US012576127B2

(12) United States Patent
Kley et al.

(10) Patent No.: US 12,576,127 B2
(45) Date of Patent: Mar. 17, 2026

(54) FIBROBLAST BINDING AGENTS AND USE THEREOF

(71) Applicants: Orionis Biosciences, Inc., Waltham, MA (US); VIB VZW, Ghent (BE); Universiteit Gent, Ghent (BE)

(72) Inventors: Nikolai Kley, Waltham, MA (US); Jan Tavernier, Balegem (BE); Anje Cauwels, Merelbeke (BE)

(73) Assignees: Orionis Biosciences, Inc., Waltham, MA (US); VIB VZW, Ghent (BE); Universiteit Gent, Ghent (BE)

( * ) Notice: Subject to any disclaimer, the term of this patent is extended or adjusted under 35 U.S.C. 154(b) by 0 days.

(21) Appl. No.: 18/402,252

(22) Filed: Jan. 2, 2024

(65) Prior Publication Data

US 2024/0148824 A1 May 9, 2024

Related U.S. Application Data

(63) Continuation of application No. 16/967,288, filed as application No. PCT/US2019/016629 on Feb. 5, 2019, now Pat. No. 11,896,643.

(60) Provisional application No. 62/626,453, filed on Feb. 5, 2018.

(51) Int. Cl.
*A61K 38/16* (2006.01)
*A61K 31/704* (2006.01)
*C07K 14/555* (2006.01)

(52) U.S. Cl.
CPC ............ *A61K 38/16* (2013.01); *A61K 31/704* (2013.01); *C07K 14/555* (2013.01); *C07K 2317/24* (2013.01); *C07K 2317/565* (2013.01); *C07K 2317/569* (2013.01)

(58) Field of Classification Search
None
See application file for complete search history.

(56) References Cited

U.S. PATENT DOCUMENTS

| | | | |
|---|---|---|---|
| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 4,537,776 | A | 8/1985 | Cooper |
| 5,059,595 | A | 10/1991 | Le Grazie |
| 5,073,543 | A | 12/1991 | Marshall et al. |
| 5,120,548 | A | 6/1992 | McClelland et al. |
| 5,354,556 | A | 10/1994 | Sparks et al. |
| 5,475,096 | A | 12/1995 | Gold et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,733,556 | A | 3/1998 | Schrier et al. |
| 5,831,012 | A | 11/1998 | Nilsson et al. |
| 6,004,746 | A | 12/1999 | Brent et al. |
| 6,433,157 | B1 | 8/2002 | Shanafelt et al. |
| 6,653,104 | B2 | 11/2003 | Goldenberg |
| 6,794,144 | B1 | 9/2004 | Saksela et al. |
| 6,818,418 | B1 | 11/2004 | Lipovsek et al. |
| 6,994,982 | B1 | 2/2006 | Watt et al. |
| 7,166,697 | B1 | 1/2007 | Galanis et al. |
| 7,186,524 | B2 | 3/2007 | Kolmar et al. |
| 7,250,297 | B1 | 7/2007 | Beste et al. |
| 7,417,130 | B2 | 8/2008 | Stumpp et al. |
| 7,803,907 | B2 | 9/2010 | Stemmer et al. |
| 7,838,629 | B2 | 11/2010 | Fiedler et al. |
| 7,993,636 | B2 | 8/2011 | Mayumi et al. |
| 8,008,449 | B2 | 8/2011 | Korman et al. |
| 8,217,149 | B2 | 7/2012 | Irving et al. |
| 8,278,036 | B2 | 10/2012 | Kariko et al. |
| 8,354,509 | B2 | 1/2013 | Carven et al. |
| 8,779,108 | B2 | 7/2014 | Queva et al. |
| 8,907,053 | B2 | 12/2014 | Sasikumar et al. |
| 8,907,065 | B2 | 12/2014 | Hermans et al. |
| 9,067,991 | B2 | 6/2015 | Beirnaert |
| 9,078,860 | B2 | 7/2015 | Szkudlinski et al. |
| 9,492,562 | B2 | 11/2016 | Tavernier et al. |
| 9,732,135 | B2 | 8/2017 | Tavernier et al. |
| 9,878,014 | B2 | 1/2018 | Tavernier et al. |
| 9,914,759 | B2 | 3/2018 | Tavernier et al. |
| 9,932,409 | B2 | 4/2018 | Tavernier et al. |

(Continued)

FOREIGN PATENT DOCUMENTS

| | | | |
|---|---|---|---|
| CN | 106928368 | A | 7/2017 |
| EP | 294703 | A2 | 12/1998 |

(Continued)

OTHER PUBLICATIONS

Fischer et al ("Radioimmunotherapy of fibroblast activation protein positive tumors by rapidly internalizing antibodies." Clinical cancer research : an official journal of the American Association for Cancer Research vol. 18,22 (2012): 6208-18) (Year: 2012).*
Almagro & Fransson, Frontiers in Bioscience 2008; 13:1619-33; (Year: 2008).*
Hasegawa H et al. (mAbs 2017, 9(5) 854-873) (Year: 2017).*
Simeon et al (In vitro-engineered non-antibody protein therapeutics, Protein & Cell, vol. 9, Jan. 2018, pp. 3â14) (Year: 2018).*
Fuming ZI et al., "Fibroblast activation protein α in tumor microenvironment: Recent progression and implications (Review)", Molecular Medicine Reports 11: 3203-3211, 2015.
Spangler J. B. et al., Insights into cytokine-receptor interactions from cytokine engineering. Annu Rev Immunol, Dec. 10, 2014, vol. 33, pp. 139-167.

(Continued)

*Primary Examiner* — Zachariah Lucas
*Assistant Examiner* — Sarah A Alsomairy
(74) *Attorney, Agent, or Firm* — Morgan, Lewis & Bockius LLP

(57) ABSTRACT

The present invention relates, in part, to agents that bind fibroblast activation protein (FAP) and their use as diagnostic and therapeutic agents. The present invention further relates to pharmaceutical compositions comprising the FAP binding agents and their use in the treatment of various diseases.

8 Claims, 28 Drawing Sheets

Specification includes a Sequence Listing.

(56) References Cited

U.S. PATENT DOCUMENTS

| | | | | |
|---|---|---|---|---|
| 10,034,919 | B2 | 7/2018 | Tavernier et al. | |
| 10,035,835 | B2 | 7/2018 | Tavernier et al. | |
| 10,072,059 | B2 | 9/2018 | Tavernier et al. | |
| 10,407,480 | B2 | 9/2019 | Tavernier et al. | |
| 10,640,542 | B2 | 5/2020 | Tavernier et al. | |
| 10,787,493 | B2 | 9/2020 | Tavernier et al. | |
| 10,906,985 | B2 | 2/2021 | Kley et al. | |
| 10,946,070 | B2 | 3/2021 | Tavernier et al. | |
| 10,947,288 | B2 | 3/2021 | Tavernier et al. | |
| 10,988,538 | B2 | 4/2021 | Kley et al. | |
| 11,001,631 | B2 | 5/2021 | Tavernier et al. | |
| 11,084,859 | B2 | 8/2021 | Kley et al. | |
| 11,236,141 | B2 | 2/2022 | Kley et al. | |
| 11,236,166 | B2 | 2/2022 | Kley et al. | |
| 11,246,911 | B2 | 2/2022 | Tavernier et al. | |
| 11,358,997 | B2 | 6/2022 | Tavernier et al. | |
| 11,384,154 | B2 | 7/2022 | Kley et al. | |
| 2004/0023334 | A1 | 2/2004 | Prior | |
| 2004/0132094 | A1 | 7/2004 | Etzerodt et al. | |
| 2004/0146938 | A1 | 7/2004 | Nguyen et al. | |
| 2004/0157209 | A1 | 8/2004 | Yilmaz et al. | |
| 2004/0209243 | A1 | 10/2004 | Nixon et al. | |
| 2008/0025980 | A1 | 1/2008 | Hardy et al. | |
| 2009/0101611 | A1 | 4/2009 | Lin et al. | |
| 2010/0119446 | A1 | 5/2010 | Grabulovski et al. | |
| 2010/0239633 | A1 | 9/2010 | Strome et al. | |
| 2011/0262348 | A1 | 10/2011 | Movahedi et al. | |
| 2011/0271358 | A1 | 11/2011 | Freeman et al. | |
| 2011/0318373 | A1 | 12/2011 | Sasikumar et al. | |
| 2012/0039906 | A1 | 2/2012 | Olive | |
| 2012/0128591 | A1* | 5/2012 | Bacac | A61P 43/00 435/69.6 |
| 2012/0244112 | A1 | 9/2012 | Ast et al. | |
| 2013/0058962 | A1 | 3/2013 | Shoemaker et al. | |
| 2013/0309250 | A1 | 11/2013 | Cogswell et al. | |
| 2014/0044738 | A1 | 2/2014 | Langermann et al. | |
| 2014/0271462 | A1 | 9/2014 | Ho et al. | |
| 2014/0356353 | A1 | 12/2014 | Queva et al. | |
| 2015/0011732 | A1 | 1/2015 | Pepinsky et al. | |
| 2016/0145325 | A1 | 5/2016 | Verheesen et al. | |
| 2017/0368169 | A1 | 12/2017 | Loew et al. | |
| 2018/0002445 | A1 | 1/2018 | Bauer et al. | |
| 2018/0022822 | A1 | 1/2018 | Brokopp et al. | |
| 2018/0030120 | A1 | 2/2018 | Riazi et al. | |
| 2019/0144553 | A1 | 5/2019 | Kley et al. | |
| 2020/0231674 | A1 | 7/2020 | Kley et al. | |
| 2020/0354424 | A1 | 11/2020 | Kley et al. | |
| 2020/0407448 | A1 | 12/2020 | Kley et al. | |
| 2021/0024637 | A1 | 1/2021 | Kley et al. | |
| 2021/0238264 | A1 | 8/2021 | Kley et al. | |

FOREIGN PATENT DOCUMENTS

| | | | |
|---|---|---|---|
| EP | 2492355 | A1 | 8/2012 |
| WO | 9404678 | A1 | 3/1994 |
| WO | 96/34103 | A1 | 10/1996 |
| WO | 1997/10338 | A1 | 3/1997 |
| WO | 9937681 | A2 | 7/1999 |
| WO | 2000/023114 | A2 | 4/2000 |
| WO | 0043507 | A1 | 7/2000 |
| WO | 0190190 | A2 | 11/2001 |
| WO | 2002/018422 | A1 | 3/2002 |
| WO | 02085945 | A2 | 10/2002 |
| WO | 03025020 | A1 | 3/2003 |
| WO | 03035694 | A2 | 5/2003 |
| WO | 2004/041862 | A2 | 5/2004 |
| WO | 04049794 | A2 | 6/2004 |
| WO | 2004060965 | A2 | 7/2004 |
| WO | 2006/121168 | A1 | 11/2006 |
| WO | 2007/005874 | A2 | 1/2007 |
| WO | 2008/071447 | A2 | 6/2008 |
| WO | 2008/124086 | A2 | 10/2008 |
| WO | 2009/114335 | A2 | 9/2009 |
| WO | 2010/027827 | A2 | 3/2010 |
| WO | 2010/030671 | A1 | 3/2010 |
| WO | 2010/036959 | A2 | 4/2010 |
| WO | 2011/066342 | A2 | 6/2011 |
| WO | 2011/066389 | A1 | 6/2011 |
| WO | 2012/145493 | A1 | 10/2012 |
| WO | 2012146628 | A1 | 11/2012 |
| WO | 2013059885 | A2 | 5/2013 |
| WO | 2013107791 | A1 | 7/2013 |
| WO | 2015/007520 | A1 | 1/2015 |
| WO | 2015/007536 | A2 | 1/2015 |
| WO | 2015/007542 | A1 | 1/2015 |
| WO | 2015007903 | A1 | 1/2015 |
| WO | 2015/112900 | A1 | 7/2015 |
| WO | 2016/06272 | A1 | 1/2016 |
| WO | 2016/022630 | A1 | 2/2016 |
| WO | 2016/025385 | A1 | 2/2016 |
| WO | 2016030350 | A1 | 3/2016 |
| WO | 2016/061142 | A1 | 4/2016 |
| WO | 2016065409 | A1 | 5/2016 |
| WO | 2016/113555 | A1 | 7/2016 |
| WO | 2016/113557 | A1 | 7/2016 |
| WO | 2017134301 | A1 | 8/2017 |
| WO | 2017134305 | A1 | 8/2017 |
| WO | 2017153402 | A1 | 9/2017 |
| WO | WO 2017/194783 | A1 | 11/2017 |

OTHER PUBLICATIONS

Elliott, et al., (1997) Blood, 89:493-502.
Taylor et al., (2010) PEDS, 23(4): 251-260.
Mathew et al., (2009) Cancer Sci 100(8): 1359-65.
Blattler et al., Biochemistry 24, 1517-1524, (1984).
Hamid, et al. (2013) New England Journal of Medicine 369 (2): 134-44.
BioDrugs (2015) 29:215-239.
Chapman, Nat. Biotechnol., 54, 531-545 (2002).
Veronese and Harris, Adv. Drug Deliv. Rev. 54, 453-456 (2003).
Harris and Chess, Nat. Rev. Drug. Discov., 2, (2003).
Yang et al., Protein Engineering, 16, 10, 761-770 (2003).
Cao and Suresh, Journal of Drug Targeting, 8, 4, 257 (2000).
Chichili et al., (2013), Protein Sci. 22(2):153-167.
Chen et al., (2013), Adv Drug Deliv Rev. 65(10):1357-1369.
Crasto et al., (2000), Protein Eng. 13(5):309-312.
Journal of Pharmaceutical Science, 66, 2-19 (1977).
Langer, 1990, Science 249:1527-1533.
Agnew, Chem. Intl. Ed. Engl., 33: 183-186 (1994).
Youle, et al., Proc. Nat'l Acad. Sci. USA 77:5483 (1980).
Gilliland, et al., Proc. Nat'l Acad. Sci. USA 77:4539 (1980).
Krolick, et al., Proc. Nat'l Acad. Sci. USA 77:5419 (1980).
Brennen, et al., "Rationale Behind Targeting Fibroblast Activation Protein-Expressing Carcinoma-Associated Fibroblasts as a Novel Chemotherapeutic Strategy," Molecular Cancer Therapeutics, vol. 11, No. 2, pp. 257-266, Feb. 2012.
International Search Report & Written Opinion, PCT Application No. PCT/US19/16629, date Jun. 11, 2019, 17 pages.
Stagg, J. et. al., Immunotherapeutic approach in triple-negative breast cancer. Ther Adv Med Oncol. (2013) 5(3):169-181.

* cited by examiner

```
                     *        20         *        40         *        60         *        80         *       100         *
2HFA7  : CAGGTGCAGCTGCAGGAGTCTGGGGGAGGATTGGTAGAGGCTGAGGGCTCTCTGAGACTCTCCTGTGCAGCCTCTGGACGCACCTTCGGTAGCTATGCCATGG------GCTGGTTCCG : (SEQ ID NO: 844)
2HFA31 : CAGGTGCAGCTGCAGGAGTCTGGGGGAGGATTGGTAGAGGCTGAGGGCTCTCTGAGACTCTCCTGTGCAGCCTCTGGACGCACCTTCGGTAGCTATGCCATGG------GCTGGTTCCG : (SEQ ID NO: 845)
2HFA6  : CAGGTGCAGCTGCAGGAGTCTGGGGGAGGATTGGTGGAGGCTGAGGGCTCTCTGAGACTCTCCTGTGCAGCCTCTGGACGCACCTTCGGTACCTATGCGCTGG------CCTGGTTCCG : (SEQ ID NO: 846)
2HFA25 : CAGGTGCAGCTGCAGGAGTCTGGGGGAGGATTGGTGCAGGCTGGGGGCTCTCTGAGACTCTCCTGTGCAGCCTCTGGACGCACCTTCAGTAGCTATGCCATGG------GCTGGTTCCG : (SEQ ID NO: 847)
2HFA26 : CAGGTGCAGCTGCAGGAGTCTGGGGGAGGCTTGGTGCAGGCTGGGGGGTCTCTGAGACTCTCCTGTGCAGCCTCTGGACGCACCTTCAGTACGTATGCCATGG------GCTGGTTCCG : (SEQ ID NO: 848)
2HFA1  : CAGGTGCAGCTGCAGGAGTCTGGGGGAGGATTGGTAGAGGCTGAGGGCTCTCTGAGACTCTCCTGTATAGCCTCTGGACGCACCTTCGGTACCTATGCCATGG------GCTGGTTCCG : (SEQ ID NO: 849)
2HFA3  : CAGGTGCAGCTGCAGGAGTCTGGAGGAGGATTGGTAGAGGCTGAGGGCTCTCTGAGACTCTCCTGTATAGCCTCTGGACGCACCTTCGGTACCTATGCCATGG------GCTGGTTCCG : (SEQ ID NO: 850)
2HFA53 : CAGGTGCAGCTGCAGGAGTCTGGGGGAGGATTGGTAGAGGCTGAGGGCTCTCTGAGACTCTCCTGTGCAGCCTCTGGACGCGCCTTCGGTAGCTATGCCATGG------GCTGGTTCCG : (SEQ ID NO: 851)
2HFA55 : CAGGTGCAGCTGCAGGAGTCTGGGGGAGGATTGGTAGAGGCTGAGGGCTCTCTGAGACTCTCCTGTGCAGCCTCTGGACGCACCTTCGGTAGTTATGCCATGG------GCTGGTTCCG : (SEQ ID NO: 852)
2HFA71 : CAGGTGCAGCTGCAGGAGTCTGGGGGAGGATTGGTAGAGGCTGAGGGCTCTCTGAGACTCTCCTGTGCAGCCTCTGGACGCACCTTCGGTAGTTATGCCATGG------GCTGGTTCCG : (SEQ ID NO: 853)
2HFA60 : CAGGTGCAGCTGCAGGAGTCTGGGGGAGGATTGGTAGAGGCTGAGGGCTCTCCGAGACTCTCCTGTGCAGCCTCTGGACGCACCTTCGGTAGCTATGCCATGG------GCTGGTTCCG : (SEQ ID NO: 854)
2HFA9  : CAGGTGCAGCTGCAGGAGTCTGGGGGAGGATTGGTAGAGGCTGAGGGCTCTCTGAGACTCTCCTGTGCAGCCTCTGGACGCACCTTCGGTAGCTATGCCATGG------GCTGGTTCCG : (SEQ ID NO: 855)
2HFA73 : CAGGTGCAGCTGCAGGAGTCTGGAGGAGGCTTGGTGCAGCCTGGGGGTTCTCTGAGACTCTCCTGTGCAGCCTCTGGACGCACCTTCGGTAGCTATGCCATGG------GCTGGTTCCG : (SEQ ID NO: 856)
2HFA65 : CAGGTGCAGCTGCAGGAGTCTGGGGGAGGCTTGGTGCAGGCTGGGGGGTCTCTGAGACTCTCCTGCGCAGCCTCTGGAAACATCGACAGTATCGCTTCCATGG------GCTGGTACCG : (SEQ ID NO: 857)
2HFA49 : CAGGTGCAGCTGCAGGAGTCTGGAGGAGGATTGGTGCAGGCTGAGGGCTCTCTGAGACTCTCCTGTGCAGCCTCTGGACGCACCTTCGGTAGCTATGCCATGG------GCTGGTTCCG : (SEQ ID NO: 858)
2HFA14 : CAGGTGCAGCTGCAGGAGTCTGGGGGAGGATTGGTGCAGGCTGGGGACTCTCTGAGACTCTCCTGTGCAGCCTCTGGACGCACTTTCAGTAGCTATGTCATGG------GCTGGTTCCG : (SEQ ID NO: 859)
2HFA57 : CAGGTGCAGCTGCAGGAGTCTGGAGGAGGATTGGTGTAGGCTGGGGGCTCTCTGAGACTCTCCTGTGCAGCCTCTGGACGCACCTTCAGTGATTATGCCATGG------GCTGGTTCCG : (SEQ ID NO: 860)
2HFA5  : CAGGTGCAGCTGCAGGAGTCTGGGGGAGGCTTGGTGCAGGCTGGGGGGTCTCTGAGACTCTCCTGTGCAGTCTCTGGAAGACTCTTCAGTGCCAATACCATGG------GCTGGTACCG : (SEQ ID NO: 861)
2HFA20 : CAGGTGCAGCTGCAGGAGTCTGGGGGAGGCTTGGTGCAGGCTGGGGGGTCTCTGAGACTCTCCTGTGCAGTCTCTGGAAGACTCTTCAGTGCCAATACCATGG------GCTGGTACCG : (SEQ ID NO: 862)
2HFA51 : CAGGTGCAGCTGCAGGAGTCTGGGGGAGGCTTGGTGCAGGCTGGGGGGTCTCTGAGACTCTCCTGTGCAGTCTCTGGAATTATCTCCAGTATGAATGCCATGG------GCTGGTACCG : (SEQ ID NO: 863)
2HFA24 : CAGGTGCAGCTGCAGGAGTCTGGGGGAGGCTTGGTGCAGGCTGGGGGGTCTCTGAGACTCTCCTGTGCAGCCTCTGGAAGCATCTTCAGTAGCAATGCCATGG------GCTGGTACCG : (SEQ ID NO: 864)
2HFA23 : CAGGTGCAGCTGCAGGAGTCTGGGGGAGGCTTGGTGCAGGCTGGGGGGTCTCTGAGACTCTCCTGTGCAGCCTCTGGACGCACCTTTAGTATGTATGCCATAG------GCTGGTTCCG : (SEQ ID NO: 865)
2HFA36 : CAGGTGCAGCTGCAGGAGTCTGGGGGAGGATTGGTGCAGCCTGGGGACTCTCTGAGACTCTCCTGTGCAGCCTCTGAACGCACCTTTAGTATGTATGCCATAG------GCTGGTTCCG : (SEQ ID NO: 866)
2HFA63 : CAGGTGCAGCTGCAGGAGTCTGGGGGAGGCTTGGTGCAGGCTGGGGGGTCTCTGAGACTCTCCTGTGTAGTCTCTGGAACCATCTTGAGTAGCAATTCCATGG------GCTGGTACCG : (SEQ ID NO: 867)
2HFA19 : CAGGTGCAGCTGCAGGAGTCTGGGGGAGGCTTGGTGCAGGCTGGGGGGTCTCTGAGACTCTCCTGTGCAGCCTCTGGAAGCATCTTCGTTGGCAATGCCATGG------GCTGGTACCG : (SEQ ID NO: 868)
2HFA41 : CAGGTGCAGCTGCAGGAGTCTGGGGGAGGCTTGGTGCGGGCTGGGGGGTCTCTGAGACTCTCCTGTGCAGCCTCTGGAAGCATCTTCGTTGGCAATGCCATGG------GCTGGTACCG : (SEQ ID NO: 869)
2HFA2  : CAGGTGCAGCTGCAGGAGTCTGGGGGAGGCTTGGTGCAGACTGGGGGGTCTCTGAGACTCTCCTGTGCAGCCTCTGGAAGCATCTTCGTTGGCAATGCCATGG------GCTGGTACCG : (SEQ ID NO: 870)
2HFA42 : CAGGTGCAGCTGCAGGAGTCTGGAGGAGGCTTGGTGCAGACTGGGGGGTCTCTGAGACTCTCCTGTGCAGCCTCTGGAAGCATCTTCGTTGGCAATGCCATGG------GCTGGTACCG : (SEQ ID NO: 871)
2HFA67 : CAGGTGCAGCTGCAGGAGTCTGGGGGAGGCTTGGTGCAGGCTGGGGGGTCTCTGAGACTCTCCTGTGTAGTCTCTGGAAGCTTCGACAGTCGCAATGCCATGG------CCTGGTACCG : (SEQ ID NO: 872)
2HFA12 : CAGGTGCAGCTGCAGGAGTCTGGGGGAGGCTTGGTGCAGGCTGGGGGGTCTCTGAGACTCTCGTGTGCAGCCTCTGGAAGCATCTCCATGCTCAATAGTATGG------GCTGGTACCG : (SEQ ID NO: 873)
2HFA29 : CAGGTGCAGCTGCAGGAGTCTGGGGGAGGCTTGGTGCAGGCTGGGGGGTCTCTGAGACTCTCCTGTGCAGCCTCTGGAACCATGTCCAGTATCAATGCCATGG------GCTGGTACCG : (SEQ ID NO: 874)
2HFA11 : CAGGTGCAGCTGCAGGAGTCTGGGGGAGGCTTGGTGCAGGCTGGGGGGTCTCTGAGACTCTCGTGTGCAGCCTCTGGAAGCTTCGACAGTCGCAATGCCATGG------GCTGGTACCG : (SEQ ID NO: 875)
2HFA44 : CAGGTGCAGCTGCAGGAGTCTGGGGGAGGCTTGGTGCAGGCTGGGGGGTCTCTGAGACTCTCGTGTGCAGCCTCTGGAGGCTTCGACAGTCGCAATGCCATGG------GCTGGTACCG : (SEQ ID NO: 876)
2HFA46 : CAGGTGCAGCTGCAGGAGTCTGGAGGAGGCTTGGTGCAGGCTGGGGGGTCTCTGAGACTCTCGTGTGCAGCCTCTGGAAGCATCGACAGTCGCAATACCATGG------GCTGGTACCG : (SEQ ID NO: 877)
2HFA52 : CAGGTGCAGCTGCAGGAGTCTGGAGGAGGCTTGGTGCGGGCTGGGGGGTCTCTGAGACTCTCGTGTGCAGCCTCTGGAACGTTCGATAGTCGCAATGCCATGG------GCTGGTACCG : (SEQ ID NO: 878)
2HFA4  : CAGGTGCAGCTGCAGGAGTCTGGGGGAGGCTTGGTACAGGCTGGGGGGTCTCTGAGACTCTCGTGTGCAGCCTCTGGAAGCATCGACATTCGCAATGCCATGG------GCTGGTACCG : (SEQ ID NO: 879)
2HFA38 : CAGGTGCAGCTGCAGGAGTCTGGGGGGGGCTTGGTGCGGGTTGGGGGGTCTCTGAGACTCTCGTGTGCAGTTTCTGGAAGCTTCGACAGTCGCAACAGCATGG------GCTGGTACCG : (SEQ ID NO: 880)
2HFA10 : CAGGTGCAGCTGCAGGAGTCTGGGGGAGGCTTGGTGCAGGCTGGGGGGTCTCTGAGACTCTCCTGTACAGTCGCTGAAAGCATCGACGTTCGCAATGCCATGG------GCTGGTACCG : (SEQ ID NO: 881)
2HFA43 : CAGGTGCAGCTGCAGGAGTCTGGAGGAGGCTTGGTGCAGGCTGGGGGGTCTCTGAGACTCTCCTGTGTAGCCTCTGGAACCATCTTCAGTAGCGGAGCCATGGCCATGGGCTGGTACCG : (SEQ ID NO: 882)
2HFA50 : CAGGTGCAGCTGCAGGAGTCTGGGGGAGGCTTGGTGCAGGCTGGGGGGTCTCTGAGACTCTCCTGTGTAGCCTCTGGAACCATC---AGTAGTGGAGCCATGG------GCTGGTACCG : (SEQ ID NO: 883)
2HFA62 : CAGGTGCAGCTGCAGGAGTCTGGAGGAGGATTGGTGCAGGCTGGGGGCTCTCTGAGACTCTCCTGTGCAGCCTCTAGAAGCATCTTCAGTATCGGCACCATGG------GCTGGTACCG : (SEQ ID NO: 884)
```

Figure 10 (CONT.):

```
         120         *        140         *        160         *        180         *        200         *        220         *
2HFA7  : CCAGGCTCCAGGAAAGTCGCGCGAGTTGGTCGCAGCTATTAGTAGTGGTGGT---ACCACATACTATGCAGACTCTGTGAAGGGCCGATTCACCATCTCCAGAGACAACGCCAGGAACA : (SEQ ID NO: 844)
2HFA31 : CCAGGCTCCAGGAAAGTCGCGCGAGTTGGTCGCAGCTATTAGTAGTGGTGGT---ACCACATACTATGCAGACTCTGTGAAGGGCCGATTCACCATCTCCAGAGACAACGCCAGGAACA : (SEQ ID NO: 845)
2HFA6  : CCAGGCTCCAGGAAAGTCGCGCGAGTTGGTCGCAGCTATTAGTAGTGGTGGT---AGCACATACTATGCAGACTCTGTGAAGGGCCGATTCACCATCTCCAGAGACAACGCCAGGAACA : (SEQ ID NO: 846)
2HFA25 : CCAGGCTCCAGGGAAGGAGCGCGAGTTGGTCGCAGCTATTAGTAATGGTGGT---AGCGCATACTATGCAGACTCTGTGAAGGGCCGATTCACCATCTCCAGAGACAACGCCAGGAACA : (SEQ ID NO: 847)
2HFA26 : CCAGGCTCCAGGGAAGGAGCGCGAGTTGGTCGCAGCTATTAGTAATGGTGGT---AGCGCATACTATGCAGACTCTGTGAAGGGCCGATTCACCATCTCCAGAGACAACGCCAGGAACA : (SEQ ID NO: 848)
2HFA1  : CCAGGCTCCAGGAAAGGAGCGCGAGTTGGTCGCAGCTATTAGTAGTGGTGGT---AGCGCATATTATGCAGACTCTGTGAAGGGCCGATTCACCATCTCCAGAGACAACGCCAGGAACA : (SEQ ID NO: 849)
2HFA3  : CCAGGCTCCAGGAAAGGAGCGCGAGTTGGTCGCAGCTATTAGTACTGGTGGT---AGCACATACTATGCAGACTCTGTGAAGGGCCGATTCACCATCTCCAGAGACAACGCCAGGAACA : (SEQ ID NO: 850)
2HFA53 : CCAGGCTCCAGGCTTGGAGCGCGAGCTGGTCGCAGCTATTAGTAGTGGTGGT---ACCACATACTATGCAGACTCTGTGAAGGGCCGATTCACCATCTCCAGAGACAACGCCAGGAACA : (SEQ ID NO: 851)
2HFA55 : CCAGGCTCCAGGAAAGGAGCGCGAGTTGGTCGCAGCTATTAGTAGTGGTGGT---AGCACATTGTATGCAGACTCTGTGAAGGGCCGATTCACCATCTCCAGAGACAACGCCAAGAACA : (SEQ ID NO: 852)
2HFA71 : CCAGGCTCCAGGAAAGGAGCGCGAGTTGGTCGCAGCTATTAGTAGTGGTGGT---AGCACATTGTATGCAGGCTCTGTGAAGGGCCGATTCACCATTTCCAAAGACAACGCCAAGAACA : (SEQ ID NO: 853)
2HFA60 : CCAGGCTCCAGGAAAGGAGCGCGAGTTGGTCGCAGCTATTAGTAGTGGTGGT---ATTACATACTATGCAGACTCTGTGAAGGGCCGATTCACCATCTCCAGAGACAACGCCAAGAACA : (SEQ ID NO: 854)
2HFA9  : CCAGGCTGCAGGAAAGGAGCGCGAGTTGGTCGCAGCTATTAGTGCTGGTGGT---AGCACACTCTATGCTGACAATGTGAAGGGCCGATTCACCATCTCCAGAGACAACGCCAGGAACA : (SEQ ID NO: 855)
2HFA73 : CCAGGCTGCAGGAAAGGAGCGCGAGTTGGTCGCAGCTATTAGTGCTGGTGGT---AGCACACTCTATGCTGACAATGTGAAGGGCCGATTCACCATCTCCAGAGACAACGCCAGGAACA : (SEQ ID NO: 856)
2HFA65 : CCAGGCTCCAGGGAAGCAGCGCGAATTGGTCGCAGCGATTAGTGTTGGTGGT---AGCACATACTATGCAGACTCTGTGAAGGGCCGATTCACCATCTCCAGAGACAACGCCAGGAACA : (SEQ ID NO: 857)
2HFA49 : CCAGGCTCCAGGGAAGGAGCGCGAGTTGGTCGCAGGTATTAGTAGTGGTGGT---ATTACAAACTATGCACACTCTGTGAAGGGCCGATTCACCATCTCCAGAGACATTGACAAGAACA : (SEQ ID NO: 858)
2HFA14 : CCAGGTTCCAGGGAAGCAGCGCGAGTTGGTCGCAGCGATTACTAGTGGTCTT---AGCACATACTATGCAGACTCCCTGAAGGGCCGATTCACCATCTCCAGAGACAACGCCAAGAACA : (SEQ ID NO: 859)
2HFA57 : CCAGGCTCCAGGGAAGGAGCGTGAGTTTATAGCAGGTATTAGTTGGGGGGGTTCAAGCACATACTATGCAGACTCCGTGAAGGGCCGATTCACCATCTCCAGAGACAACGCCAAGAACA : (SEQ ID NO: 860)
2HFA5  : CCAGGCTCCAGGGAAGCGGCGCGAGTTGGTCGCGACTATTTTGAGTAGTGGT---AGCACAAACTATGCAGACTCCGTGAAGGGCCGATTCACCATCTCCAGAGACGACGGCAAGAACA : (SEQ ID NO: 861)
2HFA20 : CCAGGCTCCAGGGAAGCGGCGCGAGTTGGTCGCGACTATTTTGAGTAGCGGT---AGCACAAACTATGCAGACTCCGTGAAGGGCCGATTCACCATCTCCAGAGACGACGCCAAGAACA : (SEQ ID NO: 862)
2HFA51 : CCAGGCTCCAGGGAAGCGGCGCGAGTTGGTCGCAGGTCTTGGTAGTGGGGTT---AGTACAACTTATGCAGACGCCGTGAAGGGCCGCTTCACCATCTCCAGAGACAACGCCAAGAACA : (SEQ ID NO: 863)
2HFA24 : CCAGGCCGCAGGGAAGCGGCGCGAGTTGGTCGCAGGTATCCGTAGTGATGGT---AACACAAACTATGTAGACTCCGTGAAGGGCCGATTCACCATCTCCAGAGACCGTGCCAAGAACA : (SEQ ID NO: 864)
2HFA23 : CCAGGCTCCAGGGAAGGAGCGCGAGTTGGTCGCAAGTATTAGTAGTGGTGGT---AGCACAAACTATGCAGACTCTGTGAAGGGCCGATTCACCATCTCCAGAGACAACGCCGAGAAAA : (SEQ ID NO: 865)
2HFA36 : CCAGGCTCCAGGGAAGGAGCGCGAGTTGGTCGCAGGTATTAGTAGTGGTGGT---AGCACAAACTATGCAGACTCTGTGAAGGGCCGATTCACCATCTCCAGAGACAACCCCAAGAAAA : (SEQ ID NO: 866)
2HFA63 : CCAGGCTCCAGGGAAGCGCCGCGAATTGGTCGCAAGTATTAGTACGGATGGT---AGCACCAACTATGCAGACTCCGTGAAGGGCCGATTCACCATCTCCAGAGACAATGCCAAGAGCA : (SEQ ID NO: 867)
2HFA19 : CCAGGCTCTAGGGAACCAGCGCGAGTTGGTCGCTGGCATTACCAGTGATGGT---ACCACATACTATCCAGACTCCGTGAAGGGCCGATTCACCATCTCCAGAGACAATGACAAGAACA : (SEQ ID NO: 868)
2HFA41 : CCAGGCTCTAGGGAACCAGCGCGAGTTGGTCGCTGGCATTACCAGTGATGGT---ACCACATACTATCCAGACTCCGTGAAGGGCCGATTCACCATCTCCAGAGACAATGACAAGAACA : (SEQ ID NO: 869)
2HFA2  : CCAGGCTCTAGGGAACCAGCGCGAGTTGGTCGCTGGCATTACCAGTGATGGT---ACCACATACTATCCAGACTCCGTGAAGGGCCGATTCACCATCTCCAGAGACAATGACAAGAACA : (SEQ ID NO: 870)
2HFA42 : CCAGGCTCTAGGGAACCAGCGCGAGTTGGTCGCTGGCATTACCAGTGATGGT---ACCACATACTATCCAGACTCCGTGAAGGGCCGATTCACCATCTCCAGAGACAATGACAAGAACA : (SEQ ID NO: 871)
2HFA67 : CCAGGCTCTAGGGAAGGAGCGCGTGTGGGTCGCTGGCATTATCAGTGATGGT---AGCACAAACTATGCAGACGCCGTGAAGGGCCGATTCACCATCTCCAGAGACAATGACAAGAATA : (SEQ ID NO: 872)
2HFA12 : CCAGGCTCTAGGGAAGCAGCGCGAGTTCGTCGCTGGCATTACCAGTGGTGGG---CGCACAAACTATGCGGACTCCGTGAAGGGCCGATTCGCCATCTCCAGAGACAATGACAAGAACA : (SEQ ID NO: 873)
2HFA29 : CCAGGCTCCAGGGAAGCAGCGCGAGTTGGTCGCAGGTATTCTAAGTGATGGT---ACCACAAAGTATGTTGAATCCGTGAAGGGCCGATTCACCATCTCCAGAGACAATGCCAAGAATA : (SEQ ID NO: 874)
2HFA11 : CCAGGCTCCAGGGAAGCGCCGCGAGTGGGTCGCAACTATTACTACTGATGGT---CGCACAAACTATGCAGACTCCGTAAAGGCCCGATTCACCGTCTCCAGAGACAATGCCAAGAACA : (SEQ ID NO: 875)
2HFA44 : CCAGGCTCCAGGGAAGCGCCGCGAGTGGGTCGCAACTATTACTAGTGATGGT---CGCACAAACTATGCAGACTCCGTGAAGGCCCGATTCACCATCTCCAGAGACAATTCCAAGAACA : (SEQ ID NO: 876)
2HFA46 : CCAGGCTCCAGGGAAGCGCCGCGAGTGGGTCGCAACTATTACTACTGGTGGT---CGCACAAACTATGCAGACTCCGTGAAGGCCCGATTCACCATCTCCAGAGACAATGCCAAGAACA : (SEQ ID NO: 877)
2HFA52 : CCAGGCTCCAGGGAAGCGCCGCGAGTGGGTCGCGACTATTACTACTGATGGT---CGCACAAACTATGCAGACTCCGTGAAGGCCCGATTCACCATCTCCAGAGACAATGCCAAGAACA : (SEQ ID NO: 878)
2HFA4  : CCAGGCTCCGGGGACGCGCCGCGAGTGGGTCGCAACTATTACTACGGATGGT---CGCACAAACTATGCAGACTCCGTGAAGGCCCGATTCACCATCTCCAGAGACAATGCCAAGAACA : (SEQ ID NO: 879)
2HFA38 : CCAGGCTCCAGGGAAGCGCCGCGAGTGGGTCGCAACTATTACTAGTGGTAGT---CGCACAAACTATGCAGACTCCGTGAAGGCCCGATTCACCATCTCCAGAGACAATGCCAAGAACA : (SEQ ID NO: 880)
2HFA10 : CCAGGCTCCAGGGAAGCGCCGCGAGTGGGTCGCAACTATTACTACTGGTGGA---CGCACAAACTATGCAGACTCCGTGAAGGCCCGATTCACCATCTCCAGAGACAATGCCAAGAACA : (SEQ ID NO: 881)
2HFA43 : CCAGGCTCCAGGGAAACAGCGCGAGTGGGTCGCAGGTATTACTGGTAGTCGT---ACAACAACCTATGCAGACTCCGTGAAGGGCCGATTCACCATCTCCAGAGACAACGCCGAGAACA : (SEQ ID NO: 882)
2HFA50 : CCAGGTTCCAGGGAAGCAGCGCGAGTGGGTCGCAGGTATTACTGGTAGTCGT---ACAACAATGTATACAGAATCCGTGAAGGGCCGATTCACCATCTCCAGAGACAACGCCGAGAACA : (SEQ ID NO: 883)
2HFA62 : CCAGGCTCCAGGGAAGCGGCGCGAGTTGGTCGCATTTATTACTGTTGATCAT---AATACATACTATACAGACTCCGTGAAAGGCCGATTCACCATCTCCACAGAGAATGACAAGAACA : (SEQ ID NO: 884)
```

Figure 10 (CONT.)

```
             240         *        260         *        280         *        300         *        320         *        340         *
2HFA7  : CGGTGTATCTGCAAACGAACAGCCTGAAACCTGAGGACACGGCCGTTTATTACTGCGCAGCTAGAACAGGGAGTGCCTACTACACTAATCGTATTGACTGGCC--CTACTGGGGCCAGG : (SEQ ID NO: 844)
2HFA31 : CGGTGTATCTGCAAACGAACAGCCCGAAACCTGAGGACACGGCCGTTTATTACTGCGCAGCTAGAACAGGGAGTGCCTACTACACTAATCGTATTGACTGGCC--CTACTGGGGCCAGG : (SEQ ID NO: 845)
2HFA6  : CGGTGTATCTGCAAACGAACAGCCTGAAACCTGAGGACACGGCCGTTTATTACTGCGCAGCAAAAACAGGGAGTGCCTACTACACTAATCGTATTGACTGGCC--CTACTGGGGCCAGG : (SEQ ID NO: 846)
2HFA25 : CGGTGTATCTGCAAACGAACAGCCTGAAACCTGAGGACACGGCCGTTTATTACTGCGCAGCTAGAAGAGGGAGTGCCTACTACACTAATCGTATTGACTGGCC--CTACTGGGGCCAGG : (SEQ ID NO: 847)
2HFA26 : CGGTGTATCTGCAAACGAACAGCCTGAAACCTGAGGACACGGCCGTTTATTACTGCGCAGCTAGAAGAGGGAGTGCCTACTACACTAATCGTATTGACTGGCC--CTACTGGGGCCAGG : (SEQ ID NO: 848)
2HFA1  : CGGTGTATCTGCAAACGAACAGCCTGAAACCTGAGGACACGGCTGTTTATTACTGCGCAGCTAGAAGAGGGAGTGCCTACTACACTAATCGTATTGATTGGCC--CTACTGGGGCCAGG : (SEQ ID NO: 849)
2HFA3  : CGGTGTATCTGCAAACGAACAGCCTGAAACCTGAGGACACGGCCGTTTATTACTGCGCAGCTAGAAGAGGTAGTGCCTACTACACTAATCACGTTGACTGGCC--CTACTGGGGCCAGG : (SEQ ID NO: 850)
2HFA53 : CGGTGTATTTGCAAACGAACAGCCTGAAACCTGAGGACACGGCCGTTTATTACTGCGCAGCTAGAACAGGGGGTGCCGCCTACACTAGGCGTATTGACTGGCC--CTACTGGGGCCAGG : (SEQ ID NO: 851)
2HFA55 : CGGTGTATCTGCAAATGAACAGCCTGAAACCTGAGGACACGGCCGTTTATTACTGCGCAGCTAGAAGTGGGGGTGCCTACTACACTGCCCGTGTTGACTGGCC--CTACTGGGGCCAGG : (SEQ ID NO: 852)
2HFA71 : CGGTGTATCTGCAAATGAACAGCCTGAAACCTGAGGACACGGCCGTTTATTACTGCGCAGCTAGAAGTGGGGGTGCCTACTACACTGCCCGTGTTGACTGGCC--CTACTGGGGCCAGG : (SEQ ID NO: 853)
2HFA60 : CGGTGTATCTGCAAATGAACAGCCTGAAACCTGAGGACACGGCCGTTTATTACTGCGCAGCTAGAAGTGGGAGTGCCTACTACACTACCCGTGTTGACTGGCC--CTACTGGGGCCAGG : (SEQ ID NO: 854)
2HFA9  : CGGTGTATCTGCTATCGAACAGCCTGAAGCCTGAGGACACGGCCGTTTATTACTGCGCAGCTAGAAGAGGAAGTGCCTACTACACTAATCATATTGACTGGCC--CTACTGGGGCCAGG : (SEQ ID NO: 855)
2HFA73 : CGGTGTATCTGCTATCGAACAGCCTGAAGCCTGAGGACACGGCCGTTTATTACTGCGCAGCTAGAAGAGGAAGTGCCTACTACACTAATCATATTGACTGGCC--CTACTGGGGCCAGG : (SEQ ID NO: 856)
2HFA65 : CGGTGTATCTGCAAACGAACAGCCTGAAGCCTGAGGACACGGCCGTTTATTACTGCGCAGCTAGAAGAGGGAGTGCCTACTACACTAGTCGTATTGACTGGCC--CTACTGGGGCCAGG : (SEQ ID NO: 857)
2HFA49 : CGGTGTTCCTGCAAATGAACAGCCTGAAACCTGAGGACACGGCCGTTTATTACTGTGCAGCTAGAAGTGGGGGTGCCTACTACACTTCCCGTGTTGACTGGCC--CTACTGGGGCCAGG : (SEQ ID NO: 858)
2HFA14 : CGATGTATCTGCAAATGAACAGCCTGAAACTTGAGGACACGGCCGTTTATTACTGTGCAGCCAGGGAGGGTGGAGGTATATGGACTAGTTCTACTCAGTATGA--CTACTGGGGCCAGG : (SEQ ID NO: 859)
2HFA57 : CGATGTATCTGCAAATGAACAGCCTGAAACCTGAGGACACGGCCGTTTATTACTGTGCAGCGCGCTTAAGTGGTG-----TAAGTAGATCCGACCGGCCGTATGACTACTGGGGCCAGG : (SEQ ID NO: 860)
2HFA5  : CGGTGTATCTGCAAATGAACAGCCTGAAACCTGACGACACAGCCGTCTATTACTGTA---------------------ATTTCGCCCCCCCGCCTGAGGGG-----TACTGGGGCCAGG : (SEQ ID NO: 861)
2HFA20 : CGGTGTATCTGCAAATGAACAGCCTGAAACCTGAGGACACTGCCGTCTATTACTGTA---------------------ATTTAGCCCCCCCGCCTGAGGGG-----TACTGGGGCCAGG : (SEQ ID NO: 862)
2HFA51 : CGCTGTATCTGCAAATGAACAGCCTGAAACCTGAGGACACAGCCGTCTATTACTGT--------AATCGATGGCCCCCCCCGTATGA------------------CTACTGGGGCCAGG : (SEQ ID NO: 863)
2HFA24 : CGGTGTATCTTCAGATGACCAGCCTAAAACCTGAGGACACGGCCGTCTATTACTGT--AACTACTGGCCCCCGCCCCTACGACAAGGGGGGGACTA------TGCCTACTGGGGCCAGG : (SEQ ID NO: 864)
2HFA23 : CGGTGTATCTGCAAATGATGAGCCTAGAACCTGAAGCTACGGGTGTTTATTACTGTGCAGCACGAGACGGATCTGCATTGTATACCGCACATAGCGACTGG--GACTATTGGGGCCAGG : (SEQ ID NO: 865)
2HFA36 : CGGTGTATCTGCAAATGATGAGCCTAGAACCTGAAGACACGGGCGTTTATTACTGTGCAGCACGATCCGGATCTGCATACTTTAGTGGACGTTACTACTGG--AACTATTGGGGCCAGG : (SEQ ID NO: 866)
2HFA63 : CGGTGTTTCTGCAAATGAACAGCCTGAAACCTGAGGACACGGCCGTCTATTACTGTAATTTC-----------CATCCCCCCGTCGTTCGGGATTGGGGGGATACCTACTGGGGCCAGG : (SEQ ID NO: 867)
2HFA19 : CGATATATCTGCAAATGAACAGTCTGAAACCTGAGGACACGGCCGTCTATTACTGTAATTTATGGCCCCCGCGTATAGGCTTCGCT--------------------TCCTGGGGCCAGG : (SEQ ID NO: 868)
2HFA41 : CGATATATCTGCAAATGAACAGTCTGAAACCTGAGGACACGGCCGTCTATTACTGTAATTTATGGCCCCCGCGTATAGGCTTCGCT--------------------TCCTGGGGCCAGG : (SEQ ID NO: 869)
2HFA2  : CGATATATCTGCAAATGAACAGTCTGAAACCTGAGGACACGGCCGTCTATTACTGTAATTTATGGCCCCCGCGTATAGGCTTCGCT--------------------TCCTGGGGCCAGG : (SEQ ID NO: 870)
2HFA42 : CGATATATCTGCAAATGAACAGTCTGAAACCTGAGGACACGGCCGTCTATTACTGTAATTTATGGCCCCCGCGTATAGGCTTCGCT--------------------TCCTGGGGCCAGG : (SEQ ID NO: 871)
2HFA67 : CGGTGTATCTGCAAATGAACAGTCTGAAACCTGAGGACACGGCCGTCTATTACTGCAATGCATGGCCCCCGCGTATAGGCTTGGGT--------------------TCCTGGGGCCAGG : (SEQ ID NO: 872)
2HFA12 : CGGTGTATCTGCAAATGAACAGTCTGAAACCTGAGGACACGGCCGTCTATTACTGTAATACATGGCCCCCGCGTATAGCGTTCGAT--------------------TCCTGGGGCCAGG : (SEQ ID NO: 873)
2HFA29 : CGGTGCATCTGCAAATGAACAGCCTGAAAGTTGAGGACACGGCCGTCTATTATTGTAATTTTTTTCCCCCCCCTGT---CCCTGCT--------------------TCCTGGGGCCAGG : (SEQ ID NO: 874)
2HFA11 : CGGTGTATCTGCAGATGAACAGCCTGAAACCAGACGACACGGCCGTCTATTACTGTAATGCAGCGCCTCCG------ATCTTCAAT--------------------TCCTGGGGCCAGG : (SEQ ID NO: 875)
2HFA44 : CGGTGTATCTGCAGATGAACAGCCTGAAACCAGAGGACACGGCCGTCTATTACTGTAATGCAGCGCCTCCG------ATCTTCGGT--------------------TCCTGGGGCCAGG : (SEQ ID NO: 876)
2HFA46 : CGGTGTATCTGCAGATGAACAGCCTGAAACCAGAGGACACGGCCGTCTATTACTGTAATCTAGCGCCTCCG------ATCTTCAAT--------------------TCCTGGGGCCAGG : (SEQ ID NO: 877)
2HFA52 : CGGTGTATCTGCAGATGAACAGCCTGAAACCAGAGGACACGGCCGTCTATTACTGTAATGCGGCGCCTCCG------ATCTTCGGT--------------------TCCTGGGGCCAGG : (SEQ ID NO: 878)
2HFA4  : CGGTGTATCTGCAGATGAACAGCCTGAAACCAGAGGACACGGCCGTCTATTACTGTAATTTAGCGCCTCCG------ATCTTCGGT--------------------TCCTGGGGCCAGG : (SEQ ID NO: 879)
2HFA38 : CGGTGTATCTGCAGATGGACAGCCTGAAACCAGAGGACACGGCCGTCTATTACTGTAATGCAGCGCCTCCG------ATCTTCAAT--------------------TCCTGGGGCCAGG : (SEQ ID NO: 880)
2HFA10 : CGGTGTATCTACAGATGAACAGCCTGAAACCAGAGGACACGGCCGTCTATTATTGTAATGCAGCGCCTCCG------ATCCTCAAT--------------------TCCTGGGGCCAGG : (SEQ ID NO: 881)
2HFA43 : CGGTTTTTCTGCAAATGAACAACCTGAAATCTGAAGACACAGCCGTCTATTACTGTAATCTATGGCCACC-----------------------CTCGAGGCCCGACCACTGGGGCCAGG : (SEQ ID NO: 882)
2HFA50 : CGGTTTTTCTGCAAATGAACAACCTGAAATCTGAAGACACAGCCGTCTATTACTGTAATCTATGGCCACC-----------------------CTCGAGGCCCGACTACTGGGGTCAGG : (SEQ ID NO: 883)
2HFA62 : CGGTGTATCTGCAAATGAACAGCCTGAAACCTGAAGATACGGCCGTCTATTACTGTAATCGAGCTCCTCCATCGACCGACGGGGAT--------------------CGATGGGGCCAGG : (SEQ ID NO: 884)
```

Figure 10 (CONT.)

```
                360         *        380         *        400         *        420         *        440
2HFA7  : GGACCCAGGTCACCGTCTCCTCAGCGGCCGCATACCCGTACGACGTTCCGGACTACGGTTCCCACCACCATCACCATCACTAG : (SEQ ID NO: 844)
2HFA31 : GGACCCAGGTCACCGTCTCCTCAGCGGCCGCATACCCGTACGACGTTCCGGACTACGGTTCCCACCACCATCACCATCACTAG : (SEQ ID NO: 845)
2HFA6  : GGACCCAGGTCACCGTCTCCTCAGCGGCCGCATACCCGTACGACGTTCCGGACTACGGTTCCCACCACCATCACCATCACTAG : (SEQ ID NO: 846)
2HFA25 : GGACCCAGGTCACCGTCTCCTCAGCGGCCGCATACCCGTACGACGTTCCGGACTACGGTTCCCACCACCATCACCATCACTAG : (SEQ ID NO: 847)
2HFA26 : GGACCCAGGTCACCGTCTCCTCAGCGGCCGCATACCCGTACGACGTTCCGGACTACGGTTCCCACCACCATCACCATCACTAG : (SEQ ID NO: 848)
2HFA1  : GGACCCAGGTCACCGTCTCCTCAGCGGCCGCATACCCGTACGACGTTCCGGACTACGGTTCCCACCACCATCACCATCACTAG : (SEQ ID NO: 849)
2HFA3  : GGACCCAGGTCACCGTCTCCTCAGCGGCCGCATACCCGTACGACGTTCCGGACTACGGTTCCCACCACCATCACCATCACTAG : (SEQ ID NO: 850)
2HFA53 : GGACCCAGGTCACCGTCTCCTCAGCGGCCGCATACCCGTACGACGTTCCGGACTACGGTTCCCACCACCATCACCATCACTAG : (SEQ ID NO: 851)
2HFA55 : GGACCCAGGTCACCGTCTCCTCAGCGGCCGCATACCCGTACGACGTTCCGGACTACGGTTCCCACCACCATCACCATCACTAG : (SEQ ID NO: 852)
2HFA71 : GGACCCAGGTCACCGTCTCCTCAGCGGCCGCATACCCGTACGACGTTCCGGACTACGGTTCCCACCACCATCACCATCACTAG : (SEQ ID NO: 853)
2HFA60 : GGACCCAGGTCACCGTCTCCTCAGCGGCCGCATACCCGTACGACGTTCCGGACTACGGTTCCCACCACCATCACCATCACTAG : (SEQ ID NO: 854)
2HFA9  : GGACCCAGGTCACCGTCTCCTCAGCGGCCGCATACCCGTACGACGTTCCGGACTACGGTTCCCACCACCATCACCATCACTAG : (SEQ ID NO: 855)
2HFA73 : GGACCCAGGTCACCGTCTCCTCAGCGGCCGCATACCCGTACGACGTTCCGGACTACGGTTCCCACCACCATCACCATCACTAG : (SEQ ID NO: 856)
2HFA65 : GGACCCAGGTCACCGTCTCCTCAGCGGCCGCATACCCGTACGACGTTCCGGACTACGGTTCCCACCACCATCACCATCACTAG : (SEQ ID NO: 857)
2HFA49 : GGACCCAGGTCACCGTCTCCTCAGCGGCCGCATACCCGTACGACGTTCCGGACTACGGTTCCCACCACCATCACCATCACTAG : (SEQ ID NO: 858)
2HFA14 : GGACCCAGGTCACCGTCTCCTCAGCGGCCGCATACCCGTACGACGTTCCGGACTACGGTTCCCACCACCATCACCATCACTAG : (SEQ ID NO: 859)
2HFA57 : GGACCCAGGTCACCGTCTCCTCAGCGGCCGCATACCCGTACGACGTTCCGGACTACGGTTCCCACCACCATCACCATCACTAG : (SEQ ID NO: 860)
2HFA5  : GGACCCAGGTCACCGTCTCCTCAGCGGCCGCATACCCGTACGACGTTCCGGACTACGGTTCCCACCACCATCACCATCACTAG : (SEQ ID NO: 861)
2HFA20 : GGACCCAGGTCACCGTCTCCTCAGCGGCCGCATACCCGTACGACGTTCCGGACTACGGTTCCCACCACCATCACCATCACTAG : (SEQ ID NO: 862)
2HFA51 : GGACCCAGGTCACCGTCTCCTCAGCGGCCGCATACCCGTACGACGTTCCGGACTACGGTTCCCACCACCATCACCATCACTAG : (SEQ ID NO: 863)
2HFA24 : GGACCCAGGTCACCGTCTCCTCAGCGGCCGCATACCCGTACGACGTTCCGGACTACGGTTCCCACCACCATCACCATCACTAG : (SEQ ID NO: 864)
2HFA23 : GGACCCAGGTCACCGTCTCCTCAGCGGCCGCATACCCGTACGACGTTCCGGACTACGGTTCCCACCACCATCACCATCACTAG : (SEQ ID NO: 865)
2HFA36 : GGACCCAGGTCACCGTCTCCTCAGCGGCCGCATACCCGTACGACGTTCCGGACTACGGTTCCCACCACCATCACCATCACTAG : (SEQ ID NO: 866)
2HFA63 : GGACCCAGGTCACCGTCTCCTCAGCGGCCGCATACCCGTACGACGTTCCGGACTACGGTTCCCACCACCATCACCATCACTAG : (SEQ ID NO: 867)
2HFA19 : GGACCCAGGTCACCGTCTCCTCAGCGGCCGCATACCCGTACGACGTTCCGGACTACGGTTCCCACCACCATCACCATCACTAG : (SEQ ID NO: 868)
2HFA41 : GGACCCAGGTCACCGTCTCCTCAGCGGCCGCATACCCGTACGACGTTCCGGACTACGGTTCCCACCACCATCACCATCACTAG : (SEQ ID NO: 869)
2HFA2  : GGACCCAGGTCACCGTCTCCTCAGCGGCCGCATACCCGTACGACGTTCCGGACTACGGTTCCCACCACCATCACCATCACTAG : (SEQ ID NO: 870)
2HFA42 : GGACCCAGGTCACCGTCTCCTCAGCGGCCGCATACCCGTACGACGTTCCGGACTACGGTTCCCACCACCATCACCATCACTAG : (SEQ ID NO: 871)
2HFA67 : GGACCCAGGTCACCGTCTCCTCAGCGGCCGCATACCCGTACGACGTTCCGGACTACGGTTCCCACCACCATCACCATCACTAG : (SEQ ID NO: 872)
2HFA12 : GGACCCAGGTCACCGTCTCCTCAGCGGCCGCATACCCGTACGACGTTCCGGACTACGGTTCCCACCACCATCACCATCACTAG : (SEQ ID NO: 873)
2HFA29 : GGACCCAGGTCACCGTCTCCTCAGCGGCCGCATACCCGTACGACGTTCCGGACTACGGTTCCCACCACCATCACCATCACTAG : (SEQ ID NO: 874)
2HFA11 : GGACCCAGGTCACCGTCTCCTCAGCGGCCGCATACCCGTACGACGTTCCGGACTACGGTTCCCACCACCATCACCATCACTAG : (SEQ ID NO: 875)
2HFA44 : GGACCCAGGTCACCGTCTCCTCAGCGGCCGCATACCCGTACGACGTTCCGGACTACGGTTCCCACCACCATCACCATCACTAG : (SEQ ID NO: 876)
2HFA46 : GGACCCAGGTCACCGTCTCCTCAGCGGCCGCATACCCGTACGACGTTCCGGACTACGGTTCCCACCACCATCACCATCACTAG : (SEQ ID NO: 877)
2HFA52 : GGACCCAGGTCACCGTCTCCTCAGCGGCCGCATACCCGTACGACGTTCCGGACTACGGTTCCCACCACCATCACCATCACTAG : (SEQ ID NO: 878)
2HFA4  : GGACCCAGGTCACCGTCTCCTCAGCGGCCGCATACCCGTACGACGTTCCGGACTACGGTTCCCACCACCATCACCATCACTAG : (SEQ ID NO: 879)
2HFA38 : GGACCCAGGTCACCGTCTCCTCAGCGGCCGCATACCCGTACGACGTTCCGGACTACGGTTCCCACCACCATCACCATCACTAG : (SEQ ID NO: 880)
2HFA10 : GGACCCAGGTCACCGTCTCCTCAGCGGCCGCATACCCGTACGACGTTCCGGACTACGGTTCCCACCACCATCACCATCACTAG : (SEQ ID NO: 881)
2HFA43 : GGACCCAGGTCACCGTCTCCTCAGCGGCCGCATACCCGTACGACGTTCCGGACTACGGTTCCCACCACCATCACCATCACTAG : (SEQ ID NO: 882)
2HFA50 : GGACCCAGGTCACCGTCTCCTCAGCGGCCGCATACCCGTACGACGTTCCGGACTACGGTTCCCACCACCATCACCATCACTAG : (SEQ ID NO: 883)
2HFA62 : GGACCCAGGTCACCGTCTCCTCAGCGGCCGCATACCCGTACGACGTTCCGGACTACGGTTCCCACCACCATCACCATCACTAG : (SEQ ID NO: 884)
```

Figure 11 (CONT.):

```
                         *        140
2HFA44  :  TQVTVSSAAAYPYDVPDYGSHHHHHH  :
2HFA52  :  TQVTVSSAAAYPYDVPDYGSHHHHHH  :
2HFA11  :  TQVTVSSAAAYPYDVPDYGSHHHHHH  :
2HFA4   :  TQVTVSSAAAYPYDVPDYGSHHHHHH  :
2HFA46  :  TQVTVSSAAAYPYDVPDYGSHHHHHH  :
2HFA10  :  TQVTVSSAAAYPYDVPDYGSHHHHHH  :
2HFA38  :  TQVTVSSAAAYPYDVPDYGSHHHHHH  :
2HFA20  :  TQVTVSSAAAYPYDVPDYGSHHHHHH  :
2HFA5   :  TQVTVSSAAAYPYDVPDYGSHHHHHH  :
2HFA19  :  TQVTVSSAAAYPYDVPDYGSHHHHHH  :
2HFA2   :  TQVTVSSAAAYPYDVPDYGSHHHHHH  :
2HFA41  :  TQVTVSSAAAYPYDVPDYGSHHHHHH  :
2HFA42  :  TQVTVSSAAAYPYDVPDYGSHHHHHH  :
2HFA12  :  TQVTVSSAAAYPYDVPDYGSHHHHHH  :
2HFA24  :  TQVTVSSAAAYPYDVPDYGSHHHHHH  :
2HFA67  :  TQVTVSSAAAYPYDVPDYGSHHHHHH  :
2HFA29  :  TQVTVSSAAAYPYDVPDYGSHHHHHH  :
2HFA51  :  TQVTVSSAAAYPYDVPDYGSHHHHHH  :
2HFA63  :  TQVTVSSAAAYPYDVPDYGSHHHHHH  :
2HFA62  :  TQVTVSSAAAYPYDVPDYGSHHHHHH  :
2HFA26  :  TQVTVSSAAAYPYDVPDYGSHHHHHH  :
2HFA15  :  TQVTVSSAAAYPYDVPDYGSHHHHHH  :
2HFA1   :  TQVTVSSAAAYPYDVPDYGSHHHHHH  :
2HFA3   :  TQVTVSSAAAYPYDVPDYGSHHHHHH  :
2HFA7   :  TQVTVSSAAAYPYDVPDYGSHHHHHH  :
2HFA31  :  TQVTVSSAAAYPYDVPDYGSHHHHHH  :
2HFA6   :  TQVTVSSAAAYPYDVPDYGSHHHHHH  :
2HFA53  :  TQVTVSSAAAYPYDVPDYGSHHHHHH  :
2HFA9   :  TQVTVSSAAAYPYDVPDYGSHHHHHH  :
2HFA73  :  TQVTVSSAAAYPYDVPDYGSHHHHHH  :
2HFA55  :  TQVTVSSAAAYPYDVPDYGSHHHHHH  :
2HFA71  :  TQVTVSSAAAYPYDVPDYGSHHHHHH  :
2HFA60  :  TQVTVSSAAAYPYDVPDYGSHHHHHH  :
2HFA65  :  TQVTVSSAAAYPYDVPDYGSHHHHHH  :
2HFA49  :  TQVTVSSAAAYPYDVPDYGSHHHHHH  :
2HFA57  :  TQVTVSSAAAYPYDVPDYGSHHHHHH  :
2HFA23  :  TQVTVSSAAAYPYDVPDYGSHHHHHH  :
2HFA36  :  TQVTVSSAAAYPYDVPDYGSHHHHHH  :
2HFA14  :  TQVTVSSAAAYPYDVPDYGSHHHHHH  :
2HFA43  :  TQVTVSSAAAYPYDVPDYGSHHHHHH  :
2HFA50  :  TQVTVSSAAAYPYDVPDYGSHHHHHH  :
```

FIBROBLAST BINDING AGENTS AND USE THEREOF

CROSS-REFERENCE TO RELATED APPLICATIONS

The present application is a continuation of U.S. application Ser. No. 16/967,288 (now U.S. Pat. No. 11,896,643), filed Aug. 4, 2020, which is a 371 National Stage Entry of International Application No. PCT/US19/16629, filed Feb. 5, 2019, which claims the benefit of and priority to U.S. Provisional Patent Application No. 62/626,453, filed Feb. 5, 2018, the contents of which are hereby incorporated by reference in their entirety.

FIELD

The present technology relates, in part, to binding agents which bind fibroblast activation protein (FAP) and their use as therapeutic and diagnostic agents.

DESCRIPTION OF THE TEXT FILE SUBMITTED ELECTRONICALLY

The contents of the text file submitted electronically herewith are incorporated herein by reference in their entirety: A computer readable format copy of the Sequence Listing (Filename: ORN-035PC_ST25; Date created: Jan. 28, 2019; File size: 636 KB).

BACKGROUND

Fibroblasts participate in dynamic interplay with other cells. They express a diverse array of immumodulating factors such as cytokines, lipid mediators and growth factors. Moreover, fibroblasts display numerous surface and intracellular receptors and the requisite molecular machinery to respond to extrinsic signals. Fibroblasts can be considered extensions of the 'professional' immune system in view of the fact that fibroblasts can initiate inflammation. Fibroblasts participate in numerous normal and pathological processes. Illustrative diseases that aberrant fibroblasts are known to be associated with include cancer, cardiovascular disease, and autoimmune disease.

Fibroblasts regulate the structure and function of healthy tissues, participate transiently in tissue repair after acute inflammation, and assume an aberrant stimulatory role during chronic inflammatory states including cancer. Cancer-associated fibroblasts (CAFs) modulate the tumor microenvironment and influence the behavior of neoplastic cells in either a tumor-promoting or tumor-inhibiting manner. CAFs are prominent stromal components and play important roles in modulating the tumor microenvironment and influencing the behavior of tumor cells primarily by releasing proteolytic enzymes, growth factors, and cytokines. Studies have shown that the cancer-promoting and therapy-resisting properties of the stroma can be attributed to the activity of fibroblasts.

Accordingly, there remains a need for improved therapies for treating diseases associated with aberrant fibroblasts, e.g., treating cancer by modifying CAF functions or fibrotic diseases.

SUMMARY

In one aspect, the present technology relates to a fibroblast binding agent that targets F2 fibroblasts. In some embodiments, the fibroblast binding agent directly or indirectly alters a disease microenvironment comprising the F2 fibroblasts (e.g. a tumor microenvironment comprising the F2 fibroblasts). In some embodiments, the fibroblast binding agent directly or indirectly polarizes the F2 fibroblast. In some embodiments, the fibroblast binding agent targets a FAP marker. In some embodiments, the fibroblast binding agent comprises a fibroblast activation protein (FAP) targeting moiety. In some embodiments, the FAP targeting moiety is a single domain antibody (VHH). In some embodiments, the fibroblast binding agent further comprises a signaling agent, e.g., without limitation, an interferon, an interleukin, and a tumor necrosis factor, that may be modified to attenuate activity. In some embodiments, the fibroblast binding agent comprises additional targeting moieties that bind to other targets (e.g., antigens or receptors) of interest. In another embodiment, the other targets (e.g., antigens or receptors) of interest are present on fibroblast cells. In some embodiments, the other targets (e.g., antigens or receptors) of interest are present on fibroblast cells in cancer stroma. In some embodiments, the present fibroblast binding agent may directly or indirectly recruit an immune cell (e.g., a dendritic cell) to a site of action (such as, by way of non-limiting example, the tumor microenvironment). In some embodiments, the present FAP binding agent facilitates the presentation of antigens (e.g., antigens or receptors) by immune cells (e.g., dendritic cells, macrophages) in tumor stroma or directly by fibroblast cells.

In another aspect, the present technology relates to therapeutic compositions having FAP binding agents having at least one targeting moiety that specifically binds to FAP. In some embodiments, these FAP binding agents bind to, but do not functionally modulate (e.g., partially or fully neutralize) FAP. Therefore, in some embodiments, the present FAP binding agents have use in, for instance, directly or indirectly recruiting a FAP-expressing cell to a site of interest while still allowing the FAP-expressing cell to signal via FAP (i.e., the binding of the FAP binding agent does not reduce or eliminate FAP signaling at the site of interest). Conversely, in some embodiments, the present FAP binding agents have use in, for instance, directly or indirectly recruiting a FAP-expressing cell to a site of interest while not allowing the FAP-expressing cell to signal via FAP (i.e., the binding of the FAP binding agent reduces or eliminates FAP signaling at the site of interest). In some embodiments, the FAP targeting moiety is a single domain antibody (VHH). In some embodiments, the FAP binding agent further comprises a signaling agent, e.g., without limitation, an interferon, an interleukin, and a tumor necrosis factor, that may be modified to attenuate activity. In some embodiments, the FAP binding agent comprises additional targeting moieties that bind to other targets (e.g., antigens or receptors) of interest. In another embodiment, the other targets (e.g., antigens or receptors) of interest are present on fibroblast cells. In some embodiments, the other targets (e.g., antigens or receptors) of interest are present on fibroblast cells in cancer stroma. In some embodiments, the present FAP binding agent may directly or indirectly recruit an immune cell (e.g., a dendritic cell) to a site of action (such as, by way of non-limiting example, the tumor microenvironment). In some embodiments, the present FAP binding agent facilitates the presentation of antigens (e.g., antigens or receptors) by immune cells (e.g., dendritic cells, macrophages) in tumor stroma or directly by fibroblast cells.

In another aspect, the present FAP binding agents are useful in methods for the treatment of various diseases or disorders such as cancer, infections, immune disorders, and other diseases and disorders.

BRIEF DESCRIPTION OF DRAWINGS

FIG. 5B) and bispecific compositions (nnClec-PD-L1; FIG. 5C or nnClec-FAP; FIG. 5D) on tumor growth in mice inoculated with a B16-mCD20 clone. Untreated mice (control) were treated with PBS (FIG. 5A).

FIG. 6B) and bispecific compositions in combination with doxorubicin (nnClec-PD-L1 Dox; FIG. 6C or nnClec-FAP Dox; FIG. 6D) on tumor growth in mice inoculated with a B16-mCD20 clone. Untreated mice (control) were treated with PBS (FIG. 6A). The number in the upper right corner of the graphs indicates the number of mice that were completely tumor-free after treatment.

FIG. 7B) and bispecific compositions in combination with TNF (nnClec-PD-L1 TNF; FIG. 7C or nnClec-FAP TNF;

FIG. 7D) on tumor growth in mice inoculated with a B16-mCD20 clone. Untreated mice (control) were treated with PBS (FIG. 7A). The number in the upper right corner of the graphs indicates the number of mice that were completely tumor-free after treatment.

FIG. 8B) and bispecific compositions in combination with Abs (nnClec-PD-L1 Abs; FIG. 8C or nnClec-FAP Abs;

FIG. 8D) on tumor growth in mice inoculated with a B16-mCD20 clone. Untreated mice (control) were treated with PBS (FIG. 8A). The number in the upper right corner of the graphs indicates the number of mice that were completely tumor-free after treatment.

FIG. 9A), monocytes (MO; FIG. 9B), neutrophils (PMN; FIG. 9C) and platelets (PLT;

FIG. 9E) are expressed in K/μl and red blood cells (rbc; FIG. 9D) in M/μl). For each of FIGS. 9A-E, the order of histograms lines up from left to right with the order of agents listed in the legend (i.e. in FIG. 9A from left to right is "PBS," "nnCle c9A-Q124A," nnClec9A-Q124A+dox," and so forth.

FIG. 10 shows the nucleotide sequences of 41 different human VHHs specific for recombinant Hiss-tagged extracellular domain of human FAP (SEQ ID NOs: 844-884).

FIG. 16C) and platelets (FIG. 16E) are expressed in K/p1, red blood cells (RBC; FIG. 16D) in M/p1) and mean platelet volume (mpv) in fL (FIG. 16F).

DETAILED DESCRIPTION

Figure 1:
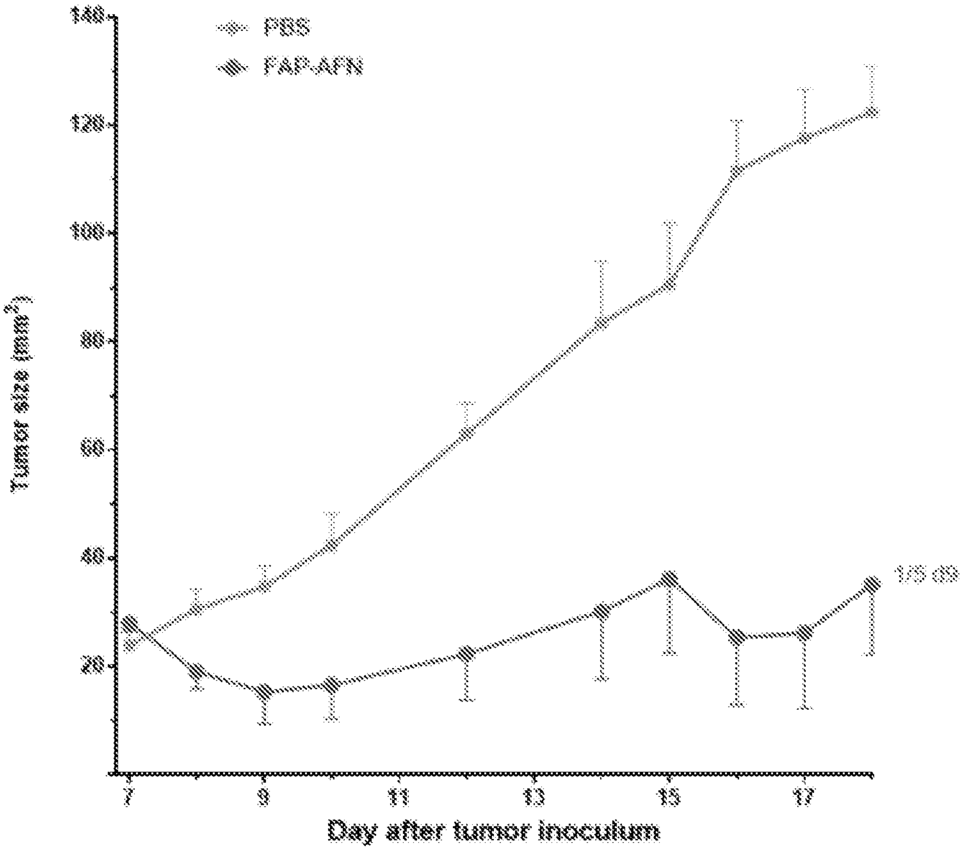
FIG. 1 is a graph showing the effect of treatment with FAP-AFN (as described in Example 2) on tumor growth in mice inoculated with a B16 tumor. Untreated mice (control) were treated with PBS. The number to the right the tumor growth curve indicates the number of mice that were completely tumor-free at the indicated day.

The present technology is based, in part, on the discovery of agents (e.g., antibodies, such as, by way of non-limiting example, VHHs) that recognize and bind to fibroblasts. In some embodiments, the present fibroblast binding agents are part of a chimeric or fusion protein with one or more targeting moieties and/or one or more signaling agents.

In some embodiments, the fibroblast binding agent targets F2 fibroblasts. In some embodiments, the fibroblast binding agent directly or indirectly alters a disease microenvironment comprising the F2 fibroblasts (e.g. a tumor microenvironment comprising the F2 fibroblasts). In some embodiments, the fibroblast binding agent directly or indirectly polarizes the F2 fibroblast into F1 fibroblast.

F2 fibroblast(s) refers to pro-tumorigenic (or tumor promoting) cancer-associated fibroblasts (CAFs) (a/k/a Type 11-CAF). F1 fibroblast(s) refers to tumor suppressive CAFs (a/k/a Type I-CAF). Polarization refers to changing the phenotype of cell, e.g. changing a tumorigenic F2 fibroblast to a tumor suppressive F1 fibroblast.

In some embodiments, the fibroblast binding agent targets a FAP marker. In some embodiments, the fibroblast binding agent comprises a FAP targeting moiety. In some embodiments, the fibroblast binding agent FAP targeting moiety is any FAP targeting moiety disclosed herein In some embodiments, fibroblast binding agent comprises an amino acid sequence having at least 90% sequence similarity with any one of SEQ ID NO: 2-42 or 46-86. In an embodiment, fibroblast binding agent comprises an amino acid sequence having at least 90% sequence similarity with SEQ ID NO: 58.

In some embodiments, fibroblast binding agent further comprises one or more signaling agents. In some embodiments, the signaling agent is selected from one or more of an interferon, an interleukin, and a tumor necrosis factor, any of which are optionally modified.

In some embodiments, a fibroblast binding agent further comprising one or more signaling agents directly or indirectly alters a disease microenvironment comprising the F2 fibroblasts (e.g. a tumor microenvironment comprising the F2 fibroblasts). In some embodiments, the fibroblast binding agent further comprising one or more signaling agents directly or indirectly polarizes the F2 fibroblast into F1 fibroblast.

In some embodiments, fibroblast binding agent further comprises one or more additional targeting moieties. In some embodiments, the one or more additional targeting moieties recognize and optionally functionally modulate a tumor antigen. In some embodiments, the one or more additional targeting moieties recognize and optionally functionally modulate an antigen on an immune cell.

In some embodiments, the immune cell is selected from a T cell, a B cell, a dendritic cell, a macrophage, neutrophil, and a NK cell.

In some embodiments, the fibroblast binding agent recruits cytotoxic T cells to tumor cells or to the tumor environment.

In some embodiments, the fibroblast binding agent recognizes and binds FAP without substantially functionally modulating its activity.

In another aspect, the present technology is based, in part, on the discovery of agents (e.g., antibodies, such as, by way of non-limiting example, VHHs) that recognize and bind to fibroblast activation protein (FAP). In some embodiments, the present FAP binding agents are part of a chimeric or fusion protein with one or more targeting moieties and/or one or more signaling agents. In some embodiments, these FAP binding agents bind to, but do not functionally modulate FAP. In some embodiments, the FAP binding agents may bind and directly or indirectly recruit immune cells to sites in need of therapeutic action (e.g., a tumor or tumor microenvironment). In some embodiments, the FAP binding agents enhance tumor antigen presentation for elicitation of effective antitumor immune response.

In some embodiments, the FAP binding agents modulate antigen presentation. In some embodiments, the FAP binding agents temper the immune response to avoid or reduce autoimmunity. In some embodiments, the FAP binding agents provide immunosuppression. In some embodiments, the FAP binding agents cause an increase a ratio of Tregs to CD8+ T cells and/or CD4+ T cells in a patient. In some embodiments, the present methods relate to reduction of auto-reactive T cells in a patient.

In some embodiments, the present technology provides pharmaceutical compositions comprising the FAP binding agents and their use in the treatment of various diseases, including fibrotic diseases. In some embodiments, the present technology provides pharmaceutical compositions comprising the FAP binding agents and their use in the treatment of various diseases, including cancer, autoimmune, and/or neurodegenerative diseases.

In some embodiments, the present FAP binding agents are used to target to cancer-associated fibroblasts (CAFs). For instance, in various embodiments, the present FAP binding agents target fibroblasts within a tumor stroma, e.g. in the treatment of a cancer, e.g. an epithelial-derived cancer such as a carcinoma. As CAFs are central to regulating the dynamic and reciprocal interactions that occur among the malignant epithelial cells, the extracellular matrix (ECM), and the numerous noncancerous cells that are frequently found within the tumor milieu, including endothelial, adipose, inflammatory, and immune cells, the present FAP binding agents provide a way to deliver crucial anti-tumor therapies (e.g. a modified cytokine and/or additional targeting moieties as described elsewhere herein) to a site of interest. In various embodiments, the present FAP binding agents target to a stromal microenvironment composed of activated fibroblasts, endothelial cells (ECs) involved in tubulogenesis, and extracellular matrix (ECM) that is constantly remodeled to accommodate growth of a tumor. Accordingly, e.g. in the context of a chimera with a cytokine, optionally with additional targeting moieties, the present FAP binding agents can deliver an anti-tumor signal to the stromal microenvironment which is crucial for tumor development. In various embodiments, the FAP-binding agents are used to target to the membranes of cells critical to tumor niche formation in primary tumors or metastases, such as, cancer-associated fibroblasts, MSCs, selected cancer cells, and endothelial cells.

FAP Binding Agents

Fibroblast activation protein (FAP) is a 170 kDa melanoma membrane-bound gelatinase that belongs to the serine protease family. FAP is selectively expressed in reactive stromal fibroblasts of epithelial cancers, granulation tissue of healing wounds, and malignant cells of bone and soft tissue sarcomas. FAP is believed to be involved in the control of fibroblast growth or epithelial-mesenchymal interactions during development, tissue repair, and epithelial carcinogenesis In some embodiments, the present FAP binding agent is a protein-based agent capable of specific binding to FAP. In some embodiments, the present FAP binding agent is a protein-based agent capable of specific binding to FAP without functional modulation (e.g., partial or full neutralization) of FAP.

In some embodiments, the FAP binding agent of the present technology comprises a targeting moiety having an antigen recognition domain that recognizes an epitope present on FAP. In some embodiments, the antigen-recognition domain recognizes one or more linear epitopes present on FAP. As used herein, a linear epitope refers to any continuous sequence of amino acids present on FAP. In another embodiment, the antigen-recognition domain recognizes one or more conformational epitopes present on FAP. As used herein, a conformation epitope refers to one or more sections of amino acids (which may be discontinuous), which form a three-dimensional surface with features and/or shapes and/or tertiary structures capable of being recognized by an antigen recognition domain.

In some embodiments, the FAP binding agent of the present technology may bind to the full-length and/or mature forms and/or isoforms and/or splice variants and/or fragments and/or any other naturally occurring or synthetic analogs, variants, or mutants of human FAP. In some embodiments, the FAP binding agent of the present technology may bind to any forms of the human FAP, including monomeric, dimeric, heterodimeric, multimeric and associated forms. In an embodiment, the FAP binding agent binds to the monomeric form of FAP. In another embodiment, the FAP binding agent binds to a dimeric form of FAP. In a further embodiment, the FAP binding agent binds to glycosylated form of FAP, which may be either monomeric or dimeric.

In an embodiment, the present FAP binding agent comprises a targeting moiety with an antigen recognition domain that recognizes one or more epitopes present on human FAP. In some embodiments, the human FAP comprises the amino acid sequence of:

(SEQ ID NO: 1)
MKTWVKIVFGVATSAVLALLVMCIVLRPSRVHNSEENTMRALTLKDILNG

TFSYKTFFPNWISGQEYLHQSADNNIVLYNIETGQSYTILSNRTMKSVNA

SNYGLSPDRQFVYLESDYSKLWRYSYTATYYIYDLSNGEFVRGNELPRPI

QYLCWSPVGSKLAYVYQNNIYLKQRPGDPPFQITFNGRENKIFNGIPDWV

YEEEMLPTKYALWWSPNGKFLAYAEFNDKDIPVIAYSYYGDEQYPRTINI

PYPKAGAKNPVVRIFIIDTTYPAYVGPQEVPVPAMIASSDYYFSWLTWVT

DERVCLQWLKRVQNVSVLSICDFREDWQTWDCPKTQEHIEESRTGWAGGF

-continued

FVSRPVFSYDAISYYKIFSDKDGYKHIHYIKDTVENAIQITSGKWEAINI

FRVTQDSLFYSSNEFEEYPGRRNIYRISIGSYPPSKKCVTCHLRKERCQY

YTASFSDYAKYYALVCYGPGIPISTLHDGRTDQEIKILEENKELENALKN

IQLPKEEIKKLEVDEITLWYKMILPPQFDRSKKYPLLIQVYGGPCSQSVR

SVFAVNWISYLASKEGMVIALVDGRGTAFQGDKLLYAVYRKLGVYEVEDQ

ITAVRKFIEMGFIDEKRIAIWGWSYGGYVSSLALASGTGLFKCGIAVAPV

SSWEYYASVYTERFMGLPTKDDNLEHYKNSTVMARAEYFRNVDYLLIHGT

ADDNVHFQNSAQIAKALVNAQVDFQAMWYSDQNHGLSGLSTNHLYTHMTH

FLKQCFSLSD.

In some embodiments, the present FAP binding agent comprises a targeting moiety capable of specific binding. In some embodiments, the FAP binding agent comprises a targeting moiety having an antigen recognition domain such as an antibody or derivatives thereof. In an embodiment, the FAP binding agent comprises a targeting moiety which is an antibody. In some embodiments, the antibody is a full-length multimeric protein that includes two heavy chains and two light chains. Each heavy chain includes one variable region (e.g., $V_H$) and at least three constant regions (e.g., $CH_1$, $CH_2$ and $CH_3$), and each light chain includes one variable region ($V_L$) and one constant region ($C_L$). The variable regions determine the specificity of the antibody. Each variable region comprises three hypervariable regions also known as complementarity determining regions (CDRs) flanked by four relatively conserved framework regions (FRs). The three CDRs, referred to as CDR1, CDR2, and CDR3, contribute to the antibody binding specificity. In some embodiments, the antibody is a chimeric antibody. In some embodiments, the antibody is a humanized antibody.

In some embodiments, the FAP binding agent comprises a targeting moiety which is an antibody derivative or format. In some embodiments, the present FAP binding agent comprises a targeting moiety which is a single-domain antibody, a recombinant heavy-chain-only antibody (VHH), a single-chain antibody (scFv), a shark heavy-chain-only antibody (VNAR), a microprotein (cysteine knot protein, knottin), a DARPin; a Tetranectin; an Affibody; a Transbody; an Anticalin; an AdNectin; an Affilin; an Affimer, a Microbody; an aptamer; an alterase; a plastic antibody; a phylomer; a stradobody; a maxibody; an evibody; a fynomer, an armadillo repeat protein, a Kunitz domain, an avimer, an atrimer, a probody, an immunobody, a triomab, a troybody; a pepbody; a vaccibody, a UniBody; a DuoBody, a Fv, a Fab, a Fab', a F(ab')2, a peptide mimetic molecule, or a synthetic molecule, as described in U.S. Pat. No. 7,417,130, US 2004/132094, U.S. Pat. No. 5,831,012, US 2004/023334, U.S. Pat. Nos. 7,250,297, 6,818,418, US 2004/209243, U.S. Pat. Nos. 7,838,629, 7,186,524, 6,004,746, 5,475,096, US 2004/146938, US 2004/157209, U.S. Pat. Nos. 6,994,982, 6,794,144, US 2010/239633, U.S. Pat. No. 7,803,907, US 2010/119446, and/or U.S. Pat. No. 7,166,697, the contents of which are hereby incorporated by reference in their entireties. See also, Storz MAbs. 2011 May-June; 3(3): 310-317.

In some embodiments, the FAP binding agent comprises a targeting moiety which is a single-domain antibody, such as a VHH. The VHH may be derived from, for example, an organism that produces VHH antibody such as a camelid, a shark, or the VHH may be a designed VHH. VHHs are antibody-derived therapeutic proteins that contain the unique structural and functional properties of naturally-occurring heavy-chain antibodies. VHH technology is based on fully functional antibodies from camelids that lack light chains. These heavy-chain antibodies contain a single variable domain (VHH) and two constant domains (CH2 and CH3). VHHs are commercially available under the trademark of NANOBODY or NANOBODIES.

In an embodiment, the FAP binding agent comprises a VHH. In some embodiments, the VHH is a humanized VHH or camelized VHH.

In some embodiments, the VHH comprises a fully human VH domain, e.g. a HUMABODY (Crescendo Biologics, Cambridge, UK). In some embodiments, fully human VH domain, e.g. a HUMABODY is monovalent, bivalent, or trivalent. In some embodiments, the fully human VH domain, e.g. a HUMABODY is mono- or multi-specific such as monospecific, bispecific, or trispecific. Illustrative fully human VH domains, e.g. a HUMABODIES are described in, for example, WO 2016/113555 and WO 2016/113557, the entire disclosures of which are incorporated by reference.

By way of example, but not by way of limitation, in some embodiments, a human VHH FAP binding agent comprises an amino acid sequence selected from the following sequences:

```
2HFA44:
                                    (SEQ ID NO: 2)
QVQLQESGGGLVQAGGSLRLSCAASGGFDSRNAMGWYRQAPGKRREWVAT

ITSDGRTNYADSVKARFTISRDNSKNTVYLQMNSLKPEDTAVYYCNAAPP

IFGSWGQGTQVTVSSAAAYPYDVPDYGSHHHHHH;

2HFA52:
                                    (SEQ ID NO: 3)
QVQLQESGGGLVRAGGSLRLSCAASGTFDSRNAMGWYRQAPGKRREWVAT

ITTDGRTNYADSVKARFTISRDNAKNTVYLQMNSLKPEDTAVYYCNAAPP

IFGSWGQGTQ VTVSSAAAYPYDVPDYGSHHHHHH;

2HFA11:
                                    (SEQ ID NO: 4)
QVQLQESGGGLVQAGGSLRLSCAASGSFDSRNAMGWYRQAPGKRREWVAT

ITTDGRTNYADSVKARFTVSRDNAKNTVYLQMNSLKPDDTAVYYCNAAPP

IFNSWGQGT QVTVSSAAAYPYDVPDYGSHHHHHH;

2HFA4:
                                    (SEQ ID NO: 5)
QVQLQESGGGLVQAGGSLRLSCAASGSIDIRNAMGWYRQAPGTRREWVAT

ITTDGRTNYADSVKARFTISRDNAKNTVYLQMNSLKPEDTAVYYCNLAPP

IFGSWGQGTQ VTVSSAAAYPYDVPDYGSHHHHHH;

2HFA46:
                                    (SEQ ID NO: 6)
QVQLQESGGGLVQAGGSLRLSCAASGSIDSRNTMGWYRQAPGKRREWVAT

ITTGGRTNYADSVKARFTISRDNAKNTVYLQMNSLKPEDTAVYYCNLAPP

IFNSWGQGTQ VTVSSAAAYPYDVPDYGSHHHHHH;

2HFA10:
                                    (SEQ ID NO: 7)
QVQLQESGGGLVQAGGSLRLSCTVAESIDVRNAMGWYRQAPGKRREWVAT

ITTGGRTNYADSVKARFTISRDNAKNTVYLQMNSLKPEDTAVYYCNAAPP

ILNSWGQGT QVTVSSAAAYPYDVPDYGSHHHHHH;
```

```
-continued
2HFA38:
                                    (SEQ ID NO: 8)
QVQLQESGGGLVRVGGSLRLSCAVSGSFDSRNSMGWYRQAPGKRREWVAT

ITSGSRTNYADSVKARFTISRDNAKNTVYLQMDSLKPEDTAVYYCNAAPP

IFNSWGQG TQVTVSSAAAYPYDVPDYGSHHHHHH;

2HFA20:
                                    (SEQ ID NO: 9)
QVQLQESGGGLVQAGGSLRLSCAVSGRLFSANTMGWYRQAPGKRRELVAT

ILSSGSTNYADSVKGRFTISRDDAKNTVYLQMNSLKPEDTAVYYCNLAPP

PEGYWGQG TQVTVSSAAAYPYDVPDYGSHHHHHH;

2HFAS:
                                    (SEQ ID NO: 10)
QVQLQESGGGLVQAGGSLRLSCAVSGRLFSANTMGWYRQAPGKRRELVAT

ILSSGSTNYADSVKGRFTISRDDGKNTVYLQMNSLKPDDTAVYYCNFAPP

PEGYWGQG TQVTVSSAAAYPYDVPDYGSHHHHHH;

2HFA19:
                                    (SEQ ID NO: 11)
QVQLQESGGGLVQAGGSLRLSCAASGSIFVGNAMGWYRQALGNQRELVAG

ITSDGITYYPDSVKGRFTISRDNDKNTIYLQMNSLKPEDTAVYYCNLWPP

RIGFASWGQG TQVTVSSAAAYPYDVPDYGSHHHHHH;

2HFA2:
                                    (SEQ ID NO: 12)
QVQLQESGGGLVQTGGSLRLSCAASGSIFVGNAMGWYRQALGNQRELVAG

ITSDGITYYPDSVKGRFTISRDNDKNTIYLQMNSLKPEDTAVYYCNLWPP

RIGFASWGQG TQVTVSSAAAYPYDVPDYGSHHHHHH;

2HFA41:
                                    (SEQ ID NO: 13)
QVQLQESGGGLVRAGGSLRLSCAASGSIFVGNAMGWYRQALGNQRELVAG

ITSDGITYYPDSVKGRFTISRDNDKNTIYLQMNSLKPEDTAVYYCNLWPP

RIGFASWGQGTQVTVSSAAAYPYDVPDYGSHHHHHH;

2HFA42:
                                    (SEQ ID NO: 14)
QVQLQESGGGLVQTGGSLRLSCAASGSIFVGNAMGWYRQALGNQRELVAG

ITSDGITYYPDSVKGRFTISRDNDKNTIYLQMNSLKPEDTAVYYCNLWPP

RIGFASWGQG TQVTVSSAAAYPYDVPDYGSHHHHHH;

2HFA12:
                                    (SEQ ID NO: 15)
QVQLQESGGGLVQAGGSLRLSCAASGSISMLNSMGWYRQALGKQREFVAG

ITSGGRTNYADSVKGRFAISRDNDKNTVYLQMNSLKPEDTAVYYCNTWPP

RIAFDSWGQG TQVTVSSAAAYPYDVPDYGSHHHHHH;

2HFA24:
                                    (SEQ ID NO: 16)
QVQLQESGGGLVQAGGSLRLSCAASGSIFSSNAMGWYRQAAGKRRELVAG

IRSDGNTNYVDSVKGRFTISRDRAKNTVYLQMTSLKPEDTAVYYCNYWPP

PLRQGGDYAYWGQGTQVTVSSAAAYPYDVPDYGSHHHHHH;

2HFA67:
                                    (SEQ ID NO: 17)
QVQLQESGGGLVQAGGSLRLSCWSGSFDSRNAMAWYRQALGKERVWVAGI

ISDGSTNYADAVKGRFTISRDNDKNTVYLQMNSLKPEDTAVYYCNAWPPR

IGLGSWGQGTQVTVSSAAAYPYDVPDYGSHHHHHH;
```

-continued

2HFA29:
(SEQ ID NO: 18)
QVQLQESGGGLVQAGGSLRLSCAASGTMSSINAMGWYRQAPGKQRELVAG
ILSDGTTKYVESVKGRFTISRDNAKNTVHLQMNSLKVEDTAVYYCNFFPP
PVPASWGQGTQVTVSSAAAYPYDVPDYGSHHHHHH;

2HFA51:
(SEQ ID NO: 19)
QVQLQESGGGLVQAGGSLRLSCAVSGIISSMNAMGWYRQAPGKRRELVAG
LGSGVSTTYADAVKGRFTISRDNAKNTLYLQMNSLKPEDTAVYYCNRWPP
PYDYWGQGTQVTVSSAAAYPYDVPDYGSHHHHHH;

2HFA63:
(SEQ ID NO: 20)
QVQLQESGGGLVQAGGSLRLSCWSGTILSSNSMGWYRQAPGKRRELVASI
STDGSTNYADSVKGRFTISRDNAKSTVFLQMNSLKPEDTAVYYCNFHPPW
RDWGDTYWGTQVTVSSAAAYPYDVPDYGSHHHHHHQG;

2HFA62:
(SEQ ID NO: 21)
QVQLQESGGGLVQAGGSLRLSCAASRSIFSIGTMGWYRQAPGKRRELVAF
ITVDHNTYYTDSVKGRFTISTENDKNTVYLQMNSLKPEDTAVYYCNRAPP
STDGDRWGQG TQVTVSSAAAYPYDVPDYGSHHHHHH;

2HFA26:
(SEQ ID NO: 22)
QVQLQESGGGLVQAGGSLRLSCAASGRTFSTYAMGWFRQAPGKERELVAA
ISNGGSAYYADSVKGRFTISRDNARNTVYLQTNSLKPEDTAVYYCAARRG
SAYYTNRIDWPYWGQGTQVTVSSAAAYPYDVPDYGSHHHHHH;

2HFA25:
(SEQ ID NO: 23)
QVQLQESGGGLVQAGGSLRLSCAASGRTFSSYAMGWFRQAPGKERELVAA
ISNGGSAYYADSVKGRFTISRDNARNTVYLQTNSLKPEDTAVYYCAARRG
SAYYTNRIDWPYWGQGTQVTVSSAAAYPYDVPDYGSHHHHHH;

2HFA1:
(SEQ ID NO: 24)
QVQLQESGGGLVEAEGSLRLSCIASGRTFGTYAMGWFRQAPGKERELVAA
ISSGGSAYYADSVKGRFTISRDNARNTVYLQTNSLKPEDTAVYYCAARRG
SAYYTNRIDWPYWGQGTQVTVSSAAAYPYDVPDYGSHHHHHH;

2HFA3:
(SEQ ID NO: 25)
QVQLQESGGGLVEAEGSLRLSCIASGRTFGTYAMGWFRQAPGKERELVAA
ISTGGSTYYADSVKGRFTISRDNARNTVYLQTNSLKPEDTAVYYCAARRG
SAYYTNHVDWPYWGQGTQVTVSSAAAYPYDVPDYGSHHHHHH;

2HFA7:
(SEQ ID NO: 26)
QVQLQESGGGLVEAEGSLRLSCAASGRTFGSYAMGWFRQAPGKSRELVAA
ISSGGTTYYADSVKGRFTISRDNARNTVYLQTNSLKPEDTAVYYCAARTG
SAYYTNRIDWPYWGQGTQVTVSSAAAYPYDVPDYGSHHHHHH;

2HFA31:
(SEQ ID NO: 27)
QVQLQESGGGLVEAEGSLRLSCAASGRTFGSYAMGWFRQAPGKSRELVAA
ISSGGTTYYADSVKGRFTISRDNARNTVYLQTNSPKPEDTAVYYCAARTG
SAYYTNRIDWPYWGQGTQVTVSSAAAYPYDVPDYGSHHHHHH;

-continued

2HFA6:
(SEQ ID NO: 28)
QVQLQESGGGLVEAEGSLRLSCAASGRTFGTYALAWFRQAPGKSRELVAA
ISSGGSTYYADSVKGRFTISRDNARNTVYLQTNSLKPEDTAVYYCAAKTG
SAYYTNRIDWPYWGQGTQVTVSSAAAYPYDVPDYGSHHHHHH;

2HFA53:
(SEQ ID NO: 29)
QVQLQESGGGLVEAEGSLRLSCAASGRAFGSYAMGWFRQAPGLERELVAA
ISSGGTTYYADSVKGRFTISRDNARNTVYLQTNSLKPEDTAVYYCAARTG
GAAYTRRIDWPYWGQGTQVTVSSAAAYPYDVPDYGSHHHHHH;

2HFA9:
(SEQ ID NO: 30)
QVQLQESGGGLVEAEGSLRLSCAASGRTFGSYAMGWFRQAAGKERELVAA
ISAGGSTLYADNVKGRFTISRDNARNTVYLLSNSLKPEDTAVYYCAARRG
SAYYTNHIDWPYWGQGTQVTVSSAAAYPYDVPDYGSHHHHHH;

2HFA73:
(SEQ ID NO: 31)
QVQLQESGGGLVQPGGSLRLSCAASGRTFGSYAMGWFRQAAGKERELVAA
ISAGGSTLYADNVKGRFTISRDNARNTVYLLSNSLKPEDTAVYYCAARRG
SAYYTNHIDWPYWGQGTQVTVSSAAAYPYDVPDYGSHHHHHH;

2HFA55:
(SEQ ID NO: 32)
QVQLQESGGGLVEAEGSLRLSCAASGRTFGSYAMGWFRQAPGKERELVAA
ISSGGSTLYADSVKGRFTISRDNAKNTVYLQMNSLKPEDTAVYYCAARSG
GAYYTARVDWPYWGQGTQVTVSSAAAYPYDVPDYGSHHHHHH;

2HFA71:
(SEQ ID NO: 33)
QVQLQESGGGLVEAEGSLRLSCAASGRTFGSYAMGWFRQAPGKERELVAA
ISSGGSTLYAGSVKGRFTISKDNAKNTVYLQMNSLKPEDTAVYYCAARSG
GAYYTARVDWPYWGQGTQVTVSSAAAYPYDVPDYGSHHHHHH;

2HFA60:
(SEQ ID NO: 34)
QVQLQESGGGLVEAEGSPRLSCAASGRTFGSYAMGWFRQAPGKERELVAA
ISSGGITYYADSVKGRFTISRDNAKNTVYLQMNSLKPEDTAVYYCAARSG
SAYYTTRVDWPYWGQGTQVTVSSAAAYPYDVPDYGSHHHHHH;

2HFA65:
(SEQ ID NO: 35)
QVQLQESGGGLVQAGGSLRLSCAASGNIDSIASMGWYRQAPGKQRELVAA
ISVGGSTYYADSVKGRFTISRDNARNTVYLQTNSLKPEDTAVYYCAARRG
SAYYTSRIDWPYWGQGTQVTVSSAAAYPYDVPDYGSHHHHHH;

2HFA49:
(SEQ ID NO: 36)
QVQLQESGGGLVQAEGSLRLSCAASGRTFGSYAMGWFRQAPGKERELVAG
ISSGGITNYAHSVKGRFTISRDIDKNTVFLQMNSLKPEDTAVYYCAARSG
GAYYTSRVDWPYWGQGTQVTVSSAAAYPYDVPDYGSHHHHHH;

2HFA57:
(SEQ ID NO: 37)
QVQLQESGGGLVXAGGSLRLSCAASGRTFSDYAMGWFRQAPGKEREFIAG
ISWGGSSTYYADSVKGRFTISRDNAKNTMYLQMNSLKPEDTAVYYCAARL
SGVSRSDRPYDYWGQGTQVTVSSAAAYPYDVPDYGSHHHHHH;

-continued

2HFA23:

(SEQ ID NO: 38)
QVQLQESGGGLVQAGGSLRLSCAASGRTFSMYAIGWFRQAPGKERELVAS

ISSGGSTNYADSVKGRFTISRDNAEKTVYLQMMSLEPEATGVYYCAARDG

SALYTAHSDWDYWGQGTQVTVSSAAAYPYDVPDYGSHHHHHH;

2HFA36:

(SEQ ID NO: 39)
QVQLQESGGGLVQPGDSLRLSCAASERTFSMYAIGWFRQAPGKERELVAG

ISSGGSTNYADSVKGRFTISRDNPKKTVYLQMMSLEPEDTGVYYCAARSG

SAYFSGRYYWNYWGQGTQVTVSSAAAYPYDVPDYGSHHHHHH;

2HFA14:

(SEQ ID NO: 40)
QVQLQESGGGLVQAGDSLRLSCAASGRTFSSYVMGWFRQVPGKQRELVAA

ITSGLSTYYADSLKGRFTISRDNAKNTMYLQMNSLKLEDTAVYYCAAREG

GGIWTSSTQYDYWGQGTQVTVSSAAAYPYDVPDYGSHHHHHH;

2HFA43:

(SEQ ID NO: 41)
QVQLQESGGGLVQAGGSLRLSCVASGTIFSSGAMAMGWYRQAPGKQREWV

AGITGSRTITYADSVKGRFTISRDNAENTVFLQMNNLKSEDTAVYYCNLW

PPSRPDHWGQGTQVTVSSAAAYPYDVPDYGSHHHHHH;
and

2HFA50:

(SEQ ID NO: 42)
QVQLQESGGGLVQAGGSLRLSCVASGTISSGAMGWYRQVPGKQREWVAGI

TGSRTTMYTESVKGRFTISRDNAENTVFLQMNNLKSEDTAVYYCNLWPPS

RPDYWGQG TQVTVSSAAAYPYDVPDYGSHHHHHH.

In various illustrative embodiments, the FAP binding agent comprises an amino acid sequence selected from any one of the sequences provided above without the terminal histidine tag sequence (i.e., HHHHHH; SEQ ID NO: 43).

In various illustrative embodiments, the FAP binding agent comprises an amino acid sequence selected from any one of the sequences provided above without the HA tag (i.e., YPYDVPDYGS; SEQ ID NO: 44).

In various illustrative embodiments, the FAP binding agent comprises an amino acid sequence selected from any one of the sequences provided above without the MA linker (i.e., AAA).

In various illustrative embodiments, the FAP binding agent comprises an amino acid sequence selected from any one of the sequences provided above without the AM linker, HA tag, and terminal histidine tag sequence (i.e., AAAY-PYDVPDYGSHHHHHH; SEQ ID NO: 45).

By way of example, but not by way of limitation, in some embodiments, a human VHH FAP binding agent comprises an amino acid sequence selected from the following sequences:

2HFA44:

(SEQ ID NO: 46)
QVQLQESGGGLVQAGGSLRLSCAASGGFDSRNAMGWYRQAPGKRREWVA

TITSDGRTNYADSVKARFTISRDNSKNTVYLQMNSLKPEDTAVYYCNAA

PPIFGSWGQGTQVTVSS;

-continued

2HFA52:

(SEQ ID NO: 47)
QVQLQESGGGLVRAGGSLRLSCAASGTFDSRNAMGWYRQAPGKRREWVA

TITTDGRTNYADSVKARFTISRDNAKNTVYLQMNSLKPEDTAVYYCNAA

PPIFGSWGQGTQVTVSS;

2HFA11:

(SEQ ID NO: 48)
QVQLQESGGGLVQAGGSLRLSCAASGSFDSRNAMGWYRQAPGKRREWVA

TITTDGRTNYADSVKARFTVSRDNAKNTVYLQMNSLKPDDTAVYYCNAA

PPIFNSWGQGT QVTVSS;

2HFA4:

(SEQ ID NO: 49)
QVQLQESGGGLVQAGGSLRLSCAASGSIDIRNAMGWYRQAPGTRREWVA

TITTDGRTNYADSVKARFTISRDNAKNTVYLQMNSLKPEDTAVYYCNLA

PPIFGSWGQGTQ VTVSS;

2HFA46:

(SEQ ID NO: 50)
QVQLQESGGGLVQAGGSLRLSCAASGSIDSRNTMGWYRQAPGKRREWVA

TITTGGRTNYADSVKARFTISRDNAKNTVYLQMNSLKPEDTAVYYCNLA

PPIFNSWGQGTQ VTVSS;

2HFA10:

(SEQ ID NO: 51)
QVQLQESGGGLVQAGGSLRLSCTVAESIDVRNAMGWYRQAPGKRREWVA

TITTGGRTNYADSVKARFTISRDNAKNTVYLQMNSLKPEDTAVYYCNAA

PPILNSWGQGT QVTVSS;

2HFA38:

(SEQ ID NO: 52)
QVQLQESGGGLVRVGGSLRLSCAVSGSFDSRNSMGWYRQAPGKRREWVA

TITSGSRTNYADSVKARFTISRDNAKNTVYLQMDSLKPEDTAVYYCNAA

PPIFNSWGQG TQVTVSS;

2HFA20:

(SEQ ID NO: 53)
QVQLQESGGGLVQAGGSLRLSCAVSGRLFSANTMGWYRQAPGKRRELVA

TILSSGSTNYADSVKGRFTISRDDAKNTVYLQMNSLKPEDTAVYYCNLA

PPPEGYWGQG TQVTVSS;

2HFA5:

(SEQ ID NO: 54)
QVQLQESGGGLVQAGGSLRLSCAVSGRLFSANTMGWYRQAPGKRRELVA

TILSSGSTNYADSVKGRFTISRDDGKNTVYLQMNSLKPDDTAVYYCNFA

PPPEGYWGQG TQVTVSS;

2HFA19:

(SEQ ID NO: 55)
QVQLQESGGGLVQAGGSLRLSCAASGSIFVGNAMGWYRQALGNQRELVA

GITSDGITYYPDSVKGRFTISRDNDKNTIYLQMNSLKPEDTAVYYCNLW

PPRIGFASWGQG TQVTVSS;

2HFA2:

(SEQ ID NO: 56)
QVQLQESGGGLVQTGGSLRLSCAASGSIFVGNAMGWYRQALGNQRELVA

GITSDGITYYPDSVKGRFTISRDNDKNTIYLQMNSLKPEDTAVYYCNLW

PPRIGFASWGQG TQVTVSS;

-continued

2HFA41:

(SEQ ID NO: 57)

QVQLQESGGGLVRAGGSLRLSCAASGSIFVGNAMGWYRQALGNQRELVA

GITSDGITYYPDSVKGRFTISRDNDKNTIYLQMNSLKPEDTAVYYCNLW

PPRIGFASWGQGTQVTVSS;

2HFA42:

(SEQ ID NO: 58)

QVQLQESGGGLVQTGGSLRLSCAASGSIFVGNAMGWYRQALGNQRELVA

GITSDGITYYPDSVKGRFTISRDNDKNTIYLQMNSLKPEDTAVYYCNLW

PPRIGFASWGQGTQVTVSS;

2HFA12:

(SEQ ID NO: 59)

QVQLQESGGGLVQAGGSLRLSCAASGSISMLNSMGWYRQALGKQREFVA

GITSGGRTNYADSVKGRFAISRDNDKNTVYLQMNSLKPEDTAVYYCNTW

PPRIAFDSWGQG TQVTVSS;

2HFA24:

(SEQ ID NO: 60)

QVQLQESGGGLVQAGGSLRLSCAASGSIFSSNAMGWYRQAAGKRRELVA

GIRSDGNTNYVDSVKGRFTISRDRAKNTVYLQMTSLKPEDTAVYYCNYW

PPPLRQGGDYAYWGQGTQVTVSS;

2HFA67:

(SEQ ID NO: 61)

QVQLQESGGGLVQAGGSLRLSCWSGSFDSRNAMAWYRQALGKERVWVAG

IISDGSTNYADAVKGRFTISRDNDKNTVYLQMNSLKPEDTAVYYCNAWP

PRIGLGSWGQGTQVTVSS;

2HFA29:

(SEQ ID NO: 62)

QVQLQESGGGLVQAGGSLRLSCAASGTMSSINAMGWYRQAPGKQRELVA

GILSDGTTKYVESVKGRFTISRDNAKNTVHLQMNSLKVEDTAVYYCNFF

PPPVPASWGQGTQVTVSS;

2HFA51:

(SEQ ID NO: 63)

QVQLQESGGGLVQAGGSLRLSCAVSGIISSMNAMGWYRQAPGKRRELVA

GLGSGVSTTYADAVKGRFTISRDNAKNTLYLQMNSLKPEDTAVYYCNRW

PPPYDYWGQGTQVTVSS;

2HFA63:

(SEQ ID NO: 64)

QVQLQESGGGLVQAGGSLRLSCVVSGTILSSNSMGWYRQAPGKRRELVA

SISTDGSTNYADSVKGRFTISRDNAKSTVFLQMNSLKPEDTAVYYCNFH

PPWRDWGDTYWGTQVTVSS QG;

2HFA62:

(SEQ ID NO: 65)

QVQLQESGGGLVQAGGSLRLSCAASRSIFSIGTMGWYRQAPGKRRELVA

FITVDHNTYYTDSVKGRFTISTENDKNTVYLQMNSLKPEDTAVYYCNRA

PPSTDGDRWGQG TQVTVSS;

2HFA26:

(SEQ ID NO: 66)

QVQLQESGGGLVQAGGSLRLSCAASGRTFSTYAMGWFRQAPGKERELVA

AISNGGSAYYADSVKGRFTISRDNARNTVYLQTNSLKPEDTAVYYCAAR

RGSAYYTNRIDWPYWGQGTQVTVSS;

-continued

2HFA25:

(SEQ ID NO: 67)

QVQLQESGGGLVQAGGSLRLSCAASGRTFSSYAMGWFRQAPGKERELVA

AISNGGSAYYADSVKGRFTISRDNARNTVYLQTNSLKPEDTAVYYCAAR

RGSAYYTNRIDWPYWGQGTQVTVSS;

2HFA1:

(SEQ ID NO: 68)

QVQLQESGGGLVEAEGSLRLSCIASGRTFGTYAMGWFRQAPGKERELVA

AISSGGSAYYADSVKGRFTISRDNARNTVYLQTNSLKPEDTAVYYCAAR

RGSAYYTNRIDWPYWGQGTQVTVSS;

2HFA3:

(SEQ ID NO: 69)

QVQLQESGGGLVEAEGSLRLSCIASGRTFGTYAMGWFRQAPGKERELVA

AISTGGSTYYADSVKGRFTISRDNARNTVYLQTNSLKPEDTAVYYCAAR

RGSAYYTNHVDWPYWGQGTQVTVSS;

2HFA7:

(SEQ ID NO: 70)

QVQLQESGGGLVEAEGSLRLSCAASGRTFGSYAMGWFRQAPGKSRELVA

AISSGGTTYYADSVKGRFTISRDNARNTVYLQTNSLKPEDTAVYYCAAR

TGSAYYTNRIDWPYWGQGTQVTVSS;

2HFA31:

(SEQ ID NO: 71)

QVQLQESGGGLVEAEGSLRLSCAASGRTFGSYAMGWFRQAPGKSRELVA
AISSGGTTYYADSVKGRFTISRDNARNTVYLQTNSPKPEDTAVYYCAAR
TGSAYYTNRIDWPYWGQGTQVTVSS;

2HFA6:

(SEQ ID NO: 72)

QVQLQESGGGLVEAEGSLRLSCAASGRTFGTYALAWFRQAPGKSRELVA

AISSGGSTYYADSVKGRFTISRDNARNTVYLQTNSLKPEDTAVYYCAAK

TGSAYYTNRIDWPYWGQGTQVTVSS;

2HFA53:

(SEQ ID NO: 73)

QVQLQESGGGLVEAEGSLRLSCAASGRAFGSYAMGWFRQAPGLERELVA

AISSGGTTYYADSVKGRFTISRDNARNTVYLQTNSLKPEDTAVYYCAAR

TGGAAYTRRIDWPYWGQGTQVTVSS;

2HFA9:

(SEQ ID NO: 74)

QVQLQESGGGLVEAEGSLRLSCAASGRTFGSYAMGWFRQAAGKERELVA

AISAGGSTLYADNVKGRFTISRDNARNTVYLLSNSLKPEDTAVYYCAAR

RGSAYYTNHIDWPYWGQGTQVTVSS;

2HFA73:

(SEQ ID NO: 75)

QVQLQESGGGLVQPGGSLRLSCAASGRTFGSYAMGWFRQAAGKERELVA

AISAGGSTLYADNVKGRFTISRDNARNTVYLLSNSLKPEDTAVYYCAAR

RGSAYYTNHIDWPYWGQGTQVTVSS;

2HFA55:

(SEQ ID NO: 76)

QVQLQESGGGLVEAEGSLRLSCAASGRTFGSYAMGWFRQAPGKERELVA

AISSGGSTLYADSVKGRFTISRDNAKNTVYLQMNSLKPEDTAVYYCAAR

SGGAYYTARVDWPYWGQGTQVTVSS;

-continued

2HFA71:

(SEQ ID NO: 77)
QVQLQESGGGLVEAEGSLRLSCAASGRTFGSYAMGWFRQAPGKERELVA

AISSGGSTLYAGSVKGRFTISKDNAKNTVYLQMNSLKPEDTAVYYCAAR

SGGAYYTARVDWPYWGQGTQVTVSS;

2HFA60:

(SEQ ID NO: 78)
QVQLQESGGGLVEAEGSPRLSCAASGRTFGSYAMGWFRQAPGKERELVA

AISSGGITYYADSVKGRFTISRDNAKNTVYLQMNSLKPEDTAVYYCAAR

SGSAYYTTRVDWPYWGQGTQVTVSS;

2HFA65:

(SEQ ID NO: 79)
QVQLQESGGGLVQAGGSLRLSCAASGNIDSIASMGWYRQAPGKQRELVA

AISVGGSTYYADSVKGRFTISRDNARNTVYLQTNSLKPEDTAVYYCAAR

RGSAYYTSRIDWPYWGQGTQVTVSS;

2HFA49:

(SEQ ID NO: 80)
QVQLQESGGGLVQAEGSLRLSCAASGRTFGSYAMGWFRQAPGKERELVA

GISSGGITNYAHSVKGRFTISRDIDKNTVFLQMNSLKPEDTAVYYCAAR

SGGAYYTSRVDWPYWGQGTQVTVSS;

2HFA57:

(SEQ ID NO: 81)
QVQLQESGGGLVXAGGSLRLSCAASGRTFSDYAMGWFRQAPGKEREFIA

GISWGGSSTYYADSVKGRFTISRDNAKNTMYLQMNSLKPEDTAVYYCAA

RLSGVSRSDRPYDYWGQGTQVTVSS;

2HFA23:

(SEQ ID NO: 82)
QVQLQESGGGLVQAGGSLRLSCAASGRTFSMYAIGWFRQAPGKERELVA

SISSGGSTNYADSVKGRFTISRDNAEKTVYLQMMSLEPEATGVYYCAAR

DGSALYTAHSDWDYW GQGTQVTVSS;

2HFA36:

(SEQ ID NO: 83)
QVQLQESGGGLVQPGDSLRLSCAASERTFSMYAIGWFRQAPGKERELVA

GISSGGSTNYADSVKGRFTISRDNPKKTVYLQMMSLEPEDTGVYYCAAR

SGSAYFSGRYYWNYWGQGTQVTVSS;

2HFA14:

(SEQ ID NO: 84)
QVQLQESGGGLVQAGDSLRLSCAASGRTFSSYVMGWFRQVPGKQRELVA

AITSGLSTYYADSLKGRFTISRDNAKNTMYLQMNSLKLEDTAVYYCAAR

EGGGIWTSSTQYDYWGQGTQVTVSS;

2HFA43:

(SEQ ID NO: 85)
QVQLQESGGGLVQAGGSLRLSCVASGTIFSSGAMAMGWYRQAPGKQREW

VAGITGSRTITYADSVKGRFTISRDNAENTVFLQMNNLKSEDTAVYYCN

LWPPSRPDHWG QGTQVTVSS;

and

2HFA50:

(SEQ ID NO: 86)
QVQLQESGGGLVQAGGSLRLSCVASGTISSGAMGWYRQVPGKQREWVAG

ITGSRTTMYTESVKGRFTISRDNAENTVFLQMNNLKSEDTAVYYCNLWP

PSRPDYWGQG TQVTVSS.

By way of example, but not by way of limitation, in some embodiments, a human VHH FAP binding agent is encoded by a nucleotide sequence selected from the sequences in FIG. 10 (i.e., SEQ ID NOs: 844-884). In some embodiments, the FAP binding agent comprises a nucleotide sequence selected from any one of the sequences in FIG. 10 without the MA linker, HA tag, and terminal histidine tag sequences.

In some embodiments, the FAP binding agent comprises a targeting moiety which is a VHH comprising a single amino acid chain having four "framework regions" or FRs and three "complementary determining regions" or CDRs. As used herein, "framework region" or "FR" refers to a region in the variable domain which is located between the CDRs. As used herein, "complementary determining region" or "CDR" refers to variable regions in VHHs that contains the amino acid sequences capable of specifically binding to antigenic targets.

In some embodiments, the FAP binding agent comprises a VHH having a variable domain comprising at least one CDR1, CDR2, and/or CDR3 sequences. In some embodiments, the FAP binding agent comprises a VHH having a variable region comprising at least one FR1, FR2, FR3, and FR4 sequences.

In some embodiments, a human FAP binding agent comprises a CDR1 sequence selected from:

(SEQ ID NO: 87)
GGFDSRNAMG;

(SEQ ID NO: 88)
GTFDSRNAMG;

(SEQ ID NO: 89)
GSFDSRNAMG;

(SEQ ID NO: 90)
GSIDIRNAMG;

(SEQ ID NO: 91)
GSIDSRNTMG;

(SEQ ID NO: 92)
ESIDVRNAMG;

(SEQ ID NO: 93)
GSFDSRNSMG;

(SEQ ID NO: 94)
GRLFSANTMG;

(SEQ ID NO: 95)
GSIFVGNAMG;

(SEQ ID NO: 96)
GSISMLNSMG;

(SEQ ID NO: 97)
GSIFSSNAMG;

(SEQ ID NO: 98)
GSFDSRNAMA;

(SEQ ID NO: 99)
GTMSSINAMG;

(SEQ ID NO: 100)
GIISSMNAMG;

(SEQ ID NO: 101)
GTILSSNSMG;

(SEQ ID NO: 102)
RSIFSIGTMG;

-continued (SEQ ID NO: 103)
GRTFSTYAMG;

(SEQ ID NO: 104)
GRTFSSYAMG;

(SEQ ID NO: 105)
GRTFGTYAMG;

(SEQ ID NO: 106)
GRTFGSYAMG;

(SEQ ID NO: 107)
GRTFGTYALA;

(SEQ ID NO: 108)
GRAFGSYAMG;

(SEQ ID NO: 109)
GNIDSIASMG;

(SEQ ID NO: 110)
GRTFSDYAMG;

(SEQ ID NO: 111)
GRTFSMYAIG;

(SEQ ID NO: 112)
ERTFSMYAIG;

(SEQ ID NO: 113)
GRTFSSYVMG;

(SEQ ID NO: 114)
GTIFSSGAMAMG;
and (SEQ ID NO: 115)
GTISSGAMG.

In some embodiments, a human FAP binding agent comprises a CDR2 sequence selected from:

(SEQ ID NO: 116)
TITSDGRTN;

(SEQ ID NO: 117)
TITTDGRTN;

(SEQ ID NO: 118)
TITTGGRTN;

(SEQ ID NO: 119)
TITSGSRTN;

(SEQ ID NO: 120)
TILSSGSTN;

(SEQ ID NO: 121)
GITSDGTTY;

(SEQ ID NO: 122)
GITSGGRTN;

(SEQ ID NO: 123)
GIRSDGNTN;

(SEQ ID NO: 124)
GIISDGSTN;

(SEQ ID NO: 125)
GILSDGTTK;

(SEQ ID NO: 126)
GLGSGVSTT;

(SEQ ID NO: 127)
SISTDGSTN;

-continued (SEQ ID NO: 128)
FITVDHNTY;

(SEQ ID NO: 129)
AISNGGSAY;

(SEQ ID NO: 130)
AISSGGSAY;

(SEQ ID NO: 131)
AISTGGSTY;

(SEQ ID NO: 132)
AISSGGTTY;

(SEQ ID NO: 133)
AISSGGSTY;

(SEQ ID NO: 134)
AISAGGSTL;

(SEQ ID NO: 135)
AISSGGSTL;

(SEQ ID NO: 136)
AISSGGITY;

(SEQ ID NO: 137)
AISVGGSTY;

(SEQ ID NO: 138)
GISSGGITN;

(SEQ ID NO: 139)
GISWGGSSTY;

(SEQ ID NO: 140)
SISSGGSTN;

(SEQ ID NO: 141)
GISSGGSTN;

(SEQ ID NO: 142)
AITSGLSTY;

(SEQ ID NO: 143)
GITGSRTTT;
and (SEQ ID NO: 144)
GITGSRTTM.

In some embodiments, a human FAP binding agent comprises a CDR3 sequence selected from:

(SEQ ID NO: 145)
NAAPPIFGS;

(SEQ ID NO: 146)
NAAPPIFNS;

(SEQ ID NO: 147)
NLAPPIFGS;

(SEQ ID NO: 148)
NLAPPIFNS;

(SEQ ID NO: 149)
NAAPPILNS;

(SEQ ID NO: 150)
NLAPPPEGY;

(SEQ ID NO: 151)
NFAPPPEGY;

(SEQ ID NO: 152)
NLWPPRIGFAS;

-continued (SEQ ID NO: 153)
NTWPPRIAFDS;

(SEQ ID NO: 154)
NYWPPPLRQGGDYAY;

(SEQ ID NO: 155)
NAWPPRIGLGS;

(SEQ ID NO: 156)
NFFPPPVPAS;

(SEQ ID NO: 157)
NRWPPPYDY;

(SEQ ID NO: 158)
NFHPPWRDWGDTY;

(SEQ ID NO: 159)
NRAPPSTDGDR;

(SEQ ID NO: 160)
AARRGSAYYTNRIDWPY;

(SEQ ID NO: 161)
AARRGSAYYTNHVDWPY;

(SEQ ID NO: 162)
AARTGSAYYTNRIDWPY;

(SEQ ID NO: 163)
AAKTGSAYYTNRIDWPY;

(SEQ ID NO: 164)
AARTGGAAYTRRIDWPY;

(SEQ ID NO: 165)
AARRGSAYYTNHIDWPY;

(SEQ ID NO: 166)
AARSGGAYYTARVDWPY;

(SEQ ID NO: 167)
AARSGSAYYTTRVDWPY;

(SEQ ID NO: 168)
AARRGSAYYTSRIDWPY;

(SEQ ID NO: 169)
AARSGGAYYTSRVDWPY;

(SEQ ID NO: 170)
AARLSGVSRSDR-PYDY;

(SEQ ID NO: 171)
AARDGSALYTAHSDWDY;

(SEQ ID NO: 172)
AARSGSAYFSGRYYWNY;

(SEQ ID NO: 173)
AAREGGGIWTSSTQYDY;

(SEQ ID NO: 174)
NLWPPSRPDH;
and (SEQ ID NO: 175)
NLWPPSRPDY.

In some embodiments, the FAP binding agent has at least 90% identity with any amino acid sequence selected from SEQ ID NOS: 2-42 or 46-86. In some embodiments, the FAP binding agent has about 90%, about 91%, about 92%, about 93%, about 94%, about 95%, about 96%, about 97%, about 98%, about 99% identity with any amino acid selected from SEQ ID NOS: 2-42 or 46-86.

In an embodiment, for example, the FAP binding agent has up to five substitutions, deletions, or insertions in any amino acid sequence selected from SEQ ID NOS: 87-175. For example, the FAP binding agent includes up to five substitutions, deletions, or insertions in any amino acid sequence selected of CDR1, e.g., from SEQ ID NOS: 87-115 (e.g., one, two, three, four or five total amino acid substitutions, deletions or insertions). Similarly, in another embodiment, the FAP binding agent includes up to five substitutions, deletions, or insertions in any amino acid sequence selected of CDR2, e.g., from SEQ ID NOS: 116-144 (e.g., one, two, three, four or five total amino acid substitutions, deletions or insertions). Similarly, in another embodiment, the FAP binding agent includes up to five substitutions, deletions, or insertions in any amino acid sequence selected of CDR3, e.g., from SEQ ID NOS: 145-175 (e.g., one, two, three, four or five total amino acid substitutions, deletions or insertions). An amino acid substitution refers to the replacement of one or more amino acid residues with another residue(s) in a peptide sequence. An amino acid deletion refers to removal of one or more amino acid residues from a peptide sequence. An amino acid insertion refers to addition of one or more amino acid residues into a peptide sequence.

In various illustrative embodiments, the murine FAP binding agent has at least 90% identity with the amino acid sequence of sibrotuzumab.

In some embodiments, the present technology contemplates the use of any natural or synthetic analogs, mutants, variants, alleles, homologs and orthologs (herein collectively referred to as "analogs") of the FAP binding agent of the present technology as described herein. In some embodiments, the amino acid sequence of the FAP binding agent further includes an amino acid analog, an amino acid derivative, or other non-classical amino acids.

In some embodiments, the FAP binding agent comprises a targeting moiety comprising a sequence that is at least 60% identical to any one of the FAP sequences disclosed herein. For example, the FAP binding agent may comprise a targeting moiety comprising a sequence that is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to any of the FAP sequences disclosed herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, about 99% or about 100% sequence identity to any one of the sequences disclosed herein).

In some embodiments, the FAP binding agent comprises a targeting moiety comprising an amino acid sequence having one or more amino acid mutations with respect to any one of the sequences disclosed herein. In some embodiments, the FAP binding agent comprises a targeting moiety comprising an amino acid sequence having one, or two, or three, or four, or five, or six, or seen, or eight, or nine, or ten, or fifteen, or twenty amino acid mutations with respect to any one of the sequences disclosed herein. In some embodiments, the one or more amino acid mutations may be independently selected from substitutions, insertions, deletions, and truncations.

In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic:Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

In some embodiments, the substitutions include non-classical amino acids. Illustrative non-classical amino acids include, but are not limited to, selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general.

In some embodiments, one or more amino acid mutations are in the CDRs of the targeting moiety (e.g., the CDR1, CDR2 or CDR3 regions). In another embodiment, one or more amino acid mutations are in the framework regions (FRs) of the targeting moiety (e.g., the FR1, FR2, FR3, or FR4 regions).

Modification of the amino acid sequences may be achieved using any known technique in the art e.g., site-directed mutagenesis or PCR based mutagenesis. Such techniques are described, for example, in Sambrook et al., Molecular Cloning: A Laboratory Manual, Cold Spring Harbor Press, Plainview, N.Y., 1989 and Ausubel et al., Current Protocols in Molecular Biology, John Wiley & Sons, New York, N.Y., 1989.

In some embodiments, the mutations do not substantially reduce the present FAP binding agent's capability to specifically bind to FAP. In some embodiments, the mutations do not substantially reduce the present FAP binding agent's capability to specifically bind to FAP and without functionally modulating (e.g., partially or fully neutralizing) FAP.

In some embodiments, the binding affinity of the FAP binding agent of the present technology for the full-length and/or mature forms and/or isoforms and/or splice variants and/or fragments and/or monomeric and/or dimeric forms and/or any other naturally occurring or synthetic analogs, variants, or mutants (including monomeric and/or dimeric forms) of human FAP may be described by the equilibrium dissociation constant ($K_D$). In some embodiments, the FAP binding agent comprises a targeting moiety that binds to the full-length and/or mature forms and/or isoforms and/or splice variants and/or fragments and/or any other naturally occurring or synthetic analogs, variants, or mutants (including monomeric and/or dimeric forms) of human FAP with a $K_D$ of less than about 1 μM, about 900 nM, about 800 nM, about 700 nM, about 600 nM, about 500 nM, about 400 nM, about 300 nM, about 200 nM, about 100 nM, about 90 nM, about 80 nM, about 70 nM, about 60 nM, about 50 nM, about 40 nM, about 30 nM, about 20 nM, about 10 nM, or about 5 nM, or about 1 nM.

In some embodiments, the FAP binding agent comprises a targeting moiety that binds but does not functionally modulate (e.g., partially or fully neutralize) the antigen of interest, i.e., FAP. For instance, in some embodiments, the targeting moiety of the FAP binding agent simply targets the antigen but does not substantially functionally modulate (e.g. partially or fully inhibit, reduce or neutralize) a biological effect that the antigen has. In some embodiments, the targeting moiety of the FAP binding agent binds an epitope that is physically separate from an antigen site that is important for its biological activity (e.g. an antigen's active site).

Such binding without significant function modulation finds use in some embodiments of the present technology, including methods in which the present FAP binding agent is used to directly or indirectly recruit active immune cells to a site of need via an effector antigen. For example, in some embodiments, the present FAP binding agent may be used to directly or indirectly recruit dendritic cells via FAP to a tumor cell in a method of reducing or eliminating a tumor (e.g. the FAP binding agent may comprise a targeting moiety having an anti-FAP antigen recognition domain and a targeting moiety having a recognition domain (e.g. antigen recognition domain) directed against a tumor antigen or receptor). In such embodiments, it is desirable to directly or indirectly recruit dendritic cells but not to functionally modulate or neutralize the FAP activity. In these embodiments, FAP signaling is an important piece of the tumor reducing or eliminating effect.

In some embodiments, the FAP binding agent enhances antigen-presentation by dendritic cells. For example, in some embodiments, the present FAP binding agent directly or indirectly recruits dendritic cells via FAP to a tumor cell, where tumor antigens are subsequently endocytosed and presented on the dendritic cell for induction of potent humoral and cytotoxic T cell responses.

In other embodiments (for example, related to treating cancer, autoimmune, or neurodegenerative disease), the FAP binding agent comprises a targeting moiety that binds and neutralizes the antigen of interest, i.e., FAP. For instance, in some embodiments, the present methods may inhibit or reduce FAP signaling or expression, e.g. to cause a reduction in an immune response.

Therapeutic Agents Comprising the Present FAP Binding Agents

Chimeras and Fusions with Signaling Agents

In some embodiments, the FAP binding agent of the present technology is part of a chimera or fusion protein with one or more signaling agents. Accordingly, the present technology provides for chimeric or fusion proteins that include, for example, a targeting moiety against FAP and one or more signaling agents.

In some embodiments, the signaling agent is modified to have reduced affinity or activity for one or more of its receptors, which allows for attenuation of activity (inclusive of agonism or antagonism) and/or prevents non-specific signaling or undesirable sequestration of the chimeric or fusion protein. In some embodiments, the signaling agent is antagonistic in its wild type form and bears one or more mutations that attenuate its antagonistic activity. In some embodiments, the signaling agent is antagonistic due to one or more mutations, e.g. an agonistic signaling agent is converted to an antagonistic signaling agent and, such a converted signaling agent, optionally, also bears one or more mutations that attenuate its antagonistic activity (e.g. as described in WO 2015/007520, the entire contents of which are hereby incorporated by reference).

Accordingly, in some embodiments, the signaling agent is a modified (e.g. mutant) form of the signaling agent having one or more modifications (e.g. mutations). In some embodiments, the mutations allow for the modified signaling agent to have one or more of attenuated activity such as one or more of reduced binding affinity, reduced endogenous activity, and reduced specific bioactivity relative to unmutated, i.e., the wild type form of the signaling agent (e.g. comparing the same signaling agent in a wild type form versus a modified (e.g. mutant) form). In some embodiments, the mutations which attenuate or reduce binding or affinity include those mutations which substantially reduce or ablate binding or activity. In some embodiments, the mutations which attenuate or reduce binding or affinity are different than those mutations which substantially reduce or ablate binding or activity. Consequentially, in some embodiments, the mutations allow for the signaling agent to have improved safety, e.g. reduced systemic toxicity, reduced side effects, and reduced off-target effects relative to unmutated, i.e., wild type, signaling agent (e.g. comparing the same signaling agent in a wild type form versus a modified (e.g. mutant) form).

As described herein, the agent may have improved safety due to one of more modifications, e.g. mutations. In some embodiments, improved safety means that the present chimeric protein provides lower toxicity (e.g. systemic toxicity and/or tissue/organ-associated toxicities); and/or lessened or substantially eliminated side effects; and/or increased tolerability, lessened or substantially eliminated adverse events; and/or reduced or substantially eliminated off-target effects; and/or an increased therapeutic window.

In some embodiments, the signaling agent is modified to have one or more mutations that reduce its binding affinity or activity for one or more of its receptors. In some embodiments, the signaling agent is modified to have one or more mutations that substantially reduce or ablate binding affinity or activity for the receptors. In some embodiments, the activity provided by the wild type signaling agent is agonism at the receptor (e.g. activation of a cellular effect at a site of therapy). For example, the wild type signaling agent may activate its receptor. In such embodiments, the mutations result in the modified signaling agent to have reduced or ablated activating activity at the receptor. For example, the mutations may result in the modified signaling agent to deliver a reduced activating signal to a target cell or the activating signal could be ablated. In some embodiments, the activity provided by the wild type signaling agent is antagonism at the receptor (e.g. blocking or dampening of a cellular effect at a site of therapy). For example, the wild type signaling agent may antagonize or inhibit the receptor. In these embodiments, the mutations result in the modified signaling agent to have a reduced or ablated antagonizing activity at the receptor. For example, the mutations may result in the modified signaling agent to deliver a reduced inhibitory signal to a target cell or the inhibitory signal could be ablated. In some embodiments, the signaling agent is antagonistic due to one or more mutations, e.g. an agonistic signaling agent is converted to an antagonistic signaling agent (e.g. as described in WO 2015/007520, the entire contents of which are hereby incorporated by reference) and, such a converted signaling agent, optionally, also bears one or mutations that reduce its binding affinity or activity for one or more of its receptors or that substantially reduce or ablate binding affinity or activity for one or more of its receptors.

In some embodiments, the reduced affinity or activity at the receptor is restorable by attachment with one or more of the targeting moieties as described herein (e.g., targeting moiety against FAP). In other embodiments, the reduced affinity or activity at the receptor is not substantially restorable by the activity of one or more of the targeting moieties.

In some embodiments, the chimeric proteins of the present technology reduce off-target effects because their signaling agents have mutations that weaken or ablate binding affinity or activity at a receptor. In some embodiments, this reduction in side effects is observed relative with, for example, the wild type signaling agents. In some embodiments, the signaling agent is active on target cells because the targeting moiety(ies) compensates for the missing/insufficient binding (e.g., without limitation and/or avidity) required for substantial activation. In some embodiments, the modified signaling agent is substantially inactive enroute to the site of therapeutic activity and has its effect substantially on specifically targeted cell types which greatly reduces undesired side effects.

In some embodiments, the signaling agent may include one or more mutations that attenuate or reduce binding or affinity for one receptor (i.e., a therapeutic receptor) and one or more mutations that substantially reduce or ablate binding or activity at a second receptor. In such embodiments, these mutations may be at the same or at different positions (i.e., the same mutation or multiple mutations). In some embodiments, the mutation(s) that reduce binding and/or activity at one receptor is different than the mutation(s) that substantially reduce or ablate at another receptor. In some embodiments, the mutation(s) that reduce binding and/or activity at one receptor is the same as the mutation(s) that substantially reduce or ablate at another receptor. In some embodiments, the present chimeric proteins have a modified signaling agent that has both mutations that attenuate binding and/or activity at a therapeutic receptor and therefore allow for a more controlled, on-target therapeutic effect (e.g. relative wild type signaling agent) and mutations that substantially reduce or ablate binding and/or activity at another receptor and therefore reduce side effects (e.g. relative to wild type signaling agent).

In some embodiments, the substantial reduction or ablation of binding or activity is not substantially restorable with a targeting moiety (e.g., a targeting moiety against FAP or any other targeting moiety described herein). In some embodiments, the substantial reduction or ablation of binding or activity is restorable with a targeting moiety. In some embodiments, substantially reducing or ablating binding or activity at a second receptor also may prevent deleterious effects that are mediated by the other receptor. Alternatively, or in addition, substantially reducing or ablating binding or activity at the other receptor causes the therapeutic effect to improve as there is a reduced or eliminated sequestration of the therapeutic chimeric proteins away from the site of therapeutic action. For instance, in some embodiments, this obviates the need of high doses of the present chimeric proteins that compensate for loss at the other receptor. Such ability to reduce dose further provides a lower likelihood of side effects.

In some embodiments, the modified signaling agent comprises one or more mutations that cause the signaling agent to have reduced, substantially reduced, or ablated affinity, e.g. binding (e.g. KD) and/or activation (for instance, when the modified signaling agent is an agonist of its receptor, measurable as, for example, KA and/or EC50) and/or inhibition (for instance, when the modified signaling agent is an antagonist of its receptor, measurable as, for example, Ki and/or 1050), for one or more of its receptors. In some embodiments, the reduced affinity at the immumodulating agent's receptor allows for attenuation of activity (inclusive of agonism or antagonism). In such embodiments, the modified signaling agent has about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, about 95%, or about 10%-20%, about 20%-40%, about 50%, about 40%-60%, about 60%-80%, about 80%-100% of the affinity for the receptor relative to the wild type signaling agent. In some embodiments, the binding affinity is at least about 2-fold lower, about 3-fold lower, about 4-fold lower, about 5-fold lower, about 6-fold lower, about 7-fold lower, about 8-fold lower, about 9-fold lower, at least about 10-fold lower, at least about 15-fold lower, at least about 20-fold lower, at least about 25-fold lower, at least about 30-fold lower, at least about 35-fold lower, at least about 40-fold lower, at least about 45-fold lower, at least about 50-fold lower, at least about 100-fold lower, at least about 150-fold lower, or about 10-50-fold lower, about 50-100-fold lower, about 100-150-fold lower, about 150-200-fold lower, or more than 200-fold lower relative to the wild type signaling agent.

In embodiments wherein the modified signaling agent has mutations that reduce binding at one receptor and substantially reduce or ablate binding at a second receptor, the attenuation or reduction in binding affinity of a modified signaling agent for one receptor is less than the substantial reduction or ablation in affinity for the other receptor. In some embodiments, the attenuation or reduction in binding affinity of a modified signaling agent for one receptor is less than the substantial reduction or ablation in affinity for the other receptor by about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, or about 95%. In some embodiments, substantial reduction or ablation refers to a greater reduction in binding affinity and/or activity than attenuation or reduction.

In some embodiments, the modified signaling agent comprises one or more mutations that reduce the endogenous activity of the signaling agent to about 75%, or about 70%, or about 60%, or about 50%, or about 40%, or about 30%, or about 25%, or about 20%, or about 10%, or about 5%, or about 3%, or about 1%, e.g., relative to the wild type signaling agent.

In some embodiments, the modified signaling agent comprises one or more mutations that cause the signaling agent to have reduced affinity for its receptor that is lower than the binding affinity of the targeting moiety(ies) for its(their) receptor(s). In some embodiments, this binding affinity differential is between signaling agent/receptor and targeting moiety/receptor on the same cell. In some embodiments, this binding affinity differential allows for the signaling agent, e.g. mutated signaling agent, to have localized, on-target effects and to minimize off-target effects that underlie side effects that are observed with wild type signaling agent. In some embodiments, this binding affinity is at least about 2-fold, or at least about 5-fold, or at least about 10-fold, or at least about 15-fold lower, or at least about 25-fold, or at least about 50-fold lower, or at least about 100-fold, or at least about 150-fold.

Receptor binding activity may be measured using methods known in the art. For example, affinity and/or binding activity may be assessed by Scatchard plot analysis and computer-fitting of binding data (e.g. Scatchard, 1949) or by reflectometric interference spectroscopy under flow through conditions, as described by Brecht et al. (1993), the entire contents of all of which are hereby incorporated by reference.

In various embodiments, the additional signaling agent is selected from modified versions of cytokines, growth factors, and hormones. Illustrative examples of such cytokines, growth factors, and hormones include, but are not limited to, lymphokines, monokines, traditional polypeptide hormones, such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and tumor necrosis factor-β; mullerian-inhibiting substance; mouse gonadotropin-associated peptide; inhibin; activin; vascular endothelial growth factor; integrin; thrombopoietin (TPO); nerve growth factors such as NGF-α; platelet-growth factor; transforming growth factors (TGFs) such as TGF-α and TGF-β; insulin-like growth factor-I and -II; osteo inductive factors; interferons such as, for example, interferon-α, interferon-β and interferon-γ (and interferon type I, II, and III), colony stimulating factors (CSFs) such as macrophage-CSF (M-CSF); granulocyte-macrophage-CSF (GM-CSF); and granulocyte-CSF (G-CSF); interleukins (ILs) such as, for example, IL-1, IL-1a, IL-2, IL-3, IL-4, IL-5, IL-6, IL-7, IL-8, IL-9, IL-10, IL-11, IL-12, IL-13, and IL-18; a tumor necrosis factor such as, for example, TNF-α or TNF-β; and other polypeptide factors including, for example, LIF and kit ligand (KL). As used herein, cytokines, growth factors, and hormones include proteins obtained from natural sources or produced from recombinant bacterial, eukaryotic or mammalian cell culture systems and biologically active equivalents of the native sequence cytokines.

In some embodiments, the additional signaling agent is a modified version of a growth factor selected from, but not limited to, transforming growth factors (TGFs) such as TGF-α and TGF-β, epidermal growth factor (EGF), insulin-like growth factor such as insulin-like growth factor-I and -II, fibroblast growth factor (FGF), heregulin, platelet-derived growth factor (PDGF), vascular endothelial growth factor (VEGF).

In an embodiment, the growth factor is a modified version of a fibroblast growth factor (FGF). Illustrative FGFs include, but are not limited to, FGF1, FGF2, FGF3, FGF4, FGF5, FGF6, FGF7, FGF8, FGF9, FGF10, FGF11, FGF12, FGF13, FGF14, murine FGF15, FGF16, FGF17, FGF18, FGF19, FGF20, FGF21, FGF22, and FGF23.

In an embodiment, the growth factor is a modified version of a transforming growth factor (TGF). Illustrative TGFs include, but are not limited to, TGF-α and TGF-β and subtypes thereof including the various subtypes of TGF-β including TGFβ1, TGFβ2, and TGFβ3.

In some embodiments, the additional signaling agent is a modified version of a hormone selected from, but not limited to, human chorionic gonadotropin, gonadotropin releasing hormone, an androgen, an estrogen, thyroid-stimulating hormone, follicle-stimulating hormone, luteinizing hormone, prolactin, growth hormone, adrenocorticotropic hormone, antidiuretic hormone, oxytocin, thyrotropin-releasing hormone, growth hormone releasing hormone, corticotropin-releasing hormone, somatostatin, dopamine, melatonin, thyroxine, calcitonin, parathyroid hormone, glucocorticoids, mineralocorticoids, adrenaline, noradrenaline, progesterone, insulin, glucagon, amylin, calcitriol, calciferol, atrial-natriuretic peptide, gastrin, secretin, cholecystokinin, neuropeptide Y, ghrelin, PYY3-36, insulin-like growth factor (IGF), leptin, thrombopoietin, erythropoietin (EPO), and angiotensinogen.

In some embodiments, the signaling agent is an immune-modulating agent, e.g. one or more of an interleukin, interferon, and tumor necrosis factor.

In some embodiments, the signaling agent is an interleukin or a modified interleukin, including for example IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; IL-36 or a fragment, variant, analogue, or family-member thereof. Interleukins are a group of multi-functional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. Interleukin activity can be determined using assays known in the art: Matthews et al., in Lymphokines and Interferens: A Practical Approach, Clemens et al., eds, IRL Press, Washington, D.C. 1987, pp. 221-225; and Orencole & Dinarello (1989) Cytokine 1, 14-20.

In some embodiments, the signaling agent is an interferon or a modified version of an interferon such as interferon types I, II, and III. Illustrative interferons, including for example, interferon-a-1, 2, 4, 5, 6, 7, 8, 10, 13, 14, 16, 17, and 21, interferon-β and interferon-γ, interferon κ, interferon ε, interferon τ, and interferon ω.

In some embodiments, the signaling agent is a tumor necrosis factor (TN F) or a modified version of a tumor necrosis factor (TNF) or a protein in the TNF family, including but not limited to, TNF-α, TNF-β, LT-β, CD40L, CD27L, CD30L, FASL, 4-1BBL, OX40L, and TRAIL.

The amino acid sequences of the wild type signaling agents described herein are well known in the art. Accordingly, in some embodiments the modified signaling agent comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74% or at least about 75% or at least about 76%, or at least about 77%, or at least about 78%, or at least about 79%, or at least about 80%, or at least about 81%, or at least about 82%, or at least about 83% at least about 84%, or at least at least about 85%, or at least about 86%, or at least about 87%, or at least about 88%, or at least about 89%, or at least about 90%, or at least about 91% or at least about 92%, or at least about 93%, or at least about 94%, or at least about 95%, or at least about 96%, or at least about 97%, or at least about 98%, or at least about 99% sequence identity with the known wild type amino acid sequences of the signaling agents described herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In some embodiments the modified signaling agent comprises an amino acid sequence that has at least about 60%, or at least about 61%, 65%, or at least about 66%, 70%, or at least about 71%, 75%, or at least about 76%, 80%, or at least about 81%, 85%, or at least about 86%, 90%, or at least about 91%, or at least about 62%, or at least about 67%, or at least about 72%, or at least about 77%, or at least about 82%, or at least about 87%, or at least about 92% or at least about 63%, or at least about 68%, or at least about 73%, or at least about 78%, or at least about 83%, or at least about 88%, or at least about 93% or at least about 64%, or at least about 69%, or at least about 74%, or at least about 79%, or at least about 84%, or at least about 89%, or at least about 94% or at least about or at least about or at least about or at least about or at least about or at least about or at least about 95%, or at least about 96%, or at least about 97%, or at least about 98%, or at least about 99% sequence identity with any amino acid sequences of the signaling agents described herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In some embodiments, the modified signaling agent comprises an amino acid sequence having one or more amino acid mutations. In some embodiments, the one or more amino acid mutations may be independently selected from substitutions, insertions, deletions, and truncations. In some embodiments, the amino acid mutations are amino acid substitutions, and may include conservative and/or non-conservative substitutions, as described elsewhere herein. In some embodiments, the substitutions may also include non-classical amino acids as described elsewhere herein.

As described herein, the modified signaling agents bear mutations that affect affinity and/or activity at one or more receptors. In some embodiments, there is reduced affinity and/or activity at a therapeutic receptor, e.g. a receptor through which a desired therapeutic effect is mediated (e.g. agonism or antagonism). In some embodiments, the modified signaling agents bear mutations that substantially reduce or ablate affinity and/or activity at a receptor, e.g. a receptor through which a desired therapeutic effect is not mediated (e.g. as the result of promiscuity of binding). The receptors of any modified signaling agents, e.g. one of the cytokines, growth factors, and hormones as described herein, are known in the art.

Illustrative mutations which provide reduced affinity and/or activity (e.g. agonistic) at a receptor are found in WO 2013/107791 and PCT/EP2017/061544 (e.g. with regard to interferons), WO 2015/007542 (e.g. with regard to interleukins), and WO 2015/007903 (e.g. with regard to TN F), the entire contents of each of which are hereby incorporated by reference. Illustrative mutations which provide reduced affinity and/or activity (e.g. antagonistic) at a therapeutic receptor are found in WO 2015/007520, the entire contents of which are hereby incorporated by reference.

In some embodiments, the modified signaling agent comprises one or more mutations that cause the signaling agent to have reduced affinity and/or activity for a type I cytokine receptor, a type II cytokine receptor, a chemokine receptor, a receptor in the Tumor Necrosis Factor Receptor (TNFR) superfamily, TGF-beta Receptors, a receptor in the immunoglobulin (Ig) superfamily, and/or a receptor in the tyrosine kinase superfamily.

In some embodiments, the receptor for the signaling agent is a Type I cytokine receptor. Type I cytokine receptors are known in the art and include, but are not limited to receptors for IL2 (beta-subunit), IL3, IL4, IL5, IL6, IL7, IL9, IL11, IL12, GM-CSF, G-CSF, LIF, CNTF, and also the receptors for Thrombopoietin (TPO), Prolactin, and Growth hormone. Illustrative type I cytokine receptors include, but are not limited to, GM-CSF receptor, G-CSF receptor, LIF receptor, CNTF receptor, TPO receptor, and type I IL receptors.

In some embodiments, the receptor for the signaling agent is a Type II cytokine receptor. Type II cytokine receptors are multimeric receptors composed of heterologous subunits, and are receptors mainly for interferons. This family of receptors includes, but is not limited to, receptors for interferon-a, interferon-13 and interferon-y, IL10, IL22, and tissue factor. Illustrative type II cytokine receptors include, but are not limited to, IFN-α receptor (e.g. IFNAR1 and IFNAR2), IFN-3 receptor, IFN-y receptor (e.g. IFNGR1 and IFNGR2), and type II IL receptors.

In some embodiments, the receptor for the signaling agent is a G protein-coupled receptor. Chemokine receptors are G protein-coupled receptors with seven transmembrane structure and coupled to G-protein for signal transduction. Chemokine receptors include, but are not limited to, CC chemokine receptors, CXC chemokine receptors, CX3C chemokine receptors, and XC chemokine receptor (XCR1). Illustrative chemokine receptors include, but are not limited to, CCR1, CCR2, CCR3, CCR4, CCR5, CCR6, CCR7, CCR8, CCR9, CCR10, CXCR1, CXCR2, CXCR3, CXCR3B, CXCR4, CXCR5, CSCR6, CXCR7, XCR1, and CX3CR1.

In some embodiments, the receptor for the signaling agent is a TNFR family member. Tumor necrosis factor receptor (TN FR) family members share a cysteine-rich domain (CRD) formed of three disulfide bonds surrounding a core motif of CXXCXXC creating an elongated molecule. Illustrative tumor necrosis factor receptor family members include: CDI 20a (TN FRSFIA), CD 120b (TNFRSFIB), Lymphotoxin beta receptor (LTBR, TNFRSF3), CD 134 (TNFRSF4), CD40 (C D40, TNFRSFS), FAS (FAS, TNFRSF6), TNFRSF6B (TNFRSF6B), CD27 (CD27, TNFRSF7), CD30 (TNFRSF8), CD137 (TNFRSF9), TNFRSFIOA (TNFRSFIOA), TNFRSFIOB, (TNFRSFIOB), TNFRSFIOC (TNFRSFIOC), TNFRSFIOD (TNFRSFIOD), RANK (TNFRSFI IA), Osteoprotegerin (TNFRSFI IB), TNFRSF12A (TNFRSF12A), TNFRSF13B (TNFRSF13B), TNFRSF13C (TNFRSF130), TNFRSF14 (TNFRSF14), Nerve growth factor receptor (NGFR, TNFRSF16), TNFRSF17 (TNFRSF17), TNFRSF18 (TNFRSF18), TNFRSF19 (TNFRSF19), TNFRSF21 (TNFRSF21), and TNFRSF25 (TNFRSF25). In an embodiment, the TNFR family member is CD120a (TNFRSF1A) or TNF-R1. In another embodiment, the TNFR family member is CD 120b (TNFRSFIB) or TNF-R2.

In some embodiments, the receptor for the signaling agent is a TGF-beta receptor. TGF-beta receptors are single pass serine/threonine kinase receptors. TGF-beta receptors include, but are not limited to, TGFBR1, TGFBR2, and TGFBR3.

In some embodiments, the receptor for the signaling agent is an Ig superfamily receptor. Receptors in the immunoglobulin (Ig) superfamily share structural homology with immunoglobulins. Receptors in the Ig superfamily include, but are not limited to, interleukin-1 receptors, CSF-1R, PDGFR (e.g. PDGFRA and PDGFRB), and SCFR.

In some embodiments, the receptor for the signaling agent is a tyrosine kinase superfamily receptor. Receptors in the tyrosine kinase superfamily are well known in the art. There are about 58 known receptor tyrosine kinases (RTKs), grouped into 20 subfamilies. Receptors in the tyrosine kinase superfamily include, but are not limited to, FGF receptors and their various isoforms such as FGFR1, FGFR2, FGFR3, FGFR4, and FGFR5.

In some embodiments, the modified signaling agent is interferon a. In some embodiments, the modified IFN-α agent has reduced affinity and/or activity for the IFN-α/β receptor (IFNAR), i.e., IFNAR1 and/or IFNAR2 chains. In some embodiments, the modified IFN-α agent has substantially reduced or ablated affinity and/or activity for the IFN-α/β receptor (IFNAR), i.e., IFNAR1 and/or IFNAR2 chains. In some embodiments, the modified IFN-α agent is a human modified IFN-α agent.

Mutant forms of interferon are known to the person skilled in the art. By way of example, but not by way of limitation, in some embodiments, the modified signaling agent is the allelic form IFN-α2a having the amino acid sequence of: SEQ ID NO: 176.

By way of example, but not by way of limitation, in some embodiments, the modified signaling agent is the allelic form IFN-α2b having the amino acid sequence of: SEQ ID NO: 177; which differs from IFN-α2a at amino acid position 23.

In some embodiments, a modified IFN-α2 signaling agent is a human IFN-α2 mutant (IFN-α2a or IFN-α2b). In some embodiments, the human IFN-α2 mutant (IFN-α2a or IFN-α2b) is mutated at one or more amino acids at positions 144-154, e.g., such as amino acid positions 148, 149 and/or 153. In some embodiments, the human IFN-α2 mutant comprises one or more mutations selected from L153A, R149A, and M148A.

In some embodiments, the IFN-α2 mutants have reduced affinity and/or activity for IFNAR1. In some embodiments, the IFN-α 2 mutant is a human IFN-α 2 mutant comprising one or more mutations selected from F64A, N65A, T69A, L80A, Y85A, and Y89A, as described in WO2010/030671, the entire contents of which is hereby incorporated by reference.

In some embodiments, the IFN-α2 mutant is a human IFN-α2 mutant comprising one or more mutations selected from K133A, R144A, R149A, and L153A, as described in WO2008/124086, the entire contents of which is hereby incorporated by reference.

In some embodiments, the IFN-α2 mutant is a human IFN-α2 mutant comprising one or more mutations selected from R120E and R120E/K121E, as described in WO2015/007520 and WO2010/030671, the entire contents of which are hereby incorporated by reference.

In some embodiments, the IFN-α2 mutant antagonizes wild type IFN-α2 activity. In some embodiments, said mutant IFN-α2 has reduced affinity and/or activity for IFNAR1, while affinity and/or activity of IFNR2 is retained.

In some embodiments, a human IFN-α2 mutant comprises (1) one or more mutations selected from R120E and R120E/K121E, which, without wishing to be bound by theory, create an antagonistic effect and (2) one or more mutations selected from K133A, R144A, R149A, and L153A, which, without wishing to be bound by theory, allow for an attenuated effect at, for example, IFNAR2. In some embodiments, the human IFN-α2 mutant comprises R120E and L153A.

In some embodiments, the human IFN-α2 mutant comprises one or more mutations selected from L15A, A19W, R22A, R23A, L26A, F27A, L30A, L30V, K31A, D32A, R33K, R33A, R33Q, H34A, D35A, Q40A, D114R, L117A, R120A, R125A, K134A, R144A, A145G, A145M, M148A, R149A, S152A, L153A, and N156A as disclosed in WO 2013/059885, the entire disclosures of which are hereby incorporated by reference. In some embodiments, the human IFN-α2 mutant comprises the mutations H57Y, E58N, Q61S, and/or L30A as disclosed in WO 2013/059885. In some embodiments, the human IFN-α2 mutant comprises the mutations H57Y, E58N, Q61S, and/or R33A as disclosed in WO 2013/059885. In some embodiments, the human IFN-α2 mutant comprises the mutations H57Y, E58N, Q61S, and/or M148A as disclosed in WO 2013/059885. In some embodiments, the human IFN-α2 mutant comprises the mutations H57Y, E58N, Q61S, and/or L153A as disclosed in WO 2013/059885. In some embodiments, the human IFN-α2 mutant comprises the mutations N65A, L80A, Y85A, and/or Y89A as disclosed in WO 2013/059885. In some embodiments, the human IFN-α2 mutant comprises the mutations N65A, L80A, Y85A, Y89A, and/or D114A as disclosed in WO 2013/059885. In some embodiments, the human IFN-α2 mutant comprises the mutations R144X1, A145X2, and R33A, wherein X, is selected from A, S, T, Y, L, and I, and wherein X2 is selected from G, H, Y, K, and D.

In an embodiment, the modified signaling agent is interferon β. In such embodiments, the modified interferon β agent has reduced affinity and/or activity for the IFN-α/β receptor (IFNAR), i.e., IFNAR1 and/or IFNAR2 chains. In some embodiments, the modified interferon β agent has substantially reduced or ablated affinity and/or activity for the IFN-α/β receptor (IFNAR), i.e., IFNAR1 and/or IFNAR2 chains.

In an illustrative embodiment, the modified signaling agent is IFN-β. In some embodiments, the IFN-β encompasses functional derivatives, analogs, precursors, isoforms, splice variants, or fragments of IFN-β. In some embodiments, the IFN-β encompasses IFN-β derived from any species. In an embodiment, the chimeric protein comprises a modified version of mouse IFN-β. In another embodiment, the chimeric protein comprises a modified version of human IFN-β. Human IFN-β is a polypeptide with a molecular weight of about 22 kDa comprising 166 amino acid residues. The amino acid sequence of human IFN-β is shown as SEQ ID NO: 178.

In some embodiments, the human IFN-β is IFN-β-1a, which is a glycosylated form of human IFN-β. In some embodiments, the human IFN-β is IFN-β-1b, which is a non-glycosylated form of human IFN-β that has a Met-1 deletion and a Cys-17 to Ser mutation.

In some embodiments, the modified IFN-β has one or more mutations that reduce its binding to or its affinity for the IFNAR1 subunit of IFNAR. In some embodiments, the modified IFN-β has reduced affinity and/or activity at IFNAR1.

In some embodiments, the modified IFN-β with reduced affinity and/or activity at IFNAR1 is human IFN-β and has one or more mutations at positions F67, R71, L88, Y92, 195, N96, K123, and R124. In some embodiments, the one or more mutations are substitutions selected from F67G, F67S, R71A, L88G, L885, Y92G, Y92S, 195A, N96G, K123G, and R124G. In some embodiments, the modified human IFN-β comprises the F67G mutation. In some embodiments, the modified human IFN-β comprises the K123G mutation. In some embodiments, the modified human IFN-β comprises the F67G and R71A mutations. In some embodiments, the modified human IFN-β comprises the L88G and Y92G mutations. In some embodiments, the modified human IFN-β comprises the Y92G, 195A, and N96G mutations. In some embodiments, the modified human IFN-β comprises the K123G and R124G mutations. In some embodiments, the modified human IFN-β comprises the F67G, L88G, and Y92G mutations. In some embodiments, the modified human IFN-β comprises the F67S, L88S, and Y92S mutations.

In some embodiments, the modified IFN-β has one or more mutations that reduce its binding to or its affinity for the IFNAR2 subunit of IFNAR. In some embodiments, the modified IFN-β has reduced affinity and/or activity at IFNAR2.

In some embodiments, the modified IFN-β reduced affinity and/or activity at IFNAR2 is human IFN-β and has one or more mutations at positions W22, R27, L32, R35, V148, L151, R152, and Y155. In some embodiments, the one or more mutations are substitutions selected from W22G, R27G, L32A, L32G, R35A, R35G, V148G, L151G, R152A, R152G, and Y155G. In some embodiments, the modified human IFN-β comprises the W22G mutation. In some embodiments, the modified human IFN-β comprises the L32A mutation. In some embodiments, the modified human IFN-β comprises the L32G mutation. In some embodiments, the modified human IFN-β comprises the R35A mutation. In some embodiments, the modified human IFN-β comprises the R35G mutation. In some embodiments, the modified human IFN-β comprises the V148G mutation. In some embodiments, the modified human IFN-β comprises the R152A mutation. In some embodiments, the modified human IFN-β comprises the R152G mutation. In some embodiments, the modified human IFN-β comprises the Y155G mutation. In some embodiments, the modified human IFN-β comprises the W22G and R27G mutations. In some embodiments, the modified human IFN-β comprises the L32A and R35A mutation. In some embodiments, the modified human IFN-β comprises the L151G and R152A mutations. In some embodiments, the modified human IFN-β comprises the V148G and R152A mutations.

In some embodiments, the modified IFN-β has one or more of the following mutations: R35A, R35T, E42K, M621, G78S, A141Y, A142T, E149K, and R152H. In some embodiments, the modified IFN-β has one or more of the following mutations: R35A, R35T, E42K, M621, G78S, A141Y, A142T, E149K, and R152H in combination with C175 or MA.

In some embodiments, the modified IFN-β has one or more of the following mutations: R35A, R35T, E42K, M621, G78S, A141Y A142T, E149K, and R152H in combination with any of the other IFN-β mutations described herein.

The crystal structure of human IFN-β is known and is described in Karpusas et al., (1998) PNAS, 94(22): 11813-1818. Specifically, the structure of human IFN-β has been shown to include five a-helices (i.e., A, B, C, D, and E) and four loop regions that connect these helices (i.e., AB, BC, CD, and DE loops). In some embodiments, the modified IFN-β has one or more mutations in the A, B, C, D, E helices and/or the AB, BC, CD, and DE loops, which reduce its binding affinity or activity at a therapeutic receptor such as IFNAR. Illustrative mutations are described in WO 2000/023114 and US 20150011732, the entire contents of which are hereby incorporated by reference.

In an illustrative embodiment, the modified IFN-β is human IFN-β comprising alanine substitutions at amino acid positions 15, 16, 18, 19, 22, and/or 23. In an illustrative embodiment, the modified IFN-β is human IFN-β comprising alanine substitutions at amino acid positions 28-30, 32, and 33. In an illustrative embodiment, the modified IFN-β is human IFN-β comprising alanine substitutions at amino acid positions 36, 37, 39, and 42. In an illustrative embodiment, the modified IFN-β is human IFN-β comprising alanine substitutions at amino acid positions 64 and 67 and a serine substitution at position 68. In an illustrative embodiment, the modified IFN-β is human IFN-β comprising alanine substitutions at amino acid positions 71-73. In an illustrative embodiment, the modified IFN-β is human IFN-β comprising alanine substitutions at amino acid positions 92, 96, 99, and 100. In an illustrative embodiment, the modified IFN-β is human IFN-β comprising alanine substitutions at amino acid positions 128, 130, 131, and 134. In an illustrative embodiment, the modified IFN-β is human IFN-β comprising alanine substitutions at amino acid positions 149, 153, 156, and 159. In some embodiments, the mutant IFN-β comprises SEQ ID NO: 178 and a mutation at W22, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 178 and a mutation at R27, wherein the mutations is an aliphatic hydrophobic residue selected from glycine (G), alanine (A), leucine (L), isoleucine (I), methionine (M), and valine (V).

In some embodiments, the mutant IFN-β comprises SEQ ID NO: 178 and a mutation at W22, wherein the mutations is an aliphatic hydrophobic residue selected from glycine (G), alanine (A), leucine (L), isoleucine (I), methionine (M), and valine (V) and a mutation at R27, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 178 and a mutation at L32, the mutation being an aliphatic hydrophobic residue selected from glycine (G), alanine (A), isoleucine (I), methionine (M), and valine (V).

In some embodiments, the mutant IFN-β comprises SEQ ID NO: 178 and a mutation at R35, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 178 and a mutation at L32, the mutation being an aliphatic hydrophobic residue selected from glycine (G), alanine (A), isoleucine (I), methionine (M), and valine (V) and a mutation at R35, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 178 and a mutation at F67, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 178 and a mutation at R71, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 178 and a mutation at F67, the mutation being an aliphatic hydrophobic residue selected from glycine (G), alanine (A), leucine (L), isoleucine (I), methionine (M), and valine (V) and a mutation at R71, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 178 and a mutation at L88, the mutation being an aliphatic hydrophobic residue selected from glycine (G), alanine (A), isoleucine (I), methionine (M), and valine (V).

In some embodiments, the mutant IFN-β comprises SEQ ID NO: 178 and a mutation at Y92, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 178 and a mutation at F67, the mutation being an aliphatic hydrophobic residue selected from glycine (G), alanine (A), leucine (L), isoleucine (I), methionine (M), and valine (V) and a mutation at L88, the mutation being an aliphatic hydrophobic residue selected from glycine (G), alanine (A), isoleucine (I), methionine (M), and valine (V) and a mutation at Y92, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 178 and a mutation at L88, the mutation being an aliphatic hydrophobic residue selected from glycine (G), alanine (A), isoleucine (I), methionine (M), and valine (V) and a mutation at Y92, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 178 and a mutation at 195, the mutation being an aliphatic hydrophobic residue selected from glycine (G), alanine (A), leucine (L), methionine (M), and valine (V) and a mutation at Y92, the mutation being an aliphatic hydrophobic residue selected from glycine (G), alanine (A), leucine (L), isoleucine (1), methionine (M), and valine (V).

In some embodiments, the mutant IFN-β comprises SEQ ID NO: 178 and a mutation at N96, the mutation being an aliphatic hydrophobic residue selected from glycine (G), alanine (A), leucine (L), isoleucine (I), methionine (M), and valine (V) and a mutation at Y92, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 178 and a mutation at Y92, the mutation being an aliphatic hydrophobic residue selected from glycine (G), alanine (A), leucine (L), isoleucine (I), methionine (M), and valine (V) and a mutation at 195, the mutation being an aliphatic hydrophobic residue selected from glycine (G), alanine (A), leucine (L), methionine (M), and valine (V) and a mutation at N96, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 178 and a mutation at K123, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 178 and a mutation at R124, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 178 and a mutation at K123, the mutation being an aliphatic hydrophobic residue selected from glycine (G), alanine (A), leucine (L), isoleucine (I), methionine (M), and valine (V) and a mutation at R124, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 178 and a mutation at L151, the mutation being an aliphatic hydrophobic residue selected from glycine (G), alanine (A), isoleucine (I), methionine (M), and valine (V).

In some embodiments, the mutant IFN-β comprises SEQ ID NO: 178 and a mutation at R152, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 178 and a mutation at L151, the mutation being an aliphatic hydrophobic residue selected from glycine (G), alanine (A), isoleucine (I), methionine (M), and valine (V) and a mutation at R152, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 178 and a mutation at V148, the mutation being an aliphatic hydrophobic residue selected from glycine (G), alanine (A), leucine (L), isoleucine (I), and methionine (M).

In some embodiments, the mutant IFN-β comprises SEQ ID NO: 178 and a mutation at V148, the mutation being an aliphatic hydrophobic residue selected from glycine (G), alanine (A), leucine (L), isoleucine (I), methionine (M), and valine (V) and a mutation at R152, the mutation being an aliphatic hydrophobic residue selected from glycine (G), alanine (A), leucine (L), isoleucine (I), methionine (M), and valine (V).

In some embodiments, the mutant IFN-β comprises SEQ ID NO: 178 and a mutation at Y155, the mutation being an aliphatic hydrophobic residue selected from glycine (G), alanine (A), leucine (L), isoleucine (I), methionine (M), and valine (V).

In some embodiments, the present technology relates to a chimeric protein comprising: (a) a modified IFN-β, having the amino acid sequence of SEQ ID NO: 178 and a mutation at position W22, wherein the mutation is an aliphatic hydrophobic residue; and (b) one or more targeting moieties, said targeting moieties comprising recognition domains which specifically bind to antigens or receptors of interest (e.g., FAP), the modified IFN-β and the one or more targeting moieties are optionally connected with one or more linkers. In some embodiments the mutation at position W22 is aliphatic hydrophobic residue is selected from G, A, L, I, M, and V. In some embodiments the mutation at position W22 is G.

Additional illustrative IFN-β mutants are provided in PCT/EP2017/061544, the entire disclosure of which is incorporated by reference herein.

In an embodiment, the modified signaling agent is interferon γ. In such embodiments, the modified interferon γ agent has reduced affinity and/or activity for the interferon-gamma receptor (IFNGR), i.e., IFNGR1 and IFNGR2 chains. In some embodiments, the modified interferon γ agent has substantially reduced or ablated affinity and/or activity for the interferon-gamma receptor (IFNGR), i.e., IFNGR1 and/or IFNGR2 chains.

In an embodiment, the modified signaling agent is consensus interferon. In some embodiments, the consensus interferon comprises the amino acid of SEQ ID NO: 179.

In some embodiments, the consensus interferon is modified to have a mutation at one or more amino acids at positions 33 and/or 145-155, such as amino acid positions 145, 146, 149, 150 and/or 154, with reference to SEQ ID NO: 179. In some embodiments, the consensus interferon is modified to have a mutation at one or more amino acids at positions 33 and/or 145-155, such as amino acid positions 145, 146, 149, 150 and/or 154, with reference to SEQ ID NO: 179, the substitutions optionally being hydrophobic and selected from alanine, valine, leucine, and isoleucine. In some embodiments, the consensus interferon mutant comprises one or more mutations selected from R33A, R145$X_1$, A146$X_2$, M149A, R150A, and L154A, wherein $X_1$ is selected from A, S, T, Y, L, and I, and wherein $X_2$ is selected from G, H, Y, K, and D with reference to SEQ ID NO: 179.

In an embodiment, the consensus interferon is modified to have a mutation at amino acid position 121 (i.e., K121), with reference to SEQ ID NO: 179. In an embodiment, the consensus interferon comprises a K121E mutation, with reference to SEQ ID NO: 179.

In an embodiment, the modified signaling agent comprises any of the consensus interferon variants as disclosed in U.S. Pat. Nos. 4,695,623, 4,897,471, 5,541,293, and 8,496,921, the entire contents of all of which are hereby incorporated by reference. For example, the consensus interferon variant may comprise the amino acid sequence of IFN-CON2 or IFN-CON3 as disclosed in U.S. Pat. Nos. 4,695,623, 4,897,471, and 5,541,293.

In some embodiments, the modified signaling agent is vascular endothelial growth factor (VEGF). VEGF is a potent growth factor that plays major roles in physiological but also pathological angiogenesis, regulates vascular permeability and can act as a growth factor on cells expressing VEGF receptors. Additional functions include, among others, stimulation of cell migration in macrophage lineage and endothelial cells. Several members of the VEGF family of growth factors exist, as well as at least three receptors (VEGFR-1, VEGFR-2, and VEGFR-3). Members of the VEGF family can bind and activate more than one VEGFR type. For example, VEGF-A binds VEGFR-1 and-2, while VEGF-C can bind VEGFR-2 and -3. VEGFR-1 and -2 activation regulates angiogenesis while VEGFR-3 activation is associated with lymphangiogenesis. The major pro-angiogenic signal is generated from activation of VEGFR-2. VEGFR-1 activation has been reported to be possibly associated with negative role in angiogenesis. It has also been reported that VEGFR-1 signaling is important for progression of tumors in vivo via bone marrow-derived VEGFR-1 positive cells (contributing to formation of premetastatic niche in the bone). Several therapies based on VEGF-A directed/neutralizing therapeutic antibodies have been developed, primarily for use in treatment of various human tumors relying on angiogenesis. These are not without side effects though. This may not be surprising considering that these operate as general, non-cell/tissue specific VEGFNEGFR interaction inhibitors. Hence, it would be desirable to restrict VEGF (e.g., VEGF-A) NEGFR-2 inhibition to specific target cells (e.g., tumor vasculature endothelial cells).

In some embodiments, the VEGF is VEGF-A, VEGF-B, VEFG-C, VEGF-D, or VEGF-E and isoforms thereof including the various isoforms of VEGF-A such as VEGF121, VEGF121b, VEGF145, VEGF165, VEGF165b, VEGF189, and VEGF206. In some embodiments, the modified signaling agent has reduced affinity and/or activity for VEGFR-1 (Flt-1) and/or VEGFR-2 (KDR/Flk-1). In some embodiments, the modified signaling agent has substantially reduced or ablated affinity and/or activity for VEGFR-1 (Flt-1) and/or VEGFR-2 (KDR/Flk-1). In an embodiment, the modified signaling agent has reduced affinity and/or activity for VEGFR-2 (KDR/Flk-1) and/or substantially reduced or ablated affinity and/or activity for VEGFR-1 (Flt-1). Such an embodiment finds use, for example, in wound healing methods or treatment of ischmia-related diseases (without wishing to be bound by theory, mediated by VEGFR-2's effects on endothelial cell function and angiogenesis). In some embodiments, binding to VEGFR-1 (Flt-1), which is linked to cancers and pro-inflammatory activities, is avoided. In some embodiments, VEGFR-1 (Flt-1) acts a decoy receptor and therefore substantially reduces or ablates affinity at this receptor avoids sequestration of the therapeutic agent. In an embodiment, the modified signaling agent has substantially reduced or ablated affinity and/or activity for VEGFR-1 (Flt-1) and/or substantially reduced or ablated affinity and/or activity for VEGFR-2 (KDR/Flk-1). In some embodiments, the VEGF is VEGF-C or VEGF-D. In such embodiments, the modified signaling agent has reduced affinity and/or activity for VEGFR-3. Alternatively, the modified signaling agent has substantially reduced or ablated affinity and/or activity for VEGFR-3.

Proangiogenic therapies are also important in various diseases (e.g. ischemic heart disease, bleeding etc.), and include VEGF-based therapeutics. Activation of VEGFR-2 is proangiogenic (acting on endothelial cells). Activation of VEFGR-1 can cause stimulation of migration of inflammatory cells (including, for example, macrophages) and lead to inflammation associated hypervascular permeability. Activation of VEFGR-1 can also promote bone marrow associated tumor niche formation. Thus, VEGF based therapeutic selective for VEGFR-2 activation would be desirable in this case. In addition, cell specific targeting, e.g. to endothelial cells, would be desirable.

In some embodiments, the modified signaling agent has reduced affinity and/or activity (e.g. antagonistic) for VEGFR-2 and/or has substantially reduced or ablated affinity and/or activity for VEGFR-1. When targeted to tumor vasculature endothelial cells via a targeting moiety that binds to a tumor endothelial cell marker (e.g. PSMA and others), such construct inhibits VEGFR-2 activation specifically on such marker-positive cells, while not activating VEGFR-1 en route and on target cells (if activity ablated), thus eliminating induction of inflammatory responses, for example. This would provide a more selective and safe anti-angiogenic therapy for many tumor types as compared to VEGF-A neutralizing therapies.

In some embodiments, the modified signaling agent has reduced affinity and/or activity (e.g. agonistic) for VEGFR-2 and/or has substantially reduced or ablated affinity and/or activity for VEGFR-1. Through targeting to vascular endothelial cells, such construct, in some embodiments, promotes angiogenesis without causing VEGFR-1 associated induction of inflammatory responses. Hence, such a construct would have targeted proangiogenic effects with substantially reduced risk of side effects caused by systemic activation of VEGFR-2 as well as VEGFR-1.

In an illustrative embodiment, the modified signaling agent is VEGF165 (wild type), which has the amino acid sequence: of SEQ ID NO: 180.

In another illustrative embodiment, the modified signaling agent is VEGF165b (wild type), which has the amino acid sequence of SEQ ID NO: 181.

In these embodiments, the modified signaling agent has a mutation at amino acid 183 (e.g., a substitution mutation at 183, e.g., 183K, 183R, or 183H). Without wishing to be bound by theory, it is believed that such mutations may result in reduced receptor binding affinity. See, for example, U.S. Pat. No. 9,078,860, the entire contents of which are hereby incorporated by reference.

In an embodiment, the modified signaling agent is TNF-α. TNF is a pleiotropic cytokine with many diverse functions, including regulation of cell growth, differentiation, apoptosis, tumorigenesis, viral replication, autoimmunity, immune cell functions and trafficking, inflammation, and septic shock. It binds to two distinct membrane receptors on target cells: TNFR1 (p55) and TNFR2 (p75). TNFR1 exhibits a very broad expression pattern whereas TNFR2 is expressed preferentially on certain populations of lymphocytes, Tregs, endothelial cells, certain neurons, microglia, cardiac myocytes and mesenchymal stem cells. Very distinct biological pathways are activated in response to receptor activation, although there is also some overlap. As a general rule, without wishing to be bound by theory, TNFR1 signaling is associated with induction of apoptosis (cell death) and TNFR2 signaling is associated with activation of cell survival signals (e.g. activation of NFκB pathway).

Administration of TNF is systemically toxic, and this is largely due to TNFR1 engagement. However, it should be noted that activation of TNFR2 is also associated with a broad range of activities and, as with TNFR1, in the context of developing TNF based therapeutics, control over TNF targeting and activity is important.

In some embodiments, the modified signaling agent has reduced affinity and/or activity for TNFR1 and/or TNFR2. In some embodiments, the modified signaling agent has substantially reduced or ablated affinity and/or activity for TNFR1 and/or TNFR2. TNFR1 is expressed in most tissues, and is involved in cell death signaling while, by contrast, TNFR2 is involved in cell survival signaling. Accordingly, in embodiments directed to methods of treating cancer, the modified signaling agent has reduced affinity and/or activity for TNFR1 and/or substantially reduced or ablated affinity and/or activity for TNFR2. In these embodiments, the chimeric proteins may be targeted to a cell for which apoptosis is desired, e.g. a tumor cell or a tumor vasculature endothelial cell. In embodiments directed to methods of promoting cell survival, for example, in neurogenesis for the treatment of neurodegenerative disorders, the modified signaling agent has reduced affinity and/or activity for TNFR2 and/or substantially reduced or ablated affinity and/or activity for TNFR1. Stated another way, the present chimeric proteins, in some embodiments, comprise modified TNF-α agent that allows of favoring either death or survival signals.

In some embodiments, the chimeric protein has a modified TNF having reduced affinity and/or activity for TNFR1 and/or substantially reduced or ablated affinity and/or activity for TNFR2. Such a chimera, in some embodiments, is a more potent inducer of apoptosis as compared to a wild type TNF and/or a chimera bearing only mutation(s) causing reduced affinity and/or activity for TNFR1. Such a chimera, in some embodiments, finds use in inducing tumor cell death or a tumor vasculature endothelial cell death (e.g. in the treatment of cancers). Also, in some embodiments, these chimeras avoid or reduce activation of Treg cells via TNFR2, for example, thus, further supporting TNFR1-mediated antitumor activity in vivo.

In some embodiments, the chimeric protein has a modified TNF having reduced affinity and/or activity for TNFR2 and/or substantially reduced or ablated affinity and/or activity for TNFR1. Such a chimera, in some embodiments, is a more potent activator of cell survival in some cell types, which may be a specific therapeutic objective in various disease settings, including without limitation, stimulation of neurogenesis. In addition, such a TNFR2-favoring chimeras also are useful in the treatment of autoimmune diseases (e.g. Crohn's, diabetes, MS, colitis etc. and many others described herein). In some embodiments, the chimera is targeted to auto-reactive T cells. In some embodiments, the chimera promotes Treg cell activation and indirect suppression of cytotoxic T cells.

In some embodiments, the chimera causes the death of auto-reactive T cells, e.g. by activation of TNFR2 and/or avoidance of TNFR1 (e.g. a modified TNF having reduced affinity and/or activity for TNFR2 and/or substantially reduced or ablated affinity and/or activity for TNFR1). Without wishing to be bound by theory these auto-reactive T cells, have their apoptosis/survival signals altered e.g. by NFκB pathway activity/signaling alterations. In some embodiments, the chimera causes the death of autoreactive T cells having lesions or modifications in the NFκB pathway, which underlie an imbalance of their cell death (apoptosis)/survival signaling properties and, optionally, altered susceptibility to certain death-inducing signals (e.g., TNFR2 activation).

In some embodiments, a TNFR2 based chimera has additional therapeutic applications in diseases, including various autoimmune diseases, heart disease, de-myelinating and neurodegenerative disorders, and infectious disease, among others.

In an embodiment, the wild type TNF-β has the amino acid sequence of: SEQ ID NO: 182.

In such embodiments, the modified TNF-β agent has mutations at one or more amino acid positions 29, 31, 32, 84, 85, 86, 87, 88, 89, 145, 146 and 147, which produces a modified TNF-β with reduced receptor binding affinity. See, for example, U.S. Pat. No. 7,993,636, the entire contents of which are hereby incorporated by reference.

In some embodiments, the modified human TNF-β moiety has mutations at one or more amino acid positions R32, N34, Q67, H73, L75, T77, S86, Y87, V91, 197, T105, P106, A109, P113, Y115, E127, N137, D143, A145, and E146, as described, for example, in WO/2015/007903, the entire contents of which is hereby incorporated by reference (numbering according to the human TNF sequence, Genbank accession number BAG70306, version BAG70306.1 GI: 197692685). In some embodiments, the modified human TNF-α moiety has substitution mutations selected from L295, R32G, R32W, N34G, Q67G, H73G, L75G, L75A, L755, T77A, S86G, S86T, Y87Q, Y87L, Y87A, Y87F, Y87H, V91G, V91A, 197A, 197Q, 197S, T105G, P106G, A109Y, P113G, Y115G, Y115A, E127G, N137G, D143N, A145G, A145R, A145T, E146D, E146K, and S147D. In an embodiment, the human TNF-α moiety has a mutation selected from Y87Q, Y87L, Y87A, Y87F, and Y87H. In another embodiment, the human TNF-β moiety has a mutation selected from 197A, 197Q, and 197S. In a further embodiment, the human TNF-α moiety has a mutation selected from Y115A and Y115G. In an embodiment, the human TNF-α moiety has an E146K mutation. In an embodiment, the human INF-α moiety has an Y87H and an E146K mutation. In an embodiment, the human TNF-α moiety has an Y87H and an A145R mutation. In an embodiment, the human INF-α moiety has a R32W and a S86T mutation. In an embodiment, the human INF-α moiety has a R32W and an E146K mutation. In an embodiment, the human INF-α moiety has a L295 and a R32W mutation. In an embodiment, the human INF-α moiety has a D143N and an A145R mutation. In an embodiment, the human INF-α moiety has a D143N and an A145R mutation. In an embodiment, the human INF-α moiety has an A145T, an E146D, and a S147D mutation. In an embodiment, the human INF-α moiety has an A145T and a S147D mutation.

In some embodiments, the modified INF-α agent has one or more mutations selected from N39Y, S147Y, and Y87H, as described in WO 2008/124086, the entire contents of which is hereby incorporated by reference.

In some embodiments, the modified human INF-α moiety has mutations that provide receptor selectivity as described in PCT/162016/001668, the entire contents of which are hereby incorporated by reference. In some embodiments, the mutations to TNF are TNF-R1 selective. In some embodiments, the mutations to TNF which are TNF-R1 selective are at one or more of positions R32, S86, and E146. In some embodiments, the mutations to TNF which are TNF-R1 selective are one or more of R32W, S86T, and E146K. In some embodiments, the mutations to TNF which are TNF-R1 selective are one or more of R32W, R32W/S86T, R32W/E146K and E146K. In some embodiments, the mutations to TNF are TNF-R2 selective. In some embodiments, the mutations to TNF which are TNF-R2 selective are at one or more of positions A145, E146, and S147. In some embodiments, the mutations to TNF which are TNF-R2 selective are one or more of A145T, A145R, E146D, and S147D.

In some embodiments, the mutations to TNF which are TNF-R2 selective are one or more of A145R, A145T/S147D, and A145T/E146D/S 147 D.

In some embodiments, the modified signaling agent is TNF-β. TNF-β forms a homotrimer or a heterotrimer with LT-β (LT-α1 β2). In some embodiments, the modified signaling agent has substantially reduced or ablated affinity and/or activity for TNFR1 and/or TNFR2 and/or herpes virus entry mediator (HEVM) and/or LT-βR.

In an embodiment, the wild type TNF-β has the amino acid sequence of: SEQ ID NO: 183.

In such embodiments, the modified soluble agent may comprise mutations at one or more amino acids at positions 106-113, which produce a modified TNF-β with reduced receptor binding affinity to TNFR2. In an embodiment, the modified soluble agent has one or more substitution mutations at amino acid positions 106-113. In some embodiments, the substitution mutations are selected from Q107E, Q107D, S106E, S106D, Q107R, Q107N, Q107E/S106E, Q107E/S106D, Q107D/S106E, and Q107D/S106D. In another embodiment, the modified soluble agent has an insertion of about 1 to about 3 amino acids at positions 106-113.

In some embodiments, the modified agent is a TNF family member (e.g. TNF-alpha, TNF-beta), which can be a single chain trimeric version as described in WO 2015/007903, the entire contents of which are incorporated by reference.

In some embodiments, the modified agent is a TNF family member (e.g. TNF-alpha, TNF-beta), which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at TNFR1. In these embodiments, the modified agent is a TNF family member (e.g. TNF-alpha, TNF-beta), which also, optionally, has substantially reduced or ablated affinity and/or activity for TNFR2. In some embodiments, the modified agent is a TNF family member (e.g. TNF-alpha, TNF-beta) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at TNFR2. In these embodiments, the modified agent is a TNF family member (e.g. TNF-alpha, TNF-beta) which also, optionally, has substantially reduced or ablated affinity and/or activity for TN FR1. The constructs of such embodiments find use in, for example, methods of dampening TNF response in a cell specific manner. In some embodiments, the antagonistic TNF family member (e.g. TNF-alpha, TNF-beta) is a single chain trimeric version as described in WO 2015/007903.

In an embodiment, the modified signaling agent is TRAIL. In some embodiments, the modified TRAIL agent has reduced affinity and/or activity for DR4 (TRAIL-RI) and/or DR5 (TRAIL-RII) and/or DcR1 and/or DcR2. In some embodiments, the modified TRAIL agent has substantially reduced or ablated affinity and/or activity for DR4 (TRAIL-RI) and/or DR5 (TRAIL-RII) and/or DcR1 and/or DcR2.

In an embodiment, the wild type TRAIL has the amino acid sequence of: SEQ ID NO: 184.

In such embodiments, the modified TRAIL agent may comprise a mutation at amino acid positions T127-R132, E144-R149, E155-H161, Y189-Y209, T214-1220, K224-A226, W231, E236-L239, E249-K251, T261-H264 and H270-E271 (Numbering based on the human sequence, Genbank accession number NP_003801, version 10 NP_003801.1, GI: 4507593; see above).

In some embodiments, the modified TRAIL agent may comprise one or more mutations that sustantially reduce its affinity and/or activity for TRAIL-R1. In such embodiments, the modified TRAIL agent may specifically bind to TRIL-R2. Illustrative mutations include mutations at one or more amino acid positions Y189, R191, Q193, H264, 1266, and D267. For example, the mutations may be one or more of Y189Q, R191K, Q193R, H264R, 1266L and D267Q. In an embodiment, the modified TRAIL agent comprises the mutations Y189Q, R191K, Q193R, H264R, 1266L and D267Q.

In some embodiments, the modified TRAIL agent may comprise one or more mutations that substantially reduce its affinity and/or activity for TRAIL-R2. In such embodiments, the modified TRAIL agent may specifically bind to TRIL-R1. Illustrative mutations include mutations at one or more amino acid positions G131, R149, S159, N199, K201, and S215. For example, the mutations may be one or more of G131R, R1491, S159R, N199R, K201H, and S215D. In an embodiment, the modified TRAIL agent comprises the mutations G131R, R1491, S159R, N199R, K201H, and S215D. Additional TRAIL mutations are described in, for example, Trebing et al., (2014) Cell Death and Disease, 5:e1035, the entire disclosure of which is hereby incorporated by reference.

In some embodiments, the modified signaling agent is TGFα. In such embodiments, the modified TGFα agent has reduced affinity and/or activity for the epidermal growth factor receptor (EGFR). In some embodiments, the modified TGFα agent has substantially reduced or ablated affinity and/or activity for the epidermal growth factor receptor (EGFR).

In some embodiments, the modified signaling agent is TGFβ. In such embodiments, the modified signaling agent has reduced affinity and/or activity for TGFBR1 and/or TGFBR2. In some embodiments, the modified signaling agent has substantially reduced or ablated affinity and/or activity for TGFBR1 and/or TGFBR2. In some embodiments, the modified signaling agent optionally has reduced or substantially reduced or ablated affinity and/or activity for TGFBR3 which, without wishing to be bound by theory, may act as a reservoir of ligand for TGF-beta receptors. In some embodiments, the TGF favors TGFBR1 over TGFBR2 or TGFBR2 over TGFBR1. Similarly, LAP, without wishing to be bound by theory, may act as a reservoir of ligand for TGF-beta receptors. In some embodiments, the modified signaling agent has reduced affinity and/or activity for TGFBR1 and/or TGFBR2 and/or substantially reduced or ablated affinity and/or activity for Latency Associated Peptide (LAP). In some embodiments, such chimeras find use in Camurati-Engelmann disease, or other diseases associated with inappropriate TGF signaling.

In some embodiments, the modified agent is a TGF family member (e.g. TGFα, TGFβ), which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at one or more of TGFBR1, TGFBR2, TGFBR3. In these embodiments, the modified agent is a TGF family member (e.g. TGFα, TGFβ) which also, optionally, has substantially reduced or ablated affinity and/or activity at one or more of TGFBR1, TGFBR2, TGFBR3.

In some embodiments, the modified agent is a TGF family member (e.g. TGFα, TGFβ) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at TGFBR1 and/or TGFBR2. In these embodiments, the modified agent is a TGF family member (e.g. TGFα, TGFβ) which also, optionally, has substantially reduced or ablated affinity and/or activity at TGFBR3.

In some embodiments, the modified signaling agent is an interleukin. In an embodiment, the modified signaling agent is IL-1. In some embodiments, the modified signaling agent is IL-1a or IL-1(3. In some embodiments, the modified signaling agent has reduced affinity and/or activity for IL-1R1 and/or IL-1RAcP. In some embodiments, the modified signaling agent has substantially reduced or ablated affinity and/or activity for IL-1R1 and/or IL-1RAcP.

In some embodiments, the modified signaling agent has reduced affinity and/or activity for IL-1R2. In some embodiments, the modified signaling agent has substantially reduced or ablated affinity and/or activity for IL-1R2. For instance, in some embodiments, the present modified IL-1 agents avoid interaction at IL-1R2 and therefore substantially reduce its function as a decoy and/or sink for therapeutic agents.

In an embodiment, the wild type IL-1p has the amino acid sequence of: SEQ ID NO: 185.

IL1 is a proinflammatory cytokine and an important immune system regulator. It is a potent activator of CD4 T cell responses, increases proportion of Th17 cells and expansion of IFNγ and IL-4 producing cells. IL-1 is also a potent regulator of CD8+ T cells, enhancing antigen-specific CD8+ T cell expansion, differentiation, migration to periphery and memory. IL-1 receptors comprise IL-1R1 and IL-1R2. Binding to and signaling through the IL-1R1 constitutes the mechanism whereby IL-1 mediates many of its biological (and pathological) activities. IL1-R2 can function as a decoy receptor, thereby reducing IL-1 availability for interaction and signaling through the IL-1R1.

In some embodiments, the modified IL-1 has reduced affinity and/or activity (e.g. agonistic activity) for IL-1R1. In some embodiments, the modified IL-1 has substantially reduced or ablated affinity and/or activity for IL-1R2. In such embodiments, there is restorable IL-1/IL-1R1 signaling and prevention of loss of therapeutic chimeras at IL-R2 and therefore a reduction in dose of IL-1 that is required (e.g. relative to wild type or a chimera bearing only an attenuation mutation for IL-R1). Such constructs find use in, for example, methods of treating cancer, including, for example, stimulating the immune system to mount an anti-cancer response.

In some embodiments, the modified IL-1 has reduced affinity and/or activity (e.g. antagonistic activity, e.g. natural antagonistic activity or antagonistic activity that is the result of one or more mutations, see, e.g., WO 2015/007520, the entire contents of which are hereby incorporated by reference) for IL-1R1. In some embodiments, the modified IL-1 has substantially reduced or ablated affinity and/or activity for IL-1R2. In such embodiments, there is the IL-1/IL-1R1 signaling is not restorable and prevention of loss of therapeutic chimeras at IL-R2 and therefore a reduction in dose of IL-1 that is required (e.g. relative to wild type or a chimera bearing only an attenuation mutation for IL-R1). Such constructs find use in, for example, methods of treating autoimmune diseases, including, for example, suppressing the immune system.

In such embodiments, the modified signaling agent has a deletion of amino acids 52-54 which produces a modified human IL-1β with reduced binding affinity for type I IL-1R and reduced biological activity. See, for example, WO 1994/000491, the entire contents of which are hereby incorporated by reference. In some embodiments, the modified human IL-1p has one or more substitution mutations selected from A117G/P118G, R120X, L122A, T125G/L126G, R127G, Q130X, Q131G, K132A, S137G/Q138Y, L145G, H146X, L145A/L147A, Q148X, Q148G/Q150G, Q150G/D151A, M152G, F162A, F162A/Q164E, F166A, Q164E/E167K, N169G/D170G, 1172A, V174A, K208E, K209X, K209A/K210A, K219X, E221X, E221 S/N224A, N224S/K225S, E244K, N245Q (where X can be any change in amino acid, e.g., a non-conservative change), which exhibit reduced binding to IL-1R, as described, for example, in WO 2015/007542 and WO/2015/007536, the entire contents of which is hereby incorporated by reference (numbering base on the human IL-1β sequence, Genbank accession number NP_000567, version NP-000567.1, GI: 10835145). In some embodiments, the modified human IL-1β may have one or more mutations selected from R120A, R120G, Q130A, Q130W, H146A, H146G, H146E, H146N, H146R, Q148E, Q148G, Q148L, K209A, K209D, K219S, K219Q, E221S and E221K. In an embodiment, the modified human IL-1p comprises the mutations Q131G and Q148G. In an embodiment, the modified human IL-1β comprises the mutations Q148G and K208E. In an embodiment, the modified human IL-1β comprises the mutations R120G and Q131G. In an embodiment, the modified human IL-1β comprises the mutations R120G and H146A. In an embodiment, the modified human IL-1β comprises the mutations R120G and H146N. In an embodiment, the modified human IL-1β comprises the mutations R120G and H146R. In an embodiment, the modified human IL-1R comprises the mutations R120G and H146E. In an embodiment, the modified human IL-1R comprises the mutations R120G and H146G. In an embodiment, the modified human IL-1β comprises the mutations R120G and K208E. In an embodiment, the modified human IL-1β comprises the mutations R120G, F162A, and Q164E.

In some embodiments, the modified signaling agent is IL-2. In such an embodiment, the modified signaling agent has reduced affinity and/or activity for IL-2Rα and/or IL-2Rβ and/or IL-2Rγ. In some embodiments, the modified signaling agent has reduced affinity and/or activity for IL-2Rβ and/or IL-2Rγ. In some embodiments, the modified signaling agent has substantially reduced or ablated affinity and/or activity for IL-2Rα. Such embodiments may be relevant for treatment of cancer, for instance when the modified IL-2 is agonistic at IL-2Rβ and/or IL-2Rγ. For instance, the present constructs may favor attenuated activation of C D8+ T cells (which can provide an anti-tumor effect), which have IL2 receptors β and γ and disfavor Tregs (which can provide an immune suppressive, pro-tumor effect), which have IL2 receptors α, β, and γ. Further, in some embodiments, the preference for IL-2Rβ and/or IL-2Rγ over IL-2Rα avoids IL-2 side effects such as pulmonary edema. Also, IL-2-based chimeras are useful for the treatment of autoimmune diseases, for instance when the modified IL-2 is antagonistic (e.g. natural antagonistic activity or antagonistic activity that is the result of one or more mutations, see, e.g., WO 2015/007520, the entire contents of which are hereby incorporated by reference) at IL-2Rβ and/or IL-2Rγ. For instance, the present constructs may favor attenuated suppression of CD8+ T cells (and therefore dampen the immune response), which have IL2 receptors β and γ and disfavor Tregs which have IL2 receptors α, β, and γ. Alternatively, in some embodiments, the chimeras bearing IL-2 favor the activation of Tregs, and therefore immune suppression, and activation of disfavor of CD8+ T cells. For instance, these constructs find use in the treatment of diseases or diseases that would benefit from immune suppression, e.g. autoimmune disorders.

In some embodiments, the chimeric protein has targeting moieties as described herein directed to FAP+ dendritic cells as well as a modified IL-2 agent having reduced affinity and/or activity for IL-2Rβ, and/or IL-2Rγ and/or substantially reduced or ablated affinity and/or activity for IL-2Rα. In some embodiments, these constructs provide targeted FAP+ dendritic cell activity and are generally inactive (or have substantially reduced activity) towards Treg cells. In some embodiments, such constructs have enhanced immune stimulatory effect compared to wild type IL-2 (e.g., without wishing to be bound by theory, by not stimulating Tregs), whilst eliminating or reducing the systemic toxicity associated with IL-2.

In some embodiments, the wild type IL-2 has the amino acid sequence of: SEQ ID NO: 186.

In such embodiments, the modified IL-2 agent has one or more mutations at amino acids L72 (L72G, L72A, L725, L721, L72Q, L72E, L72N, L72D, L72R, or L72K), F42 (F42A, F42G, F42S, F42T, F42Q, F42E, F42N, F42D, F42R, or F42K) and Y45 (Y45A, Y45G, Y45S, Y45T, Y45Q, Y45E, Y45N, Y45D, Y45R or Y45K). Without wishing to be bound by theory, it is believed that these modified IL-2 agents have reduced affinity for the high-affinity IL-2 receptor and preserves affinity to the intermediate-affinity IL-2 receptor, as compared to the wild-type IL-2. See, for example, US Patent Publication No. 2012/0244112, the entire contents of which are hereby incorporated by reference.

In some embodiments, the modified IL-2 agent has one or more mutations at amino acids R38, F42, Y45, and E62. For example, the modified IL-2 agent may comprise one or more of R38A, F42A, Y45A, and E62A. In some embodiments, the modified IL-2 agent may comprise a mutation at C125. For example, the mutation may be C125S. In such embodiments, the modified IL-2 agent may have substantially reduced affinity and/or activity for IL-2Rα, as described in, for example, Carmenate et al. (2013) The Journal of Immunology, 190:6230-6238, the entire disclosure of which is hereby incorporated by reference. In some embodiments, the modified IL-2 agent with mutations at R38, F42, Y45, and/or E62 is able to induce an expansion of effector cells including CD8+ T cells and NK cells but not Treg cells. In some embodiments, the modified IL-2 agent with mutations at R38, F42, Y45, and/or E62 is less toxic than wildtype IL-2 agents. A chimeric protein comprising the modified IL-2 agent with substantially reduced affinity and/or activity for IL-2Rα may find application in oncology for example.

In other embodiments, the modified IL-2 agent may have substantially reduced affinity and/or activity for IL-2Rβ, as described in, for example, WO 2016/025385, the entire disclosure of which is hereby incorporated by reference. In such embodiments, the modified IL-2 agent may induce an expansion of Treg cells but not effector cells such as CD8+ T cells and NK cells. A chimeric protein comprising the modified IL-2 agent with substantially reduced affinity and/or activity for IL-2Rβ may find application in the treatment of autoimmune disease for example. In some embodiments, the modified IL-2 agent may comprise one or more mutations at amino acids N88, D20, and/or A126. For example, the modified IL-2 agent may comprise one or more of N88R, N881, N88G, D2OH, Q126L, and Q126F.

In some embodiments, the modified IL-2 agent may comprise a mutation at D109 or C125. For example, the mutation may be D109C or C125S. In some embodiments, the modified IL-2 with a mutation at D109 or C125 may be utilized for attachment to a PEG moiety.

In some embodiments, the modified signaling agent is IL-3. In some embodiments, the modified signaling agent has reduced affinity and/or activity for the IL-3 receptor, which is a heterodimer with a unique alpha chain paired with the common beta (beta c or C D131) subunit. In some embodiments, the modified signaling agent has substantially reduced or ablated affinity and/or activity for the IL-3 receptor, which is a heterodimer with a unique alpha chain paired with the common beta (beta c or CD131) subunit.

In some embodiments, the modified signaling agent is IL-4. In such an embodiment, the modified signaling agent has reduced affinity and/or activity for type 1 and/or type 2 IL-4 receptors. In such an embodiment, the modified signaling agent has substantially reduced or ablated affinity and/or activity for type 1 and/or type 2 IL-4 receptors. Type 1 IL-4 receptors are composed of the IL-4Rα subunit with a common γ chain and specifically bind IL-4. Type 2 IL-4 receptors include an IL-4Rα subunit bound to a different subunit known as IL-13Rα1. In some embodiments, the modified signaling agent has substantially reduced or ablated affinity and/or activity the type 2 IL-4 receptors.

In some embodiments, the wild type IL-4 has the amino acid sequence of: SEQ ID NO: 187.

In such embodiments, the modified IL-4 agent has one or more mutations at amino acids R121 (R121A, R121D, R121E, R121F, R121H, R1211, R121K, R121N, R121P, R121T, R121W), E122 (E122F), Y124 (Y124A, Y124Q, Y124R, Y124S, Y124T), and S125 (S125A). Without wishing to be bound by theory, it is believed that these modified IL-4 agents maintain the activity mediated by the type I receptor, but significantly reduces the biological activity mediated by the other receptors. See, for example, U.S. Pat. No. 6,433,157, the entire contents of which are hereby incorporated by reference.

In some embodiments, the modified signaling agent is IL-6. IL-6 signals through a cell-surface type I cytokine receptor complex including the ligand-binding IL-6R chain (0D126), and the signal-transducing component gp130. IL-6 may also bind to a soluble form of IL-6R (sIL-6R), which is the extracellular portion of IL-6R. The sIL-6R/IL-6 complex may be involved in neurites outgrowth and survival of neurons and, hence, may be important in nerve regeneration through remyelination. Accordingly, in some embodiments, the modified signaling agent has reduced affinity and/or activity for IL-6R/gp130 and/or sIL-6R. In some embodiments, the modified signaling agent has substantially reduced or ablated affinity and/or activity for IL-6R/gp130 and/or sIL-6R.

In some embodiments, the wild type IL-6 has the amino acid sequence of SEQ ID NO: 188.

In such embodiments, the modified signaling agent has one or more mutations at amino acids 58, 160, 163, 171 or 177. Without wishing to be bound by theory, it is believed that these modified IL-6 agents exhibit reduced binding affinity to IL-6R-alpha and reduced biological activity. See, for example, WO 97/10338, the entire contents of which are hereby incorporated by reference.

In some embodiments, the modified signaling agent is IL-10. In such an embodiment, the modified signaling agent has reduced affinity and/or activity for IL-10 receptor-1 and IL-10 receptor-2. In some embodiments, the modified signaling agent has substantially reduced or ablated affinity and/or activity for IL-10 receptor-1 and IL-10 receptor-2

In some embodiments, the modified signaling agent is IL-11. In such an embodiment, the modified signaling agent has reduced affinity and/or activity for IL-11Rα and/or IL-11Rβ and/or gp130. In such an embodiment, the modified signaling agent has substantially reduced or ablated affinity and/or activity for IL-11Rα and/or IL-11Rβ and/or gp130.

In some embodiments, the modified signaling agent is IL-12. In such an embodiment, the modified signaling agent has reduced affinity and/or activity for IL-12Rβ1 and/or IL-12Rβ2. In such an embodiment, the modified signaling agent has substantially reduced or ablated affinity and/or activity for IL-12Rβ1 and/or IL-12Rβ2.

In some embodiments, the modified signaling agent is IL-13. In such an embodiment, the modified signaling agent has reduced affinity and/or activity for the IL-4 receptor (IL-4Rα) and IL-13Rα1. In some embodiments, the modified signaling agent has substantially reduced or ablated affinity and/or activity for IL-4 receptor (IL-4Rα) or IL-13Rα1.

In some embodiments, the wild type IL-13 has the amino acid sequence: SEQ ID NO: 189.

In such embodiments, the modified IL-13 agent has one or more mutations at amino acids 13, 16, 17, 66, 69, 99, 102, 104, 105, 106, 107, 108, 109, 112, 113 and 114. Without wishing to be bound by theory, it is believed that these modified IL-13 agents exhibit reduced biological activity. See, for example, WO 2002/018422, the entire contents of which are hereby incorporated by reference.

In some embodiments, the modified signaling agent is IL-18. In some embodiments, the modified signaling agent has reduced affinity and/or activity for IL-18Rα and/or IL-18Rβ. In some embodiments, the modified signaling agent has substantially reduced or ablated affinity and/or activity for IL-18Rα and/or IL-18Rβ. In some embodiments, the modified signaling agent has substantially reduced or ablated affinity and/or activity for IL-18Rα type II, which is an isoform of IL-18Rα that lacks the TIR domain required for signaling.

In some embodiments, the wild type IL-18 has the amino acid sequence: SEQ ID NO: 190.

In such embodiments, the modified IL-18 agent may comprise one or more mutations in amino acids or amino acid regions selected from Y37-K44, R49-Q54, D59-R63, E67-074, R80, M87-A97, N 27-K129, Q139-M149, K165-K171, R183 and Q190-N191, as described in WO/2015/007542, the entire contents of which are hereby incorporated by reference (numbering based on the human IL-18 sequence, Genbank accession number AAV38697, version AAV38697.1, GI: 54696650).

In some embodiments, the modified signaling agent is IL-33. In such an embodiment, the modified signaling agent has reduced affinity and/or activity for the ST-2 receptor and IL-1RAcP. In some embodiments, the modified signaling agent has substantially reduced or ablated affinity and/or activity for the ST-2 receptor and IL-1RAcP.

In some embodiments, the wild type IL-33 has the amino acid sequence of: SEQ ID NO: 191.

In such embodiments, the modified IL-33 agent may comprise one or more mutations in amino acids or amino acid regions selected from 1113-Y122, 5127-E139, E144-D157, Y163-M183, E200, Q215, L220-0227 and T260-E269, as described in WO/2015/007542, the entire contents of which are hereby incorporated by reference (numbering based on the human sequence, Genbank accession number NP_254274, version NP_254274.1, GI:15559209).

In some embodiments, the modified signaling agent is epidermal growth factor (EGF). EGF is a member of a family of potent growth factors. Members include EGF, HB-EGF, and others such as TGFalpha, amphiregulin, neuregulins, epiregulin, betacellulin. EGF family receptors include EGFR (ErbB1), ErbB2, ErbB3 and ErbB4. These may function as homodimeric and/or heterodimeric receptor subtypes. The different EGF family members exhibit differential selectivity for the various receptor subtypes. For example, EGF associates with ErbB1/ErbB1, ErbB1/ErbB2, ErbB4/ErbB2 and some other heterodimeric subtypes. HB-EGF has a similar pattern, although it also associates with ErbB4/4. Modulation of EGF (EGF-like) growth factor signaling, positively or negatively, is of considerable therapeutic interest. For example, inhibition of EGFRs signaling is of interest in the treatment of various cancers where EGFR signaling constitutes a major growth promoting signal. Alternatively, stimulation of EGFRs signaling is of therapeutic interest in, for example, promoting wound healing (acute and chronic), oral mucositis (a major side-effect of various cancer therapies, including, without limitation radiation therapy).

In some embodiments, the modified signaling agent has reduced affinity and/or activity for ErbB1, ErbB2, ErbB3, and/or ErbB4. Such embodiments find use, for example, in methods of treating wounds. In some embodiments, the modified signaling agent binds to one or more ErbB1, ErbB2, ErbB3, and ErbB4 and antagonizes the activity of the receptor. In such embodiments, the modified signaling agent has reduced affinity and/or activity for ErbB1, ErbB2, ErbB3, and/or ErbB4 which allows for the activity of the receptor to be antagonized in an attenuated fashion. Such embodiments find use in, for example, treatments of cancer. In an embodiment, the modified signaling agent has reduced affinity and/or activity for ErbB1. ErbB1 is the therapeutic target of kinase inhibitors most have side effects because they are not very selective (e.g., gefitinib, erlotinib, afatinib, brigatinib and icotinib). In some embodiments, attenuated antagonistic ErbB1 signaling is more on-target and has less side effects than other agents targeting receptors for EGF.

In some embodiments, the modified signaling agent has reduced affinity and/or activity (e.g. antagonistic e.g. natural antagonistic activity or antagonistic activity that is the result of one or more mutations, see, e.g., WO 2015/007520, the entire contents of which are hereby incorporated by reference) for ErbB1 and/or substantially reduced or ablated affinity and/or activity for ErbB4 or other subtypes it may interact with. Through specific targeting via the targeting moiety, cell-selective suppression (antagonism e.g. natural antagonistic activity or antagonistic activity that is the result of one or more mutations, see, e.g., WO 2015/007520, the entire contents of which are hereby incorporated by reference) of ErbB1/ErbB1 receptor activation would be achieved while not engaging other receptor subtypes potentially associated with inhibition-associated side effects. Hence, in contrast to EGFR kinase inhibitors, which inhibit EGFR activity in all cell types in the body, such a construct would provide a cell-selective (e.g., tumor cell with activated EGFR signaling due to amplification of receptor, overexpression etc.) anti-EGFR (ErbB1) drug effect with reduced side effects.

In some embodiments, the modified signaling agent has reduced affinity and/or activity (e.g. agonistic) for ErbB4 and/or other subtypes it may interact with. Through targeting to specific target cells through the targeting moiety, a selective activation of ErbB1 signaling is achieved (e.g. epithelial cells). Such a construct finds use, in some embodiments, in the treatment of wounds (promoting would healing) with reduced side effects, especially for treatment of chronic conditions and application other than topical application of a therapeutic (e.g. systemic wound healing).

In an embodiment, the modified signaling agent is insulin or insulin analogs. In some embodiments, the modified insulin or insulin analog has reduced affinity and/or activity for the insulin receptor and/or IGF1 or IGF2 receptor. In some embodiments, the modified insulin or insulin analog has substantially reduced or ablated affinity and/or activity for the insulin receptor and/or IGF1 or IGF2 receptor. Attenuated response at the insulin receptor allows for the control of diabetes, obesity, metabolic disorders and the like while directing away from IGF1 or IGF2 receptor avoids pro-cancer effects.

In an embodiment, the modified signaling agent is insulin-like growth factor-I or insulin-like growth factor-II (IGF-1 or IGF-2). In an embodiment, the modified signaling agent is IGF-1. In such an embodiment, the modified signaling agent has reduced affinity and/or activity for the insulin receptor and/or IGF1 receptor. In an embodiment, the modified signaling agent may bind to the IGF1 receptor and antagonize the activity of the receptor. In such an embodiment, the modified signaling agent has reduced affinity and/or activity for IGF1 receptor which allows for the activity of the receptor to be antagonized in an attenuated fashion. In some embodiments, the modified signaling agent has substantially reduced or ablated affinity and/or activity for the insulin receptor and/or IGF1 receptor. In some embodiments, the modified signaling agent has reduced affinity and/or activity for IGF2 receptor which allows for the activity of the receptor to be antagonized in an attenuated fashion. In an embodiment, the modified signaling agent has substantially reduced or ablated affinity and/or activity for the insulin receptor and accordingly does not interfere with insulin signaling. In some embodiments, this applies to cancer treatment. In some embodiments, the present agents may prevent IR isoform A from causing resistance to cancer treatments.

In an embodiment, the modified signaling agent is EPO. In various embodiments, the modified EPO agent has reduced affinity and/or activity for the EPO receptor (EPOR) receptor and/or the ephrin receptor (EphR) relative to wild type EPO or other EPO based agents described herein. In some embodiments, the modified EPO agent has substantially reduced or ablated affinity and/or activity for the EPO receptor (EPOR) receptor and/or the Eph receptor (EphR). Illustrative EPO receptors include, but are not limited to, an EPOR homodimer or an EPOR/CD131 heterodimer. Also included as an EPO receptor is beta-common receptor (βcR). Illustrative Eph receptors include, but are not limited to, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, and EPHB6. In some embodiments, the modified EPO protein comprises one or more mutations that cause the EPO protein to have reduced affinity for receptors that comprise one or more different EPO receptors or Eph receptors (e.g., heterodimer, heterotrimers, etc., including by way of non-limitation: EPOR-EPHB4, EPOR-βcR-EPOR). Also provided are the receptors of EP Patent Publication No. 2492355 the entire contents of which are hereby incorporated by reference, including by way of non-limitation, NEPORs.

The structure of the human EPO protein is predicted to comprise four-helix bundles including helices A, B, C, and D. In various embodiments, the modified EPO protein comprises one or more mutations located in four regions of the EPO protein which are important for bioactivity, i.e., amino acid residues 10-20, 44-51, 96-108, and 142-156. In some embodiments, the one or more mutations are located at residues 11-15, 44-51, 100-108, and 147-151. These residues are localized to helix A (Val11, Arg14, and Tyr15), helix C (Ser100, Arg103, Ser104, and Leu108), helix D (Asn147, Arg150, Gly151, and Leu155), and the A/B connecting loop (residues 42-51). In some embodiments, the modified EPO protein comprises mutations in residues between amino acids 41-52 and amino acids 147, 150, 151, and 155. Without wishing to be bound by theory, it is believed that mutations of these residues have substantial effects on both receptor binding and in vitro biological activity. In some embodiments, the modified EPO protein comprises mutations at residues 11, 14, 15, 100, 103, 104, and 108. Without wishing to be bound by theory, it is believed that mutations of these residues have modest effects on receptor binding activity and much greater effects on in vitro biological activity. Illustrative substitutions include, but are not limited to, one or more of Val11Ser, Arg14Ala, Arg14Gln, Tyr15Ile, Pro42Asn, Thr44Ile, Lys45Asp, Val46Ala, Tyr51Phe, Ser100Glu, Ser100Thr, Arg103Ala, Ser104Ile, Ser104Ala, Leu108Lys, Asn147Lys, Arg150Ala, Gly151Ala, and Leu155Ala.

In some embodiments, the modified EPO protein comprises mutations that effect bioactivity and not binding, e.g., those listed in Eliot, et al. Mapping of the Active Site of Recombinant Human Erythropoietin Jan. 15, 1997*; Blood:* 89 (2), the entire contents of which are hereby incorporated by reference.

In some embodiments, the modified EPO protein comprises one or more mutations involving surface residues of the EPO protein which are involved in receptor contact. Without wishing to be bound by theory, it is believed that mutations of these surface residues are less likely to affect protein folding thereby retaining some biological activity. Illustrative surface residues that may be mutated include, but are not limited to, residues 147 and 150. In illustrative embodiments, the mutations are substitutions including, one or more of N147A, N147K, R150A and R150E.

In some embodiments, the modified EPO protein comprises one or more mutations at residues N59, E62, L67, and L70, and one or more mutations that affect disulfide bond formation. Without wishing to be bound by theory, it is believed that these mutations affect folding and/or are predicted be in buried positions and thus affects biological activity indirectly.

In an embodiment, the modified EPO protein comprises a K20E substitution which significantly reduces receptor binding. See Elliott, et al., (1997) *Blood,* 89:493-502, the entire contents of which are hereby incorporated by reference.

Additional EPO mutations that may be incorporated into the chimeric EPO protein of the invention are disclosed in, for example, Elliott, et al., (1997) *Blood,* 89:493-502, the entire contents of which are hereby incorporated by reference and Taylor et al., (2010) *PEDS,* 23(4): 251-260, the entire contents of which are hereby incorporated by reference.

In one embodiment, the present chimeric protein has (i) a targeting moiety against FAP and (ii) a targeting moiety which is directed against a tumor cell, along with any of the modified or mutant signaling agents described herein. In an embodiment, the present chimeric protein has a targeting moiety directed against FAP on dendritic cells and a second targeting moiety directed against PD-L1 or PD-L2 on tumor cells.

In one embodiment, the present chimeric protein has (i) a targeting moiety against FAP and (ii) a targeting moiety which is directed against a checkpoint inhibitor marker, along with any of the modified or mutant interferons described herein. In an embodiment, the present chimeric protein has a targeting moiety directed against FAP on dendritic cells and a second targeting moiety directed against PD-1.

In some embodiments, the signaling agent is a toxin or toxic enzyme. In some embodiments, the toxin or toxic enzyme is derived from plants and bacteria. Illustrative toxins or toxic enzymes include, but are not limited to, the diphtheria toxin, *Pseudomonas* toxin, anthrax toxin, ribosome-inactivating proteins (RIPs) such as ricin and saporin, modeccin, abrin, gelonin, and poke weed antiviral protein. Additional toxins include those disclosed in Mathew et al., (2009) Cancer Sci 100(8): 1359-65, the entire disclosures are hereby incorporated by reference. In such embodiments, the chimeric proteins of the present technology may be utilized to induce cell death in cell-type specific manner. In such embodiments, the toxin may be modified, e.g. mutated, to reduce affinity and/or activity of the toxin for an attenuated effect, as described with other signaling agents herein.

Multi-Specific Chimeras and Fusions with Signaling Agents

In some embodiments, the FAP binding agent of the present technology is part of a chimera or fusion with one or more signaling agents as described herein and/or one or more additional targeting moieties. Accordingly, the present technology provides for chimeric or fusion proteins that include one or more signaling agents and a targeting moiety against FAP and/or one or more additional targeting moieties.

In some embodiments, the FAP binding agent of the present technology is multispecific, i.e., the FAP binding agent comprises two or more targeting moieties having recognition domains that recognize and bind two or more targets, e.g. antigens, or receptors, or epitopes. In such embodiments, the FAP binding agent of the present technology may comprise two more targeting moieties having recognition domains that recognize and bind two or more epitopes on the same antigen or on different antigens. In some embodiments, such multi-specific FAP binding agents exhibit advantageous properties such as increased avidity and/or improved selectivity. In an embodiment, the FAP binding agent of the present technology comprises two targeting moieties and is bispecific, i.e., binds and recognizes two epitopes on the same antigen or on different antigens.

In some embodiments, the multispecific FAP binding agent of the present technology comprises two or more targeting moieties with each targeting moiety being an antibody or an antibody derivative as described herein. In an embodiment, the multispecific FAP binding agent of the present technology comprises at least one VHH comprising an antigen recognition domain against FAP and one antibody or antibody derivative comprising an antigen recognition domain against a tumor antigen.

In some embodiments, the present multispecific FAP binding agents have two or more targeting moieties that target different antigens or receptors, and one targeting moiety may be attenuated for its antigen or receptor, e.g. the targeting moiety binds its antigen or receptor with a low affinity or avidity (including, for example, at an affinity or avidity that is less than the affinity or avidity the other targeting moiety has for its for its antigen or receptor, for instance the difference between the binding affinities may be about 10-fold, or 25-fold, or 50-fold, or 100-fold, or 300-fold, or 500-fold, or 1000-fold, or 5000-fold; for instance the lower affinity or avidity targeting moiety may bind its antigen or receptor at a KD in the mid- to high-nM or low- to mid-pM range while the higher affinity or avidity targeting moiety may bind its antigen or receptor at a KD in the mid- to high-pM or low- to mid-nM range). For instance, in some embodiments, the present multispecific FAP binding agents comprises an attenuated targeting moiety that is directed against a promiscuous antigen or receptor, which may improve targeting to a cell of interest (e.g. via the other targeting moiety) and prevent effects across multiple types of cells, including those not being targeted for therapy (e.g. by binding promiscuous antigen or receptor at a higher affinity than what is provided in these embodiments).

The multispecific FAP binding agent of the present technology may be constructed using methods known in the art, see for example, U.S. Pat. No. 9,067,991, U.S. Patent Publication No. 20110262348 and WO 2004/041862, the entire contents of which are hereby incorporated by reference. In an illustrative embodiment, the multispecific FAP binding agent of the present technology comprising two or more targeting moieties may be constructed by chemical crosslinking, for example, by reacting amino acid residues with an organic derivatizing agent as described by Blattler et al., Biochemistry 24,1517-1524 and EP294703, the entire contents of which are hereby incorporated by reference. In another illustrative embodiment, the multispecific FAP binding agent comprising two or more targeting moieties is constructed by genetic fusion, i.e., constructing a single polypeptide which includes the polypeptides of the individual targeting moieties. For example, a single polypeptide construct may be formed which encodes a first VHH with an antigen recognition domain against FAP and a second antibody or antibody derivative with an antigen recognition domain against a tumor antigen. A method for producing bivalent or multivalent VHH polypeptide constructs is disclosed in PCT patent application WO 96/34103, the entire contents of which is hereby incorporated by reference. In a further illustrative embodiment, the multispecific FAP binding agent of the present technology may be constructed by using linkers. For example, the carboxy-terminus of a first VHH with an antigen recognition domain against FAP may be linked to the amino-terminus of a second antibody or antibody derivative with an antigen recognition domain against a tumor antigen (or vice versa). Illustrative linkers that may be used are described herein. In some embodiments, the components of the multispecific FAP binding agent of the present technology are directly linked to each other without the use of linkers.

In some embodiments, the multi-specific FAP binding agent of the present technology recognizes and binds to FAP and one or more antigens found on one or more immune cells, which can include, without limitation, megakaryocytes, thrombocytes, erythrocytes, mast cells, basophils, neutrophils, eosinophils, monocytes, macrophages, natural killer cells, T lymphocytes (e.g., cytotoxic T lymphocytes, T helper cells, natural killer T cells), B lymphocytes, plasma cells, dendritic cells, or subsets thereof. In some embodiments, the FAP binding agent specifically binds to an antigen of interest and effectively directly or indirectly recruits one of more immune cells.

In some embodiments, the multi-specific FAP binding agent of the present technology recognizes and binds to FAP and one or more antigens found on tumor cells. In these embodiments, the present FAP binding agents may directly or indirectly recruit an immune cell to a tumor cell or the tumor microenvironment. In some embodiments, the present FAP binding agents may directly or indirectly recruit an immune cell, e.g. an immune cell that can kill and/or suppress a tumor cell (e.g., a CTL), to a site of action (such as, by way of non-limiting example, the tumor microenvironment).

In some embodiments, the present FAP binding agents are capable of, or find use in methods involving, shifting the balance of immune cells in favor of immune attack of a tumor. For instance, the present FAP binding agents can shift the ratio of immune cells at a site of clinical importance in favor of cells that can kill and/or suppress a tumor (e.g. T cells, cytotoxic T lymphocytes, T helper cells, natural killer (NK) cells, natural killer T (NKT) cells, anti-tumor macrophages (e.g. M1 macrophages), neutrophils, B cells, dendritic cells or subsets thereof and in opposition to cells that protect tumors (e.g. myeloid-derived suppressor cells (MDSCs), regulatory T cells (Tregs); tumor associated neutrophils (TANs), M2 macrophages, tumor associated macrophages (TAMs), or subsets thereof). In some embodiments, the present FAP binding agent is capable of increasing a ratio of effector T cells to regulatory T cells.

In some embodiments, the multi-specific FAP binding agent of the present technology comprises a targeting moiety having an antigen recognition domain that specifically binds to an antigen associated with tumor cells. In some embodiments, the targeting moiety directly or indirectly recruits tumor cells. For instance, in some embodiments, the recruitment of the tumor cell is to one or more effector cell (e.g. an immune cell as described herein) that can kill and/or suppress the tumor cell. In some embodiments, the targeting moiety directly or indirectly recruits T cells to a tumor cell, for example, by virtue of the two targeting moieties interacting with their respective antigens on a tumor and FAP-positive immune cell (e.g. dendritic cells).

Tumor cells, or cancer cells refer to an uncontrolled growth of cells or tissues and/or an abnormal increased in cell survival and/or inhibition of apoptosis which interferes with the normal functioning of bodily organs and systems. For example, tumor cells include benign and malignant cancers, polyps, hyperplasia, as well as dormant tumors or micrometastases. Illustrative tumor cells include, but are not limited to cells of: basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g. that associated with brain tumors), and Meigs' syndrome.

Tumor cells, or cancer cells also include, but are not limited to, carcinomas, e.g. various subtypes, including, for example, adenocarcinoma, basal cell carcinoma, squamous cell carcinoma, and transitional cell carcinoma), sarcomas (including, for example, bone and soft tissue), leukemia (including, for example, acute myeloid, acute lymphoblastic, chronic myeloid, chronic lymphocytic, and hairy cell), lymphomas and myelomas (including, for example, Hodgkin and non-Hodgkin lymphomas, light chain, non-secretory, MGUS, and plasmacytomas), and central nervous system cancers (including, for example, brain (e.g. gliomas (e.g. astrocytoma, oligodendroglioma, and ependymoma), meningioma, pituitary adenoma, and neuromas, and spinal cord tumors (e.g. meningiomas and neurofibroma).

Illustrative tumor antigens include, but are not limited to, MART-1/Melan-A, gp100, Dipeptidyl peptidase IV (DP-PIV), adenosine deaminase-binding protein (ADAbp), cyclophilin b, Colorectal associated antigen (CRC)-0017-1A/GA733, Carcinoembryonic Antigen (CEA) and its immunogenic epitopes CAP-1 and CAP-2, etv6, am11, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-Al2, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, a-fetoprotein, E-cadherin, a-catenin, 3-catenin and y-catenin, p120ctn, gp100 Pme1117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, NA, EBV-encoded nuclear antigen (EBNA)-1, brain glycogen phosphorylase, SSX-1, SSX-2 (HOM-MEL-40), SSX-1, SSX-4, SSX-5, SCP-1 CT-7, c-erbB-2, CD19, CD20, CD22, CD30, CD33, CD37, CD56, CD70, CD74, CD138, AGS16, MUC1, GPNMB, Ep-CAM, PD-L1, PD-L2, PMSA, and BCMA (TNFRSF17). In some embodiments, the FAP binding agent comprises a targeting moiety that binds one or more of these tumor antigens.

In some embodiments, the present multi-specific FAP binding agent recognizes and binds to FAP as well as an antigen on a tumor cell. In some embodiments, the multi-specific FAP binding agent directly or indirectly recruits CTLs to the tumor cell or tumor microenvironment.

In some embodiments, the present multi-specific FAP binding agent has targeting moieties which target two different cells (e.g. to make a synapse) or the same cell (e.g. to get a more concentrated signaling agent effect).

In some embodiments, the multi-specific FAP binding agent of the present technology comprises a targeting moiety having an antigen recognition domain that specifically binds to a target (e.g. antigen, receptor) associated with T cells. In some embodiments, the targeting moiety recruits directly or indirectly T cells. In an embodiment, the antigen recognition domains specifically bind to effector T cells. In some embodiments, the antigen recognition domain directly or indirectly recruits effector T cells, e.g., in some embodiments, to a therapeutic site (e.g. a locus with one or more disease cell or cell to be modulated for a therapeutic effect). Illustrative effector T cells include cytotoxic T cells (e.g. $\alpha\beta$ TCR, CD3+, CD8+, CD45R0+); CD4+ effector T cells (e.g. $\alpha\beta$ TCR, CD3+, CD4+, CCR7+, CD62Lhi, IL-7R/CD127+); CD8+ effector T cells (e.g. $\alpha\beta$ TCR, CD3+, CD8+, CCR7+, CD62Lhi, IL-7R/CD127+); effector memory T cells (e.g. CD62Llow, CD44+, TCR, CD3+, IL-7R/CD127+, IL-15R+, CCR7low); central memory T cells (e.g. CCR7+, CD62L+, CD27+; or CCR7hi, CD44+, CD62Lhi, TCR, CD3+, IL-7R/CD127+, IL-15R+); CD62L+ effector T cells; CD8+ effector memory T cells (TEM)

including early effector memory T cells (CD27+CD62L−) and late effector memory T cells (CD27-CD62L−) (TemE and TemL, respectively); CD127(+)CD25(low/−) effector T cells; CD127(−)CD25(−) effector T cells; CD8+ stem cell memory effector cells (TSCM) (e.g. CD44(low)CD62L (high)CD122(high)sca(+)); TH1 effector T-cells (e.g. CXCR3+, CXCR6+ and CCR5+; or αβ TCR, CD3+, CD4+, IL-12R+, IFNγR+, CXCR3+), TH2 effector T cells (e.g. CCR3', CCR4' and CCR8+; or αβ TCR, CD3+, CD4+, IL-4R+, IL-33R+, CCR4+, IL-17RB+, CRTH2+); TH9 effector T cells (e.g. αβ TCR, CD3+, CD4+); TH17 effector T cells (e.g. αβ TCR, CD3+, CD4+, IL-23R+, CCR6+, IL-1R+); CD4+CD45RO+CCR7+ effector T cells, ICOS+ effector T cells; CD4+CD45RO+CCR7(−) effector T cells; and effector T cells secreting IL-2, IL-4 and/or IFN-γ.

Illustrative T cell antigens of interest include, for example (and inclusive of the extracellular domains, where applicable): CD8, CD3, SLAMF4, IL-2Rα, 4-1BB/TNFRSF9, IL-2 Rβ, ALCAM, B7-1, IL-4 R, B7-H3, BLAME/SLAMFS, CEACAM1, IL-6 R, CCR3, IL-7 Rα, CCR4, CXCRI/IL-S RA, CCR5, CCR6, IL-10Rα, CCR 7, IL-10 R β, CCR5, IL-12 R β1, CCR9, IL-12 R β2, CD2, IL-13 R α 1, IL-13, CD3, CD4, ILT2/CDS5j, ILT3/CDS5k, ILT4/CDS5d, ILT5/CDS5a, lutegrin a 4/CD49d, CDS, Integrin a E/CD103, CD6, Integrin α M/CD 11 b, CDS, Integrin α X/CD11c, Integrin β 2/CDIS, KIR/CD15S, CD27/TNFRSF7, KIR2DL1, CD2S, KIR2DL3, CD30/TNFRSF5, KIR2DL4/CD15Sd, CD31/PECAM-1, KIR2DS4, CD40 Ligand/TNFSF5, LAG-3, CD43, LAIR1, CD45, LAIR2, CDS3, Leukotriene B4-R1, CDS4/SLAMF5, NCAM-L1, CD94, NKG2A, CD97, NKG2C, CD229/SLAMF3, NKG2D, CD2F-10/SLAMF9, NT-4, CD69, NTB-A/SLAMF6, Common γ Chain/IL-2 Rγ, Osteopontin, CRACC/SLAMF7, PD-1, CRTAM, PSGL-1, CTLA-4, RANK/TNFRSF11A, CX3CR1, CX3CL1, L-Selectin, CXCR3, SIRP β 1, CXCR4, SLAM, CXCR6, TCCRNVSX-1, DNAM-1, Thymopoietin, EMMPRIN/CD147, TIM-1, EphB6, TIM-2, Fas/TNFRSF6, TIM-3, Fas Ligand/TNFSF6, TIM-4, Fcγ RIII/CD16, TIM-6, TNFR1/TNFRSF1A, Granulysin, TNF RIII/TNFRSF1B, TRAIL RI/TNFRSFIOA, ICAM-1/CD54, TRAIL R2/TNFRSF10B, ICAM-2/CD102, TRAILR3/TNFRSF10C, IFN-γR1, TRAILR4/TNFRSF10D, IFN-γ R2, TSLP, IL-1 R1 and TSLP R. In some embodiments, the FAP binding agent comprises a targeting moiety that binds one or more of these illustrative T cell antigens.

In some embodiments, the multi-specific FAP binding agent of the present technology comprises a targeting moiety against CD8 which is a VHH comprising a single amino acid chain having four "framework regions" or FRs and three "complementary determining regions" or CDRs. As used herein, "framework region" or "FR" refers to a region in the variable domain which is located between the CDRs. As used herein, "complementary determining region" or "CDR" refers to variable regions in VHHs that contains the amino acid sequences capable of specifically binding to antigenic targets.

In some embodiments, the multi-specific FAP binding agent of the present technology comprises a VHH against CD8 having a variable domain comprising at least one CD8 CDR1, CD8 CDR2, and/or CD8 CDR3 sequences.

In some embodiments, the CD8 CDR1 sequence is selected from: SEQ ID NO: 192 or SEQ ID NO: 193.

In some embodiments, the CD8 CDR2 sequence is selected from: SEQ ID NO: 194 or SEQ ID NO: 195.

In some embodiments, the CD8 CDR3 sequence is selected from: SEQ ID NO: 196 or SEQ ID NO: 197 or SEQ ID NO: 198.

In some embodiments, the CD8 targeting moiety comprises an amino acid sequence selected from the following sequences: R3HCD27 (SEQ ID NO: 199); or R3HCD129: (SEQ ID NO: 200); or R2HCD26: (SEQ ID NO: 201).

In some embodiments, the CD8 targeting moiety comprises a VHH having a variable domain comprising at least one CD8 CDR1, CD8 CDR2, and/or CD8 CDR3 sequences as described below.

In some embodiments, the CD8 CDR1 sequence is selected from: SEQ ID NO: 202 to SEQ ID NO: 270.

In some embodiments, the CD8 CDR2 sequence is selected from: SEQ ID NO: 271 to SEQ ID NO: 339.

In some embodiments, the CD8 CDR3 sequence is selected from: SEQ ID NO: 340 to SEQ ID NO: 408.

In some embodiments, the CD8 targeting moiety comprises an amino acid sequence selected from the following sequences 1CDA 7 (SEQ ID NO: 409); or 1CDA 12 (SEQ ID NO: 410); or 1CDA 14 (SEQ ID NO: 411); or 1CDA 15 (SEQ ID NO: 412); or 1CDA 17 (SEQ ID NO: 413); or 1CDA 18 (SEQ ID NO: 414); or 1CDA 19 (SEQ ID NO: 415); or 1CDA 24(SEQ ID NO: 416); or 1CDA 26 (SEQ ID NO: 417); or 1CDA 28 (SEQ ID NO: 418); or 1CDA 37 (SEQ ID NO: 419); or 1CDA 43 (SEQ ID NO: 420); or 1CDA 45 (SEQ ID NO: 421); or 1CDA 47 (SEQ ID NO: 422); or 1CDA 48 (SEQ ID NO: 423); or 1CDA 58 (SEQ ID NO: 424); or 1CDA 65 (SEQ ID NO: 425); or 1CDA 68 (SEQ ID NO: 426); or 1CDA 73 (SEQ ID NO: 427); or 1CDA 75 (SEQ ID NO: 428); or 1CDA 86 (SEQ ID NO: 429); or 1CDA 87 (SEQ ID NO: 430); or 1CDA 88 (SEQ ID NO: 431); or 1CDA 89 (SEQ ID NO: 432); or 1CDA 92 (SEQ ID NO: 433); or 1CDA 93 (SEQ ID NO: 434); or 2CDA 1 (SEQ ID NO: 435); or 2CDA 5 (SEQ ID NO: 436); or 2CDA 22 (SEQ ID NO: 437); or 2CDA 28 (SEQ ID NO: 438); or 2CDA 62 (SEQ ID NO: 439); or 2CDA 68 (SEQ ID NO: 440); or 2CDA 73 (SEQ ID NO: 441); or 2CDA 74 (SEQ ID NO: 442); or 2CDA 75 (SEQ ID NO: 443); or 2CDA 77 (SEQ ID NO: 444); or 2CDA 81 (SEQ ID NO: 445); or 2CDA 87 (SEQ ID NO: 446); or 2CDA 88 (SEQ ID NO: 447); or 2CDA 89 (SEQ ID NO: 448); or 2CDA 91 (SEQ ID NO: 449); or 2CDA 92 (SEQ ID NO: 450); or 2CDA 93 (SEQ ID NO: 451); or 2CDA 94 (SEQ ID NO: 452); or 2CDA 95 (SEQ ID NO: 453); or 3CDA 3 (SEQ ID NO: 454); or 3CDA 8 (SEQ ID NO: 455); or 3CDA 11 (SEQ ID NO: 456); or 3CDA 18 (SEQ ID NO: 457); or 3CDA 19 (SEQ ID NO: 458); or 3CDA 21 (SEQ ID NO: 459); or 3CDA 24 (SEQ ID NO: 460); or 3CDA 28 (SEQ ID NO: 461); or 3CDA 29 (SEQ ID NO: 462); or 3CDA 31 (SEQ ID NO: 463); or 3CDA 32 (SEQ ID NO: 464); or 3CDA 33 (SEQ ID NO: 465); or 3CDA 37 (SEQ ID NO: 466); or 3CDA 40 (SEQ ID NO: 467); or 3CDA 41 (SEQ ID NO: 468); or 3CDA 48 (SEQ ID NO: 469); or 3CDA 57 (SEQ ID NO: 470); or 3CDA 65 (SEQ ID NO: 471); or 3CDA 70 (SEQ ID NO: 472); or 3CDA 73 (SEQ ID NO: 473); or 3CDA 83 (SEQ ID NO: 474); or 3CDA 86 (SEQ ID NO: 475); or 3CDA 88 (SEQ ID NO: 476); or 3CDA 90 (SEQ ID NO: 477).

In various illustrative embodiments, the CD8 targeting moiety comprises an amino acid sequence selected from any one of the above sequences without the terminal histidine tag sequence (i.e., HHHHHH; SEQ ID NO: 43).

In some embodiments, the CD8 targeting moiety comprises an amino acid sequence described in US Patent Publication No. 2014/0271462, the entire contents of which are incorporated by reference. In some embodiments, the CD8 targeting moiety comprises an amino acid sequence described in Table 0.1, Table 0.2, Table 0.3, and/or FIGS. 1A-121 of US Patent Publication No. 2014/0271462, the entire contents of which are incorporated by reference. In some embodiments, the CD8 targeting moiety comprises a HCDR1 of a HCDR1 of SEQ ID NO: 478 or 479 and/or a HCDR2 of HCDR1 of SEQ ID NO: 478 or 479 and/or a HCDR3 of HCDR1 of SEQ ID NO: 478 or 479 and/or a LCDR1 of LCDR1 of SEQ ID NO: 480 and/or a LCDR2 of LCDR1 of SEQ ID NO: 480 and/or a LCDR3 of LCDR1 of SEQ ID NO: 480.

In some embodiments, the present technology contemplates the use of any natural or synthetic analogs, mutants, variants, alleles, homologs and orthologs (herein collectively referred to as "analogs") of the targeting moiety directed against CD8 as described herein. In some embodiments, the amino acid sequence of the targeting moiety directed against CD8 further includes an amino acid analog, an amino acid derivative, or other non-classical amino acids.

In some embodiments, the multi-specific FAP binding agent of the present technology comprises a targeting moiety having an antigen recognition domain that specifically binds to a target (e.g., antigen, receptor) associated with B cells. In some embodiments, the targeting moiety directly or indirectly recruits B cells, e.g., to a therapeutic site (e.g. a locus with one or more disease cell or cell to be modulated for a therapeutic effect). By way of example, but not by way of limitation, in some embodiments, the B cell antigens include, for example, CD10, CD19, CD20, CD21, CD22, CD23, CD24, CD37, CD38, CD39, CD40, CD70, CD72, CD73, CD74, CDw75, CDw76, CD77, CD78, CD79a/b, CD80, CD81, CD82, CD83, CD84, CD85, CD86, CD89, CD98, CD126, CD127, CDw130, CD138, CDw150, and B-cell maturation antigen (BCMA). In some embodiments, the FAP binding agent comprises a targeting moiety that binds one or more of the above disclosed B cell antigens.

In some embodiments, the multi-specific FAP binding agent of the present technology comprises a targeting moiety having an antigen recognition domain that specifically bind to a target (e.g. antigen, receptor) associated with Natural Killer cells. In some embodiments, the targeting moiety directly or indirectly recruits Natural Killer cells, e.g., to a therapeutic site (e.g. a locus with one or more disease cell or cell to be modulated for a therapeutic effect). By way of example, but not by way of limitation, in some embodiments, the Natural Killer cell antigens include, for example, TIGIT, 2B4/SLAMF4, KIR2DS4, CD155/PVR, KIR3DL1, CD94, LMIR1/CD300A, CD69, LMIR2/CD300c, CRACC/SLAMF7, LMIR3/CD300LF, Kidalpha, DNAM-1, LMIR5/CD300LB, Fc-epsilon RII, LMIR6/CD300LE, Fc-γ RI/CD64, MICA, Fc-γ RIIB/CD32b, MICB, Fc-γ RIIC/CD32c, MULT-1, Fc-γ RIIA/CD32a, Nectin-2/0D112, Fc-γ RIII/CD16, NKG2A, FcRH1/IRTA5, NKG2C, FcRH2/IRTA4, NKG2D, FcRH4/IRTA1, NKp30, FcRH5/IRTA2, NKp44, Fc-Receptor-like 3/CD16-2, NKp46/NCR1, NKp80/KLRF1, NTB-A/SLAMF6, Rae-1, Rae-1 a, Rae-1 p, Rae-1 delta, H60, Rae-1 epsilon, ILT2/CD85j, Rae-1 y, ILT3/CD85k, TREM-1, ILT4/CD85d, TREM-2, ILT5/CD85a, TREM-3, KIR/CD158, TREML1/TLT-1, KIR2DL1, ULBP-1, KIR2DL3, ULBP-2, KIR2DL4/CD158d and ULBP-3. In some embodiments, the FAP binding agent comprises a targeting moiety that binds one or more of the above disclosed NK cell antigens.

In some embodiments, the multi-specific FAP binding agent of the present technology comprises a targeting moiety having an antigen recognition domain that specifically binds to a target (e.g. antigen, receptor) associated with macrophages/monocytes. In some embodiments, the targeting moiety directly or indirectly recruits macrophages/monocytes, e.g., to a therapeutic site (e.g. a locus with one or more disease cell or cell to be modulated for a therapeutic effect). By way of example, but not by way of limitation, in some embodiments, the macrophages/monocyte antigens include, for example, SIRP1a, B7-1/CD80, ILT4/CD85d, B7-H1, ILT5/CD85a, Common 3 Chain, Integrin a 4/CD49d, BLAME/SLAMF8, Integrin a X/CDIIc, CCL6/C10, Integrin 3 2/CD18, CD155/PVR, Integrin 3 3/CD61, CD31/PECAM-1, Latexin, CD36/SR-B3, Leukotriene B4 R1, CD40/TNFRSF5, LIMPIIISR-B2, CD43, LMIR1/CD300A, CD45, LMIR2/CD300c, CD68, LMIR3/CD300LF, CD84/SLAMF5, LMIR5/CD300LB, CD97, LMIR6/CD300LE, CD163, LRP-1, CD2F-10/SLAMF9, MARCO, CRACC/SLAMF7, MD-1, ECF-L, MD-2, EMMPRIN/CD147, MGL2, Endoglin/CD105, Osteoactivin/GPNMB, Fc-γ RI/CD64, Osteopontin, Fc-γ RIIB/CD32b, PD-L2, Fc-γ RIIC/CD32c, Siglec-3/CD33, Fc-γ RIIA/CD32a, SIGNR1/CD209, Fc-γ RIII/CD16, SLAM, GM-CSF R a, TCCRNVSX-1, ICAM-2/CD102, TLR3, IFN-γ RI, TLR4, IFN-gamma R2, TREM-I, IL-I RII, TREM-2, ILT2/CD85j, TREM-3, ILT3/CD85k, TREML1/TLT-1, 2B4/SLAMF 4, IL-10 R a, ALCAM, IL-10 R p, AminopeptidaseN/ANPEP, ILT2/CD85j, Common 3 Chain, ILT3/CD85k, C1q R1/CD93, ILT4/CD85d, CCR1, ILT5/CD85a, CCR2, CD206, Integrin a 4/CD49d, CCR5, Integrin a M/CDII b, CCR8, Integrin a X/CDIIc, CD155/PVR, Integrin 3 2/CD18, CD14, Integrin 13 3/CD61, CD36/SR-B3, LAIR1, CD43, LAIR2, CD45, Leukotriene B4-R1, CD68, LIMPIIISR-B2, CD84/SLAMFS, LMIR1/CD300A, CD97, LMIR2/CD300c, CD163, LMIR3/CD300LF, Coagulation Factor III/Tissue Factor, LMIR5/CD300LB, CX3CR1, CX3CL1, LMIR6/CD300LE, CXCR4, LRP-1, CXCR6, M-CSF R, DEP-1/CD148, MD-1, DNAM-1, MD-2, EMMPRIN/CD147, MMR, Endoglin/CD105, NCAM-L1, Fc-γ RI/CD64, PSGL-1, Fc-γ RIIICD16, RP105, G-CSF R, L-Selectin, GM-CSF R a, Siglec-3/CD33, HVEM/TNFRSF14, SLAM, ICAM-1/CD54, TCCRANSX-1, ICAM-2/CD102, TREM-I, IL-6 R, TREM-2, CXCRI/IL-8 RA, TREM-3 and TREMLITTLT-1. In some embodiments, the FAP binding agent comprises a targeting moiety that binds one or more of the above disclosed macrophage/monocyte antigens.

In some embodiments, the multi-specific FAP binding agent of the present technology comprises a targeting moiety having an antigen recognition domain that specifically binds to a target (e.g. antigen, receptor) associated with dendritic cells. In some embodiments, the targeting moiety directly or indirectly recruits dendritic cells, e.g., to a therapeutic site (e.g. a locus with one or more disease cell or cell to be modulated for a therapeutic effect). By way of example, but not by way of limitation, in some embodiments, the dendritic cell (DC) antigens include, for example, FAP, XCR1, RANK, CD36/SRB3, LOX-1/SR-El, CD68, MARCO, CD163, SR-A1/MSR, CD5L, SREC-1, CL-PI/C0LEC12, SREC-II, LIMPIIISRB2, RP105, TLR4, TLR1, TLR5, TLR2, TLR6, TLR3, TLR9, 4-IBB Ligand/TNFSF9, IL-12/1L-23 p40, 4-Amino-1,8-naphthalimide, ILT2/CD85j, CCL21/6Ckine, ILT3/CD85k, 8-oxo-dG, ILT4/CD85d, 8D6A, ILT5/CD85a, A2B5, lutegrin a 4/CD49d, Aag, Integrin p 2/CD18, AMICA, Langerin, B7-2/CD86, Leukotriene B4 RI, B7-H3, LMIR1/CD300A, BLAME/SLAMF8, LMIR2/CD300c, C1q R1/CD93, LMIR3/CD300LF, CCR6, LMIR5/CD300LB CCR7, LMIR6/CD300LE, CD40/TNFRSF5, MAG/Siglec-4-a, CD43, MCAM, CD45, MD-1, CD68, MD-2, CD83, MDL-1/CLEC5A, CD84/SLAMF5, MMR, CD97, NCAMLI, CD2F-10/SLAMF9, Osteoactivin GPNMB, Chern 23, PD-L2, CLEC-1, RP105, CLEC-2, CLEC-8, Siglec-2/CD22, CRACC/SLAMF7, Siglec-3/CD33, DC-SIGN, DEC-205, Siglec-5, DC-SIGNR/CD299, Siglec-6, DCAR, Siglec-7, DCIR/CLEC4A, Siglec-9, DEC-205, Siglec-10, Dectin-1/CLEC7A, Siglec-F, Dectin-2/CLEC6A, SIGNR1/CD209, DEP-1/CD148, SIGNR4, DLEC, SLAM, EMMPRIN/CD147, TCCRNVSX-1, Fc-y R1/CD64, TLR3, Fc-y RIIB/CD32b, TREM-1, Fc-y RIIC/CD32c, TREM-2, Fc-y RIIA/CD32a, TREM-3, Fc-y RIII/CD16, TREML1/TLT-1, ICAM-2/CD102, DEC205, and Vanilloid R1. In some embodiments, the FAP binding agent comprises a targeting moiety that binds one or more of the above disclosed DC antigens.

In some embodiments, the present chimeric protein comprises a targeting moiety comprising an amino acid sequence that is at least 60% identical to any one of the sequences disclosed herein. For example, in some embodiments, the chimeric protein comprises a targeting moiety comprising an amino acid sequence that is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to any one of the sequences discloses herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, about 99% or about 100% sequence identity to any one of the sequences disclosed herein).

In some embodiments, the multi-specific FAP binding agent of the present technology comprises a targeting moiety having an antigen recognition domain that specifically binds a target (e.g. antigen, receptor) on immune cells selected from, but not limited to, megakaryocytes, thrombocytes, erythrocytes, mast cells, basophils, neutrophils, and eosinophils. In some embodiments, the antigen recognition domains directly or indirectly recruit megakaryocytes, thrombocytes, erythrocytes, mast cells, basophils, neutrophils, and eosinophil, e.g., to a therapeutic site (e.g. a locus with one or more disease cell or cell to be modulated for a therapeutic effect).

In some embodiments, the multi-specific FAP binding agent of the present technology comprises a targeting moiety having an antigen recognition domain that specifically binds to a target (e.g. antigen, receptor) associated with megakaryocytes and/or thrombocytes. By way of example, but not by way of limitation, in some embodiments, the megakaryocyte and/or thrombocyte antigens include, for example, GP 11b/111a, GP1b, vWF, PF4, and TSP. In some embodiments, the FAP binding agent comprises a targeting moiety that binds one or more of the above disclosed megakaryocyte and/or thrombocyte antigens.

In some embodiments, the multi-specific FAP binding agent of the present technology comprises a targeting moiety having an antigen recognition domain that specifically binds to a target (e.g. antigen, receptor) associated with erythrocytes. By way of example, but not by way of limitation, in some embodiments, the erythrocyte antigens include, for example, CD34, C D36, CD38, CD41a (platelet glycoprotein 11b/111a), CD41b (GPIIb), CD71 (transferrin receptor), CD105, glycophorin A, glycophorin C, c-kit, HLA-DR, H2 (MHC-I1), and Rhesus antigens. In some embodiments, the FAP binding agent comprises a targeting moiety that binds one or more of the above disclosed erythrocyte antigens.

In some embodiments, the multi-specific FAP binding agent of the present technology comprises a targeting moiety having an antigen recognition domain that specifically binds to a target (e.g. antigen, receptor) associated with mast cells. By way of example, but not by way of limitation, in some embodiments, the mast cells antigens include, for example, SCFR/CD117, Fca, CD2, CD25, CD35, CD88, CD203c, C5R1, CMAI, FCERIA, FCER2, TPSABI. In some embodiments, the FAP binding agent comprises a targeting moiety that binds one or more of the above disclosed mast cell antigens.

In some embodiments, the multi-specific FAP binding agent of the present technology comprises a targeting moiety having an antigen recognition domain that specifically binds to a target (e.g. antigen, receptor) associated with basophils. By way of example, but not by way of limitation, in some embodiments, the basophils antigens include, for example, Fca, CD203c, CD123, CD13, CD107a, CD107b, and CD164. In some embodiments, the FAP binding agent comprises a targeting moiety that binds one or more of the above disclosed basophil antigens.

In some embodiments, the multi-specific FAP binding agent of the present technology comprises a targeting moiety having an antigen recognition domain that specifically binds to a target (e.g. antigen, receptor) associated with neutrophils. By way of example, but not by way of limitation, in some embodiments, the neutrophils antigens include, for example, 7D5, CD10/CALLA, CD13, CD16 (FcRIII), CD18 proteins (LFA-1, CR3, and p150, 95), CD45, CD67, and CD177. In some embodiments, the FAP binding agent comprises a targeting moiety that binds one or more of the above disclosed neutrophil antigens.

In some embodiments, the multi-specific FAP binding agent of the present technology comprises a targeting moiety having an antigen recognition domain that specifically binds to a target (e.g. antigen, receptor) associated with eosinophils. By way of example, but not by way of limitation, in some embodiments, the eosinophils antigens include, for example, CD35, CD44 and CD69. In some embodiments, the FAP binding agent comprises a targeting moiety that binds one or more of the above disclosed eosinophil antigens.

In some embodiments, the multi-specific FAP binding agent of the present technology comprises a targeting moiety having an antigen recognition domain that specifically binds to any appropriate antigen or receptor or cell surface markers known by the skilled artisan. In some embodiments, the antigen or cell surface marker is a tissue-specific marker. By way of example, but not by way of limitation, in some embodiments, the tissue-specific markers include, but are not limited to, endothelial cell surface markers (such as, e.g., ACE, CD14, CD34, CDHS, ENG, ICAM2, MCAM, NOS3, PECAMI, PROCR, SELE, SELP, TEK, THBD, VCAMI, VWF); smooth muscle cell surface markers (such as, e.g., ACTA2, MYHIO, MYHI 1, MYH9, MYOCD); fibroblast (stromal) cell surface markers (such as, e.g., ALCAM, CD34, COLIAI, COL1A2, COL3A1, FAP, PH-4); epithelial cell surface markers (such as, e.g., CDID, K61RS2, KRTIO, KRT13, KRT17, KRT18, KRT19, KRT4, KRT5, KRT8, MUCI, TACSTDI); neovasculature markers (such as, e.g., CD13, TFNA, Alpha-v beta-3 (av33), E-selectin); and adipocyte surface markers (such as, e.g., ADIPOQ, FABP4, and REIN). In some embodiments, the FAP binding agent comprises a targeting moiety that binds one or more of the above disclosed antigens.

In some embodiments, the multi-specific FAP binding agent of the present technology comprises a targeting moiety having an antigen recognition domain that specifically binds to a checkpoint marker expressed on a T cell. In some embodiments, the checkpoint marker is one or more checkpoint marker selected from PD-1, CD28, CTLA4, ICOS, BILA, KIR, LAG3, CD137, 0X40, CD27, CD40L, TIM3, and A2aR.

In some embodiments, the multi-specific FAP binding agent of the present technology comprises a targeting moiety having an antigen recognition domain that specifically binds to a checkpoint marker. In some embodiments, the checkpoint marker is one or more checkpoint marker selected from PD-1/PD-L1 or PD-L2, CD28/CD80 or CD86, CTLA4/CD80 or CD86, ICOS/ICOSL or B7RP1, BTLA/HVEM, KIR, LAG3, CD137/CD137L, OX40/0X40L, CD27, CD40L, TIM3/Ga19, and A2aR.

By way of example, but not by way of limitation, in some embodiments, the present multispecific FAP binding agent comprises a targeting moiety directed against (i) CD8; (ii) a checkpoint marker expressed on a T cell, e.g. one or more of PD-1, CD28, CTLA4, ICOS, BILA, KIR, LAG3, CD137, 0X40, Cd27, CD40L, TIM3, and A2aR and/or (iii) a targeting moiety is directed against a tumor cell, along with any of the modified (e.g. mutant) signaling agents described herein.

In some embodiments, the present multi-specific FAP binding agent has one or more targeting moieties directed against PD-1. In some embodiments, the FAP binding agent has one or more targeting moieties that selectively bind a PD-1 polypeptide. In some embodiments, the FAP binding agent comprises one or more antibodies, antibody derivatives or formats, peptides or polypeptides, or fusion proteins that selectively bind a PD-1 polypeptide.

In some embodiments, the multi-specific FAP binding agent of the present technology comprises a VHH against PD-1 having a variable domain comprising at least one PD-1 CDR1, PD-1 CDR2, and/or PD-1 CDR3 sequences.

In some embodiments, the PD-1 CDR1 sequence is selected from SEQ ID NO: 481 to SEQ ID NO: 494.

In some embodiments, the PD-1 CDR2 sequence is selected from: SEQ ID NO: 495 to SEQ ID NO: 508.

In some embodiments, the PD-1 CDR3 sequence is selected from: SEQ ID NO: 509 to SEQ ID NO: 521.

In various illustrative embodiments, the PD-1 targeting moiety comprises an amino acid sequence selected from the following sequences: 2PD23: (SEQ ID NO: 522); or 2PD26: (SEQ ID NO: 523); or 2PD90: (SEQ ID NO: 524); or 2PD-106: (SEQ ID NO: 525); or 2PD-16: (SEQ ID NO: 526); or 2PD71: (SEQ ID NO: 527); or 2PD-152: (SEQ ID NO: 528); or 2PD-12: (SEQ ID NO: 529); or 3PD55: (SEQ ID NO: 530); or 3PD82: (SEQ ID NO: 531); or 2PD8: (SEQ ID NO: 532); or 2PD27: (SEQ ID NO: 533); or 2PD82: (SEQ ID NO: 534); or 3PD36: (SEQ ID NO: 535).

In various illustrative embodiments, the PD-1 targeting moiety comprises an amino acid sequence selected from any one of the above without the terminal histidine tag sequence (i.e., without HHHHHH, SEQ ID NO: 43).

In some embodiments, the targeting moiety comprises the anti-PD-1 antibody pembrolizumab (a/k/a M K-3475, KEYTRUDA®, or fragments thereof. In some embodiments, the targeting moiety is one or more of pembrolizumab and other humanized anti-PD-1 antibodies disclosed in Hamid, et al. (2013) New England Journal of Medicine 369 (2): 134-44, U.S. Pat. No. 8,354,509, and WO 2009/114335, the entire disclosures of which are hereby incorporated by reference. By way of example, but not by way of limitation, in some embodiments, the pembrolizumab or an antigen-binding fragment thereof for use in the methods provided herein comprises a heavy chain comprising the amino acid sequence of: (SEQ ID NO: 536); and/or a light chain comprising the amino acid sequence of: (SEQ ID NO: 537).

In some embodiments, the targeting moiety comprises the anti-PD-1 antibody, nivolumab (a/k/a BMS-936558, MDX-1106, ONO-4538, OPDIVO®), or fragments thereof. In some embodiments, the targeting moiety is one or more of the nivolumab (clone 5C4) and other human monoclonal antibodies that specifically bind to PD-1 disclosed in U.S. Pat. No. 8,008,449 and WO 2006/121168, the entire disclosures of which are hereby incorporated by reference. By way of example, but not by way of limitation, in some embodiments, the nivolumab or an antigen-binding fragment thereof for use in the methods provided herein comprises a heavy chain comprising the amino acid sequence of: (SEQ ID NO: 538); and/or a light chain comprising the amino acid sequence of: (SEQ ID NO: 539).

In some embodiments, the targeting moiety comprises the anti-PD-1 antibody pidilizumab (a/k/a CT-011, hBAT or hBAT-1), or fragments thereof. In some embodiments, the pidilizumab and other humanized anti-PD-I monoclonal antibodies are selected from pidilizumab and other humanized anti-PD-I monoclonal antibodies disclosed in US 2008/0025980 and WO 2009/101611, the entire disclosures of which are hereby incorporated by reference. By way of example, but not by way of limitation, in some embodiments, the anti-PD-1 antibody or an antigen-binding fragment thereof for use in the methods provided herein comprises one or more light chain variable regions comprising an amino acid sequence selected from the following sequences disclosed in US 2008/0025980: (SEQ ID NO: 540); (SEQ ID NO: 541); (SEQ ID NO: 542); and (SEQ ID NO: 543);

and/or a heavy chain comprising an amino acid sequence selected from the following sequences disclosed in US 2008/0025980: (SEQ ID NO: 544); (SEQ ID NO: 545); (SEQ ID NO: 546); (SEQ ID NO: 547); and (SEQ ID NO: 548).

In some embodiments, the targeting moiety comprises a light chain comprising: (SEQ ID NO: 549); and a heavy chain comprising: (SEQ ID NO: 550).

In some embodiments, the targeting moiety comprises AMP-514 (a/k/a MEDT-0680).

In some embodiments, the targeting moiety comprises the PD-L2-Fc fusion protein AMP-224 or fragments thereof, which are disclosed in WO 2010/027827 and WO 2011/066342, the entire disclosures of which are hereby incorporated by reference.

In some embodiments, the targeting moiety comprises: (SEQ ID NO: 551) and/or a B7-DC fusion protein comprising: (SEQ ID NO: 552).

In some embodiments, the targeting moiety comprises the peptide AUNP 12 or any other peptides disclosed in US 2011/0318373 or U.S. Pat. No. 8,907,053. By way of example, but not by way of limitation, in some embodiments, the targeting moiety comprises the AUNP 12 sequence of:

(SEQ ID NO: 553)
SNTSESFK(SNTSESF)FRVTQLAPKAQIKE-$NH_2$

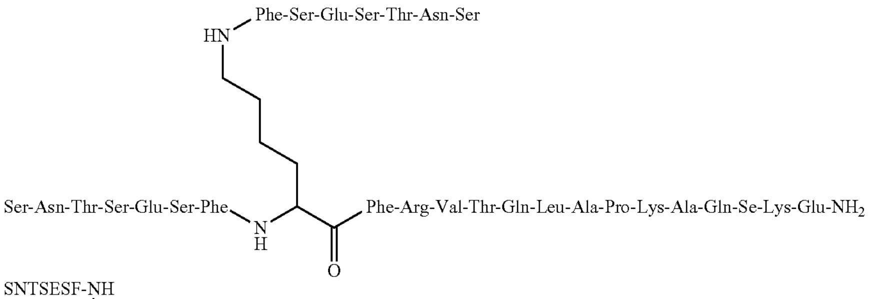

or:

SNTSESF-NH
SNTSESFKFRVTQLAPKAQIKE-$NH_2$.

(i.e., Compound 8 of US 2011/0318373).

In some embodiments, the targeting moiety comprises the anti-PD-1 antibody 1E3, or fragments thereof, disclosed in US 2014/0044738, the entire disclosures of which are hereby incorporated by reference. By way of example, but not by way of limitation, in some embodiments, the 1E3 or an antigen-binding fragment thereof for use in the methods provided herein comprises a heavy chain variable region comprising the amino acid sequence of: (SEQ ID NO: 554); and/or a light chain variable region comprising the amino acid sequence of: (SEQ ID NO: 555).

In an embodiment, the targeting moiety comprises the anti-PD-1 antibody 1E8, or fragments thereof, disclosed in US 2014/0044738, the entire disclosures of which are hereby incorporated by reference. By way of example, but not by way of limitation, in some embodiments, the 1E8 or an antigen-binding fragment thereof for use in the methods provided herein comprises a heavy chain variable region comprising the amino acid sequence of: (SEQ ID NO: 556); and/or a light chain variable region comprising the amino acid sequence of: (SEQ ID NO: 557).

In some embodiments, the targeting moiety comprises the anti-PD-1 antibody 1H3, or fragments thereof, disclosed in US 2014/0044738, the entire disclosures of which are hereby incorporated by reference. By way of example, but not by way of limitation, in some embodiments, the 1H3 or an antigen-binding fragment thereof for use in the methods provided herein comprises a heavy chain variable region comprising the amino acid sequence of: (SEQ ID NO: 558);

and/or light chain variable region comprising the amino acid sequence of: (SEQ ID NO: 559).

In some embodiments, the targeting moiety comprises a VHH directed against PD-1 disclosed in U.S. Pat. No. 8,907,065 and WO 2008/071447, the entire disclosures of which are hereby incorporated by reference. By way of example, but not by way of limitation, in some embodiments, the VHHs against PD-1 comprise one or more of the following sequences disclosed in U.S. Pat. No. 8,907,065: (SEQ ID NO: 560); (SEQ ID NO: 561); (SEQ ID NO: 562); (SEQ ID NO: 563); or (SEQ ID NO: 564).

In some embodiments, the targeting moiety comprises any one of the anti-PD-1 antibodies, or fragments thereof, disclosed in US 2011/0271358 and WO 2010/036959, the entire contents of which are hereby incorporated by reference. By way of example, but not by way of limitation, in some embodiments, the antibody or an antigen-binding fragment thereof for use in the methods provided herein comprises a heavy chain comprising one or more amino acid sequences selected from the following sequences in US 2011/0271358: (SEQ ID NO: 565); (SEQ ID NO: 566); (SEQ ID NO: 567); (SEQ ID NO: 568); or (SEQ ID NO: 569); and/or a light chain comprising one or more amino acid sequences selected from the following sequences in US 2011/0271358: (SEQ ID NO: 570); (SEQ ID NO: 571); (SEQ ID NO: 572); or (SEQ ID NO: 573).

In some embodiments, the present multi-specific FAP binding agent comprises one or more antibodies directed against PD-1, or antibody fragments thereof, selected from TSR-042 (Tesaro, Inc.), REGN2810 (Regeneron Pharmaceuticals, Inc.), PDR001 (Novartis Pharmaceuticals), and BGB-A317 (BeiGene Ltd.)

In some embodiments, the present multi-specific FAP binding agent has one or more targeting moieties directed against PD-L1. In some embodiments, the FAP binding agent has one or more targeting moieties that selectively bind a PD-L1 polypeptide. In some embodiments, the FAP binding agent comprises one or more antibodies, antibody derivatives or formats, peptides or polypeptides, or fusion proteins that selectively bind a PD-L1 polypeptide.

In some embodiments, the multi-specific FAP binding agent of the present technology comprises a VHH against PD-L1 having a variable domain comprising at least one PD-L1 CDR1, PD-L1 CDR2, and/or PD-L1 CDR3 sequences.

In some embodiments, the PD-L1 CDR1 sequence is selected from: SEQ ID NO: 574 to SEQ ID NO: 604.

In some embodiments, the PD-L1 CDR2 sequence is selected from: SEQ ID NO: 605 to SEQ ID NO: 635.

In some embodiments, the PD-L1 CDR3 sequence is selected from: SEQ ID NO: 636 to SEQ ID NO: 666.

In some embodiments, the PD-L1 targeting moiety comprises an amino acid sequence selected from the following sequences: 2LIG2: (SEQ ID NO: 667); or 2LIG3: (SEQ ID NO: 668); or 2LIG16: (SEQ ID NO: 669); or 2LIG22: (SEQ ID NO: 670); or 2LIG27: (SEQ ID NO: 671); or 2LIG29: (SEQ ID NO: 672); or 2LIG30: (SEQ ID NO: 673); or 2LIG34: (SEQ ID NO: 674); or 2LIG35: (SEQ ID NO: 675); or 2LIG48: (SEQ ID NO: 676); or 2LIG65: (SEQ ID NO:

677); or 2LIG85: (SEQ ID NO: 678); or 2LIG86: (SEQ ID NO: 679); or 2LIG89: (SEQ ID NO: 680); or 2LIG97: (SEQ ID NO: 681); or 2LIG99: (SEQ ID NO: 682); or 2LIG109: (SEQ ID NO: 683); or 2LIG127: (SEQ ID NO: 684); or 2LIG139: (SEQ ID NO: 685); or 2LIG176: (SEQ ID NO: 686); or 2LIG189: (SEQ ID NO: 687); or 3LIG3: (SEQ ID NO: 688); or 3LIG7: (SEQ ID NO: 689); or 3LIG8: (SEQ ID NO: 690); or 3LIG9: (SEQ ID NO: 691); or 3LIG18: (SEQ ID NO: 692); or 3LIG20: (SEQ ID NO: 693); or 3LIG28: (SEQ ID NO: 694); or 3LIG29: (SEQ ID NO: 695); or 3LIG30: (SEQ ID NO: 696); or 3LIG33: (SEQ ID NO: 697).

In some embodiments, the PD-L1 targeting moiety comprises an amino acid sequence selected from any one of the above sequences without the terminal histidine tag sequence (i.e., HHHHHH; SEQ ID NO: 43).

In some embodiment, the targeting moiety comprises the anti-PD-L1 antibody MED14736 (a/k/a durvalumab), or fragments thereof. MED14736 is selective for PD-L1 and blocks the binding of PD-L1 to the PD-1 and CD80 receptors. In some embodiments, the MED14736 and antigen-binding fragments thereof for use in the methods provided herein comprises a heavy chain and a light chain or a heavy chain variable region and a light chain variable region. The sequence of MED14736 is disclosed in WO/2016/06272, the entire contents of which are hereby incorporated by reference. By way of example, but not by way of limitation, in some embodiments, the MED14736 or an antigen-binding fragment thereof for use in the methods provided herein comprises a heavy chain comprising the amino acid sequence of: (SEQ ID NO: 698); and/or a light chain comprising the amino acid sequence of: (SEQ ID NO: 699).

In some embodiments, the MED14736 or an antigen-binding fragment thereof for use in the methods provided herein comprises a heavy chain variable region comprising the amino acid sequence: (SEQ ID NO: 885); and/or a light chain variable region comprising the amino acid sequence: (SEQ ID NO: 886).

In some embodiments, the targeting moiety comprises the anti-PD-L1 antibody atezolizumab (a/k/a MPDL3280A, RG7446), or fragments thereof. By way of example, but not by way of limitation, in some embodiments, the atezolizumab or an antigen-binding fragment thereof for use in the methods provided herein comprises a heavy chain comprising the amino acid sequence of: (SEQ ID NO: 887); and/or a light chain comprising the amino acid sequence of: (SEQ ID NO: 888).

In some embodiments, the targeting moiety comprises the anti-PD-L1 antibody avelumab (a/k/a MSB00107180), or fragments thereof. By way of example, but not by way of limitation, in some embodiments, the avelumab or an antigen-binding fragment thereof for use in the methods provided herein comprises a heavy chain comprising the amino acid sequence of: (SEQ ID NO: 889); and/or a light chain comprising the amino acid sequence of: (SEQ ID NO: 890).

In some embodiments, the targeting moiety comprises the anti-PD-L1 antibody BMS-936559 (a/k/a 12A4, MDX-1105), or fragments thereof, disclosed in US 2013/0309250 and WO 2007/005874, the entire disclosures of which are hereby incorporated by reference. By way of example, but not by way of limitation, in some embodiments, the BMS-936559 or an antigen-binding fragment thereof for use in the methods provided herein comprises a heavy chain variable region comprising the amino acid sequence of: (SEQ ID NO: 891); and/or a light chain variable region comprising the amino acid sequence of: (SEQ ID NO: 892).

In some embodiments, the targeting moiety comprises the anti-PD-L1 antibody 3G10, or fragments thereof, disclosed in US 2013/0309250 and WO 2007/005874, the entire disclosures of which are hereby incorporated by reference. By way of example, but not by way of limitation, in some embodiments, the 3G10 or an antigen-binding fragment thereof for use in the methods provided herein comprises a heavy chain variable region comprising the amino acid sequence of: (SEQ ID NO: 893); and/or a light chain variable region comprising the amino acid sequence of: (SEQ ID NO: 894).

In some embodiments, the targeting moiety comprises the anti-PD-L1 antibody 10A5, or fragments thereof, disclosed in US 2013/0309250 and WO 2007/005874, the entire disclosures of which are hereby incorporated by reference. By way of example, but not by way of limitation, in some embodiments, the 10A5 or an antigen-binding fragment thereof for use in the methods provided herein comprises a heavy chain variable region comprising the amino acid sequence of: (SEQ ID NO: 895); and/or a light chain variable region comprising the amino acid sequence of: (SEQ ID NO: 896).

In some embodiments, the targeting moiety comprises the anti-PD-L1 antibody 5F8, or fragments thereof, disclosed in US 2013/0309250 and WO 2007/005874, the entire disclosures of which are hereby incorporated by reference. By way of example, but not by way of limitation, in some embodiments, the 5F8 or an antigen-binding fragment thereof for use in the methods provided herein comprises a heavy chain variable region comprising the amino acid sequence of: (SEQ ID NO: 897); and/or a light chain variable region comprising the amino acid sequence of: (SEQ ID NO: 898).

In some embodiments, the targeting moiety comprises the anti-PD-L1 antibody 10H10, or fragments thereof, disclosed in US 2013/0309250 and WO 2007/005874, the entire disclosures of which are hereby incorporated by reference. By way of example, but not by way of limitation, in some embodiments, the 10H10 or an antigen-binding fragment thereof for use in the methods provided herein comprises a heavy chain variable region comprising the amino acid sequence of: (SEQ ID NO: 899); and/or a light chain variable region comprising the amino acid sequence of: (SEQ ID NO: 900).

In some embodiments, the targeting moiety comprises the anti-PD-L1 antibody 1612, or fragments thereof, disclosed in US 2013/0309250 and WO 2007/005874, the entire disclosures of which are hereby incorporated by reference. By way of example, but not by way of limitation, in some embodiments, the 1612 or an antigen-binding fragment thereof for use in the methods provided herein comprises a heavy chain variable region comprising the amino acid sequence of: (SEQ ID NO: 901); and/or a light chain variable region comprising the amino acid sequence of: (SEQ ID NO: 902).

In some embodiments, the targeting moiety comprises the anti-PD-L1 antibody 7H1, or fragments thereof, disclosed in US 2013/0309250 and WO 2007/005874, the entire disclosures of which are hereby incorporated by reference. By way of example, but not by way of limitation, in some embodiments, the 7H1 or an antigen-binding fragment thereof for use in the methods provided herein comprises a heavy chain variable region comprising the amino acid sequence of: (SEQ ID NO: 903); and/or a light chain variable region comprising the amino acid sequence of: (SEQ ID NO: 904).

In some embodiments, the targeting moiety comprises the anti-PD-L1 antibody 11E6, or fragments thereof, disclosed in US 2013/0309250 and WO 2007/005874, the entire disclosures of which are hereby incorporated by reference. By way of example, but not by way of limitation, in some embodiments, the 11E6 or an antigen-binding fragment thereof for use in the methods provided herein comprises a heavy chain variable region comprising the amino acid sequence of: (SEQ ID NO: 905); and/or a light chain variable region comprising the amino acid sequence of: (SEQ ID NO: 906).

In some embodiments, the targeting moiety comprises the anti-PD-L1 antibody 1267, or fragments thereof, disclosed in US 2013/0309250 and WO 2007/005874, the entire disclosures of which are hereby incorporated by reference. By way of example, but not by way of limitation, in some embodiments, the 1267 or an antigen-binding fragment thereof for use in the methods provided herein comprises a heavy chain variable region comprising the amino acid sequence of: (SEQ ID NO: 907); and/or a light chain variable region comprising the amino acid sequence of: (SEQ ID NO: 908).

In some embodiments, the targeting moiety comprises the anti-PD-L1 antibody 13G4, or fragments thereof, disclosed in US 2013/0309250 and WO 2007/005874, the entire disclosures of which are hereby incorporated by reference. By way of example, but not by way of limitation, in some embodiments, the 13G4 or an antigen-binding fragment thereof for use in the methods provided herein comprises a heavy chain variable region comprising the amino acid sequence of: (SEQ ID NO: 909); and/or a light chain variable region comprising the amino acid sequence of: (SEQ ID NO: 910).

In some embodiments, the targeting moiety comprises the anti-PD-L1 antibody 1E12, or fragments thereof, disclosed in US 2014/0044738, the entire disclosures of which are hereby incorporated by reference. By way of example, but not by way of limitation, in some embodiments, the 1E12 or an antigen-binding fragment thereof for use in the methods provided herein comprises a heavy chain variable region comprising the amino acid sequence of: (SEQ ID NO: 911); and/or a light chain variable region comprising the amino acid sequence of: (SEQ ID NO: 912).

In some embodiments, the targeting moiety comprises the anti-PD-L1 antibody 1F4, or fragments thereof, disclosed in US 2014/0044738, the entire disclosures of which are hereby incorporated by reference. By way of example, but not by way of limitation, in some embodiments, the 1F4 or an antigen-binding fragment thereof for use in the methods provided herein comprises a heavy chain variable region comprising the amino acid sequence of: (SEQ ID NO: 913); and/or a light chain variable region comprising the amino acid sequence of: (SEQ ID NO: 914).

In some embodiments, the targeting moiety comprises the anti-PD-L1 antibody 2G11, or fragments thereof, disclosed in US 2014/0044738, the entire disclosures of which are hereby incorporated by reference. By way of example, but not by way of limitation, in some embodiments, the 2G11 or an antigen-binding fragment thereof for use in the methods provided herein comprises a heavy chain variable region comprising the amino acid sequence of: (SEQ ID NO: 700); and/or a light chain variable region comprising the amino acid sequence of: (SEQ ID NO: 701).

In some embodiments, the targeting moiety comprises the anti-PD-L1 antibody 3B6, or fragments thereof, disclosed in US 2014/0044738, the entire disclosures of which are hereby incorporated by reference. By way of example, but not by way of limitation, in some embodiments, the 3B6 or an antigen-binding fragment thereof for use in the methods provided herein comprises a heavy chain variable region comprising the amino acid sequence of: (SEQ ID NO: 702); and/or a light chain variable region comprising the amino acid sequence of: (SEQ ID NO: 703).

In some embodiments, the targeting moiety comprises the anti-PD-L1 antibody 3D10, or fragments thereof, disclosed in US 2014/0044738 and WO 2012/145493, the entire disclosures of which are hereby incorporated by reference. By way of example, but not by way of limitation, in some embodiments, the 3D10 or an antigen-binding fragment thereof for use in the methods provided herein comprises a heavy chain variable region comprising the amino acid sequence of: (SEQ ID NO: 704); and/or a light chain variable region comprising the amino acid sequence of: (SEQ ID NO: 705).

In some embodiments, the targeting moiety comprises any one of the anti-PD-L1 antibodies disclosed in US2011/0271358 and WO 2010/036959, the entire contents of which are hereby incorporated by reference. By way of example, but not by way of limitation, in some embodiments, the antibody or an antigen-binding fragment thereof for use in the methods provided herein comprises a heavy chain comprising one or more amino acid sequences selected from the following sequences in US2011/0271358: (SEQ ID NO: 706); (SEQ ID NO: 707); (SEQ ID NO: 708); (SEQ ID NO: 709); or (SEQ ID NO: 710); and/or a light chain comprising one or more amino acid sequences selected from the following sequences in US2011/0271358: (SEQ ID NO: 711); (SEQ ID NO: 712); (SEQ ID NO: 713); or (SEQ ID NO: 714).

In some embodiments, the targeting moiety comprises the anti-PD-L1 antibody 2.7A4, or fragments thereof, disclosed in WO 2011/066389, U.S. Pat. No. 8,779,108, and US 2014/0356353, the entire disclosures of which are hereby incorporated by reference. By way of example, but not by way of limitation, in some embodiments, the 2.7A4 or an antigen-binding fragment thereof for use in the methods provided herein comprises a heavy chain variable region comprising the amino acid sequence of: (SEQ ID NO: 715); and/or a light chain variable region comprising the amino acid sequence of: (SEQ ID NO: 716).

In some embodiments, the targeting moiety comprises the anti-PD-L1 antibody 2.9D10, or fragments thereof, disclosed in WO 2011/066389, U.S. Pat. No. 8,779,108, and US 2014/0356353, the entire disclosures of which are hereby incorporated by reference. By way of example, but not by way of limitation, in some embodiments, the 2.9D10 or an antigen-binding fragment thereof for use in the methods provided herein comprises a heavy chain variable region comprising the amino acid sequence of: (SEQ ID NO: 717); and/or a light chain variable region comprising the amino acid sequence of: (SEQ ID NO: 718).

In some embodiments, the targeting moiety comprises the anti-PD-L1 antibody 2.14H9, or fragments thereof, disclosed in WO 2011/066389, U.S. Pat. No. 8,779,108, and US 2014/0356353, the entire disclosures of which are hereby incorporated by reference. By way of example, but not by way of limitation, in some embodiments, the 2.14H9 or an antigen-binding fragment thereof for use in the methods provided herein comprises a heavy chain variable region comprising the amino acid sequence of: (SEQ ID NO: 719); and/or a light chain variable region comprising the amino acid sequence of: (SEQ ID NO: 720).

In some embodiments, the targeting moiety comprises the anti-PD-L1 antibody 2.20A8, or fragments thereof, disclosed in WO 2011/066389, U.S. Pat. No. 8,779,108, and US 2014/0356353, the entire disclosures of which are hereby incorporated by reference. By way of example, but not by way of limitation, in some embodiments, the 2.20A8 or an antigen-binding fragment thereof for use in the methods provided herein comprises a heavy chain variable region comprising the amino acid sequence of: (SEQ ID NO: 721); and/or a light chain variable region comprising the amino acid sequence of: (SEQ ID NO: 722).

In some embodiments, the targeting moiety comprises the anti-PD-L1 antibody 3.15G8, or fragments thereof, disclosed in WO 2011/066389, U.S. Pat. No. 8,779,108, and US 2014/0356353, the entire disclosures of which are hereby incorporated by reference. By way of example, but not by way of limitation, in some embodiments, the 3.15G8 or an antigen-binding fragment thereof for use in the methods provided herein comprises a heavy chain variable region comprising the amino acid sequence of: (SEQ ID NO: 723); and/or a light chain variable region comprising the amino acid sequence of: (SEQ ID NO: 724).

In some embodiments, the targeting moiety comprises the anti-PD-L1 antibody 3.18G1, or fragments thereof, disclosed in WO 2011/066389, U.S. Pat. No. 8,779,108, and US 2014/0356353, the entire disclosures of which are hereby incorporated by reference. By way of example, but not by way of limitation, in some embodiments, the 3.18G1 or an antigen-binding fragment thereof for use in the methods provided herein comprises a heavy chain variable region comprising the amino acid sequence of: (SEQ ID NO: 725); and/or a light chain variable region comprising the amino acid sequence of: (SEQ ID NO: 726).

In some embodiments, the targeting moiety comprises the anti-PD-L1 antibody 2.7A4OPT, or fragments thereof, disclosed in WO 2011/066389, U.S. Pat. No. 8,779,108, and US 2014/0356353, the entire disclosures of which are hereby incorporated by reference. By way of example, but not by way of limitation, in some embodiments, the 2.7A4OPT or an antigen-binding fragment thereof for use in the methods provided herein comprises a heavy chain variable region comprising the amino acid sequence of: (SEQ ID NO: 727); and/or a light chain variable region comprising the amino acid sequence of: (SEQ ID NO: 728).

In some embodiments, the targeting moiety comprises the anti-PD-L1 antibody 2.14H90PT, or fragments thereof, as disclosed in WO 2011/066389, U.S. Pat. No. 8,779,108, and US 2014/0356353, the entire disclosures of which are hereby incorporated by reference. By way of example, but not by way of limitation, in some embodiments, the 2.14H90PT or an antigen-binding fragment thereof for use in the methods provided herein comprises a heavy chain variable region comprising the amino acid sequence of: (SEQ ID NO: 729); and/or a light chain variable region comprising the amino acid sequence of: (SEQ ID NO: 730).

In some embodiments, the targeting moiety comprises any one of the anti-PD-L1 antibodies disclosed in WO 2016/061142, the entire contents of which are hereby incorporated by reference. By way of example, but not by way of limitation, in some embodiments, the antibody or an antigen-binding fragment thereof for use in the methods provided herein comprises a heavy chain comprising one or more amino acid sequences selected from the following sequences in WO 2016/061142: (SEQ ID NO: 731); (SEQ ID NO: 732); (SEQ ID NO: 733); (SEQ ID NO: 734); (SEQ ID NO: 735); (SEQ ID NO: 736); (SEQ ID NO: 737); (SEQ ID NO: 738); or (SEQ ID NO: 739); and/or a light chain comprising one or more amino acid sequences selected from the following sequences in WO 2016/061142: (SEQ ID NO: 740); (SEQ ID NO: 741); (SEQ ID NO: 742); (SEQ ID NO: 743); (SEQ ID NO: 744); (SEQ ID NO: 745); (SEQ ID NO: 746); (SEQ ID NO: 747); or (SEQ ID NO: 748).

In some embodiments, the targeting moiety comprises any one of the anti-PD-L1 antibodies disclosed in WO 2016/022630, the entire contents of which are hereby incorporated by reference. By way of example, but not by way of limitation, in some embodiments, the antibody or an antigen-binding fragment thereof for use in the methods provided herein comprises a heavy chain comprising one or more amino acid sequences selected from the following sequences in WO 2016/022630: (SEQ ID NO: 749); (SEQ ID NO: 750); (SEQ ID NO: 751); (SEQ ID NO: 752); (SEQ ID NO: 753); (SEQ ID NO: 754); (SEQ ID NO: 755); (SEQ ID NO: 756); (SEQ ID NO: 757); (SEQ ID NO: 758); (SEQ ID NO: 759); (SEQ ID NO: 760); and/or a light chain comprising one or more amino acid sequences selected from the following sequences in WO 2016/022630: (SEQ ID NO: 761); (SEQ ID NO: 762); (SEQ ID NO: 763); (SEQ ID NO: 764); (SEQ ID NO: 765); (SEQ ID NO: 766); (SEQ ID NO: 767); (SEQ ID NO: 768); (SEQ ID NO: 769); (SEQ ID NO: 770); (SEQ ID NO: 771); and (SEQ ID NO: 772).

In some embodiments, the targeting moiety comprises any one of the anti-PD-L1 antibodies disclosed in WO 2015/112900, the entire contents of which are hereby incorporated by reference. By way of example, but not by way of limitation, in some embodiments, the antibody or an antigen-binding fragment thereof for use in the methods provided herein comprises a heavy chain comprising one or more amino acid sequences selected from the following sequences in WO 2015/112900: (SEQ ID NO: 773); (SEQ ID NO: 774); (SEQ ID NO: 775); or (SEQ ID NO: 776); and/or a light chain comprising one or more amino acid sequences selected from the following sequences in WO 2015/112900: (SEQ ID NO: 777); (SEQ ID NO: 778); (SEQ ID NO: 779); (SEQ ID NO: 780); (SEQ ID NO: 781); (SEQ ID NO: 782); (SEQ ID NO: 783); (SEQ ID NO: 784); or (SEQ ID NO: 785).

In some embodiments, the targeting moiety comprises any one of the anti-PD-L1 antibodies disclosed in WO 2010/077634 and U.S. Pat. No. 8,217,149, the entire disclosures of which are hereby incorporated by reference. By way of example, but not by way of limitation, in some embodiments, the anti-PD-L1 antibody or an antigen-binding fragment thereof for use in the methods provided herein comprises a heavy chain region comprising the amino acid sequence of: (SEQ ID NO: 786); and/or a light chain variable region comprising the amino acid sequence of: (SEQ ID NO: 787).

In some embodiments, the targeting moiety comprises any one of the anti-PD-L1 antibodies obtainable from the hybridoma accessible under CNCM deposit numbers CNCM 1-4122, CNCM 1-4080 and CNCM 1-4081 disclosed in US 20120039906, the entire disclosures of which are hereby incorporated by reference.

In some embodiments, the targeting moiety comprises a VHH directed against PD-L1 disclosed, in U.S. Pat. No. 8,907,065 and WO 2008/071447, the entire disclosures of which are hereby incorporated by reference. By way of example, but not by way of limitation, in some embodiments, the VHHs against PD-L1 comprise one or more of the following sequences in U.S. Pat. No. 8,907,065: (SEQ ID NO: 788); (SEQ ID NO: 789); (SEQ ID NO: 790); (SEQ ID NO: 791); (SEQ ID NO: 792); and (SEQ ID NO: 793).

In some embodiments, the present multi-specific FAP binding agent has one or more targeting moieties directed against PD-L2. In some embodiments, the FAP binding agent has one or more targeting moieties that selectively bind a PD-L2 polypeptide. In some embodiments, the FAP binding agent comprises one or more antibodies, antibody derivatives or formats, peptides or polypeptides, or fusion proteins that selectively bind a PD-L2 polypeptide.

In some embodiments, the targeting moiety comprises a VHH directed against PD-L2 disclosed in U.S. Pat. No. 8,907,065 and WO 2008/071447, the entire disclosures of which are hereby incorporated by reference. By way of example, but not by way of limitation, in some embodiments, the VHHs against PD-1 comprise one or more of the following sequences in U.S. Pat. No. 8,907,065: (SEQ ID NO: 794); (SEQ ID NO: 795); (SEQ ID NO: 796); (SEQ ID NO: 797); (SEQ ID NO: 798); (SEQ ID NO: 799); and (SEQ ID NO: 800).

In some embodiments, the targeting moiety comprises any one of the anti-PD-L2 antibodies disclosed in US2011/0271358 and WO2010/036959, the entire contents of which are hereby incorporated by reference. By way of example, but not by way of limitation, in some embodiments, the antibody or an antigen-binding fragment thereof for use in the methods provided herein comprises a heavy chain comprising one or more amino acid sequences selected from the following sequences in US 2011/0271358: (SEQ ID NO: 801); (SEQ ID NO: 802); (SEQ ID NO: 803); (SEQ ID NO: 804); or (SEQ ID NO: 805); and/or a light chain comprising one or more amino acid sequences selected from the following sequences in US 2011/0271358: (SEQ ID NO: 806); (SEQ ID NO: 807); (SEQ ID NO: 808); or (SEQ ID NO: 809).

In some embodiments, the targeting moieties of the present technology comprises a sequence that targets PD-1, PD-L1, and/or PD-L2 that is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to any of the sequences disclosed herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, about 99% or about 100% sequence identity with any of the sequences disclosed herein).

In some embodiments, the targeting moieties of the present technology comprise any combination of heavy chain, light chain, heavy chain variable region, light chain variable region, complementarity determining region (CDR), and framework region sequences that target PD-1, PD-L1, and/or PD-L2 as disclosed herein.

In some embodiments, the targeting moiety is one or more antibodies, antibody derivatives or formats, peptides or polypeptides, or fusion proteins that selectively bind or target PD-1, PD-L1 and/or PD-L2 disclosed in WO 2011/066389, US 2008/0025980, US 2013/0034559, U.S. Pat. No. 8,779,108, US 2014/0356353, U.S. Pat. No. 8,609,089, US 2010/028330, US 2012/0114649, WO 2010/027827, WO 2011/066342, U.S. Pat. No. 8,907,065, WO 2016/062722, WO 2009/101611, WO2010/027827, WO 2011/066342, WO 2007/005874, WO 2001/014556, US2011/0271358, WO 2010/036959, WO 2010/077634, U.S. Pat. No. 8,217,149, US 2012/0039906, WO 2012/145493, US 2011/0318373, U.S. Pat. No. 8,779,108, US 20140044738, WO 2009/089149, WO 2007/00587, WO 2016061142, WO 2016,02263, WO 2010/077634, and WO 2015/112900, the entire disclosures of which are hereby incorporated by reference.

In some embodiments, the multi-specific FAP binding agent of the present technology comprises a targeting moiety having an antigen recognition domain that specifically binds to XCR1, e.g. on dendritic cells. In some embodiments, the multi-specific FAP binding agent of the present technology comprises a targeting moiety having an antigen recognition domain that comprise all of or part of XCL1.

In some embodiments, the multi-specific FAP binding agents have targeting moieties having recognition domains which specifically bind to a target (e.g. antigen, receptor) that is part of a non-cellular structure. In some embodiments, the antigen or receptor is not an integral component of an intact cell or cellular structure. In some embodiments, the antigen or receptor is an extracellular antigen or receptor. In some embodiments, the target is a non-proteinaceous, non-cellular marker, including, without limitation, nucleic acids, inclusive of DNA or RNA, such as, for example, DNA released from necrotic tumor cells or extracellular deposits such as cholesterol.

In some embodiments, the target (e.g. antigen, receptor) of interest is part of the non-cellular component of the stroma or the extracellular matrix (ECM) or the markers associated therewith. As used herein, stroma refers to the connective and supportive framework of a tissue or organ. Stroma may include a compilation of cells such as fibroblasts/myofibroblasts, glial, epithelia, fat, immune, vascular, smooth muscle, and immune cells along with the extracellular matrix (ECM) and extracellular molecules. In some embodiments, the target (e.g. antigen, receptor) of interest is part of the non-cellular component of the stroma such as the extracellular matrix and extracellular molecules. As used herein, the ECM refers to the non-cellular components present within all tissues and organs. The ECM is composed of a large collection of biochemically distinct components including, without limitation, proteins, glycoproteins, proteoglycans, and polysaccharides. These components of the ECM are usually produced by adjacent cells and secreted into the ECM via exocytosis. Once secreted, the ECM components often aggregate to form a complex network of macromolecules. In some embodiments, the chimeric protein of the present technology comprises a targeting moiety that recognizes a target (e.g., an antigen or receptor or non-proteinaceous molecule) located on any component of the ECM. Illustrative components of the ECM include, without limitation, the proteoglycans, the non-proteoglycan polysaccharides, fibers, and other ECM proteins or ECM non-proteins, e.g. polysaccharides and/or lipids, or ECM associated molecules (e.g. proteins or non-proteins, e.g. polysaccharides, nucleic acids and/or lipids).

In some embodiments, the targeting moiety recognizes a target (e.g. antigen, receptor) on ECM proteoglycans. Proteoglycans are glycosylated proteins. The basic proteoglycan unit includes a core protein with one or more covalently attached glycosaminoglycan (GAG) chains. Proteoglycans have a net negative charge that attracts positively charged sodium ions (Na+), which attracts water molecules via osmosis, keeping the ECM and resident cells hydrated. Proteoglycans may also help to trap and store growth factors within the ECM. Illustrative proteoglycans that may be targeted by the chimeric proteins of the present technology include, but are not limited to, heparan sulfate, chondroitin sulfate, and keratan sulfate. In an embodiment, the targeting moiety recognizes a target (e.g. antigen, receptor) on non-proteoglycan polysaccharides such as hyaluronic acid.

In some embodiments, the targeting moiety recognizes a target (e.g. antigen, receptor) on ECM fibers. ECM fibers include collagen fibers and elastin fibers. In some embodiments, the targeting moiety recognizes one or more epitopes on collagens or collagen fibers. Collagens are the most abundant proteins in the ECM. Collagens are present in the ECM as fibrillar proteins and provide structural support to resident cells. In one or more embodiments, the targeting moiety recognizes and binds to various types of collagens present within the ECM including, without limitation, fibrillar collagens (types I, II, III, V, XI), facit collagens (types IX, XII, XIV), short chain collagens (types VIII, X), basement membrane collagens (type IV), and/or collagen types VI, VII, or XIII. Elastin fibers provide elasticity to tissues, allowing them to stretch when needed and then return to their original state. In some embodiments, the target moiety recognizes one or more epitopes on elastins or elastin fibers.

In some embodiments, the targeting moiety recognizes one or more ECM proteins including, but not limited to, a tenascin, a fibronectin, a fibrin, a laminin, or a nidogen/entactin.

In some embodiments, the targeting moiety recognizes and binds to tenascin. The tenascin (TN) family of glycoproteins includes at least four members, tenascin-C, tenascin-R, tenascin-X, and tenascin W. The primary structures of tenascin proteins include several common motifs ordered in the same consecutive sequence: amino-terminal heptad repeats, epidermal growth factor (EGF)-like repeats, fibronectin type III domain repeats, and a carboxyl-terminal fibrinogen-like globular domain. Each protein member is associated with typical variations in the number and nature of EGF-like and fibronectin type III repeats. Isoform variants also exist particularly with respect to tenascin-C. Over 27 splice variants and/or isoforms of tenascin-C are known. In a particular embodiment, the targeting moiety recognizes and binds to tenascin-CA1. Similarly, tenascin-R also has various splice variants and isoforms. Tenascin-R usually exists as dimers or trimers. Tenascin-X is the largest member of the tenascin family and is known to exist as trimers. Tenascin-W exists as trimers. In some embodiments, the targeting moiety recognizes one or more epitopes on a tenascin protein. In some embodiments, the targeting moiety recognizes the monomeric and/or the dimeric and/or the trimeric and/or the hexameric forms of a tenascin protein.

In an embodiment, the targeting moieties recognize and bind to fibronectin. Fibronectins are glycoproteins that connect cells with collagen fibers in the ECM, allowing cells to move through the ECM. Upon binding to integrins, fibronectins unfold to form functional dimers. In some embodiments, the targeting moiety recognizes the monomeric and/or the dimeric forms of fibronectin. In some embodiments, the targeting moiety recognizes one or more epitopes on fibronectin. By way of example, but not by way of limitation, in some embodiments, the targeting moiety recognizes fibronectin extracellular domain A (EDA) or fibronectin extracellular domain B (EDB). Elevated levels of EDA are associated with various diseases and disorders including psoriasis, rheumatoid arthritis, diabetes, and cancer. In some embodiments, the targeting moiety recognizes fibronectin that contains the EDA isoform and may be utilized to target the chimeric protein to diseased cells including cancer cells. In some embodiments, the targeting moiety recognizes fibronectin that contains the EDB isoform. In some embodiments, such targeting moieties may be utilized to target the chimeric protein to tumor cells including the tumor neovasculature.

In some embodiments, the targeting moiety recognizes and binds to fibrin. Fibrin is another protein substance often found in the matrix network of the ECM. Fibrin is formed by the action of the protease thrombin on fibrinogen which causes the fibrin to polymerize. In some embodiments, the targeting moiety recognizes one or more epitopes on fibrin. In some embodiments, the targeting moiety recognizes the monomeric as well as the polymerized forms of fibrin.

In some embodiments, the targeting moiety recognizes and binds to laminin. Laminin is a major component of the basal lamina, which is a protein network foundation for cells and organs. Laminins are heterotrimeric proteins that contain an a-chain, a 3-chain, and a y-chain. In some embodiments, the targeting moiety recognizes one or more epitopes on laminin. In some embodiments, the targeting moiety recognizes the monomeric, the dimeric as well as the trimeric forms of laminin.

In some embodiments, the targeting moiety recognizes and binds to a nidogen or entactin. Nidogens/entactins are a family of highly conserved, sulfated glycoproteins. They make up the major structural component of the basement membranes and function to link laminin and collagen IV networks in basement membranes. Members of this family include nidogen-1 and nidogen-2. In some embodiments, the targeting moiety recognizes an epitope on nidogen-1 and/or nidogen-2.

In some embodiments, the targeting moiety comprises an antigen recognition domain that recognizes an epitope present on any of the targets (e.g., ECM proteins) described herein. In some embodiments, the antigen-recognition domain recognizes one or more linear epitopes present on the protein. As used herein, a linear epitope refers to any continuous sequence of amino acids present on the protein. In another embodiment, the antigen-recognition domain recognizes one or more conformational epitopes present on the protein. As used herein, a conformation epitope refers to one or more sections of amino acids (which may be discontinuous) that form a three-dimensional surface with features and/or shapes and/or tertiary structures capable of being recognized by an antigen recognition domain.

In some embodiments, the targeting moiety binds to the full-length and/or mature forms and/or isoforms and/or splice variants and/or fragments and/or any other naturally occurring or synthetic analogs, variants, or mutants of any of the targets (e.g., ECM proteins) described herein. In some embodiments, the targeting moiety may bind to any forms of the proteins described herein, including monomeric, dimeric, trimeric, tetrameric, heterodimeric, multimeric and associated forms. In some embodiments, the targeting moiety may bind to any post-translationally modified forms of the proteins described herein, such as glycosylated and/or phosphorylated forms.

In some embodiments, the targeting moiety comprises an antigen recognition domain that recognizes extracellular molecules such as DNA. In some embodiments, the targeting moiety comprises an antigen recognition domain that recognizes DNA. In some embodiments, the DNA is shed into the extracellular space from necrotic or apoptotic tumor cells or other diseased cells.

In some embodiments, the targeting moiety comprises an antigen recognition domain that recognizes one or more non-cellular structures associated with atherosclerotic plaques. Two types of atherosclerotic plaques are known. The fibro-lipid (fibro-fatty) plaque is characterized by an accumulation of lipid-laden cells underneath the intima of the arteries. Beneath the endothelium there is a fibrous cap covering the atheromatous core of the plaque. The core includes lipid-laden cells (macrophages and smooth muscle cells) with elevated tissue cholesterol and cholesterol ester content, fibrin, proteoglycans, collagen, elastin, and cellular debris. In advanced plaques, the central core of the plaque usually contains extracellular cholesterol deposits (released from dead cells), which form areas of cholesterol crystals with empty, needle-like clefts. At the periphery of the plaque are younger foamy cells and capillaries. A fibrous plaque is also localized under the intima, within the wall of the artery resulting in thickening and expansion of the wall and, sometimes, spotty localized narrowing of the lumen with some atrophy of the muscular layer. The fibrous plaque contains collagen fibers (eosinophilic), precipitates of calcium (hematoxylinophilic) and lipid-laden cells. In some embodiments, the targeting moiety recognizes and binds to one or more of the non-cellular components of these plaques such as the fibrin, proteoglycans, collagen, elastin, cellular debris, and calcium or other mineral deposits or precipitates. In some embodiments, the cellular debris is a nucleic acid, e.g. DNA or RNA, released from dead cells.

In some embodiments, the targeting moiety comprises an antigen recognition domain that recognizes one or more non-cellular structures found in the brain plaques associated with neurodegenerative diseases. In some embodiments, the targeting moiety recognizes and binds to one or more non-cellular structures located in the amyloid plaques found in the brains of patients with Alzheimer's disease. For example, the targeting moiety may recognize and bind to the peptide amyloid beta, which is a major component of the amyloid plaques. In some embodiments, the targeting moiety recognizes and binds to one or more non-cellular structures located in the brains plaques found in patients with Huntington's disease. In some embodiments, the targeting moiety recognizes and binds to one or more non-cellular structures found in plaques associated with other neurodegenerative or musculoskeletal diseases such as Lewy body dementia and inclusion body myositis.

Linkers and Functional Groups

In some embodiments, the FAP binding agent may include one or more functional groups, residues, or moieties. In some embodiments, the one or more functional groups, residues, or moieties are attached or genetically fused to any of the signaling agents or targeting moieties described herein. In some embodiments, such functional groups, residues or moieties confer one or more desired properties or functionalities to the FAP binding agent of the present technology. Examples of such functional groups and of techniques for introducing them into the FAP binding agent are known in the art, for example, see Remington's Pharmaceutical Sciences, 16th ed., Mack Publishing Co., Easton, Pa. (1980).

In some embodiments, the FAP binding agent may by conjugated and/or fused with another agent to extend half-life or otherwise improve pharmacodynamic and pharmacokinetic properties. In some embodiments, the FAP binding agent may be fused or conjugated with one or more of PEG, XTEN (e.g., as rPEG), polysialic acid (POLYXEN), albumin (e.g., human serum albumin or HAS), elastin-like protein (ELP), PAS, HAP, GLK, CTP, transferrin, and the like. In some embodiments, the FAP binding agent may be fused or conjugated with an antibody or an antibody fragment such as an Fc fragment. For example, the chimeric protein may be fused to either the N-terminus or the C-terminus of the Fc domain of human immunoglobulin (Ig) G. In some embodiments, each of the individual chimeric proteins is fused to one or more of the agents described in BioDrugs (2015) 29:215-239, the entire contents of which are hereby incorporated by reference.

In some embodiments, the functional groups, residues, or moieties comprise a suitable pharmacologically acceptable polymer, such as poly(ethyleneglycol) (PEG) or derivatives thereof (such as methoxypoly(ethyleneglycol) or mPEG). In some embodiments, attachment of the PEG moiety increases the half-life and/or reduces the immunogenecity of the FAP binding protein. Generally, any suitable form of pegylation can be used, such as the pegylation used in the art for antibodies and antibody fragments (including but not limited to single domain antibodies such as VHHs); see, for example, Chapman, Nat. Biotechnol., 54, 531-545 (2002); by Veronese and Harris, Adv. Drug Deliv. Rev. 54, 453-456 (2003), by Harris and Chess, Nat. Rev. Drug. Discov., 2, (2003) and in WO04060965, the entire contents of which are hereby incorporated by reference. Various reagents for pegylation of proteins are also commercially available, for example, from Nektar Therapeutics, USA. In some embodiments, site-directed pegylation is used, in particular via a cysteine-residue (see, for example, Yang et al., Protein Engineering, 16, 10, 761-770 (2003), the entire contents of which is hereby incorporated by reference). For example, for this purpose, PEG may be attached to a cysteine residue that naturally occurs in the FAP binding agent of the present technology. In some embodiments, the FAP binding agent of the present technology is modified so as to suitably introduce one or more cysteine residues for attachment of PEG, or an amino acid sequence comprising one or more cysteine residues for attachment of PEG may be fused to the amino- and/or carboxy-terminus of the FAP binding agent, using techniques known in the art.

In some embodiments, the functional groups, residues, or moieties comprise N-linked or O-linked glycosylation. In some embodiments, the N-linked or O-linked glycosylation is introduced as part of a co-translational and/or post-translational modification.

In some embodiments, the functional groups, residues, or moieties comprise one or more detectable labels or other signal-generating groups or moieties. Suitable labels and techniques for attaching, using and detecting them are known in the art and, include, but are not limited to, fluorescent labels (such as fluorescein, isothiocyanate, rhodamine, phycoerythrin, phycocyanin, allophycocyanin, o-phthaldehyde, and fluorescamine and fluorescent metals such as Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes, metals, metals chelates or metallic cations or other metals or metallic cations that are particularly suited for use in vivo, in vitro, or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels include moieties that can be detected using NMR or ESR spectroscopy. Such labeled VHHs and polypeptides of the present technology may, for example, be used for in vitro, in vivo, or in situ assays (including immunoassays known per se such as ELISA, RIA, EIA and other "sandwich assays," etc.) as well as in vivo diagnostic and imaging purposes, depending on the choice of the specific label.

In some embodiments, the functional groups, residues, or moieties comprise a tag that is attached or genetically fused to the FAP binding agent. In some embodiments, the FAP binding agent may include a single tag or multiple tags. The tag for example is a peptide, sugar, or DNA molecule that does not inhibit or prevent binding of the FAP binding agent to FAP or any other antigen of interest such as tumor antigens. In some embodiments, the tag is at least about: three to five amino acids long, five to eight amino acids long, eight to twelve amino acids long, twelve to fifteen amino acids long, or fifteen to twenty amino acids long. Illustrative tags are described for example, in U.S. Patent Publication No. US2013/0058962. In some embodiment, the tag is an affinity tag such as glutathione-S-transferase (GST) and histidine (His) tag. In an embodiment, the FAP binding agent comprises a His tag.

In some embodiments, the functional groups, residues, or moieties comprise a chelating group, for example, to chelate one of the metals or metallic cations. By way of example, but not by way of limitation, in some embodiments, the chelating groups are diethyl-enetriaminepentaacetic acid (DTPA) or ethylenediaminetetraacetic acid (EDTA).

In some embodiments, the functional groups, residues, or moieties comprise a functional group that is one part of a specific binding pair, such as the biotin-(strept)avidin binding pair. Such a functional group may be used to link the FAP binding agent of the present technology to another protein, polypeptide or chemical compound that is bound to the other half of the binding pair, i.e., through formation of the binding pair. For example, in some embodiments, a FAP binding agent of the present technology may be conjugated to biotin, and linked to another protein, polypeptide, compound or carrier conjugated to avidin or streptavidin. For example, such a conjugated FAP binding agent may be used as a reporter, for example, in a diagnostic system where a detectable signal-producing agent is conjugated to avidin or streptavidin. Such binding pairs may, for example, also be used to bind the FAP binding agent to a carrier, including carriers suitable for pharmaceutical purposes. One non-limiting example are the liposomal formulations described by Cao and Suresh, Journal of Drug Targeting, 8, 4, 257 (2000). Such binding pairs may also be used to link a therapeutically active agent to the FAP binding agent of the present technology.

In some embodiments, the present FAP binding agent optionally comprises one or more linkers. In some embodiments, the FAP binding agent includes a linker that connects each binding region and/or targeting moieties. In some embodiments, the FAP binding agent includes a linker that connects each signaling agent and targeting moiety (or, if more than one targeting moiety, a signaling agent to one of the targeting moieties). In some embodiments, the linker may be utilized to link various functional groups, residues, or moieties as described herein to the FAP binding agent. In some embodiments, the linker is a single amino acid or a plurality of amino acids that does not affect or reduce the stability, orientation, binding, neutralization, and/or clearance characteristics of the binding regions and the binding protein. In some embodiments, the linker is selected from a peptide, a protein, a sugar, or a nucleic acid.

In some embodiments, the present FAP binding agent comprises a linker connecting the targeting moiety and the signaling agent. In some embodiments, the present chimeric protein comprises a linker within the signaling agent (e.g. in the case of single chain TNF, which can comprise two linkers to yield a trimer).

The present technology contemplates the use of a variety of linker sequences. In some embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et al., (2000), Protein Eng. 13(5):309-312, the entire contents of which are hereby incorporated by reference. In some embodiments, the linker may be functional. For example, without limitation, the linker may function to improve the folding and/or stability, improve the expression, improve the pharmacokinetics, and/or improve the bioactivity of the present FAP binding agent.

In some embodiments, the linker is a polypeptide. In some embodiments, the linker is less than about 100 amino acids long. For example, in some embodiments, the linker is less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is a polypeptide. In some embodiments, the linker is greater than about 100 amino acids long. For example, in some embodiments, the linker is greater than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is flexible. In another embodiment, the linker is rigid.

In some embodiments, the linker length allows for efficient binding of a targeting moiety and the signaling agent to their receptors. For instance, in some embodiments, the linker length allows for efficient binding of one of the targeting moieties and the signaling agent to receptors on the same cell as well as the efficient binding of the other targeting moiety to another cell. Illustrative pairs of cells are provided elsewhere herein.

In some embodiments, the linker length is at least equal to the minimum distance between the binding sites of one of the targeting moieties and the signaling agent to receptors on the same cell. In some embodiments, the linker length is at least twice, or three times, or four times, or five times, or ten times, or twenty times, or 25 times, or 50 times, or one hundred times, or more the minimum distance between the binding sites of one of the targeting moieties and the signaling agent to receptors on the same cell.

In some embodiments, a linker connects the two targeting moieties to each other and this linker has a short length and a linker connects a targeting moiety and a signaling agent this linker is longer than the linker connecting the two targeting moieties. For example, in some embodiments, the difference in amino acid length between the linker connecting the two targeting moieties and the linker connecting a targeting moiety and a signaling agent may be about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids. In some embodiments, the linker is flexible. In another embodiment, the linker is rigid.

In some embodiments, the linker is substantially comprised of glycine and serine residues (e.g. about 30%, or about 40%, or about 50%, or about 60%, or about 70%, or about 80%, or about 90%, or about 95%, or about 97% glycines and serines). For example, in some embodiments, the linker is $(Gly4Ser)_n$, where n is from about 1 to about 8, e.g. 1, 2, 3, 4, 5, 6, 7, or 8 (SEQ ID NO: 810 to SEQ ID NO: 817). In some embodiments, the linker sequence is GGSGGSGGGGSGGGGS (SEQ ID NO: 818). In some embodiments, the linkers include, but are not limited to, linkers having the sequence LE, GGGGS (SEQ ID NO: 810), $(GGGGS)_n$ (n=1-4) (SEQ ID NO: 810-813), $(Gly)_8$ (SEQ ID NO: 819), $(Gly)_6$ (SEQ ID NO: 820), $(EAAAK)_n$ (n=1-3) (SEQ ID NO: 821-823):, $A(EAAAK)_nA$ (n=2-5) (SEQ ID NO: 824-827), AEAAAKEAAAKA (SEQ ID NO: 824), $A(EAAAK)_4ALEA(EAAAK)_4A$ (SEQ ID NO: 828), PAPAP (SEQ ID NO: 829), KESGSVSSEQLAQFRSLD (SEQ ID NO: 830), EGKSSGSGSESKST (SEQ ID NO: 831), GSAGSAAGSGEF (SEQ ID NO: 832), and $(XP)_n$, with X designating any amino acid, e.g., Ala, Lys, or Glu. In some embodiments, the linker is GGS.

In some embodiments, the linker is one or more of GGGSE (SEQ ID NO: 833), GSESG (SEQ ID NO: 834), GSEGS (SEQ ID NO: 835), GEGGSGEGSSGEGSSSEGGGSEGGGSEGGGSEGGS (SEQ ID NO: 836), and a linker of randomly placed G, S, and E every 4 amino acid intervals.

In some embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). In some embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). Without wishing to be bound by theory, in some embodiments, the hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges.

IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2.

According to crystallographic studies, the immunoglobulin hinge region can be further subdivided functionally into three regions: the upper hinge region, the core region, and the lower hinge region. See Shin et al., 1992 Immunological Reviews 130:87. The upper hinge region includes amino acids from the carboxyl end of CH, to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the CH2 domain and includes residues in CH2. The core hinge region of wild-type human IgG1 contains the sequence Cys-Pro-Pro-Cys, which, when dimerized by disulfide bond formation, results in a cyclic octapeptide believed to act as a pivot, thus conferring flexibility. In some embodiments, the present linker comprises, one, or two, or three of the upper hinge region, the core region, and the lower hinge region of any antibody (e.g., of IgG, IgA, IgD, and IgE, inclusive of subclasses (e.g. IgG1, IgG2, IgG3, and IgG4, and IgA1 and IgA2)). The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin. In some embodiments, the linker of the present technology comprises one or more glycosylation sites. In some embodiments, the linker is a hinge-CH2-CH3 domain of a human IgG4 antibody.

In some embodiments, the present FAP binding agent is linked to an antibody Fc region, comprising one or both of CH2 and CH3 domains, and optionally a hinge region. For example, vectors encoding the present FAP binding agents linked as a single nucleotide sequence to an Fc region can be used to prepare such polypeptides.

In some embodiments, the linker is a synthetic linker such as PEG.

In some embodiments, the linker may be functional. For example, in some embodiments, the linker functions to improve the folding and/or stability, improve the expression, improve the pharmacokinetics, and/or improve the bioactivity of the present FAP binding agent. In another example, the linker may function to target the FAP binding agent to a particular cell type or location.

Modifications and Production of FAP Binding Agents

In some embodiments, the FAP binding agent comprises a targeting moiety that is a VHH. In some embodiments, the VHH is not limited to a specific biological source or to a specific method of preparation. For example, the VHH can generally be obtained: (1) by isolating the VHH domain of a naturally occurring heavy chain antibody; (2) by expression of a nucleotide sequence encoding a naturally occurring VHH domain; (3) by "humanization" of a naturally occurring VHH domain or by expression of a nucleic acid encoding a such humanized VHH domain; (4) by "camelization" of a naturally occurring VH domain from any animal species, such as from a mammalian species, such as from a human being, or by expression of a nucleic acid encoding such a camelized VH domain; (5) by "camelization" of a "domain antibody" or "Dab" as described in the art, or by expression of a nucleic acid encoding such a camelized VH domain; (6) by using synthetic or semi-synthetic techniques for preparing proteins, polypeptides or other amino acid sequences known in the art; (7) by preparing a nucleic acid encoding a VHH using techniques for nucleic acid synthesis known in the art, followed by expression of the nucleic acid thus obtained; and/or (8) by any combination of one or more of the foregoing.

In an embodiment, the FAP binding agent comprises a VHH that corresponds to the VHH domains of naturally occurring heavy chain antibodies directed against human FAP. In some embodiments, such VHH sequences can generally be generated or obtained by suitably immunizing a species of Camelid with a FAP molecule, (i.e., so as to raise an immune response and/or heavy chain antibodies directed against FAP), by obtaining a suitable biological sample from the Camelid (such as a blood sample, or any sample of B-cells), and by generating VHH sequences directed against FAP, starting from the sample, using any suitable known techniques. In some embodiments, naturally occurring VHH domains against FAP can be obtained from naive libraries of Camelid VHH sequences, for example, by screening such a library using FAP or at least one part, fragment, antigenic determinant or epitope thereof using one or more screening techniques known in the art. Such libraries and techniques are, for example, described in WO 9937681, WO 0190190, WO 03025020 and WO 03035694, the entire contents of which are hereby incorporated by reference. In some embodiments, improved synthetic or semi-synthetic libraries derived from naive VHH libraries may be used, such as VHH libraries obtained from naive VHH libraries by techniques such as random mutagenesis and/or CDR shuffling, as for example, described in WO 0043507, the entire contents of which are hereby incorporated by reference. In some embodiments, another technique for obtaining VHH sequences directed against a FAP involves suitably immunizing a transgenic mammal that is capable of expressing heavy chain antibodies (i.e., so as to raise an immune response and/or heavy chain antibodies directed against FAP), obtaining a suitable biological sample from the transgenic mammal (such as a blood sample, or any sample of B-cells), and then generating VHH sequences directed against FAP starting from the sample, using any suitable known techniques. For example, for this purpose, the heavy chain antibody-expressing mice and the further methods and techniques described in WO 02085945 and in WO 04049794 (the entire contents of which are hereby incorporated by reference) can be used.

In an embodiment, the FAP binding agent comprises a VHH that has been "humanized" i.e., by replacing one or more amino acid residues in the amino acid sequence of the naturally occurring VHH sequence (and in particular in the framework sequences) by one or more of the amino acid residues that occur at the corresponding position(s) in a VH domain from a conventional 4-chain antibody from a human being. This can be performed using humanization techniques known in the art. In some embodiments, possible humanizing substitutions or combinations of humanizing substitutions may be determined by methods known in the art, for example, by a comparison between the sequence of a VHH and the sequence of a naturally occurring human VH domain. In some embodiments, the humanizing substitutions are chosen such that the resulting humanized VHHs still retain advantageous functional properties. Generally, as a result of humanization, the VHHs of the present technology may become more "human-like," while still retaining favorable properties such as a reduced immunogenicity, compared to the corresponding naturally occurring VHH domains. In some embodiments, the humanized VHHs of the present technology can be obtained in any suitable manner known in the art and thus are not strictly limited to polypeptides that have been obtained using a polypeptide that comprises a naturally occurring VHH domain as a starting material.

In some embodiments, the FAP binding agent comprises a VHH that has been "camelized," i.e., by replacing one or more amino acid residues in the amino acid sequence of a naturally occurring VH domain from a conventional 4-chain antibody by one or more of the amino acid residues that occur at the corresponding position(s) in a VHH domain of a heavy chain antibody of a camelid. In some embodiments, such "camelizing" substitutions are inserted at amino acid positions that form and/or are present at the VH-VL interface, and/or at the so-called Camelidae hallmark residues (see, for example, WO 9404678, the entire contents of which are hereby incorporated by reference). In some embodiments, the VH sequence that is used as a starting material or starting point for generating or designing the camelized VHH is a VH sequence from a mammal, for example, the VH sequence of a human being, such as a VH3 sequence. In some embodiments, the camelized VHHs can be obtained in any suitable manner known in the art (i.e., as indicated under points (1)-(8) above) and thus are not strictly limited to polypeptides that have been obtained using a polypeptide that comprises a naturally occurring VH domain as a starting material.

In some embodiments, both "humanization" and "camelization" can be performed by providing a nucleotide sequence that encodes a naturally occurring VHH domain or VH domain, respectively, and then changing, in a manner known in the art, one or more codons in the nucleotide sequence in such a way that the new nucleotide sequence encodes a "humanized" or "camelized" VHH, respectively. This nucleic acid can then be expressed in a manner known in the art, so as to provide the desired VHH of the present technology. Alternatively, based on the amino acid sequence of a naturally occurring VHH domain or VH domain, respectively, the amino acid sequence of the desired humanized or camelized VHH of the present technology, respectively, can be designed and then synthesized de novo using techniques for peptide synthesis known in the art. Also, based on the amino acid sequence or nucleotide sequence of a naturally occurring VHH domain or VH domain, respectively, a nucleotide sequence encoding the desired humanized or camelized VHH, respectively, can be designed and then synthesized de novo using techniques for nucleic acid synthesis known in the art, after which the nucleic acid thus obtained can be expressed in a manner known in the art, so as to provide the desired VHH of the present technology. Other suitable methods and techniques for obtaining the VHHs of the present technology and/or nucleic acids encoding the same, starting from naturally occurring VH sequences or VHH sequences, are known in the art, and may, for example, comprise combining one or more parts of one or more naturally occurring VH sequences (such as one or more FR sequences and/or CDR sequences), one or more parts of one or more naturally occurring VHH sequences (such as one or more FR sequences or CDR sequences), and/or one or more synthetic or semi-synthetic sequences, in a suitable manner, so as to provide a VHH of the present technology or a nucleotide sequence or nucleic acid encoding the same.

Methods for producing the FAP binding agents of the present technology are described herein. For example, DNA sequences encoding the FAP binding agents of the present technology can be chemically synthesized using methods known in the art. Synthetic DNA sequences can be ligated to other appropriate nucleotide sequences, including, e.g., expression control sequences, to produce gene expression constructs encoding the desired FAP binding agents. Accordingly, in some embodiments, the present technology provides for isolated nucleic acids comprising a nucleotide sequence encoding the FAP binding agent of the present technology.

Nucleic acids encoding the FAP binding agent of the present technology can be incorporated (ligated) into expression vectors, which can be introduced into host cells through transfection, transformation, or transduction techniques. For example, nucleic acids encoding the FAP binding agent of the present technology can be introduced into host cells by retroviral transduction. Illustrative host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells. Transformed host cells can be grown under conditions that permit the host cells to express the genes that encode the FAP binding agent of the present technology. Accordingly, in some embodiments, the present technology provides expression vectors comprising nucleic acids that encode the FAP binding agent of the present technology. In some embodiments, the present technology additional provides host cells comprising such expression vectors.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. In another example, if the engineered gene is to be expressed in eukaryotic host cells, e.g., CHO cells, it is first inserted into an expression vector containing for example, a suitable eukaryotic promoter, a secretion signal, enhancers, and various introns. The gene construct can be introduced into the host cells using transfection, transformation, or transduction techniques.

The FAP binding agent of the present technology can be produced by growing a host cell transfected with an expression vector encoding the FAP binding agent under conditions that permit expression of the protein. Following expression, the protein can be harvested and purified using techniques well known in the art, e.g., affinity tags such as glutathione-S-transferase (GST) and histidine (His) tags or by chromatography. In an embodiment, the FAP binding agent comprises a His tag. In some embodiments, the FAP binding agent comprises a His tag and a proteolytic site to allow cleavage of the His tag.

Accordingly, in some embodiments, the present technology provides for a nucleic acid encoding a FAP binding agent of the present technology. In some embodiments, the present technology provides for a host cell comprising a nucleic acid encoding a FAP binding agent of the present technology.

In some embodiments, the present FAP binding agent or chimeric protein comprising the same may be expressed in vivo, for instance, in a patient. For example, in some embodiments, the present FAP binding agent or chimeric protein comprising the same may administered in the form of nucleic acid which encodes the present FAP binding agents or chimeric proteins comprising the same. In some embodiments, the nucleic acid is DNA or RNA. In some embodiments, present FAP binding agent or chimeric protein comprising the same is encoded by a modified mRNA, i.e. an mRNA comprising one or more modified nucleotides. In some embodiments, the modified mRNA comprises one or modifications found in U.S. Pat. No. 8,278,036, the entire contents of which are hereby incorporated by reference. In some embodiments, the modified mRNA comprises one or more of m5C, m5U, m6A, s2U, ψ, and 2'-O-methyl-U. In some embodiments, the present technology relates to administering a modified mRNA encoding one or more of the present chimeric proteins. In some embodiments, the present technology relates to gene therapy vectors comprising the same. In some embodiments, the present technology relates to gene therapy methods comprising the same. In some embodiments, the nucleic acid is in the form of an oncolytic virus, e.g. an adenovirus, reovirus, measles, herpes simplex, Newcastle disease virus or vaccinia.

Pharmaceutically Acceptable Salts and Excipients

The FAP binding agents (and/or any other therapeutic agents) described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, Journal of Pharmaceutical Science, 66, 2-19 (1977) and The Handbook of Pharmaceutical Salts; Properties, Selection, and Use. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, a-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term “pharmaceutically acceptable salt” also refers to a salt of the compositions of the present technology having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-0H-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl) amine; N-methyl-D-glucamine; and amino acids such as arginine, lysine, and the like.

In some embodiments, the compositions described herein are in the form of a pharmaceutically acceptable salt.

Pharmaceutical Compositions and Formulations

In some embodiments, the present technology pertains to pharmaceutical compositions comprising the FAP binding agents (and/or any other therapeutic agents) described herein and a pharmaceutically acceptable carrier or excipient. In some embodiments, the present technology pertains to pharmaceutical compositions comprising the present FAP binding agents. In another embodiment, the present technology pertains to pharmaceutical compositions comprising any other therapeutic agents described herein. In a further embodiment, the present technology pertains to pharmaceutical compositions comprising a combination of the present FAP binding agents and any other therapeutic agents described herein. Any pharmaceutical compositions described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

In some embodiments, pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents. Other examples of suitable pharmaceutical excipients are described in Remington's Pharmaceutical Sciences 1447-1676 (Alfonso R. Gennaro eds., 19th ed. 1995), incorporated herein by reference.

The present technology includes the described pharmaceutical compositions (and/or additional therapeutic agents) in various formulations. Any inventive pharmaceutical composition (and/or additional therapeutic agents) described herein can take the form of solutions, suspensions, emulsion, drops, tablets, pills, pellets, capsules, capsules containing liquids, gelatin capsules, powders, sustained-release formulations, suppositories, emulsions, aerosols, sprays, suspensions, lyophilized powder, frozen suspension, desiccated powder, or any other form suitable for use. In one embodiment, the composition is in the form of a capsule. In another embodiment, the composition is in the form of a tablet. In yet another embodiment, the pharmaceutical composition is formulated in the form of a soft-gel capsule. In a further embodiment, the pharmaceutical composition is formulated in the form of a gelatin capsule. In yet another embodiment, the pharmaceutical composition is formulated as a liquid.

In some embodiments, the inventive pharmaceutical compositions (and/or additional agents) can also include a solubilizing agent. Also, the agents can be delivered with a suitable vehicle or delivery device as known in the art. Combination therapies outlined herein can be co-delivered in a single delivery vehicle or delivery device.

The formulations comprising the inventive pharmaceutical compositions (and/or additional agents) of the present technology may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

In some embodiments, any pharmaceutical compositions (and/or additional agents) described herein is formulated in accordance with routine procedures as a composition adapted for a mode of administration described herein.

In some embodiments, the routes of administration include, for example: oral, intradermal, intramuscular, intraperitoneal, intravenous, subcutaneous, intranasal, epidural, sublingual, intranasal, intracerebral, intravaginal, transdermal, rectally, by inhalation, or topically. Administration can be local or systemic. In some embodiments, the administering is effected orally. In another embodiment, the administration is by parenteral injection. The mode of administration can be left to the discretion of the practitioner, and depends in-part upon the site of the medical condition. In most instances, administration results in the release of any agent described herein into the bloodstream.

In some embodiments, the FAP binding agent described herein is formulated in accordance with routine procedures as a composition adapted for oral administration. By way of example, but not by way of limitation, in some embodiments, compositions for oral delivery are in the form of tablets, lozenges, aqueous or oily suspensions, granules, powders, emulsions, capsules, syrups, or elixirs. In some embodiments, orally administered compositions include one or more agents, for example, sweetening agents such as fructose, aspartame or saccharin; flavoring agents such as peppermint, oil of wintergreen, or cherry; coloring agents; and preserving agents, to provide a pharmaceutically palatable preparation. In some embodiments, the compositions, when in tablet or pill form, are coated to delay disintegration and absorption in the gastrointestinal tract thereby providing a sustained action over an extended period of time. Selectively permeable membranes surrounding an osmotically active driving any FAP binding agents described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. In some embodiments, the oral compositions include a time-delay material, such as, e.g., glycerol monostearate or glycerol stearate. In some embodiments, oral compositions include standard excipients such as mannitol, lactose, starch, magnesium stearate, sodium saccharin, cellulose, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art. Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor EL™ (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

The compositions provided herein, alone or in combination with other suitable components, can be made into aerosol formulations (i.e., "nebulized") to be administered via inhalation. Aerosol formulations can be placed into pressurized acceptable propellants, such as dichlorodifluoromethane, propane, nitrogen, and the like.

Any inventive pharmaceutical compositions (and/or additional agents) described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropyl cellulose, hydropropylmethyl cellulose, polyvinylpyrrolidone, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the agents described herein. The present technology, thus, provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, a controlled-release system can be placed in proximity of the target area to be treated, thus requiring only a fraction of the systemic dose (see, e.g., Goodson, in Medical Applications of Controlled Release, supra, vol. 2, pp. 115-138 (1984)). Other controlled-release systems discussed in the review by Langer, 1990, Science 249:1527-1533) may be used.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

Administration and Dosage

It will be appreciated that the actual dose of the FAP binding agent and/or any therapeutic agents described herein to be administered according to the present technology will vary according to the particular dosage form, and the mode of administration. Many factors that may modify the action of the FAP binding agent (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

In some embodiments, a suitable dosage of the FAP binding agent and/or any therapeutic agents described herein is in a range of about 0.01 mg/kg to about 10 g/kg of body weight of the subject, about 0.01 mg/kg to about 1 g/kg of body weight of the subject, about 0.01 mg/kg to about 100 mg/kg of body weight of the subject, about 0.01 mg/kg to about 10 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, about 100 mg/kg body weight, about 1 g/kg of body weight, about 10 g/kg of body weight, inclusive of all values and ranges therebetween.

In some embodiments, individual doses of the FAP binding agent and/or any therapeutic agents described herein are administered in unit dosage forms containing, for example, from about 0.01 mg to about 100 g, from about 0.01 mg to about 75 g, from about 0.01 mg to about 50 g, from about 0.01 mg to about 25 g, about 0.01 mg to about 10 g, about 0.01 mg to about 7.5 g, about 0.01 mg to about 5 g, about 0.01 mg to about 2.5 g, about 0.01 mg to about 1 g, about 0.01 mg to about 100 mg, from about 0.1 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg active ingredient, from about 0.1 mg to about 30 mg, from about 0.1 mg to about 20 mg, from about 0.1 mg to about 10 mg, from about 0.1 mg to about 5 mg, from about 0.1 mg to about 3 mg, from about 0.1 mg to about 1 mg per unit dosage form, or from about 5 mg to about 80 mg per unit dosage form. For example, a unit dosage form can be about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 500 mg, about 1 g, about 2.5 g, about 5 g, about 10 g, about 25 g, about 50 g, about 75 g, about 100 g, inclusive of all values and ranges therebetween.

In one embodiment, the FAP binding agent and/or any therapeutic agents described herein are administered at an amount of from about 0.01 mg to about 100 g daily, from about 0.01 mg to about 75 g daily, from about 0.01 mg to about 50 g daily, from about 0.01 mg to about 25 g daily, from about 0.01 mg to about 10 g daily, from about 0.01 mg to about 7.5 g daily, from about 0.01 mg to about 5 g daily, from about 0.01 mg to about 2.5 g daily, from about 0.01 mg to about 1 g daily, from about 0.01 mg to about 100 mg daily, from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, from about 0.1 mg to about 1 mg daily, or from about 5 mg to about 80 mg daily. In some embodiments, the FAP binding agent is administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 500 mg, about 1 g, about 2.5 g, about 5 g, about 7.5 g, about 10 g, about 25 g, about 50 g, about 75 g, about 100 g, inclusive of all values and ranges therebetween.

In accordance with certain embodiments of the present technology, the pharmaceutical composition comprising the FAP binding agent and/or any therapeutic agents described herein may be administered, for example, more than once daily (e.g., about two times, about three times, about four times, about five times, about six times, about seven times, about eight times, about nine times, or about ten times daily), about once per day, about every other day, about every third day, about once a week, about once every two weeks, about once every month, about once every two months, about once every three months, about once every six months, or about once every year.

Combination Therapy and Additional Therapeutic Agents

In some embodiments, the pharmaceutical composition of the present technology is co-administered in conjunction with one or more additional therapeutic agents. In some embodiments, co-administration can be simultaneous or sequential.

In one embodiment, the additional therapeutic agent and the FAP binding agent of the present technology are administered to a subject simultaneously. The term "simultaneously" as used herein, means that the additional therapeutic agent and the FAP binding agent are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and the FAP binding agent can be by simultaneous administration of a single formulation (e.g., a formulation comprising the additional therapeutic agent and the FAP binding agent) or of separate formulations (e.g., a first formulation including the additional therapeutic agent and a second formulation including the FAP binding agent).

Co-administration does not require the therapeutic agents to be administered simultaneously, if the timing of their administration is such that the pharmacological activities of the additional therapeutic agent and the FAP binding agent overlap in time, thereby exerting a combined therapeutic effect. For example, the additional therapeutic agent and the FAP binding agent can be administered sequentially. The term "sequentially" as used herein means that the additional therapeutic agent and the FAP binding agent are administered with a time separation of more than about 60 minutes. For example, the time between the sequential administration of the additional therapeutic agent and the FAP binding agent can be more than about 60 minutes, more than about 2 hours, more than about 5 hours, more than about 10 hours, more than about 1 day, more than about 2 days, more than about 3 days, more than about 1 week, or more than about 2 weeks, or more than about one month apart. The optimal administration times will depend on the rates of metabolism, excretion, and/or the pharmacodynamic activity of the additional therapeutic agent and the FAP binding agent being administered. Either the additional therapeutic agent or the FAP binding agent cell may be administered first.

Co-administration also does not require the therapeutic agents to be administered to the subject by the same route of administration. Rather, each therapeutic agent can be administered by any appropriate route, for example, parenterally or non-parenterally.

In some embodiments, the FAP binding agent described herein acts synergistically when co-administered with another therapeutic agent. As used herein, a "synergistically" refers to a greater-than-additive therapeutic effect, which is produced by a combination of at least two agents, and which exceeds that which would otherwise result from the individual administration of the agents. For example, lower doses of one or more agents may be used in treating a disease or disorder, resulting in increased therapeutic efficacy and decreased side-effects. In such embodiments, the FAP binding agent and the additional therapeutic agent may be administered at doses that are lower than the doses employed when the agents are used in the context of monotherapy.

In some embodiments, the present technology pertains to chemotherapeutic agents as additional therapeutic agents. For example, without limitation, such combination of the present FAP binding agents and chemotherapeutic agent find use in the treatment of cancers, as described elsewhere herein. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; toxoids (e.g., TAXOL, paclitaxel (Bristol-Myers Squibb Oncology, Princeton, N.J.), ABRAXANE®, Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France)); chloranbucil; GEMZAR (gemcitabine); 6-thioguanine; mercaptopurine; methotrexate; platinum analogs (such as, e.g., cisplatin, oxaliplatin and carboplatin); vinblastine; platinum; etoposide (VP-16); ifosfamide; mitoxantrone; vincristine; NAVELBINE (vinorelbine); novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-a, Raf, H-Ras, EGFR (e.g., erlotinib (Tarceva®)) and VEGF-A that reduce cell proliferation and pharmaceutically acceptable salts, acids or derivatives of any of the above. In addition, in some embodiments, the methods of treatment further include the use of radiation. In addition, in some embodiments, the methods of treatment further include the use of photodynamic therapy.

Accordingly, in some embodiments, the present technology relates to combination therapies using the FAP binding agent and a chemotherapeutic agent. In some embodiments, the present technology relates to administration of the FAP binding agent to a patient undergoing treatment with a chemotherapeutic agent. In some embodiments, the chemotherapeutic agent is a DNA-intercalating agent, such as, without limitation, doxorubicin, cisplatin, daunorubicin, and epirubicin. In some embodiments, the DNA-intercalating agent is doxorubicin.

In some embodiments, the FAP binding agent acts synergistically when co-administered with doxorubicin. In some embodiments, the FAP binding agent acts synergistically when co-administered with doxorubicin for use in treating tumor or cancer. For example, co-administration of the FAP binding agent and doxorubicin may act synergistically to reduce or eliminate the tumor or cancer, or slow the growth and/or progression and/or metastasis of the tumor or cancer. In some embodiments, the combination of the FAP binding agent and doxorubicin may exhibit improved safety profiles when compared to the agents used alone in the context of monotherapy. In some embodiments, the FAP binding agent and doxorubicin are administered at doses that are lower than the doses employed when the agents are used in the context of monotherapy. In some embodiments, the FAP binding agent comprises a mutated interferon such as a mutated IFNα. In some embodiments, the mutated IFNα comprises one or more mutations at positions 148, 149, and 153 with reference to SEQ ID NO: 688 or SEQ ID NO: 689, such as the substitutions M148A, R149A, and L153A.

In some embodiments, the present technology relates to combination therapy with one or more immune-modulating agents, for example, without limitation, agents that modulate immune checkpoint. In some embodiments, the immune-modulating agent targets one or more of PD-1, PD-L1, and PD-L2. In some embodiments, the immune-modulating agent is PD-1 inhibitor. In some embodiments, the immune-modulating agent is an antibody specific for one or more of PD-1, PD-L1, and PD-L2. For instance, in some embodiments, the immune-modulating agent is an antibody such as, by way of non-limitation, nivolumab, (ONO-4538/BMS-936558, MDX1106, OPDIVO, BRISTOL MYERS SQUIBB), pembrolizumab (KEYTRUDA, MERCK), pidilizumab (CT-011, CURE TECH), MK-3475 (MERCK), BMS 936559 (BRISTOL MYERS SQUIBB), MPDL3280A (ROCHE). In some embodiments, the immune-modulating agent targets one or more of CD137 or CD137L. In some embodiments, the immune-modulating agent is an antibody specific for one or more of CD137 or CD137L. For instance, in some embodiments, the immune-modulating agent is an antibody such as, by way of non-limitation, urelumab (also known as BMS-663513 and anti-4-1BB antibody). In some embodiments, the present chimeric protein is combined with urelumab (optionally with one or more of nivolumab, lirilumab, and urelumab) for the treatment of solid tumors and/or B-cell non-Hodgkins lymphoma and/or head and neck cancer and/or multiple myeloma. In some embodiments, the immune-modulating agent is an agent that targets one or more of CTLA-4, AP2M1, CD80, CD86, SHP-2, and PPP2R5A. In some embodiments, the immune-modulating agent is an antibody specific for one or more of CTLA-4, AP2M1, CD80, CD86, SHP-2, and PPP2R5A. For instance, in some embodiments, the immune-modulating agent is an antibody such as, by way of non-limitation, ipilimumab (MDX-010, MDX-101, Yervoy, BMS) and/or tremelimumab (Pfizer). In some embodiments, the present chimeric protein is combined with ipilimumab (optionally with bavituximab) for the treatment of one or more of melanoma, prostate cancer, and lung cancer. In some embodiments, the immune-modulating agent targets CD20. In some embodiments, the immune-modulating agent is an antibody specific CD20. For instance, in some embodiments, the immune-modulating agent is an antibody such as, by way of non-limitation, Ofatumumab (GENMAB), obinutuzumab (GAZYVA), AME-133v (APPLIED MOLECULAR EVOLUTION), Ocrelizumab (GENENTECH), TRU-015 (TRUBION/EMERGENT), veltuzumab (IMMU-106).

In some embodiments, the present technology relates to combination therapy using the FAP binding agent and a checkpoint inhibitor. In some embodiments, the present technology relates to administration of the FAP binding agent to a patient undergoing treatment with a checkpoint inhibitor. In some embodiments, the checkpoint inhibitor is an agent that targets one or more of PD-1, PD-L1, PD-L2, and CTLA-4 (including any of the anti-PD-1, anti-PD-L1, anti-PD-L2, and anti-CTLA-4 agents described herein). In some embodiment, the checkpoint inhibitor is one or more of nivolumab, (ONO-4538/BMS-936558, MDX1106, OPDIVO, BRISTOL MYERS SQUIBB), pembrolizumab (KEYTRUDA, MERCK), pidilizumab (CT-011, CURE TECH), MK-3475 (MERCK), BMS 936559 (BRISTOL MYERS SQUIBB), MPDL3280A (ROCHE), ipilimumab (MDX-010, MDX-101, Yervoy, BMS) and tremelimumab (Pfizer). In some embodiments, the checkpoint inhibitor is an antibody against PD-L1.

In some embodiments, the FAP binding agent acts synergistically when co-administered with the anti-PD-L1 antibody. In some embodiments, the FAP binding agent acts synergistically when co-administered with the anti-PD-L1 antibody for use in treating tumor or cancer. For example, co-administration of the FAP binding agent and the anti-PD-L1 antibody may act synergistically to reduce or eliminate the tumor or cancer, or slow the growth and/or progression and/or metastasis of the tumor or cancer. In some embodiments, the combination of the FAP binding agent and the anti-PD-L1 antibody may exhibit improved safety profiles when compared to the agents used alone in the context of monotherapy. In some embodiments, the FAP binding agent and the anti-PD-L1 antibody may be administered at doses that are lower than the doses employed when the agents are used in the context of monotherapy. In some embodiments, the FAP binding agent comprises a mutated interferon such as a mutated IFNα. In illustrative embodiments, the mutated IFNα comprises one or more mutations at positions 148,149, and 153 with reference to SEQ ID NO: 688 or SEQ ID NO: 689, such as the substitutions M148A, R149A, and L153A.

In some embodiments, the present technology relates to combination therapies using the FAP binding agent and an immunosuppressive agent. In some embodiments, the present technology relates to administration of the FAP binding agent to a patient undergoing treatment with an immunosuppressive agent. In some embodiments, the immunosuppressive agent is TNF.

In illustrative embodiments, the FAP binding agent acts synergistically when co-administered with TNF. In an illustrative embodiment, the FAP binding agent acts synergistically when co-administered with TNF for use in treating tumor or cancer. For example, co-administration of the FAP binding agent and TNF may act synergistically to reduce or eliminate the tumor or cancer, or slow the growth and/or progression and/or metastasis of the tumor or cancer. In some embodiments, the combination of the FAP binding agent and TNF may exhibit improved safety profiles when compared to the agents used alone in the context of monotherapy. In some embodiments, the FAP binding agent and TNF may be administered at doses that are lower than the doses employed when the agents are used in the context of monotherapy. In some embodiments, the FAP binding agent comprises a mutated interferon such as a mutated IFNα. In illustrative embodiments, the mutated IFNα comprises one or more mutations at positions 148,149, and 153 with reference to SEQ ID NO: 688 or SEQ ID NO: 689, such as the substitutions M148A, R149A, and L153A.

In some embodiments, the FAP binding agent acts synergistically when used in combination with Chimeric Antigen Receptor (CAR) T-cell therapy. In an illustrative embodiment, the FAP binding agent acts synergistically when used in combination with CAR T-cell therapy in treating tumor or cancer. In an embodiment, the FAP binding agent acts synergistically when used in combination with CAR T-cell therapy in treating blood-based tumors. In an embodiment, the FAP binding agent acts synergistically when used in combination with CAR T-cell therapy in treating solid tumors. For example, use of the FAP binding agent and CAR T-cells may act synergistically to reduce or eliminate the tumor or cancer, or slow the growth and/or progression and/or metastasis of the tumor or cancer. In some embodiments, the FAP binding agent of the present technology induces CAR T-cell division. In some embodiments, the FAP binding agent of the present technology induces CAR T-cell proliferation. In some embodiments, the FAP binding agent of the present technology prevents anergy of the CART cells.

In some embodiments, the CAR T-cell therapy comprises CART cells that target antigens (e.g., tumor antigens) such as, but not limited to, carbonic anhydrase IX (CAIX), 5T4, CD19, CD20, CD22, CD30, CD33, CD38, CD47, CS1, CD138, Lewis-Y, L1-CAM, MUC16, ROR-1, IL13Ra2, gp100, prostate stem cell antigen (PSCA), prostate-specific membrane antigen (PSMA), B-cell maturation antigen (BCMA), human papillomavirus type 16 E6 (HPV-16 E6), CD171, folate receptor alpha (FR-a), GD2, human epidermal growth factor receptor 2 (HER2), mesothelin, EGFRvIII, fibroblast activation protein (FAP), carcinoembryonic antigen (CEA), and vascular endothelial growth factor receptor 2 (VEGF-R2), as well as other tumor antigens well known in the art. Additional illustrative tumor antigens include, but are not limited to MART-1/Melan-A, gp100, Dipeptidyl peptidase IV (DPPIV), adenosine deaminase-binding protein (ADAbp), cyclophilin b, Colorectal associated antigen (CRC)-0017-1A/GA733, Carcinoembryonic Antigen (CEA) and its immunogenic epitopes CAP-1 and CAP-2, etv6, am11, Prostate Specific Antigen (PSA) and its immunogenic epitopes PSA-1, PSA-2, and PSA-3, T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-Al2, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, a-fetoprotein, E-cadherin, a-catenin, 3-catenin and y-catenin, p120ctn, gp100 Pme1117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, NA, EBV-encoded nuclear antigen (EBNA)-1, brain glycogen phosphorylase, SSX-1, SSX-2 (HOM-MEL-40), SSX-1, SSX-4, SSX-5, SCP-1 CT-7, c-erbB-2, CD19, CD37, CD56, CD70, CD74, CD138, AGS16, MUC1, GPNMB, Ep-CAM, PD-L1, and PD-L2.

Illustrative CAR T-cell therapy include, but are not limited to, JCAR014 (Juno Therapeutics), JCAR015 (Juno Therapeutics), JCAR017 (Juno Therapeutics), JCAR018 (Juno Therapeutics), JCAR020 (Juno Therapeutics), JCAR023 (Juno Therapeutics), JCAR024 (Juno Therapeutics), CTL019 (Novartis), KTE-C19 (Kite Pharma), BPX-401 (Bellicum Pharmaceuticals), BPX-501 (Bellicum Pharmaceuticals), BPX-601 (Bellicum Pharmaceuticals), bb2121 (Bluebird Bio), CD-19 Sleeping Beauty cells (Ziopharm Oncology), UCART19 (Cellectis), UCART123 (Cellectis), UCART38 (Cellectis), UCARTCS1 (Cellectis), OXB-302 (Oxford BioMedica, MB-101 (Mustang Bio) and CAR T-cells developed by Innovative Cellular Therapeutics.

In some embodiments, the present technology relates to combination therapy with one or more chimeric agents described in WO 2013/10779, WO 2015/007536, WO 2015/007520, WO 2015/007542, and WO 2015/007903, the entire contents of which are hereby incorporated by reference in their entireties.

In some embodiments, inclusive of, without limitation, infectious disease applications, the present technology pertains to anti-infectives as additional therapeutic agents. In some embodiments, the anti-infective is an anti-viral agent including, but not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet. In some embodiments, the anti-infective is an anti-bacterial agent including, but not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In some embodiments, the anti-infectives include anti-malarial agents (e.g., chloroquine, quinine, mefloquine, primaquine, doxycycline, artemether/lumefantrine, atovaquone/proguanil and sulfadoxine/pyrimethamine), metronidazole, tinidazole, ivermectin, pyrantel pamoate, and albendazole.

In some embodiments, inclusive, without limitation, of autoimmmune applications, the additional therapeutic agent is an immunosuppressive agent. In some embodiments, the immunosuppressive agent is an anti-inflammatory agent such as a steroidal anti-inflammatory agent or a non-steroidal anti-inflammatory agent (NSAID). Steroids, particularly the adrenal corticosteroids and their synthetic analogues, are well known in the art. Examples of corticosteroids useful in the present technology include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluoromethalone, fluperolone, fluprednisolone, hydrocortisone, meprednisone, paramethasone, prednisolone, prednisone, beclomethasone dipropionate. (NSAIDS) that may be used in the present technology, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. In some embodiments, the immunosupressive agent may be cytostatics such as alkylating agents, antimetabolites (e.g., azathioprine, methotrexate), cytotoxic antibiotics, antibodies (e.g., basiliximab, daclizumab, and muromonab), anti-immunophilins (e.g., cyclosporine, tacrolimus, sirolimus), inteferons, opioids, TNF binding proteins, mycophenolates, and small biological agents (e.g., fingolimod, myriocin). Additional anti-inflammatory agents are described, for example, in U.S. Pat. No. 4,537,776, the entire contents of which is incorporated by reference herein.

In some embodiments, the FAP binding agent described herein, include derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of tunicamycin, etc.

In still other embodiments, the FAP binding agent described herein further comprise a cytotoxic agent, comprising, in illustrative embodiments, a toxin, a chemotherapeutic agent, a radioisotope, and an agent that causes apoptosis or cell death. Such agents may be conjugated to a composition described herein.

The FAP binding agent described herein may thus be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Illustrative cytotoxic agents include, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the *vinca* alkaloids, vincristine and vinblastine. Other cytotoxic agents include paclitaxel (taxol), ricin, *pseudomonas* exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, *vinca* alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Toxin conjugated monoclonal antibodies, tumor antigen specific monoclonal antibodies, Erbitux, Avastin, Pertuzumab, anti-C D20 antibodies, Rituxan, ocrelizumab, ofatumumab, DXL625, HERCEPTIN®, or any combination thereof. Toxic enzymes from plants and bacteria such as ricin, diphtheria toxin and *Pseudomonas* toxin may be conjugated to the therapeutic agents (e.g. antibodies) to generate cell-type-specific-killing reagents (Youle, et al., Proc. Nat'l Acad. Sci. USA 77:5483 (1980); Gilliland, et al., Proc. Nat'l Acad. Sci. USA 77:4539 (1980); Krolick, et al., Proc. Nat'l Acad. Sci. USA 77:5419 (1980)).

Other cytotoxic agents include cytotoxic ribonucleases as described by Goldenberg in U.S. Pat. No. 6,653,104. Embodiments of the present technology also relate to radioimmunoconjugates where a radionuclide that emits alpha or beta particles is stably coupled to the FAP binding agent, with or without the use of a complex-forming agent. Such radionuclides include beta-emitters such as Phosphorus-32, Scandium-47, Copper-67, Gallium-67, Yttrium-88, Yttrium-90, Iodine-125, Iodine-131, Samarium-153, Lutetium-177, Rhenium-186 or Rhenium-188, and alpha-emitters such as Astatine-211, Lead-212, Bismuth-212, Bismuth-213 or Actinium-225.

Illustrative detectable moieties further include, but are not limited to, horseradish peroxidase, acetylcholinesterase, alkaline phosphatase, beta-galactosidase and luciferase. Further illustrative fluorescent materials include, but are not limited to, rhodamine, fluorescein, fluorescein isothiocyanate, umbelliferone, dichlorotriazinylamine, phycoerythrin and dansyl chloride. Further illustrative chemiluminescent moieties include, but are not limited to, luminol. Further illustrative bioluminescent materials include, but are not limited to, luciferin and aequorin. Further illustrative radioactive materials include, but are not limited to, Iodine-125, Carbon-14, Sulfur-35, Tritium and Phosphorus-32.

Methods of Treatment

Methods and compositions described herein have application to treating various diseases and disorders, including, but not limited to cancer, infections, immune disorders, fibrotic diseases, inflammatory diseases or conditions, anemia, autoimmune diseases, cardiovascular diseases, wound healing, ischemia-related diseases, neurodegenerative diseases, metabolic diseases and many other diseases and disorders.

Further, any of the present agents may be for use in the treating, or the manufacture of a medicament for treating, various diseases and disorders, including, but not limited to cancer, infections, immune disorders, inflammatory diseases or conditions, fibrotic diseases, and autoimmune diseases.

In some embodiments, the present invention relates to the treatment of, or a patient having one or more of chronic granulomatous disease, osteopetrosis, idiopathic pulmonary fibrosis, Friedreich's ataxia, atopic dermatitis, Chagas disease, cancer, heart failure, autoimmune disease, sickle cell disease, thalassemia, blood loss, transfusion reaction, diabetes, vitamin B12 deficiency, collagen vascular disease, Shwachman syndrome, thrombocytopenic purpura, Celiac disease, endocrine deficiency state such as hypothyroidism or Addison's disease, autoimmune disease such as Crohn's Disease, systemic lupus erythematosis, rheumatoid arthritis or juvenile rheumatoid arthritis, ulcerative colitis immune disorders such as eosinophilic fasciitis, hypoimmunoglobulinemia, or thymoma/thymic carcinoma, graft versus host disease, preleukemia, Nonhematologic syndrome (e.g., Down's, Dubowwitz, Seckel), Felty syndrome, hemolytic uremic syndrome, myelodysplasic syndrome, nocturnal paroxysmal hemoglobinuria, osteomyelofibrosis, pancytopenia, pure red-cell aplasia, Schoenlein-Henoch purpura, malaria, protein starvation, menorrhagia, systemic sclerosis, liver cirrhosis, hypometabolic states, and congestive heart failure.

In some embodiments, the present invention relates to the treatment of, or a patient having one or more of chronic granulomatous disease, osteopetrosis, idiopathic pulmonary fibrosis, Friedreich's ataxia, atopic dermatitis, Chagas disease, mycobacterial infections, cancer, scleroderma, hepatitis, hepatitis C, septic shock, and rheumatoid arthritis.

In some embodiments, the present technology relates to the treatment of, or a patient having cancer. As used herein, cancer refers to any uncontrolled growth of cells that may interfere with the normal functioning of the bodily organs and systems, and includes both primary and metastatic tumors. Primary tumors or cancers that migrate from their original location and seed vital organs can eventually lead to the death of the subject through the functional deterioration of the affected organs. A metastasis is a cancer cell or group of cancer cells, distinct from the primary tumor location, resulting from the dissemination of cancer cells from the primary tumor to other parts of the body. Metastases may eventually result in death of a subject. For example, cancers can include benign and malignant cancers, polyps, hyperplasia, as well as dormant tumors or micrometastases.

Illustrative cancers that may be treated include, but are not limited to, leukemias (including, for example, acute myeloid, acute lymphoblastic, chronic myeloid, chronic lymphocytic, and hairy cell), lymphomas and myelomas (including, for example, Hodgkin and non-Hodgkin lymphomas, light chain, non-secretory, MGUS, and plasmacytomas), and central nervous system cancers (including, for example, brain (e.g., gliomas (e.g., astrocytoma, oligodendroglioma, and ependymoma), meningioma, pituitary adenoma, and neuromas, and spinal cord tumors (e.g., meningiomas and neurofibroma).

Illustrative cancers that may be treated include, but are not limited to, basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); acute myeloid leukemia (AML); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g. that associated with brain tumors), and Meigs' syndrome.

In some embodiments, the present technology provides FAP binding agents which are part of a chimera that further comprises modified signaling agents for the treatment of cancer. In some embodiments, the FAP binding agents of the present technology significantly reduce and/or eliminate tumors. In some embodiments, the present FAP binding agents significant reduce and/or eliminate tumors when administered to a subject in combination with other anti-cancer agents such as chemotherapeutic agents, checkpoint inhibitors, and immunosuppressive agents. In some embodiments, the combination of FAP binding agents and other anti-cancer agents synergistically reduced tumor size and/or eliminated tumor cells.

In some embodiments, the present technology relates to cancer combination therapies with a FAP binding agent that is part of a chimera comprising one or more targeting moieties and one or more modified signaling agents. Accordingly, the present technology provides for chimeric or fusion proteins that include, for example, a targeting moiety against FAP and one or more signaling agents and uses thereof in combination with anti-cancer agents.

For instance, in some embodiments, the present technology pertains to combination therapies for cancer involving chimeras of a FAP binding agent described herein and a modified signaling agent, including, without limitation a mutated human interferon, such as IFN alpha, including human interferon alpha 2.

In other embodiments, the present FAP binding agent is part of a chimera that comprises multiple targeting moieties and therefore be present in bispecific or trispecific formats. For instance, in some embodiments, the present technology pertains to combination therapies for cancer involving chimeras of a FAP binding agent and a checkpoint inhibitor binding agent (e.g. anti-PD-L1, anti-PD-1, anti-PD-L2, or anti-CTLA) described herein and a modified signaling agent, including, without limitation a mutated human interferon, such as IFN alpha, including human interferon alpha 2.

In some embodiments, the signaling agent is modified to have reduced affinity or activity for one or more of its receptors, which allows for attenuation of activity (inclusive of agonism or antagonism) and/or prevents non-specific signaling or undesirable sequestration of the chimeric protein. In some embodiments, the reduced affinity or activity at the receptor is restorable by attachment with one or more of the targeting moieties described herein.

In some embodiments, the present technology relates to the treatment of, or a patient having a microbial infection and/or chronic infection. Illustrative infections include, but are not limited to, HIV/AIDS, tuberculosis, osteomyelitis, hepatitis B, hepatitis C, Epstein-Barr virus or parvovirus, T cell leukemia virus, bacterial overgrowth syndrome, fungal or parasitic infections.

In some embodiments, the present compositions are used to treat or prevent one or more inflammatory diseases or conditions, such as inflammation, acute inflammation, chronic inflammation, respiratory disease, atherosclerosis, restenosis, asthma, allergic rhinitis, atopic dermatitis, septic shock, rheumatoid arthritis, inflammatory bowel disease, inflammatory pelvic disease, pain, ocular inflammatory disease, celiac disease, Leigh Syndrome, Glycerol Kinase Deficiency, Familial eosinophilia (FE), autosomal recessive spastic ataxia, laryngeal inflammatory disease; Tuberculosis, Chronic cholecystitis, Bronchiectasis, Silicosis and other pneumoconioses.

In some embodiments, the present technology has application to treating autoimmune and/or neurodegenerative diseases.

In some embodiments, the present compositions are used to treat or prevent one or more conditions characterized by undesirable CTL activity, and/or conditions characterized by high levels of cell death. For instance, in some embodiments, the present compositions are used to treat or prevent one or more conditions associated with uncontrolled or overactive immune response.

In some embodiments, the present compositions are used to treat or prevent one or more autoimmune and/or neurodegenerative diseases or conditions, such as MS, diabetes mellitus, lupus, celiac disease, Crohn's disease, ulcerative colitis, Guillain-Barre syndrome, scleroderms, Goodpasture's syndrome, Wegener's granulomatosis, autoimmune epilepsy, Rasmussen's encephalitis, Primary biliary sclerosis, Sclerosing cholangitis, Autoimmune hepatitis, Addison's disease, Hashimoto's thyroiditis, Fibromyalgia, Menier's syndrome; transplantation rejection (e.g., prevention of allograft rejection) pernicious anemia, rheumatoid arthritis, systemic lupus erythematosus, dermatomyositis, Sjogren's syndrome, lupus erythematosus, myasthenia gravis, Reiter's syndrome, Grave's disease, and other autoimmune diseases.

In some embodiments, the present technology is used to treat or prevent various autoimmune and/or neurodegenerative diseases. In some embodiments, the autoimmune and/or neurodegenerative diseases selected from MS, Alzheimer's disease (including, without limitation, Early-onset Alzheimer's, Late-onset Alzheimer's, and Familial Alzheimer's disease (FAD), Parkinson's disease and parkinsonism (including, without limitation, Idiopathic Parkinson's disease, Vascular parkinsonism, Drug-induced parkinsonism, Dementia with Lewy bodies, Inherited Parkinson's, Juvenile Parkinson's), Huntington's disease, Amyotrophic lateral sclerosis (ALS, including, without limitation, Sporadic ALS, Familial ALS, Western Pacific ALS, Juvenile ALS, Hiramaya Disease).

In an embodiment, the present invention provides methods for the treatment or prevention of one or more liver disorders, selected from viral hepatitis, alcohol hepatitis, autoimmune hepatitis, alcohol liver disease, fatty liver disease, steatosis, steatohepatitis, non-alcohol fatty liver disease, drug-induced liver disease, cirrhosis, fibrosis, liver failure, drug induced liver failure, metabolic syndrome, hepatocellular carcinoma, cholangiocarcinoma, primary biliary cirrhosis (primary biliary cholangitis), bile capillaries, Gilbert's syndrome, jaundice, and any other liver toxicity-associated indication. In some embodiments, the present invention provides methods for the treatment or prevention of liver fibrosis. In some embodiments, the present invention provides methods for the treatment or prevention of primary sclerosing cholangitis (PSC), chronic liver disease, nonalcoholic fatty liver disease (NAFLD), nonalcoholic steatohepatitis (NASH), hepatitis C infection, alcoholic liver disease, liver damage, optionally due to progressive fibrosis and liver fibrosis. In some embodiments, the present invention provides methods for the treatment or prevention of nonalcoholic steatohepatitis (NASH). In some embodiments, the present invention provides methods that reduce or prevent fibrosis. In some embodiments, the present invention provides methods that reduce or prevent cirrhosis. In some embodiments, the present invention provides methods that reduce or prevent hepatocellular carcinoma.

In some embodiments, the present invention provides methods that treat or prevent a fibrotic disease is optionally selected from liver fibrosis, lung fibrosis, primary sclerosing cholangitis (PSC), chronic liver disease, nonalcoholic fatty liver disease (NAFLD), nonalcoholic steatohepatitis (NASH), hepatitis C infection, alcoholic liver disease, liver damage, liver cirrhosis, and myelodysplastic syndrome In various embodiments, the present invention provides methods for the treatment or prevention of cardiovascular disease, such as a disease or condition affecting the heart and vasculature, including but not limited to, coronary heart disease (CHD), cerebrovascular disease (CVD), aortic stenosis, peripheral vascular disease, atherosclerosis, arteriosclerosis, myocardial infarction (heart attack), cerebrovascular diseases (stroke), transient ischaemic attacks (TIA), angina (stable and unstable), atrial fibrillation, arrhythmia, vavular disease, and/or congestive heart failure. In various embodiments, the present invention provides methods for the treatment or prevention of cardiovascular disease which involves inflammation.

In various embodiments, the present invention provides methods for the treatment or prevention of one or more respiratory diseases, such as asthma, chronic obstructive pulmonary disease (COPD), bronchiectasis, allergic rhinitis, sinusitis, pulmonary vasoconstriction, inflammation, allergies, impeded respiration, respiratory distress syndrome, cystic fibrosis, pulmonary hypertension, pulmonary vasoconstriction, emphysema, Hantavirus pulmonary syndrome (HPS), Loeffler's syndrome, Goodpasture's syndrome, Pleurisy, pneumonitis, pulmonary edema, pulmonary fibrosis, Sarcoidosis, complications associated with respiratory syncitial virus infection, and other respiratory diseases.

In some embodiments, methods of the present technology are useful in treatment a human subject. In some embodiments, the human is a pediatric human. In other embodiments, the human is an adult human. In other embodiments, the human is a geriatric human. In other embodiments, the human may be referred to as a patient. In some embodiments, the human is a female. In some embodiments, the human is a male.

In certain embodiments, the human has an age in a range of from about 1 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old. In some embodiments, the human has an age of more than 30 years old.

Immune Modulation

In some embodiments, the present compositions are capable of, or find use in methods of, immune modulation. For example, in some embodiments, the present methods of treatment may involve the immune modulation described herein. In some embodiments, the immune modulation involves IFN signaling, including modified IFN signaling, in the context of a dendritic cell (DC).

In some embodiments, a multi-specific FAP binding agent is provided. In some embodiments, such multi-specific FAP binding agent of the present technology recognizes and binds to FAP and one or more antigens found on one or more immune cells, which can include, without limitation, megakaryocytes, thrombocytes, erythrocytes, mast cells, basophils, neutrophils, eosinophils, monocytes, macrophages, natural killer cells, T lymphocytes (e.g., cytotoxic T lymphocytes, T helper cells, natural killer T cells), B lymphocytes, plasma cells, dendritic cells, or subsets thereof. In some embodiments, the FAP binding agent specifically binds to an antigen of interest and effectively directly or indirectly recruits one of more immune cells.

In some embodiments, the FAP binding agent specifically binds to an antigen of interest and effectively directly or indirectly recruits one of more immune cells to cause an immunosuppressive effect, e.g. the FAP binding agent directly or indirectly recruits an immunosuppressive immune cell. In some embodiments, the immunosuppressive immune cell is a regulatory T cell (or "Tregs" which, as used herein, refers to a subpopulation of T cells which modulate the immune system, abrogate autoimmune disease, maintain tolerance to self-antigens and thwart anti-tumor immune responses). Other immunosuppressive immune cells include myeloid suppressor cells (or "MSC," which, as used herein, refers to a heterogeneous population of cells, defined by their myeloid origin, immature state, and ability to potently suppress T cell responses); tumor associated neutrophils (or "TANs" which, as used herein, refers to a subset of neutrophils that are capable of suppressing immune responses); tumor associated macrophages (or "TAMs" which, as used herein, refers to a subset of macrophages that may reduce an immune response), M2 macrophages, and/or tumor-inducing mast cells (which as used herein, refers to a subset of bone marrow-derived, long-lived, heterogeneous cellular population). Also, immunosuppressive immune cells include Th2 cells and Th17 cells. Additionally, immunosuppressive immune cells include immune cells, e.g., CD4+ and/or CD8+ T cells, expressing one or more checkpoint inhibitory receptors (e.g. receptors, including CTLA-4, B7-H3, B7-H4, TIM-3, expressed on immune cells that prevent or inhibit uncontrolled immune responses). See Stagg, J. et. al., Immunotherapeutic approach in triple-negative breast cancer. Ther Adv Med Oncol. (2013) 5(3):169-181).

In some embodiments, the FAP binding agent stimulates regulatory T cell (Treg) proliferation. Treg cells are characterized by the expression of the Foxp3 (Forkhead box p3) transcription factor. Most Treg cells are C D4+ and CD25+, and can be regarded as a subset of helper T cells, although a small population may be CD8+. Thus the immune response which is to be modulated by a method of the present technology may comprise inducing proliferation of Treg cells, optionally in response to an antigen. Thus the method may comprise administering to the subject a composition comprising the antigen, wherein the antigen is associated with a binding agent having affinity for FAP. The antigen may be administered with an adjuvant which promotes proliferation of Treg cells.

Insofar as this method involves stimulating proliferation and differentiation of Treg cells in response to a specific antigen, it can be considered to be a method of stimulating an immune response. However, given that Treg cells may be capable of modulating the response of other cells of the immune system against an antigen in other ways, e.g. inhibiting or suppressing their activity, the effect on the immune system as a whole may be to modulate (e.g. suppress or inhibit) the response against that antigen. Thus, the methods of this aspect of the present technology can equally be referred to as methods of modulating (e.g. inhibiting or suppressing) an immune response against an antigen.

In some embodiments, the methods therapeutically or prophylactically inhibit or suppress an undesirable immune response against a particular antigen, even in a subject with pre-existing immunity or an on-going immune response to that antigen. This may be particularly useful, for example, in the treatment of autoimmune disease.

Under certain conditions, it may also be possible to tolerize a subject against a particular antigen by targeting the antigen to an antigen presenting cell expressing FAP. The present technology thus provides a method for inducing tolerance in a subject towards an antigen, comprising administering to the subject a composition comprising the antigen, wherein the antigen is associated with a binding agent having affinity for FAP and wherein the antigen is administered in the absence of an adjuvant. Tolerance in this context typically involves depletion of immune cells which would otherwise be capable of responding to that antigen, or inducing a lasting reduction in responsiveness to an antigen in such immune cells.

It may be particularly desirable to raise a Treg response against an antigen to which the subject exhibits, or is at risk of developing, an undesirable immune response. For example, it may be a self-antigen against which an immune response occurs in an autoimmune disease. Examples of autoimmune diseases in which specific antigens have been identified as potentially pathogenically significant include multiple sclerosis (myelin basic protein), insulin-dependent diabetes mellitus (glutamic acid decarboxylase), insulin-resistant diabetes mellitus (insulin receptor), celiac disease (gliadin), bullous pemphigoid (collagen type XVII), auto-immune haemolytic anaemia (Rh protein), auto-immune thrombocytopenia (GpIIb/IIIa), myaesthenia gravis (acetylcholine receptor), Graves' disease (thyroid-stimulating hormone receptor), glomerulonephritis, such as Goodpasture's disease (alpha3(IV)NC1 collagen), and pernicious anaemia (intrinsic factor). Alternatively, the target antigen may be an exogenous antigen which stimulates a response which also causes damage to host tissues. For example, acute rheumatic fever is caused by an antibody response to a Streptococcal antigen which cross-reacts with a cardiac muscle cell antigen. Thus, these antigens, or particular fragments or epitopes thereof, may be suitable antigens for use in the present technology.

In some embodiments, the present agents, or methods using these agents, disrupt FAP signaling (e.g. via neutralization of FAP), e.g. by reducing or inhibiting FAP binding to its ligand. Some autoimmune diseases are characterized by unusually high levels of cell death and it is believed that immune responses against self antigens associated with these cells may contribute to the pathogenesis of these conditions. FAP antagonists may therefore be used to prevent FAP from binding to the ligand exposed in dead and dying cells (e.g. those undergoing immunogenic cell death) and may thus inhibit or prevent stimulation of immune responses against these antigens.

In some embodiments, the present agents, or methods using these agents, reduce or suppress autoreactive T cells. In some embodiments, the multi-specific FAP binding agent, optionally through an interferon signaling in the context of a chimera, causes this immunosuppression. In some embodiments, the multi-specific FAP binding agent stimulates PD-L1 or PD-L2 signaling and/or expression which may suppress autoreactive T cells. In some embodiments, the FAP binding agent, optionally through an interferon signaling in the context of a chimera, causes this immunosuppression. In some embodiments, the FAP binding agent stimulates PD-L1 or PD-L2 signaling and/or expression which may suppress autoreactive T cells.

In some embodiments, the present methods comprise modulating the ratio of regulatory T cells to effector T cells in favor of immunosuppression, for instance, to treat autoimmune diseases. For instance, the present methods, in some embodiments, reduce and/or suppress one or more of cytotoxic T cells; effector memory T cells; central memory T cells; CD8+ stem cell memory effector cells; TH1 effector T-cells; TH2 effector T cells; TH9 effector T cells; TH17 effector T cells. For instance, the present methods, in some embodiments, increase and/or stimulate one or more of CD4+CD25+FOXP3+ regulatory T cells, CD4+CD25+ regulatory T cells, CD4+CD25-regulatory T cells, CD4+

CD25high regulatory T cells, TIM-3+PD-1+ regulatory T cells, lymphocyte activation gene-3 (LAG-3)' regulatory T cells, CTLA-4/CD152+ regulatory T cells, neuropilin-1 (Nrp-1)±regulatory T cells, CCR4+CCR8+ regulatory T cells, CD62L (L-selectin)' regulatory T cells, CD45RBlow regulatory T cells, CD127low regulatory T cells, LRRC32/GARP+ regulatory T cells, CD39+ regulatory T cells, GITR+ regulatory T cells, LAP' regulatory T cells, 1611+ regulatory T cells, BTLA+ regulatory T cells, type 1 regulatory T cells (Tr1 cells), T helper type 3 (Th3) cells, regulatory cell of natural killer T cell phenotype (NKTregs), CD8+ regulatory T cells, CD8+CD28-regulatory T cells and/or regulatory T-cells secreting IL-10, IL-35, TGF-3, TNF-α, Galectin-1, IFN-γ and/or MCP1.

In some embodiments, the present methods favor immune inhibitory signals over immune stimulatory signals. In some embodiments, the present methods allow for reversing or suppressing immune activating or co-stimulatory signals. In some embodiments, the present methods allow for providing immune inhibitory signals. For instance, in some embodiments, the present agents and methods reduce the effects of an immune stimulatory signal, which, without limitation, is one or more of 4-166, OX-40, HVEM, GITR, CD27, CD28, CD30, CD40, ICOS ligand; OX-40 ligand, LIGHT (0D258), GITR ligand, CD70, 67-1, B7-2, CD30 ligand, CD40 ligand, ICOS, ICOS ligand, CD137 ligand and TL1A. Further, in some embodiments, the present agents and methods increase the effects of an immune inhibitory signal, which, without limitation, is one or more of CTLA-4, PD-L1, PD-L2, PD-1, BTLA, HVEM, TI M3, GAL9, LAG3, VISTA, KIR, 2B4, CD160 (also referred to as BY55), CGEN-15049, CHK 1 and CH K2 kinases, A2aR, CEACAM (e.g., CEACAM-1, CEACAM-3 and/or CEACAM-5), and various B-7 family ligands (including, but are not limited to, 67-1, B7-2, B7-DC, 137-H1, B7-H2, B7-H3, B7-H4, B7-H5, B7-H6 and B7-H7.

Kits

The present technology also provides kits for the administration of any FAP binding agent described herein (e.g. with or without additional therapeutic agents). The kit is an assemblage of materials or components, including at least one of the inventive pharmaceutical compositions described herein. Thus, in some embodiments, the kit contains at least one of the pharmaceutical compositions described herein.

The exact nature of the components configured in the kit depends on its intended purpose. In one embodiment, the kit is configured for the purpose of treating human subjects.

Instructions for use may be included in the kit. Instructions for use typically include a tangible expression describing the technique to be employed in using the components of the kit to effect a desired therapeutic outcome, such as to treat cancer. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials and components assembled in the kit can be provided to the practitioner stored in any convenience and suitable ways that preserve their operability and utility. For example, the components can be provided at room, refrigerated or frozen temperatures. The components are typically contained in suitable packaging materials. In some embodiments, the packaging material is constructed by well-known methods, preferably to provide a sterile, contaminant-free environment. The packaging material may have an external label which indicates the contents and/or purpose of the kit and/or its components.

Definitions

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

As used herein, the term "effective amount" refers to a quantity sufficient to achieve a desired therapeutic and/or prophylactic effect, e.g., an amount which results in the prevention of, or a decrease in a disease or disorder or one or more signs or symptoms associated with a disease or disorder. In the context of therapeutic or prophylactic applications, the amount of a composition administered to the subject will depend on the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compounds may be administered to a subject having one or more signs or symptoms of a disease or disorder.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the present technology, the present technology, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As used herein, a "therapeutically effective amount," or "pharmacologically effective amount," or "pharmacologically effective dose" of a compound refers to compound levels in which the physiological effects of a disease or disorder are, at a minimum, ameliorated. Therapeutic benefit also includes halting or slowing the progression of the underlying disease or disorder, regardless of whether improvement is realized. A therapeutically effective amount can be given in one or more administrations. The amount of a compound which constitutes a therapeutically effective amount will vary depending on the compound, the disorder and its severity, and the general health, age, sex, body weight and tolerance to drugs of the subject to be treated, but can be determined routinely by one of ordinary skill in the art.

Effective amounts, toxicity, and therapeutic efficacy can be determined by standard pharmaceutical procedures in cell cultures or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

As used herein, "methods of treatment" are equally applicable to use of a composition for treating the diseases or disorders described herein and/or compositions for use and/or uses in the manufacture of a medicaments for treating the diseases or disorders described herein.

EXAMPLES

Example 1. Making Human FAP Binding Agents

A VHH library was constructed and screened for the presence of antigen-specific VHHs. To this end, total RNA from peripheral blood lymphocytes was used as template for first strand cDNA synthesis with oligo(dT) primer. Using this cDNA, the VHH encoding sequences were amplified by PCR, digested with PstI and NotI, and cloned into the PstI and NotI sites of the phagemid vector pMECS. A VHH library of about $10^8$ independent transformants was obtained. About 87% of transformants harbored the vector with the right insert size.

Figure 11:
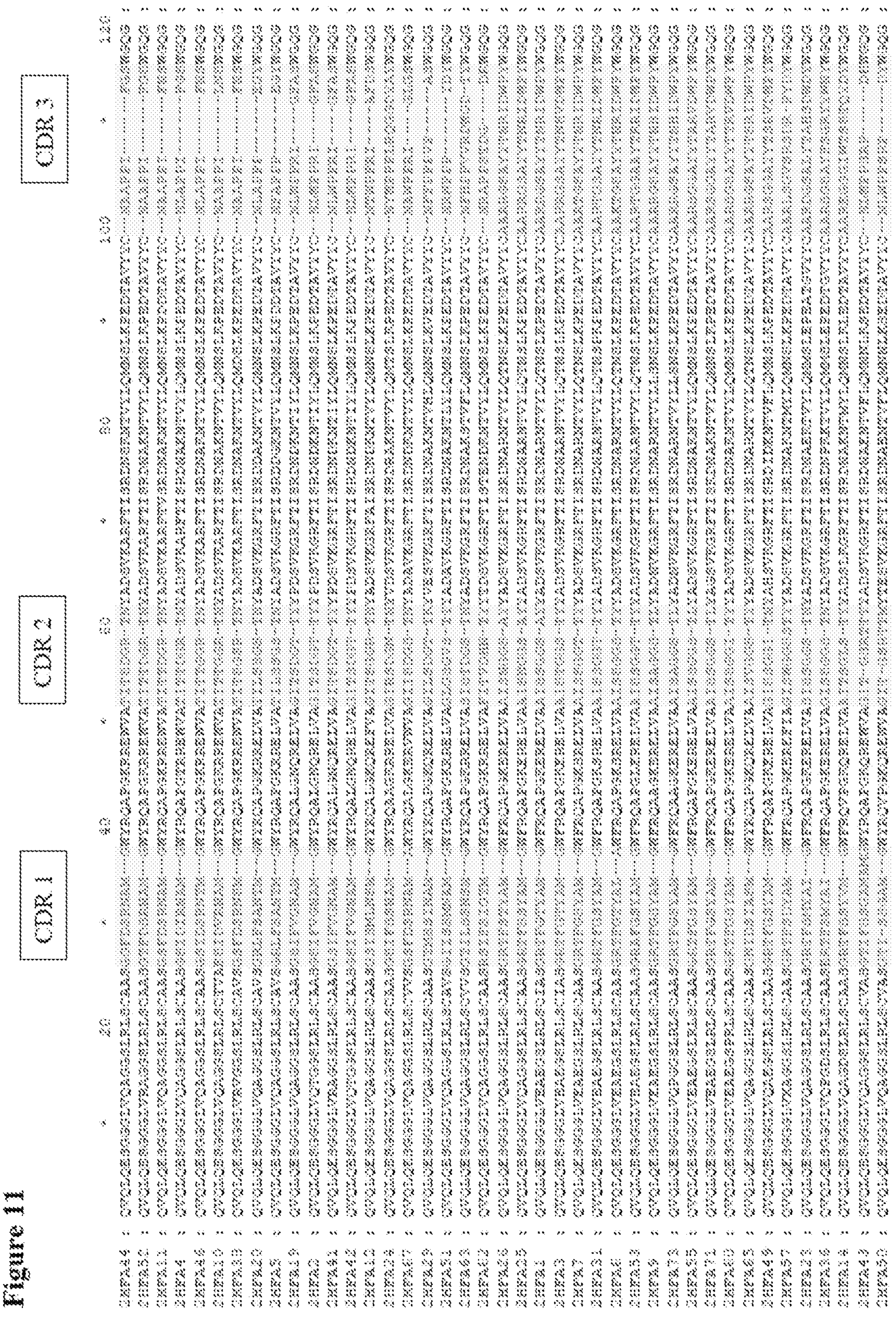
FIG. 11 shows the amino acid sequences of 41 different human VHHs specific for recombinant Hiss-tagged extracellular domain of human FAP (SEQ ID NOs: 2-42). CDRs (i.e., CDR 1, 2, and 3) in the VHHs are labeled accordingly. For example, the top sequence 2HFA44 is SEQ ID NO: 2, and the bottom sequence 2HFA50 is SEQ ID NO: 42.

The library was subject to three consecutive rounds of panning on solid-phase coated antigen (200 μg/ml, 20 μg/well). The enrichment for antigen-specific phages was assessed after each round of panning by comparing the number of phagemid particles eluted from antigen-coated wells with the number of phagemid particles eluted from only-blocked wells (negative control wells). These experiments suggested that the phage population was enriched about 5-fold, $2\times10^2$-fold and $5\times10^2$-fold for antigen-specific phages after $1^{st}$, $2^{nd}$ and $3^{rd}$ rounds of panning, respectively. 95 colonies from $2^{nd}$ round were randomly selected and analyzed by ELISA for the presence of antigen-specific VHHs in their periplasmic extracts (ELISA using crude periplasmic extracts including soluble VHHs). Out of these 95 colonies, 84 colonies scored positive in this assay. The antigen used for the panning and ELISA screening was the same as the one used for immunization. Based on sequence data, the 84 ELISA-positive colonies represented 41 different VHHs (Table 2). The 41 different VHHs belong to 7 different CDR3 groups (see Table 1, SEQ ID Nos: 2-42, and FIGS. 10-11).

TABLE 1

| Group | Member(s) |
|---|---|
| 1 | 2HFA44, 2HFA52, 2HFA11, 2HFA4, 2HFA46. 2HFA10, 2HFA38, 2HFA20, 2HFA5, 2HFA51 |
| 2 | 2HFA19, 2HFA2, 2HFA41, 2HFA42, 2HFA12, 2HFA67, 2HFA62 |
| 3 | 2HFA24 |
| 4 | 2HFA29, 2HFA43, 2HFA50 |
| 5 | 2HFA63 |
| 6 | 2HFA26, 2HFA25, 2HFA1, 2HFA3, 2HFA7, 2HFA31, 2HFA6, 2HFA53, 2HFA9, 2HFA73, 2HFA55, 2HFA71, 2HFA60, 2HFA65, 2HFA49, 2HFA23, 2HFA36, 2HFA14 |
| 7 | 2HFA57 |

*E. coli* TG1 harboring recombinant phagemid pMECS containing anti-human FAP-ECD-$His_6$ VHH sequences as in the following table (store at −80° C.).

TABLE 2

| *E. coli* strain + Vector | VHH | NSF glycerol stock No. |
|---|---|---|
| TG1, pMECS | 2HFA1 | 3030 |
| TG1, pMECS | 2HFA2 | 3031 |
| TG1, pMECS | 2HFA3 | 3032 |
| TG1, pMECS | 2HFA4 | 3033 |
| TG1, pMECS | 2HFA5 | 3034 |
| TG1, pMECS | 2HFA6 | 3035 |
| TG1, pMECS | 2HFA7 | 3036 |
| TG1, pMECS | 2HFA9 | 3037 |
| TG1, pMECS | 2HFA10 | 3038 |
| TG1, pMECS | 2HFA11 | 3039 |
| TG1, pMECS | 2HFA12 | 3040 |

TABLE 2-continued

| *E. coli* strain + Vector | VHH | NSF glycerol stock No. |
|---|---|---|
| TG1, pMECS | 2HFA14 | 3041 |
| TG1, pMECS | 2HFA19 | 3042 |
| TG1, pMECS | 2HFA20 | 3043 |
| TG1, pMECS | 2HFA23 | 3044 |
| TG1, pMECS | 2HFA24 | 3045 |
| TG1, pMECS | 2HFA25 | 3046 |
| TG1, pMECS | 2HFA26 | 3047 |
| TG1, pMECS | 2HFA29 | 3048 |
| TG1, pMECS | 2HFA31 | 3049 |
| TG1, pMECS | 2HFA36 | 3050 |
| TG1, pMECS | 2HFA38 | 3051 |
| TG1, pMECS | 2HFA41 | 3052 |
| TG1, pMECS | 2HFA42 | 3053 |
| TG1, pMECS | 2HFA43 | 3054 |
| TG1, pMECSV | 2HFA44 | 3055 |
| TG1, pMECS | 2HFA46 | 3056 |
| TG1, pMECS | 2HFA49 | 3057 |
| TG1, pMECS | 2HFA50 | 3058 |
| TG1, pMECS | 2HFA51 | 3059 |
| TG1, pMECS | 2HFA52 | 3060 |
| TG1, pMECS | 2HFA53 | 3061 |
| TG1, pMECS | 2HFA55 | 3062 |
| TG1, pMECS | 2HFA57 | 3063 |
| TG1, pMECS | 2HFA60 | 3064 |
| TG1, pMECS | 2HFA62 | 3065 |
| TG1, pMECS | 2HFA63 | 3066 |
| TG1, pMECS | 2HFA65 | 3067 |
| TG1, pMECS | 2HFA67 | 3068 |
| TG1, pMECS | 2HFA71 | 3069 |
| TG1, pMECS | 2HFA73 | 3070 |

Table 2 shows a description of 41 clones representing 41 different anti-human FAP-ECD-$His_6$ VHHs genes that encode human FAP binding agents. The vector pMECS codes for ampicillin resistance.

The VHH gene cloned in pMECS vector contains PeIB signal sequence at the N-terminus and HA tag and $His_6$ tag at the C-terminus (PeIB leader-VHH-HA-$His_6$). The PeIB leader sequence directs the VHH to the periplasmic space of the *E. coli* and the HA and $His_6$ tags can be used for the purification and detection of the VHH (e.g., in ELISA, Western Blot, etc.).

In pMECS vector, the $His_6$ tag was followed by an amber stop codon (TAG) and this amber stop codon is followed by gene III of M13 phage. In suppressor *E. coli* strains (e.g., TG1), the amber stop codon was read as glutamine and therefore the VHH was expressed as fusion protein with protein III of the phage, which allows the display of the VHH on the phage coat for panning (in TG1 suppressor strains, the efficiency of suppression is not 100% and therefore the expression of VHHs in suppressor strains lead to two different types of VHH molecules, i.e., fused to protein III and without protein 111). In non-suppressor *E. coli* strains (e.g., WK6), the amber stop codon was read as stop codon and therefore the resulting VHH was not fused to protein III.

To express and purify VHHs cloned in pMECS vector, pMECS containing the gene of the VHH of interest was prepared and transform into a non-suppressor strain (e.g., WK6) with this plasmid. Sequence the VHH of the resulting clone was verified using MP057 primer (5'-TTATGCTTCCGGCTCGTATG-3' (SEQ ID NO: 837).

Recloning VHH Genes from pMECS to pHEN6c Vector

Primer sequences (R stands for A or G):

```
Primer A6E
                                        (SEQ ID NO: 838)
(5' GATGTGCAGCTGCAGGAGTCTGGRGGAGG 3').

Primer PMCF
                                        (SEQ ID NO: 839)
(5' CTAGTGCGGCCGCTGAGGAGACGGTGACCTGGGT 3')..

Universal reverse primer
                                        (SEQ ID NO: 840)
(5' TCACACAGGAAACAGCTATGAC 3').

Universal forward primer
                                        (SEQ ID NO: 841)
(5 CGCCAGGGTTTTCCCAGTCACGAC 3').
```

The VHH gene was amplified by PCR using *E. coli* containing recombinant pMECS harboring the VHH gene as template and primers A6E and PMCF (about 30 cycles of PCR were performed, each cycle consisting of 30 seconds at 94° C., 30 seconds at 55° C. and 45 seconds at 72° C., followed by 10 minutes extension at 72° C. at the end of PCR). A fragment of about 400 bp was amplified. (Primers A6E and PMCF are framework) and framework4 primers, respectively).

The PCR product was purified by Qiaquick PCR purification kit from Qiagen and digest overnight with PstI, BstEII, or with Eco91I.

The PCR product was ligated using the following protocol.:

Digest pHEN6c vector with PstI for 3 hours, purify the digested vector as above and then digest it with BstEII for 2 to 3 hours.

Run digested vector on 1% agarose gel. Cut the vector band out of gel and purify (e.g. by Qiaquick gel extraction kit from Qiagen).

Ligate PCR fragment and vector.

Transform electrocompetent WK6 cells with the ligation reaction.

Select for the transformants using LB/agar/ampicillin (100 μg/ml)/glucose (1-2%) plates.

Screen for positive clones by PCR using universal reverse and universal forward primers. A fragment of about 550 bp is amplified, if the insert is present.

Sequence at least 2 clones per each VHH using universal reverse primer to verify the identity of the clones.

Retest antigen binding capacity by ELISA or any other appropriate assay.

After following the above protocol, the VHH gene was cloned in pHEN6c vector contains PeIB signal sequence at the N-terminus and $His_6$ tag at the C-terminus. The PeIB leader sequence directs the VHH to the periplasmic space of the *E. coli* and the $His_6$ tag can be used for the purification and detection of VHH (e.g. in ELISA, Western Blot, etc.).

Expression and Purification of VHHs

Day 1:

The following protocol was followed:

Inoculate 10-20 ml of LB+ampicillin (100 μg/ml)+glucose (1%) with a freshly transformed WK6 colony.

Incubate at 37° C. overnight with shaking at 200-250 rpm (this is the pre-culture).

Day 2:

TB per liter: 2.3 g $KH_2PO_4$; 16.4 g $K_2HPO_4 \cdot 3H_2O$, 12 g Tryptone (Duchefa Biochemie); 24 g Yeast (Duchefa Biochemie); and 4 ml 100% glycerol (Duchefa Biochemie).

The following protocol was followed:

A baffled shaker flask of 1 liter was filled with 330 ml TB and autoclaved.

Add 1 ml of the pre-culture to 330 ml TB supplemented with 100 μg/ml Ampicillin, 2 mM $MgCl_2$ and 0.1% glucose and grow at 37° C. with shaking (200-250 rpm) till an $OD_{600}$ of 0.6-0.9 is reached.

Induce VHH expression by addition of IPTG to final concentration of 1 mM.

Incubate at 28° C. with shaking overnight (about 16-18 hours) (The $OD_{600}$ after overnight induction should ideally be between 25 and 30).

Day 3:

Extraction of VHH from Periplasm of *E. coli:*

Solutions:

TES: 0.2 M Tris pH 8.0; 0.5 mM EDTA; and 0.5 M sucrose.

TES/4: TES diluted 4 times in water

Method:

The following protocol was followed:

Centrifuge the overnight induced cultures for 8 minutes at 8000 rpm.

Resuspend the cell pellet from 1 liter culture in 12 ml TES by pipetting up and down, shake for 1 hour on ice.

Per each 12 ml TES used, add 18 ml TES/4 and incubate further on ice for an additional hour (with shaking).

Centrifuge for 30 min at 8000 rpm at 4° C.

Transfer the supernatant to fresh falcon tubes (The supernatant contains proteins extracted from the periplasmic space).

Purification by IMAC:

Solutions Used:

HIS-select (SIGMA); PBS; and 50 mM NaAcetate pH 4.6

Method:

The following protocol was followed:

Equilibrate His-select with PBS: per periplasmic extract derived from 1 liter culture, add 1 ml Resin (about 2 ml His-select solution) to a 50 ml falcon tube, add PBS to final volume of 50 ml and mix.

Centrifuge at 2000 rpm for 2 min. Discard the supernatant.

Wash the resin with PBS as above.

Wash the resin with PBS as above again.

Add periplasmic extract to the resin, incubate for 30 minutes to 1 hour at room temperature with gentle shaking (longer incubation times may result in non-specific binding).

Load sample on PD-10 column with a filter at the bottom (GE healthcare, cat. No. 17-0435-01)

Wash with 50 to 100 ml PBS (50-100 ml PBS per 1 ml resin used).

Elute 3 times, each time with 1 ml PBS/0.5 M imidazole per 1 ml resin used (for efficient elution, resuspend the beads and leave overnight at 4° C. with the bottom of the column closed).

Dialyses overnight at 4° C. against PBS (cutoff 3500 daltons) to remove imidazole. For efficient dialysis, change the dialysis buffer (PBS) 2-3 times.

The amount of protein was estimated by $OD_{280}$ measurement of eluted sample. Extinction coefficient of each clone was determined by protParam tool under primary structure analysis at the Expasy proteomics server. Further purification of the VHHs can be achieved by additional methods.

Example 2. Use of Fusion Protein Having a FAP Binding Agent to Treat Cancer

This example shows that a fusion protein having a FAP targeting moiety and a mutated cytokine, wherein the mutation in the cytokine results in the reduced activity of the cytokine, can reduce tumor growth. This example shows that the FAP targeting moiety leads to the recovery of the activity of the mutated cytokine.

Preparation of Fusion Protein with FAP Targeting Moiety

FAP-targeted AcTaferon ("FAP-AFN"), a human IFNα2 with a mutation at Q124R coupled via a 20×GGS-linker to an N-terminal neutralizing VHH (also called single domain antibody (sdAb)) specific for FAP (mFAP_R3FAP85), was constructed in a pHen6 vector.

```
mFAP_R3FAP85:
                                        (SEQ ID NO: 842)
QVQLQESGGGLVQAGDSLRLSCKGSGRNFGSYNMGWYRQAPGKEREFVAA

VAWIGGTTYYADSVKGRFTISRDNAERMVYLQMTNLKPEDTAIYYCNADI

E---RRPLFGSWGPGTQVTVSSAAAYPYDVPDYGSHHHHHH.
```

The Q124R mutation in human IFNα2 results in the reduced affinity of human IFNα2 to the its receptor, thus reducing its activity (see PCT/EP2013/050787). The Q124R mutant is representative of an attenuated human IFN alpha 2 mutant that can be assayed in vivo in a murine model. Specifically, Q124R is a human IFN mutation that is suitable for use in the mouse (i.e. it is a human mutant IFN that functions in mouse). See *Nat. Comm.* 2014; 5:3016. doi: 10.1038/ncomms4016, the entire contents of which are hereby incorporated by reference.

Large scale productions of His-tagged pHen6-FAP-AFN constructs were performed in *E. coli*. The bacteria were cultured until stationary phase (OD600 of 0.7-0.8) and then IPTG (BioScientific) was added to activate the LacZ promoter. Cell supernatant was collected after overnight culture.

The proteins in the periplasmic fraction were released by osmotic shock using a sucrose solution and were purified by immobilized metal ion chromatography (IMAC) on a HiTrap Sepharose resin loaded with Kobalt ions (Clontech, Takara Biotechnology). After binding of the proteins, columns were washed with 0.5% EMPIGEN (Calbiochem, Millipore), 0.5% CHAPS (Sigma-Aldrich) and PBS. Imidazole (Merck) was used for elution and removed using PD-10 gel filtration columns (GE Healthcare). Protein concentration was determined using the absorbance at 280 nm and purity was assessed via SDS-PAGE.

LPS levels were quantified using Limulus Amebocyte Lysate (LAL) QCL-1000 (Lonza). If still present, LPS was removed using Endotoxin Removal Resin (Thermo Scientific). Biological activities of all products were assessed by a functional assay using the mouse luciferase reporter cell line LL171 against the WHO International mouse IFNα standard Ga02-901-511 as described in Garcin et al., Nat. Commun. (2014).

Treatment of Tumors with FAP-AFN

Mice were maintained in pathogen-free conditions in a temperature-controlled environment with 12/12 hour light/dark cycles and received food and water ad *libitum*. Female C57BL/6J mice (Charles River Laboratories, Saint-Germain sur l'Arbresle, France) were inoculated with $5\times10^6$ cells of the B16-mCD20 clone (B16 cells stably transfected with a plasmid containing the expression cassette for mCD20), or parental B16 cells, at the age of 8 weeks, using a 30G insulin syringe, in 50 μl suspension, on the shaved flank of briefly sedated mice (using 4% isoflurane). B16 cells are a murine melanoma cell line that are typically used as a model for human skin cancers.

Figure 2:
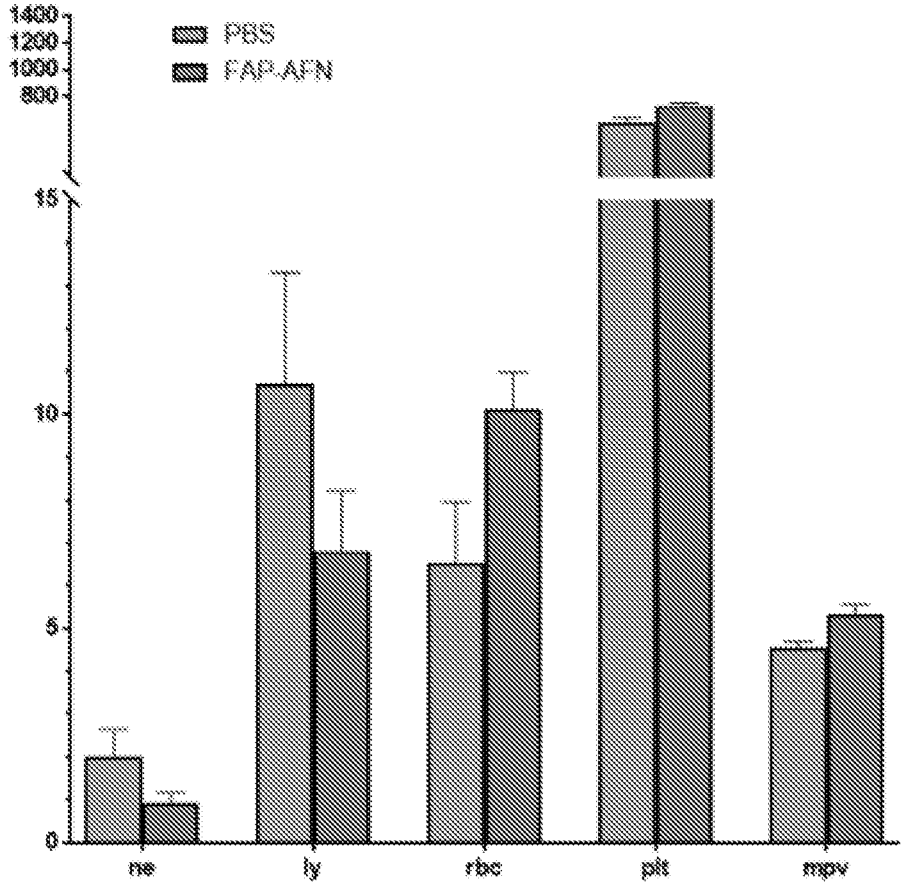
FIG. 2 is a graph showing hematological data from mice treated with FAP-AFN or PBS (neutrophils (ne), lymphocytes (ly), and platelets (plt) are expressed in K/μl; red blood cells (rbc) in M/μl; and mean platelet volume (mpv) in fL). The parameters tested are: neutrophil count ("ne"), lymphocytes count ("ly"), red blood cell count ("rbc"), platelets ("plt"), and mean platelet volume ("mpv").

Tumor treatments were done perilesionally (p.l.), which is s.c. at the tumor border, starting at day 7 after tumor inoculation. Mice (n=5) received FAP-AFN treatments on days 7, 8, 9, 10, 12, 14, 15 and 16. Control mice were treated with 100 μl PBS (n=6) on the same days. FAP-AFN were given at 5,000 IU per treatment, corresponding to 37 μg protein (1.8 mg/kg). One day after the last tumor treatment, blood was collected from the tail vein in EDTA-coated microvette tubes (Sarstedt), and analyzed in a Hemavet 950FS (Drew Scientific, Waterbury, USA) whole blood counter. Neutrophils (ne), platelets (plt), and lymphocytes (ly) are expressed in K/μl; red blood cells (rbc) in M/μl; and mean platelet volume (mpv) in fL. FIG. 1 shows the means+/−s.e.m. for tumor growth and FIG. 2 shows the hematological data. To the right of the tumor growth curve in FIG. 1, the number of mice that were completely tumor-free at the indicated day is shown (i.e., 1 out of the 5 treated mice was tumor-free on day 9).

FIG. 1 shows that mice treated with FAP-AFN had reduced tumor growth as compared to untreated mice (control mice). Additionally, 1 of 5 mice treated with FAP-AFN was tumor free by day 9.

FIG. 2 shows that the FAP-AFN construct was safe. Specifically, the FAP-AFN altered hematological parameters comparably to PBS. Wild type interferon is known to suffer from safety deficiencies that are reflected in changes in hematological parameters.

These results show that a fusion protein having a FAP targeting moiety and a mutated IFNα2 with reduced affinity for its receptor can reduce tumor growth. Additionally, the data shows that the FAP targeting moiety restores the ability of the mutated IFNα2 to activate it receptor. Accordingly, the fusion proteins having a FAP targeting moiety and at least one mutated cytokine disclosed herein are useful in the treatment of the diseases and disorders disclosed herein (e.g., cancer).

Example 3. Combination Therapy with FAP-AFN

This example shows that combination treatment with a fusion protein having a FAP targeting moiety and a mutated a cytokine, wherein the mutation in the cytokine results in the reduced activity of the cytokine, and at least one additional therapeutic agent can reduce tumor growth.

Methods

The FAP-AFN disclosed in Example 2 above was used in combination therapy to reduce tumor growth. The mouse model disclosed in Example 2 was used. For the combination therapy treatment, mice (n=4 per experimental group), were treated with either:

1) PBS (100 μl) (control);
2) FAP-AFN alone (1.8 mg/kg) (FAP-Q124R);
3) FAP-AFN (1.8 mg/kg) and doxorubicin (3 mg/kg) (FAP+dox);
4) FAP-AFN (1.8 mg/kg) and recombinant mouse TNF (28 μg/kg) (FAP+TNF);
5) FAP-AFN (1.8 mg/kg) and anti-PD-L1 sdAb (5.5 mg/kg) (FAP+PD-L1); or
6) FAP-AFN (1.8 mg/kg), anti-PD-L1 sdAb (5.5 mg/kg), and anti-CTLA4 Ab (45 μg/kg) plus anti-OX40 Ab (1.8 mg/kg) (anti-CTLA4 Ab plus anti-OX40 Ab designated as Treg-depleting (TregD)) (FAP+PD-L1+TregD).

Treatment started at 6 days after tumor inoculation.

Figure 3A:
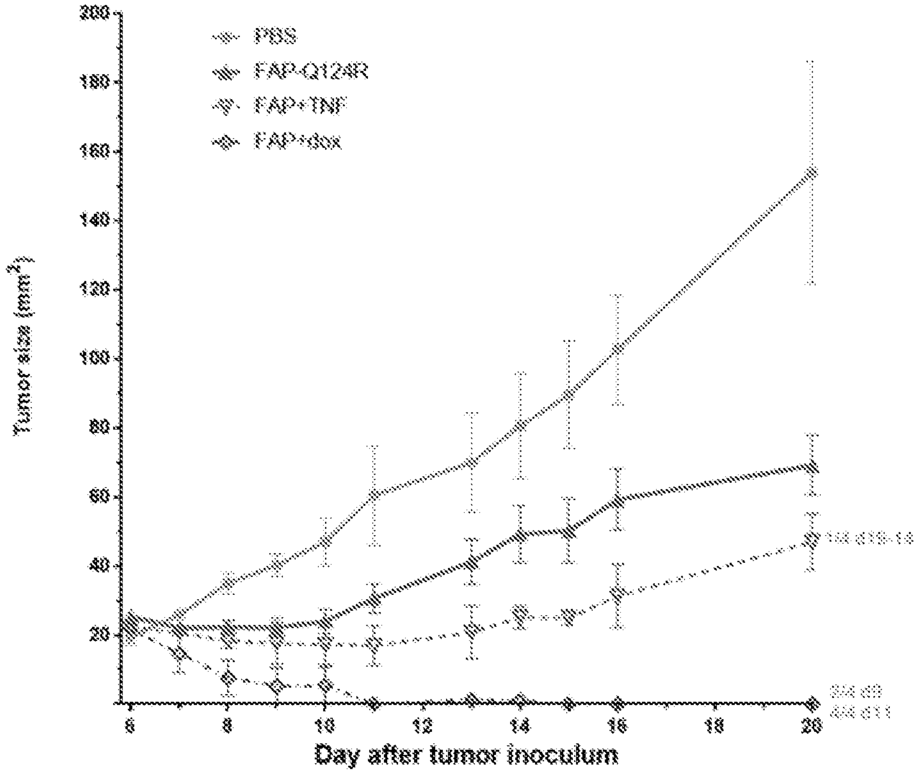
FIG. 3A is a graph comparing the effect of treatment with FAP-AFN (as described in Example 2) alone, FAP-AFN and doxorubicin (FAP+dox), and FAP-AFN and recombinant mouse TNF (FAP+TNF) on tumor growth in mice inoculated with a B16-mCD20 clone. Untreated mice (control) were treated with PBS. The number to the right a tumor growth curve indicates the number of mice that were completely tumor-free at the indicated day.
Figure 3B:
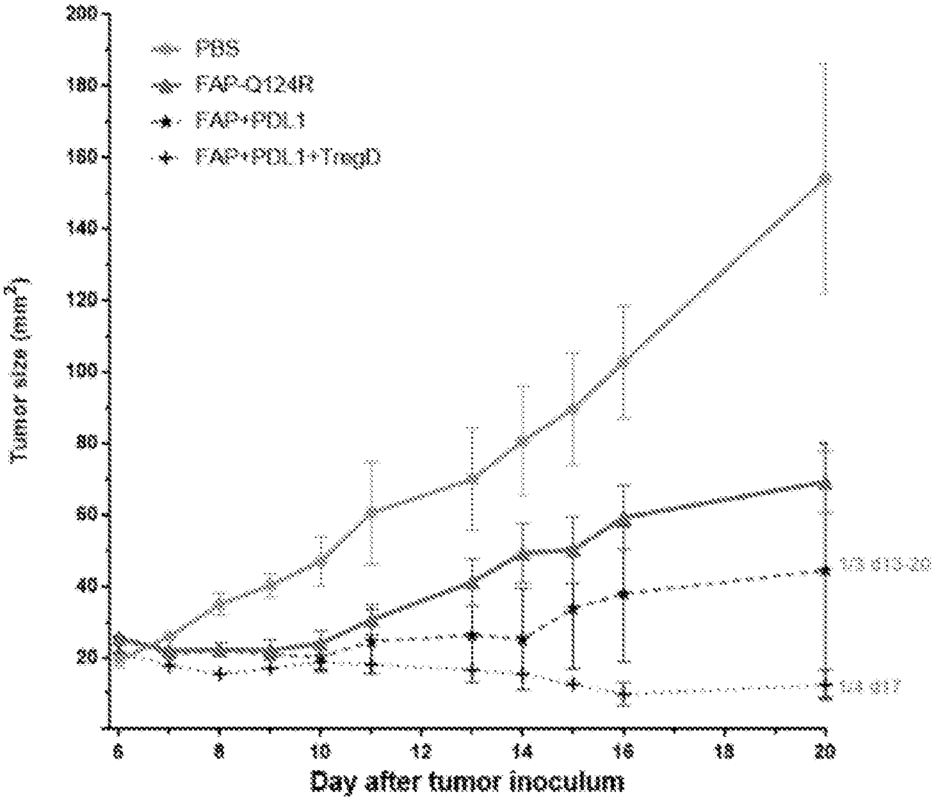
FIG. 3B is a graph comparing the effect of treatment with FAP-AFN (as described in Example 2) alone, FAP-AFN and anti-PD-L1 sdAb (FAP+PD-L1), and FAP-AFN, anti-PD-L1 sdAb, and anti-CTLA4 Ab plus anti-OX40 Ab (FAP+PD-L1+TregD) on tumor growth in mice inoculated with a B16-mCD20 clone. Untreated mice (control) were treated with PBS. The number to the right the tumor growth curve indicates the number of mice that were completely tumor-free at the indicated day.

FAP-AFN treatments in these combination therapies were given on days 6, 7, 8, 9, 10, 11, 13, 14 and 15 (via p.l. injections). The additional therapeutic agents were injected every 2-3 days (via p.l.) with a total of 3×/week. FIGS. 3A and 3B show the means+/−s.e.m. for tumor growth. To the right of the curves, the number of mice are shown that were completely tumor-free at the indicated day.

Results

FIGS. 3A-B shows that mice treated with FAP-AFN and at least one other therapeutic agent (e.g., TNF, dox, PD-L1, or PD-L1+TregD) had increased reduced tumor growth as compared to FAP-AFN alone (FAP-Q124R) and untreated mice (control mice). Additionally, 1 of 4 mice treated with FAP+TNF was tumor-free on day 9-14; 4 of 4 mice treated with FAP+dox were tumor-free by day 11 (2 were tumor free on day 9; all 4 were tumor-free at day 11); 1 of 3 mice treated with FAP+PD-L1 was tumor-free on day 13-20; and 1 of 4 mice treated with FAP+PD-L1+TregD was tumor-free on day 17. The data also shows that mice treated with FAP-AFN alone had greater reduction in tumor growth as compared to untreated mice (control mice).

These results show that treatment with a fusion protein having a FAP targeting moiety and a mutated a cytokine alone or in combination with at least one additional therapeutic agent can reduce tumor growth. Additionally, the data shows that there is a synergistic effect as mice subject to combination treatments with FAP-AFN had greater reduction in tumor growth as compare to mice treated with FAP-AFN alone. Accordingly, the fusion proteins having a FAP targeting moiety and at least one mutated cytokine disclosed herein alone or in combined with at least one additional therapeutic agent are useful in the treatment of the diseases and disorders disclosed herein (e.g., cancer).

Example 4. Treatment with a Bispecific FAP-AFN

This example shows that a bispecific fusion protein having at least one FAP targeting moiety and a mutated a cytokine, wherein the mutation in the cytokine results in the reduced activity of the cytokine, can reduce tumor growth.

Methods

A bispecific fusion protein having a FAP targeting moiety (described in Example 2), a PD-L1 targeting moiety, and a human IFNα2 with a mutation at Q124R (FAP-PD-L1-Q124R) were used in the mouse model disclosed in Example 2. Mice (n=5 per experimental group), were treated with either:

1) PBS (100 μl) (control);
2) FAP-AFN alone (1.8 mg/kg) (FAP-Q124R); or
3) FAP-PD-L1-Q124R (55 μg/injection).

Figure 4:
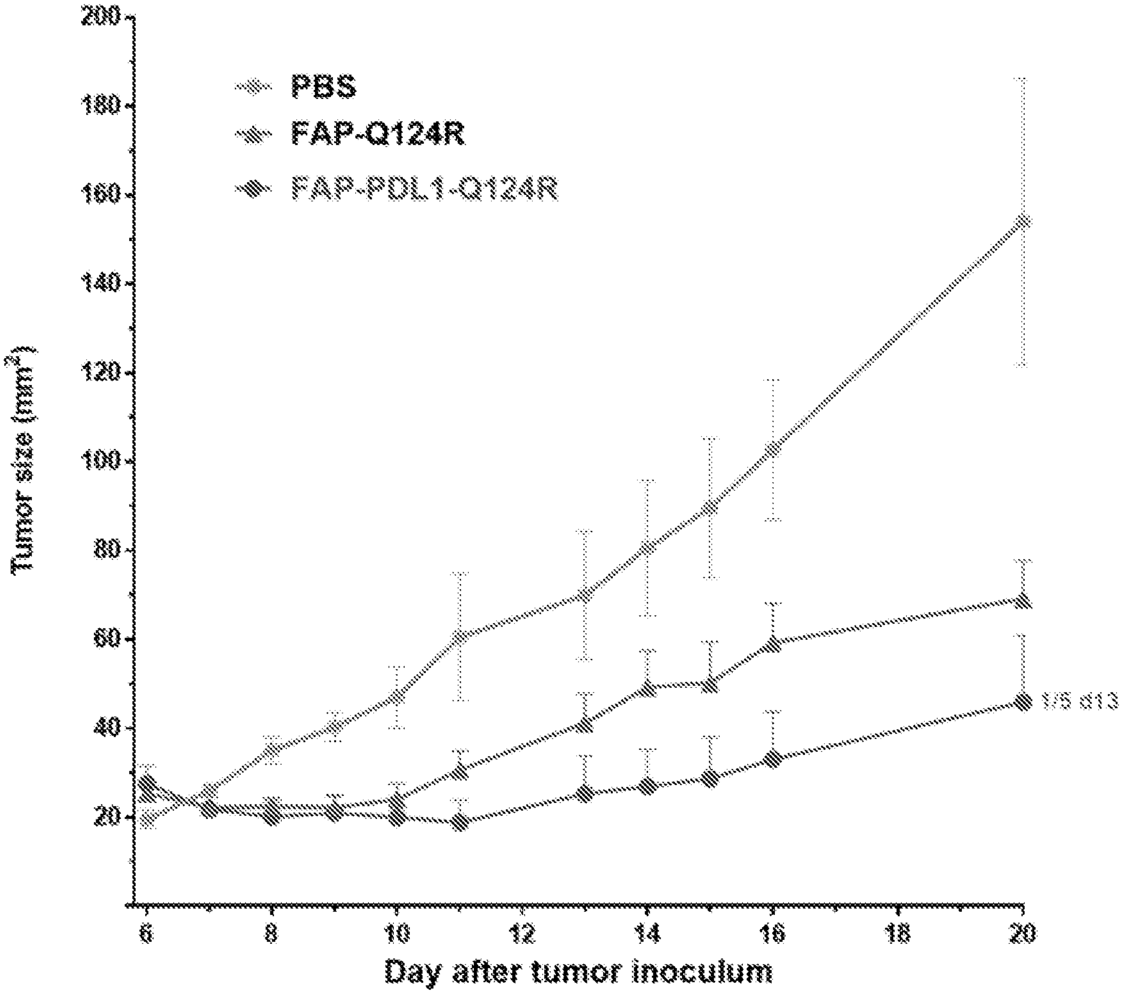
FIG. 4 is a graph comparing the effect of treatment with FAP-AFN (as described in Example 2) alone and a bispecific composition having a FAP binding agent (FAP-PD-L1-Q124R) on tumor growth in mice inoculated with a B16-mCD20 clone. Untreated mice (control) were treated with PBS. The number to the right the tumor growth curve indicates the number of mice that were completely tumor-free at the indicated day.
Figure 5:
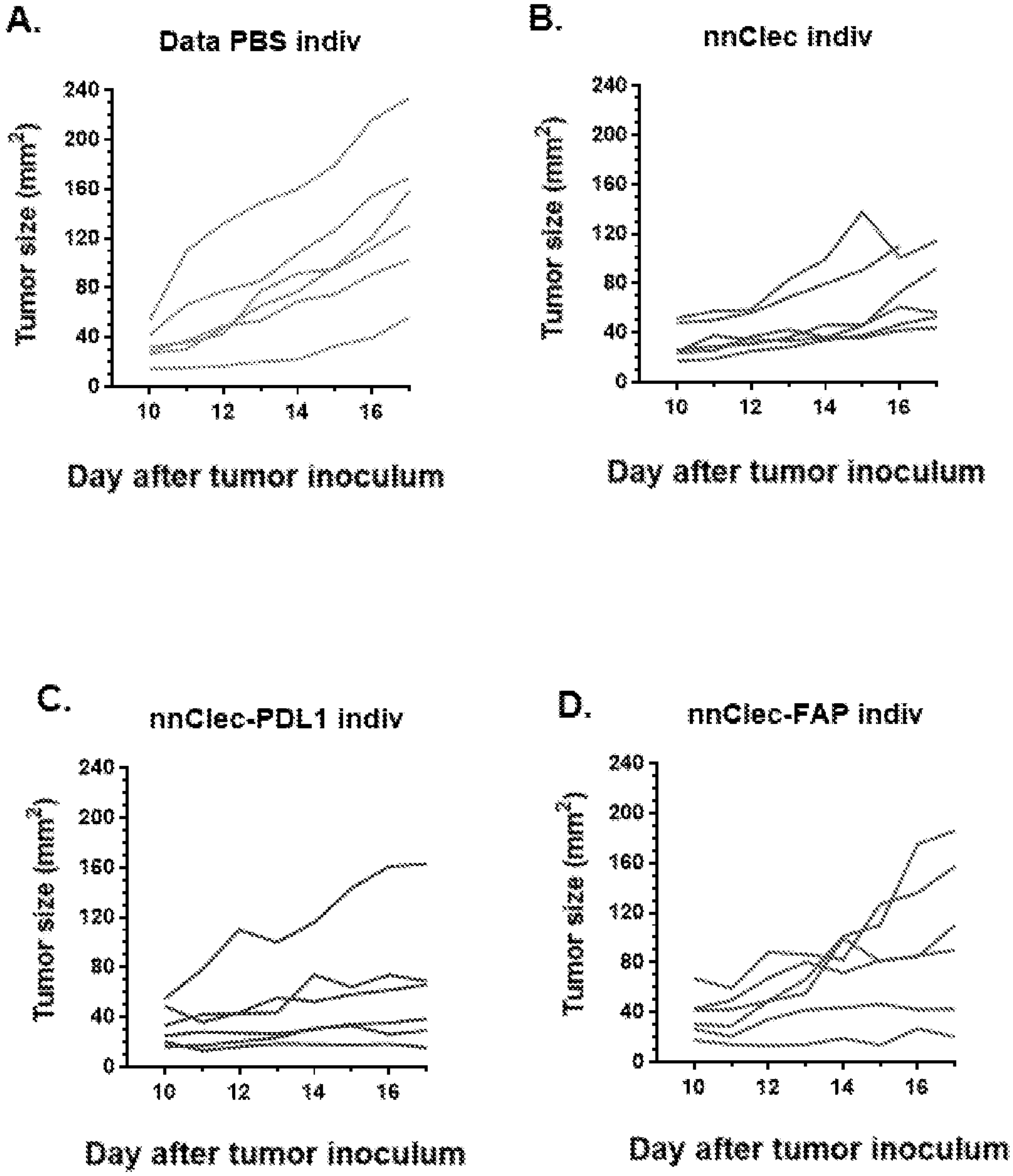
FIGS. 5A-D are graphs showing the effect of treatment with a monospecific composition (nnClec.
Figure 6:
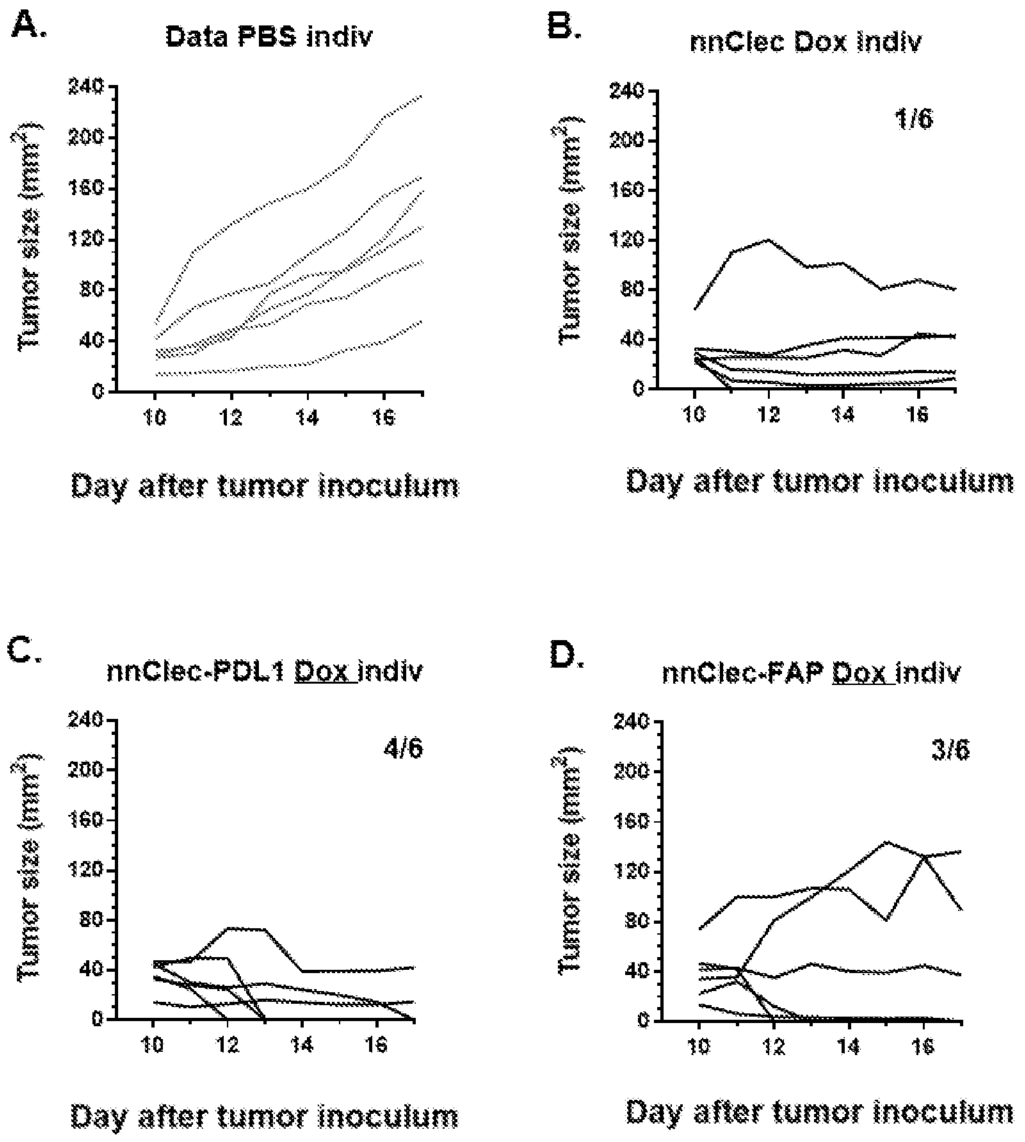
FIGS. 6A-D are graphs showing the effect of treatment with a monospecific composition in combination with doxorubicin (nnClec Dox.
Figure 7:
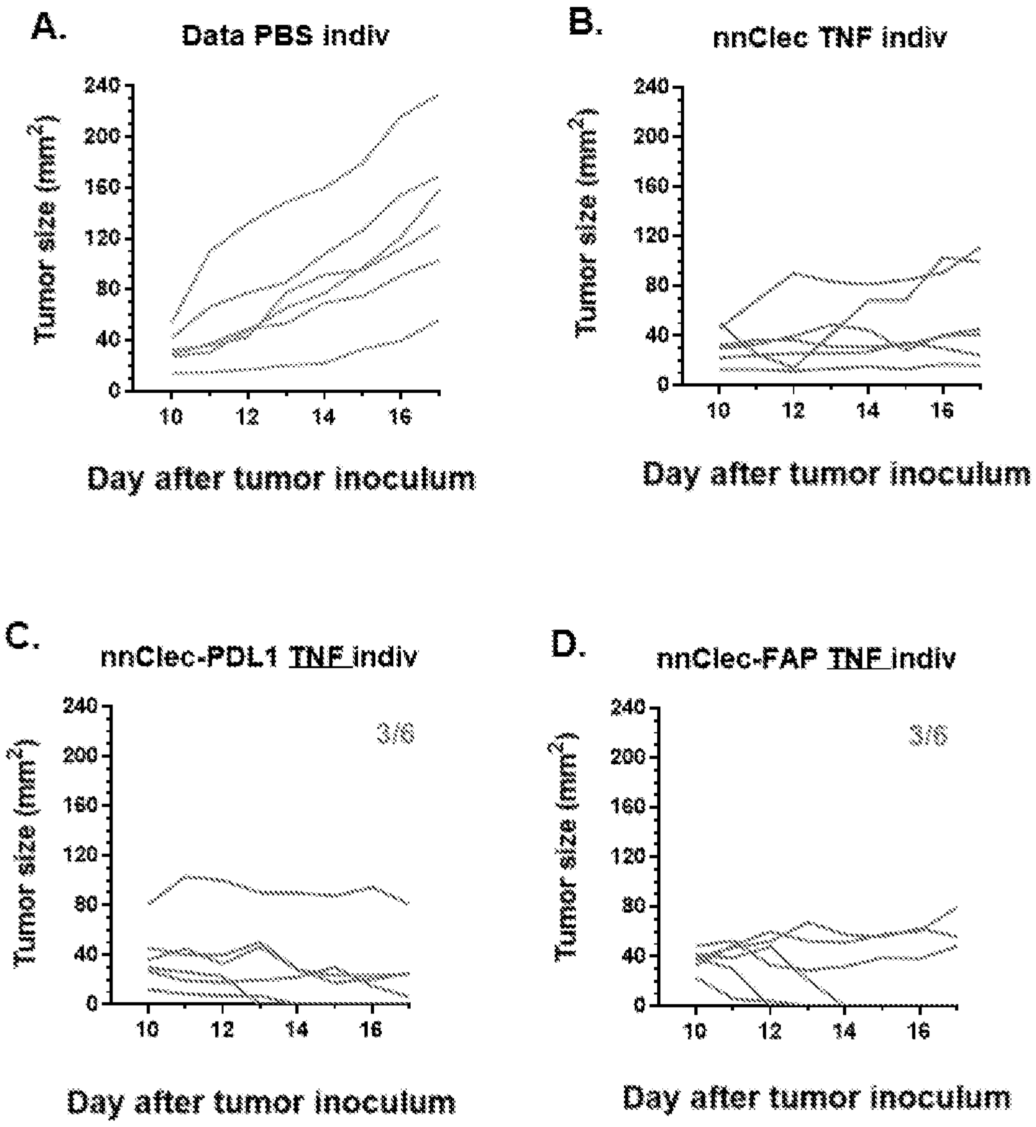
FIGS. 7A-D are graphs showing the effect of treatment with a monospecific composition in combination with TNF (nnClec TNF.
Figure 8:
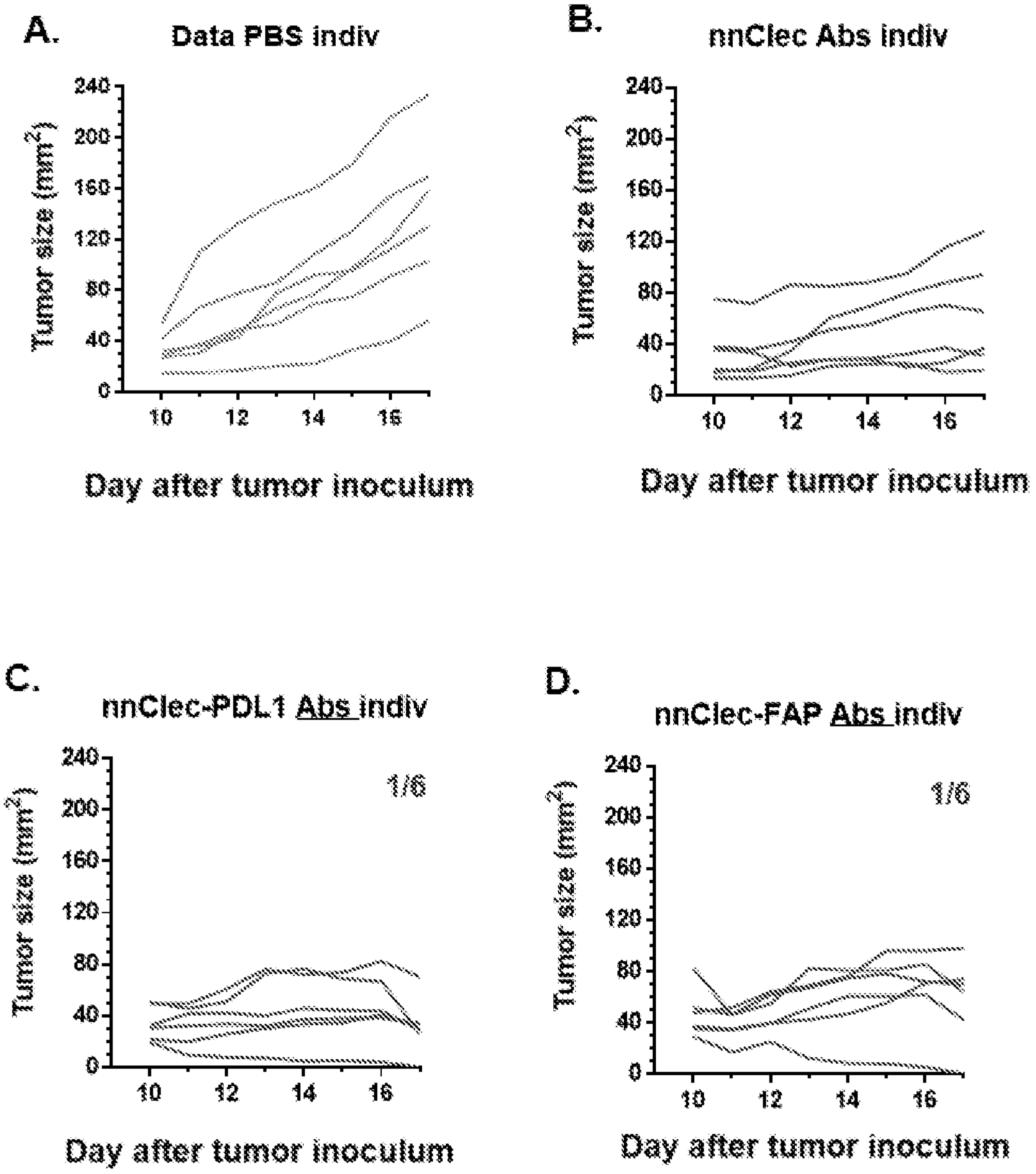
FIGS. 8A-D are graphs showing the effect of treatment with a monospecific composition in combination with Abs (nnClec Abs.
Figure 9:
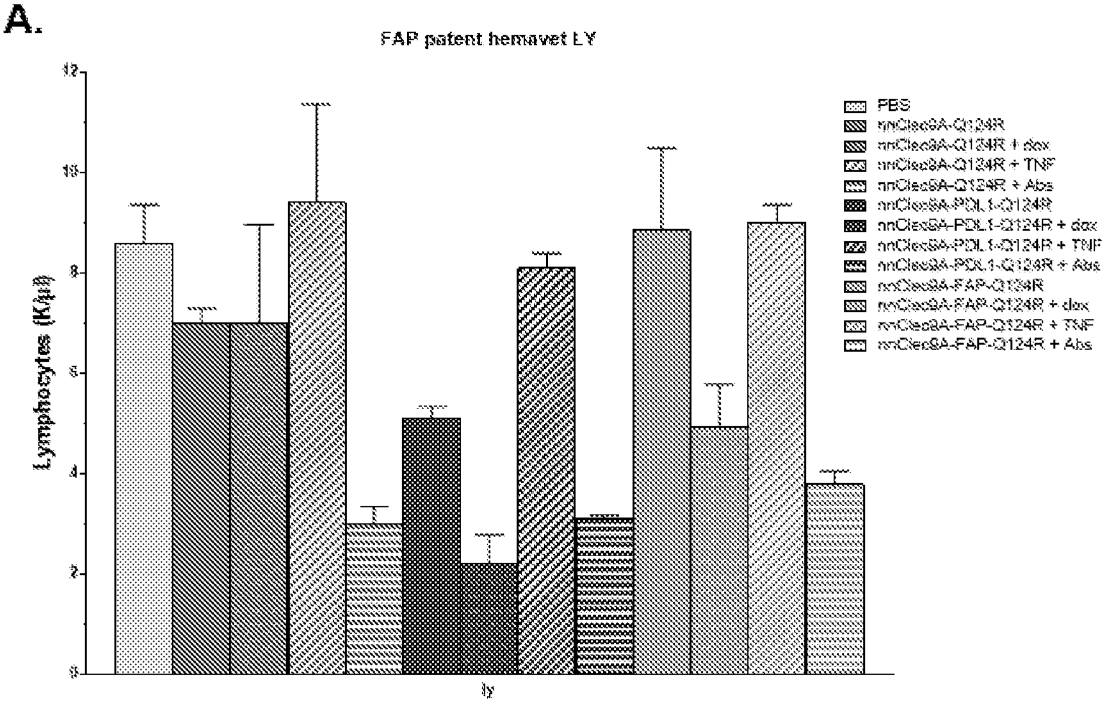
FIGS. 9A-E are graphs showing the hematological data from mice treated with a monospecific composition (nnClec), either alone or in combination with at least one additional therapeutic agent (i.e., doxorubicin, TNF, Abs) or a bispecific composition (nnClec-PD-L1 or nnClec-FAP, either alone or in combination with at least one additional therapeutic agent (i.e., doxorubicin, TNF, Abs) (lymphocytes (LY.
Figure 9:
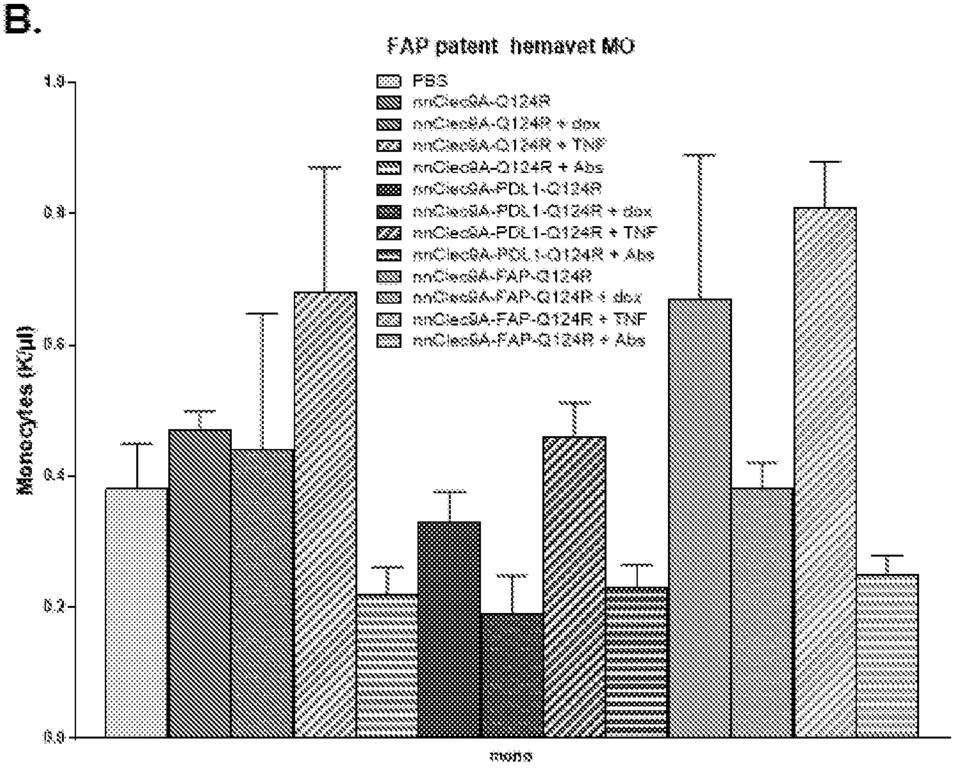
Figure 9:
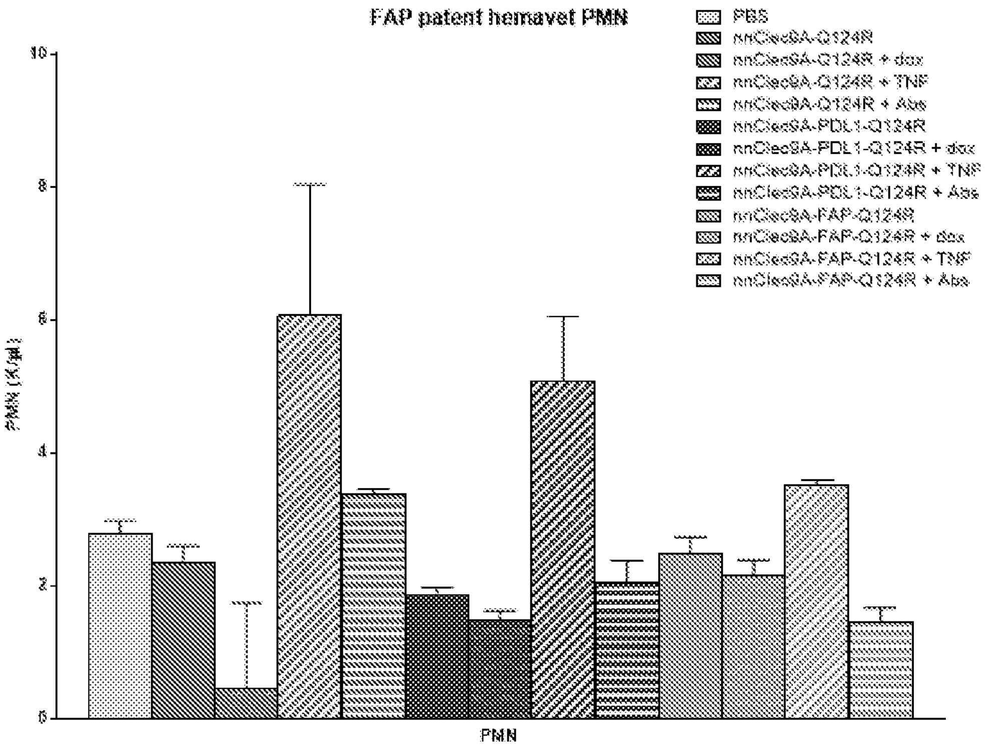
Figure 9:
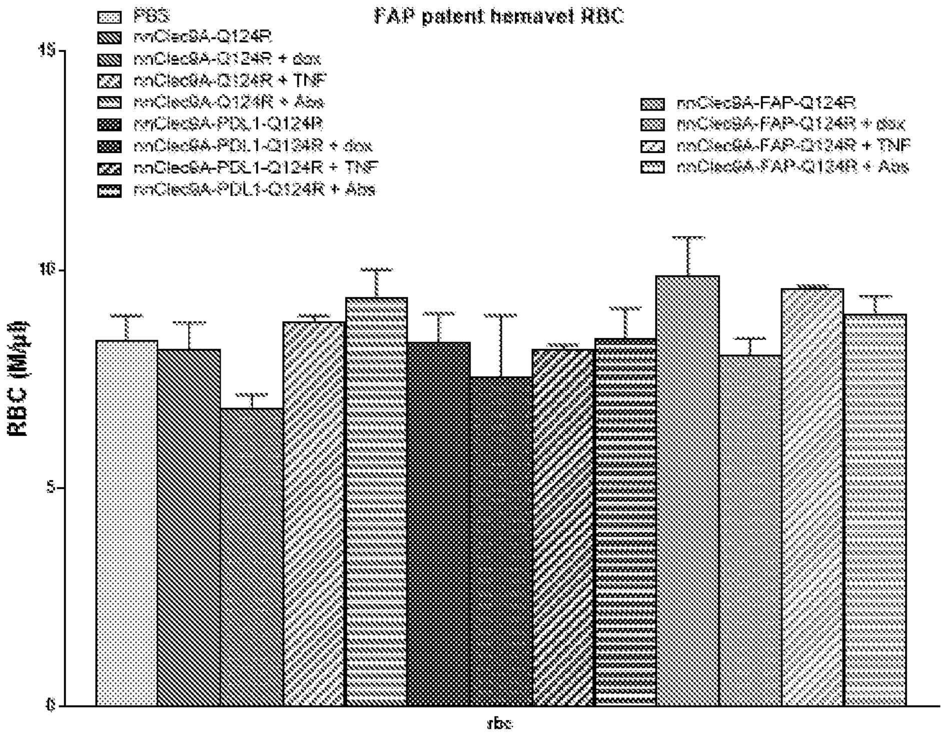
Figure 9:
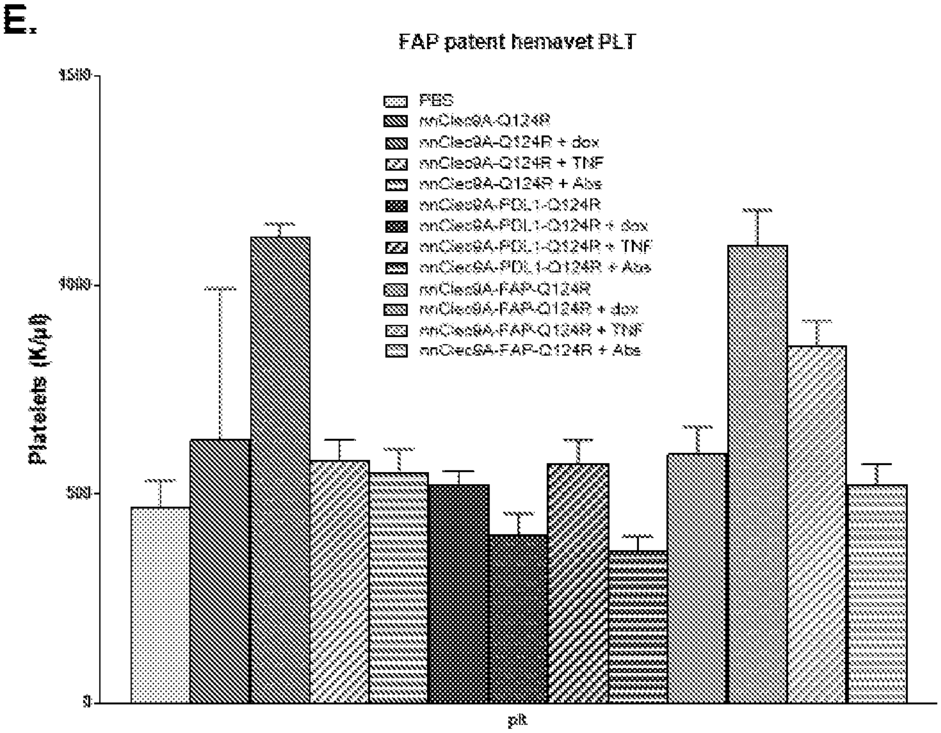

FAP-PD-L1-Q124R was given at 55 μg/injection, to correct for the presence of 2 VHHs (sdAbs) instead of 1 VHH (sdAb) in the monospecific FAP-AFN. Treatments started at 6 days after tumor inoculation. Treatments were given on days 6, 7, 8, 9, 10, 11, 13, 14 and 15 via p.l. injections. FIG. 4 shows the means+/−s.e.m. for tumor growth. In FIG. 4, to the right of the tumor growth curve, the number of mice that were completely tumor-free at the indicated day is shown.

FIG. 4 shows that mice treated with bispecific FAP-PD-L1-Q124R had a greater reduction in tumor growth as compared to FAP-Q124R treated mice and untreated mice (control mice). Additionally, 1 of 5 mice treated with FAP-PD-L1-Q124R was tumor-free on day 13. The data also shows that mice treated with FAP-Q124R had greater reduction in tumor growth as compared to untreated mice (control mice).

These results show that treatment with a bispecific fusion protein or a monospecific fusion protein having at least one FAP targeting moiety and at least one mutated cytokine can reduce tumor growth. The results also show that the bispecific fusion protein has a stronger therapeutic effect as compared to the monospecific fusion protein. Accordingly, a bispecific and monospecific fusion proteins having a FAP targeting moiety and at least one mutated cytokine disclosed herein are useful in the treatment of the diseases and disorders disclosed herein (e.g., cancer).

Example 5. Treatment with a Bispecific FAP-AFN

This example compares the efficacy of bispecific nnClec9A-FAP-Q124R as compared to bispecific nnClec9A-PD-L1-Q124R as compared to monospecific nnClec9A-Q124R in large tumors. This example shows that the bispecific composition disclosed herein are useful to treat cancer.

The mouse model disclosed in Example 2 was used. Mice (n=6 per experimental group), were treated with either:

1) PBS (100 μl) (control);
2) nnClec9A-Q124R alone (40 μg/injection) (nnClec);
3) nnClec9A-PD-L1-Q124R alone (60 μg/injection) (nnClec-PD-L1);
4) nnClec9A-FAP-Q124R alone (60 μg/injection) (nnClec-FAP);
5) nnClec9A-Q124R (40 μg/injection) and doxorubicin (3 mg/kg) (nnClec Dox);
6) nnClec9A-PD-L1-Q124R (60 μg/injection) and doxorubicin (3 mg/kg) (nnClec-PD-L1 Dox);
7) nnClec9A-FAP-Q124R (60 μg/injection) and doxorubicin (3 mg/kg) (nnClec-FAP Dox);
8) nnClec9A-Q124R (40 μg/injection) and recombinant mouse TNF (28 μg/kg) (nnClec TNF);
9) nnClec9A-PD-L1-Q124R (60 μg/injection) and recombinant mouse TNF (28 μg/kg) (nnClec-PD-L1 TNF);
10) nnClec9A-FAP-Q124R (60 μg/injection) and recombinant mouse TNF (28 μg/kg) (nnClec-FAP TNF);
11) nnClec9A-Q124R (40 μg/injection) and anti-CTLA4 Ab (45 μg/kg) plus anti-OX40 Ab (1.8 mg/kg) (anti-CTLA4 Ab plus anti-OX40 Ab designated as Treg-depleting antibodies) (nnClec Abs);
12) nnClec9A-PD-L1-Q124R (60 μg/injection) and anti-CTLA4 Ab (45 μg/kg) plus anti-OX40 Ab (1.8 mg/kg) (nnClec-PD-L1 Abs); or
13) nnClec9A-FAP-Q124R (60 μg/injection) and anti-CTLA4 Ab (45 μg/kg) plus anti-OX40 Ab (1.8 mg/kg) (nnClec-FAP Abs).

Tumors were grown to greater the 30 $mm^2$ before treatment began. Mice were treated daily with PBS, nnClec, nnClec-PD-L1, and nnClec-FAP via p.l. on days 10-16 after tumor inoculation. Groups (i.e., Groups 5-12) that received additional therapeutic agents (i.e., doxorubicin, TNF, or Treg-depleting antibodies) received the additional therapeutic agent via p.l. every 2-3 days, with a total of 3×/week. One day after the last tumor treatment, blood was collected from the tail vein in EDTA-coated microvette tubes (Sarstedt), and analyzed in a Hemavet 950FS (Drew Scientific, Waterbury, USA) whole blood counter. Lymphocytes, monocytes and neutrophils are expressed in K/μl, red blood cells (rbc) in M/μl; platelets in K/μl.

FIGS. 5A-D show that mice treated with nnClec, nnClec-PD-L1, and nnClec-FAP had reduced tumor growth as compared to untreated mice (control mice). The data also shows that tumor growth was slowed in mice treated with nnClec, whereas tumor growth stopped (i.e., tumor is in stasis) in 3 of 6 nnClec-PD-L1 treated mice and 2 of 6 nnClec-FAP treated mice (see FIGS. 5B-D).

FIG. 6A-D shows that mice treated with nnClec+Dox (nnClec Dox), nnClec-PD-L1+Dox (nnClec-PD-L1 Dox), and nnClec-FAP+Dox (nnClec-FAP Dox) had reduced tumor growth as compared to untreated mice (control mice). The data also shows that the mice treated with bispecific compositions had a greater incident of tumor-free mice (see Table 3).

TABLE 3

| Tumor Status | nnClec Dox | nnClec-PD-L1 Dox | nnClec-FAP Dox |
|---|---|---|---|
| Tumor Stasis | 2/6 | 2/6 | 2/6 |
| Tumor Shrinkage | 3/6 | 4/6 | 3/6 |
| Tumor Free | 1/6 | 4/6 | 3/6 |

The comparison of the results in FIGS. 5A-D and FIGS. 6A-D show that the combination of a monospecific or bispecific fusion protein with at least one additional therapeutic agent has a synergistic effect as mice subject to combination treatments had greater reduction in tumor growth as compared to mice treatment with a monospecific or bispecific fusion protein alone (compare FIGS. 5B and 6B, FIGS. 5C and 6C, and FIGS. 5D and 6D).

FIG. 7A-D shows that mice treated with nnClec+TNF (nnClec TNF), nnClec-PD-L1+TNF (nnClec-PD-L1 TNF), and nnClec-FAP+TNF (nnClec-FAP TNF) had reduced tumor growth as compared to untreated mice (control mice). The data also shows that the mice treated with bispecific compositions had a greater incident of tumor-free mice (see Table 4).

TABLE 4

| Tumor Status | nnClec TNF | nnClec-PD-L1 TNF | nnClec-FAP TNF |
|---|---|---|---|
| Tumor Stasis | 4/6 | 2/6 | 3/6 |
| Tumor Shrinkage | 1/6 | 4/6 | 3/6 |
| Tumor Free | 0/6 | 3/6 | 3/6 |

FIG. 8A-D shows that mice treated with nnClec Abs, nnClec-PD-L1 Abs, and nnClec-FAP Abs had reduced tumor growth as compared to untreated mice (control mice). The data also shows that the mice treated with bispecific compositions had a greater incident of tumor-free mice and mice with tumor stasis (see Table 5).

TABLE 5

| Tumor Status | nnClec Abs | nnClec-PD-L1 Abs | nnClec-FAP Abs |
|---|---|---|---|
| Tumor Stasis | 2/6 | 4/6 | 4/6 |
| Tumor Shrinkage | 1/6 | 1/6 | 1/6 |
| Tumor Free | 0/6 | 1/6 | 1/6 |

FIGS. 9A-E show the analysis of lymphocytes (LY), monocytes (MO), neutrophils (PMN), red blood cells (rbc), and platelets (PLT). FIGS. 9A-E show that the tested constructs were safe. Specifically, the tested constructs altered hematological parameters comparably to PBS. Wild type interferon is known to suffer from safety deficiencies that are reflected in changes in hematological parameters.

These results show that treatment with a bispecific fusion protein or a monospecific fusion protein having at least one FAP targeting moiety and at least one mutated cytokine can reduce tumor growth. The results also show that the combination of a bispecific fusion protein with at least one additional therapeutic agent has a synergistic effect as mice subject to combination treatments had greater reduction in tumor growth as compared to mice treated with a bispecific fusion protein or monospecific fusion protein alone. Furthermore, the data shows that the combination treatment with a bispecific fusion protein and at least one additional therapeutic agent resulted in the higher incidents of tumor-free mice. Accordingly, a bispecific and monospecific fusion proteins having a FAP targeting moiety and at least one mutated cytokine disclosed herein are useful in the treatment of the diseases and disorders disclosed herein (e.g., cancer).

Example 6. Human FAP VHH Binds to Membrane Bound FAP in Cells

Figure 12:
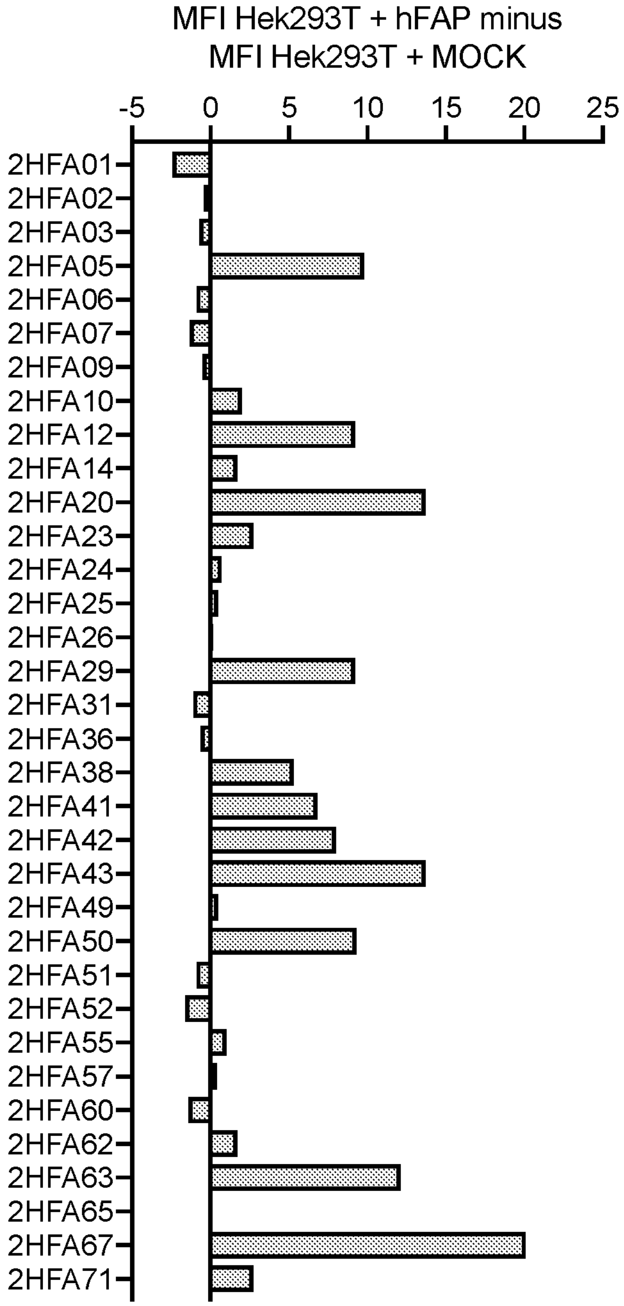
FIG. 12 shows FAP VHH binding analysis done using fluorescence activated cell sorting (FACS). FAP VHH periplasmic extracts were applied to HEK293T cells transiently transfected with human FAP or an empty vector (MOCK). Binding was measured using a fluorescently labeled anti-His Ab in FACS and plotted as the difference in mean fluorescent intensity (MFI) between FAP and MOCK transfected cells.

Expression-vectors (pMECS) encoding 34 VHH representing all 7 different CDR3 groups of the human FAP VHHs from Example 1 were transformed to WK6 cells. VHHs (with a C-terminal His-tag) were expressed in periplasmic extracts upon IPTG overnight stimulation. These extracts were applied at a 1/5 dilution in a FACS binding-assay: HEK293T cells were transiently transfected with a full length human FAP plasmid (pMET7 FLAG-huFAP) or an empty vector (MOCK). Two days after transfections, cells were resuspended and incubated with a 1 over 5 dilution periplasmic extracts in FACS buffer (PBS+0.5 mM EDTA+3% FBS). VHH binding was detected using a FITC-coupled anti-His Ab (Genscript). Samples were acquired with a MACSQuant X instrument (Miltenyi Biotec) and analyzed using the FlowLogic software (Miltenyi Biotec). Data are summarized in FIG. 12.

Example 7. Human Specific FAP VHH AcTakines

One FAP VHH, 2HFA42, was cloned into an AFN format in the pHEN6C expression plasmid as follows: FAP VHH 2HFA42-$(GGS)_{20}$-hIFNα2_R149A-GGS-$(His)_6$ (see sequence below). AFN expression in WK6 cells was induced overnight with 1 mM IPTG, cells were pelleted, and periplasmic extracts prepared using TES (0.2 M Tris pH 8.0, 0.5 mM EDTA, 0.5 M sucrose) and TES/4 buffers. Proteins were purified from extracts using the TALON Metal affinity resin according to the manufacturer's guidelines and imidazole was removed from the samples using PD10 columns (GE Healthcare).

Figure 13A:
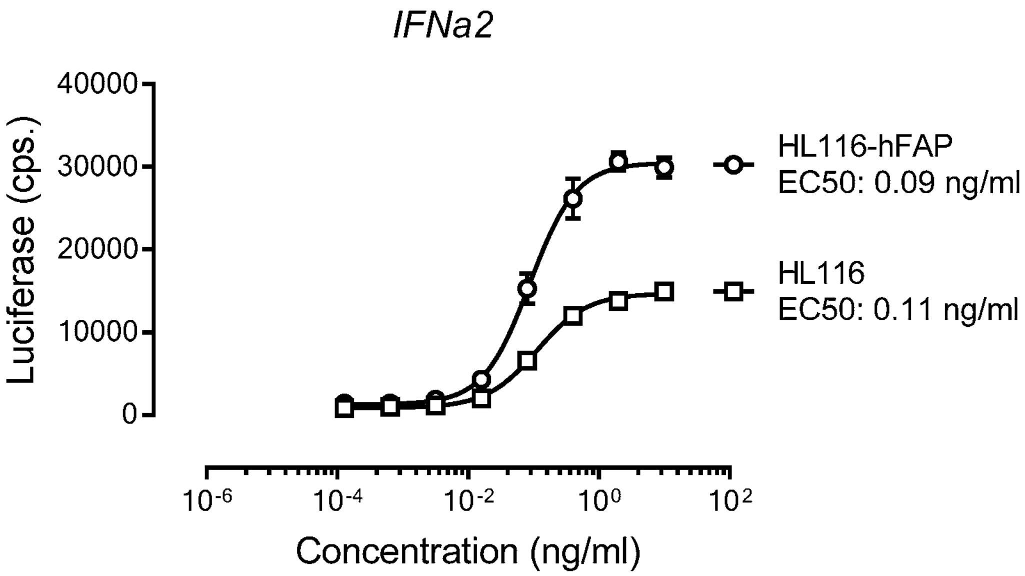
FIGS. 13A and B show biological activity of FAP VHH AFN. HL116 or HL116-hFAP cells were stimulated for 6 hours with serial dilution wild type IFNa2 (left) or FAP VHH AFN (right). Average luciferase activities (±STDEV) are plotted.
Figure 13B:
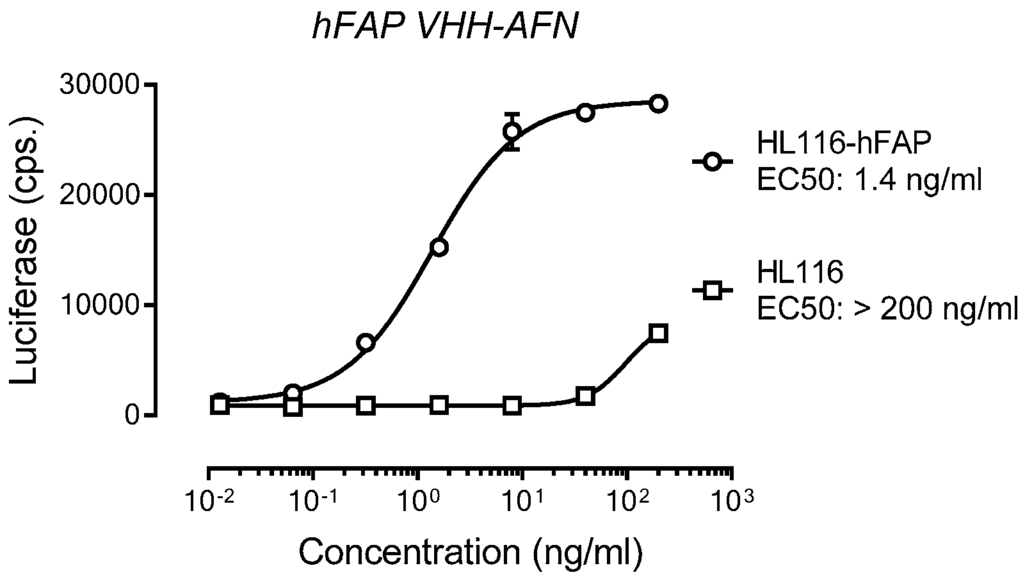

Biological activity was measured on parental HL116 cells (an IFN responsive cell-line stably transfected with a p6-16 luciferase reporter) and the derived, stably transfected HL116-hFAP cells. Cells were seeded overnight and stimulated for 6 hours with a serial dilution FAP VHH AFN. Luciferase activity was measured on an EnSight Multimode Plate Reader (Perkin Elmer). Data in FIGS. 13A and B clearly show that AFN is more active on cells expressing hFAP compared to parental cells, illustrating that it is possible to, at least in part, to restore signalling of an IFNα2 mutant by specific targeting to hFAP. Of note, parental HL116 and HL116-hFAP cells are comparable sensitive to wild type, untargeted IFNα2, as also indicated by the targeting index of about 1 compared to a targeting index of >140 for the FAP VHH AFN (FIGS. 13A and 13B; Table 6).

TABLE 6

| | EC50 HL116 (ng/ml) | EC50 HL116-FAP (ng/ml) | Targeting Index (ratio EC50 HL116/ HL116-FAP) |
|---|---|---|---|
| Wild type IFN | 0.11 | 0.09 | 1.2 |
| FAP VHH AFN | >200 | 1.4 | >140 |

The structure for FAP VHH AFN is shown below:

FAP VHH 2HFA42—$(GGS)_{20}$-hIFNα2 R149A-$His_6$

The sequence for FAP VHH AFN is shown below (the sequence for FAPVHH 2HFA42 is shown in bold letters, the sequence for $(GGS)_{20}$ is shown in italicized letters, and the sequence for hIFNα2_R149A is shown with underlined letters):

(SEQ ID NO: 843)

QVQLQESGGGLVQTGGSLRLSCAASGSIFVGNAMGWYRQALGNQRELVAG

ITSDGITYYPDSVKGRFTISRDNDKNTIYLQMNSLKPEDTAVYYCNLWPP

RIGFASWGQGTQVTVSSVD*GGSGGSGGSGGSGGSGGSRSGGSGGSGGSGG*

*SGGSGGSGGSGGSGGSGGSGGSGGSGGS*AAAMCDLPQTHSLGSRRTLMLL

AQMRRISLFSCLKDRHDFGFPQEEFGNQFQKAETIPVLHEMIQQIFNLFS

TKDSSAAWDETLLDKFYTELYQQLNDLEACVIQGVGVTETPLMKEDSILA

VRKYFQRITLYLKEKKYSPCAWEWRAEIMASFSLSTNLQESLRSKELEHH

HHHH.

Example 8. Tolerability and Efficacy of FAP-AFN in the Presence or Absence of Chemotherapy in Different Tumor Models Mice were maintained in pathogen-free conditions in a temperature-controlled environment with 12/12 hour light/dark cycles and received food and water ad libitum. Female C57BL/6J mice (Charles River Laboratories, Saint-Germain sur l'Arbresle, France) were inoculated with B16BL6 or MC38 or Panc02 cells, at the age of 8 weeks, using a 30G insulin syringe, in 50 μl suspension, on the shaved flank of briefly sedated mice (using 4% isoflurane). B16BL6 cells are a murine melanoma cell line that are typically used as a model for human skin cancers with increased resistance to doxorubicin. MC38 cells are derived from a murine colon adenocarcinoma and are typically used as a model for human colon cancers. Panc02 cells are derived from a murine pancreatic ductal adenocarcinoma and are typically used as a model for human pancreatic cancers.

All tumor treatments were done perilesionally (p.l.), which is s.c. at the tumor border, starting at day 7 after tumor inoculation. Mice received FAP-AFN or FAP-WTmIFN treatments on days 7, 8, 9, 10, 12, 13, 14 and 15. Control mice were treated with PBS on the same days. FAP-AFN or FAP-VVTmIFN were given about 3714 protein (1.8 mg/kg). Doxorubicin treatments were done at 3 mg/kg, 3 times per week.

1) PBS (100 μl) (control), 7-8 mice;
2) FAP-AFN alone (1.8 mg/kg) (FAP-Q124R), 5 mice;
3) FAP-AFN (1.8 mg/kg) and doxorubicin (3 mg/kg) (FAP-AFN+dox), 5 mice;
4) FAP-WTmIFN (1.8 mg/kg) (FAP-WTmIFN), 5 mice;
5) FAP-WTmIFN (1.8 mg/kg) and doxorubicin (3 mg/kg) (FAP-WTmIFN+dox), 5 mice.

The FAP-AFN fusion protein disclosed in Example 2 was used while the FAP-WTmIFN is a similar his-tagged fusion consisting out of the N-terminal VHH mFAP_R3FAP8 and the mouse IFNα11 coupled via a 20×GGS-linker and produced as described for the FAP-AFN in Example 2.

In the B16BL6 experiments, blood was collected one day after the last tumor treatment from the tail vein in EDTA-coated microvette tubes (Sarstedt), and analyzed in a Hemavet 950FS (Drew Scientific, Waterbury, USA) whole blood counter. Monocytes, neutrophils, platelets and lymphocytes are expressed in K/μ1; red blood cells (rbc) in M/µl; and mean platelet volume (mpv) in fL. This analysis was performed on 4 animals of the control group or groups with FAP-AFN based treatments and 3 animals in case of FAP-VVTmIFN based treatments.

B16Bl6 Tumor Model

Figure 14A:
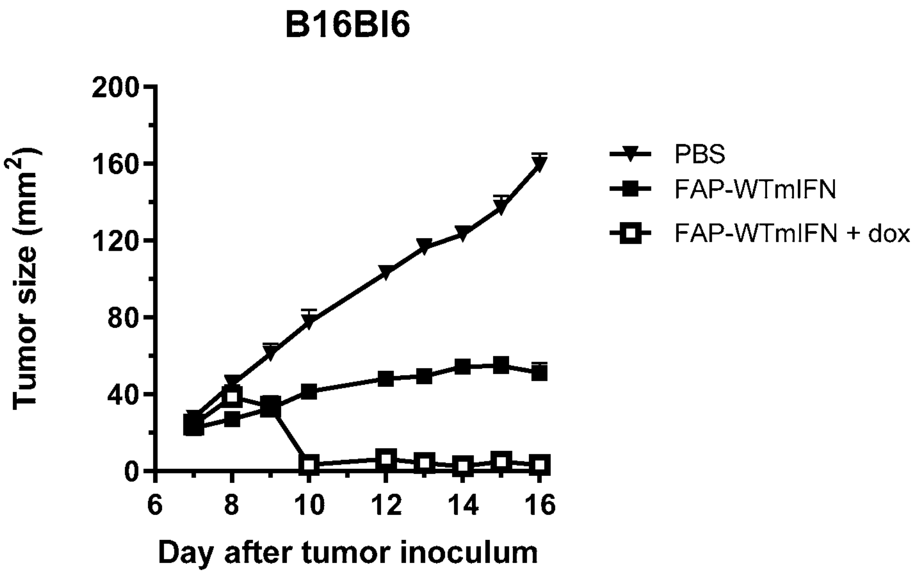
FIGS. 14A and B show the effects of FAP-VVTmIFN alone or combined with doxorubicin (FIG. 14A) and FAP-AFN alone or combined with doxorubicin (FIG. 14B) on tumor growth in mice inoculated with a B16BL6 cell line. Control mice were treated with PBS. Average tumor sizes (+SEM) are plotted.
Figure 14B:
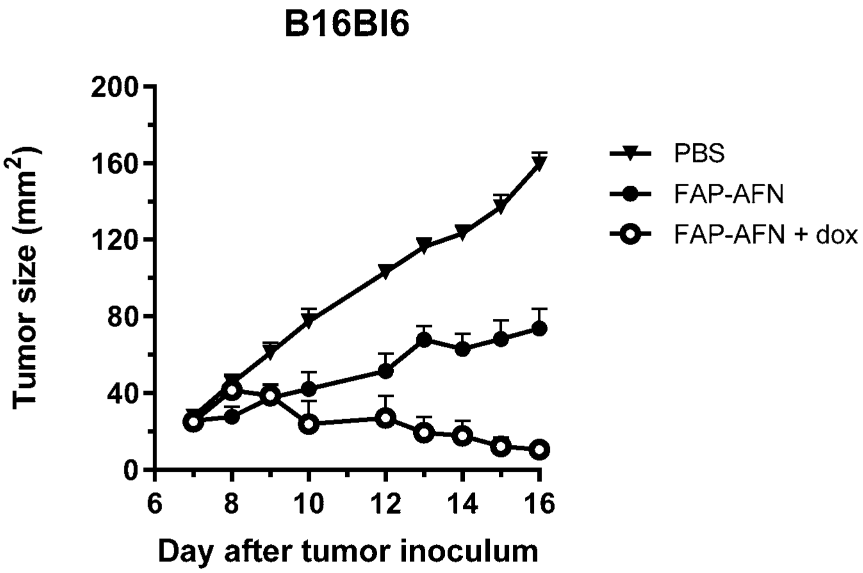
Figure 15A:
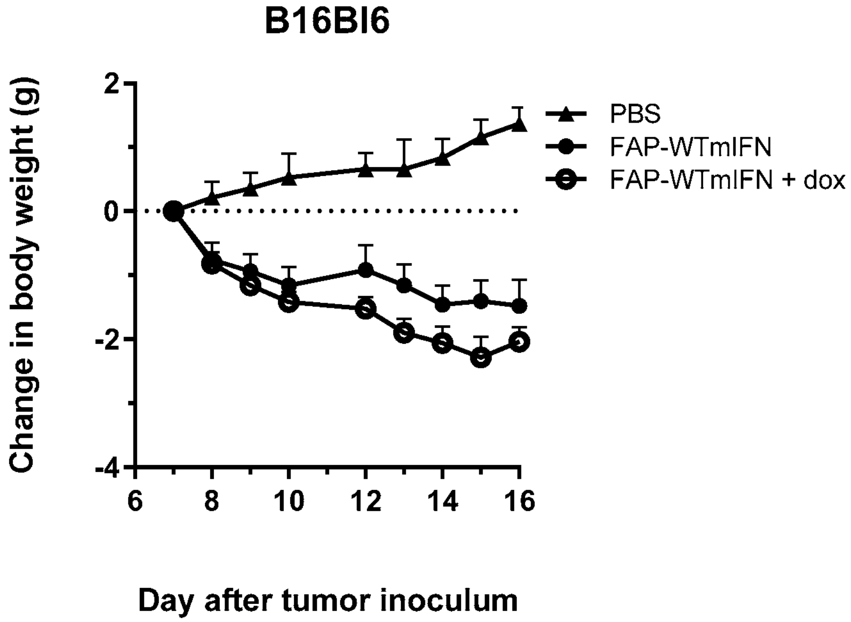
FIGS. 15A and B show the effects of FAP-WTmIFN alone or combined with doxorubicin (FIG. 15A) and FAP-AFN alone or combined with doxorubicin (FIG. 15B) on body weight in mice inoculated with a B16BL6 cell line. Control mice were treated with PBS. Average change in body weight as of day 7 (+SEM) are plotted.
Figure 15B:
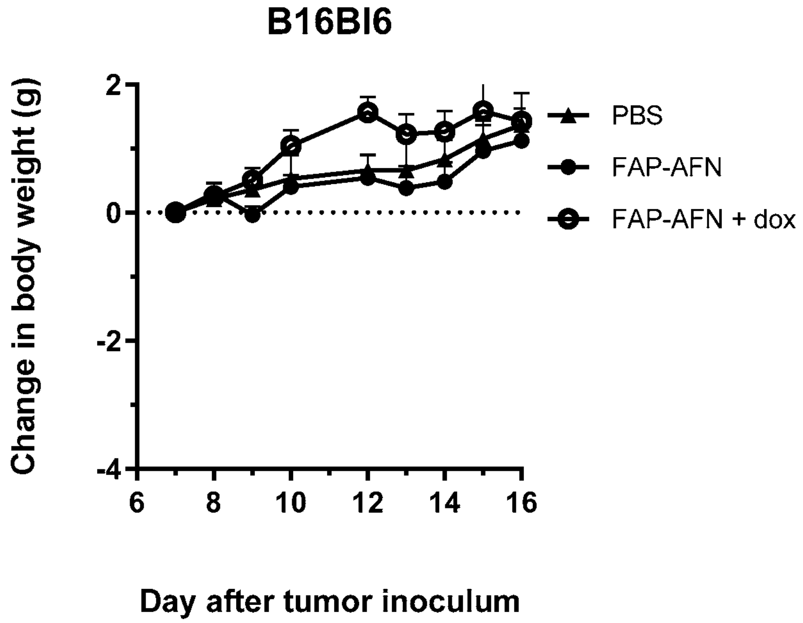
Figure 16A:
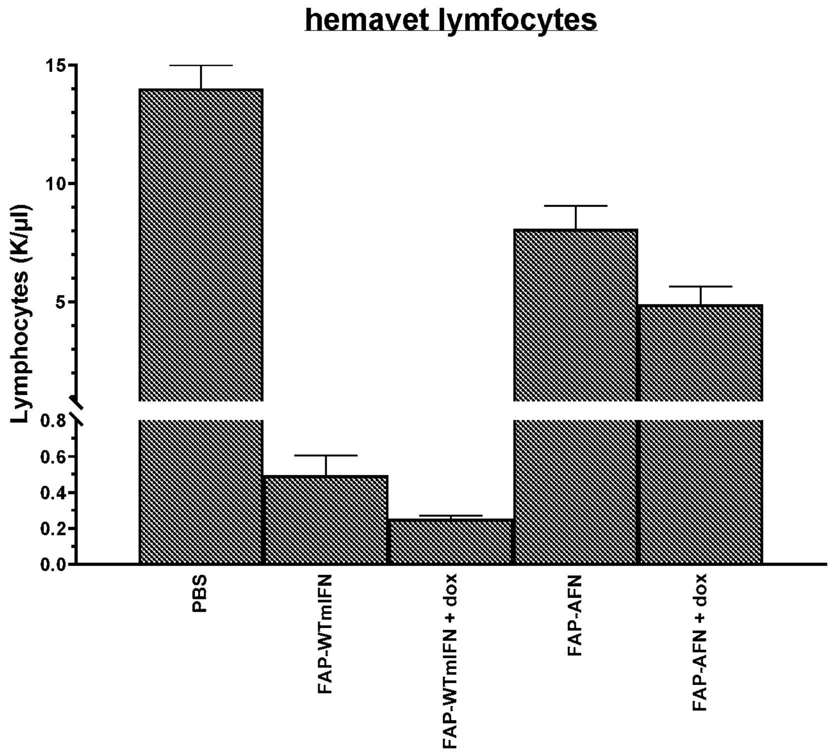
FIGS. 16A-F shows the haematological data from mice treated with FAP-WTmIFN alone or combined with doxorubicin AFN and FAP-AFN alone or combined with doxorubicin:lymphocytes (FIG. 16A), monocytes (FIG. 16B), neutrophils (PMN.
Figure 16B:
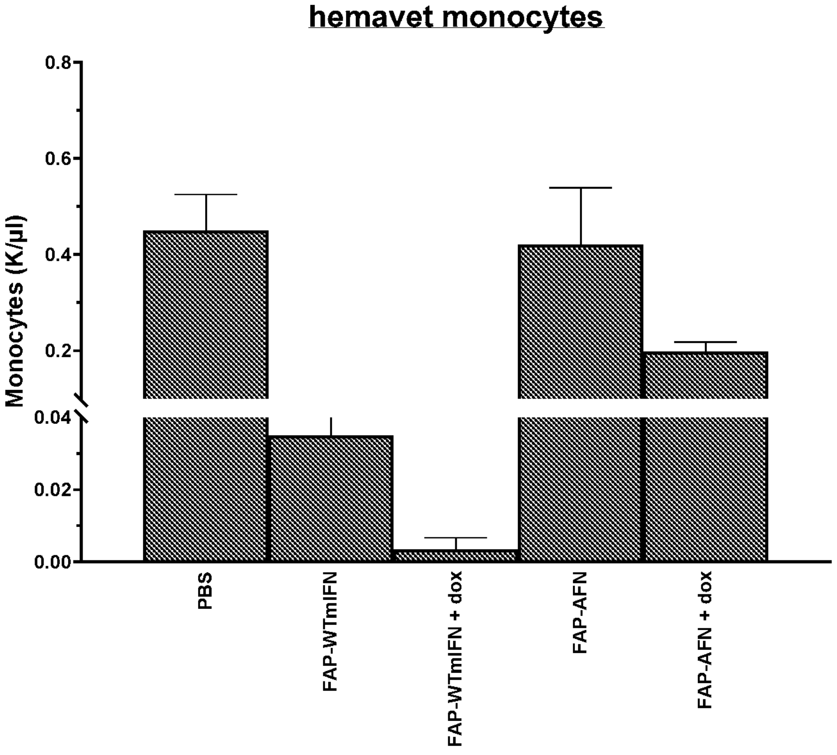
Figure 16C:
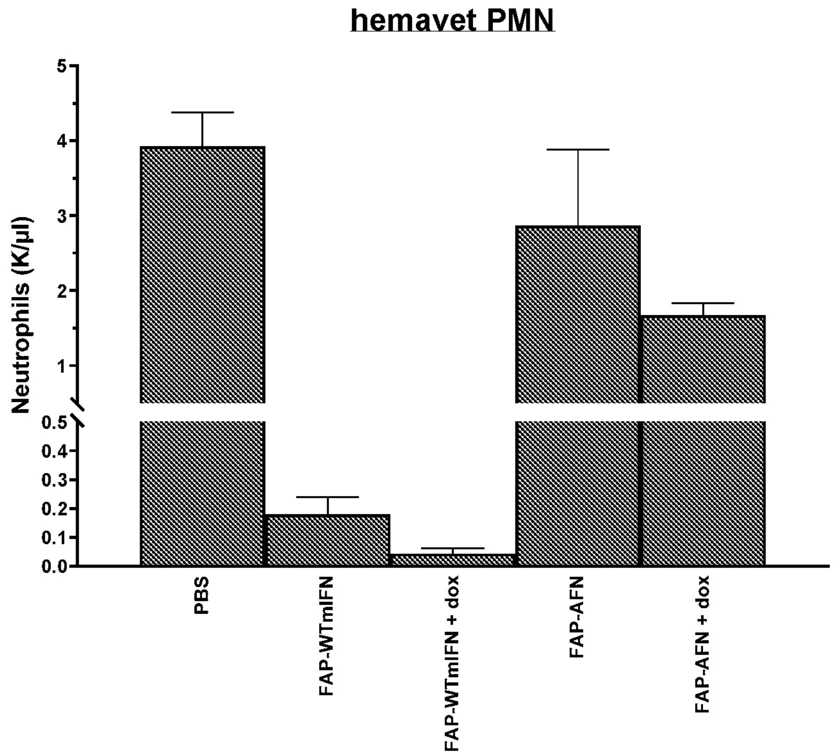
Figure 16D:
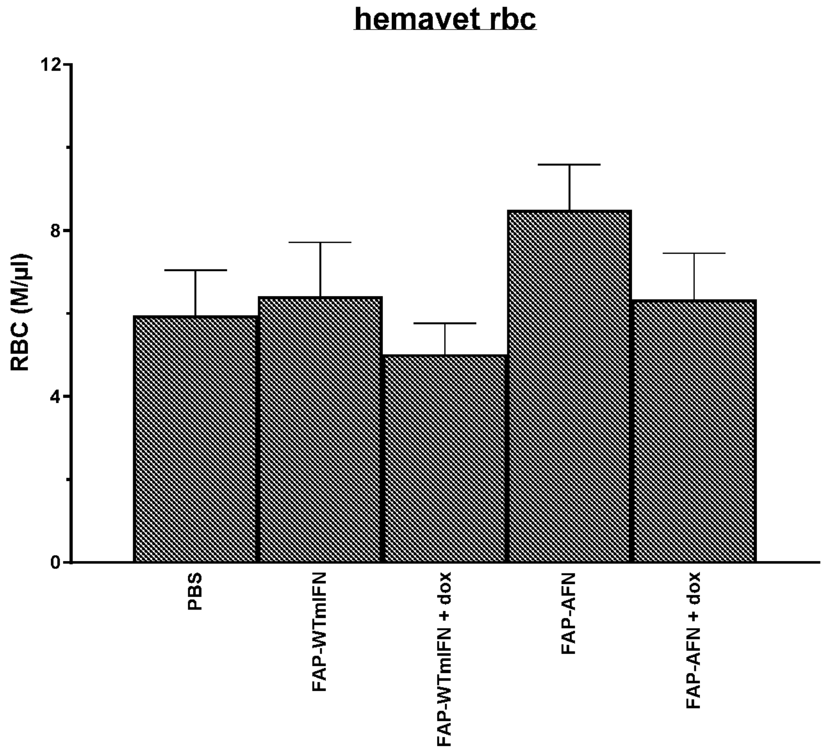
Figure 16E:
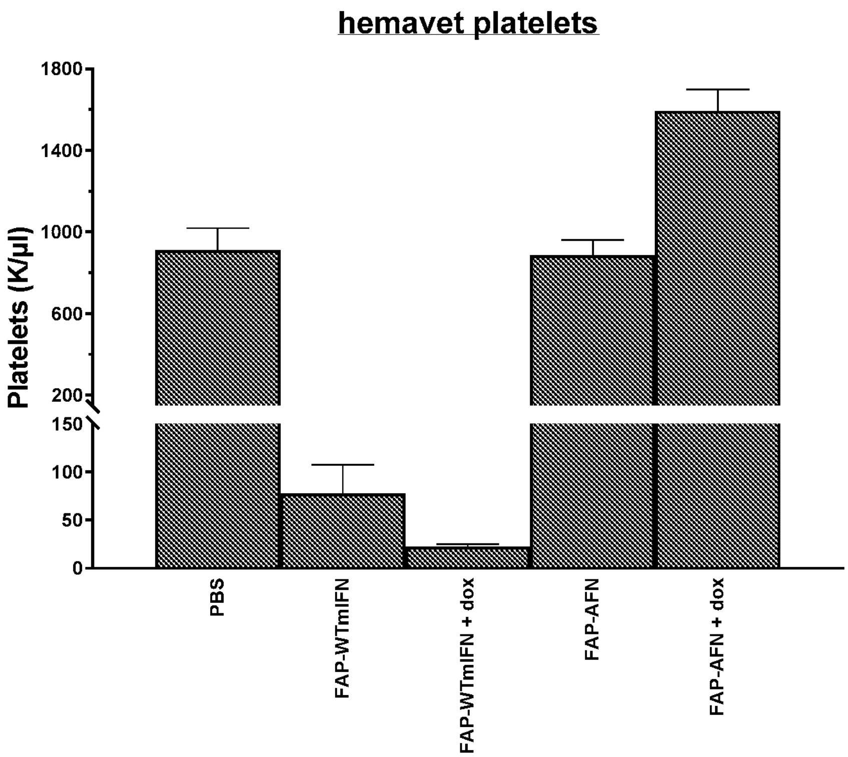
Figure 16F:
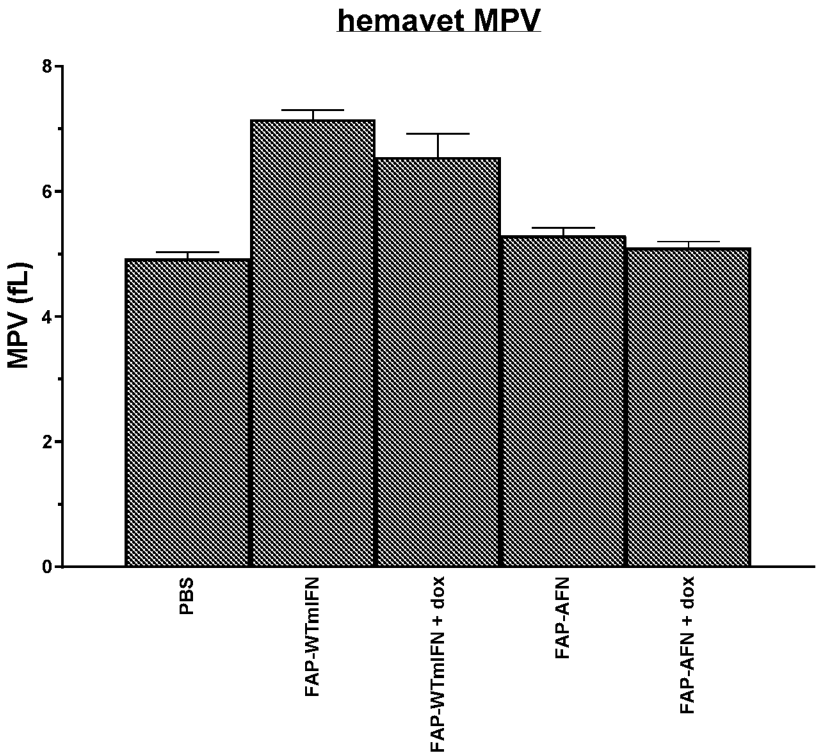

FIGS. 14A-B show that mice treated with either FAP-AFN or FAP-VVTmIFN had a strong reduced tumor growth as compared to PBS. Combination with doxorubicin enhanced the tumor growth reduction further showing a shift to tumor shrinkage. Treatment with doxorubicin alone in this model typically leads to tumor stasis at best, but no tumor regression (data not shown). Of note 20% of the mice died on day 17 in the group treated with FAP-VVTmIFN and even 80% in the group of mice treated with the combination of FAP-WTmIFN and doxorubicin, while in none of the other treatment groups mice died. The lack of tolerability of the FAP-WTmIFN treatments is further shown in FIGS. 15A-B which shows the change of body weight as of the first day of treatment. Both groups treated with FAP-VVTmIFN show a drastic reduction in body weight compared to a gain in body weight in the FAP-AFN treated groups. Additionally, also the hematology data support the improved tolerability profile of the FAP-AFN based treatments compared to the FAP-WTmIFN based treatments (FIGS. 16A-F).

MC38 Tumor Model

Figure 17:
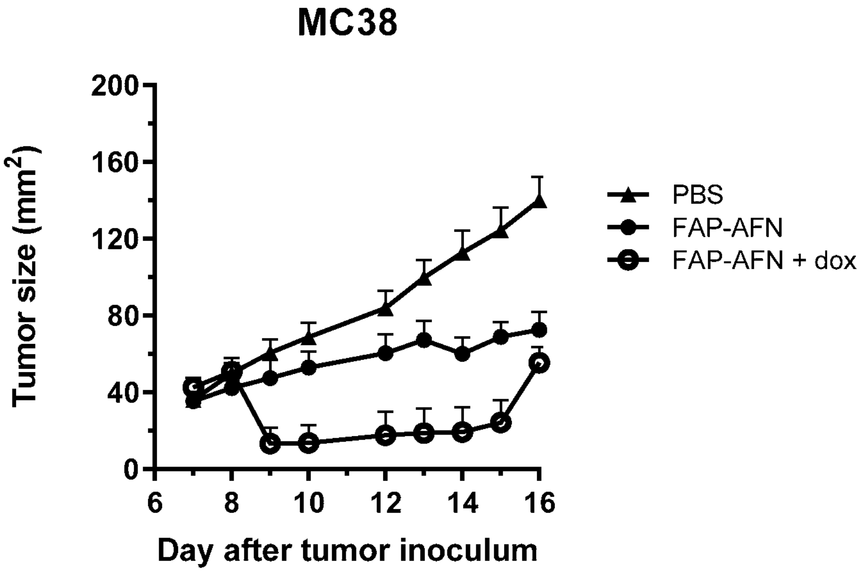
FIG. 17 shows the effects of FAP-AFN alone or combined with doxorubicin on tumor growth in mice inoculated with a MC38 cell line. Control mice were treated with PBS. Average tumor sizes (+SEM) are plotted.
Figure 18:
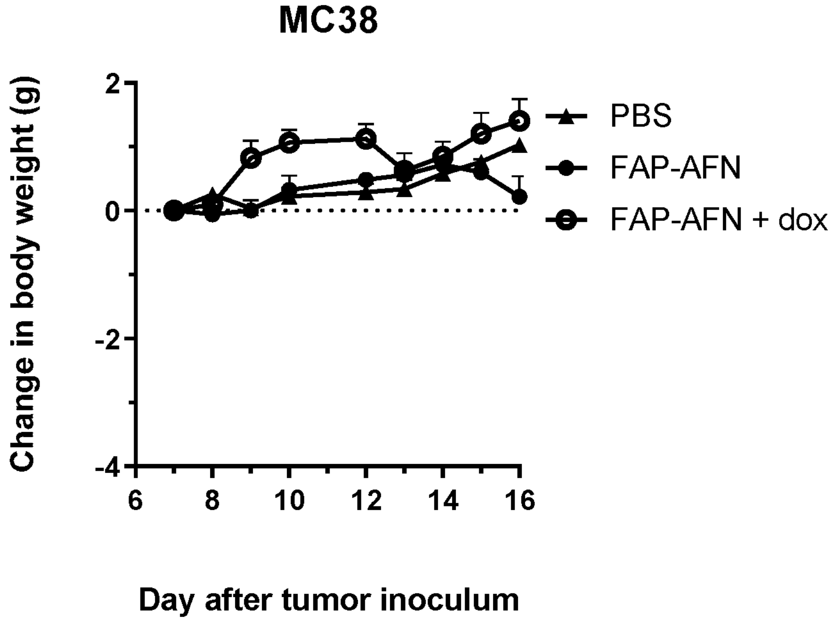
FIG. 18 shows the effects of FAP-AFN alone or combined with doxorubicin on body weight in mice inoculated with a MC38 cell line. Control mice were treated with PBS. Average change in body weight as of day 7 (+SEM) are plotted.

FIG. 17 shows that mice treated with FAP-AFN had a strong reduced tumor growth as compared to PBS. Combination with doxorubicin enhanced the tumor growth reduction further showing a shift to tumor shrinkage. The tolerability of the FAP-AFN treatment is supported by the change in body weight (FIG. 18).

EQUIVALENTS

While the present technology has been described in connection with specific embodiments thereof, it will be understood that it is capable of further modifications and this application is intended to cover any variations, uses, or adaptations of the present technology following, in general, the principles of the present technology and including such departures from the present disclosure as come within known or customary practice within the art to which the present technology pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

What is claimed is:

1. A fibroblast activation protein (FAP) binding agent comprising a recombinant heavy-chain-only antibody (VHH) comprising three complementarity determining regions (CDR1, CDR2, and CDR3), wherein:

(a) CDR1 comprises an amino acid sequence of SEQ ID NO: 95 or any one of SEQ ID NOS: 87 to 94 or SEQ ID NOS: 96 to 115;

(b) CDR2 comprises an amino acid sequence of SEQ ID NO: 121 or any one of SEQ ID NOS: 116 to 120 or SEQ ID NOS: 122 to 144; and (c) CDR3 comprises an amino acid sequence of SEQ ID NO: 152 or any one of SEQ ID NOS: 145 to 151 or SEQ ID NOS: 153 to 175.

2. The FAP binding agent of claim 1, wherein the binding agent further comprises the amino acid sequence of SEQ ID NO: 58 or any one of SEQ ID NOS: 2 to 42, 46 to 57, or 59 to 86.

3. A recombinant nucleic acid encoding the FAP binding agent of claim 1, or a component thereof.

4. A host cell comprising the nucleic acid of claim 3.

5. The FAP binding agent of claim 1, wherein:

CDR1 comprises the amino acid sequence of SEQ ID NO: 95; CDR2 comprises the amino acid sequence of SEQ ID NO: 121; CDR3 comprises the amino acid sequence of SEQ ID NO: 152;

CDR1 comprises the amino acid sequence of SEQ ID NO: 87; CDR2 comprises the amino acid sequence of SEQ ID NO: 116; CDR3 comprises the amino acid sequence of SEQ ID NO: 145;

CDR1 comprises the amino acid sequence of SEQ ID NO: 89; CDR2 comprises the amino acid sequence of SEQ ID NO: 117; CDR3 comprises the amino acid sequence of SEQ ID NO: 146;

CDR1 comprises the amino acid sequence of SEQ ID NO: 90; CDR2 comprises the amino acid sequence of SEQ ID NO: 117; CDR3 comprises the amino acid sequence of SEQ ID NO: 147;

CDR1 comprises the amino acid sequence of SEQ ID NO: 91; CDR2 comprises the amino acid sequence of SEQ ID NO: 118; CDR3 comprises the amino acid sequence of SEQ ID NO: 148;

CDR1 comprises the amino acid sequence of SEQ ID NO: 92; CDR2 comprises the amino acid sequence of SEQ ID NO: 118; CDR3 comprises the amino acid sequence of SEQ ID NO: 149;

CDR1 comprises the amino acid sequence of SEQ ID NO: 93; CDR2 comprises the amino acid sequence of SEQ ID NO: 119; CDR3 comprises the amino acid sequence of SEQ ID NO: 146;

CDR1 comprises the amino acid sequence of SEQ ID NO: 94; CDR2 comprises the amino acid sequence of SEQ ID NO: 120; CDR3 comprises the amino acid sequence of SEQ ID NO: 150;

CDR1 comprises the amino acid sequence of SEQ ID NO: 94; CDR2 comprises the amino acid sequence of SEQ ID NO: 120; CDR3 comprises the amino acid sequence of SEQ ID NO: 151;

CDR1 comprises the amino acid sequence of SEQ ID NO: 96; CDR2 comprises the amino acid sequence of SEQ ID NO: 122; CDR3 comprises the amino acid sequence of SEQ ID NO: 153;

CDR1 comprises the amino acid sequence of SEQ ID NO: 97; CDR2 comprises the amino acid sequence of SEQ ID NO: 123; CDR3 comprises the amino acid sequence of SEQ ID NO: 154;

CDR1 comprises the amino acid sequence of SEQ ID NO: 98; CDR2 comprises the amino acid sequence of SEQ ID NO: 124; CDR3 comprises the amino acid sequence of SEQ ID NO:155;

CDR1 comprises the amino acid sequence of SEQ ID NO: 99; CDR2 comprises the amino acid sequence of SEQ ID NO: 125; CDR3 comprises the amino acid sequence of SEQ ID NO: 156;

CDR1 comprises the amino acid sequence of SEQ ID NO: 100; CDR2 comprises the amino acid sequence of SEQ ID NO: 126; CDR3 comprises the amino acid sequence of SEQ ID NO: 157;

CDR1 comprises the amino acid sequence of SEQ ID NO: 101; CDR2 comprises the amino acid sequence of SEQ ID NO: 127; CDR3 comprises the amino acid sequence of SEQ ID NO: 158;

CDR1 comprises the amino acid sequence of SEQ ID NO: 102; CDR2 comprises the amino acid sequence of SEQ ID NO: 128; CDR3 comprises the amino acid sequence of SEQ ID NO: 159;

CDR1 comprises the amino acid sequence of SEQ ID NO: 103; CDR2 comprises the amino acid sequence of SEQ ID NO: 129; CDR3 comprises the amino acid sequence of SEQ ID NO: 160;

CDR1 comprises the amino acid sequence of SEQ ID NO: 104; CDR2 comprises the amino acid sequence of SEQ ID NO: 129; CDR3 comprises the amino acid sequence of SEQ ID NO: 160;

CDR1 comprises the amino acid sequence of SEQ ID NO: 105; CDR2 comprises the amino acid sequence of SEQ ID NO: 130; CDR3 comprises the amino acid sequence of SEQ ID NO: 160;

CDR1 comprises the amino acid sequence of SEQ ID NO: 105; CDR2 comprises the amino acid sequence of SEQ ID NO: 131; CDR3 comprises the amino acid sequence of SEQ ID NO: 161;

CDR1 comprises the amino acid sequence of SEQ ID NO: 106; CDR2 comprises the amino acid sequence of SEQ ID NO: 132; CDR3 comprises the amino acid sequence of SEQ ID NO: 162;

CDR1 comprises the amino acid sequence of SEQ ID NO: 107; CDR2 comprises the amino acid sequence of SEQ ID NO: 133; CDR3 comprises the amino acid sequence of SEQ ID NO: 163;

CDR1 comprises the amino acid sequence of SEQ ID NO: 108; CDR2 comprises the amino acid sequence of SEQ ID NO: 132; CDR3 comprises the amino acid sequence of SEQ ID NO: 164;

CDR1 comprises the amino acid sequence of SEQ ID NO: 106; CDR2 comprises the amino acid sequence of SEQ ID NO: 134; CDR3 comprises the amino acid sequence of SEQ ID NO: 165;

CDR1 comprises the amino acid sequence of SEQ ID NO: 106; CDR2 comprises the amino acid sequence of SEQ ID NO: 135; CDR3 comprises the amino acid sequence of SEQ ID NO: 166;

CDR1 comprises the amino acid sequence of SEQ ID NO: 106; CDR2 comprises the amino acid sequence of SEQ ID NO: 136; CDR3 comprises the amino acid sequence of SEQ ID NO: 167;

CDR1 comprises the amino acid sequence of SEQ ID NO: 109; CDR2 comprises the amino acid sequence of SEQ ID NO: 137; CDR3 comprises the amino acid sequence of SEQ ID NO: 168;

CDR1 comprises the amino acid sequence of SEQ ID NO: 106; CDR2 comprises the amino acid sequence of SEQ ID NO: 138; CDR3 comprises the amino acid sequence of SEQ ID NO: 169;

CDR1 comprises the amino acid sequence of SEQ ID NO: 110; CDR2 comprises the amino acid sequence of SEQ ID NO: 139; CDR3 comprises the amino acid sequence of SEQ ID NO: 170;

CDR1 comprises the amino acid sequence of SEQ ID NO: 111; CDR2 comprises the amino acid sequence of SEQ ID NO: 140; CDR3 comprises the amino acid sequence of SEQ ID NO: 171;

CDR1 comprises the amino acid sequence of SEQ ID NO: 112; CDR2 comprises the amino acid sequence of SEQ ID NO: 141; CDR3 comprises the amino acid sequence of SEQ ID NO: 172;

CDR1 comprises the amino acid sequence of SEQ ID NO: 113; CDR2 comprises the amino acid sequence of SEQ ID NO: 142; CDR3 comprises the amino acid sequence of SEQ ID NO: 173;

CDR1 comprises the amino acid sequence of SEQ ID NO: 114; CDR2 comprises the amino acid sequence of SEQ ID NO: 143; CDR3 comprises the amino acid sequence of SEQ ID NO: 174; or CDR1 comprises the amino acid sequence of SEQ ID NO: 115; CDR2 comprises the amino acid sequence of SEQ ID NO: 144; CDR3 comprises the amino acid sequence of SEQ ID NO: 175.

6. The FAP binding agent of claim 5, wherein the binding agent further comprises the amino acid sequence of SEQ ID NO: 58 or any one of SEQ ID NOS: 2 to 42, 46 to 57, or 59 to 86.

7. A recombinant nucleic acid encoding the FAP binding agent of claim 5, or a component thereof.

8. A host cell comprising the nucleic acid of claim 7.

* * * * *

SEQUENCE LISTING

```
Sequence total quantity: 914
SEQ ID NO: 1           moltype = AA  length = 760
FEATURE                Location/Qualifiers
REGION                 1..760
                       note = Synthetic polymer.
source                 1..760
                       mol_type = protein
                       organism = synthetic construct
SEQUENCE: 1
MKTWVKIVFG VATSAVLALL VMCIVLRPSR VHNSEENTMR ALTLKDILNG TFSYKTFFPN  60
WISGQEYLHQ SADNNIVLYN IETGQSYTIL SNRTMKSVNA SNYGLSPDRQ FVYLESDYSK  120
LWRYSYTATY YIYDLSNGEF VRGNELPRPI QYLCWSPVGS KLAYVYQNNI YLKQRPGDPP  180
FQITFNGREN KIFNGIPDWV YEEEMLPTKY ALWWSPNGKF LAYAEFNDKD IPVIAYSYYG  240
DEQYPRTINI PYPKAGAKNP VVRIFIIDTT YPAYVGPQEV PVPAMIASSD YYFSWLTWVT  300
DERVCLQWLK RVQNVSVLSI CDFREDWQTW DCPKTQEHIE ESRTGWAGGF FVSRPVFSYD  360
AISYYKIFSD KDGYKHIHYI KDTVENAIQI TSGKWEAINI FRVTQDSLFY SSNEFEEYPG  420
RRNIYRISIG SYPPSKKCVT CHLRKERCQY YTASFSDYAK YYALVCYGPG IPISTLHDGR  480
TDQEIKILEE NKELENALKN IQLPKEEIKK LEVDEITLWY KMILPPQFDR SKKYPLLIQV  540
YGGPCSQSVR SVFAVNWISY LASKEGMVIA LVDGRGTAFQ GDKLLYAVYR KLGVYEVEDQ  600
ITAVRKFIEM GFIDEKRIAI WGWSYGGYVS SLALASGTGL FKCGIAVAPV SSWEYYASVY  660
TERFMGLPTK DDNLEHYKNS TVMARAEYFR NVDYLLIHGT ADDNVHFQNS AQIAKALVNA  720
QVDFQAMWYS DQNHGLSGLS TNHLYTHMTH FLKQCFSLSD                       760

SEQ ID NO: 2           moltype = AA  length = 134
FEATURE                Location/Qualifiers
REGION                 1..134
                       note = Synthetic polymer.
source                 1..134
                       mol_type = protein
                       organism = synthetic construct
SEQUENCE: 2
QVQLQESGGG LVQAGGSLRL SCAASGGFDS RNAMGWYRQA PGKRREWVAT ITSDGRTNYA  60
DSVKARFTIS RDNSKNTVYL QMNSLKPEDT AVYYCNAAPP IFGSWGQGTQ VTVSSAAAYP  120
YDVPDYGSHH HHHH                                                   134

SEQ ID NO: 3           moltype = AA  length = 134
FEATURE                Location/Qualifiers
REGION                 1..134
                       note = Synthetic polymer.
source                 1..134
                       mol_type = protein
                       organism = synthetic construct
SEQUENCE: 3
```

-continued

```
QVQLQESGGG LVRAGGSLRL SCAASGTFDS RNAMGWYRQA PGKRREWVAT ITTDGRTNYA  60
DSVKARFTIS RDNAKNTVYL QMNSLKPEDT AVYYCNAAPP IFGSWGQGTQ VTVSSAAAYP  120
YDVPDYGSHH HHHH                                                    134

SEQ ID NO: 4           moltype = AA  length = 134
FEATURE                Location/Qualifiers
REGION                 1..134
                       note = Synthetic polymer.
source                 1..134
                       mol_type = protein
                       organism = synthetic construct
SEQUENCE: 4
QVQLQESGGG LVQAGGSLRL SCAASGSFDS RNAMGWYRQA PGKRREWVAT ITTDGRTNYA  60
DSVKARFTVS RDNAKNTVYL QMNSLKPDDT AVYYCNAAPP IFNSWGQGTQ VTVSSAAAYP  120
YDVPDYGSHH HHHH                                                    134

SEQ ID NO: 5           moltype = AA  length = 134
FEATURE                Location/Qualifiers
REGION                 1..134
                       note = Synthetic polymer.
source                 1..134
                       mol_type = protein
                       organism = synthetic construct
SEQUENCE: 5
QVQLQESGGG LVQAGGSLRL SCAASGSIDI RNAMGWYRQA PGTRREWVAT ITTDGRTNYA  60
DSVKARFTIS RDNAKNTVYL QMNSLKPEDT AVYYCNLAPP IFGSWGQGTQ VTVSSAAAYP  120
YDVPDYGSHH HHHH                                                    134

SEQ ID NO: 6           moltype = AA  length = 134
FEATURE                Location/Qualifiers
REGION                 1..134
                       note = Synthetic polymer.
source                 1..134
                       mol_type = protein
                       organism = synthetic construct
SEQUENCE: 6
QVQLQESGGG LVQAGGSLRL SCAASGSIDS RNTMGWYRQA PGKRREWVAT ITTGGRTNYA  60
DSVKARFTIS RDNAKNTVYL QMNSLKPEDT AVYYCNLAPP IFNSWGQGTQ VTVSSAAAYP  120
YDVPDYGSHH HHHH                                                    134

SEQ ID NO: 7           moltype = AA  length = 134
FEATURE                Location/Qualifiers
REGION                 1..134
                       note = Synthetic polymer.
source                 1..134
                       mol_type = protein
                       organism = synthetic construct
SEQUENCE: 7
QVQLQESGGG LVQAGGSLRL SCTVAESIDV RNAMGWYRQA PGKRREWVAT ITTGGRTNYA  60
DSVKARFTIS RDNAKNTVYL QMNSLKPEDT AVYYCNAAPP ILNSWGQGTQ VTVSSAAAYP  120
YDVPDYGSHH HHHH                                                    134

SEQ ID NO: 8           moltype = AA  length = 134
FEATURE                Location/Qualifiers
REGION                 1..134
                       note = Synthetic polymer.
source                 1..134
                       mol_type = protein
                       organism = synthetic construct
SEQUENCE: 8
QVQLQESGGG LVRVGGSLRL SCAVSGSFDS RNSMGWYRQA PGKRREWVAT ITSGSRTNYA  60
DSVKARFTIS RDNAKNTVYL QMDSLKPEDT AVYYCNAAPP IFNSWGQGTQ VTVSSAAAYP  120
YDVPDYGSHH HHHH                                                    134

SEQ ID NO: 9           moltype = AA  length = 134
FEATURE                Location/Qualifiers
REGION                 1..134
                       note = Synthetic polymer.
source                 1..134
                       mol_type = protein
                       organism = synthetic construct
SEQUENCE: 9
QVQLQESGGG LVQAGGSLRL SCAVSGRLFS ANTMGWYRQA PGKRRELVAT ILSSGSTNYA  60
DSVKGRFTIS RDDAKNTVYL QMNSLKPEDT AVYYCNLAPP PEGYWGQGTQ VTVSSAAAYP  120
YDVPDYGSHH HHHH                                                    134

SEQ ID NO: 10          moltype = AA  length = 134
FEATURE                Location/Qualifiers
REGION                 1..134
```

```
                         note = Synthetic polymer.
source                   1..134
                         mol_type = protein
                         organism = synthetic construct
SEQUENCE: 10
QVQLQESGGG LVQAGGSLRL SCAVSGRLFS ANTMGWYRQA PGKRRELVAT ILSSGSTNYA  60
DSVKGRFTIS RDDGKNTVYL QMNSLKPDDT AVYYCNFAPP PEGYWGQGTQ VTVSSAAAYP  120
YDVPDYGSHH HHHH                                                   134

SEQ ID NO: 11            moltype = AA  length = 136
FEATURE                  Location/Qualifiers
REGION                   1..136
                         note = Synthetic polymer.
source                   1..136
                         mol_type = protein
                         organism = synthetic construct
SEQUENCE: 11
QVQLQESGGG LVQAGGSLRL SCAASGSIFV GNAMGWYRQA LGNQRELVAG ITSDGTTYYP  60
DSVKGRFTIS RDNDKNTIYL QMNSLKPEDT AVYYCNLWPP RIGFASWGQG TQVTVSSAAA  120
YPYDVPDYGS HHHHHH                                                 136

SEQ ID NO: 12            moltype = AA  length = 136
FEATURE                  Location/Qualifiers
REGION                   1..136
                         note = Synthetic polymer.
source                   1..136
                         mol_type = protein
                         organism = synthetic construct
SEQUENCE: 12
QVQLQESGGG LVQTGGSLRL SCAASGSIFV GNAMGWYRQA LGNQRELVAG ITSDGTTYYP  60
DSVKGRFTIS RDNDKNTIYL QMNSLKPEDT AVYYCNLWPP RIGFASWGQG TQVTVSSAAA  120
YPYDVPDYGS HHHHHH                                                 136

SEQ ID NO: 13            moltype = AA  length = 136
FEATURE                  Location/Qualifiers
REGION                   1..136
                         note = Synthetic polymer.
source                   1..136
                         mol_type = protein
                         organism = synthetic construct
SEQUENCE: 13
QVQLQESGGG LVRAGGSLRL SCAASGSIFV GNAMGWYRQA LGNQRELVAG ITSDGTTYYP  60
DSVKGRFTIS RDNDKNTIYL QMNSLKPEDT AVYYCNLWPP RIGFASWGQG TQVTVSSAAA  120
YPYDVPDYGS HHHHHH                                                 136

SEQ ID NO: 14            moltype = AA  length = 136
FEATURE                  Location/Qualifiers
REGION                   1..136
                         note = Synthetic polymer.
source                   1..136
                         mol_type = protein
                         organism = synthetic construct
SEQUENCE: 14
QVQLQESGGG LVQTGGSLRL SCAASGSIFV GNAMGWYRQA LGNQRELVAG ITSDGTTYYP  60
DSVKGRFTIS RDNDKNTIYL QMNSLKPEDT AVYYCNLWPP RIGFASWGQG TQVTVSSAAA  120
YPYDVPDYGS HHHHHH                                                 136

SEQ ID NO: 15            moltype = AA  length = 136
FEATURE                  Location/Qualifiers
REGION                   1..136
                         note = Synthetic polymer.
source                   1..136
                         mol_type = protein
                         organism = synthetic construct
SEQUENCE: 15
QVQLQESGGG LVQAGGSLRL SCAASGSISM LNSMGWYRQA LGKQREFVAG ITSGGRTNYA  60
DSVKGRFAIS RDNDKNTVYL QMNSLKPEDT AVYYCNTWPP RIAFDSWGQG TQVTVSSAAA  120
YPYDVPDYGS HHHHHH                                                 136

SEQ ID NO: 16            moltype = AA  length = 140
FEATURE                  Location/Qualifiers
REGION                   1..140
                         note = Synthetic polymer.
source                   1..140
                         mol_type = protein
                         organism = synthetic construct
SEQUENCE: 16
QVQLQESGGG LVQAGGSLRL SCAASGSIFS SNAMGWYRQA AGKRRELVAG IRSDGNTNYV  60
DSVKGRFTIS RDRAKNTVYL QMTSLKPEDT AVYYCNYWPP PLRQGGDYAY WGQGTQVTVS  120
```

```
SAAAYPYDVP DYGSHHHHHH                                         140

SEQ ID NO: 17          moltype = AA  length = 136
FEATURE                Location/Qualifiers
REGION                 1..136
                       note = Synthetic polymer.
source                 1..136
                       mol_type = protein
                       organism = synthetic construct
SEQUENCE: 17
QVQLQESGGG LVQAGGSLRL SCVVSGSFDS RNAMAWYRQA LGKERVWVAG IISDGSTNYA  60
DAVKGRFTIS RDNDKNTVYL QMNSLKPEDT AVYYCNAWPP RIGLGSWGQG TQVTVSSAAA  120
YPYDVPDYGS HHHHHH                                             136

SEQ ID NO: 18          moltype = AA  length = 135
FEATURE                Location/Qualifiers
REGION                 1..135
                       note = Synthetic polymer.
source                 1..135
                       mol_type = protein
                       organism = synthetic construct
SEQUENCE: 18
QVQLQESGGG LVQAGGSLRL SCAASGTMSS INAMGWYRQA PGKQRELVAG ILSDGTTKYV  60
ESVKGRFTIS RDNAKNTVHL QMNSLKVEDT AVYYCNFFPP PVPASWGQGT QVTVSSAAAY  120
PYDVPDYGSH HHHHH                                              135

SEQ ID NO: 19          moltype = AA  length = 134
FEATURE                Location/Qualifiers
REGION                 1..134
                       note = Synthetic polymer.
source                 1..134
                       mol_type = protein
                       organism = synthetic construct
SEQUENCE: 19
QVQLQESGGG LVQAGGSLRL SCAVSGIISS MNAMGWYRQA PGKRRELVAG LGSGVSTTYA  60
DAVKGRFTIS RDNAKNTLYL QMNSLKPEDT AVYYCNRWPP PYDYWGQGTQ VTVSSAAAYP  120
YDVPDYGSHH HHHH                                               134

SEQ ID NO: 20          moltype = AA  length = 139
FEATURE                Location/Qualifiers
REGION                 1..139
                       note = Synthetic polymer.
source                 1..139
                       mol_type = protein
                       organism = synthetic construct
SEQUENCE: 20
QVQLQESGGG LVQAGGSLRL SCVVSGTILS SNSMGWYRQA PGKRRELVAS ISTDGSTNYA  60
DSVKGRFTIS RDNAKSTVFL QMNSLKPEDT AVYYCNFHPP VVRDWGDTYW GTQVTVSSAA  120
AYPYDVPDYG SHHHHHHQG                                          139

SEQ ID NO: 21          moltype = AA  length = 136
FEATURE                Location/Qualifiers
REGION                 1..136
                       note = Synthetic polymer.
source                 1..136
                       mol_type = protein
                       organism = synthetic construct
SEQUENCE: 21
QVQLQESGGG LVQAGGSLRL SCAASRSIFS IGTMGWYRQA PGKRRELVAF ITVDHNTYYT  60
DSVKGRFTIS TENDKNTVYL QMNSLKPEDT AVYYCNRAPP STDGDRWGQG TQVTVSSAAA  120
YPYDVPDYGS HHHHHH                                             136

SEQ ID NO: 22          moltype = AA  length = 142
FEATURE                Location/Qualifiers
REGION                 1..142
                       note = Synthetic polymer.
source                 1..142
                       mol_type = protein
                       organism = synthetic construct
SEQUENCE: 22
QVQLQESGGG LVQAGGSLRL SCAASGRTFS TYAMGWFRQA PGKERELVAA ISNGGSAYYA  60
DSVKGRFTIS RDNARNTVYL QTNSLKPEDT AVYYCAARRG SAYYTNRIDW PYWGQGTQVT  120
VSSAAAYPYD VPDYGSHHHH HH                                      142

SEQ ID NO: 23          moltype = AA  length = 142
FEATURE                Location/Qualifiers
REGION                 1..142
                       note = Synthetic polymer.
source                 1..142
```

```
                         mol_type = protein
                         organism = synthetic construct
SEQUENCE: 23
QVQLQESGGG LVQAGGSLRL SCAASGRTFS SYAMGWFRQA PGKERELVAA ISNGGSAYYA  60
DSVKGRFTIS RDNARNTVYL QTNSLKPEDT AVYYCAARRG SAYYTNRIDW PYWGQGTQVT  120
VSSAAAYPYD VPDYGSHHHH HH                                           142

SEQ ID NO: 24            moltype = AA  length = 142
FEATURE                  Location/Qualifiers
REGION                   1..142
                         note = Synthetic polymer.
source                   1..142
                         mol_type = protein
                         organism = synthetic construct
SEQUENCE: 24
QVQLQESGGG LVEAEGSLRL SCIASGRTFG TYAMGWFRQA PGKERELVAA ISSGGSAYYA  60
DSVKGRFTIS RDNARNTVYL QTNSLKPEDT AVYYCAARRG SAYYTNRIDW PYWGQGTQVT  120
VSSAAAYPYD VPDYGSHHHH HH                                           142

SEQ ID NO: 25            moltype = AA  length = 142
FEATURE                  Location/Qualifiers
REGION                   1..142
                         note = Synthetic polymer.
source                   1..142
                         mol_type = protein
                         organism = synthetic construct
SEQUENCE: 25
QVQLQESGGG LVEAEGSLRL SCIASGRTFG TYAMGWFRQA PGKERELVAA ISTGGSTYYA  60
DSVKGRFTIS RDNARNTVYL QTNSLKPEDT AVYYCAARRG SAYYTNHVDW PYWGQGTQVT  120
VSSAAAYPYD VPDYGSHHHH HH                                           142

SEQ ID NO: 26            moltype = AA  length = 142
FEATURE                  Location/Qualifiers
REGION                   1..142
                         note = Synthetic polymer.
source                   1..142
                         mol_type = protein
                         organism = synthetic construct
SEQUENCE: 26
QVQLQESGGG LVEAEGSLRL SCAASGRTFG SYAMGWFRQA PGKSRELVAA ISSGGTTYYA  60
DSVKGRFTIS RDNARNTVYL QTNSLKPEDT AVYYCAARTG SAYYTNRIDW PYWGQGTQVT  120
VSSAAAYPYD VPDYGSHHHH HH                                           142

SEQ ID NO: 27            moltype = AA  length = 142
FEATURE                  Location/Qualifiers
REGION                   1..142
                         note = Synthetic polymer.
source                   1..142
                         mol_type = protein
                         organism = synthetic construct
SEQUENCE: 27
QVQLQESGGG LVEAEGSLRL SCAASGRTFG SYAMGWFRQA PGKSRELVAA ISSGGTTYYA  60
DSVKGRFTIS RDNARNTVYL QTNSPKPEDT AVYYCAARTG SAYYTNRIDW PYWGQGTQVT  120
VSSAAAYPYD VPDYGSHHHH HH                                           142

SEQ ID NO: 28            moltype = AA  length = 142
FEATURE                  Location/Qualifiers
REGION                   1..142
                         note = Synthetic polymer.
source                   1..142
                         mol_type = protein
                         organism = synthetic construct
SEQUENCE: 28
QVQLQESGGG LVEAEGSLRL SCAASGRTFG TYALAWFRQA PGKSRELVAA ISSGGSTYYA  60
DSVKGRFTIS RDNARNTVYL QTNSLKPEDT AVYYCAAKTG SAYYTNRIDW PYWGQGTQVT  120
VSSAAAYPYD VPDYGSHHHH HH                                           142

SEQ ID NO: 29            moltype = AA  length = 142
FEATURE                  Location/Qualifiers
REGION                   1..142
                         note = Synthetic polymer.
source                   1..142
                         mol_type = protein
                         organism = synthetic construct
SEQUENCE: 29
QVQLQESGGG LVEAEGSLRL SCAASGRAFG SYAMGWFRQA PGLERELVAA ISSGGTTYYA  60
DSVKGRFTIS RDNARNTVYL QTNSLKPEDT AVYYCAARTG GAAYTRRIDW PYWGQGTQVT  120
VSSAAAYPYD VPDYGSHHHH HH                                           142
```

```
SEQ ID NO: 30          moltype = AA  length = 142
FEATURE                Location/Qualifiers
REGION                 1..142
                       note = Synthetic polymer.
source                 1..142
                       mol_type = protein
                       organism = synthetic construct
SEQUENCE: 30
QVQLQESGGG LVEAEGSLRL SCAASGRTFG SYAMGWFRQA AGKERELVAA ISAGGSTLYA  60
DNVKGRFTIS RDNARNTVYL LSNSLKPEDT AVYYCAARRG SAYYTNHIDW PYWGQGTQVT  120
VSSAAAYPYD VPDYGSHHHH HH                                           142

SEQ ID NO: 31          moltype = AA  length = 142
FEATURE                Location/Qualifiers
REGION                 1..142
                       note = Synthetic polymer.
source                 1..142
                       mol_type = protein
                       organism = synthetic construct
SEQUENCE: 31
QVQLQESGGG LVQPGGSLRL SCAASGRTFG SYAMGWFRQA AGKERELVAA ISAGGSTLYA  60
DNVKGRFTIS RDNARNTVYL LSNSLKPEDT AVYYCAARRG SAYYTNHIDW PYWGQGTQVT  120
VSSAAAYPYD VPDYGSHHHH HH                                           142

SEQ ID NO: 32          moltype = AA  length = 142
FEATURE                Location/Qualifiers
REGION                 1..142
                       note = Synthetic polymer.
source                 1..142
                       mol_type = protein
                       organism = synthetic construct
SEQUENCE: 32
QVQLQESGGG LVEAEGSLRL SCAASGRTFG SYAMGWFRQA PGKERELVAA ISSGGSTLYA  60
DSVKGRFTIS RDNAKNTVYL QMNSLKPEDT AVYYCAARSG GAYYTARVDW PYWGQGTQVT  120
VSSAAAYPYD VPDYGSHHHH HH                                           142

SEQ ID NO: 33          moltype = AA  length = 142
FEATURE                Location/Qualifiers
REGION                 1..142
                       note = Synthetic polymer.
source                 1..142
                       mol_type = protein
                       organism = synthetic construct
SEQUENCE: 33
QVQLQESGGG LVEAEGSLRL SCAASGRTFG SYAMGWFRQA PGKERELVAA ISSGGSTLYA  60
GSVKGRFTIS KDNAKNTVYL QMNSLKPEDT AVYYCAARSG GAYYTARVDW PYWGQGTQVT  120
VSSAAAYPYD VPDYGSHHHH HH                                           142

SEQ ID NO: 34          moltype = AA  length = 142
FEATURE                Location/Qualifiers
REGION                 1..142
                       note = Synthetic polymer.
source                 1..142
                       mol_type = protein
                       organism = synthetic construct
SEQUENCE: 34
QVQLQESGGG LVEAEGSPRL SCAASGRTFG SYAMGWFRQA PGKERELVAA ISSGGITYYA  60
DSVKGRFTIS RDNAKNTVYL QMNSLKPEDT AVYYCAARSG SAYYTTRVDW PYWGQGTQVT  120
VSSAAAYPYD VPDYGSHHHH HH                                           142

SEQ ID NO: 35          moltype = AA  length = 142
FEATURE                Location/Qualifiers
REGION                 1..142
                       note = Synthetic polymer.
source                 1..142
                       mol_type = protein
                       organism = synthetic construct
SEQUENCE: 35
QVQLQESGGG LVQAGGSLRL SCAASGNIDS IASMGWYRQA PGKQRELVAA ISVGGSTYYA  60
DSVKGRFTIS RDNARNTVYL QTNSLKPEDT AVYYCAARRG SAYYTSRIDW PYWGQGTQVT  120
VSSAAAYPYD VPDYGSHHHH HH                                           142

SEQ ID NO: 36          moltype = AA  length = 142
FEATURE                Location/Qualifiers
REGION                 1..142
                       note = Synthetic polymer.
source                 1..142
                       mol_type = protein
                       organism = synthetic construct
```

-continued

```
SEQUENCE: 36
QVQLQESGGG LVQAEGSLRL SCAASGRTFG SYAMGWFRQA PGKERELVAG ISSGGITNYA  60
HSVKGRFTIS RDIDKNTVFL QMNSLKPEDT AVYYCAARSG GAYYTSRVDW PYWGQGTQVT  120
VSSAAAYPYD VPDYGSHHHH HH                                          142

SEQ ID NO: 37          moltype = AA  length = 142
FEATURE                Location/Qualifiers
REGION                 1..142
                       note = Synthetic polymer.
SITE                   13
                       note = misc_feature - Xaa can be any naturally occurring
                        amino acid
source                 1..142
                       mol_type = protein
                       organism = synthetic construct
SEQUENCE: 37
QVQLQESGGG LVXAGGSLRL SCAASGRTFS DYAMGWFRQA PGKEREFIAG ISWGGSSTYY  60
ADSVKGRFTI SRDNAKNTMY LQMNSLKPED TAVYYCAARL SGVSRSDRPY DYWGQGTQVT  120
VSSAAAYPYD VPDYGSHHHH HH                                          142

SEQ ID NO: 38          moltype = AA  length = 142
FEATURE                Location/Qualifiers
REGION                 1..142
                       note = Synthetic polymer.
source                 1..142
                       mol_type = protein
                       organism = synthetic construct
SEQUENCE: 38
QVQLQESGGG LVQAGGSLRL SCAASGRTFS MYAIGWFRQA PGKERELVAS ISSGGSTNYA  60
DSVKGRFTIS RDNAEKTVYL QMMSLEPEAT GVYYCAARDG SALYTAHSDW DYWGQGTQVT  120
VSSAAAYPYD VPDYGSHHHH HH                                          142

SEQ ID NO: 39          moltype = AA  length = 142
FEATURE                Location/Qualifiers
REGION                 1..142
                       note = Synthetic polymer.
source                 1..142
                       mol_type = protein
                       organism = synthetic construct
SEQUENCE: 39
QVQLQESGGG LVQPGDSLRL SCAASERTFS MYAIGWFRQA PGKERELVAG ISSGGSTNYA  60
DSVKGRFTIS RDNPKKTVYL QMMSLEPEDT GVYYCAARSG SAYFSGRYYW NYWGQGTQVT  120
VSSAAAYPYD VPDYGSHHHH HH                                          142

SEQ ID NO: 40          moltype = AA  length = 142
FEATURE                Location/Qualifiers
REGION                 1..142
                       note = Synthetic polymer.
source                 1..142
                       mol_type = protein
                       organism = synthetic construct
SEQUENCE: 40
QVQLQESGGG LVQAGDSLRL SCAASGRTFS SYVMGWFRQV PGKQRELVAA ITSGLSTYYA  60
DSLKGRFTIS RDNAKNTMYL QMNSLKLEDT AVYYCAAREG GGIWTSSTQY DYWGQGTQVT  120
VSSAAAYPYD VPDYGSHHHH HH                                          142

SEQ ID NO: 41          moltype = AA  length = 137
FEATURE                Location/Qualifiers
REGION                 1..137
                       note = Synthetic polymer.
source                 1..137
                       mol_type = protein
                       organism = synthetic construct
SEQUENCE: 41
QVQLQESGGG LVQAGGSLRL SCVASGTIFS SGAMAMGWYR QAPGKQREWV AGITGSRTTT  60
YADSVKGRFT ISRDNAENTV FLQMNNLKSE DTAVYYCNLW PPSRPDHWGQ GTQVTVSSAA  120
AYPYDVPDYG SHHHHHH                                                137

SEQ ID NO: 42          moltype = AA  length = 134
FEATURE                Location/Qualifiers
REGION                 1..134
                       note = Synthetic polymer.
source                 1..134
                       mol_type = protein
                       organism = synthetic construct
SEQUENCE: 42
QVQLQESGGG LVQAGGSLRL SCVASGTISS GAMGWYRQVP GKQREWVAGI TGSRTTMYTE  60
SVKGRFTISR DNAENTVFLQ MNNLKSEDTA VYYCNLWPPS RPDYWGQGTQ VTVSSAAAYP  120
YDVPDYGSHH HHHH                                                   134
```

```
SEQ ID NO: 43          moltype = AA  length = 6
FEATURE                Location/Qualifiers
REGION                 1..6
                       note = Synthetic polymer.
source                 1..6
                       mol_type = protein
                       organism = synthetic construct
SEQUENCE: 43
HHHHHH                                                       6

SEQ ID NO: 44          moltype = AA  length = 10
FEATURE                Location/Qualifiers
REGION                 1..10
                       note = Synthetic polymer.
source                 1..10
                       mol_type = protein
                       organism = synthetic construct
SEQUENCE: 44
YPYDVPDYGS                                                   10

SEQ ID NO: 45          moltype = AA  length = 19
FEATURE                Location/Qualifiers
REGION                 1..19
                       note = Synthetic polymer.
source                 1..19
                       mol_type = protein
                       organism = synthetic construct
SEQUENCE: 45
AAAYPYDVPD YGSHHHHHH                                         19

SEQ ID NO: 46          moltype = AA  length = 115
FEATURE                Location/Qualifiers
REGION                 1..115
                       note = Synthetic polymer.
source                 1..115
                       mol_type = protein
                       organism = synthetic construct
SEQUENCE: 46
QVQLQESGGG LVQAGGSLRL SCAASGGFDS RNAMGWYRQA PGKRREWVAT ITSDGRTNYA  60
DSVKARFTIS RDNSKNTVYL QMNSLKPEDT AVYYCNAAPP IFGSWGQGTQ VTVSS       115

SEQ ID NO: 47          moltype = AA  length = 115
FEATURE                Location/Qualifiers
REGION                 1..115
                       note = Synthetic polymer.
source                 1..115
                       mol_type = protein
                       organism = synthetic construct
SEQUENCE: 47
QVQLQESGGG LVRAGGSLRL SCAASGTFDS RNAMGWYRQA PGKRREWVAT ITTDGRTNYA  60
DSVKARFTIS RDNAKNTVYL QMNSLKPEDT AVYYCNAAPP IFGSWGQGTQ VTVSS       115

SEQ ID NO: 48          moltype = AA  length = 115
FEATURE                Location/Qualifiers
REGION                 1..115
                       note = Synthetic polymer.
source                 1..115
                       mol_type = protein
                       organism = synthetic construct
SEQUENCE: 48
QVQLQESGGG LVQAGGSLRL SCAASGSFDS RNAMGWYRQA PGKRREWVAT ITTDGRTNYA  60
DSVKARFTVS RDNAKNTVYL QMNSLKPDDT AVYYCNAAPP IFNSWGQGTQ VTVSS       115

SEQ ID NO: 49          moltype = AA  length = 115
FEATURE                Location/Qualifiers
REGION                 1..115
                       note = Synthetic polymer.
source                 1..115
                       mol_type = protein
                       organism = synthetic construct
SEQUENCE: 49
QVQLQESGGG LVQAGGSLRL SCAASGSIDI RNAMGWYRQA PGTRREWVAT ITTDGRTNYA  60
DSVKARFTIS RDNAKNTVYL QMNSLKPEDT AVYYCNLAPP IFGSWGQGTQ VTVSS       115

SEQ ID NO: 50          moltype = AA  length = 115
FEATURE                Location/Qualifiers
REGION                 1..115
                       note = Synthetic polymer.
```

```
source                  1..115
                        mol_type = protein
                        organism = synthetic construct
SEQUENCE: 50
QVQLQESGGG LVQAGGSLRL SCAASGSIDS RNTMGWYRQA PGKRREWVAT ITTGGRTNYA  60
DSVKARFTIS RDNAKNTVYL QMNSLKPEDT AVYYCNLAPP IFNSWGQGTQ VTVSS       115

SEQ ID NO: 51           moltype = AA  length = 115
FEATURE                 Location/Qualifiers
REGION                  1..115
                        note = Synthetic polymer.
source                  1..115
                        mol_type = protein
                        organism = synthetic construct
SEQUENCE: 51
QVQLQESGGG LVQAGGSLRL SCTVAESIDV RNAMGWYRQA PGKRREWVAT ITTGGRTNYA  60
DSVKARFTIS RDNAKNTVYL QMNSLKPEDT AVYYCNAAPP ILNSWGQGTQ VTVSS       115

SEQ ID NO: 52           moltype = AA  length = 115
FEATURE                 Location/Qualifiers
REGION                  1..115
                        note = Synthetic polymer.
source                  1..115
                        mol_type = protein
                        organism = synthetic construct
SEQUENCE: 52
QVQLQESGGG LVRVGGSLRL SCAVSGSFDS RNSMGWYRQA PGKRREWVAT ITSGSRTNYA  60
DSVKARFTIS RDNAKNTVYL QMDSLKPEDT AVYYCNAAPP IFNSWGQGTQ VTVSS       115

SEQ ID NO: 53           moltype = AA  length = 115
FEATURE                 Location/Qualifiers
REGION                  1..115
                        note = Synthetic polymer.
source                  1..115
                        mol_type = protein
                        organism = synthetic construct
SEQUENCE: 53
QVQLQESGGG LVQAGGSLRL SCAVSGRLFS ANTMGWYRQA PGKRRELVAT ILSSGSTNYA  60
DSVKGRFTIS RDDAKNTVYL QMNSLKPEDT AVYYCNLAPP PEGYWGQGTQ VTVSS       115

SEQ ID NO: 54           moltype = AA  length = 115
FEATURE                 Location/Qualifiers
REGION                  1..115
                        note = Synthetic polymer.
source                  1..115
                        mol_type = protein
                        organism = synthetic construct
SEQUENCE: 54
QVQLQESGGG LVQAGGSLRL SCAVSGRLFS ANTMGWYRQA PGKRRELVAT ILSSGSTNYA  60
DSVKGRFTIS RDDGKNTVYL QMNSLKPDDT AVYYCNFAPP PEGYWGQGTQ VTVSS       115

SEQ ID NO: 55           moltype = AA  length = 117
FEATURE                 Location/Qualifiers
REGION                  1..117
                        note = Synthetic polymer.
source                  1..117
                        mol_type = protein
                        organism = synthetic construct
SEQUENCE: 55
QVQLQESGGG LVQAGGSLRL SCAASGSIFV GNAMGWYRQA LGNQRELVAG ITSDGTTYYP  60
DSVKGRFTIS RDNDKNTIYL QMNSLKPEDT AVYYCNLWPP RIGFASWGQG TQVTVSS     117

SEQ ID NO: 56           moltype = AA  length = 117
FEATURE                 Location/Qualifiers
REGION                  1..117
                        note = Synthetic polymer.
source                  1..117
                        mol_type = protein
                        organism = synthetic construct
SEQUENCE: 56
QVQLQESGGG LVQTGGSLRL SCAASGSIFV GNAMGWYRQA LGNQRELVAG ITSDGTTYYP  60
DSVKGRFTIS RDNDKNTIYL QMNSLKPEDT AVYYCNLWPP RIGFASWGQG TQVTVSS     117

SEQ ID NO: 57           moltype = AA  length = 117
FEATURE                 Location/Qualifiers
REGION                  1..117
                        note = Synthetic polymer.
source                  1..117
                        mol_type = protein
```

-continued

```
                        organism = synthetic construct
SEQUENCE: 57
QVQLQESGGG LVRAGGSLRL SCAASGSIFV GNAMGWYRQA LGNQRELVAG ITSDGTTYYP  60
DSVKGRFTIS RDNDKNTIYL QMNSLKPEDT AVYYCNLWPP RIGFASWGQG TQVTVSS     117

SEQ ID NO: 58           moltype = AA  length = 117
FEATURE                 Location/Qualifiers
REGION                  1..117
                        note = Synthetic polymer.
source                  1..117
                        mol_type = protein
                        organism = synthetic construct
SEQUENCE: 58
QVQLQESGGG LVQTGGSLRL SCAASGSIFV GNAMGWYRQA LGNQRELVAG ITSDGTTYYP  60
DSVKGRFTIS RDNDKNTIYL QMNSLKPEDT AVYYCNLWPP RIGFASWGQG TQVTVSS     117

SEQ ID NO: 59           moltype = AA  length = 117
FEATURE                 Location/Qualifiers
REGION                  1..117
                        note = Synthetic polymer.
source                  1..117
                        mol_type = protein
                        organism = synthetic construct
SEQUENCE: 59
QVQLQESGGG LVQAGGSLRL SCAASGSISM LNSMGWYRQA LGKQREFVAG ITSGGRTNYA  60
DSVKGRFAIS RDNDKNTVYL QMNSLKPEDT AVYYCNTWPP RIAFDSWGQG TQVTVSS     117

SEQ ID NO: 60           moltype = AA  length = 121
FEATURE                 Location/Qualifiers
REGION                  1..121
                        note = Synthetic polymer.
source                  1..121
                        mol_type = protein
                        organism = synthetic construct
SEQUENCE: 60
QVQLQESGGG LVQAGGSLRL SCAASGSIFS SNAMGWYRQA AGKRRELVAG IRSDGNTNYV  60
DSVKGRFTIS RDRAKNTVYL QMTSLKPEDT AVYYCNYWPP PLRQGGDYAY WGQGTQVTVS  120
S                                                                  121

SEQ ID NO: 61           moltype = AA  length = 117
FEATURE                 Location/Qualifiers
REGION                  1..117
                        note = Synthetic polymer.
source                  1..117
                        mol_type = protein
                        organism = synthetic construct
SEQUENCE: 61
QVQLQESGGG LVQAGGSLRL SCVVSGSFDS RNAMAWYRQA LGKERVWVAG IISDGSTNYA  60
DAVKGRFTIS RDNDKNTVYL QMNSLKPEDT AVYYCNAWPP RIGLGSWGQG TQVTVSS     117

SEQ ID NO: 62           moltype = AA  length = 116
FEATURE                 Location/Qualifiers
REGION                  1..116
                        note = Synthetic polymer.
source                  1..116
                        mol_type = protein
                        organism = synthetic construct
SEQUENCE: 62
QVQLQESGGG LVQAGGSLRL SCAASGTMSS INAMGWYRQA PGKQRELVAG ILSDGTTKYV  60
ESVKGRFTIS RDNAKNTVHL QMNSLKVEDT AVYYCNFFPP PVPASWGQGT QVTVSS      116

SEQ ID NO: 63           moltype = AA  length = 115
FEATURE                 Location/Qualifiers
REGION                  1..115
                        note = Synthetic polymer.
source                  1..115
                        mol_type = protein
                        organism = synthetic construct
SEQUENCE: 63
QVQLQESGGG LVQAGGSLRL SCAVSGIISS MNAMGWYRQA PGKRRELVAG LGSGVSTTYA  60
DAVKGRFTIS RDNAKNTLYL QMNSLKPEDT AVYYCNRWPP PYDYWGQGTQ VTVSS       115

SEQ ID NO: 64           moltype = AA  length = 120
FEATURE                 Location/Qualifiers
REGION                  1..120
                        note = Synthetic polymer.
source                  1..120
                        mol_type = protein
                        organism = synthetic construct
```

-continued

```
SEQUENCE: 64
QVQLQESGGG LVQAGGSLRL SCVVSGTILS SNSMGWYRQA PGKRRELVAS ISTDGSTNYA  60
DSVKGRFTIS RDNAKSTVFL QMNSLKPEDT AVYYCNFHPP VVRDWGDTYW GTQVTVSSQG  120

SEQ ID NO: 65          moltype = AA  length = 117
FEATURE                Location/Qualifiers
REGION                 1..117
                       note = Synthetic polymer.
source                 1..117
                       mol_type = protein
                       organism = synthetic construct
SEQUENCE: 65
QVQLQESGGG LVQAGGSLRL SCAASRSIFS IGTMGWYRQA PGKRRELVAF ITVDHNTYYT  60
DSVKGRFTIS TENDKNTVYL QMNSLKPEDT AVYYCNRAPP STDGDRWGQG TQVTVSS     117

SEQ ID NO: 66          moltype = AA  length = 123
FEATURE                Location/Qualifiers
REGION                 1..123
                       note = Synthetic polymer.
source                 1..123
                       mol_type = protein
                       organism = synthetic construct
SEQUENCE: 66
QVQLQESGGG LVQAGGSLRL SCAASGRTFS TYAMGWFRQA PGKERELVAA ISNGGSAYYA  60
DSVKGRFTIS RDNARNTVYL QTNSLKPEDT AVYYCAARRG SAYYTNRIDW PYWGQGTQVT  120
VSS                                                                123

SEQ ID NO: 67          moltype = AA  length = 123
FEATURE                Location/Qualifiers
REGION                 1..123
                       note = Synthetic polymer.
source                 1..123
                       mol_type = protein
                       organism = synthetic construct
SEQUENCE: 67
QVQLQESGGG LVQAGGSLRL SCAASGRTFS SYAMGWFRQA PGKERELVAA ISNGGSAYYA  60
DSVKGRFTIS RDNARNTVYL QTNSLKPEDT AVYYCAARRG SAYYTNRIDW PYWGQGTQVT  120
VSS                                                                123

SEQ ID NO: 68          moltype = AA  length = 123
FEATURE                Location/Qualifiers
REGION                 1..123
                       note = Synthetic polymer.
source                 1..123
                       mol_type = protein
                       organism = synthetic construct
SEQUENCE: 68
QVQLQESGGG LVEAEGSLRL SCIASGRTFG TYAMGWFRQA PGKERELVAA ISSGGSAYYA  60
DSVKGRFTIS RDNARNTVYL QTNSLKPEDT AVYYCAARRG SAYYTNRIDW PYWGQGTQVT  120
VSS                                                                123

SEQ ID NO: 69          moltype = AA  length = 123
FEATURE                Location/Qualifiers
REGION                 1..123
                       note = Synthetic polymer.
source                 1..123
                       mol_type = protein
                       organism = synthetic construct
SEQUENCE: 69
QVQLQESGGG LVEAEGSLRL SCIASGRTFG TYAMGWFRQA PGKERELVAA ISTGGSTYYA  60
DSVKGRFTIS RDNARNTVYL QTNSLKPEDT AVYYCAARRG SAYYTNHVDW PYWGQGTQVT  120
VSS                                                                123

SEQ ID NO: 70          moltype = AA  length = 123
FEATURE                Location/Qualifiers
REGION                 1..123
                       note = Synthetic polymer.
source                 1..123
                       mol_type = protein
                       organism = synthetic construct
SEQUENCE: 70
QVQLQESGGG LVEAEGSLRL SCAASGRTFG SYAMGWFRQA PGKSRELVAA ISSGGTTYYA  60
DSVKGRFTIS RDNARNTVYL QTNSLKPEDT AVYYCAARTG SAYYTNRIDW PYWGQGTQVT  120
VSS                                                                123

SEQ ID NO: 71          moltype = AA  length = 123
FEATURE                Location/Qualifiers
REGION                 1..123
                       note = Synthetic polymer.
```

-continued

```
source                  1..123
                        mol_type = protein
                        organism = synthetic construct
SEQUENCE: 71
QVQLQESGGG LVEAEGSLRL SCAASGRTFG SYAMGWFRQA PGKSRELVAA ISSGGTTYYA  60
DSVKGRFTIS RDNARNTVYL QTNSPKPEDT AVYYCAARTG SAYYTNRIDW PYWGQGTQVT  120
VSS                                                               123

SEQ ID NO: 72           moltype = AA  length = 123
FEATURE                 Location/Qualifiers
REGION                  1..123
                        note = Synthetic polymer.
source                  1..123
                        mol_type = protein
                        organism = synthetic construct
SEQUENCE: 72
QVQLQESGGG LVEAEGSLRL SCAASGRTFG TYALAWFRQA PGKSRELVAA ISSGGSTYYA  60
DSVKGRFTIS RDNARNTVYL QTNSLKPEDT AVYYCAAKTG SAYYTNRIDW PYWGQGTQVT  120
VSS                                                               123

SEQ ID NO: 73           moltype = AA  length = 123
FEATURE                 Location/Qualifiers
REGION                  1..123
                        note = Synthetic polymer.
source                  1..123
                        mol_type = protein
                        organism = synthetic construct
SEQUENCE: 73
QVQLQESGGG LVEAEGSLRL SCAASGRAFG SYAMGWFRQA PGLERELVAA ISSGGTTYYA  60
DSVKGRFTIS RDNARNTVYL QTNSLKPEDT AVYYCAARTG GAAYTRRIDW PYWGQGTQVT  120
VSS                                                               123

SEQ ID NO: 74           moltype = AA  length = 123
FEATURE                 Location/Qualifiers
REGION                  1..123
                        note = Synthetic polymer.
source                  1..123
                        mol_type = protein
                        organism = synthetic construct
SEQUENCE: 74
QVQLQESGGG LVEAEGSLRL SCAASGRTFG SYAMGWFRQA AGKERELVAA ISAGGSTLYA  60
DNVKGRFTIS RDNARNTVYL LSNSLKPEDT AVYYCAARRG SAYYTNHIDW PYWGQGTQVT  120
VSS                                                               123

SEQ ID NO: 75           moltype = AA  length = 123
FEATURE                 Location/Qualifiers
REGION                  1..123
                        note = Synthetic polymer.
source                  1..123
                        mol_type = protein
                        organism = synthetic construct
SEQUENCE: 75
QVQLQESGGG LVQPGGSLRL SCAASGRTFG SYAMGWFRQA AGKERELVAA ISAGGSTLYA  60
DNVKGRFTIS RDNARNTVYL LSNSLKPEDT AVYYCAARRG SAYYTNHIDW PYWGQGTQVT  120
VSS                                                               123

SEQ ID NO: 76           moltype = AA  length = 123
FEATURE                 Location/Qualifiers
REGION                  1..123
                        note = Synthetic polymer.
source                  1..123
                        mol_type = protein
                        organism = synthetic construct
SEQUENCE: 76
QVQLQESGGG LVEAEGSLRL SCAASGRTFG SYAMGWFRQA PGKERELVAA ISSGGSTLYA  60
DSVKGRFTIS RDNAKNTVYL QMNSLKPEDT AVYYCAARSG GAYYTARVDW PYWGQGTQVT  120
VSS                                                               123

SEQ ID NO: 77           moltype = AA  length = 123
FEATURE                 Location/Qualifiers
REGION                  1..123
                        note = Synthetic polymer.
source                  1..123
                        mol_type = protein
                        organism = synthetic construct
SEQUENCE: 77
QVQLQESGGG LVEAEGSLRL SCAASGRTFG SYAMGWFRQA PGKERELVAA ISSGGSTLYA  60
GSVKGRFTIS KDNAKNTVYL QMNSLKPEDT AVYYCAARSG GAYYTARVDW PYWGQGTQVT  120
VSS                                                               123
```

```
SEQ ID NO: 78          moltype = AA  length = 123
FEATURE                Location/Qualifiers
REGION                 1..123
                       note = Synthetic polymer.
source                 1..123
                       mol_type = protein
                       organism = synthetic construct
SEQUENCE: 78
QVQLQESGGG LVEAEGSPRL SCAASGRTFG SYAMGWFRQA PGKERELVAA ISSGGITYYA  60
DSVKGRFTIS RDNAKNTVYL QMNSLKPEDT AVYYCAARSG SAYYTTRVDW PYWGQGTQVT  120
VSS                                                               123

SEQ ID NO: 79          moltype = AA  length = 123
FEATURE                Location/Qualifiers
REGION                 1..123
                       note = Synthetic polymer.
source                 1..123
                       mol_type = protein
                       organism = synthetic construct
SEQUENCE: 79
QVQLQESGGG LVQAGGSLRL SCAASGNIDS IASMGWYRQA PGKQRELVAA ISVGGSTYYA  60
DSVKGRFTIS RDNARNTVYL QTNSLKPEDT AVYYCAARRG SAYYTSRIDW PYWGQGTQVT  120
VSS                                                               123

SEQ ID NO: 80          moltype = AA  length = 123
FEATURE                Location/Qualifiers
REGION                 1..123
                       note = Synthetic polymer.
source                 1..123
                       mol_type = protein
                       organism = synthetic construct
SEQUENCE: 80
QVQLQESGGG LVQAEGSLRL SCAASGRTFG SYAMGWFRQA PGKERELVAG ISSGGITNYA  60
HSVKGRFTIS RDIDKNTVFL QMNSLKPEDT AVYYCAARSG GAYYTSRVDW PYWGQGTQVT  120
VSS                                                               123

SEQ ID NO: 81          moltype = AA  length = 123
FEATURE                Location/Qualifiers
REGION                 1..123
                       note = Synthetic polymer.
SITE                   13
                       note = misc_feature - Xaa can be any naturally occurring
                        amino acid
source                 1..123
                       mol_type = protein
                       organism = synthetic construct
SEQUENCE: 81
QVQLQESGGG LVXAGGSLRL SCAASGRTFS DYAMGWFRQA PGKEREFIAG ISWGGSSTYY  60
ADSVKGRFTI SRDNAKNTMY LQMNSLKPED TAVYYCAARL SGVSRSDRPY DYWGQGTQVT  120
VSS                                                               123

SEQ ID NO: 82          moltype = AA  length = 123
FEATURE                Location/Qualifiers
REGION                 1..123
                       note = Synthetic polymer.
source                 1..123
                       mol_type = protein
                       organism = synthetic construct
SEQUENCE: 82
QVQLQESGGG LVQAGGSLRL SCAASGRTFS MYAIGWFRQA PGKERELVAS ISSGGSTNYA  60
DSVKGRFTIS RDNAEKTVYL QMMSLEPEAT GVYYCAARDG SALYTAHSDW DYWGQGTQVT  120
VSS                                                               123

SEQ ID NO: 83          moltype = AA  length = 123
FEATURE                Location/Qualifiers
REGION                 1..123
                       note = Synthetic polymer.
source                 1..123
                       mol_type = protein
                       organism = synthetic construct
SEQUENCE: 83
QVQLQESGGG LVQPGDSLRL SCAASERTFS MYAIGWFRQA PGKERELVAG ISSGGSTNYA  60
DSVKGRFTIS RDNPKKTVYL QMMSLEPEDT GVYYCAARSG SAYFSGRYYW NYWGQGTQVT  120
VSS                                                               123

SEQ ID NO: 84          moltype = AA  length = 123
FEATURE                Location/Qualifiers
REGION                 1..123
```

-continued

```
                        note = Synthetic polymer.
source                  1..123
                        mol_type = protein
                        organism = synthetic construct
SEQUENCE: 84
QVQLQESGGG LVQAGDSLRL SCAASGRTFS SYVMGWFRQV PGKQRELVAA ITSGLSTYYA  60
DSLKGRFTIS RDNAKNTMYL QMNSLKLEDT AVYYCAAREG GGIWTSSTQY DYWGQGTQVT  120
VSS                                                                123

SEQ ID NO: 85           moltype = AA  length = 118
FEATURE                 Location/Qualifiers
REGION                  1..118
                        note = Synthetic polymer.
source                  1..118
                        mol_type = protein
                        organism = synthetic construct
SEQUENCE: 85
QVQLQESGGG LVQAGGSLRL SCVASGTIFS SGAMAMGWYR QAPGKQREWV AGITGSRTTT  60
YADSVKGRFT ISRDNAENTV FLQMNNLKSE DTAVYYCNLW PPSRPDHWGQ GTQVTVSS    118

SEQ ID NO: 86           moltype = AA  length = 115
FEATURE                 Location/Qualifiers
REGION                  1..115
                        note = Synthetic polymer.
source                  1..115
                        mol_type = protein
                        organism = synthetic construct
SEQUENCE: 86
QVQLQESGGG LVQAGGSLRL SCVASGTISS GAMGWYRQVP GKQREWVAGI TGSRTTMYTE  60
SVKGRFTISR DNAENTVFLQ MNNLKSEDTA VYYCNLWPPS RPDYWGQGTQ VTVSS       115

SEQ ID NO: 87           moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 87
GGFDSRNAMG                                                         10

SEQ ID NO: 88           moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 88
GTFDSRNAMG                                                         10

SEQ ID NO: 89           moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 89
GSFDSRNAMG                                                         10

SEQ ID NO: 90           moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 90
GSIDIRNAMG                                                         10

SEQ ID NO: 91           moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 91
```

```
GSIDSRNTMG                                                      10

SEQ ID NO: 92           moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 92
ESIDVRNAMG                                                      10

SEQ ID NO: 93           moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 93
GSFDSRNSMG                                                      10

SEQ ID NO: 94           moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 94
GRLFSANTMG                                                      10

SEQ ID NO: 95           moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 95
GSIFVGNAMG                                                      10

SEQ ID NO: 96           moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 96
GSISMLNSMG                                                      10

SEQ ID NO: 97           moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 97
GSIFSSNAMG                                                      10

SEQ ID NO: 98           moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 98
GSFDSRNAMA                                                      10

SEQ ID NO: 99           moltype = AA  length = 10
FEATURE                 Location/Qualifiers
REGION                  1..10
                        note = Synthetic polymer.
source                  1..10
                        mol_type = protein
                        organism = synthetic construct
```

-continued

```
SEQUENCE: 99
GTMSSINAMG                                                          10

SEQ ID NO: 100          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 100
GIISSMNAMG                                                          10

SEQ ID NO: 101          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 101
GTILSSNSMG                                                          10

SEQ ID NO: 102          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 102
RSIFSIGTMG                                                          10

SEQ ID NO: 103          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 103
GRTFSTYAMG                                                          10

SEQ ID NO: 104          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 104
GRTFSSYAMG                                                          10

SEQ ID NO: 105          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 105
GRTFGTYAMG                                                          10

SEQ ID NO: 106          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 106
GRTFGSYAMG                                                          10

SEQ ID NO: 107          moltype = AA  length = 10
FEATURE                 Location/Qualifiers
REGION                  1..10
                        note = Synthetic polymer.
source                  1..10
                        mol_type = protein
```

```
                        organism = synthetic construct
SEQUENCE: 107
GRTFGTYALA                                                            10

SEQ ID NO: 108          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 108
GRAFGSYAMG                                                            10

SEQ ID NO: 109          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 109
GNIDSIASMG                                                            10

SEQ ID NO: 110          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 110
GRTFSDYAMG                                                            10

SEQ ID NO: 111          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 111
GRTFSMYAIG                                                            10

SEQ ID NO: 112          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 112
ERTFSMYAIG                                                            10

SEQ ID NO: 113          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 113
GRTFSSYVMG                                                            10

SEQ ID NO: 114          moltype = AA  length = 12
FEATURE                 Location/Qualifiers
REGION                  1..12
                        note = Synthetic polymer.
source                  1..12
                        mol_type = protein
                        organism = synthetic construct
SEQUENCE: 114
GTIFSSGAMA MG                                                         12

SEQ ID NO: 115          moltype = AA  length = 9
FEATURE                 Location/Qualifiers
REGION                  1..9
                        note = Synthetic polymer.
source                  1..9
```

```
                        mol_type = protein
                        organism = synthetic construct
SEQUENCE: 115
GTISSGAMG                                                    9

SEQ ID NO: 116          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 116
TITSDGRTN                                                    9

SEQ ID NO: 117          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 117
TITTDGRTN                                                    9

SEQ ID NO: 118          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 118
TITTGGRTN                                                    9

SEQ ID NO: 119          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 119
TITSGSRTN                                                    9

SEQ ID NO: 120          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 120
TILSSGSTN                                                    9

SEQ ID NO: 121          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 121
GITSDGTTY                                                    9

SEQ ID NO: 122          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 122
GITSGGRTN                                                    9

SEQ ID NO: 123          moltype = AA  length = 9
FEATURE                 Location/Qualifiers
REGION                  1..9
                        note = Synthetic polymer.
```

```
source                1..9
                      mol_type = protein
                      organism = synthetic construct
SEQUENCE: 123
GIRSDGNTN                                                                9

SEQ ID NO: 124        moltype = AA  length = 9
FEATURE               Location/Qualifiers
REGION                1..9
                      note = Synthetic polymer.
source                1..9
                      mol_type = protein
                      organism = synthetic construct
SEQUENCE: 124
GIISDGSTN                                                                9

SEQ ID NO: 125        moltype = AA  length = 9
FEATURE               Location/Qualifiers
REGION                1..9
                      note = Synthetic polymer.
source                1..9
                      mol_type = protein
                      organism = synthetic construct
SEQUENCE: 125
GILSDGTTK                                                                9

SEQ ID NO: 126        moltype = AA  length = 9
FEATURE               Location/Qualifiers
REGION                1..9
                      note = Synthetic polymer.
source                1..9
                      mol_type = protein
                      organism = synthetic construct
SEQUENCE: 126
GLGSGVSTT                                                                9

SEQ ID NO: 127        moltype = AA  length = 9
FEATURE               Location/Qualifiers
REGION                1..9
                      note = Synthetic polymer.
source                1..9
                      mol_type = protein
                      organism = synthetic construct
SEQUENCE: 127
SISTDGSTN                                                                9

SEQ ID NO: 128        moltype = AA  length = 9
FEATURE               Location/Qualifiers
REGION                1..9
                      note = Synthetic polymer.
source                1..9
                      mol_type = protein
                      organism = synthetic construct
SEQUENCE: 128
FITVDHNTY                                                                9

SEQ ID NO: 129        moltype = AA  length = 9
FEATURE               Location/Qualifiers
REGION                1..9
                      note = Synthetic polymer.
source                1..9
                      mol_type = protein
                      organism = synthetic construct
SEQUENCE: 129
AISNGGSAY                                                                9

SEQ ID NO: 130        moltype = AA  length = 9
FEATURE               Location/Qualifiers
REGION                1..9
                      note = Synthetic polymer.
source                1..9
                      mol_type = protein
                      organism = synthetic construct
SEQUENCE: 130
AISSGGSAY                                                                9

SEQ ID NO: 131        moltype = AA  length = 9
FEATURE               Location/Qualifiers
REGION                1..9
```

```
                        note = Synthetic polymer.
source                  1..9
                        mol_type = protein
                        organism = synthetic construct
SEQUENCE: 131
AISTGGSTY                                                         9

SEQ ID NO: 132          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 132
AISSGGTTY                                                         9

SEQ ID NO: 133          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 133
AISSGGSTY                                                         9

SEQ ID NO: 134          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 134
AISAGGSTL                                                         9

SEQ ID NO: 135          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 135
AISSGGSTL                                                         9

SEQ ID NO: 136          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 136
AISSGGITY                                                         9

SEQ ID NO: 137          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 137
AISVGGSTY                                                         9

SEQ ID NO: 138          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 138
GISSGGITN                                                         9

SEQ ID NO: 139          moltype = AA  length = 10
FEATURE                 Location/Qualifiers
```

```
REGION                1..10
                      note = Synthetic polymer.
source                1..10
                      mol_type = protein
                      organism = synthetic construct
SEQUENCE: 139
GISWGGSSTY                                                                10

SEQ ID NO: 140        moltype = AA  length = 9
FEATURE               Location/Qualifiers
REGION                1..9
                      note = Synthetic polymer.
source                1..9
                      mol_type = protein
                      organism = synthetic construct
SEQUENCE: 140
SISSGGSTN                                                                 9

SEQ ID NO: 141        moltype = AA  length = 9
FEATURE               Location/Qualifiers
REGION                1..9
                      note = Synthetic polymer.
source                1..9
                      mol_type = protein
                      organism = synthetic construct
SEQUENCE: 141
GISSGGSTN                                                                 9

SEQ ID NO: 142        moltype = AA  length = 9
FEATURE               Location/Qualifiers
REGION                1..9
                      note = Synthetic polymer.
source                1..9
                      mol_type = protein
                      organism = synthetic construct
SEQUENCE: 142
AITSGLSTY                                                                 9

SEQ ID NO: 143        moltype = AA  length = 9
FEATURE               Location/Qualifiers
REGION                1..9
                      note = Synthetic polymer.
source                1..9
                      mol_type = protein
                      organism = synthetic construct
SEQUENCE: 143
GITGSRTTT                                                                 9

SEQ ID NO: 144        moltype = AA  length = 9
FEATURE               Location/Qualifiers
REGION                1..9
                      note = Synthetic polymer.
source                1..9
                      mol_type = protein
                      organism = synthetic construct
SEQUENCE: 144
GITGSRTTM                                                                 9

SEQ ID NO: 145        moltype = AA  length = 9
FEATURE               Location/Qualifiers
REGION                1..9
                      note = Synthetic polymer.
source                1..9
                      mol_type = protein
                      organism = synthetic construct
SEQUENCE: 145
NAAPPIFGS                                                                 9

SEQ ID NO: 146        moltype = AA  length = 9
FEATURE               Location/Qualifiers
REGION                1..9
                      note = Synthetic polymer.
source                1..9
                      mol_type = protein
                      organism = synthetic construct
SEQUENCE: 146
NAAPPIFNS                                                                 9

SEQ ID NO: 147        moltype = AA  length = 9
```

-continued

```
FEATURE                 Location/Qualifiers
REGION                  1..9
                        note = Synthetic polymer.
source                  1..9
                        mol_type = protein
                        organism = synthetic construct
SEQUENCE: 147
NLAPPIFGS                                                                   9

SEQ ID NO: 148          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 148
NLAPPIFNS                                                                   9

SEQ ID NO: 149          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 149
NAAPPILNS                                                                   9

SEQ ID NO: 150          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 150
NLAPPPEGY                                                                   9

SEQ ID NO: 151          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 151
NFAPPPEGY                                                                   9

SEQ ID NO: 152          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 152
NLWPPRIGFA S                                                                11

SEQ ID NO: 153          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 153
NTWPPRIAFD S                                                                11

SEQ ID NO: 154          moltype = AA  length = 15
FEATURE                 Location/Qualifiers
REGION                  1..15
                        note = Synthetic polymer.
source                  1..15
                        mol_type = protein
                        organism = synthetic construct
SEQUENCE: 154
NYWPPPLRQG GDYAY                                                            15
```

-continued

```
SEQ ID NO: 155          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 155
NAWPPRIGLG S                                                         11

SEQ ID NO: 156          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 156
NFFPPPVPAS                                                           10

SEQ ID NO: 157          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 157
NRWPPPYDY                                                            9

SEQ ID NO: 158          moltype = AA  length = 14
FEATURE                 Location/Qualifiers
REGION                  1..14
                        note = Synthetic polymer.
source                  1..14
                        mol_type = protein
                        organism = synthetic construct
SEQUENCE: 158
NFHPPVVRDW GDTY                                                      14

SEQ ID NO: 159          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 159
NRAPPSTDGD R                                                         11

SEQ ID NO: 160          moltype = AA  length = 17
FEATURE                 Location/Qualifiers
REGION                  1..17
                        note = Synthetic polymer.
source                  1..17
                        mol_type = protein
                        organism = synthetic construct
SEQUENCE: 160
AARRGSAYYT NRIDWPY                                                   17

SEQ ID NO: 161          moltype = AA  length = 17
FEATURE                 Location/Qualifiers
REGION                  1..17
                        note = Synthetic polymer.
source                  1..17
                        mol_type = protein
                        organism = synthetic construct
SEQUENCE: 161
AARRGSAYYT NHVDWPY                                                   17

SEQ ID NO: 162          moltype = AA  length = 17
FEATURE                 Location/Qualifiers
REGION                  1..17
                        note = Synthetic polymer.
source                  1..17
                        mol_type = protein
                        organism = synthetic construct
SEQUENCE: 162
AARTGSAYYT NRIDWPY                                                   17
```

```
SEQ ID NO: 163          moltype = AA  length = 17
FEATURE                 Location/Qualifiers
REGION                  1..17
                        note = Synthetic polymer.
source                  1..17
                        mol_type = protein
                        organism = synthetic construct
SEQUENCE: 163
AAKTGSAYYT NRIDWPY                                                17

SEQ ID NO: 164          moltype = AA  length = 17
FEATURE                 Location/Qualifiers
REGION                  1..17
                        note = Synthetic polymer.
source                  1..17
                        mol_type = protein
                        organism = synthetic construct
SEQUENCE: 164
AARTGGAAYT RRIDWPY                                                17

SEQ ID NO: 165          moltype = AA  length = 17
FEATURE                 Location/Qualifiers
REGION                  1..17
                        note = Synthetic polymer.
source                  1..17
                        mol_type = protein
                        organism = synthetic construct
SEQUENCE: 165
AARRGSAYYT NHIDWPY                                                17

SEQ ID NO: 166          moltype = AA  length = 17
FEATURE                 Location/Qualifiers
REGION                  1..17
                        note = Synthetic polymer.
source                  1..17
                        mol_type = protein
                        organism = synthetic construct
SEQUENCE: 166
AARSGGAYYT ARVDWPY                                                17

SEQ ID NO: 167          moltype = AA  length = 17
FEATURE                 Location/Qualifiers
REGION                  1..17
                        note = Synthetic polymer.
source                  1..17
                        mol_type = protein
                        organism = synthetic construct
SEQUENCE: 167
AARSGSAYYT TRVDWPY                                                17

SEQ ID NO: 168          moltype = AA  length = 17
FEATURE                 Location/Qualifiers
REGION                  1..17
                        note = Synthetic polymer.
source                  1..17
                        mol_type = protein
                        organism = synthetic construct
SEQUENCE: 168
AARRGSAYYT SRIDWPY                                                17

SEQ ID NO: 169          moltype = AA  length = 17
FEATURE                 Location/Qualifiers
REGION                  1..17
                        note = Synthetic polymer.
source                  1..17
                        mol_type = protein
                        organism = synthetic construct
SEQUENCE: 169
AARSGGAYYT SRVDWPY                                                17

SEQ ID NO: 170          moltype = AA  length = 16
FEATURE                 Location/Qualifiers
REGION                  1..16
                        note = Synthetic polymer.
source                  1..16
                        mol_type = protein
                        organism = synthetic construct
SEQUENCE: 170
```

```
AARLSGVSRS DRPYDY                                           16

SEQ ID NO: 171          moltype = AA  length = 17
FEATURE                 Location/Qualifiers
REGION                  1..17
                        note = Synthetic polymer.
source                  1..17
                        mol_type = protein
                        organism = synthetic construct
SEQUENCE: 171
AARDGSALYT AHSDWDY                                          17

SEQ ID NO: 172          moltype = AA  length = 17
FEATURE                 Location/Qualifiers
REGION                  1..17
                        note = Synthetic polymer.
source                  1..17
                        mol_type = protein
                        organism = synthetic construct
SEQUENCE: 172
AARSGSAYFS GRYYWNY                                          17

SEQ ID NO: 173          moltype = AA  length = 17
FEATURE                 Location/Qualifiers
REGION                  1..17
                        note = Synthetic polymer.
source                  1..17
                        mol_type = protein
                        organism = synthetic construct
SEQUENCE: 173
AAREGGGIWT SSTQYDY                                          17

SEQ ID NO: 174          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 174
NLWPPSRPDH                                                  10

SEQ ID NO: 175          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 175
NLWPPSRPDY                                                  10

SEQ ID NO: 176          moltype = AA  length = 165
FEATURE                 Location/Qualifiers
REGION                  1..165
                        note = Synthetic polymer.
source                  1..165
                        mol_type = protein
                        organism = synthetic construct
SEQUENCE: 176
CDLPQTHSLG SRRTLMLLAQ MRKISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE             165

SEQ ID NO: 177          moltype = AA  length = 165
FEATURE                 Location/Qualifiers
REGION                  1..165
                        note = Synthetic polymer.
source                  1..165
                        mol_type = protein
                        organism = synthetic construct
SEQUENCE: 177
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE             165

SEQ ID NO: 178          moltype = AA  length = 166
FEATURE                 Location/Qualifiers
REGION                  1..166
```

-continued

```
                        note = Synthetic polymer.
source                  1..166
                        mol_type = protein
                        organism = synthetic construct
SEQUENCE: 178
MSYNLLGFLQ RSSNFQCQKL LWQLNGRLEY CLKDRMNFDI PEEIKQLQQF QKEDAALTIY  60
EMLQNIFAIF RQDSSSTGWN ETIVENLLAN VYHQINHLKT VLEEKLEKED FTRGKLMSSL  120
HLKRYYGRIL HYLKAKEYSH CAWTIVRVEI LRNFYFINRL TGYLRN                 166

SEQ ID NO: 179          moltype = AA  length = 166
FEATURE                 Location/Qualifiers
REGION                  1..166
                        note = Synthetic polymer.
source                  1..166
                        mol_type = protein
                        organism = synthetic construct
SEQUENCE: 179
CDLPQTHSLG NRRALILLAQ MRRISPFSCL KDRHDFGFPQ EEFDGNQFQK AQAISVLHEM  60
IQQTFNLFST KDSSAAWDES LLEKFYTELY QQLNDLEACV IQEVGVEETP LMNVDSILAV  120
KKYFQRITLY LTEKKYSPCA WEVVRAEIMR SFSLSTNLQE RLRRKE                 166

SEQ ID NO: 180          moltype = AA  length = 165
FEATURE                 Location/Qualifiers
REGION                  1..165
                        note = Synthetic polymer.
source                  1..165
                        mol_type = protein
                        organism = synthetic construct
SEQUENCE: 180
APMAEGGGQN HHEVVKFMDV YQRSYCHPIE TLVDIFQEYP DEIEYIFKPS CVPLMRCGGC  60
CNDEGLECVP TEESNITMQI MRIKPHQGQH IGEMSFLQHN KCECRPKKDR ARQENPCGPC  120
SERRKHLFVQ DPQTCKCSCK NTDSRCKARQ LELNERTCRC DKPRR                  165

SEQ ID NO: 181          moltype = AA  length = 165
FEATURE                 Location/Qualifiers
REGION                  1..165
                        note = Synthetic polymer.
source                  1..165
                        mol_type = protein
                        organism = synthetic construct
SEQUENCE: 181
APMAEGGGQN HHEVVKFMDV YQRSYCHPIE TLVDIFQEYP DEIEYIFKPS CVPLMRCGGC  60
CNDEGLECVP TEESNITMQI MRIKPHQGQH IGEMSFLQHN KCECRPKKDR ARQENPCGPC  120
SERRKHLFVQ DPQTCKCSCK NTDSRCKARQ LELNERTCRS LTRKD                  165

SEQ ID NO: 182          moltype = AA  length = 156
FEATURE                 Location/Qualifiers
REGION                  1..156
                        note = Synthetic polymer.
source                  1..156
                        mol_type = protein
                        organism = synthetic construct
SEQUENCE: 182
VRSSSRTPSD KPVAHWANPQ AEGQLQWLNR RANALLANGV ELRDNQLVVP SEGLYLIYSQ  60
VLFKGQGCPS THVLLTHTIS RIAVSYQTKV NLLSAIKSPC QRETPEGAEA KPWYEPIYLG  120
GVFQLEKGDR LSAEINRPDY LDFAESGQVY FGIIAL                            156

SEQ ID NO: 183          moltype = AA  length = 170
FEATURE                 Location/Qualifiers
REGION                  1..170
                        note = Synthetic polymer.
source                  1..170
                        mol_type = protein
                        organism = synthetic construct
SEQUENCE: 183
LPGVGLTPSA AQTARQHPKM HLAHSNLKPA AHLIGDPSKQ NSLLWRANTD RAFLQDGFSL  60
SNNSLLVPTS GIYFVYSQWF SGKAYSPKAT SSPLYLAHEV QLFSSQYPFH VPLLSSQKMV  120
YPGLQEPWLH SMYHGAAFQL TQGDQLSTHT DGIPHLVLSP STVFFGAFAL             170

SEQ ID NO: 184          moltype = AA  length = 281
FEATURE                 Location/Qualifiers
REGION                  1..281
                        note = Synthetic polymer.
source                  1..281
                        mol_type = protein
                        organism = synthetic construct
SEQUENCE: 184
MAMMEVQGGP SLGQTCVLIV IFTVLLQSLC VAVTYVYFTN ELKQMQDKYS KSGIACFLKE  60
DDSYWDPNDE ESMNSPCWQV KWQLRQLVRK MILRTSEETI STVQEKQQNI SPLVRERGPQ  120
```

-continued

```
RVAAHITGTR GRSNTLSSPN SKNEKALGRK INSWESSRSG HSFLSNLHLR NGELVIHEKG  180
FYYIYSQTYF RFQEEIKENT KNDKQMVQYI YKYTSYPDPI LLMKSARNSC WSKDAEYGLY  240
SIYQGGIFEL KENDRIFVSV TNEHLIDMDH EASFFGAFLV G                      281

SEQ ID NO: 185         moltype = AA  length = 153
FEATURE                Location/Qualifiers
REGION                 1..153
                       note = Synthetic polymer.
source                 1..153
                       mol_type = protein
                       organism = synthetic construct
SEQUENCE: 185
APVRSLNCTL RDSQQKSLVM SGPYELKALH LQGQDMEQQV VFSMSFVQGE ESNDKIPVAL  60
GLKEKNLYLS CVLKDDKPTL QLESVDPKNY PKKKMEKRFV FNKIELNNKL EFESAQFPNW  120
YISTSQAENM PVFLGGTKGG QDITDFTMQF VSS                               153

SEQ ID NO: 186         moltype = AA  length = 133
FEATURE                Location/Qualifiers
REGION                 1..133
                       note = Synthetic polymer.
source                 1..133
                       mol_type = protein
                       organism = synthetic construct
SEQUENCE: 186
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 187         moltype = AA  length = 129
FEATURE                Location/Qualifiers
REGION                 1..129
                       note = Synthetic polymer.
source                 1..129
                       mol_type = protein
                       organism = synthetic construct
SEQUENCE: 187
HKCDITLQEI IKTLNSLTEQ KTLCTELTVT DIFAASKNTT EKETFCRAAT VLRQFYSHHE  60
KDTRCLGATA QQFHRHKQLI RFLKRLDRNL WGLAGLNSCP VKEANQSTLE NFLERLKTIM  120
REKYSKCSS                                                          129

SEQ ID NO: 188         moltype = AA  length = 185
FEATURE                Location/Qualifiers
REGION                 1..185
                       note = Synthetic polymer.
source                 1..185
                       mol_type = protein
                       organism = synthetic construct
SEQUENCE: 188
APVPPGEDSK DVAAPHRQPL TSSERIDKQI RYILDGISAL RKETCNKSNM CESSKEALAE  60
NNLNLPKMAE KDGCFQSGFN EETCLVKIIT GLLEFEVYLE YLQNRFESSE EQARAVQMST  120
KVLIQFLQKK AKNLDAITTP DPTTNASLTT KLQAQNQWLQ DMTTHLILRS FKEFLQSSLR  180
ALRQM                                                              185

SEQ ID NO: 189         moltype = AA  length = 114
FEATURE                Location/Qualifiers
REGION                 1..114
                       note = Synthetic polymer.
source                 1..114
                       mol_type = protein
                       organism = synthetic construct
SEQUENCE: 189
SPGPVPPSTA LRELIEELVN ITQNQKAPLC NGSMVWSINL TAGMYCAALE SLINVSGCSA  60
IEKTQRMLSG FCPHKVSAGQ FSSLHVRDTK IEVAQFVKDL LLHLKKLFRE GRFN        114

SEQ ID NO: 190         moltype = AA  length = 194
FEATURE                Location/Qualifiers
REGION                 1..194
                       note = Synthetic polymer.
source                 1..194
                       mol_type = protein
                       organism = synthetic construct
SEQUENCE: 190
MAAEPVEDNC INFVAMKFID NTLYFIAEDD ENLESDYFGK LESKLSVIRN LNDQVLFIDQ  60
GNRPLFEDMT DSDCRDNAPR TIFLISMYKD SQPRGMAVTI SVKCEKISTL SCENKIISFK  120
EMNPPDNIKD TKSDIIFFQR SVPGHDNKMQ FESSSYEGYF LACEKERDLF KLILKKEDEL  180
GDRSIMFTVQ NEDL                                                    194

SEQ ID NO: 191         moltype = AA  length = 270
FEATURE                Location/Qualifiers
```

```
REGION                 1..270
                       note = Synthetic polymer.
source                 1..270
                       mol_type = protein
                       organism = synthetic construct
SEQUENCE: 191
MKPKMKYSTN KISTAKWKNT ASKALCFKLG KSQQKAKEVC PMYFMKLRSG LMIKKEACYF  60
RRETTKRPSL KTGRKHKRHL VLAACQQQST VECFAFGISG VQKYTRALHD SSITGISPIT  120
EYLASLSTYN DQSITFALED ESYEIYVEDL KKDEKKDKVL LSYYESQHPS NESGDGVDGK  180
MLMVTLSPTK DFWLHANNKE HSVELHKCEK PLPDQAFFVL HNMHSNCVSF ECKTDPGVFI  240
GVKDNHLALI KVDSSENLCT ENILFKLSET                                  270

SEQ ID NO: 192         moltype = AA  length = 10
FEATURE                Location/Qualifiers
REGION                 1..10
                       note = Synthetic polymer.
source                 1..10
                       mol_type = protein
                       organism = synthetic construct
SEQUENCE: 192
GFTFDDYAMS                                                        10

SEQ ID NO: 193         moltype = AA  length = 10
FEATURE                Location/Qualifiers
REGION                 1..10
                       note = Synthetic polymer.
source                 1..10
                       mol_type = protein
                       organism = synthetic construct
SEQUENCE: 193
GFTFDDYAIG                                                        10

SEQ ID NO: 194         moltype = AA  length = 17
FEATURE                Location/Qualifiers
REGION                 1..17
                       note = Synthetic polymer.
source                 1..17
                       mol_type = protein
                       organism = synthetic construct
SEQUENCE: 194
TINWNGGSAE YAEPVKG                                                17

SEQ ID NO: 195         moltype = AA  length = 17
FEATURE                Location/Qualifiers
REGION                 1..17
                       note = Synthetic polymer.
source                 1..17
                       mol_type = protein
                       organism = synthetic construct
SEQUENCE: 195
CIRVSDGSTY YADPVKG                                                17

SEQ ID NO: 196         moltype = AA  length = 11
FEATURE                Location/Qualifiers
REGION                 1..11
                       note = Synthetic polymer.
source                 1..11
                       mol_type = protein
                       organism = synthetic construct
SEQUENCE: 196
KDADLVWYNL S                                                      11

SEQ ID NO: 197         moltype = AA  length = 11
FEATURE                Location/Qualifiers
REGION                 1..11
                       note = Synthetic polymer.
source                 1..11
                       mol_type = protein
                       organism = synthetic construct
SEQUENCE: 197
KDADLVWYNL R                                                      11

SEQ ID NO: 198         moltype = AA  length = 23
FEATURE                Location/Qualifiers
REGION                 1..23
                       note = Synthetic polymer.
source                 1..23
                       mol_type = protein
                       organism = synthetic construct
```

-continued

```
SEQUENCE: 198
AGSLYTCVQS IWVPARPYYD MDY                                         23

SEQ ID NO: 199          moltype = AA  length = 132
FEATURE                 Location/Qualifiers
REGION                  1..132
                        note = Synthetic polymer.
source                  1..132
                        mol_type = protein
                        organism = synthetic construct
SEQUENCE: 199
QVQLQESGGG SVQPGGSLRL SCAASGFTFD DYAMSWVRQV PGKGLEWVST INWNGGSAEY  60
AEPVKGRFTI SRDNAKNTVY LQMNSLKLED TAVYYCAKDA DLVWYNLSTG QGTQVTVSSA  120
AAYPYDVPDY GS                                                     132

SEQ ID NO: 200          moltype = AA  length = 132
FEATURE                 Location/Qualifiers
REGION                  1..132
                        note = Synthetic polymer.
source                  1..132
                        mol_type = protein
                        organism = synthetic construct
SEQUENCE: 200
QVQLQESGGG LVQPGGSLRL SCAASGFTFD DYAMSWVRQV PGKGLEWVST INWNGGSAEY  60
AEPVKGRFTI SRDNAKNTVY LQMNSLKLED TAVYYCAKDA DLVWYNLRTG QGTQVTVSSA  120
AAYPYDVPDY GS                                                     132

SEQ ID NO: 201          moltype = AA  length = 145
FEATURE                 Location/Qualifiers
REGION                  1..145
                        note = Synthetic polymer.
source                  1..145
                        mol_type = protein
                        organism = synthetic construct
SEQUENCE: 201
QVQLQESGGG LVQAGGSLRL SCAASGFTFD DYAIGWFRQA PGKEREGVSC IRVSDGSTYY  60
ADPVKGRFTI SSDNAKNTVY LQMNSLKPED AAVYYCAAGS LYTCVQSIVV VPARPYYDMD  120
YWGKGTQVTV SSAAAYPYDV PDYGS                                       145

SEQ ID NO: 202          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 202
GRSFSSYTLA                                                        10

SEQ ID NO: 203          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 203
GRTFSSYTMG                                                        10

SEQ ID NO: 204          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 204
GRTFSSYIMG                                                        10

SEQ ID NO: 205          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 205
GRTFSSYTMG                                                        10
```

-continued

```
SEQ ID NO: 206          moltype = AA  length = 14
FEATURE                 Location/Qualifiers
REGION                  1..14
                        note = Synthetic polymer.
source                  1..14
                        mol_type = protein
                        organism = synthetic construct
SEQUENCE: 206
GRTSGRTFSS YTMG                                                   14

SEQ ID NO: 207          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 207
GRTFSSYAMG                                                        10

SEQ ID NO: 208          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 208
GLTFSNYIMG                                                        10

SEQ ID NO: 209          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 209
GRTFSSYTMG                                                        10

SEQ ID NO: 210          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 210
GRTFSSDTMG                                                        10

SEQ ID NO: 211          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 211
GLTFSNYIMG                                                        10

SEQ ID NO: 212          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 212
GFTLDYYGIG                                                        10

SEQ ID NO: 213          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 213
GHTFSSYTMG                                                        10
```

```
SEQ ID NO: 214          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 214
GRTFSSYVIG                                                          10

SEQ ID NO: 215          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 215
GFAFDGYAIG                                                          10

SEQ ID NO: 216          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 216
GFAFGFFDMT                                                          10

SEQ ID NO: 217          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 217
GRTFSNYVIG                                                          10

SEQ ID NO: 218          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 218
GSIFSINVMG                                                          10

SEQ ID NO: 219          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 219
GRTFSNYNVG                                                          10

SEQ ID NO: 220          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 220
GHTFSSYTMG                                                          10

SEQ ID NO: 221          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 221
```

```
GRTFSTYPVG                                                       10

SEQ ID NO: 222          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 222
GRTFSNYAMG                                                       10

SEQ ID NO: 223          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 223
GRTFSDYRMG                                                       10

SEQ ID NO: 224          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 224
GLTFSNYIMA                                                       10

SEQ ID NO: 225          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 225
GRTFSNSVMG                                                       10

SEQ ID NO: 226          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 226
GRTFSSYIIG                                                       10

SEQ ID NO: 227          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 227
GRTFSSYVMG                                                       10

SEQ ID NO: 228          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 228
GGTFSNYVMG                                                       10

SEQ ID NO: 229          moltype = AA  length = 10
FEATURE                 Location/Qualifiers
REGION                  1..10
                        note = Synthetic polymer.
source                  1..10
                        mol_type = protein
                        organism = synthetic construct
```

```
SEQUENCE: 229
GRTFSNYGIG                                                        10

SEQ ID NO: 230          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 230
GFTFDDYAIA                                                        10

SEQ ID NO: 231          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 231
GRTFSSYTVA                                                        10

SEQ ID NO: 232          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 232
GFPFDDYAIA                                                        10

SEQ ID NO: 233          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 233
GRTFSSYVMG                                                        10

SEQ ID NO: 234          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 234
GRTLSSNPMA                                                        10

SEQ ID NO: 235          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 235
GFTFDNYAIG                                                        10

SEQ ID NO: 236          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 236
GRAFSSYFMG                                                        10

SEQ ID NO: 237          moltype = AA  length = 10
FEATURE                 Location/Qualifiers
REGION                  1..10
                        note = Synthetic polymer.
source                  1..10
                        mol_type = protein
```

```
                        organism = synthetic construct
SEQUENCE: 237
TPTFSSYNMG                                                               10

SEQ ID NO: 238          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 238
GFTFDDYAIA                                                               10

SEQ ID NO: 239          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 239
GGTFSGYIMG                                                               10

SEQ ID NO: 240          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 240
GRSFSSYTIA                                                               10

SEQ ID NO: 241          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 241
GFSSDDYTIG                                                               10

SEQ ID NO: 242          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 242
GFTFDDYTIG                                                               10

SEQ ID NO: 243          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 243
GFSSDDYTIG                                                               10

SEQ ID NO: 244          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 244
GFTFDQYTIA                                                               10

SEQ ID NO: 245          moltype = AA  length = 10
FEATURE                 Location/Qualifiers
REGION                  1..10
                        note = Synthetic polymer.
source                  1..10
```

```
                       mol_type = protein
                       organism = synthetic construct
SEQUENCE: 245
GRTFSSYAMA                                                                  10

SEQ ID NO: 246         moltype = AA  length = 10
FEATURE                Location/Qualifiers
REGION                 1..10
                       note = Synthetic polymer.
source                 1..10
                       mol_type = protein
                       organism = synthetic construct
SEQUENCE: 246
GFAFDGYAIG                                                                  10

SEQ ID NO: 247         moltype = AA  length = 10
FEATURE                Location/Qualifiers
REGION                 1..10
                       note = Synthetic polymer.
source                 1..10
                       mol_type = protein
                       organism = synthetic construct
SEQUENCE: 247
GFSSDDYTIA                                                                  10

SEQ ID NO: 248         moltype = AA  length = 10
FEATURE                Location/Qualifiers
REGION                 1..10
                       note = Synthetic polymer.
source                 1..10
                       mol_type = protein
                       organism = synthetic construct
SEQUENCE: 248
GFSSDDYTIG                                                                  10

SEQ ID NO: 249         moltype = AA  length = 10
FEATURE                Location/Qualifiers
REGION                 1..10
                       note = Synthetic polymer.
source                 1..10
                       mol_type = protein
                       organism = synthetic construct
SEQUENCE: 249
GFTFDDYTIG                                                                  10

SEQ ID NO: 250         moltype = AA  length = 10
FEATURE                Location/Qualifiers
REGION                 1..10
                       note = Synthetic polymer.
source                 1..10
                       mol_type = protein
                       organism = synthetic construct
SEQUENCE: 250
GFSSDDYTIG                                                                  10

SEQ ID NO: 251         moltype = AA  length = 10
FEATURE                Location/Qualifiers
REGION                 1..10
                       note = Synthetic polymer.
source                 1..10
                       mol_type = protein
                       organism = synthetic construct
SEQUENCE: 251
GFSSDDYTIG                                                                  10

SEQ ID NO: 252         moltype = AA  length = 10
FEATURE                Location/Qualifiers
REGION                 1..10
                       note = Synthetic polymer.
source                 1..10
                       mol_type = protein
                       organism = synthetic construct
SEQUENCE: 252
GFSFDDYAIA                                                                  10

SEQ ID NO: 253         moltype = AA  length = 10
FEATURE                Location/Qualifiers
REGION                 1..10
                       note = Synthetic polymer.
```

```
source                  1..10
                        mol_type = protein
                        organism = synthetic construct
SEQUENCE: 253
GFSSDDYTIG                                                              10

SEQ ID NO: 254          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 254
GFTGNDLAIG                                                              10

SEQ ID NO: 255          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 255
GFSSDDYTIA                                                              10

SEQ ID NO: 256          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 256
EGTLSSYGIG                                                              10

SEQ ID NO: 257          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 257
GFSSDDYTIA                                                              10

SEQ ID NO: 258          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 258
GFTFDDYAIA                                                              10

SEQ ID NO: 259          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 259
GLSSDDYTIG                                                              10

SEQ ID NO: 260          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 260
GLSSDDYTIG                                                              10

SEQ ID NO: 261          moltype = AA  length = 10
FEATURE                 Location/Qualifiers
REGION                  1..10
```

```
                          note = Synthetic polymer.
source                    1..10
                          mol_type = protein
                          organism = synthetic construct
SEQUENCE: 261
GFSSDDYTIG                                                          10

SEQ ID NO: 262            moltype = AA  length = 10
FEATURE                   Location/Qualifiers
REGION                    1..10
                          note = Synthetic polymer.
source                    1..10
                          mol_type = protein
                          organism = synthetic construct
SEQUENCE: 262
GFSFDDYTIG                                                          10

SEQ ID NO: 263            moltype = AA  length = 10
FEATURE                   Location/Qualifiers
REGION                    1..10
                          note = Synthetic polymer.
source                    1..10
                          mol_type = protein
                          organism = synthetic construct
SEQUENCE: 263
GFTFDDYAIA                                                          10

SEQ ID NO: 264            moltype = AA  length = 10
FEATURE                   Location/Qualifiers
REGION                    1..10
                          note = Synthetic polymer.
source                    1..10
                          mol_type = protein
                          organism = synthetic construct
SEQUENCE: 264
GFTFDDYAIG                                                          10

SEQ ID NO: 265            moltype = AA  length = 10
FEATURE                   Location/Qualifiers
REGION                    1..10
                          note = Synthetic polymer.
source                    1..10
                          mol_type = protein
                          organism = synthetic construct
SEQUENCE: 265
GFTFGDYTIG                                                          10

SEQ ID NO: 266            moltype = AA  length = 10
FEATURE                   Location/Qualifiers
REGION                    1..10
                          note = Synthetic polymer.
source                    1..10
                          mol_type = protein
                          organism = synthetic construct
SEQUENCE: 266
EGTFSSYGIG                                                          10

SEQ ID NO: 267            moltype = AA  length = 10
FEATURE                   Location/Qualifiers
REGION                    1..10
                          note = Synthetic polymer.
source                    1..10
                          mol_type = protein
                          organism = synthetic construct
SEQUENCE: 267
GFSSDDYTIG                                                          10

SEQ ID NO: 268            moltype = AA  length = 10
FEATURE                   Location/Qualifiers
REGION                    1..10
                          note = Synthetic polymer.
source                    1..10
                          mol_type = protein
                          organism = synthetic construct
SEQUENCE: 268
GVSIGDYNIG                                                          10

SEQ ID NO: 269            moltype = AA  length = 10
FEATURE                   Location/Qualifiers
```

```
REGION              1..10
                    note = Synthetic polymer.
source              1..10
                    mol_type = protein
                    organism = synthetic construct
SEQUENCE: 269
GFTFDDYTIA                                                         10

SEQ ID NO: 270      moltype = AA  length = 10
FEATURE             Location/Qualifiers
REGION              1..10
                    note = Synthetic polymer.
source              1..10
                    mol_type = protein
                    organism = synthetic construct
SEQUENCE: 270
GFTFDDYTIA                                                         10

SEQ ID NO: 271      moltype = AA  length = 11
FEATURE             Location/Qualifiers
REGION              1..11
                    note = Synthetic polymer.
source              1..11
                    mol_type = protein
                    organism = synthetic construct
SEQUENCE: 271
ASITWGGGNT Y                                                       11

SEQ ID NO: 272      moltype = AA  length = 11
FEATURE             Location/Qualifiers
REGION              1..11
                    note = Synthetic polymer.
source              1..11
                    mol_type = protein
                    organism = synthetic construct
SEQUENCE: 272
AATVWTGAGT V                                                       11

SEQ ID NO: 273      moltype = AA  length = 11
FEATURE             Location/Qualifiers
REGION              1..11
                    note = Synthetic polymer.
source              1..11
                    mol_type = protein
                    organism = synthetic construct
SEQUENCE: 273
AAIGWSADIT V                                                       11

SEQ ID NO: 274      moltype = AA  length = 11
FEATURE             Location/Qualifiers
REGION              1..11
                    note = Synthetic polymer.
source              1..11
                    mol_type = protein
                    organism = synthetic construct
SEQUENCE: 274
AFIDWSGGGT Y                                                       11

SEQ ID NO: 275      moltype = AA  length = 11
FEATURE             Location/Qualifiers
REGION              1..11
                    note = Synthetic polymer.
source              1..11
                    mol_type = protein
                    organism = synthetic construct
SEQUENCE: 275
ATITWGGGST Y                                                       11

SEQ ID NO: 276      moltype = AA  length = 11
FEATURE             Location/Qualifiers
REGION              1..11
                    note = Synthetic polymer.
source              1..11
                    mol_type = protein
                    organism = synthetic construct
SEQUENCE: 276
AAISWSGGPT V                                                       11

SEQ ID NO: 277      moltype = AA  length = 11
```

-continued

```
FEATURE                 Location/Qualifiers
REGION                  1..11
                        note = Synthetic polymer.
source                  1..11
                        mol_type = protein
                        organism = synthetic construct
SEQUENCE: 277
AAITWGGGST V                                                       11

SEQ ID NO: 278          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 278
AAITWSGVST V                                                       11

SEQ ID NO: 279          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 279
GAIMWSGAFT H                                                       11

SEQ ID NO: 280          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 280
AAITWGGGST V                                                       11

SEQ ID NO: 281          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 281
SCISSSDRNT Y                                                       11

SEQ ID NO: 282          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 282
AFIDWSGGGT Y                                                       11

SEQ ID NO: 283          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 283
AVITWSGDST Y                                                       11

SEQ ID NO: 284          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 284
ACISSKDGST Y                                                       11
```

-continued

```
SEQ ID NO: 285          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 285
SGINSIGGST T                                                        11

SEQ ID NO: 286          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 286
AWTWSGDSTY                                                          10

SEQ ID NO: 287          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 287
AKITNFGITS                                                          10

SEQ ID NO: 288          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 288
SFISWISDIT Y                                                        11

SEQ ID NO: 289          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 289
AFIDWSGGGT Y                                                        11

SEQ ID NO: 290          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 290
AVILWSGVST Y                                                        11

SEQ ID NO: 291          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 291
AAIVWSGGST Y                                                        11

SEQ ID NO: 292          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 292
AAISSSGYHT Y                                                        11
```

```
SEQ ID NO: 293          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 293
SCISSPDGST Y                                                          11

SEQ ID NO: 294          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 294
AAVLWSGVST A                                                          11

SEQ ID NO: 295          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 295
VAITWDGSAT T                                                          11

SEQ ID NO: 296          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 296
AAIGWNGGIT Y                                                          11

SEQ ID NO: 297          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 297
GFITWSGAST Y                                                          11

SEQ ID NO: 298          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 298
AGINWSGESA D                                                          11

SEQ ID NO: 299          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 299
SCIERSDGST Y                                                          11

SEQ ID NO: 300          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 300
```

```
SCISNTDSST Y                                                11

SEQ ID NO: 301          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 301
SCISNTDSST Y                                                11

SEQ ID NO: 302          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 302
AQISWSAGSI Y                                                11

SEQ ID NO: 303          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 303
AGMSWNPGPA V                                                11

SEQ ID NO: 304          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 304
SCISRSDGST Y                                                11

SEQ ID NO: 305          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 305
ANIGWTGDMT Y                                                11

SEQ ID NO: 306          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 306
AAIIWSGSMT Y                                                11

SEQ ID NO: 307          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 307
SCISNTDSST Y                                                11

SEQ ID NO: 308          moltype = AA  length = 11
FEATURE                 Location/Qualifiers
REGION                  1..11
                        note = Synthetic polymer.
source                  1..11
                        mol_type = protein
                        organism = synthetic construct
```

```
SEQUENCE: 308
AANTWSGGPT Y                                                    11

SEQ ID NO: 309          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 309
SCISSDGSTG                                                      10

SEQ ID NO: 310          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 310
SCYSSSDGST G                                                    11

SEQ ID NO: 311          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 311
SCISSDGSTG                                                      10

SEQ ID NO: 312          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 312
GCIKSSDGTT G                                                    11

SEQ ID NO: 313          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 313
SCISNTDSST Y                                                    11

SEQ ID NO: 314          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 314
AAIAWSAGST Y                                                    11

SEQ ID NO: 315          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 315
SCISSKEGST Y                                                    11

SEQ ID NO: 316          moltype = AA  length = 11
FEATURE                 Location/Qualifiers
REGION                  1..11
                        note = Synthetic polymer.
source                  1..11
                        mol_type = protein
```

```
                        organism = synthetic construct
SEQUENCE: 316
SCISSSDGST G                                                        11

SEQ ID NO: 317          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 317
SCYSSRDGTT G                                                        11

SEQ ID NO: 318          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 318
SCISSDGSTG                                                          10

SEQ ID NO: 319          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 319
SCYSSSDGST G                                                        11

SEQ ID NO: 320          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 320
SCFSSSDGST G                                                        11

SEQ ID NO: 321          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 321
SCISNTDSST F                                                        11

SEQ ID NO: 322          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 322
SCYSSSDGST G                                                        11

SEQ ID NO: 323          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 323
SCISNTDSST Y                                                        11

SEQ ID NO: 324          moltype = AA  length = 11
FEATURE                 Location/Qualifiers
REGION                  1..11
                        note = Synthetic polymer.
source                  1..11
```

```
                        mol_type = protein
                        organism = synthetic construct
SEQUENCE: 324
SCISSSDGST G                                              11

SEQ ID NO: 325          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 325
GGINWSGDST D                                              11

SEQ ID NO: 326          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 326
SCFSSSDGSA G                                              11

SEQ ID NO: 327          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 327
SCISNTDSST Y                                              11

SEQ ID NO: 328          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 328
SCFSTRDGNA G                                              11

SEQ ID NO: 329          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 329
SCFSSRDGST G                                              11

SEQ ID NO: 330          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 330
SCFSSRDGST G                                              11

SEQ ID NO: 331          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 331
SCISSDGSTG                                                10

SEQ ID NO: 332          moltype = AA  length = 11
FEATURE                 Location/Qualifiers
REGION                  1..11
                        note = Synthetic polymer.
```

-continued

```
source                  1..11
                        mol_type = protein
                        organism = synthetic construct
SEQUENCE: 332
SCISNTDSST Y                                                              11

SEQ ID NO: 333          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 333
SCISSPDGST Y                                                              11

SEQ ID NO: 334          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 334
SCYSSSDGNT G                                                              11

SEQ ID NO: 335          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 335
GGINWSGDST D                                                              11

SEQ ID NO: 336          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 336
SCFSSSDGST G                                                              11

SEQ ID NO: 337          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 337
SCISSGDGTT Y                                                              11

SEQ ID NO: 338          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 338
SCISSDGSTG                                                                10

SEQ ID NO: 339          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 339
SCISSDGSTG                                                                10

SEQ ID NO: 340          moltype = AA  length = 19
FEATURE                 Location/Qualifiers
REGION                  1..19
```

```
                        note = Synthetic polymer.
source                  1..19
                        mol_type = protein
                        organism = synthetic construct
SEQUENCE: 340
AKGLRNSDWD LRRGYEYDY                                             19

SEQ ID NO: 341          moltype = AA  length = 25
FEATURE                 Location/Qualifiers
REGION                  1..25
                        note = Synthetic polymer.
source                  1..25
                        mol_type = protein
                        organism = synthetic construct
SEQUENCE: 341
ADQASVPPPY GSERYDIASP SEYDY                                      25

SEQ ID NO: 342          moltype = AA  length = 21
FEATURE                 Location/Qualifiers
REGION                  1..21
                        note = Synthetic polymer.
source                  1..21
                        mol_type = protein
                        organism = synthetic construct
SEQUENCE: 342
ANSRAYYSSS YDLGRLASYD Y                                          21

SEQ ID NO: 343          moltype = AA  length = 16
FEATURE                 Location/Qualifiers
REGION                  1..16
                        note = Synthetic polymer.
source                  1..16
                        mol_type = protein
                        organism = synthetic construct
SEQUENCE: 343
AAQRLGSVTD YTKYDY                                                16

SEQ ID NO: 344          moltype = AA  length = 20
FEATURE                 Location/Qualifiers
REGION                  1..20
                        note = Synthetic polymer.
source                  1..20
                        mol_type = protein
                        organism = synthetic construct
SEQUENCE: 344
ASVKWAGSGI DISGSRNYDY                                            20

SEQ ID NO: 345          moltype = AA  length = 21
FEATURE                 Location/Qualifiers
REGION                  1..21
                        note = Synthetic polymer.
source                  1..21
                        mol_type = protein
                        organism = synthetic construct
SEQUENCE: 345
AKRLDYSATD KGVDLSDEYD Y                                          21

SEQ ID NO: 346          moltype = AA  length = 19
FEATURE                 Location/Qualifiers
REGION                  1..19
                        note = Synthetic polymer.
source                  1..19
                        mol_type = protein
                        organism = synthetic construct
SEQUENCE: 346
AAGGSGRLRD LKVGQNYDY                                             19

SEQ ID NO: 347          moltype = AA  length = 23
FEATURE                 Location/Qualifiers
REGION                  1..23
                        note = Synthetic polymer.
source                  1..23
                        mol_type = protein
                        organism = synthetic construct
SEQUENCE: 347
ADSPPRTYSS GSVNLEDGSE YDY                                        23

SEQ ID NO: 348          moltype = AA  length = 21
FEATURE                 Location/Qualifiers
```

```
REGION               1..21
                     note = Synthetic polymer.
source               1..21
                     mol_type = protein
                     organism = synthetic construct
SEQUENCE: 348
VIPGRGSALP IDVGKSDEYE Y                                          21

SEQ ID NO: 349       moltype = AA  length = 19
FEATURE              Location/Qualifiers
REGION               1..19
                     note = Synthetic polymer.
source               1..19
                     mol_type = protein
                     organism = synthetic construct
SEQUENCE: 349
AAGASGRLRD LKVGQNYDY                                             19

SEQ ID NO: 350       moltype = AA  length = 23
FEATURE              Location/Qualifiers
REGION               1..23
                     note = Synthetic polymer.
source               1..23
                     mol_type = protein
                     organism = synthetic construct
SEQUENCE: 350
ADGNVWSPPI CGSAGPPPGG MDY                                        23

SEQ ID NO: 351       moltype = AA  length = 16
FEATURE              Location/Qualifiers
REGION               1..16
                     note = Synthetic polymer.
source               1..16
                     mol_type = protein
                     organism = synthetic construct
SEQUENCE: 351
AAQRLGSVTD YTKYDY                                                16

SEQ ID NO: 352       moltype = AA  length = 22
FEATURE              Location/Qualifiers
REGION               1..22
                     note = Synthetic polymer.
source               1..22
                     mol_type = protein
                     organism = synthetic construct
SEQUENCE: 352
AIPPRAYSGG SYSLKDQSKY EY                                         22

SEQ ID NO: 353       moltype = AA  length = 23
FEATURE              Location/Qualifiers
REGION               1..23
                     note = Synthetic polymer.
source               1..23
                     mol_type = protein
                     organism = synthetic construct
SEQUENCE: 353
ADGNVWSPPI CSSAGPPPGG MDY                                        23

SEQ ID NO: 354       moltype = AA  length = 9
FEATURE              Location/Qualifiers
REGION               1..9
                     note = Synthetic polymer.
source               1..9
                     mol_type = protein
                     organism = synthetic construct
SEQUENCE: 354
KSRSSYSNN                                                        9

SEQ ID NO: 355       moltype = AA  length = 22
FEATURE              Location/Qualifiers
REGION               1..22
                     note = Synthetic polymer.
source               1..22
                     mol_type = protein
                     organism = synthetic construct
SEQUENCE: 355
AMPPRAYTGR SVSLKDQSKY EY                                         22

SEQ ID NO: 356       moltype = AA  length = 13
```

```
FEATURE                Location/Qualifiers
REGION                 1..13
                       note = Synthetic polymer.
source                 1..13
                       mol_type = protein
                       organism = synthetic construct
SEQUENCE: 356
LDTTGWGPPP YQY                                                      13

SEQ ID NO: 357         moltype = AA  length = 22
FEATURE                Location/Qualifiers
REGION                 1..22
                       note = Synthetic polymer.
source                 1..22
                       mol_type = protein
                       organism = synthetic construct
SEQUENCE: 357
AHPPDPSRGG EWRLQTPSEY DY                                            22

SEQ ID NO: 358         moltype = AA  length = 16
FEATURE                Location/Qualifiers
REGION                 1..16
                       note = Synthetic polymer.
source                 1..16
                       mol_type = protein
                       organism = synthetic construct
SEQUENCE: 358
AAQRLGSVTD YTKYDY                                                   16

SEQ ID NO: 359         moltype = AA  length = 24
FEATURE                Location/Qualifiers
REGION                 1..24
                       note = Synthetic polymer.
source                 1..24
                       mol_type = protein
                       organism = synthetic construct
SEQUENCE: 359
VPRSHFTTAQ DMGQDMGAPS WYEY                                          24

SEQ ID NO: 360         moltype = AA  length = 22
FEATURE                Location/Qualifiers
REGION                 1..22
                       note = Synthetic polymer.
source                 1..22
                       mol_type = protein
                       organism = synthetic construct
SEQUENCE: 360
AVLIRYYSGG YQGLSDANEY DY                                            22

SEQ ID NO: 361         moltype = AA  length = 16
FEATURE                Location/Qualifiers
REGION                 1..16
                       note = Synthetic polymer.
source                 1..16
                       mol_type = protein
                       organism = synthetic construct
SEQUENCE: 361
WKYLSGSYSY AGQYNF                                                   16

SEQ ID NO: 362         moltype = AA  length = 23
FEATURE                Location/Qualifiers
REGION                 1..23
                       note = Synthetic polymer.
source                 1..23
                       mol_type = protein
                       organism = synthetic construct
SEQUENCE: 362
ADFNVWSPPI CGSVGPPPGG MDY                                           23

SEQ ID NO: 363         moltype = AA  length = 21
FEATURE                Location/Qualifiers
REGION                 1..21
                       note = Synthetic polymer.
source                 1..21
                       mol_type = protein
                       organism = synthetic construct
SEQUENCE: 363
AHESTYYSGT YYLTDPRRYV Y                                             21
```

```
SEQ ID NO: 364          moltype = AA  length = 19
FEATURE                 Location/Qualifiers
REGION                  1..19
                        note = Synthetic polymer.
source                  1..19
                        mol_type = protein
                        organism = synthetic construct
SEQUENCE: 364
AVPARGLTMD LENSDIYDH                                              19

SEQ ID NO: 365          moltype = AA  length = 22
FEATURE                 Location/Qualifiers
REGION                  1..22
                        note = Synthetic polymer.
source                  1..22
                        mol_type = protein
                        organism = synthetic construct
SEQUENCE: 365
AATLQVTGSY YLDLSTVDIY DN                                          22

SEQ ID NO: 366          moltype = AA  length = 20
FEATURE                 Location/Qualifiers
REGION                  1..20
                        note = Synthetic polymer.
source                  1..20
                        mol_type = protein
                        organism = synthetic construct
SEQUENCE: 366
ATLFRSNGPK DLSSGYEYDY                                             20

SEQ ID NO: 367          moltype = AA  length = 13
FEATURE                 Location/Qualifiers
REGION                  1..13
                        note = Synthetic polymer.
source                  1..13
                        mol_type = protein
                        organism = synthetic construct
SEQUENCE: 367
AGESGVWVGG LDY                                                    13

SEQ ID NO: 368          moltype = AA  length = 22
FEATURE                 Location/Qualifiers
REGION                  1..22
                        note = Synthetic polymer.
source                  1..22
                        mol_type = protein
                        organism = synthetic construct
SEQUENCE: 368
VGSANSGEFR FGWVLKPDLY NY                                          22

SEQ ID NO: 369          moltype = AA  length = 23
FEATURE                 Location/Qualifiers
REGION                  1..23
                        note = Synthetic polymer.
source                  1..23
                        mol_type = protein
                        organism = synthetic construct
SEQUENCE: 369
ADGNVWSPPI CGSAGPPPGG MDY                                         23

SEQ ID NO: 370          moltype = AA  length = 23
FEATURE                 Location/Qualifiers
REGION                  1..23
                        note = Synthetic polymer.
source                  1..23
                        mol_type = protein
                        organism = synthetic construct
SEQUENCE: 370
ADGNVWSPPI CGSAGPPPGG MDY                                         23

SEQ ID NO: 371          moltype = AA  length = 20
FEATURE                 Location/Qualifiers
REGION                  1..20
                        note = Synthetic polymer.
source                  1..20
                        mol_type = protein
                        organism = synthetic construct
SEQUENCE: 371
ERGYAYCSDD GCQRTQDYDY                                             20
```

```
SEQ ID NO: 372          moltype = AA  length = 21
FEATURE                 Location/Qualifiers
REGION                  1..21
                        note = Synthetic polymer.
source                  1..21
                        mol_type = protein
                        organism = synthetic construct
SEQUENCE: 372
GAARAWWSGS YDYTRMNNYD Y                                             21

SEQ ID NO: 373          moltype = AA  length = 23
FEATURE                 Location/Qualifiers
REGION                  1..23
                        note = Synthetic polymer.
source                  1..23
                        mol_type = protein
                        organism = synthetic construct
SEQUENCE: 373
AETSADSGEF RFGWVLKPSL YDY                                           23

SEQ ID NO: 374          moltype = AA  length = 21
FEATURE                 Location/Qualifiers
REGION                  1..21
                        note = Synthetic polymer.
source                  1..21
                        mol_type = protein
                        organism = synthetic construct
SEQUENCE: 374
AAGSAYSGSY WNITMAANYD Y                                             21

SEQ ID NO: 375          moltype = AA  length = 18
FEATURE                 Location/Qualifiers
REGION                  1..18
                        note = Synthetic polymer.
source                  1..18
                        mol_type = protein
                        organism = synthetic construct
SEQUENCE: 375
AQRIFGAQPM DLSGDYEY                                                 18

SEQ ID NO: 376          moltype = AA  length = 23
FEATURE                 Location/Qualifiers
REGION                  1..23
                        note = Synthetic polymer.
source                  1..23
                        mol_type = protein
                        organism = synthetic construct
SEQUENCE: 376
ADGNVWSPPI CGSAGPPPGG MDY                                           23

SEQ ID NO: 377          moltype = AA  length = 18
FEATURE                 Location/Qualifiers
REGION                  1..18
                        note = Synthetic polymer.
source                  1..18
                        mol_type = protein
                        organism = synthetic construct
SEQUENCE: 377
ARDYRGIKDL DLKGDYDY                                                 18

SEQ ID NO: 378          moltype = AA  length = 25
FEATURE                 Location/Qualifiers
REGION                  1..25
                        note = Synthetic polymer.
source                  1..25
                        mol_type = protein
                        organism = synthetic construct
SEQUENCE: 378
ADFNVWSPPI CGSIWYGPPP RGMDY                                         25

SEQ ID NO: 379          moltype = AA  length = 25
FEATURE                 Location/Qualifiers
REGION                  1..25
                        note = Synthetic polymer.
source                  1..25
                        mol_type = protein
                        organism = synthetic construct
SEQUENCE: 379
```

```
ADSNVWSPPI CGSRWYGPPP GGMAY                                   25

SEQ ID NO: 380          moltype = AA  length = 25
FEATURE                 Location/Qualifiers
REGION                  1..25
                        note = Synthetic polymer.
source                  1..25
                        mol_type = protein
                        organism = synthetic construct
SEQUENCE: 380
ADFNVWSPPI CGSNWYGPPP GGMDY                                   25

SEQ ID NO: 381          moltype = AA  length = 25
FEATURE                 Location/Qualifiers
REGION                  1..25
                        note = Synthetic polymer.
source                  1..25
                        mol_type = protein
                        organism = synthetic construct
SEQUENCE: 381
ADFNVWSPPI CGSIWYGPPP GGMDY                                   25

SEQ ID NO: 382          moltype = AA  length = 23
FEATURE                 Location/Qualifiers
REGION                  1..23
                        note = Synthetic polymer.
source                  1..23
                        mol_type = protein
                        organism = synthetic construct
SEQUENCE: 382
ADGNVWSPPI CGSAGPPPGG MDY                                     23

SEQ ID NO: 383          moltype = AA  length = 17
FEATURE                 Location/Qualifiers
REGION                  1..17
                        note = Synthetic polymer.
source                  1..17
                        mol_type = protein
                        organism = synthetic construct
SEQUENCE: 383
ARIITVATMR LDSDYDY                                            17

SEQ ID NO: 384          moltype = AA  length = 23
FEATURE                 Location/Qualifiers
REGION                  1..23
                        note = Synthetic polymer.
source                  1..23
                        mol_type = protein
                        organism = synthetic construct
SEQUENCE: 384
ADGNVWSPPI CGSAGPPPGG MDY                                     23

SEQ ID NO: 385          moltype = AA  length = 25
FEATURE                 Location/Qualifiers
REGION                  1..25
                        note = Synthetic polymer.
source                  1..25
                        mol_type = protein
                        organism = synthetic construct
SEQUENCE: 385
ADSNVWSPPI CGRTWYGPPP GGMDY                                   25

SEQ ID NO: 386          moltype = AA  length = 25
FEATURE                 Location/Qualifiers
REGION                  1..25
                        note = Synthetic polymer.
source                  1..25
                        mol_type = protein
                        organism = synthetic construct
SEQUENCE: 386
ADFNVWSPPI CGSIWYGPPP GGMAY                                   25

SEQ ID NO: 387          moltype = AA  length = 25
FEATURE                 Location/Qualifiers
REGION                  1..25
                        note = Synthetic polymer.
source                  1..25
                        mol_type = protein
                        organism = synthetic construct
```

```
SEQUENCE: 387
ADFNVWSPPI CGSNWYGPPP GGMDY                                    25

SEQ ID NO: 388          moltype = AA  length = 25
FEATURE                 Location/Qualifiers
REGION                  1..25
                        note = Synthetic polymer.
source                  1..25
                        mol_type = protein
                        organism = synthetic construct
SEQUENCE: 388
ADFNVWSPPI CGSSWYGPPP GGMDY                                    25

SEQ ID NO: 389          moltype = AA  length = 25
FEATURE                 Location/Qualifiers
REGION                  1..25
                        note = Synthetic polymer.
source                  1..25
                        mol_type = protein
                        organism = synthetic construct
SEQUENCE: 389
ADFNVWSPPI CGSRWYGPPP GGMEY                                    25

SEQ ID NO: 390          moltype = AA  length = 23
FEATURE                 Location/Qualifiers
REGION                  1..23
                        note = Synthetic polymer.
source                  1..23
                        mol_type = protein
                        organism = synthetic construct
SEQUENCE: 390
ADGNVWSPPI CGSAGPPPGG MDY                                      23

SEQ ID NO: 391          moltype = AA  length = 25
FEATURE                 Location/Qualifiers
REGION                  1..25
                        note = Synthetic polymer.
source                  1..25
                        mol_type = protein
                        organism = synthetic construct
SEQUENCE: 391
ADFNVWSPPI CGSRWYGPPP GGMAY                                    25

SEQ ID NO: 392          moltype = AA  length = 23
FEATURE                 Location/Qualifiers
REGION                  1..23
                        note = Synthetic polymer.
source                  1..23
                        mol_type = protein
                        organism = synthetic construct
SEQUENCE: 392
ADGNVWSPPI CGSAGPPPGG MDY                                      23

SEQ ID NO: 393          moltype = AA  length = 25
FEATURE                 Location/Qualifiers
REGION                  1..25
                        note = Synthetic polymer.
source                  1..25
                        mol_type = protein
                        organism = synthetic construct
SEQUENCE: 393
ADSNVWSPPI CGKTWYGPPP GGMDY                                    25

SEQ ID NO: 394          moltype = AA  length = 13
FEATURE                 Location/Qualifiers
REGION                  1..13
                        note = Synthetic polymer.
source                  1..13
                        mol_type = protein
                        organism = synthetic construct
SEQUENCE: 394
AGESGVWVGG LDY                                                 13

SEQ ID NO: 395          moltype = AA  length = 25
FEATURE                 Location/Qualifiers
REGION                  1..25
                        note = Synthetic polymer.
source                  1..25
                        mol_type = protein
```

```
                        organism = synthetic construct
SEQUENCE: 395
ADSNVWSPPI CGSTWYGPPP GGMAY                                           25

SEQ ID NO: 396          moltype = AA  length = 23
FEATURE                 Location/Qualifiers
REGION                  1..23
                        note = Synthetic polymer.
source                  1..23
                        mol_type = protein
                        organism = synthetic construct
SEQUENCE: 396
ADGNVWSPPI CGSAGPPPGG MDY                                             23

SEQ ID NO: 397          moltype = AA  length = 25
FEATURE                 Location/Qualifiers
REGION                  1..25
                        note = Synthetic polymer.
source                  1..25
                        mol_type = protein
                        organism = synthetic construct
SEQUENCE: 397
ADFNVWSPPI CGSRWYGPPP GGMDY                                           25

SEQ ID NO: 398          moltype = AA  length = 25
FEATURE                 Location/Qualifiers
REGION                  1..25
                        note = Synthetic polymer.
source                  1..25
                        mol_type = protein
                        organism = synthetic construct
SEQUENCE: 398
ADFNVWSPPI CGSRWYGPPP GGMDY                                           25

SEQ ID NO: 399          moltype = AA  length = 25
FEATURE                 Location/Qualifiers
REGION                  1..25
                        note = Synthetic polymer.
source                  1..25
                        mol_type = protein
                        organism = synthetic construct
SEQUENCE: 399
ADFNVWSPPI CGSRWYGPPP GGMDY                                           25

SEQ ID NO: 400          moltype = AA  length = 25
FEATURE                 Location/Qualifiers
REGION                  1..25
                        note = Synthetic polymer.
source                  1..25
                        mol_type = protein
                        organism = synthetic construct
SEQUENCE: 400
ADFNVWSPPI CGSIWYGPPP GGMDY                                           25

SEQ ID NO: 401          moltype = AA  length = 23
FEATURE                 Location/Qualifiers
REGION                  1..23
                        note = Synthetic polymer.
source                  1..23
                        mol_type = protein
                        organism = synthetic construct
SEQUENCE: 401
ADGNVWSPPI CGSAGPPPGG MDY                                             23

SEQ ID NO: 402          moltype = AA  length = 23
FEATURE                 Location/Qualifiers
REGION                  1..23
                        note = Synthetic polymer.
source                  1..23
                        mol_type = protein
                        organism = synthetic construct
SEQUENCE: 402
ADFNVWSPPI CGSVGPPPGG MDY                                             23

SEQ ID NO: 403          moltype = AA  length = 25
FEATURE                 Location/Qualifiers
REGION                  1..25
                        note = Synthetic polymer.
source                  1..25
```

```
                         mol_type = protein
                         organism = synthetic construct
SEQUENCE: 403
ADFNVWSPPI CGSSWYGPPP GGMAY                                      25

SEQ ID NO: 404           moltype = AA  length = 13
FEATURE                  Location/Qualifiers
REGION                   1..13
                         note = Synthetic polymer.
source                   1..13
                         mol_type = protein
                         organism = synthetic construct
SEQUENCE: 404
AGESGVWVGG LDY                                                   13

SEQ ID NO: 405           moltype = AA  length = 25
FEATURE                  Location/Qualifiers
REGION                   1..25
                         note = Synthetic polymer.
source                   1..25
                         mol_type = protein
                         organism = synthetic construct
SEQUENCE: 405
ADFNVWSPPI CGSSWYGPPP GGMEY                                      25

SEQ ID NO: 406           moltype = AA  length = 23
FEATURE                  Location/Qualifiers
REGION                   1..23
                         note = Synthetic polymer.
source                   1..23
                         mol_type = protein
                         organism = synthetic construct
SEQUENCE: 406
ADGNVWSPPI CGSAGPPPGG MDY                                        23

SEQ ID NO: 407           moltype = AA  length = 25
FEATURE                  Location/Qualifiers
REGION                   1..25
                         note = Synthetic polymer.
source                   1..25
                         mol_type = protein
                         organism = synthetic construct
SEQUENCE: 407
ADFNVWSPPI CSSNWYGPPP RGMDY                                      25

SEQ ID NO: 408           moltype = AA  length = 25
FEATURE                  Location/Qualifiers
REGION                   1..25
                         note = Synthetic polymer.
source                   1..25
                         mol_type = protein
                         organism = synthetic construct
SEQUENCE: 408
ADFNVWSPPI CGSIWYGPPP RGMDY                                      25

SEQ ID NO: 409           moltype = AA  length = 146
FEATURE                  Location/Qualifiers
REGION                   1..146
                         note = Synthetic polymer.
source                   1..146
                         mol_type = protein
                         organism = synthetic construct
SEQUENCE: 409
QVQLQESGGG LVQAGGSLRL SCAASGRSFS SYTLAWFRQA PGKEREFVAS ITWGGGNTYY  60
PDSVKGRFTI SRDDAKNTVY LQMNSLKPED TAVYYCAAKG LRNSDWDLRR GYEYDYWGQG  120
TQVTVSSAAA YPYDVPDYGS HHHHHH                                     146

SEQ ID NO: 410           moltype = AA  length = 152
FEATURE                  Location/Qualifiers
REGION                   1..152
                         note = Synthetic polymer.
source                   1..152
                         mol_type = protein
                         organism = synthetic construct
SEQUENCE: 410
QVQLQESGGG LVQDGGSLRL SCAFSGRTFS SYTMGWFRQG PGKEREFVAA TVWTGAGTVY  60
ADSVKGRFTI SRDNAKNTVY LQMNSLRPED TAVYYCAADQ ASVPPPYGSE RYDIASPSEY  120
DYWGQGTQVT VSSAAAYPYD VPDYGSHHHH HH                              152
```

```
SEQ ID NO: 411          moltype = AA  length = 148
FEATURE                 Location/Qualifiers
REGION                  1..148
                        note = Synthetic polymer.
source                  1..148
                        mol_type = protein
                        organism = synthetic construct
SEQUENCE: 411
QVQLQESGGG LVQAGASLRL SCAASGRTFS SYIMGWFRQA PGKEREFVAA IGWSADITVY  60
ADSVKGRFTI SRDNAENMVY LQMNSLNPED TAVYYCAANS RAYYSSSYDL GRLASYDYWG  120
QGTQVTVSSA AAYPYDVPDY GSHHHHHH                                    148

SEQ ID NO: 412          moltype = AA  length = 143
FEATURE                 Location/Qualifiers
REGION                  1..143
                        note = Synthetic polymer.
source                  1..143
                        mol_type = protein
                        organism = synthetic construct
SEQUENCE: 412
QVQLQESGGG LVQAGGSLRL SCAASGRTFS SYTMGWFRQA PGKEREFVAF IDWSGGGTYY  60
DDSVKGRFTI SRDNAENTVY LQMNNLEPED TAVYYCAAAQ RLGSVTDYTK YDYWGQGTQV  120
TVSSAAAYPY DVPDYGSHHH HHH                                         143

SEQ ID NO: 413          moltype = AA  length = 152
FEATURE                 Location/Qualifiers
REGION                  1..152
                        note = Synthetic polymer.
source                  1..152
                        mol_type = protein
                        organism = synthetic construct
SEQUENCE: 413
QVQLQESGGG LVQAGGSLRL SCAASGRTSG RTFSSYTMGW FRQAPGKERE FVATITWGGG  60
STYYADSVKG RFTISRDNAN NTVYLQMNSL KPEDTAVYYC AASVKVVAGS GIDISGSRNY  120
DYWGQGTQVT VSSAAAYPYD VPDYGSHHHH HH                               152

SEQ ID NO: 414          moltype = AA  length = 148
FEATURE                 Location/Qualifiers
REGION                  1..148
                        note = Synthetic polymer.
source                  1..148
                        mol_type = protein
                        organism = synthetic construct
SEQUENCE: 414
QVQLQESGGG LVQPGGSLRL SCLASGRTFS SYAMGWFRQA PGKEREFVAA ISWSGGPTVY  60
ADHVKGRFTI SRDNAKNTVY LQVNSLKPED TADYYCAAKR LDYSATDKGV DLSDEYDYWG  120
QGTQVTVSSA AAYPYDVPDY GSHHHHHH                                    148

SEQ ID NO: 415          moltype = AA  length = 146
FEATURE                 Location/Qualifiers
REGION                  1..146
                        note = Synthetic polymer.
source                  1..146
                        mol_type = protein
                        organism = synthetic construct
SEQUENCE: 415
QVQLQESGGG LVQAGDSLRL SCAASGLTFS NYIMGWFRQA PGKEREFVAA ITWGGGSTVY  60
ADSVEGRFTI SRDGTKNTVS LQMNSLLPED TAVYYCAAAG GSGRLRDLKV GQNYDYWGQG  120
TQVTVSSAAA YPYDVPDYGS HHHHHH                                      146

SEQ ID NO: 416          moltype = AA  length = 150
FEATURE                 Location/Qualifiers
REGION                  1..150
                        note = Synthetic polymer.
source                  1..150
                        mol_type = protein
                        organism = synthetic construct
SEQUENCE: 416
QVQLQESGGG LVQAGGSLRL SCAASGRTFS SYTMGWFRQA PGREREFVAA ITWSGVSTVY  60
TDSVKGRFTV SRDNAKNTVY LQMNSLKPED TAVYYCAADS PPRTYSSGSV NLEDGSEYDY  120
WGQGTQVTVS SAAAYPYDVP DYGSHHHHHH                                  150

SEQ ID NO: 417          moltype = AA  length = 148
FEATURE                 Location/Qualifiers
REGION                  1..148
                        note = Synthetic polymer.
source                  1..148
                        mol_type = protein
                        organism = synthetic construct
```

-continued

```
SEQUENCE: 417
QVQLQESGGG LVQAGGSLRL SCAASGRTFS SDTMGWFRQA PGKEREFVGA IMWSGAFTHY  60
ADSVKGRFTI SRDNAKNTVY LQMNALKPED TAVYYCAVIP GRGSALPIDV GKSDEYEYWG  120
QGTQVTVSSA AAYPYDVPDY GSHHHHHH                                     148

SEQ ID NO: 418         moltype = AA  length = 146
FEATURE                Location/Qualifiers
REGION                 1..146
                       note = Synthetic polymer.
source                 1..146
                       mol_type = protein
                       organism = synthetic construct
SEQUENCE: 418
QVQLQESGGG LVQAGDSLRL SCAASGLTFS NYIMGWFRQA PGKEREFVAA ITWGGGSTVY  60
ADSVEGRFTI SRDGTKNTVS LQMNSLQPED TAVYYCAAAG ASGRLRDLKV GQNYDYWGQG  120
TQVTVSSAAA YPYDVPDYGS HHHHHH                                       146

SEQ ID NO: 419         moltype = AA  length = 150
FEATURE                Location/Qualifiers
REGION                 1..150
                       note = Synthetic polymer.
source                 1..150
                       mol_type = protein
                       organism = synthetic construct
SEQUENCE: 419
QVQLQESGGG LVQAGGSLRL SCAGSGFTLD YYGIGWFRQA PGKEREGVSC ISSSDRNTYY  60
ADSVKGRFTI SGDNAKNTVY LQMNNLKPED TAVYYCAADG NVWSPPICGS AGPPPGGMDY  120
WGKGTQVTVS SAAAYPYDVP DYGSHHHHHH                                   150

SEQ ID NO: 420         moltype = AA  length = 143
FEATURE                Location/Qualifiers
REGION                 1..143
                       note = Synthetic polymer.
source                 1..143
                       mol_type = protein
                       organism = synthetic construct
SEQUENCE: 420
QVQLQESGGG LVQAGGSLRL SCVASGHTFS SYTMGWFRQA PGKEREFVAF IDWSGGGTYY  60
ANSVKGRFTI SRDNAENTVY LQMNNLKPED TAVYYCAAAQ RLGSVTDYTK YDYWGQGTQV  120
TVSSAAAYPY DVPDYGSHHH HHH                                          143

SEQ ID NO: 421         moltype = AA  length = 149
FEATURE                Location/Qualifiers
REGION                 1..149
                       note = Synthetic polymer.
source                 1..149
                       mol_type = protein
                       organism = synthetic construct
SEQUENCE: 421
QVQLQESGGG LVQAGGSLRL SCAASGRTFS SYVIGWFRQA PGKEREFVAV ITWSGDSTYS  60
SDSLKGRFTI SRDNAKNTVY LQMNALNPED TAVYYCAAIP PRAYSGGSYS LKDQSKYEYW  120
GQGTQVTVSS AAAYPYDVPD YGSHHHHHH                                    149

SEQ ID NO: 422         moltype = AA  length = 149
FEATURE                Location/Qualifiers
REGION                 1..149
                       note = Synthetic polymer.
source                 1..149
                       mol_type = protein
                       organism = synthetic construct
SEQUENCE: 422
QVQLQESGGG LVQAEGSLKL SCISGFAFDG YAIGWFRQAP GKEREGVACI SSKDGSTYYA  60
DSVKGRFTMS VDKTKNTVYL QMSSLKPEDT AVYYCAADGN VWSPPICSSA GPPPGGMDYW  120
GKGTQVTVSS AAAYPYDVPD YGSHHHHHH                                    149

SEQ ID NO: 423         moltype = AA  length = 139
FEATURE                Location/Qualifiers
REGION                 1..139
                       note = Synthetic polymer.
source                 1..139
                       mol_type = protein
                       organism = synthetic construct
SEQUENCE: 423
QVQLQESGGG LVQPGGSLTL SCAASGFAFG FFDMTWVRQA PGKGLEWVSG INSIGGSTTY  60
ADSVKGRFTI SRDNAKNELY LQMNSLKPDD TAVYYCAKSR SSYSNNWRPP GQGTQVTVSS  120
AAAYPYDVPD YGSHHHHHH                                               139

SEQ ID NO: 424         moltype = AA  length = 149
FEATURE                Location/Qualifiers
```

```
REGION                  1..149
                        note = Synthetic polymer.
source                  1..149
                        mol_type = protein
                        organism = synthetic construct
SEQUENCE: 424
QVQLQESGGG LVQARGSLTL SCAASGRTFS NYVIGWFRQA PGEEREFVAV VTWSGDSTYS  60
SDSLKGRFTI SRDNAKNTVY LQMNNLNPED TAVYYCAAMP PRAYTGRSVS LKDQSKYEYW  120
GQGTQVTVSS AAAYPYDVPD YGSHHHHHH                                  149

SEQ ID NO: 425          moltype = AA  length = 139
FEATURE                 Location/Qualifiers
REGION                  1..139
                        note = Synthetic polymer.
source                  1..139
                        mol_type = protein
                        organism = synthetic construct
SEQUENCE: 425
QVQLQESGGG LVQPGGSLRL SCAASGSIFS INVMGWYRQT PGKERELVAK ITNFGITSYA  60
DSAQGRFTIS RGNAKNTVYL QMNSLKPEDT AVYYCNLDTT GWGPPPYQYW GQGTQVTVSS  120
AAAYPYDVPD YGSHHHHHH                                             139

SEQ ID NO: 426          moltype = AA  length = 149
FEATURE                 Location/Qualifiers
REGION                  1..149
                        note = Synthetic polymer.
source                  1..149
                        mol_type = protein
                        organism = synthetic construct
SEQUENCE: 426
QVQLQESGGG LVQAGASLRL SCAASGRTFS NYNVGWFRQA PGKEREFVSF ISWISDITYY  60
SDSVKGRFII SRDNAKNMVY LQMNSLKPED TAVYYCAAHP PDPSRGGEWR LQTPSEYDYW  120
GQGTQVTVSS AAAYPYDVPD YGSHHHHHH                                  149

SEQ ID NO: 427          moltype = AA  length = 143
FEATURE                 Location/Qualifiers
REGION                  1..143
                        note = Synthetic polymer.
source                  1..143
                        mol_type = protein
                        organism = synthetic construct
SEQUENCE: 427
QVQLQESGGG LVQAGGSLRL SCAASGHTFS SYTMGWFRQA PGKEREFVAF IDWSGGGTYY  60
ADSVKGRFTI SRDNAENTVY LQMNNLKPED TAVYYCAAAQ RLGSVTDYTK YDYWGQGTQV  120
TVSSAAAYPY DVPDYGSHHH HHH                                        143

SEQ ID NO: 428          moltype = AA  length = 151
FEATURE                 Location/Qualifiers
REGION                  1..151
                        note = Synthetic polymer.
source                  1..151
                        mol_type = protein
                        organism = synthetic construct
SEQUENCE: 428
QVQLQESGGG LVQAGGSLRL SCAASGRTFS TYPVGWFRQA PGKEREFVAV ILWSGVSTYY  60
ADSVKGRFTI SRDNAQNTVY LQMDSLKPED TAVYYCAVPR SHFTTAQDMG QDMGAPSWYE  120
YWGQGTQVTV SSAAAYPYDV PDYGSHHHHH H                               151

SEQ ID NO: 429          moltype = AA  length = 149
FEATURE                 Location/Qualifiers
REGION                  1..149
                        note = Synthetic polymer.
source                  1..149
                        mol_type = protein
                        organism = synthetic construct
SEQUENCE: 429
QVQLQESGGG LVQAGGSLRL SCAASGRTFS NYAMGWFRQA PGKEREFVAA IVWSGGSTYY  60
ADSVKGRFTI SRDNAKNTVY LQMNSLKPED TAVYYCAAVL IRYYSGGYQG LSDANEYDYW  120
GQGTQVTVSS AAAYPYDVPD YGSHHHHHH                                  149

SEQ ID NO: 430          moltype = AA  length = 145
FEATURE                 Location/Qualifiers
REGION                  1..145
                        note = Synthetic polymer.
source                  1..145
                        mol_type = protein
                        organism = synthetic construct
SEQUENCE: 430
QVQLQESGGG LVQAGASLRL SCSASGRTFS DYRMGWFRQA PGKEREIWVA AISSSGYHTY  60
```

-continued

```
YADSVKGRFT ISRDNAKNTG YLQMSSLKPE DTAVYYCAVV KYLSGSYSYA GQYNFWGQGT  120
QVTVSSAAAY PYDVPDYGSH HHHHH                                        145

SEQ ID NO: 431          moltype = AA  length = 150
FEATURE                 Location/Qualifiers
REGION                  1..150
                        note = Synthetic polymer.
source                  1..150
                        mol_type = protein
                        organism = synthetic construct
SEQUENCE: 431
QVQLQESGGG LVQAGDSLKL SCAASGLTFS NYIMAWFRQA PGKEREGVSC ISSPDGSTYY  60
ADSVKGRFTI SSDNAKNTVY LQMNSLKPED TAVYYCAADF NVWSPPICGS VGPPPGGMDY  120
WGKGTQVTVS SAAAYPYDVP DYGSHHHHHH                                   150

SEQ ID NO: 432          moltype = AA  length = 148
FEATURE                 Location/Qualifiers
REGION                  1..148
                        note = Synthetic polymer.
source                  1..148
                        mol_type = protein
                        organism = synthetic construct
SEQUENCE: 432
QVQLQESGGG LVQAGGSLRL SCAASGRTFS NSVMGWFRQP PGKEREFVAA VLWSGVSTAY  60
ADSVKGRFTI SRDNAKNTVY LQMNNLKPDD TAVYYCAAHE STYYSGTYYL TDPRRYVYWG  120
QGTQVTVSSA AAYPYDVPDY GSHHHHHH                                     148

SEQ ID NO: 433          moltype = AA  length = 146
FEATURE                 Location/Qualifiers
REGION                  1..146
                        note = Synthetic polymer.
source                  1..146
                        mol_type = protein
                        organism = synthetic construct
SEQUENCE: 433
QVQLQESGGG LVQAGGSLRL SCVGDGRTFS SYLIGWFRQA PGNEREFVVA ITWDGSATTY  60
ADSVKGRFTV SRDSAKNTAY LQMNSLKPED TAVYYCAAVP ARGLTMDLEN SDIYDHWGRG  120
TQVTVSSAAA YPYDVPDYGS HHHHHH                                       146

SEQ ID NO: 434          moltype = AA  length = 149
FEATURE                 Location/Qualifiers
REGION                  1..149
                        note = Synthetic polymer.
source                  1..149
                        mol_type = protein
                        organism = synthetic construct
SEQUENCE: 434
QVQLQESGGG LVQAGGSLRL SCAASGRTFS SYVMGWFRQA LGKEREFVAA IGWNGGITYY  60
ADSVKGRFAI SRDNAKNTVY LQMNSLKPED TAVYYCAAAT LQVTGSYYLD LSTVDIYDNW  120
GQGTQVTVSS AAAYPYDVPD YGSHHHHHH                                    149

SEQ ID NO: 435          moltype = AA  length = 147
FEATURE                 Location/Qualifiers
REGION                  1..147
                        note = Synthetic polymer.
source                  1..147
                        mol_type = protein
                        organism = synthetic construct
SEQUENCE: 435
QVQLQESGGG LVQAGGSLRL SCAASGGTFS NYVMGWFRQA PGKEREFVGF ITWSGASTYY  60
ADSVKGRFTI SRDNAENTVY LQMNSLKPED TAVYYCAATL FRSNGPKDLS SGYEYDYWGQ  120
GTQVTVSSAA AYPYDVPDYG SHHHHHH                                      147

SEQ ID NO: 436          moltype = AA  length = 140
FEATURE                 Location/Qualifiers
REGION                  1..140
                        note = Synthetic polymer.
SITE                    112
                        note = misc_feature - Xaa can be any naturally occurring
                         amino acid
source                  1..140
                        mol_type = protein
                        organism = synthetic construct
SEQUENCE: 436
QVQLQESGGG LVQAGDSLRL TCTASGRTFS NYGIGWFRQA PGKEREFVAG INWSGESADY  60
ADSVKGRFTI SRDNAKNTVY LQMNSLKPED TAVYYCAAGE SGVWVGGLDY WXQGTQVTVS  120
SAAAYPYDVP DYGSHHHHHH                                              140

SEQ ID NO: 437          moltype = AA  length = 149
```

-continued

```
FEATURE              Location/Qualifiers
REGION               1..149
                     note = Synthetic polymer.
source               1..149
                     mol_type = protein
                     organism = synthetic construct
SEQUENCE: 437
QVQLQESGGG LVQAGGSLRL SCAASGFTFD DYAIAWFRQA PGKEREGVSC IERSDGSTYY  60
ADSVKGRFTI SSDNAKNTVY LQMNSLKPED TAVYYCAVGS ANSGEFRFGW VLKPDLYNYW  120
GQGTQVTVSS AAAYPYDVPD YGSHHHHHH                                    149

SEQ ID NO: 438      moltype = AA  length = 150
FEATURE              Location/Qualifiers
REGION               1..150
                     note = Synthetic polymer.
source               1..150
                     mol_type = protein
                     organism = synthetic construct
SEQUENCE: 438
QVQLQESGGG LVQAGGSLRL SCTASGRTFS SYTVAWFRQS PGKEREGISC ISNTDSSTYY  60
ADSVKGRFTI SSDNAKSTVH LQMSSLKPED TAVYYCAADG NVWSPPICGS AGPPPGGMDY  120
WGKGTQVTVS SAAAYPYDVP DYGSHHHHHH                                   150

SEQ ID NO: 439      moltype = AA  length = 150
FEATURE              Location/Qualifiers
REGION               1..150
                     note = Synthetic polymer.
source               1..150
                     mol_type = protein
                     organism = synthetic construct
SEQUENCE: 439
QVQLQESGGG LVQPGGSLRL SCATFGFPFD DYAIAWFRQA PGKEREGVSC ISNTDSSTYY  60
ADSVKGRFTI SSDNAKNTVH LQMSSLKPED TAVYYCAADG NVWSPPICGS AGPPPGGMDY  120
WGKGTQVTVS SAAAYPYDVP DYGSHHHHHH                                   150

SEQ ID NO: 440      moltype = AA  length = 147
FEATURE              Location/Qualifiers
REGION               1..147
                     note = Synthetic polymer.
source               1..147
                     mol_type = protein
                     organism = synthetic construct
SEQUENCE: 440
QVQLQESGGG LVQAGGSLRL SCAASGRTFS SYVMGWFRQA PGKEREFVAQ ISWSAGSIYY  60
ADSVKGRFTI SNDNAKRTVY LQMNSLKPED TAVYYCAERG YAYCSDDGCQ RTQDYDYWGQ  120
GTQVTVSSAA AYPYDVPDYG SHHHHHH                                      147

SEQ ID NO: 441      moltype = AA  length = 148
FEATURE              Location/Qualifiers
REGION               1..148
                     note = Synthetic polymer.
source               1..148
                     mol_type = protein
                     organism = synthetic construct
SEQUENCE: 441
QVQLQESGGG LVQAGGSLRL SCAASGRTLS SNPMAWFRQA AGKEREFVAG MSWNPGPAVY  60
ADSVKGRFTI SRDSAENTVY LQMNSLKPED TAVYYCAGAA RAWWSGSYDY TRMNNYDYWG  120
PGTQVTVSSA AAYPYDVPDY GSHHHHHH                                     148

SEQ ID NO: 442      moltype = AA  length = 150
FEATURE              Location/Qualifiers
REGION               1..150
                     note = Synthetic polymer.
source               1..150
                     mol_type = protein
                     organism = synthetic construct
SEQUENCE: 442
QVQLQESGGG LVQAGGSLRL SCAVSGFTFD NYAIGWFRQA PGKEREGVSC ISRSDGSTYY  60
ADSVRGRFTI SSDNAKNTVY LQMNSLKPED TAVYYCAAET SADSGEFRFG WVLKPSLYDY  120
WGQGTQVTVS SAAAYPYDVP DYGSHHHHHH                                   150

SEQ ID NO: 443      moltype = AA  length = 148
FEATURE              Location/Qualifiers
REGION               1..148
                     note = Synthetic polymer.
source               1..148
                     mol_type = protein
                     organism = synthetic construct
SEQUENCE: 443
```

-continued

```
QVQLQESGGG LVQAGGSLRL SCAASGRAFS SYFMGWFRQT PGKEREFVAN IGWTGDMTYY  60
ADSVKGRFTI SRDNAKNTVY LQMNSLKPED TAVYYCAAAG SAYSGSYWNI TMAANYDYWG  120
QGTQVTVSSA AAYPYDVPDY GSHHHHHH                                     148

SEQ ID NO: 444         moltype = AA  length = 145
FEATURE                Location/Qualifiers
REGION                 1..145
                       note = Synthetic polymer.
source                 1..145
                       mol_type = protein
                       organism = synthetic construct
SEQUENCE: 444
QVQLQESGGG LVQAGGSLRL SCAASTPTFS SYNMGWFRQA PGKEREFVAA IIWSGSMTYY  60
ADSMKGRFTV SIDNAKNTVY LQMNSLKPED TAVYYCAAQR IFGAQPMDLS GDYEYWGQGT  120
QVTVSSAAAY PYDVPDYGSH HHHHH                                        145

SEQ ID NO: 445         moltype = AA  length = 150
FEATURE                Location/Qualifiers
REGION                 1..150
                       note = Synthetic polymer.
source                 1..150
                       mol_type = protein
                       organism = synthetic construct
SEQUENCE: 445
QVQLQESGGG LVQAGGSLRL SCATFGFTFD DYAIAWFRQA PGKEREGISC ISNTDSSTYY  60
ADSVKGRFTI SSDSAKNTVH LQMSSLKPED TAVYYCAADG NVWSPPICGS AGPPPGGMDY  120
WGKGTQVTVS SAAAYPYDVP DYGSHHHHHH                                   150

SEQ ID NO: 446         moltype = AA  length = 145
FEATURE                Location/Qualifiers
REGION                 1..145
                       note = Synthetic polymer.
source                 1..145
                       mol_type = protein
                       organism = synthetic construct
SEQUENCE: 446
QVQLQESGGG LVQAGGSLRL SCKASGGTFS GYIMGWFRQA PGKEREFVAA NTWSGGPTYY  60
SDSVKGRFTI SRDNAKNTVY LQMNTLKPED TAVYQCAARD YRGIKDLDLK GDYDYWGQGT  120
QVTVSSAAAY PYDVPDYGSH HHHHH                                        145

SEQ ID NO: 447         moltype = AA  length = 151
FEATURE                Location/Qualifiers
REGION                 1..151
                       note = Synthetic polymer.
source                 1..151
                       mol_type = protein
                       organism = synthetic construct
SEQUENCE: 447
QVQLQESGGG LVQAGDSLKL SCATSGRSFS SYTIAWFRQA PGKEREGISC ISSDGSTGYA  60
DSVRGRFTIS SDNAKNTVYL QMNSLKPEDT AVYYCAADFN VWSPPICGSI WYGPPPRGMD  120
YWGKGTQVTV SSAAAYPYDV PDYGSHHHHH H                                 151

SEQ ID NO: 448         moltype = AA  length = 152
FEATURE                Location/Qualifiers
REGION                 1..152
                       note = Synthetic polymer.
source                 1..152
                       mol_type = protein
                       organism = synthetic construct
SEQUENCE: 448
QVQLQESGGG LVQAGGYLRL SCAASGFSSD DYTIGWFRQA PGKEREGISC YSSSDGSTGF  60
ADSVKGRFTI SSDNAKNTVY LQMNNLRPED TAVYYCAADS NVWSPPICGS RWYGPPPGGM  120
AYWGKGTQVT VSSAAAYPYD VPDYGSHHHH HH                                152

SEQ ID NO: 449         moltype = AA  length = 151
FEATURE                Location/Qualifiers
REGION                 1..151
                       note = Synthetic polymer.
source                 1..151
                       mol_type = protein
                       organism = synthetic construct
SEQUENCE: 449
QVQLQESGGG LAQVGGSLRL SCTASGFTFD DYTIGWFRQA PGKEREGISC ISSDGSTGYA  60
DSVKGRFTIS SDNAKNTVYL QMNSLKPEDT AVYYCAADFN VWSPPICGSN WYGPPPGGMD  120
YWGKGTQVTV SSAAAYPYDV PDYGSHHHHH H                                 151

SEQ ID NO: 450         moltype = AA  length = 152
FEATURE                Location/Qualifiers
REGION                 1..152
```

```
                         note = Synthetic polymer.
source                   1..152
                         mol_type = protein
                         organism = synthetic construct
SEQUENCE: 450
QVQLQESGGG LVQAGGSLRL SCAASGFSSD DYTIGWFRQA PGKEREGIGC IKSSDGTTGY  60
ADSVKGRFTI SSDNAKNTVY LQMNSLKPED TAVYYCAADF NVWSPPICGS IWYGPPPGGM  120
DYWGKGTQVT VSSAAAYPYD VPDYGSHHHH HH                                152

SEQ ID NO: 451           moltype = AA  length = 150
FEATURE                  Location/Qualifiers
REGION                   1..150
                         note = Synthetic polymer.
source                   1..150
                         mol_type = protein
                         organism = synthetic construct
SEQUENCE: 451
QVQLQESGGG LAQAGGSLRL SCAASGFTFD QYTIAWFRQA PGKEREGVSC ISNTDSSTYY  60
ADSVKGRFTI SSDNAKNTVY LQMSSLKPED TAVYYCAADG NVWSPPICGS AGPPPGGMDY  120
WGKGTQVTVS SAAAYPYDVP DYGSHHHHHH                                   150

SEQ ID NO: 452           moltype = AA  length = 144
FEATURE                  Location/Qualifiers
REGION                   1..144
                         note = Synthetic polymer.
source                   1..144
                         mol_type = protein
                         organism = synthetic construct
SEQUENCE: 452
QVQLQESGGG LVQAGGSLRL SCAASGRTFS SYAMAWFRQA PGKEREFVAA IAWSAGSTYY  60
ADSVKGRFAI SRDNAENTVY LQMNSLKPED TAVYYCAARI ITVATMRLDS DYDYWGQGTQ  120
VTVSSAAAYP YDVPDYGSHH HHHH                                         144

SEQ ID NO: 453           moltype = AA  length = 150
FEATURE                  Location/Qualifiers
REGION                   1..150
                         note = Synthetic polymer.
source                   1..150
                         mol_type = protein
                         organism = synthetic construct
SEQUENCE: 453
QVQLQESGGG LVQAGGSLRL SCAASGFAFD GYAIGWFRQA PGKEREGVSC ISSKEGSTYY  60
ADSVKGRFTI SSDNAKNTVY LQMSSLKPED TAVYYCAADG NVWSPPICGS AGPPPGGMDY  120
WGKGTQVTVS SAAAYPYDVP DYGSHHHHHH                                   150

SEQ ID NO: 454           moltype = AA  length = 152
FEATURE                  Location/Qualifiers
REGION                   1..152
                         note = Synthetic polymer.
source                   1..152
                         mol_type = protein
                         organism = synthetic construct
SEQUENCE: 454
QVQLQESGGG LVQAGGSLRL SCAASGFSSD DYTIAWFRRA PGKEREGISC ISSSDGSTGY  60
ADSVKGRFTI TSDSAKNTVY LQMNSLKPED TAVYYCAADS NVWSPPICGR TWYGPPPGGM  120
DYWGKGTQVT VSSAAAYPYD VPDYGSHHHH HH                                152

SEQ ID NO: 455           moltype = AA  length = 152
FEATURE                  Location/Qualifiers
REGION                   1..152
                         note = Synthetic polymer.
source                   1..152
                         mol_type = protein
                         organism = synthetic construct
SEQUENCE: 455
QVQLQESGGG LVQPGGSLRL SCAASGFSSD DYTIGWFRQA PGKEREGISC YSSRDGTTGY  60
ADSVKGRFTI SSDNAKNTVY LQMNSLKPED TAVYYCAADF NVWSPPICGS IWYGPPPGGM  120
AYWGQGTQVT VSSAAAYPYD VPDYGSHHHH HH                                152

SEQ ID NO: 456           moltype = AA  length = 151
FEATURE                  Location/Qualifiers
REGION                   1..151
                         note = Synthetic polymer.
source                   1..151
                         mol_type = protein
                         organism = synthetic construct
SEQUENCE: 456
QVQLQESGGG LVQAGGSLRL SCAASGFTFD DYTIGWFRQA PGKEREGISC ISSDGSTGYA  60
DSVKGRFTIS SDNAKNTVYL QMNSLKPEDT AVYYCAADFN VWSPPICGSN WYGPPPGGMD  120
```

-continued

```
YWGKGTQVTV SSAAAYPYDV PDYGSHHHHH H                                151

SEQ ID NO: 457         moltype = AA  length = 152
FEATURE                Location/Qualifiers
REGION                 1..152
                       note = Synthetic polymer.
source                 1..152
                       mol_type = protein
                       organism = synthetic construct
SEQUENCE: 457
QVQLQESGGG LVQAGGSLRL SCAASGFSSD DYTIGWFRQA PGKEREGISC YSSSDGSTGY  60
ADSVKGRFTI SSDNAKNTVY LQMNSLKPED TAVYYCAADF NVWSPPICGS SWYGPPPGGM  120
DYWGKGTQVT VSSAAAYPYD VPDYGSHHHH HH                               152

SEQ ID NO: 458         moltype = AA  length = 152
FEATURE                Location/Qualifiers
REGION                 1..152
                       note = Synthetic polymer.
source                 1..152
                       mol_type = protein
                       organism = synthetic construct
SEQUENCE: 458
QVQLQESGGG LVQAGGSLRL SCAASGFSSD DYTIGWFRQA PGKEREGISC FSSSDGSTGF  60
ADSVKGRFTI SSDNATNTVY LEMNSLKPED TAVYYCAADF NVWSPPICGS RWYGPPPGGM  120
EYWGKGTQVT VSSAAAYPYD VPDYGSHHHH HH                               152

SEQ ID NO: 459         moltype = AA  length = 150
FEATURE                Location/Qualifiers
REGION                 1..150
                       note = Synthetic polymer.
source                 1..150
                       mol_type = protein
                       organism = synthetic construct
SEQUENCE: 459
QVQLQESGGG LVQAGGSLRL SCATFGFSFD DYAIAWFRQA PGKEREGISC ISNTDSSTFY  60
ADSVKGRFTI SSDNAKNTVH LQMSSLKPED TAVYYCAADG NVWSPPICGS AGPPPGGMDY  120
WGKGTQVTVS SAAAYPYDVP DYGSHHHHHH                                  150

SEQ ID NO: 460         moltype = AA  length = 152
FEATURE                Location/Qualifiers
REGION                 1..152
                       note = Synthetic polymer.
source                 1..152
                       mol_type = protein
                       organism = synthetic construct
SEQUENCE: 460
QVQLQESGGG LVQAGGSLRL SCAASGFSSD DYTIGWFRQA PGKEREGISC YSSSDGSTGF  60
ADSVKGRFTI SSDNAKNTVY LQMNSLRPED TAVYYCAADF NVWSPPICGS RWYGPPPGGM  120
AYWGKGTQVT VSSAAAYPYD VPDYGSHHHH HH                               152

SEQ ID NO: 461         moltype = AA  length = 151
FEATURE                Location/Qualifiers
REGION                 1..151
                       note = Synthetic polymer.
source                 1..151
                       mol_type = protein
                       organism = synthetic construct
SEQUENCE: 461
QVQLQESGGG LVQVGGSLRL SCTISGFTGN DLAIGWFRQA PGKDQREGIS CISNTDSSTY  60
YADSVKGRFT ISSDNAKNTV HLQMSSLKPE DTAVYYCAAD GNVWSPPICG SAGPPPGGMD  120
YWGKGTQVTV SSAAAYPYDV PDYGSHHHHH H                                151

SEQ ID NO: 462         moltype = AA  length = 152
FEATURE                Location/Qualifiers
REGION                 1..152
                       note = Synthetic polymer.
source                 1..152
                       mol_type = protein
                       organism = synthetic construct
SEQUENCE: 462
QVQLQESGGG LVQAGGSLRL SCAASGFSSD DYTIAWFRRA PGKEREGISC ISSSDGSTGY  60
ADSVKGRFTI SSDNAKNTVY LQMTSLKPED TAVYYCAADS NVWSPPICGK TWYGPPPGGM  120
DYWGKGTQVT VSSAAAYPYD VPDYGSHHHH HH                               152

SEQ ID NO: 463         moltype = AA  length = 140
FEATURE                Location/Qualifiers
REGION                 1..140
                       note = Synthetic polymer.
source                 1..140
```

```
                        mol_type = protein
                        organism = synthetic construct
SEQUENCE: 463
QVQLQESGGG LVQAGDSLRL SCAGSEGTLS SYGIGWFRQA PGKEREFVGG INWSGDSTDY  60
ADSVKGRFTI SRDSAKNTVY LQMNSLKPED TAVYYCAAGE SGVWVGGLDY WGQGTQVTVS  120
SAAAYPYDVP DYGSHHHHHH                                              140

SEQ ID NO: 464          moltype = AA  length = 152
FEATURE                 Location/Qualifiers
REGION                  1..152
                        note = Synthetic polymer.
source                  1..152
                        mol_type = protein
                        organism = synthetic construct
SEQUENCE: 464
QVQLQESGGG LVQAGGSLRL SCAASGFSSD DYTIAWFRRA PGKEREGISC FSSSDGSAGY  60
ADSVKGRFTV SSDNAKNTVY LQMNSLKPED TAVYYCAADS NVWSPPICGS TWYGPPPGGM  120
AYWGKGTQVT VSSAAAYPYD VPDYGSHHHH HH                                152

SEQ ID NO: 465          moltype = AA  length = 150
FEATURE                 Location/Qualifiers
REGION                  1..150
                        note = Synthetic polymer.
source                  1..150
                        mol_type = protein
                        organism = synthetic construct
SEQUENCE: 465
QVQLQESGGG LVQAGGSLRL SCATSGFTFD DYAIAWFRQA PGKEREGVSC ISNTDSSTYY  60
ADSVKGRFTI SSDNAKNTVY LQMSSLKPED TAVYYCAADG NVWSPPICGS AGPPPGGMDY  120
WGKGTQVTVS SAAAYPYDVP DYGSHHHHHH                                   150

SEQ ID NO: 466          moltype = AA  length = 152
FEATURE                 Location/Qualifiers
REGION                  1..152
                        note = Synthetic polymer.
source                  1..152
                        mol_type = protein
                        organism = synthetic construct
SEQUENCE: 466
QVQLQESGGG LVQAGGSLRL SCEVSGLSSD DYTIGWFRQA PGKEREGFSC FSTRDGNAGY  60
ADSVKGRFTI SSDNAKNTVY LQMNNLKPED TAVYYCAADF NVWSPPICGS RWYGPPPGGM  120
DYWGKGTQVT VSSAAAYPYD VPDYGSHHHH HH                                152

SEQ ID NO: 467          moltype = AA  length = 152
FEATURE                 Location/Qualifiers
REGION                  1..152
                        note = Synthetic polymer.
source                  1..152
                        mol_type = protein
                        organism = synthetic construct
SEQUENCE: 467
QVQLQESGGG LVQAGGSLRL SCEVSGLSSD DYTIGWFRQA PGKKREGFSC FSSRDGSTGY  60
ADSVKGRFTI SSDNAKNTVY LQMNSLKPED TAVYYCAADF NVWSPPICGS RWYGPPPGGM  120
DYWGKGTQVT VSSAAAYPYD VPDYGSHHHH HH                                152

SEQ ID NO: 468          moltype = AA  length = 152
FEATURE                 Location/Qualifiers
REGION                  1..152
                        note = Synthetic polymer.
source                  1..152
                        mol_type = protein
                        organism = synthetic construct
SEQUENCE: 468
QVQLQESGGG LVQAGGSLRL SCAASGFSSD DYTIGWFRQA PGKEREGFSC FSSRDGSTGY  60
ADSVKGRFTI SSDNAKNTVY LQMNSLKPED TAVYYCAADF NVWSPPICGS RWYGPPPGGM  120
DYWGKGTQVT VSSAAAYPYD VPDYGSHHHH HH                                152

SEQ ID NO: 469          moltype = AA  length = 151
FEATURE                 Location/Qualifiers
REGION                  1..151
                        note = Synthetic polymer.
source                  1..151
                        mol_type = protein
                        organism = synthetic construct
SEQUENCE: 469
QVQLQESGGG LVQAGGSLRL SCAASGFSFD DYTIGWFRQV PGKEREGISC ISSDGSTGYA  60
DSVKGRFTIS SDNAKNTVYL QINSLKPEDT AVYYCAADFN VWSPPICGSI WYGPPPGGMD  120
YWGKGTQVTV SSAAAYPYDV PDYGSHHHHH H                                 151
```

-continued

```
SEQ ID NO: 470          moltype = AA  length = 150
FEATURE                 Location/Qualifiers
REGION                  1..150
                        note = Synthetic polymer.
source                  1..150
                        mol_type = protein
                        organism = synthetic construct
SEQUENCE: 470
QVQLQESGGG LVQAGGSLRL SCATFGFTFD DYAIAWFRQA PGKEREGISC ISNTDSSTYY  60
ADSVKGRFTI SSDNAKNTVH LQMSSLKPED TAVYYCAADG NVWSPPICGS AGPPPGGMDY  120
WGKGTQVTVS SAAAYPYDVP DYGSHHHHHH                                  150

SEQ ID NO: 471          moltype = AA  length = 150
FEATURE                 Location/Qualifiers
REGION                  1..150
                        note = Synthetic polymer.
SITE                    19
                        note = misc_feature - Xaa can be any naturally occurring
                         amino acid
source                  1..150
                        mol_type = protein
                        organism = synthetic construct
SEQUENCE: 471
QVQLQESGGG LVQAGGSLXL SCAASGFTFD DYAIGWFRQA PGKEREGVSC ISSPDGSTYY  60
ADSVKGRFTI SSDNAKNTVY LQMNSLKPED TAVYYCAADF NVWSPPICGS VGPPPGGMDY  120
WGKGTQVTVS SAAAYPYDVP DYGSHHHHHH                                  150

SEQ ID NO: 472          moltype = AA  length = 152
FEATURE                 Location/Qualifiers
REGION                  1..152
                        note = Synthetic polymer.
source                  1..152
                        mol_type = protein
                        organism = synthetic construct
SEQUENCE: 472
QVQLQESGGG LVQAGASLRL SCKASGFTFG DYTIGWFRQA PGKEREGISC YSSSDGNTGY  60
ADSVKGRFTI SSDNAKNTVY LQMNSLRPED TAVYYCAADF NVWSPPICGS SWYGPPPGGM  120
AYWGKGTQVT VSSAAAYPYD VPDYGSHHHH HH                               152

SEQ ID NO: 473          moltype = AA  length = 140
FEATURE                 Location/Qualifiers
REGION                  1..140
                        note = Synthetic polymer.
source                  1..140
                        mol_type = protein
                        organism = synthetic construct
SEQUENCE: 473
QVQLQESGGG LVQAGDSLRL SCAGSEGTFS SYGIGWFRQA PGKEREFVGG INWSGDSTDY  60
ADSVKGRFTI SRDNAKNTVY LQMNSLKPED TAVYYCAAGE SGVWVGGLDY WGQGTQVTVS  120
SAAAYPYDVP DYGSHHHHHH                                             140

SEQ ID NO: 474          moltype = AA  length = 152
FEATURE                 Location/Qualifiers
REGION                  1..152
                        note = Synthetic polymer.
source                  1..152
                        mol_type = protein
                        organism = synthetic construct
SEQUENCE: 474
QVQLQESGGG LVQAGGSLRL SCAASGFSSD DYTIGWFRQA PGKEREGISC FSSSDGSTGF  60
ADSVKGRFTI SSDNATNTVY LQMNSLKPED TAVYYCAADF NVWSPPICGS SWYGPPPGGM  120
EYWGKGTQVT VSSAAAYPYD VPDYGSHHHH HH                               152

SEQ ID NO: 475          moltype = AA  length = 150
FEATURE                 Location/Qualifiers
REGION                  1..150
                        note = Synthetic polymer.
source                  1..150
                        mol_type = protein
                        organism = synthetic construct
SEQUENCE: 475
QVQLQESGGG LVQAGDSLRL SCTASGVSIG DYNIGWFRQA PGKEREGVSC ISSGDGTTYY  60
TDSVKGRFTI STDNAKNTVY LQMNSLKPED TAVYYCAADG NVWSPPICGS AGPPPGGMDY  120
WGKGTQVTVS SAAAYPYDVP DYGSHHHHHH                                  150

SEQ ID NO: 476          moltype = AA  length = 152
FEATURE                 Location/Qualifiers
REGION                  1..152
                        note = Synthetic polymer.
```

```
source                  1..152
                        mol_type = protein
                        organism = synthetic construct
SEQUENCE: 476
QVQLQESGGG LVQAGGSLRL SCAASGFTFD DYTIAWFRQA PGGKEREGIS CISSDGSTGY  60
ADSVKGRFTI SSDNAKNMVY LQMNSLKPED TALYYCAADF NVWSPPICSS NWYGPPPRGM  120
DYWGKGTQVT VSSAAAYPYD VPDYGSHHHH HH                                152

SEQ ID NO: 477          moltype = AA  length = 151
FEATURE                 Location/Qualifiers
REGION                  1..151
                        note = Synthetic polymer.
source                  1..151
                        mol_type = protein
                        organism = synthetic construct
SEQUENCE: 477
QVQLQESGGG LVQAGGSLRL SCAASGFTFD DYTIAWFRQA PGKEREGISC ISSDGSTGYA  60
DSVRGRFTIS SDNAKNTVYL QMNSLKPEDT AVYYCAADFN VWSPPICGSI WYGPPPRGMD  120
YWGKGTQVTV SSAAAYPYDV PDYGSHHHHH H                                 151

SEQ ID NO: 478          moltype = AA  length = 118
FEATURE                 Location/Qualifiers
REGION                  1..118
                        note = Synthetic polymer.
source                  1..118
                        mol_type = protein
                        organism = synthetic construct
SEQUENCE: 478
EVQLVESGGG LVQPGGSLRL SCAASGFNIK DTYIHWVRQA PGKGLEWVAR IDPANDNTLY  60
ASKFQGRATI SADTSKNTAY LQMNSLRAED TAVYYCGRGY GYYVFDHWGQ GTLVTVSS    118

SEQ ID NO: 479          moltype = AA  length = 118
FEATURE                 Location/Qualifiers
REGION                  1..118
                        note = Synthetic polymer.
source                  1..118
                        mol_type = protein
                        organism = synthetic construct
SEQUENCE: 479
QVQLVQSGAE VKKPGATVKH SCKVSGFNHK DTYIHWVQQA PGKGLEWMGR HDPANDNTLY  60
ASKFQGRVTH TADTSTDTAY MELSSLRSED TAVYYCARGY GYYVFDHWGQ GTLVTVSS    118

SEQ ID NO: 480          moltype = AA  length = 107
FEATURE                 Location/Qualifiers
REGION                  1..107
                        note = Synthetic polymer.
source                  1..107
                        mol_type = protein
                        organism = synthetic construct
SEQUENCE: 480
DVQITQSPSS LSASVGDRVT ITCRTSRSIS QYLAWYQQKP GKVPKLLIYS GSTLQSGVPS  60
RFSGSGSGTD FTLTISSLQP EDVATYYCQQ HNENPLTFGG GTKVEIK                107

SEQ ID NO: 481          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 481
GFSMDYYAIA                                                         10

SEQ ID NO: 482          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 482
GFSMDYYAIA                                                         10

SEQ ID NO: 483          moltype = AA  length = 10
FEATURE                 Location/Qualifiers
REGION                  1..10
                        note = Synthetic polymer.
source                  1..10
                        mol_type = protein
```

```
                        organism = synthetic construct
SEQUENCE: 483
GFSVDYYAIA                                                                  10

SEQ ID NO: 484          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 484
GFSMDYYAIA                                                                  10

SEQ ID NO: 485          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 485
GGFNRVSYMG                                                                  10

SEQ ID NO: 486          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 486
GGFNRVSYMG                                                                  10

SEQ ID NO: 487          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 487
GIIKSINFMG                                                                  10

SEQ ID NO: 488          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 488
GFILDYYGIG                                                                  10

SEQ ID NO: 489          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 489
GLSLDYDGVG                                                                  10

SEQ ID NO: 490          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 490
GFILDYYGIG                                                                  10

SEQ ID NO: 491          moltype = AA  length = 10
FEATURE                 Location/Qualifiers
REGION                  1..10
                        note = Synthetic polymer.
source                  1..10
```

```
                        mol_type = protein
                        organism = synthetic construct
SEQUENCE: 491
GRTFSSLGMG                                                          10

SEQ ID NO: 492          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 492
GRTFSSLGMG                                                          10

SEQ ID NO: 493          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 493
GFAFGSYDMG                                                          10

SEQ ID NO: 494          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 494
GFSFGNNDMS                                                          10

SEQ ID NO: 495          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 495
CITGSDFMVD T                                                        11

SEQ ID NO: 496          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 496
CITGSDFMVD T                                                        11

SEQ ID NO: 497          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 497
CITGSDFMVD T                                                        11

SEQ ID NO: 498          moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 498
CITGSDFMVD T                                                        11

SEQ ID NO: 499          moltype = AA  length = 8
FEATURE                 Location/Qualifiers
REGION                  1..8
                        note = Synthetic polymer.
```

```
source                  1..8
                        mol_type = protein
                        organism = synthetic construct
SEQUENCE: 499
SVTSGGEI                                                        8

SEQ ID NO: 500          moltype = AA  length = 8
FEATURE                 Location/Qualifiers
REGION                  1..8
                        note = Synthetic polymer.
source                  1..8
                        mol_type = protein
                        organism = synthetic construct
SEQUENCE: 500
SVTSGGEI                                                        8

SEQ ID NO: 501          moltype = AA  length = 8
FEATURE                 Location/Qualifiers
REGION                  1..8
                        note = Synthetic polymer.
source                  1..8
                        mol_type = protein
                        organism = synthetic construct
SEQUENCE: 501
STTSDGRT                                                        8

SEQ ID NO: 502          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 502
CISSSDGST                                                       9

SEQ ID NO: 503          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 503
CISSSDGST                                                       9

SEQ ID NO: 504          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 504
CISSSDGST                                                       9

SEQ ID NO: 505          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 505
AIAWNGAST                                                       9

SEQ ID NO: 506          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 506
AIAWNGAST                                                       9

SEQ ID NO: 507          moltype = AA  length = 9
FEATURE                 Location/Qualifiers
REGION                  1..9
```

```
                        note = Synthetic polymer.
source                  1..9
                        mol_type = protein
                        organism = synthetic construct
SEQUENCE: 507
GINSGGRIT                                                     9

SEQ ID NO: 508          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 508
AINSGGGST                                                     9

SEQ ID NO: 509          moltype = AA  length = 19
FEATURE                 Location/Qualifiers
REGION                  1..19
                        note = Synthetic polymer.
source                  1..19
                        mol_type = protein
                        organism = synthetic construct
SEQUENCE: 509
AVRSTANTLC PSHYSVMDY                                          19

SEQ ID NO: 510          moltype = AA  length = 19
FEATURE                 Location/Qualifiers
REGION                  1..19
                        note = Synthetic polymer.
source                  1..19
                        mol_type = protein
                        organism = synthetic construct
SEQUENCE: 510
AVRSTANTLC PSHYSIMDY                                          19

SEQ ID NO: 511          moltype = AA  length = 19
FEATURE                 Location/Qualifiers
REGION                  1..19
                        note = Synthetic polymer.
source                  1..19
                        mol_type = protein
                        organism = synthetic construct
SEQUENCE: 511
AVRSTANTLC PSHYSVMDY                                          19

SEQ ID NO: 512          moltype = AA  length = 14
FEATURE                 Location/Qualifiers
REGION                  1..14
                        note = Synthetic polymer.
source                  1..14
                        mol_type = protein
                        organism = synthetic construct
SEQUENCE: 512
NADIWVSDAR MYNY                                               14

SEQ ID NO: 513          moltype = AA  length = 14
FEATURE                 Location/Qualifiers
REGION                  1..14
                        note = Synthetic polymer.
source                  1..14
                        mol_type = protein
                        organism = synthetic construct
SEQUENCE: 513
NADIWVSDAR MYNY                                               14

SEQ ID NO: 514          moltype = AA  length = 14
FEATURE                 Location/Qualifiers
REGION                  1..14
                        note = Synthetic polymer.
source                  1..14
                        mol_type = protein
                        organism = synthetic construct
SEQUENCE: 514
NADIWLPSDR MYNY                                               14

SEQ ID NO: 515          moltype = AA  length = 13
FEATURE                 Location/Qualifiers
```

```
REGION                  1..13
                        note = Synthetic polymer.
source                  1..13
                        mol_type = protein
                        organism = synthetic construct
SEQUENCE: 515
ATATLCDGGI WGY                                                    13

SEQ ID NO: 516          moltype = AA  length = 13
FEATURE                 Location/Qualifiers
REGION                  1..13
                        note = Synthetic polymer.
source                  1..13
                        mol_type = protein
                        organism = synthetic construct
SEQUENCE: 516
ATATLCDGGI WGY                                                    13

SEQ ID NO: 517          moltype = AA  length = 13
FEATURE                 Location/Qualifiers
REGION                  1..13
                        note = Synthetic polymer.
source                  1..13
                        mol_type = protein
                        organism = synthetic construct
SEQUENCE: 517
ATATLCDGGI WGY                                                    13

SEQ ID NO: 518          moltype = AA  length = 16
FEATURE                 Location/Qualifiers
REGION                  1..16
                        note = Synthetic polymer.
source                  1..16
                        mol_type = protein
                        organism = synthetic construct
SEQUENCE: 518
AASGLGSVWT ANEYDY                                                 16

SEQ ID NO: 519          moltype = AA  length = 16
FEATURE                 Location/Qualifiers
REGION                  1..16
                        note = Synthetic polymer.
source                  1..16
                        mol_type = protein
                        organism = synthetic construct
SEQUENCE: 519
AASGLGSVWT ANEYDY                                                 16

SEQ ID NO: 520          moltype = AA  length = 15
FEATURE                 Location/Qualifiers
REGION                  1..15
                        note = Synthetic polymer.
source                  1..15
                        mol_type = protein
                        organism = synthetic construct
SEQUENCE: 520
AQGDRSSWHY YGMDY                                                  15

SEQ ID NO: 521          moltype = AA  length = 13
FEATURE                 Location/Qualifiers
REGION                  1..13
                        note = Synthetic polymer.
source                  1..13
                        mol_type = protein
                        organism = synthetic construct
SEQUENCE: 521
ATKSDPMTNE YDL                                                    13

SEQ ID NO: 522          moltype = AA  length = 147
FEATURE                 Location/Qualifiers
REGION                  1..147
                        note = Synthetic polymer.
source                  1..147
                        mol_type = protein
                        organism = synthetic construct
SEQUENCE: 522
QVQLQESGGG LVQPGGSLRL SCAASGFSMD YYAIAWFRQA PGKEREEISC ITGSDFMVDT  60
YYVASVKGRF TISRDNAENT AYLQMNNLKP EDTGVYFCAV RSTANTLCPS HYSVMDYWGK  120
GTQVTVSSAA AYPYDVPDYG SHHHHHH                                     147
```

```
SEQ ID NO: 523         moltype = AA  length = 147
FEATURE                Location/Qualifiers
REGION                 1..147
                       note = Synthetic polymer.
source                 1..147
                       mol_type = protein
                       organism = synthetic construct
SEQUENCE: 523
QVQLQESGGG LVQAGGSLRL SCAASGFSMD YYAIAWFRQA PGKEREEISC ITGSDFMVDT  60
YYVASVKGRF TISRDNAENT AYLQMNNLKP EDTGVYFCAV RSTANTLCPS HYSVMDYWGK  120
GTQVTVSSAA AYPYDVPDYG SHHHHHH                                      147

SEQ ID NO: 524         moltype = AA  length = 146
FEATURE                Location/Qualifiers
REGION                 1..146
                       note = Synthetic polymer.
source                 1..146
                       mol_type = protein
                       organism = synthetic construct
SEQUENCE: 524
QVQLQESGGG LVQPGGSLRL SCSASGFSVD YYAIAWFRQA PGKEREEISC ITGSDFMVDT  60
YYVASVKGRF TISRDNAKNT AYLQMNSLKP EDTGVYFCAV RSTANTLCPS HYSIMDYWGK  120
GTQVTVSSAA AYPYDVPDYG SHHHHH                                       146

SEQ ID NO: 525         moltype = AA  length = 147
FEATURE                Location/Qualifiers
REGION                 1..147
                       note = Synthetic polymer.
source                 1..147
                       mol_type = protein
                       organism = synthetic construct
SEQUENCE: 525
QVQLQESGGG LVQPGGSLRL SCSASGFSMD YYAIAWFRQA PGKEREEISC ITGSDFMVDT  60
YYVASVKGRF TISRDNAKNT AHLQMNSLKP EDTGVYFCAV RSTANTLCPS HYSVMDYWGK  120
GTQVTVSSAA AYPYDVPDYG SHHHHHH                                      147

SEQ ID NO: 526         moltype = AA  length = 139
FEATURE                Location/Qualifiers
REGION                 1..139
                       note = Synthetic polymer.
source                 1..139
                       mol_type = protein
                       organism = synthetic construct
SEQUENCE: 526
QVQLQESGGG LVQAGGSLRL SCAASGGFNR VSYMGWYRQA PGTKRELVAS VTSGGEITIA  60
DSVKGRFTVS RDNSKNTLYL QMNGLKPEDG ATYWCNADIW VSDARMYNYW GQGTQVTVSS  120
AAAYPYDVPD YGSHHHHHH                                               139

SEQ ID NO: 527         moltype = AA  length = 139
FEATURE                Location/Qualifiers
REGION                 1..139
                       note = Synthetic polymer.
source                 1..139
                       mol_type = protein
                       organism = synthetic construct
SEQUENCE: 527
QVQLQESGGG LVQTGESLRL SCAASGGFNR VSYMGWYRQA PGSKRELVAS VTSGGEITVA  60
DSVKGRFTVS RDNNKNTLYL QMNGLKPEDG ATYWCNADIW VSDARMYNYW GQGTQVTVSS  120
AAAYPYDVPD YGSHHHHHH                                               139

SEQ ID NO: 528         moltype = AA  length = 139
FEATURE                Location/Qualifiers
REGION                 1..139
                       note = Synthetic polymer.
source                 1..139
                       mol_type = protein
                       organism = synthetic construct
SEQUENCE: 528
QVQLQESGGG LVQTGESLRL SCAASGIIKS INFMGWYRQP PGTKRELVAS TTSDGRTTVA  60
DSVKGRFTIS RDNAKNTIYL EMSSLKPEDT ATYWCNADIW LPSDRMYNYW GQGTQVTVSS  120
AAAYPYDVPD YGSHHHHHH                                               139

SEQ ID NO: 529         moltype = AA  length = 139
FEATURE                Location/Qualifiers
REGION                 1..139
                       note = Synthetic polymer.
source                 1..139
                       mol_type = protein
```

```
                         organism = synthetic construct
SEQUENCE: 529
QVQLQESGGG LVQAGGSLRL SCAVSGFILD YYGIGWFRQA PGKEREAVSC ISSSDGSTYY  60
ADSVKGRFTI SRDNALNTLY LQMNSLKPED TAVYHCATAT LCDGGIWGYW GQGTQVTVSS  120
AAAYPYDVPD YGSHHHHHH                                               139

SEQ ID NO: 530           moltype = AA  length = 139
FEATURE                  Location/Qualifiers
REGION                   1..139
                         note = Synthetic polymer.
source                   1..139
                         mol_type = protein
                         organism = synthetic construct
SEQUENCE: 530
QVQLQESGGG LAQAGGSLRL SCEGSGLSLD YDGVGWFRQA PGKEREAVSC ISSSDGSTYY  60
ADSVKGRFTI SRGNALNTLY LQMNSLKPED TAVYYCATAT LCDGGIWGYW GQGTQVTVSS  120
AAAYPYDVPD YGSHHHHHH                                               139

SEQ ID NO: 531           moltype = AA  length = 139
FEATURE                  Location/Qualifiers
REGION                   1..139
                         note = Synthetic polymer.
source                   1..139
                         mol_type = protein
                         organism = synthetic construct
SEQUENCE: 531
QVQLQESGGG SVQPGGSLRL SCAVSGFILD YYGIGWFRQA PGKEREAVSC ISSSDGSTYY  60
ADSVKGRFTI SRDNALNTLY LQMNSLKPED TAVYYCATAT LCDGGIWGYW GQGTQVTVSS  120
AAAYPYDVPD YGSHHHHHH                                               139

SEQ ID NO: 532           moltype = AA  length = 143
FEATURE                  Location/Qualifiers
REGION                   1..143
                         note = Synthetic polymer.
source                   1..143
                         mol_type = protein
                         organism = synthetic construct
SEQUENCE: 532
QVQLQESGGG SVQAGDSLRL SCTASGRTFS SLGMGWFRQA PGKEREFVSA IAWNGASTYY  60
TESVKGRFTI SRDDAKNTVY LQMNSLKPTD TAVYFCAASG LGSVVVTANE YDYWGQGTQV  120
TVSSAAAYPY DVPDYGSHHH HHH                                          143

SEQ ID NO: 533           moltype = AA  length = 143
FEATURE                  Location/Qualifiers
REGION                   1..143
                         note = Synthetic polymer.
source                   1..143
                         mol_type = protein
                         organism = synthetic construct
SEQUENCE: 533
QVQLQESGGG SVQPGKSLRL SCAASGRTFS SLGMGWFRQA PGKEREFVSA IAWNGASTYY  60
TESVKGRFTI SRDDAKNTVY LQMNSLKPTD TAVYFCAASG LGSVVVTANE YDYWGQGTQV  120
TVSSAAAYPY DVPDYGSHHH HHH                                          143

SEQ ID NO: 534           moltype = AA  length = 141
FEATURE                  Location/Qualifiers
REGION                   1..141
                         note = Synthetic polymer.
source                   1..141
                         mol_type = protein
                         organism = synthetic construct
SEQUENCE: 534
QVQLQESGGG LVQPGGSLRL SCTTSGFAFG SYDMGWVRQA PGKGPEWVSG INSGGRITDY  60
ADSVTGRFTI SRDNAKNTLY LQMNSLKPED TAVYYCAQGD RSSWHYYGMD YWGKGTQVTV  120
SSAAAYPYDV PDYGSHHHHH H                                            141

SEQ ID NO: 535           moltype = AA  length = 139
FEATURE                  Location/Qualifiers
REGION                   1..139
                         note = Synthetic polymer.
SITE                     112
                         note = misc_feature - Xaa can be any naturally occurring
                          amino acid
source                   1..139
                         mol_type = protein
                         organism = synthetic construct
SEQUENCE: 535
QVQLQESGGG LVQPGGSLRL SCAASGFSFG NNDMSWVRQA PGKGPEWVSA INSGGGSTYY  60
ADSVKGRFTI SRDNAKNTLY LQMNSLKPED TAVYYCATKS DPMTNEYDLW GXGTQVTVSS  120
```

```
AAAYPYDVPD YGSHHHHHH                                         139

SEQ ID NO: 536          moltype = AA  length = 447
FEATURE                 Location/Qualifiers
REGION                  1..447
                        note = Synthetic polymer.
source                  1..447
                        mol_type = protein
                        organism = synthetic construct
SEQUENCE: 536
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                 447

SEQ ID NO: 537          moltype = AA  length = 218
FEATURE                 Location/Qualifiers
REGION                  1..218
                        note = Synthetic polymer.
source                  1..218
                        mol_type = protein
                        organism = synthetic construct
SEQUENCE: 537
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                      218

SEQ ID NO: 538          moltype = AA  length = 440
FEATURE                 Location/Qualifiers
REGION                  1..440
                        note = Synthetic polymer.
source                  1..440
                        mol_type = protein
                        organism = synthetic construct
SEQUENCE: 538
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSLGK                                         440

SEQ ID NO: 539          moltype = AA  length = 214
FEATURE                 Location/Qualifiers
REGION                  1..214
                        note = Synthetic polymer.
source                  1..214
                        mol_type = protein
                        organism = synthetic construct
SEQUENCE: 539
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                          214

SEQ ID NO: 540          moltype = AA  length = 106
FEATURE                 Location/Qualifiers
REGION                  1..106
                        note = Synthetic polymer.
source                  1..106
                        mol_type = protein
                        organism = synthetic construct
SEQUENCE: 540
EIVLTQSPSS LSASVGDRVT ITCSARSSVS YMHWYQQKPG KAPKLLIYRT SNLASGVPSR  60
FSGSGSGTDF TLTINSLQPE DFATYYCQQR SSFPLTFGGG TKLEIK              106

SEQ ID NO: 541          moltype = AA  length = 106
FEATURE                 Location/Qualifiers
REGION                  1..106
                        note = Synthetic polymer.
source                  1..106
                        mol_type = protein
```

```
                         organism = synthetic construct
SEQUENCE: 541
EIVLTQSPSS LSASVGDRVT ITCSARSSVS YMHWFQQKPG KAPKLWIYRT SNLASGVPSR  60
FSGSGSGTDY TLTINSLQPE DFATYYCQQR SSFPLTFGGG TKLEIK                 106

SEQ ID NO: 542           moltype = AA  length = 106
FEATURE                  Location/Qualifiers
REGION                   1..106
                         note = Synthetic polymer.
source                   1..106
                         mol_type = protein
                         organism = synthetic construct
SEQUENCE: 542
EIVLTQSPSS LSASVGDRVT ITCSARSSVS YMHWFQQKPG KAPKLWIYRT SNLASGVPSR  60
FSGSGSGTDY CLTINSLQPE DFATYYCQQR SSFPLTFGGG TKLEIK                 106

SEQ ID NO: 543           moltype = AA  length = 106
FEATURE                  Location/Qualifiers
REGION                   1..106
                         note = Synthetic polymer.
source                   1..106
                         mol_type = protein
                         organism = synthetic construct
SEQUENCE: 543
EIVLTQSPSS LSASVGDRVT ITCSARSSVS YMHWFQQKPG KAPKLWIYRT SNLASGVPSR  60
FSGSGSGTSY CLTINSLQPE DFATYYCQQR SSFPLTFGGG TKLEIK                 106

SEQ ID NO: 544           moltype = AA  length = 117
FEATURE                  Location/Qualifiers
REGION                   1..117
                         note = Synthetic polymer.
source                   1..117
                         mol_type = protein
                         organism = synthetic construct
SEQUENCE: 544
QVQLVQSGSE LKKPGASVKI SCKASGYSFS NYGMNWVRQA PGQGLQWMGW INTDSGESTY  60
AEEFKGRFVF SLDTSVSTAY LQITSLTAED TGMYFCAKVG YDALDYWGQG TLVTVSS     117

SEQ ID NO: 545           moltype = AA  length = 117
FEATURE                  Location/Qualifiers
REGION                   1..117
                         note = Synthetic polymer.
source                   1..117
                         mol_type = protein
                         organism = synthetic construct
SEQUENCE: 545
QVQLVQSGSE LKKPGASVKI SCKASGYTFT NYGMNWVRQA PGQGLQWMGW INTDSGESTY  60
AEEFKGRFVF SLDTSVSTAY LQITSLTAED TGMYFCAKVG YDALDYWGQG TLVTVSS     117

SEQ ID NO: 546           moltype = AA  length = 117
FEATURE                  Location/Qualifiers
REGION                   1..117
                         note = Synthetic polymer.
source                   1..117
                         mol_type = protein
                         organism = synthetic construct
SEQUENCE: 546
QVQLVQSGSE LKKPGASVKI SCKASGYTFT NYGMNWVRQA PGQGLQWMGW INTDSGESTY  60
AEEFKGRFVF SLDTSVNTAY LQITSLTAED TGMYFCVRVG YDALDYWGQG TLVTVSS     117

SEQ ID NO: 547           moltype = AA  length = 117
FEATURE                  Location/Qualifiers
REGION                   1..117
                         note = Synthetic polymer.
source                   1..117
                         mol_type = protein
                         organism = synthetic construct
SEQUENCE: 547
QIQLVQSGSE LKKPGASVKI SCKASGYTFT NYGMNWVRQA PGQGLQWMGW INTDSGESTY  60
AEEFKGRFVF SLDTSVNTAY LQITSLTAED TGMYFCVRVG YDALDYWGQG TLVTVSS     117

SEQ ID NO: 548           moltype = AA  length = 117
FEATURE                  Location/Qualifiers
REGION                   1..117
                         note = Synthetic polymer.
source                   1..117
                         mol_type = protein
                         organism = synthetic construct
SEQUENCE: 548
```

```
QIQLVQSGSE LKKPGASVKI SCKASGYTFT NYGMNWVKQA PGQGLKWMGW INTDSGESTY  60
AEEFKGRFAF SLDTSVNTAY LQITSLNAED TGMYFCVRVG YDALDYWGQG TLVTVSS     117

SEQ ID NO: 549         moltype = AA  length = 106
FEATURE                Location/Qualifiers
REGION                 1..106
                       note = Synthetic polymer.
source                 1..106
                       mol_type = protein
                       organism = synthetic construct
SEQUENCE: 549
EIVLTQSPSS LSASVGDRVT ITCSARSSVS YMHWFQQKPG KAPKLWIYRT SNLASGVPSR  60
FSGSGSGTSY CLTINSLQPE DFATYYCQQR SSFPLTFGGG TKLEIK                106

SEQ ID NO: 550         moltype = AA  length = 117
FEATURE                Location/Qualifiers
REGION                 1..117
                       note = Synthetic polymer.
source                 1..117
                       mol_type = protein
                       organism = synthetic construct
SEQUENCE: 550
QVQLVQSGSE LKKPGASVKI SCKASGYTFT NYGMNWVRQA PGQGLQWMGW INTDSGESTY  60
AEEFKGRFVF SLDTSVNTAY LQITSLTAED TGMYFCVRVG YDALDYWGQG TLVTVSS     117

SEQ ID NO: 551         moltype = AA  length = 254
FEATURE                Location/Qualifiers
REGION                 1..254
                       note = Synthetic polymer.
source                 1..254
                       mol_type = protein
                       organism = synthetic construct
SEQUENCE: 551
LFTVTVPKEL YIIEHGSNVT LECNFDTGSH VNLGAITASL QKVENDTSPH RERATLLEEQ  60
LPLGKASFHI PQVQVRDEGQ YQCIIIYGVA WDYKYLTLKV KASYRKINTH ILKVPETDEV  120
ELTCQATGYP LAEVSWPNVS VPANTSHSRT PEGLYQVTSV LRLKPPPGRN FSCVFWNTHV  180
RELTLASIDL QSQMEPRTHP TWLLHIFIPF CITAFTFIAT VIALRKQLCQ KLYSSKDTTK  240
RPVTTTKREV NSAI                                                   254

SEQ ID NO: 552         moltype = AA  length = 453
FEATURE                Location/Qualifiers
REGION                 1..453
                       note = Synthetic polymer.
source                 1..453
                       mol_type = protein
                       organism = synthetic construct
SEQUENCE: 552
MIFLLLMLSL ELQLHQTAAL FTVTVPKELY IIEHGSNVTL ECNFDTGSHV NLGAITASLQ  60
KVENDTSPHR ERATLLEEQL PLGKASFHIP QVQVRDEGQY QCIIIYGVAW DYKYLTLKVK  120
ASYRKINTHI LKVPETDEVE LTCQATGYPL AEVSWPNVSV PANTSHSRTP EGLYQVTSVL  180
RLKPPPGRNF SCVFWNTHVR ELTLASIDLQ SQMEPRTHPT WEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                               453

SEQ ID NO: 553         moltype = AA  length = 29
FEATURE                Location/Qualifiers
REGION                 1..29
                       note = Synthetic polymer.
source                 1..29
                       mol_type = protein
                       organism = synthetic construct
SEQUENCE: 553
SNTSESFKSN TSESFFRVTQ LAPKAQIKE                                   29

SEQ ID NO: 554         moltype = AA  length = 119
FEATURE                Location/Qualifiers
REGION                 1..119
                       note = Synthetic polymer.
source                 1..119
                       mol_type = protein
                       organism = synthetic construct
SEQUENCE: 554
EVQLQQSGPV LVKPGASVKM SCKASGYTFT DYYMNWVKQS HGKSLEWIGN INPYNGGTTY  60
NQKFKGKATL TVDKSSRTAY MEINSLTSED SAVYYCARGR IYDGSLDYWG QGTALTVSS   119

SEQ ID NO: 555         moltype = AA  length = 106
FEATURE                Location/Qualifiers
```

```
REGION                  1..106
                        note = Synthetic polymer.
source                  1..106
                        mol_type = protein
                        organism = synthetic construct
SEQUENCE: 555
DIQMTQFPSS LCASQGGKVT VTCKASQDIN NYMAWYQHKP GKGPRLLIHY TSTLLSGIPS  60
RFSGSGSGRD YSFSISNLEP EDIATYYCLQ YDNLWTFGGG TKLEIK                106

SEQ ID NO: 556          moltype = AA  length = 116
FEATURE                 Location/Qualifiers
REGION                  1..116
                        note = Synthetic polymer.
source                  1..116
                        mol_type = protein
                        organism = synthetic construct
SEQUENCE: 556
QVQLQQSGAE LAKPGASVRL SCKASGYTFT NYWMHWVKQR PGQGLEWIGH INPSSGFTTY  60
NQNFKDKATL TADKSSNTAY MQLSSLTYED SAVYFCARED YDVDYWGQGT TLTVSS      116

SEQ ID NO: 557          moltype = AA  length = 107
FEATURE                 Location/Qualifiers
REGION                  1..107
                        note = Synthetic polymer.
source                  1..107
                        mol_type = protein
                        organism = synthetic construct
SEQUENCE: 557
DIVMTQSQKF MSTSVGDRVS VTCKASQSVD TNVAWYQQKP GQSPKALIFS ASYRYSGVPD  60
RFTGSGSGTD FTLTINSVQS EDLAEYFCQQ YNSYPYTFGS GTKLEIK               107

SEQ ID NO: 558          moltype = AA  length = 122
FEATURE                 Location/Qualifiers
REGION                  1..122
                        note = Synthetic polymer.
source                  1..122
                        mol_type = protein
                        organism = synthetic construct
SEQUENCE: 558
EVQLVESGGG LVKPGGSLKL SCAASGFTFS DYGMHWVRQA PEKGLEWVAY ISSGSYTIYY  60
TDTVKGRFTI SRDNAKNTLF LQMTSLRSED TAMYYCARRG YGSFYEYYFD YWGQGTTLTV  120
SS                                                                122

SEQ ID NO: 559          moltype = AA  length = 106
FEATURE                 Location/Qualifiers
REGION                  1..106
                        note = Synthetic polymer.
source                  1..106
                        mol_type = protein
                        organism = synthetic construct
SEQUENCE: 559
QIVLTQSPAL MSASPGEKVT MTCSASSSVS YMYWYQQKPR SSPKPWIYLT SNLASGVPAR  60
FSGSGSGTSY SLTISSMEAE DAATYYCQQW SSNPFTFGSG TKLEIK                106

SEQ ID NO: 560          moltype = AA  length = 119
FEATURE                 Location/Qualifiers
REGION                  1..119
                        note = Synthetic polymer.
source                  1..119
                        mol_type = protein
                        organism = synthetic construct
SEQUENCE: 560
EVQLVESGGG LVQAGKSLRL SCAASGSIFS IHAMGWFRQA PGKEREFVAA ITWSGGITYY  60
EDSVKGRFTI SRDNAKNTVY LQMNSLKPED TAIYYCAADR AESSWYDYWG QGTQVTVSS   119

SEQ ID NO: 561          moltype = AA  length = 119
FEATURE                 Location/Qualifiers
REGION                  1..119
                        note = Synthetic polymer.
source                  1..119
                        mol_type = protein
                        organism = synthetic construct
SEQUENCE: 561
EVQLVESGGG LVQAGGSLRL SCAASGSIAS IHAMGWFRQA PGKEREFVAV ITWSGGITYY  60
ADSVKGRFTI SRDNAKNTVY LQMNSLKPED TAIYYCAGDK HQSSWYDYWG QGTQVTVSS   119

SEQ ID NO: 562          moltype = AA  length = 119
FEATURE                 Location/Qualifiers
REGION                  1..119
```

```
                        note = Synthetic polymer.
source                  1..119
                        mol_type = protein
                        organism = synthetic construct
SEQUENCE: 562
EVQLVESGGG LVQAGGSLRL SCAASGSISS IHAMGWFRQA PGKEREFVAA ITWSGGITYY  60
ADSLKGRFTI SRDNAKNTGY LQMNSLKPED TAIYYCAADR AQSSWYDYWG QGTQVTVSS   119

SEQ ID NO: 563          moltype = AA  length = 119
FEATURE                 Location/Qualifiers
REGION                  1..119
                        note = Synthetic polymer.
source                  1..119
                        mol_type = protein
                        organism = synthetic construct
SEQUENCE: 563
EVQLVESGGG LVQAGGSLGL SCAASGSIFS INAMAWFRQA PGKEREFVAL ISWSGGSTYY  60
EDSVKGRFTI SRDNAKNTVY LQMNSLKPED TAIYYCAADR VDSNWYDYWG QGTQVTVSS   119

SEQ ID NO: 564          moltype = AA  length = 120
FEATURE                 Location/Qualifiers
REGION                  1..120
                        note = Synthetic polymer.
source                  1..120
                        mol_type = protein
                        organism = synthetic construct
SEQUENCE: 564
EVQLVESGGG LVQAGGSLRL SCAASGRAFS SGTMGWFRRA PGKEREFVAS IPWSGGRIYY  60
ADSVKGRFTI SRDNAQNTVY LQMNSLKPED TAVYYCAVKE RSTGWDFASW GQCTQVTVSS  120

SEQ ID NO: 565          moltype = AA  length = 121
FEATURE                 Location/Qualifiers
REGION                  1..121
                        note = Synthetic polymer.
source                  1..121
                        mol_type = protein
                        organism = synthetic construct
SEQUENCE: 565
QVQLVQSGAE LKQPGASVKM SCKASGYSFT SSWIHWVKQA PGQGLEWIGY IYPSTGFTEY  60
NQKFKDRATL TADKSTSTAY MELSSLRSED SAVYYCARWR DSSGYHAMDY WGQGTSVTVS  120
S                                                                 121

SEQ ID NO: 566          moltype = AA  length = 121
FEATURE                 Location/Qualifiers
REGION                  1..121
                        note = Synthetic polymer.
source                  1..121
                        mol_type = protein
                        organism = synthetic construct
SEQUENCE: 566
QVQLVQSGAE VKQPGASVKM SCKASGYSFT SSWIHWVKQA PGQGLEWIGY IYPSTGFTEY  60
NQKFKDRATL TADKSTSTAY MELSSLRSED TAVYYCARWR DSSGYHAMDY WGQGTSVTVS  120
S                                                                 121

SEQ ID NO: 567          moltype = AA  length = 121
FEATURE                 Location/Qualifiers
REGION                  1..121
                        note = Synthetic polymer.
source                  1..121
                        mol_type = protein
                        organism = synthetic construct
SEQUENCE: 567
QVQLVQSGHE VKQPGASVKM SCKASGYSFT SSWIHWVKQA PGQGLEWIGY IYPSTGFTEY  60
NQKFKDRATL TADKSTSTAY MELSSLRSED TAVYYCARWR DSSGYHAMDY WGQGTLVTVS  120
S                                                                 121

SEQ ID NO: 568          moltype = AA  length = 121
FEATURE                 Location/Qualifiers
REGION                  1..121
                        note = Synthetic polymer.
source                  1..121
                        mol_type = protein
                        organism = synthetic construct
SEQUENCE: 568
QVQLVQSGHE VKQPGASVKM SCKASGYSFT SSWIHWVRQA PGQGLEWIGY IYPSTGFTEY  60
NQKFKDRATL TADKSTSTAY MELSSLRSED TAVYYCARWR DSSGYHAMDY WGQGTLVTVS  120
S                                                                 121

SEQ ID NO: 569          moltype = AA  length = 121
```

```
FEATURE                Location/Qualifiers
REGION                 1..121
                       note = Synthetic polymer.
source                 1..121
                       mol_type = protein
                       organism = synthetic construct
SEQUENCE: 569
QVQLVQSGHE VKQPGASVKV SCKASGYSFT SSWIHWVRQA PGQGLEWIGY IYPSTGFTEY  60
NQKFKDRATI TADKSTSTAY MELSSLRSED TAVYYCARWR DSSGYHAMDY WGQGTLVTVS  120
S                                                                 121

SEQ ID NO: 570         moltype = AA  length = 111
FEATURE                Location/Qualifiers
REGION                 1..111
                       note = Synthetic polymer.
source                 1..111
                       mol_type = protein
                       organism = synthetic construct
SEQUENCE: 570
DIVLTQSPAS LTLSPGQRLT ISCRASQSVS TSGYSYMHWY QQKPDQSPKL LIKFGSNLES  60
GIPARFSGSG SGTDFTLTIS SLEEEDFATY YCQHSWEIPY TFGQGTKLEI K           111

SEQ ID NO: 571         moltype = AA  length = 111
FEATURE                Location/Qualifiers
REGION                 1..111
                       note = Synthetic polymer.
source                 1..111
                       mol_type = protein
                       organism = synthetic construct
SEQUENCE: 571
DIVLTQSPAT LSLSPGQRLT ISCRASQSVS TSGYSYMHWY QQKPDQSPKL LIKFGSNLES  60
GIPARFSGSG SGTDFTLTIS SLEPEDFATY YCQHSWEIPY TFGQGTKLEI K           111

SEQ ID NO: 572         moltype = AA  length = 111
FEATURE                Location/Qualifiers
REGION                 1..111
                       note = Synthetic polymer.
source                 1..111
                       mol_type = protein
                       organism = synthetic construct
SEQUENCE: 572
EIVLTQSPAT LSLSPGQRLT ISCRASQSVS TSGYSYMHWY QQKPDQSPKL LIKFGSNLES  60
GIPARFSGSG SGTDFTLTIS SLEPEDFATY YCQHSWEIPY TFGQGTKLEI K           111

SEQ ID NO: 573         moltype = AA  length = 111
FEATURE                Location/Qualifiers
REGION                 1..111
                       note = Synthetic polymer.
source                 1..111
                       mol_type = protein
                       organism = synthetic construct
SEQUENCE: 573
DIVLTQSPAT LSLSPGQRLT ISCRASQSVS TSGYSYMHWY QQKPDQSPKL LIKFGSNLES  60
GIPARFSGSG SGTDFTLTIS SLEPEDFAVY YCQHSWEIPY TFGQGTKLEI K           111

SEQ ID NO: 574         moltype = AA  length = 10
FEATURE                Location/Qualifiers
REGION                 1..10
                       note = Synthetic polymer.
source                 1..10
                       mol_type = protein
                       organism = synthetic construct
SEQUENCE: 574
GFTLDYYAIG                                                        10

SEQ ID NO: 575         moltype = AA  length = 10
FEATURE                Location/Qualifiers
REGION                 1..10
                       note = Synthetic polymer.
source                 1..10
                       mol_type = protein
                       organism = synthetic construct
SEQUENCE: 575
GTIFSINHMD                                                        10

SEQ ID NO: 576         moltype = AA  length = 10
FEATURE                Location/Qualifiers
REGION                 1..10
                       note = Synthetic polymer.
```

```
source                  1..10
                        mol_type = protein
                        organism = synthetic construct
SEQUENCE: 576
GFTFDDYGMS                                                              10

SEQ ID NO: 577          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 577
GFTLDYYAIN                                                              10

SEQ ID NO: 578          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 578
GTIFSINRMD                                                              10

SEQ ID NO: 579          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 579
GFTFSSYGMS                                                              10

SEQ ID NO: 580          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 580
GKIFSGNDMG                                                              10

SEQ ID NO: 581          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 581
GTIFSINRMD                                                              10

SEQ ID NO: 582          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 582
GFTFSSYGMS                                                              10

SEQ ID NO: 583          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 583
GFTFNDYAMS                                                              10

SEQ ID NO: 584          moltype = AA  length = 10
FEATURE                 Location/Qualifiers
REGION                  1..10
```

```
                          note = Synthetic polymer.
source                    1..10
                          mol_type = protein
                          organism = synthetic construct
SEQUENCE: 584
GFNLDPYAIA                                                              10

SEQ ID NO: 585            moltype = AA  length = 10
FEATURE                   Location/Qualifiers
REGION                    1..10
                          note = Synthetic polymer.
source                    1..10
                          mol_type = protein
                          organism = synthetic construct
SEQUENCE: 585
GFTFTAYAMS                                                              10

SEQ ID NO: 586            moltype = AA  length = 10
FEATURE                   Location/Qualifiers
REGION                    1..10
                          note = Synthetic polymer.
source                    1..10
                          mol_type = protein
                          organism = synthetic construct
SEQUENCE: 586
GFTFDYYAIG                                                              10

SEQ ID NO: 587            moltype = AA  length = 10
FEATURE                   Location/Qualifiers
REGION                    1..10
                          note = Synthetic polymer.
source                    1..10
                          mol_type = protein
                          organism = synthetic construct
SEQUENCE: 587
GFNLDPYAIA                                                              10

SEQ ID NO: 588            moltype = AA  length = 10
FEATURE                   Location/Qualifiers
REGION                    1..10
                          note = Synthetic polymer.
source                    1..10
                          mol_type = protein
                          organism = synthetic construct
SEQUENCE: 588
GTIFSINRMD                                                              10

SEQ ID NO: 589            moltype = AA  length = 10
FEATURE                   Location/Qualifiers
REGION                    1..10
                          note = Synthetic polymer.
source                    1..10
                          mol_type = protein
                          organism = synthetic construct
SEQUENCE: 589
GTIFSINRMD                                                              10

SEQ ID NO: 590            moltype = AA  length = 10
FEATURE                   Location/Qualifiers
REGION                    1..10
                          note = Synthetic polymer.
source                    1..10
                          mol_type = protein
                          organism = synthetic construct
SEQUENCE: 590
GFTFSSYGMS                                                              10

SEQ ID NO: 591            moltype = AA  length = 10
FEATURE                   Location/Qualifiers
REGION                    1..10
                          note = Synthetic polymer.
source                    1..10
                          mol_type = protein
                          organism = synthetic construct
SEQUENCE: 591
GFNLDPYAIG                                                              10

SEQ ID NO: 592            moltype = AA  length = 10
FEATURE                   Location/Qualifiers
```

```
REGION               1..10
                     note = Synthetic polymer.
source               1..10
                     mol_type = protein
                     organism = synthetic construct
SEQUENCE: 592
GFNLDPYAIA                                                              10

SEQ ID NO: 593       moltype = AA  length = 10
FEATURE              Location/Qualifiers
REGION               1..10
                     note = Synthetic polymer.
source               1..10
                     mol_type = protein
                     organism = synthetic construct
SEQUENCE: 593
ESIFSIEAMG                                                              10

SEQ ID NO: 594       moltype = AA  length = 10
FEATURE              Location/Qualifiers
REGION               1..10
                     note = Synthetic polymer.
source               1..10
                     mol_type = protein
                     organism = synthetic construct
SEQUENCE: 594
GKIFSGNDMG                                                              10

SEQ ID NO: 595       moltype = AA  length = 10
FEATURE              Location/Qualifiers
REGION               1..10
                     note = Synthetic polymer.
source               1..10
                     mol_type = protein
                     organism = synthetic construct
SEQUENCE: 595
GFTLDYYAIG                                                              10

SEQ ID NO: 596       moltype = AA  length = 10
FEATURE              Location/Qualifiers
REGION               1..10
                     note = Synthetic polymer.
source               1..10
                     mol_type = protein
                     organism = synthetic construct
SEQUENCE: 596
GFTFSSYGMS                                                              10

SEQ ID NO: 597       moltype = AA  length = 10
FEATURE              Location/Qualifiers
REGION               1..10
                     note = Synthetic polymer.
source               1..10
                     mol_type = protein
                     organism = synthetic construct
SEQUENCE: 597
GTIFSINRMD                                                              10

SEQ ID NO: 598       moltype = AA  length = 10
FEATURE              Location/Qualifiers
REGION               1..10
                     note = Synthetic polymer.
source               1..10
                     mol_type = protein
                     organism = synthetic construct
SEQUENCE: 598
GFTFSSYGMS                                                              10

SEQ ID NO: 599       moltype = AA  length = 10
FEATURE              Location/Qualifiers
REGION               1..10
                     note = Synthetic polymer.
source               1..10
                     mol_type = protein
                     organism = synthetic construct
SEQUENCE: 599
GFNLDPYAIA                                                              10

SEQ ID NO: 600       moltype = AA  length = 10
```

```
FEATURE                Location/Qualifiers
REGION                 1..10
                       note = Synthetic polymer.
source                 1..10
                       mol_type = protein
                       organism = synthetic construct
SEQUENCE: 600
GRTFSISAMG                                                           10

SEQ ID NO: 601         moltype = AA  length = 10
FEATURE                Location/Qualifiers
REGION                 1..10
                       note = Synthetic polymer.
source                 1..10
                       mol_type = protein
                       organism = synthetic construct
SEQUENCE: 601
GFTLDYYAIN                                                           10

SEQ ID NO: 602         moltype = AA  length = 10
FEATURE                Location/Qualifiers
REGION                 1..10
                       note = Synthetic polymer.
source                 1..10
                       mol_type = protein
                       organism = synthetic construct
SEQUENCE: 602
GFTFSSYGMS                                                           10

SEQ ID NO: 603         moltype = AA  length = 10
FEATURE                Location/Qualifiers
REGION                 1..10
                       note = Synthetic polymer.
source                 1..10
                       mol_type = protein
                       organism = synthetic construct
SEQUENCE: 603
GFTFNDYAMS                                                           10

SEQ ID NO: 604         moltype = AA  length = 10
FEATURE                Location/Qualifiers
REGION                 1..10
                       note = Synthetic polymer.
source                 1..10
                       mol_type = protein
                       organism = synthetic construct
SEQUENCE: 604
GFTLDYYAIG                                                           10

SEQ ID NO: 605         moltype = AA  length = 9
FEATURE                Location/Qualifiers
REGION                 1..9
                       note = Synthetic polymer.
source                 1..9
                       mol_type = protein
                       organism = synthetic construct
SEQUENCE: 605
ISSSDGSTY                                                            9

SEQ ID NO: 606         moltype = AA  length = 8
FEATURE                Location/Qualifiers
REGION                 1..8
                       note = Synthetic polymer.
source                 1..8
                       mol_type = protein
                       organism = synthetic construct
SEQUENCE: 606
ITSDGFPT                                                             8

SEQ ID NO: 607         moltype = AA  length = 9
FEATURE                Location/Qualifiers
REGION                 1..9
                       note = Synthetic polymer.
source                 1..9
                       mol_type = protein
                       organism = synthetic construct
SEQUENCE: 607
IRWNGGSTN                                                            9
```

-continued

```
SEQ ID NO: 608          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 608
ISSSDGSTY                                                          9

SEQ ID NO: 609          moltype = AA  length = 8
FEATURE                 Location/Qualifiers
REGION                  1..8
                        note = Synthetic polymer.
source                  1..8
                        mol_type = protein
                        organism = synthetic construct
SEQUENCE: 609
ITSDGTPT                                                           8

SEQ ID NO: 610          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 610
IDSGGGSTS                                                          9

SEQ ID NO: 611          moltype = AA  length = 8
FEATURE                 Location/Qualifiers
REGION                  1..8
                        note = Synthetic polymer.
source                  1..8
                        mol_type = protein
                        organism = synthetic construct
SEQUENCE: 611
ITSGGITD                                                           8

SEQ ID NO: 612          moltype = AA  length = 8
FEATURE                 Location/Qualifiers
REGION                  1..8
                        note = Synthetic polymer.
source                  1..8
                        mol_type = protein
                        organism = synthetic construct
SEQUENCE: 612
ITSDGTPT                                                           8

SEQ ID NO: 613          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 613
IDSGGGSTS                                                          9

SEQ ID NO: 614          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 614
IRSNGGYTN                                                          9

SEQ ID NO: 615          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 615
ISSSDVGTY                                                          9
```

```
SEQ ID NO: 616          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 616
INSSDGSTY                                                         9

SEQ ID NO: 617          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 617
ISGSDSSTY                                                         9

SEQ ID NO: 618          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 618
ISSSDVGTY                                                         9

SEQ ID NO: 619          moltype = AA  length = 8
FEATURE                 Location/Qualifiers
REGION                  1..8
                        note = Synthetic polymer.
source                  1..8
                        mol_type = protein
                        organism = synthetic construct
SEQUENCE: 619
ITSDGTPT                                                          8

SEQ ID NO: 620          moltype = AA  length = 8
FEATURE                 Location/Qualifiers
REGION                  1..8
                        note = Synthetic polymer.
source                  1..8
                        mol_type = protein
                        organism = synthetic construct
SEQUENCE: 620
ITSDGTPA                                                          8

SEQ ID NO: 621          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 621
IDSGGGSTS                                                         9

SEQ ID NO: 622          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 622
ISSGDGSKY                                                         9

SEQ ID NO: 623          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 623
```

```
ISSSDVGTY                                                   9

SEQ ID NO: 624          moltype = AA  length = 8
FEATURE                 Location/Qualifiers
REGION                  1..8
                        note = Synthetic polymer.
source                  1..8
                        mol_type = protein
                        organism = synthetic construct
SEQUENCE: 624
IFGGGFTN                                                    8

SEQ ID NO: 625          moltype = AA  length = 8
FEATURE                 Location/Qualifiers
REGION                  1..8
                        note = Synthetic polymer.
source                  1..8
                        mol_type = protein
                        organism = synthetic construct
SEQUENCE: 625
ITSGGITD                                                    8

SEQ ID NO: 626          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 626
ISSSDGSTY                                                   9

SEQ ID NO: 627          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 627
IDSGGGSTS                                                   9

SEQ ID NO: 628          moltype = AA  length = 8
FEATURE                 Location/Qualifiers
REGION                  1..8
                        note = Synthetic polymer.
source                  1..8
                        mol_type = protein
                        organism = synthetic construct
SEQUENCE: 628
ITSDGTPT                                                    8

SEQ ID NO: 629          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 629
IDSGGGSTS                                                   9

SEQ ID NO: 630          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 630
ISSSDVGTY                                                   9

SEQ ID NO: 631          moltype = AA  length = 9
FEATURE                 Location/Qualifiers
REGION                  1..9
                        note = Synthetic polymer.
source                  1..9
                        mol_type = protein
                        organism = synthetic construct
```

```
SEQUENCE: 631
ITWSGGSTS                                                          9

SEQ ID NO: 632          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 632
ISSSDGSTY                                                          9

SEQ ID NO: 633          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 633
IDSGGGSTS                                                          9

SEQ ID NO: 634          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 634
IRSNGGYTN                                                          9

SEQ ID NO: 635          moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 635
ISSSDGSTY                                                          9

SEQ ID NO: 636          moltype = AA  length = 16
FEATURE                 Location/Qualifiers
REGION                  1..16
                        note = Synthetic polymer.
source                  1..16
                        mol_type = protein
                        organism = synthetic construct
SEQUENCE: 636
DGWSSCRHGI NEYLYW                                                  16

SEQ ID NO: 637          moltype = AA  length = 8
FEATURE                 Location/Qualifiers
REGION                  1..8
                        note = Synthetic polymer.
source                  1..8
                        mol_type = protein
                        organism = synthetic construct
SEQUENCE: 637
SSGVYNYW                                                           8

SEQ ID NO: 638          moltype = AA  length = 12
FEATURE                 Location/Qualifiers
REGION                  1..12
                        note = Synthetic polymer.
source                  1..12
                        mol_type = protein
                        organism = synthetic construct
SEQUENCE: 638
QGYYCSGYGC PR                                                      12

SEQ ID NO: 639          moltype = AA  length = 17
FEATURE                 Location/Qualifiers
REGION                  1..17
                        note = Synthetic polymer.
source                  1..17
                        mol_type = protein
```

```
                        organism = synthetic construct
SEQUENCE: 639
SGWRLCRPTD EYDYSYW                                                         17

SEQ ID NO: 640          moltype = AA  length = 8
FEATURE                 Location/Qualifiers
REGION                  1..8
                        note = Synthetic polymer.
source                  1..8
                        mol_type = protein
                        organism = synthetic construct
SEQUENCE: 640
SSGVYNYW                                                                   8

SEQ ID NO: 641          moltype = AA  length = 14
FEATURE                 Location/Qualifiers
REGION                  1..14
                        note = Synthetic polymer.
source                  1..14
                        mol_type = protein
                        organism = synthetic construct
SEQUENCE: 641
QGYYCSGYGC SDYW                                                            14

SEQ ID NO: 642          moltype = AA  length = 7
FEATURE                 Location/Qualifiers
REGION                  1..7
                        note = Synthetic polymer.
source                  1..7
                        mol_type = protein
                        organism = synthetic construct
SEQUENCE: 642
RDRTIWW                                                                    7

SEQ ID NO: 643          moltype = AA  length = 8
FEATURE                 Location/Qualifiers
REGION                  1..8
                        note = Synthetic polymer.
source                  1..8
                        mol_type = protein
                        organism = synthetic construct
SEQUENCE: 643
SSGVYNYW                                                                   8

SEQ ID NO: 644          moltype = AA  length = 14
FEATURE                 Location/Qualifiers
REGION                  1..14
                        note = Synthetic polymer.
source                  1..14
                        mol_type = protein
                        organism = synthetic construct
SEQUENCE: 644
QGYYCSGYGC SDYW                                                            14

SEQ ID NO: 645          moltype = AA  length = 12
FEATURE                 Location/Qualifiers
REGION                  1..12
                        note = Synthetic polymer.
source                  1..12
                        mol_type = protein
                        organism = synthetic construct
SEQUENCE: 645
QGYYCSGYGC YP                                                              12

SEQ ID NO: 646          moltype = AA  length = 15
FEATURE                 Location/Qualifiers
REGION                  1..15
                        note = Synthetic polymer.
source                  1..15
                        mol_type = protein
                        organism = synthetic construct
SEQUENCE: 646
DGYYYCSDYP HPLYW                                                           15

SEQ ID NO: 647          moltype = AA  length = 15
FEATURE                 Location/Qualifiers
REGION                  1..15
                        note = Synthetic polymer.
source                  1..15
```

```
                        mol_type = protein
                        organism = synthetic construct
SEQUENCE: 647
DGWRDCTWSN EYAYW                                               15

SEQ ID NO: 648          moltype = AA  length = 15
FEATURE                 Location/Qualifiers
REGION                  1..15
                        note = Synthetic polymer.
source                  1..15
                        mol_type = protein
                        organism = synthetic construct
SEQUENCE: 648
TGWRTCRGLN EYDYW                                               15

SEQ ID NO: 649          moltype = AA  length = 15
FEATURE                 Location/Qualifiers
REGION                  1..15
                        note = Synthetic polymer.
source                  1..15
                        mol_type = protein
                        organism = synthetic construct
SEQUENCE: 649
DGYYYCSDYP HPLYW                                               15

SEQ ID NO: 650          moltype = AA  length = 8
FEATURE                 Location/Qualifiers
REGION                  1..8
                        note = Synthetic polymer.
source                  1..8
                        mol_type = protein
                        organism = synthetic construct
SEQUENCE: 650
SSGVYNYW                                                       8

SEQ ID NO: 651          moltype = AA  length = 8
FEATURE                 Location/Qualifiers
REGION                  1..8
                        note = Synthetic polymer.
source                  1..8
                        mol_type = protein
                        organism = synthetic construct
SEQUENCE: 651
SSGVYNYW                                                       8

SEQ ID NO: 652          moltype = AA  length = 14
FEATURE                 Location/Qualifiers
REGION                  1..14
                        note = Synthetic polymer.
source                  1..14
                        mol_type = protein
                        organism = synthetic construct
SEQUENCE: 652
QGYYCSGYGC SDYW                                                14

SEQ ID NO: 653          moltype = AA  length = 15
FEATURE                 Location/Qualifiers
REGION                  1..15
                        note = Synthetic polymer.
source                  1..15
                        mol_type = protein
                        organism = synthetic construct
SEQUENCE: 653
DGYYYCSDYP HPLYW                                               15

SEQ ID NO: 654          moltype = AA  length = 15
FEATURE                 Location/Qualifiers
REGION                  1..15
                        note = Synthetic polymer.
source                  1..15
                        mol_type = protein
                        organism = synthetic construct
SEQUENCE: 654
DGYYYCSDYP HPLYW                                               15

SEQ ID NO: 655          moltype = AA  length = 13
FEATURE                 Location/Qualifiers
REGION                  1..13
                        note = Synthetic polymer.
```

```
source                  1..13
                        mol_type = protein
                        organism = synthetic construct
SEQUENCE: 655
DLVSGSSRLY DYW                                                    13

SEQ ID NO: 656          moltype = AA  length = 7
FEATURE                 Location/Qualifiers
REGION                  1..7
                        note = Synthetic polymer.
source                  1..7
                        mol_type = protein
                        organism = synthetic construct
SEQUENCE: 656
RDRTIWW                                                           7

SEQ ID NO: 657          moltype = AA  length = 16
FEATURE                 Location/Qualifiers
REGION                  1..16
                        note = Synthetic polymer.
source                  1..16
                        mol_type = protein
                        organism = synthetic construct
SEQUENCE: 657
DGWSSCRHGI NEYLYW                                                 16

SEQ ID NO: 658          moltype = AA  length = 14
FEATURE                 Location/Qualifiers
REGION                  1..14
                        note = Synthetic polymer.
source                  1..14
                        mol_type = protein
                        organism = synthetic construct
SEQUENCE: 658
QGYYCSGYGC SDYW                                                   14

SEQ ID NO: 659          moltype = AA  length = 8
FEATURE                 Location/Qualifiers
REGION                  1..8
                        note = Synthetic polymer.
source                  1..8
                        mol_type = protein
                        organism = synthetic construct
SEQUENCE: 659
SSGVYNYW                                                          8

SEQ ID NO: 660          moltype = AA  length = 14
FEATURE                 Location/Qualifiers
REGION                  1..14
                        note = Synthetic polymer.
source                  1..14
                        mol_type = protein
                        organism = synthetic construct
SEQUENCE: 660
QGYYCSGYGC SDYW                                                   14

SEQ ID NO: 661          moltype = AA  length = 15
FEATURE                 Location/Qualifiers
REGION                  1..15
                        note = Synthetic polymer.
source                  1..15
                        mol_type = protein
                        organism = synthetic construct
SEQUENCE: 661
DGYYYCSDYP HPLYW                                                  15

SEQ ID NO: 662          moltype = AA  length = 18
FEATURE                 Location/Qualifiers
REGION                  1..18
                        note = Synthetic polymer.
source                  1..18
                        mol_type = protein
                        organism = synthetic construct
SEQUENCE: 662
MGRTNYGVIY DPNMYNYW                                               18

SEQ ID NO: 663          moltype = AA  length = 17
FEATURE                 Location/Qualifiers
REGION                  1..17
```

```
                        note = Synthetic polymer.
source                  1..17
                        mol_type = protein
                        organism = synthetic construct
SEQUENCE: 663
SGWRLCRPTD EYDYLYW                                                  17

SEQ ID NO: 664          moltype = AA  length = 14
FEATURE                 Location/Qualifiers
REGION                  1..14
                        note = Synthetic polymer.
source                  1..14
                        mol_type = protein
                        organism = synthetic construct
SEQUENCE: 664
QGYYCSGYGC SDYW                                                     14

SEQ ID NO: 665          moltype = AA  length = 12
FEATURE                 Location/Qualifiers
REGION                  1..12
                        note = Synthetic polymer.
source                  1..12
                        mol_type = protein
                        organism = synthetic construct
SEQUENCE: 665
QGYYCSGYGC YP                                                       12

SEQ ID NO: 666          moltype = AA  length = 16
FEATURE                 Location/Qualifiers
REGION                  1..16
                        note = Synthetic polymer.
source                  1..16
                        mol_type = protein
                        organism = synthetic construct
SEQUENCE: 666
DGWSSCRHGI NEYLYW                                                   16

SEQ ID NO: 667          moltype = AA  length = 143
FEATURE                 Location/Qualifiers
REGION                  1..143
                        note = Synthetic polymer.
source                  1..143
                        mol_type = protein
                        organism = synthetic construct
SEQUENCE: 667
QVQLQESGGG LVQAGGSLRL SCAASGFTLD YYAIGWFRQA PGKEREEVSC ISSSDGSTYY  60
ADSVKGRFTI SRDNAKNTVN LQMNSLKPED TAVYYCATDG WSSCRHGINE YLYWGQGTQV  120
TVSSAAAYPY DVPDYGSHHH HHH                                           143

SEQ ID NO: 668          moltype = AA  length = 134
FEATURE                 Location/Qualifiers
REGION                  1..134
                        note = Synthetic polymer.
source                  1..134
                        mol_type = protein
                        organism = synthetic construct
SEQUENCE: 668
QVQLQESGGG LVQAGGSLRL SCTASGTIFS INHMDWFRQA PGKQRELVAL ITSDGFPTYA  60
DSAKGRFTIS RDNTKKTVSL QMNSLKPEDT AVYYCHVSSG VYNYWGQGTQ VTVSSAAAYP  120
YDVPDYGSHH HHHH                                                     134

SEQ ID NO: 669          moltype = AA  length = 138
FEATURE                 Location/Qualifiers
REGION                  1..138
                        note = Synthetic polymer.
source                  1..138
                        mol_type = protein
                        organism = synthetic construct
SEQUENCE: 669
QVQLQESGGG LVQPGGSLRL SCAASGFTFD DYGMSWVRQA PGKGLEWVSA IRWNGGSTNY  60
ADSVKGRFTI SRDNAKNTLY LQMNSLKSED TAVYYCAQGY YCSGYGCPRG QGTQVTVSSA  120
AAYPYDVPDY GSHHHHHH                                                 138

SEQ ID NO: 670          moltype = AA  length = 144
FEATURE                 Location/Qualifiers
REGION                  1..144
                        note = Synthetic polymer.
source                  1..144
                        mol_type = protein
```

```
                        organism = synthetic construct
SEQUENCE: 670
QVQLQESGGG LVQPGGSLRL SCAASGFTLD YYAINWFRQA PGKEREEVSC ISSSDGSTYY  60
ADSVKGRFTI SRDNAKNTVY LQMNSLKPED TAVYYCATSG WRLCRPTDEY DYSYWGQGTQ  120
VTVSSAAAYP YDVPDYGSHH HHHH                                        144

SEQ ID NO: 671          moltype = AA  length = 134
FEATURE                 Location/Qualifiers
REGION                  1..134
                        note = Synthetic polymer.
source                  1..134
                        mol_type = protein
                        organism = synthetic construct
SEQUENCE: 671
QVQLQESGGG VVQAGGSLRL SCTASGTIFS INRMDWFRQA PGKQRELVAL ITSDGTPTYA  60
DSAKGRFTIS RDNTKKTVSL QMNSLKPEDT AVYYCHVSSG VYNYWGQGTQ VTVSSAAAYP  120
YDVPDYGSHH HHHH                                                   134

SEQ ID NO: 672          moltype = AA  length = 140
FEATURE                 Location/Qualifiers
REGION                  1..140
                        note = Synthetic polymer.
source                  1..140
                        mol_type = protein
                        organism = synthetic construct
SEQUENCE: 672
QVQLQESGGG LVQTGGSLRL SCAASGFTFS SYGMSWVRQT PGKGPEWVSA IDSGGGSTSY  60
ADSVKGRFTI SRDNAKNTLY LQMNSLKPED TAVYYCAQGY YCSGYGCSDY WGQGTQVTVS  120
SAAAYPYDVP DYGSHHHHHH                                             140

SEQ ID NO: 673          moltype = AA  length = 133
FEATURE                 Location/Qualifiers
REGION                  1..133
                        note = Synthetic polymer.
source                  1..133
                        mol_type = protein
                        organism = synthetic construct
SEQUENCE: 673
QVQLQESGGG LVQPGGSLRL SCAASGKIFS GNDMGWYRQA PGKQRELVGI ITSGGITDYA  60
DAVKGRFTIS RDNAKNMMYL QMNSLKPEDT AVYYCNMRDR TIWWGQGTQV TVSSAAAYPY  120
DVPDYGSHHH HHH                                                    133

SEQ ID NO: 674          moltype = AA  length = 134
FEATURE                 Location/Qualifiers
REGION                  1..134
                        note = Synthetic polymer.
source                  1..134
                        mol_type = protein
                        organism = synthetic construct
SEQUENCE: 674
QVQLQESGGG SVQAGGSLRL SCTASGTIFS INRMDWFRQA PGKQRELVAL ITSDGTPTYA  60
DSAKGRFTIS RDNTKKTVSL QMNSLKPEDT AVYYCHVSSG VYNYWGQGTQ VTVSSAAAYP  120
YDVPDYGSHH HHHH                                                   134

SEQ ID NO: 675          moltype = AA  length = 140
FEATURE                 Location/Qualifiers
REGION                  1..140
                        note = Synthetic polymer.
source                  1..140
                        mol_type = protein
                        organism = synthetic construct
SEQUENCE: 675
QVQLQESGGG LVQPGGSLRL SCAASGFTFS SYGMSWVRQT PGKGPEWVSA IDSGGGSTSY  60
ADSVKGRFTT SRDNAKNTLY LQMNSLKPED TAVYYCAQGY YCSGYGCSDY WGQGTQVTVS  120
SAAAYPYDVP DYGSHHHHHH                                             140

SEQ ID NO: 676          moltype = AA  length = 138
FEATURE                 Location/Qualifiers
REGION                  1..138
                        note = Synthetic polymer.
source                  1..138
                        mol_type = protein
                        organism = synthetic construct
SEQUENCE: 676
QVQLQESGGG LVQPGGSLRL SCAASGFTFN DYAMSWVRQA PGKGLEWVSG IRSNGGYTNY  60
ADSVKGRFTI SRDNAKNTLY LQMNSLKSED TAVYYCAQGY YCSGYGCYPG QGTQVTVSSA  120
AAYPYDVPDY GSHHHHHH                                               138

SEQ ID NO: 677          moltype = AA  length = 142
```

-continued

```
FEATURE                Location/Qualifiers
REGION                 1..142
                       note = Synthetic polymer.
source                 1..142
                       mol_type = protein
                       organism = synthetic construct
SEQUENCE: 677
QVQLQESGGG LVQAGGSLRL SCAASGFNLD PYAIAWFRQA PGKEREEVSC ISSSDVGTYY  60
ADSVKGRFTI SRDNAKKTVY LQMNSLKPED TAVYYCATDG YYYCSDYPHP LYWGQGTQVT  120
VSSAAAYPYD VPDYGSHHHH HH                                           142

SEQ ID NO: 678         moltype = AA  length = 142
FEATURE                Location/Qualifiers
REGION                 1..142
                       note = Synthetic polymer.
source                 1..142
                       mol_type = protein
                       organism = synthetic construct
SEQUENCE: 678
QVQLQESGGG LVQPGGSLRL SCAASGFTFT AYAMSWFRQA PGKEREEVSC INSSDGSTYY  60
ADSVKGRFTI SRDNAKNTVY LQMNSLKPED TAVYHCATDG WRDCTWSNEY AYWGQGTQVT  120
VSSAAAYPYD VPDYGSHHHH HH                                           142

SEQ ID NO: 679         moltype = AA  length = 142
FEATURE                Location/Qualifiers
REGION                 1..142
                       note = Synthetic polymer.
source                 1..142
                       mol_type = protein
                       organism = synthetic construct
SEQUENCE: 679
QVQLQESGGG LVQPGGSLRL SCAASGFTFD YYAIGWFRQA PGKEREEVSC ISGSDSSTYY  60
ADSVKGRFTI VRDNAQNTVY LQMNSLKPED TAIYYCAVTG WRTCRGLNEY DYWGQGTQVT  120
VSSAAAYPYD VPDYGSHHHH HH                                           142

SEQ ID NO: 680         moltype = AA  length = 142
FEATURE                Location/Qualifiers
REGION                 1..142
                       note = Synthetic polymer.
source                 1..142
                       mol_type = protein
                       organism = synthetic construct
SEQUENCE: 680
QVQLQESGGG LVQPGGSLRL SCAASGFNLD PYAIAWFRQA PGKEREEVSC ISSSDVGTYY  60
ADSVKGRFTI SRDNTKKTVY LQMNSLKPED TAVYYCATDG YYYCSDYPHP LYWGQGTQVT  120
VSSAAAYPYD VPDYGSHHHH HH                                           142

SEQ ID NO: 681         moltype = AA  length = 134
FEATURE                Location/Qualifiers
REGION                 1..134
                       note = Synthetic polymer.
source                 1..134
                       mol_type = protein
                       organism = synthetic construct
SEQUENCE: 681
QVQLQESGGG LVQAGESLRL SCTASGTIFS INRMDWFRQA PGKQRELVAL ITSDGTPTYA  60
DSAKGRFTIS RDNTKKTVSL QMNSLKPEDT AVYYCHVSSG VYNYWGQGTQ VTVSSAAAYP  120
YDVPDYGSHH HHHH                                                    134

SEQ ID NO: 682         moltype = AA  length = 134
FEATURE                Location/Qualifiers
REGION                 1..134
                       note = Synthetic polymer.
source                 1..134
                       mol_type = protein
                       organism = synthetic construct
SEQUENCE: 682
QVQLQESGGG LVQAGGSLRL SCTASGTIFS INRMDWFRQA PGKQRELVAL ITSDGTPAYA  60
DSAKGRFTIS RDNTKKTVSL QMNSLKPEDT AVYYCHVSSG VYNYWGQGTQ VTVSSAAAYP  120
YDVPDYGSHH HHHH                                                    134

SEQ ID NO: 683         moltype = AA  length = 140
FEATURE                Location/Qualifiers
REGION                 1..140
                       note = Synthetic polymer.
source                 1..140
                       mol_type = protein
                       organism = synthetic construct
SEQUENCE: 683
```

-continued

```
QVQLQESGGG LVQSGGSLRL SCKTSGFTFS SYGMSWVRQT PGKGPEWVSA IDSGGGSTSY  60
ADSVKGRFTI SRDNAKNTLY LQMNSLKPED TAVYYCAQGY YCSGYGCSDY WGQGTQVTVS  120
SAAAYPYDVP DYGSHHHHHH                                              140

SEQ ID NO: 684         moltype = AA  length = 142
FEATURE                Location/Qualifiers
REGION                 1..142
                       note = Synthetic polymer.
source                 1..142
                       mol_type = protein
                       organism = synthetic construct
SEQUENCE: 684
QVQLQESGGG LVQPGGSLRL SCAASGFNLD PYAIGWFRQA PGKEREEVSC ISSGDGSKYY  60
ADSVKGRFTM SRDNAKKTVY LQMNSLKPED TAVYYCATDG YYYCSDYPHP LYWGQGTQVT  120
VSSAAAYPYD VPDYGSHHHH HH                                           142

SEQ ID NO: 685         moltype = AA  length = 142
FEATURE                Location/Qualifiers
REGION                 1..142
                       note = Synthetic polymer.
source                 1..142
                       mol_type = protein
                       organism = synthetic construct
SEQUENCE: 685
QVQLQESGGG LVQPGGSLRL SCAVSGFNLD PYAIAWFRQA PGKEREEVSC ISSSDVGTYY  60
ADSVKGRFTI SRDNAKKTVY LQMNSLKPED TAVYYCATDG YYYCSDYPHP LYWGQGTQVT  120
VSSAAAYPYD VPDYGSHHHH HH                                           142

SEQ ID NO: 686         moltype = AA  length = 139
FEATURE                Location/Qualifiers
REGION                 1..139
                       note = Synthetic polymer.
source                 1..139
                       mol_type = protein
                       organism = synthetic construct
SEQUENCE: 686
QVQLQESGGG LVQAGGSLRL SCAASESIFS IEAMGWYRQA PGKQRELVAA IFGGGFTNYA  60
DSVKGRFTIS RDNANRTVYL QMNSLKPEDT AVYYCNADLV SGSSRLYDYW GQGTQVTVSS  120
AAAYPYDVPD YGSHHHHHH                                               139

SEQ ID NO: 687         moltype = AA  length = 133
FEATURE                Location/Qualifiers
REGION                 1..133
                       note = Synthetic polymer.
source                 1..133
                       mol_type = protein
                       organism = synthetic construct
SEQUENCE: 687
QVQLQESGGG LVQAGGSLRL SCAASGKIFS GNDMGWYRQA PGKQRELVGI ITSGGITDYA  60
DAVKGRFTIS RDNAKNMMYL QMNSLKPEDT AVYYCNMRDR TIWWGQGTQV TVSSAAAYPY  120
DVPDYGSHHH HHH                                                     133

SEQ ID NO: 688         moltype = AA  length = 143
FEATURE                Location/Qualifiers
REGION                 1..143
                       note = Synthetic polymer.
source                 1..143
                       mol_type = protein
                       organism = synthetic construct
SEQUENCE: 688
QVQLQESGGG LVQPGGSLRL SCAASGFTLD YYAIGWFRQA PGKEREEVSC ISSSDGSTYY  60
ADSVKGRFTI SRDNAKNTVN LQMNSLKPED TAVYYCATDG WSSCRHGINE YLYWGQGTQV  120
TVSSAAAYPY DVPDYGSHHH HHH                                          143

SEQ ID NO: 689         moltype = AA  length = 140
FEATURE                Location/Qualifiers
REGION                 1..140
                       note = Synthetic polymer.
source                 1..140
                       mol_type = protein
                       organism = synthetic construct
SEQUENCE: 689
QVQLQESGGG LVQAGGSLRL SCAASGFTFS SYGMSWVRQT PGKGPEWVSA IDSGGGSTSY  60
ADSVKGRFTI SRDNAKNTLY LQMNSLKPED TAVYYCAQGY YCSGYGCSDY WGQGTQVTVS  120
SAAAYPYDVP DYGSHHHHHH                                              140

SEQ ID NO: 690         moltype = AA  length = 134
FEATURE                Location/Qualifiers
REGION                 1..134
```

```
                        note = Synthetic polymer.
source                  1..134
                        mol_type = protein
                        organism = synthetic construct
SEQUENCE: 690
QVQLQESGGG LVQPGGSLRL SCTASGTIFS INRMDWFRQA PGKQRELVAL ITSDGTPTYA  60
DSAKGRFTIS RDNTKKTVSL QMNSLKPEDT AVYYCHVSSG VYNYWGQGTQ VTVSSAAAYP  120
YDVPDYGSHH HHHH                                                    134

SEQ ID NO: 691          moltype = AA  length = 140
FEATURE                 Location/Qualifiers
REGION                  1..140
                        note = Synthetic polymer.
source                  1..140
                        mol_type = protein
                        organism = synthetic construct
SEQUENCE: 691
QVQLQESGGG LVQPGGSLRL SCAASGFTFS SYGMSWVRQT PGKGPEWVSA IDSGGGSTSY  60
ADSVKGRFTI SRDNAKNTLY LQMNSLKPED TAVYYCAQGY YCSGYGCSDY WGQGTQVTVS  120
SAAAYPYDVP DYGSHHHHHH                                              140

SEQ ID NO: 692          moltype = AA  length = 142
FEATURE                 Location/Qualifiers
REGION                  1..142
                        note = Synthetic polymer.
source                  1..142
                        mol_type = protein
                        organism = synthetic construct
SEQUENCE: 692
QVQLQESGGG LVQPGGSLRL SCAASGFNLD PYAIAWFRQA PGKEREEVSC ISSSDVGTYY  60
ADSVKGRFTI SRDNAKKTVY LQMNSLKPED TAVYYCATDG YYYCSDYPHP LYWGQGTQVT  120
VSSAAAYPYD VPDYGSHHHH HH                                           142

SEQ ID NO: 693          moltype = AA  length = 145
FEATURE                 Location/Qualifiers
REGION                  1..145
                        note = Synthetic polymer.
SITE                    13
                        note = misc_feature - Xaa can be any naturally occurring
                         amino acid
source                  1..145
                        mol_type = protein
                        organism = synthetic construct
SEQUENCE: 693
QVQLQESGGG LVXAGGSLRL SCAASGRTFS ISAMGWFRQA PGKEREFVAA ITWSGGSTSY  60
TDSVKGRFTI SRDNAKNTLY LQMNSLKPED TAIYYCAAMG RTNYGVIYDP NMYNYWGQGT  120
QVTVSSAAAY PYDVPDYGSH HHHHH                                        145

SEQ ID NO: 694          moltype = AA  length = 144
FEATURE                 Location/Qualifiers
REGION                  1..144
                        note = Synthetic polymer.
source                  1..144
                        mol_type = protein
                        organism = synthetic construct
SEQUENCE: 694
QVQLQESGGG LVQPGGSLRL SCAASGFTLD YYAINWFRQA PGKEREEVSC ISSSDGSTYY  60
ADSVKGRFTI SRDNAKNTVY LQMNSLKPED TAVYYCATSG WRLCRPTDEY DYLYWGQGTQ  120
VTVSSAAAYP YDVPDYGSHH HHHH                                         144

SEQ ID NO: 695          moltype = AA  length = 140
FEATURE                 Location/Qualifiers
REGION                  1..140
                        note = Synthetic polymer.
source                  1..140
                        mol_type = protein
                        organism = synthetic construct
SEQUENCE: 695
QVQLQESGGG LVQAGGSMRL SCAASGFTFS SYGMSWVRQT PGKGPEWVSA IDSGGGSTSY  60
ADSVKGRFTI SRDNAKNTLY LQMNSLKPED TAVYYCAQGY YCSGYGCSDY WGQGTQVTVS  120
SAAAYPYDVP DYGSHHHHHH                                              140

SEQ ID NO: 696          moltype = AA  length = 138
FEATURE                 Location/Qualifiers
REGION                  1..138
                        note = Synthetic polymer.
source                  1..138
                        mol_type = protein
                        organism = synthetic construct
```

```
SEQUENCE: 696
QVQLQESGGG TVQAGGSLRL SCAASGFTFN DYAMSWVRQA PGKGLEWVSG IRSNGGYTNY  60
ADSVKGRFTI SRDNAKNTLY LQMNSLKSED TAVYYCAQGY YCSGYGCYPG QGTQVTVSSA  120
AAYPYDVPDY GSHHHHHH                                               138

SEQ ID NO: 697          moltype = AA  length = 143
FEATURE                 Location/Qualifiers
REGION                  1..143
                        note = Synthetic polymer.
source                  1..143
                        mol_type = protein
                        organism = synthetic construct
SEQUENCE: 697
QVQLQESGGG LVQPGTSLRL SCAASGFTLD YYAIGWFRQA PGKEREEVSC ISSSDGSTYY  60
ADSVKGRFTI SRDNAKNTVN LQMNSLKPED TAVYYCATDG WSSCRHGINE YLYWGQGTQV  120
TVSSAAAYPY DVPDYGSHHH HHH                                         143

SEQ ID NO: 698          moltype = AA  length = 451
FEATURE                 Location/Qualifiers
REGION                  1..451
                        note = Synthetic polymer.
source                  1..451
                        mol_type = protein
                        organism = synthetic construct
SEQUENCE: 698
EVQLVESGGG IKQDGSEKYY GWFGELAFDY KDYFPEPVTV TYICNVNHKP PKDTLMISRT  60
NSTYRVVSVL QVYTLPPSRE VLDSDGSFFL LVQPGGSLRL VDSVKGRFTI WGQGTLVTVS  120
SWNSGALTSG SNTKVDKRVE PEVTCVVVDV TVLHQDWLNG EMTKNQVSLT YSKLTVDKSR  180
SCAASGFTFS SRDNAKNSLY SASTKGPSVF VHTFPAVLQS PKSCDKTHTC SHEDPEVKFN  240
KEYKCKVSNK CLVKGFYPSD WQQGNVFSCS RYWMSWVRQA LQMNSLRAED PLAPSSKSTS  300
SGLYSLSSVV PPCPAPEFEG WYVDGVEVHN ALPASIEKTI IAVEWESNGQ VMHEALHNHY  360
PGKGLEWVAN TAVYYCAREG GGTAALGCLV TVPSSSLGTQ GPSVFLFPPK AKTKPREEQY  420
SKAKGQPREP PENNYKTTPP TQKSLSLSPG K                                451

SEQ ID NO: 699          moltype = AA  length = 215
FEATURE                 Location/Qualifiers
REGION                  1..215
                        note = Synthetic polymer.
source                  1..215
                        mol_type = protein
                        organism = synthetic construct
SEQUENCE: 699
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 700          moltype = AA  length = 118
FEATURE                 Location/Qualifiers
REGION                  1..118
                        note = Synthetic polymer.
source                  1..118
                        mol_type = protein
                        organism = synthetic construct
SEQUENCE: 700
EVKLQESGPS LVKPSQTLSL TCSVTGYSII SDYWNWIRKF PGNKLEYLGY ISYTGSTYYN  60
PSLKSRISIT RDTSKNQYYL QLNSVTTEDT ATYYCARRGG WLLPFDYWGQ GTTLTVSS   118

SEQ ID NO: 701          moltype = AA  length = 113
FEATURE                 Location/Qualifiers
REGION                  1..113
                        note = Synthetic polymer.
source                  1..113
                        mol_type = protein
                        organism = synthetic construct
SEQUENCE: 701
DIVMTQSPSS LAVSVGEKVS MGCKSSQSLL YSSNQKNSLA WYQQKPGQSP KLLIDWASTR  60
ESGVPDRFTG SGSGTDFTLT ISSVKAEDLA VYYCQQYYGY PLTFGAGTKL ELK        113

SEQ ID NO: 702          moltype = AA  length = 118
FEATURE                 Location/Qualifiers
REGION                  1..118
                        note = Synthetic polymer.
source                  1..118
                        mol_type = protein
                        organism = synthetic construct
SEQUENCE: 702
EVKLQESGPS LVKPGASVKL SCKASGYTFT SYDINWVKQR PGQGLEWIGW IFPRDNNTKY  60
NENFKGKATL TVDTSSTTAY MELHSLTSED SAVYFCTKEN WVGDFDYWGQ GTTLTLSS   118
```

```
SEQ ID NO: 703          moltype = AA  length = 106
FEATURE                 Location/Qualifiers
REGION                  1..106
                        note = Synthetic polymer.
source                  1..106
                        mol_type = protein
                        organism = synthetic construct
SEQUENCE: 703
DIVMTQSPAI MSASPGEKVT MTCSASSSIR YMHWYQQKPG TSPKRWISDT SKLTSGVPAR  60
FSGSGSGTSY ALTISSMEAE DAATYYCHQR SSYPWTFGGG TKLEIK                 106

SEQ ID NO: 704          moltype = AA  length = 114
FEATURE                 Location/Qualifiers
REGION                  1..114
                        note = Synthetic polymer.
source                  1..114
                        mol_type = protein
                        organism = synthetic construct
SEQUENCE: 704
EVQLQQSGPD LVTPGASVRI SCQASGYTFP DYYMNWVKQS HGKSLEWIGD IDPNYGGTTY  60
NQKFKGKAIL TVDRSSSTAY MELRSLTSED SAVYYCARGA LTDWGQGTSL TVSS        114

SEQ ID NO: 705          moltype = AA  length = 106
FEATURE                 Location/Qualifiers
REGION                  1..106
                        note = Synthetic polymer.
source                  1..106
                        mol_type = protein
                        organism = synthetic construct
SEQUENCE: 705
QIVLSQSPAI LSASPGEKVT MTCRASSSVS YIYWFQQKPG SSPKPWIYAT FNLASGVPAR  60
FSGSGSGTSY SLTISRVETE DAATYYCQQW SNNPLTFGAG TKLELK                 106

SEQ ID NO: 706          moltype = AA  length = 115
FEATURE                 Location/Qualifiers
REGION                  1..115
                        note = Synthetic polymer.
source                  1..115
                        mol_type = protein
                        organism = synthetic construct
SEQUENCE: 706
EVQLVQSGPE LKKPGASVKM SCKASGYTFT SYVMHWVKQA PGQRLEWIGY VNPFNDGTKY  60
NEMFKGRATL TSDKSTSTAY MELSSLRSED SAVYYCARQA WGYPWGQGTL VTVSS       115

SEQ ID NO: 707          moltype = AA  length = 115
FEATURE                 Location/Qualifiers
REGION                  1..115
                        note = Synthetic polymer.
source                  1..115
                        mol_type = protein
                        organism = synthetic construct
SEQUENCE: 707
EVQLVQSGAE VKKPGASVKM SCKASGYTFT SYVMHWVKQA PGQRLEWIGY VNPFNDGTKY  60
NEMFKGRATL TSDKSTSTAY MELSSLRSED TAVYYCARQA WGYPWGQGTL VTVSS       115

SEQ ID NO: 708          moltype = AA  length = 115
FEATURE                 Location/Qualifiers
REGION                  1..115
                        note = Synthetic polymer.
source                  1..115
                        mol_type = protein
                        organism = synthetic construct
SEQUENCE: 708
EVQLVQSGAE VKKPGASVKM SCKASGYTFT SYVMHWVRQA PGQRLEWIGY VNPFNDGTKY  60
NEMFKGRATL TSDKSTSTAY MELSSLRSED TAVYYCARQA WGYPWGQGTL VTVSS       115

SEQ ID NO: 709          moltype = AA  length = 115
FEATURE                 Location/Qualifiers
REGION                  1..115
                        note = Synthetic polymer.
source                  1..115
                        mol_type = protein
                        organism = synthetic construct
SEQUENCE: 709
EVQLVQSGAE VKKPGASVKV SCKASGYTFT SYVMHWVRQA PGQRLEWIGY VNPFNDGTKY  60
NEMFKGRATL TSDKSTSTAY MELSSLRSED TAVYYCARQA WGYPWGQGTL VTVSS       115

SEQ ID NO: 710          moltype = AA  length = 115
```

```
FEATURE                 Location/Qualifiers
REGION                  1..115
                        note = Synthetic polymer.
source                  1..115
                        mol_type = protein
                        organism = synthetic construct
SEQUENCE: 710
EVQLVQSGAE VKKPGASVKV SCKASGYTFT SYVMHWVRQA PGQRLEWIGY VNPFNDGTKY  60
NEMFKGRATI TSDKSTSTAY MELSSLRSED TAVYYCARQA WGYPWGQGTL VTVSS       115

SEQ ID NO: 711          moltype = AA  length = 111
FEATURE                 Location/Qualifiers
REGION                  1..111
                        note = Synthetic polymer.
source                  1..111
                        mol_type = protein
                        organism = synthetic construct
SEQUENCE: 711
DIVLTQSPAS LALSPGERAT LSCRATESVE YYGTSLVQWY QQKPGQPPKL LIYAASSVDS  60
GVPSRFSGSG SGTDFTLTIN SLEEEDAAMY FCQQSRRVPY TFGQGTKLEI K           111

SEQ ID NO: 712          moltype = AA  length = 111
FEATURE                 Location/Qualifiers
REGION                  1..111
                        note = Synthetic polymer.
source                  1..111
                        mol_type = protein
                        organism = synthetic construct
SEQUENCE: 712
DIVLTQSPAT LSLSPGERAT LSCRATESVE YYGTSLVQWY QQKPGQPPKL LIYAASSVDS  60
GVPSRFSGSG SGTDFTLTIN SLEAEDAAMY FCQQSRRVPY TFGQGTKLEI K           111

SEQ ID NO: 713          moltype = AA  length = 111
FEATURE                 Location/Qualifiers
REGION                  1..111
                        note = Synthetic polymer.
source                  1..111
                        mol_type = protein
                        organism = synthetic construct
SEQUENCE: 713
EIVLTQSPAT LSLSPGERAT LSCRATESVE YYGTSLVQWY QQKPGQPPKL LIYAASSVDS  60
GVPSRFSGSG SGTDFTLTIN SLEAEDAAMY FCQQSRRVPY TFGQGTKLEI K           111

SEQ ID NO: 714          moltype = AA  length = 111
FEATURE                 Location/Qualifiers
REGION                  1..111
                        note = Synthetic polymer.
source                  1..111
                        mol_type = protein
                        organism = synthetic construct
SEQUENCE: 714
DIVLTQSPAT LSLSPGERAT LSCRATESVE YYGTSLVQWY QQKPGQPPKL LIYAASSVDS  60
GVPSRFSGSG SGTDFTLTIN SLEAEDAATY FCQQSRRVPY TFGQGTKLEI K           111

SEQ ID NO: 715          moltype = AA  length = 120
FEATURE                 Location/Qualifiers
REGION                  1..120
                        note = Synthetic polymer.
source                  1..120
                        mol_type = protein
                        organism = synthetic construct
SEQUENCE: 715
EVQLVESGGG LVKPGGSLRL SCAASGFTFS TYSMNWVRQA PGKGLEWVSS ISSSGDYIYY  60
ADSVKGRFTI SRDNAKNSLF LQMNSLKAED TAVYYCARDL VTSMVAFDYW GQGTLVTVSS  120

SEQ ID NO: 716          moltype = AA  length = 108
FEATURE                 Location/Qualifiers
REGION                  1..108
                        note = Synthetic polymer.
source                  1..108
                        mol_type = protein
                        organism = synthetic construct
SEQUENCE: 716
SYELTQPPSV SVSPGQAARI TCSGDALPQK YVFWYQQKSG QAPVLVIYED SKRPSGIPER  60
FSGSSSGTMA TLTISGAQVE DEADYYCYST DRSGNHRVFG GGTRLTVL               108

SEQ ID NO: 717          moltype = AA  length = 120
FEATURE                 Location/Qualifiers
REGION                  1..120
```

```
                        note = Synthetic polymer.
source                  1..120
                        mol_type = protein
                        organism = synthetic construct
SEQUENCE: 717
EVQLVESGGG LVQPGGSLRL SCAASGFTFS SYWMSWVRQA PGKGLEWVAN IKQDGGEQYY  60
VDSVKGRFTI SRDNAKNSLY LQMNSLRAED TAVYYCARDW NYGYYDMDVW GQGTTVTVSS  120

SEQ ID NO: 718          moltype = AA  length = 108
FEATURE                 Location/Qualifiers
REGION                  1..108
                        note = Synthetic polymer.
source                  1..108
                        mol_type = protein
                        organism = synthetic construct
SEQUENCE: 718
EIVLTQSPGT LSLSPGERAT LSCRASQSVS SNYLAWFQQK PGQAPRLLIF GTSSRATGIP  60
DRFSGSGSGT DFTLTISRLE PEDFAVYYCQ QYGSSIFTFG PGTKVDIK              108

SEQ ID NO: 719          moltype = AA  length = 121
FEATURE                 Location/Qualifiers
REGION                  1..121
                        note = Synthetic polymer.
source                  1..121
                        mol_type = protein
                        organism = synthetic construct
SEQUENCE: 719
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
S                                                                  121

SEQ ID NO: 720          moltype = AA  length = 108
FEATURE                 Location/Qualifiers
REGION                  1..108
                        note = Synthetic polymer.
source                  1..108
                        mol_type = protein
                        organism = synthetic construct
SEQUENCE: 720
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTEVEIK              108

SEQ ID NO: 721          moltype = AA  length = 121
FEATURE                 Location/Qualifiers
REGION                  1..121
                        note = Synthetic polymer.
source                  1..121
                        mol_type = protein
                        organism = synthetic construct
SEQUENCE: 721
EVQLLESGGG LVQPGGSLRL SCAASGFTFS NYAMSWVRQA PGKGLEWVSA IRGSGGSTYY  60
ADSVKGRFTI SRDNSKNTLY LQMNSLRAED TAVYYCAKDL HYDSSGYLDY WGQGTLVTVS  120
S                                                                  121

SEQ ID NO: 722          moltype = AA  length = 107
FEATURE                 Location/Qualifiers
REGION                  1..107
                        note = Synthetic polymer.
source                  1..107
                        mol_type = protein
                        organism = synthetic construct
SEQUENCE: 722
DIQMTQSPSS VSASVGDRVT ITCRASQGIR SWLAWYQQKP GKAPKLLIYA ISRLQSGVPS  60
RFSGSGSGTD FTLTISSLQP EDFATYYCQQ ANSFPLTFGG GTKVEIK               107

SEQ ID NO: 723          moltype = AA  length = 119
FEATURE                 Location/Qualifiers
REGION                  1..119
                        note = Synthetic polymer.
source                  1..119
                        mol_type = protein
                        organism = synthetic construct
SEQUENCE: 723
EVQLVESGGG LVQPGGSLRL SCAASGFTFS SYWMSWVRQA PGKGLEWVAN IKQDGGEKYY  60
VDSVKGRFTI SRDNAKNSLF LQMNSLRAED TAVYYCARVQ LYSDYFDYWG QGTLVTVSS   119

SEQ ID NO: 724          moltype = AA  length = 107
FEATURE                 Location/Qualifiers
REGION                  1..107
```

```
                        note = Synthetic polymer.
source                  1..107
                        mol_type = protein
                        organism = synthetic construct
SEQUENCE: 724
DIQMTQSPSS VSASVGDRVT ITCRASQGIS SWLAWYQQKS GKAPKLLIYA ASGLQSGVPS  60
RFSGSGSGTD FTLTISSLQP EDLATYYCQQ SHSLPPTFGQ GTKVEIK                107

SEQ ID NO: 725          moltype = AA  length = 121
FEATURE                 Location/Qualifiers
REGION                  1..121
                        note = Synthetic polymer.
source                  1..121
                        mol_type = protein
                        organism = synthetic construct
SEQUENCE: 725
EVQLLESGGD LVQPGGSLRL SCAASGFTFN SYAMSWVRQA PGKGLEWVST ISGSGGFTFS  60
ADSVKGRFTI SRDNSKNTLF LQMNSLRVED SAVYSCAKVL VGFNNGCWDY WGQGTLVTVS  120
S                                                                  121

SEQ ID NO: 726          moltype = AA  length = 108
FEATURE                 Location/Qualifiers
REGION                  1..108
                        note = Synthetic polymer.
source                  1..108
                        mol_type = protein
                        organism = synthetic construct
SEQUENCE: 726
SYVLTQPPSV SVAPGQTARI TCGGNNIGSK SVHWYQQKPG QAPVLVVYDD SDRPSGIPER  60
FSGSNSGNTA TLTISRVEAG DEADYYCQVW DSSNDHVVFG GGTKLTVL               108

SEQ ID NO: 727          moltype = AA  length = 120
FEATURE                 Location/Qualifiers
REGION                  1..120
                        note = Synthetic polymer.
source                  1..120
                        mol_type = protein
                        organism = synthetic construct
SEQUENCE: 727
EVQLVESGGG LVKPGGSLRL SCAASGFTFS TYSMNWVRQA PGKGLEWVSS ISSSGDYIYY  60
ADSVKGRFTI SRDNAKNSLY LQMNSLRAED TAVYYCARDL VTSMVAFDYW GQGTLVTVSS  120

SEQ ID NO: 728          moltype = AA  length = 108
FEATURE                 Location/Qualifiers
REGION                  1..108
                        note = Synthetic polymer.
source                  1..108
                        mol_type = protein
                        organism = synthetic construct
SEQUENCE: 728
SYELTQPPSV SVSPGQTARI TCSGDALPQK YVFWYQQKSG QAPVLVIYED SKRPSGIPER  60
FSGSSSGTMA TLTISGAQVE DEADYYCYST DRSGNHRVFG GGTKLTVL               108

SEQ ID NO: 729          moltype = AA  length = 121
FEATURE                 Location/Qualifiers
REGION                  1..121
                        note = Synthetic polymer.
source                  1..121
                        mol_type = protein
                        organism = synthetic construct
SEQUENCE: 729
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
S                                                                  121

SEQ ID NO: 730          moltype = AA  length = 108
FEATURE                 Location/Qualifiers
REGION                  1..108
                        note = Synthetic polymer.
source                  1..108
                        mol_type = protein
                        organism = synthetic construct
SEQUENCE: 730
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTKVEIK               108

SEQ ID NO: 731          moltype = AA  length = 120
FEATURE                 Location/Qualifiers
REGION                  1..120
```

```
                         note = Synthetic polymer.
source                   1..120
                         mol_type = protein
                         organism = synthetic construct
SEQUENCE: 731
QVQLVQSGAE VKKPGASVKV SCKASGYTFT SYWMYWVRQA TGQGLEWMGR IDPNSGSTKY  60
NEKFKNRFTI SRDDSKNTAY LQMNSLKTED TAVYYCARDY RKGLYAMDYW GQGTTVTVSS  120

SEQ ID NO: 732           moltype = AA  length = 120
FEATURE                  Location/Qualifiers
REGION                   1..120
                         note = Synthetic polymer.
source                   1..120
                         mol_type = protein
                         organism = synthetic construct
SEQUENCE: 732
EVQLVQSGAE VKKPGATVKI SCKVSGYTFT SYWMYWVRQA TGQGLEWMGR IDPNSGSTKY  60
NEKFKNRVTI TADKSTSTAY MELSSLRSED TAVYYCARDY RKGLYAMDYW GQGTTVTVSS  120

SEQ ID NO: 733           moltype = AA  length = 120
FEATURE                  Location/Qualifiers
REGION                   1..120
                         note = Synthetic polymer.
source                   1..120
                         mol_type = protein
                         organism = synthetic construct
SEQUENCE: 733
EVQLVQSGAE VKKPGESLRI SCKGSGYTFT SYWMYWVRQA PGQGLEWMGR IDPNSGSTKY  60
NEKFKNRVTI SVDTSKNQFS LKLSSVTAAD TAVYYCARDY RKGLYAMDYW GQGTTVTVSS  120

SEQ ID NO: 734           moltype = AA  length = 120
FEATURE                  Location/Qualifiers
REGION                   1..120
                         note = Synthetic polymer.
source                   1..120
                         mol_type = protein
                         organism = synthetic construct
SEQUENCE: 734
EVQLVQSGAE VKKPGATVKI SCKVSGYTFT SYWMYWIRQS PSRGLEWLGR IDPNSGSTKY  60
NEKFKNRLTI SKDTSKNQVV LTMTNMDPVD TATYYCARDY RKGLYAMDYW GQGTTVTVSS  120

SEQ ID NO: 735           moltype = AA  length = 120
FEATURE                  Location/Qualifiers
REGION                   1..120
                         note = Synthetic polymer.
source                   1..120
                         mol_type = protein
                         organism = synthetic construct
SEQUENCE: 735
EVQLVQSGAE VKKPGESLRI SCKGSGYTFT SYWMYWIRQP PGKGLEWIGR IDPNSGSTKY  60
NEKFKNRVTI TADKSTSTAY MELSSLRSED TAVYYCARDY RKGLYAMDYW GQGTTVTVSS  120

SEQ ID NO: 736           moltype = AA  length = 120
FEATURE                  Location/Qualifiers
REGION                   1..120
                         note = Synthetic polymer.
source                   1..120
                         mol_type = protein
                         organism = synthetic construct
SEQUENCE: 736
QVQLVQSGAE VKKPGASVKV SCKASGYTFT SYWMYWIRQS PSRGLEWLGR IDPNSGSTKY  60
NEKFKNRFTI SRDDSKNTAY LQMNSLKTED TAVYYCARDY RKGLYAMDYW GQGTTVTVSS  120

SEQ ID NO: 737           moltype = AA  length = 120
FEATURE                  Location/Qualifiers
REGION                   1..120
                         note = Synthetic polymer.
source                   1..120
                         mol_type = protein
                         organism = synthetic construct
SEQUENCE: 737
EVQLVQSGAE VKKPGESLRI SCKGSGYTFT SYWMYWVRQA RGQRLEWIGR IDPNSGSTKY  60
NEKFKNRLTI SKDTSKNQVV LTMTNMDPVD TATYYCARDY RKGLYAMDYW GQGTTVTVSS  120

SEQ ID NO: 738           moltype = AA  length = 120
FEATURE                  Location/Qualifiers
REGION                   1..120
                         note = Synthetic polymer.
source                   1..120
```

```
                      mol_type = protein
                      organism = synthetic construct
SEQUENCE: 738
QITLKESGPT LVKPTQTLTL TCTFSGYTFT SYWMYWVRQA PGKGLEWVSR IDPNSGSTKY  60
NEKFKNRVTI TADKSTSTAY MELSSLRSED TAVYYCARDY RKGLYAMDYW GQGTTVTVSS  120

SEQ ID NO: 739        moltype = AA  length = 120
FEATURE               Location/Qualifiers
REGION                1..120
                      note = Synthetic polymer.
source                1..120
                      mol_type = protein
                      organism = synthetic construct
SEQUENCE: 739
EVQLVQSGAE VKKPGATVKI SCKVSGYTFT SYWMYWVRQA RGQRLEWIGR IDPNSGSTKY  60
NEKFKNRFTI SRDNSKNTLY LQMNSLRAED TAVYYCARDY RKGLYAMDYW GQGTTVTVSS  120

SEQ ID NO: 740        moltype = AA  length = 107
FEATURE               Location/Qualifiers
REGION                1..107
                      note = Synthetic polymer.
source                1..107
                      mol_type = protein
                      organism = synthetic construct
SEQUENCE: 740
DIVMTQTPLS LPVTPGEPAS ISCKASQDVG TAVAWYLQKP GQSPQLLIYW ASTRHTGIPA  60
RFSGSGSGTE FTLTISSLQS EDFAVYYCQQ YNSYPLTFGQ GTKVEIK               107

SEQ ID NO: 741        moltype = AA  length = 107
FEATURE               Location/Qualifiers
REGION                1..107
                      note = Synthetic polymer.
source                1..107
                      mol_type = protein
                      organism = synthetic construct
SEQUENCE: 741
DIQMTQSPSS LSASVGDRVT ITCKASQDVG TAVAWYLQKP GQSPQLLIYW ASTRHTGVPS  60
RFSGSGSGTD FTLTISSLQP EDFATYYCQQ YNSYPLTFGQ GTKVEIK               107

SEQ ID NO: 742        moltype = AA  length = 107
FEATURE               Location/Qualifiers
REGION                1..107
                      note = Synthetic polymer.
source                1..107
                      mol_type = protein
                      organism = synthetic construct
SEQUENCE: 742
EIVLTQSPDF QSVTPKEKVT ITCKASQDVG TAVAWYLQKP GQSPQLLIYW ASTRHTGVPD  60
RFSGSGSGTD FTLKISRVEA EDVGVYYCQQ YNSYPLTFGQ GTKVEIK               107

SEQ ID NO: 743        moltype = AA  length = 107
FEATURE               Location/Qualifiers
REGION                1..107
                      note = Synthetic polymer.
source                1..107
                      mol_type = protein
                      organism = synthetic construct
SEQUENCE: 743
EIVLTQSPDF QSVTPKEKVT ITCKASQDVG TAVAWYLQKP GQSPQLLIYW ASTRHTGVPS  60
RFSGSGSGTD FTFTISSLQP EDIATYYCQQ YNSYPLTFGQ GTKVEIK               107

SEQ ID NO: 744        moltype = AA  length = 107
FEATURE               Location/Qualifiers
REGION                1..107
                      note = Synthetic polymer.
source                1..107
                      mol_type = protein
                      organism = synthetic construct
SEQUENCE: 744
EIVLTQSPAT LSLSPGERAT LSCKASQDVG TAVAWYLQKP GQSPQLLIYW ASTRHTGIPP  60
RFSGSGYGTD FTLTINNIES EDAAYYFCQQ YNSYPLTFGQ GTKVEIK               107

SEQ ID NO: 745        moltype = AA  length = 107
FEATURE               Location/Qualifiers
REGION                1..107
                      note = Synthetic polymer.
source                1..107
                      mol_type = protein
                      organism = synthetic construct
```

-continued

```
SEQUENCE: 745
DVVMTQSPLS LPVTLGQPAS ISCKASQDVG TAVAWYQQKP GQAPRLLIYW ASTRHTGVPS  60
RFSGSGSGTE FTLTISSLQP DDFATYYCQQ YNSYPLTFGQ GTKVEIK                107

SEQ ID NO: 746          moltype = AA  length = 107
FEATURE                 Location/Qualifiers
REGION                  1..107
                        note = Synthetic polymer.
source                  1..107
                        mol_type = protein
                        organism = synthetic construct
SEQUENCE: 746
DIQMTQSPSS LSASVGDRVT ITCKASQDVG TAVAWYQQKP GQAPRLLIYW ASTRHTGVPS  60
RFSGSGSGTD FTFTISSLQP EDIATYYCQQ YNSYPLTFGQ GTKVEIK                107

SEQ ID NO: 747          moltype = AA  length = 107
FEATURE                 Location/Qualifiers
REGION                  1..107
                        note = Synthetic polymer.
source                  1..107
                        mol_type = protein
                        organism = synthetic construct
SEQUENCE: 747
AIQLTQSPSS LSASVGDRVT ITCKASQDVG TAVAWYLQKP GQSPQLLIYW ASTRHTGVPS  60
RFSGSGSGTD FTFTISSLEA EDAATYYCQQ YNSYPLTFGQ GTKVEIK                107

SEQ ID NO: 748          moltype = AA  length = 107
FEATURE                 Location/Qualifiers
REGION                  1..107
                        note = Synthetic polymer.
source                  1..107
                        mol_type = protein
                        organism = synthetic construct
SEQUENCE: 748
EIVLTQSPDF QSVTPKEKVT ITCKASQDVG TAVAWYQQKP GQAPRLLIYW ASTRHTGVPS  60
RFSGSGSGTE FTLTISSLQP DDFATYYCQQ YNSYPLTFGQ GTKVEIK                107

SEQ ID NO: 749          moltype = AA  length = 116
FEATURE                 Location/Qualifiers
REGION                  1..116
                        note = Synthetic polymer.
source                  1..116
                        mol_type = protein
                        organism = synthetic construct
SEQUENCE: 749
EVKLVESGGG LVKPGGSLKL SCAASGFIFR SYGMSWVRQT PEKRLEWVAS ISSGGSTYYP  60
DSVKGRFTIS RDNARNILYL QMSSLRSEDT AMYDCARGYD SGFAYWGQGT LVTVSE      116

SEQ ID NO: 750          moltype = AA  length = 116
FEATURE                 Location/Qualifiers
REGION                  1..116
                        note = Synthetic polymer.
source                  1..116
                        mol_type = protein
                        organism = synthetic construct
SEQUENCE: 750
EVKLVESGGG LVKPGGSLKL SCAASGFTFR SYGMSWVRQT PEKRLEWVAS ISSGGTTYYP  60
DSVKGRFIIS RDNARNILYL QMSSLRSEDT AMYYCAKGYD SGFAYWGQGT LVIVSA      116

SEQ ID NO: 751          moltype = AA  length = 116
FEATURE                 Location/Qualifiers
REGION                  1..116
                        note = Synthetic polymer.
source                  1..116
                        mol_type = protein
                        organism = synthetic construct
SEQUENCE: 751
QVQLKQSGPG LVQPSQSLSI TCTVSGFSLT TYGVHWVRQS PGKGLEWLGV IWRGVTTDYN  60
AAFMSRLTIT KDNSKSQVFF KMNSLQANDT AIYYCARLGF YAMDYWGQGT SVTVSS      116

SEQ ID NO: 752          moltype = AA  length = 116
FEATURE                 Location/Qualifiers
REGION                  1..116
                        note = Synthetic polymer.
source                  1..116
                        mol_type = protein
                        organism = synthetic construct
SEQUENCE: 752
QVQLKQSGPG LVQPSQSLSI TCTVSGFSLT SYGVHWVRQS PGKGLEWLGV IWSGGVTDYN  60
```

```
AAFISRLSIS KDNSKSQVFF KMNSLQANDT AIYYCARLGF YAMDYWGQGT SVTVSS      116

SEQ ID NO: 753         moltype = AA  length = 119
FEATURE                Location/Qualifiers
REGION                 1..119
                       note = Synthetic polymer.
source                 1..119
                       mol_type = protein
                       organism = synthetic construct
SEQUENCE: 753
EVKLFESGGG LVQPGGSLKL SCVASGFDFS TYWMHWVRQA PGQGLEWIGQ INPDSTTINY  60
APSLKDRFII SRDNAKNTLF LQMSKVRSED TALYYCAKPG DYGYDFDCWG QGTTLTVSS   119

SEQ ID NO: 754         moltype = AA  length = 119
FEATURE                Location/Qualifiers
REGION                 1..119
                       note = Synthetic polymer.
source                 1..119
                       mol_type = protein
                       organism = synthetic construct
SEQUENCE: 754
EVQLQESGPS LVKPSQTLSL TCSVTGDSIT SGYWNWIRKF PGNKLEYMGY ISYSGSTYYN  60
PSLKSRISIT RDTSKNQYYL QLNSVTTEDT ATYYCARSLL WFSTGFAYWG QGTLVTVSA   119

SEQ ID NO: 755         moltype = AA  length = 116
FEATURE                Location/Qualifiers
REGION                 1..116
                       note = Synthetic polymer.
source                 1..116
                       mol_type = protein
                       organism = synthetic construct
SEQUENCE: 755
QVQLKQSGPG LVQPSQSLSI TCTVSGFSLT SYGVHWVRQS PGKGLEWLGV IWSGGITDYN  60
AAFKSRLSIS KDNSKSQVFF KMNSLQANDT AIYFCARLGF YAMDYWGQGT SVTVSS      116

SEQ ID NO: 756         moltype = AA  length = 116
FEATURE                Location/Qualifiers
REGION                 1..116
                       note = Synthetic polymer.
source                 1..116
                       mol_type = protein
                       organism = synthetic construct
SEQUENCE: 756
EVKLVESGGG LVKPGGSLKL SCAASGFTFR SYGMSWARQI PEKRLEWVAS ISSGGTTYYL  60
GSVQGRFTIS RDNARNILYL QMSSLRSEDT AMYYCARGYD AGFAYWGQGT LVSVSE      116

SEQ ID NO: 757         moltype = AA  length = 117
FEATURE                Location/Qualifiers
REGION                 1..117
                       note = Synthetic polymer.
source                 1..117
                       mol_type = protein
                       organism = synthetic construct
SEQUENCE: 757
EVQLQESGPS LVKPSQTLSL TCSVTGDSIT SGYWTWIRKF PGNKLEYMGY ISYTGSTYYN  60
PSLKSRISIS RDTSKSQYYL QLNSVTTEDT ATYYCARQRD WLGFAYWGQG TLVTVSA     117

SEQ ID NO: 758         moltype = AA  length = 116
FEATURE                Location/Qualifiers
REGION                 1..116
                       note = Synthetic polymer.
source                 1..116
                       mol_type = protein
                       organism = synthetic construct
SEQUENCE: 758
EEKLVESGGG LVKPGGSLKL SCAASGFSFS SYGMSWVRQT PEKRLEWVAS ISSGGSIYYP  60
DSVKGRFTIS RDNARNILYL QMSSLRSEDT AMYYCARGYD AGFAFWGQGT LVTASA      116

SEQ ID NO: 759         moltype = AA  length = 116
FEATURE                Location/Qualifiers
REGION                 1..116
                       note = Synthetic polymer.
source                 1..116
                       mol_type = protein
                       organism = synthetic construct
SEQUENCE: 759
QITLKESGPT LVKPTQTLTL TCTVSGFSLS TYGVHWIRQP PGKALEWLGV IWRGVTTDYN  60
AAFMSRLTIT KDNSKNQVVL TMNNMDPVDT ATYYCARLGF YAMDYWGQGT LVTVSS      116
```

-continued

```
SEQ ID NO: 760         moltype = AA  length = 116
FEATURE                Location/Qualifiers
REGION                 1..116
                       note = Synthetic polymer.
source                 1..116
                       mol_type = protein
                       organism = synthetic construct
SEQUENCE: 760
EVQLVESGGG LVKPGGSLRL SCAASGFIFR SYGMSWVRQA PGKGLEWVAS ISSGGSTYYP  60
DSVKGRFTIS RDNAKNSLYL QMNSLRAEDT AVYDCARGYD SGFAYWGQGT LVTVSS      116

SEQ ID NO: 761         moltype = AA  length = 112
FEATURE                Location/Qualifiers
REGION                 1..112
                       note = Synthetic polymer.
source                 1..112
                       mol_type = protein
                       organism = synthetic construct
SEQUENCE: 761
DIVLTQSPAS LAVSLGQRAT ISCRASQSVS TSSSSFMHWY QQKPGQPPKL LIKYASNLES  60
GVPARFSGSG SGTDFTLNIH PVEEEDTATY YCQHSWEIPY TFGGGTKLEI KR          112

SEQ ID NO: 762         moltype = AA  length = 111
FEATURE                Location/Qualifiers
REGION                 1..111
                       note = Synthetic polymer.
source                 1..111
                       mol_type = protein
                       organism = synthetic construct
SEQUENCE: 762
DIVLTQSPPS LAVSLGQRAT ISCRASQSVS TSSSSYMHWY QQKPGQPPKL LIKYASNLES  60
GVPARFSGSG SGTDFTLNIH PVEEEDTATY YCQHSWEIPY TFGGGTKLEI K           111

SEQ ID NO: 763         moltype = AA  length = 107
FEATURE                Location/Qualifiers
REGION                 1..107
                       note = Synthetic polymer.
source                 1..107
                       mol_type = protein
                       organism = synthetic construct
SEQUENCE: 763
SIVMTQTPKF LLVSAGDRVT ITCKASQSVS NDVAWYQQKP GQSPKLLIYY AANRYTGVPD  60
RFTGSGYGTD FTFTISIVQA EDLAVYFCQQ DYTSPYTFGG GTKLEIK                107

SEQ ID NO: 764         moltype = AA  length = 107
FEATURE                Location/Qualifiers
REGION                 1..107
                       note = Synthetic polymer.
source                 1..107
                       mol_type = protein
                       organism = synthetic construct
SEQUENCE: 764
SIVMTQTPKF LLVSAGDRVT ITCKASQSVS NDVGWYQQKP GQSPKLLIYY ASNRYSGVPD  60
RFTGSGYGTD FTFTISTVQA EDLAVYFCQQ DYTSPYTFGG GTKLEIK                107

SEQ ID NO: 765         moltype = AA  length = 112
FEATURE                Location/Qualifiers
REGION                 1..112
                       note = Synthetic polymer.
source                 1..112
                       mol_type = protein
                       organism = synthetic construct
SEQUENCE: 765
DVLMTQTPLY LPVSLGDQAS ISCRSSQIIV HSNANTYLEW FLQKPGQSPK LLIYKVSNRF  60
SGVPDRFSGS GSGTDFTLKI SRVEAEDLGV YYCFQGSHVP YTFGGGTKLE IK          112

SEQ ID NO: 766         moltype = AA  length = 108
FEATURE                Location/Qualifiers
REGION                 1..108
                       note = Synthetic polymer.
source                 1..108
                       mol_type = protein
                       organism = synthetic construct
SEQUENCE: 766
QIVLTQSPAI MSASPGEKVT LTCSASSSVS SSYLYWNQQK PGSSPKVWIY NTSNLASGVP  60
ARFSGSGSGT SYSLTISSME AEDAASYFCH QWRSYPPTLG AGTKLELK               108

SEQ ID NO: 767         moltype = AA  length = 106
FEATURE                Location/Qualifiers
```

```
REGION                 1..106
                       note = Synthetic polymer.
source                 1..106
                       mol_type = protein
                       organism = synthetic construct
SEQUENCE: 767
QIVLTQSPAI MSASPGEKVT MTCSANSSVS YMHWYQQKSG TSPKRWIYDT SKLASGVPAR  60
FSGSGSGTSY SLTISSMGAE DAATYYCQQW SSNPWTFGGG TKLEIK                106

SEQ ID NO: 768         moltype = AA  length = 111
FEATURE                Location/Qualifiers
REGION                 1..111
                       note = Synthetic polymer.
source                 1..111
                       mol_type = protein
                       organism = synthetic construct
SEQUENCE: 768
DIVLTQSPAS LAVSLGQRAT ISCRASQSVS TSSYSYMHWY QQKPGQPPKL LIKYASNLES  60
GVPARFSGSG SGTDFTLNIH PVEEEDTATY YCQNSWEIPY TFGGGTKLEI K          111

SEQ ID NO: 769         moltype = AA  length = 113
FEATURE                Location/Qualifiers
REGION                 1..113
                       note = Synthetic polymer.
source                 1..113
                       mol_type = protein
                       organism = synthetic construct
SEQUENCE: 769
DIVMTQTPSS LAVSLGEKVT MSCKSSQSLL YSSNQKNSLA WYQQKPGQSP KLLIYWASNR  60
ESGVPDRFTG SSSGTDFTLT ISSVKAEDLA VYYCQQYYSY PLTFGAGTKL ELK        113

SEQ ID NO: 770         moltype = AA  length = 111
FEATURE                Location/Qualifiers
REGION                 1..111
                       note = Synthetic polymer.
source                 1..111
                       mol_type = protein
                       organism = synthetic construct
SEQUENCE: 770
DIVLTQSPAS LAVSLGQRAT ISCRASQSVS TSSYSYVHWY QQKPGQPPKL LIKYASNLES  60
GVPARFSGSG SGTDFTLNIH PVEEEDTATY YCQHSWEIPY TFGGGTKLEI K          111

SEQ ID NO: 771         moltype = AA  length = 107
FEATURE                Location/Qualifiers
REGION                 1..107
                       note = Synthetic polymer.
source                 1..107
                       mol_type = protein
                       organism = synthetic construct
SEQUENCE: 771
DIQMTQSPSS LSASVGDRVT ITCKASQSVS NDVAWYQQKP GKAPKLLIYY AANRYTGVPD  60
RFSGSGYGTD FTFTISSLQP EDIATYFCQQ DYTSPYTFGQ GTKLEIK               107

SEQ ID NO: 772         moltype = AA  length = 111
FEATURE                Location/Qualifiers
REGION                 1..111
                       note = Synthetic polymer.
source                 1..111
                       mol_type = protein
                       organism = synthetic construct
SEQUENCE: 772
DIVLTQSPAS LAVSPGQRAT ITCRASQSVS TSSSSFMHWY QQKPGQPPKL LIKYASNLES  60
GVPARFSGSG SGTDFTLTIN PVEANDTANY YCQHSWEIPY TFGQGTKLEI K          111

SEQ ID NO: 773         moltype = AA  length = 117
FEATURE                Location/Qualifiers
REGION                 1..117
                       note = Synthetic polymer.
source                 1..117
                       mol_type = protein
                       organism = synthetic construct
SEQUENCE: 773
EVQLVQSGAE VKKPGESLRI SCKGSGYTFT TYWMHWVRQA TGQGLEWMGN IYPGTGGSNF  60
DEKFKNRVTI TADKSTSTAY MELSSLRSED TAVYYCTRWT TGTGAYWGQG TTVTVSS    117

SEQ ID NO: 774         moltype = AA  length = 117
FEATURE                Location/Qualifiers
REGION                 1..117
                       note = Synthetic polymer.
```

```
source                  1..117
                        mol_type = protein
                        organism = synthetic construct
SEQUENCE: 774
EVQLVQSGAE VKKPGESLRI SCKGSGYTFT TYWMHWIRQS PSRGLEWLGN IYPGTGGSNF  60
DEKFKNRFTI SRDNSKNTLY LQMNSLRAED TAVYYCTRWT TGTGAYWGQG TTVTVSS     117

SEQ ID NO: 775          moltype = AA  length = 117
FEATURE                 Location/Qualifiers
REGION                  1..117
                        note = Synthetic polymer.
source                  1..117
                        mol_type = protein
                        organism = synthetic construct
SEQUENCE: 775
QVQLVQSGAE VKKPGASVKV SCKASGYTFT TYWMHWIRQS PSRGLEWLGN IYPGTGGSNF  60
DEKFKNRFTI SRDNSKNTLY LQMNSLRAED TAVYYCTRWT TGTGAYWGQG TTVTVSS     117

SEQ ID NO: 776          moltype = AA  length = 117
FEATURE                 Location/Qualifiers
REGION                  1..117
                        note = Synthetic polymer.
source                  1..117
                        mol_type = protein
                        organism = synthetic construct
SEQUENCE: 776
EVQLVQSGAE VKKPGESLRI SCKGSGYTFT TYWMHWVRQA PGQGLEWMGN IYPGTGGSNF  60
DEKFKNRFTI SRDNSKNTLY LQMNSLRAED TAVYYCTRWT TGTGAYWGQG TTVTVSS     117

SEQ ID NO: 777          moltype = AA  length = 113
FEATURE                 Location/Qualifiers
REGION                  1..113
                        note = Synthetic polymer.
source                  1..113
                        mol_type = protein
                        organism = synthetic construct
SEQUENCE: 777
EIVLTQSPAT LSLSPGERAT LSCKSSQSLL DSGNQKNFLT WYQQKPGQAP RLLIYWASTR  60
ESGVPSRFSG SGSGTEFTLT ISSLQPDDFA TYYCQNDYSY PYTFGQGTKV EIK         113

SEQ ID NO: 778          moltype = AA  length = 113
FEATURE                 Location/Qualifiers
REGION                  1..113
                        note = Synthetic polymer.
source                  1..113
                        mol_type = protein
                        organism = synthetic construct
SEQUENCE: 778
DIQMTQSPSS LSASVGDRVT ITCKSSQSLL DSGNQKNFLT WYQQKPGQAP RLLIYWASTR  60
ESGIPPRFSG SGYGTDFTLT INNIESEDAA YYFCQNDYSY PYTFGQGTKV EIK         113

SEQ ID NO: 779          moltype = AA  length = 113
FEATURE                 Location/Qualifiers
REGION                  1..113
                        note = Synthetic polymer.
source                  1..113
                        mol_type = protein
                        organism = synthetic construct
SEQUENCE: 779
EIVLTQSPAT LSLSPGERAT LSCKSSQSLL DSGNQKNFLT WYQQKPGKAP KLLIYWASTR  60
ESGVPSRFSG SGSGTDFTFT ISSLQPEDIA TYYCQNDYSY PYTFGQGTKV EIK         113

SEQ ID NO: 780          moltype = AA  length = 113
FEATURE                 Location/Qualifiers
REGION                  1..113
                        note = Synthetic polymer.
source                  1..113
                        mol_type = protein
                        organism = synthetic construct
SEQUENCE: 780
DIVMTQTPLS LPVTPGEPAS ISCKSSQSLL DSGNQKNFLT WYQQKPGQAP RLLIYWASTR  60
ESGVPSRFSG SGSGTDFTFT ISSLEAEDAA TYYCQNDYSY PYTFGQGTKV EIK         113

SEQ ID NO: 781          moltype = AA  length = 113
FEATURE                 Location/Qualifiers
REGION                  1..113
                        note = Synthetic polymer.
source                  1..113
                        mol_type = protein
```

```
                         organism = synthetic construct
SEQUENCE: 781
EIVLTQSPAT LSLSPGERAT LSCKSSQSLL DSGNQKNFLT WYQQKPGKAP KLLIYWASTR  60
ESGVPSRFSG SGSGTDFTFT ISSLEAEDAA TYYCQNDYSY PYTFGQGTKV EIK         113

SEQ ID NO: 782           moltype = AA  length = 113
FEATURE                  Location/Qualifiers
REGION                   1..113
                         note = Synthetic polymer.
source                   1..113
                         mol_type = protein
                         organism = synthetic construct
SEQUENCE: 782
EIVLTQSPDF QSVTPKEKVT ITCKSSQSLL DSGNQKNFLT WYQQKPGQAP RLLIYWASTR  60
ESGVPSRFSG SGSGTDFTFT ISSLEAEDAA TYYCQNDYSY PYTFGQGTKV EIK         113

SEQ ID NO: 783           moltype = AA  length = 113
FEATURE                  Location/Qualifiers
REGION                   1..113
                         note = Synthetic polymer.
source                   1..113
                         mol_type = protein
                         organism = synthetic construct
SEQUENCE: 783
EIVLTQSPAT LSLSPGERAT LSCKSSQSLL DSGNQKNFLT WYQQKPGQAP RLLIYWASTR  60
ESGVPSRFSG SGSGTDFTFT ISSLEAEDAA TYYCQNDYSY PYTFGQGTKV EIK         113

SEQ ID NO: 784           moltype = AA  length = 113
FEATURE                  Location/Qualifiers
REGION                   1..113
                         note = Synthetic polymer.
source                   1..113
                         mol_type = protein
                         organism = synthetic construct
SEQUENCE: 784
DIQMTQSPSS LSASVGDRVT ITCKSSQSLL DSGNQKNFLT WYLQKPGQSP QLLIYWASTR  60
ESGVPSRFSG SGSGTDFTFT ISSLEAEDAA TYYCQNDYSY PYTFGQGTKV EIK         113

SEQ ID NO: 785           moltype = AA  length = 113
FEATURE                  Location/Qualifiers
REGION                   1..113
                         note = Synthetic polymer.
source                   1..113
                         mol_type = protein
                         organism = synthetic construct
SEQUENCE: 785
DVVMTQSPLS LPVTLGQPAS ISCKSSQSLL DSGNQKNFLT WYQQKPGKAP KLLIYWASTR  60
ESGVPSRFSG SGSGTDFTFT ISSLEAEDAA TYYCQNDYSY PYTFGQGTKV EIK         113

SEQ ID NO: 786           moltype = AA  length = 118
FEATURE                  Location/Qualifiers
REGION                   1..118
                         note = Synthetic polymer.
source                   1..118
                         mol_type = protein
                         organism = synthetic construct
SEQUENCE: 786
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSA    118

SEQ ID NO: 787           moltype = AA  length = 108
FEATURE                  Location/Qualifiers
REGION                   1..108
                         note = Synthetic polymer.
source                   1..108
                         mol_type = protein
                         organism = synthetic construct
SEQUENCE: 787
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKR               108

SEQ ID NO: 788           moltype = AA  length = 126
FEATURE                  Location/Qualifiers
REGION                   1..126
                         note = Synthetic polymer.
source                   1..126
                         mol_type = protein
                         organism = synthetic construct
SEQUENCE: 788
```

```
EVQLVESGGG LVQPGGSLRL SCAASGFTLD YYAIGWFRQA PGKEREWASS ISSSDGSTYY  60
ADSVKGRFTI SRDNAKNTVF LQMNSLKPED TAVYSCAASQ APITIATMMK PFYDYWGQGT  120
QVTVSS                                                             126

SEQ ID NO: 789         moltype = AA  length = 123
FEATURE                Location/Qualifiers
REGION                 1..123
                       note = Synthetic polymer.
source                 1..123
                       mol_type = protein
                       organism = synthetic construct
SEQUENCE: 789
EVQLVESGGG LVQPGGSLRL SCAASGFTLD YYAKCWFRQA PGKEREWVSC ISSSDGSTYY  60
ADSVKGRFTI SRDNAKNTVY LQMNSLKPED TAVYFCAARH GGPLTVEYFF DYWGQGTQVT  120
VSS                                                                123

SEQ ID NO: 790         moltype = AA  length = 124
FEATURE                Location/Qualifiers
REGION                 1..124
                       note = Synthetic polymer.
source                 1..124
                       mol_type = protein
                       organism = synthetic construct
SEQUENCE: 790
EVQLVESGGG LVQPGGSLRL SCAASGFTFD YYAIGWFRQA PGKAREGVSC ISGGDNSTYY  60
ADSVKGRFTI SRDNAKNTVY LQMNSLKPED TAVYYCATGG WKYCSGYDPE YIYWGQGTQV  120
TVSS                                                               124

SEQ ID NO: 791         moltype = AA  length = 115
FEATURE                Location/Qualifiers
REGION                 1..115
                       note = Synthetic polymer.
source                 1..115
                       mol_type = protein
                       organism = synthetic construct
SEQUENCE: 791
EVQLVESGGG LVQAGGSLRL SCAASGSTFS QYDVGWYRQA PGKQRELVAF SSSGGRTIYP  60
DSVKGRFTFS RDNTKNTVYL QMTSLKPEDT AVYYCKIDWY LNSYWGQGTQ VTVSS       115

SEQ ID NO: 792         moltype = AA  length = 114
FEATURE                Location/Qualifiers
REGION                 1..114
                       note = Synthetic polymer.
source                 1..114
                       mol_type = protein
                       organism = synthetic construct
SEQUENCE: 792
EVQLVESGGG LVQAGGSLRL SCAASGVDAS NSAMGWYRQA PGKQREWVAR ITGGGLIAYT  60
DSVKGRFTIS RDNAKSTVYL QMNSLEPEDT AVYYCNTINS RDGWGQGTQV TVSS        114

SEQ ID NO: 793         moltype = AA  length = 111
FEATURE                Location/Qualifiers
REGION                 1..111
                       note = Synthetic polymer.
source                 1..111
                       mol_type = protein
                       organism = synthetic construct
SEQUENCE: 793
EVQLVESGGG LVQAGGSLTI SCAASGITFS DSIVSWYRRA RGKQREWVAG ISNGGTTKYA  60
ESVLGRFTIS RDNAKNNVYL QMNGLNPEDT AVYLCKVRQY WGQGTQVTVS S           111

SEQ ID NO: 794         moltype = AA  length = 130
FEATURE                Location/Qualifiers
REGION                 1..130
                       note = Synthetic polymer.
source                 1..130
                       mol_type = protein
                       organism = synthetic construct
SEQUENCE: 794
EVQLVESGGG LVQAGGSLRL SCAASESTVL INAMGWYRQA PGKQRELVAS ISSGGSTNYA  60
DSVKGRFTIS RDNAKNTVYL QMNSLKPEDT AVYYCNADVY PQDYGLGYVE GKVYYGHDYW  120
GTGTLVTVSS                                                         130

SEQ ID NO: 795         moltype = AA  length = 119
FEATURE                Location/Qualifiers
REGION                 1..119
                       note = Synthetic polymer.
source                 1..119
                       mol_type = protein
```

```
                         organism = synthetic construct
SEQUENCE: 795
EVQLVESGGG LVQAGGSLRL SCAASGSTFS NYVSNYAMGW GRQAPGTQRE LVASISNGDT  60
TNYADSVKGR FTISRDNAKN TVYLQMNSLK PEDTAVYYCF EHQVAGLTWG QGTQVTVSS   119

SEQ ID NO: 796           moltype = AA  length = 118
FEATURE                  Location/Qualifiers
REGION                   1..118
                         note = Synthetic polymer.
SITE                     27
                         note = misc_feature - Xaa can be any naturally occurring
                          amino acid
SITE                     32
                         note = misc_feature - Xaa can be any naturally occurring
                          amino acid
SITE                     75
                         note = misc_feature - Xaa can be any naturally occurring
                          amino acid
source                   1..118
                         mol_type = protein
                         organism = synthetic construct
SEQUENCE: 796
EVQLVESGGG LVQAGGSLRL SCVASGXALK IXVMGWYRQA PGKQRELVAA ITSGGRTNYS  60
DSVKGRFTIS GDNAXNTVYL QMNSLKSEDT AVYYCREWNS GYPPVDYWGQ GTQVTVSS    118

SEQ ID NO: 797           moltype = AA  length = 120
FEATURE                  Location/Qualifiers
REGION                   1..120
                         note = Synthetic polymer.
source                   1..120
                         mol_type = protein
                         organism = synthetic construct
SEQUENCE: 797
EVQLVESGGG LVQAGGSLRL SCAASGRTFS SGTMGWFRRA PGKEREFVAS IPWSGGRTYY  60
ADSVKDRFTI SRDNAQNTVF LQMNSLKPED TAVYYCAFKE RSTGWDFASW GQGIQVTVSS  120

SEQ ID NO: 798           moltype = AA  length = 127
FEATURE                  Location/Qualifiers
REGION                   1..127
                         note = Synthetic polymer.
source                   1..127
                         mol_type = protein
                         organism = synthetic construct
SEQUENCE: 798
EVQLVESGGG LVQTGGSLRL SCAASGFTLD YYGIGWFRQA PGKEREGVSF ISGSDGSTYY  60
AESVKGRFTI SRDKAKNTVY LQMNSLKPED TAVYYCAADP WGPPSIATMT SYEYKHWGQG  120
TQVTVSS                                                            127

SEQ ID NO: 799           moltype = AA  length = 113
FEATURE                  Location/Qualifiers
REGION                   1..113
                         note = Synthetic polymer.
source                   1..113
                         mol_type = protein
                         organism = synthetic construct
SEQUENCE: 799
EVQLVESGGG LVQPGGSLRL SCAASGFTFS TYTMIWLRRA PGKGFEWVST IDKDGNTNYV  60
DSVKGRFAVS RDNTKNTLYL QMNSLKPEDT AMYYCTKHGS SARGQGTRVT VSS         113

SEQ ID NO: 800           moltype = AA  length = 114
FEATURE                  Location/Qualifiers
REGION                   1..114
                         note = Synthetic polymer.
source                   1..114
                         mol_type = protein
                         organism = synthetic construct
SEQUENCE: 800
EVQLVESGGG LVEPGGSLRL SCVASGFTFS SYDMSWVRQA PGKGLEWVST INSGGGITYR  60
GSVKGRFTIS RDNAKNTLYL QMNSLKPEDT AVYYCENGGS SYRRGQGTQV TVSS        114

SEQ ID NO: 801           moltype = AA  length = 114
FEATURE                  Location/Qualifiers
REGION                   1..114
                         note = Synthetic polymer.
source                   1..114
                         mol_type = protein
                         organism = synthetic construct
SEQUENCE: 801
QVQLVQSGAE LKKPGASVKM SCKASGYTFT GYTMHWVKQA PGQGLEWIGY INPRSGYTEY  60
```

```
NQKFKDRTTL TADKSTSTAY MELSSLRSED SAVYYCARPW FAYWGQGTLV TVSS        114

SEQ ID NO: 802         moltype = AA  length = 114
FEATURE                Location/Qualifiers
REGION                 1..114
                       note = Synthetic polymer.
source                 1..114
                       mol_type = protein
                       organism = synthetic construct
SEQUENCE: 802
QVQLVQSGAE VKKPGASVKM SCKASGYTFT GYTMHWVKQA PGQGLEWIGY INPRSGYTEY  60
NQKFKDRTTL TADKSTSTAY MELSSLRSED TAVYYCARPW FAYWGQGTLV TVSS        114

SEQ ID NO: 803         moltype = AA  length = 114
FEATURE                Location/Qualifiers
REGION                 1..114
                       note = Synthetic polymer.
source                 1..114
                       mol_type = protein
                       organism = synthetic construct
SEQUENCE: 803
QVQLVQSGAE VKKPGASVKM SCKASGYTFT GYTMHWVRQA PGQGLEWIGY INPRSGYTEY  60
NQKFKDRTTL TADKSTSTAY MELSSLRSED TAVYYCARPW FAYWGQGTLV TVSS        114

SEQ ID NO: 804         moltype = AA  length = 114
FEATURE                Location/Qualifiers
REGION                 1..114
                       note = Synthetic polymer.
source                 1..114
                       mol_type = protein
                       organism = synthetic construct
SEQUENCE: 804
QVQLVQSGAE VKKPGASVKV SCKASGYTFT GYTMHWVRQA PGQGLEWIGY INPRSGYTEY  60
NQKFKDRTTL TADKSTSTAY MELSSLRSED TAVYYCARPW FAYWGQGTLV TVSS        114

SEQ ID NO: 805         moltype = AA  length = 114
FEATURE                Location/Qualifiers
REGION                 1..114
                       note = Synthetic polymer.
source                 1..114
                       mol_type = protein
                       organism = synthetic construct
SEQUENCE: 805
QVQLVQSGAE VKKPGASVKV SCKASGYTFT GYTMHWVRQA PGQGLEWIGY INPRSGYTEY  60
NQKFKDRTTI TADKSTSTAY MELSSLRSED TAVYYCARPW FAYWGQGTLV TVSS        114

SEQ ID NO: 806         moltype = AA  length = 113
FEATURE                Location/Qualifiers
REGION                 1..113
                       note = Synthetic polymer.
source                 1..113
                       mol_type = protein
                       organism = synthetic construct
SEQUENCE: 806
DIVMTQSPAS LTVTPGEKVT ITCKSSQSLL NSGNQKNYLT WYQQKPGQPP KLLIYWASTR  60
ESGVPDRFTG SGSGTDFTLT ISSLQAEDVA VYYCQNDYSY PLTFGQGTKL EIK         113

SEQ ID NO: 807         moltype = AA  length = 113
FEATURE                Location/Qualifiers
REGION                 1..113
                       note = Synthetic polymer.
source                 1..113
                       mol_type = protein
                       organism = synthetic construct
SEQUENCE: 807
DIVMTQSPAS LSVTPGEKVT ITCKSSQSLL NSGNQKNYLT WYQQKPGQPP KLLIYWASTR  60
ESGVPDRFTG SGSGTDFTLT ISSLQAEDVA VYYCQNDYSY PLTFGQGTKL EIK         113

SEQ ID NO: 808         moltype = AA  length = 113
FEATURE                Location/Qualifiers
REGION                 1..113
                       note = Synthetic polymer.
source                 1..113
                       mol_type = protein
                       organism = synthetic construct
SEQUENCE: 808
DIVMTQSPAF LSVTPGEKVT ITCKSSQSLL NSGNQKNYLT WYQQKPGQPP KLLIYWASTR  60
ESGVPDRFTG SGSGTDFTLT ISSLQAEDVA VYYCQNDYSY PLTFGQGTKL EIK         113
```

-continued

```
SEQ ID NO: 809          moltype = AA  length = 113
FEATURE                 Location/Qualifiers
REGION                  1..113
                        note = Synthetic polymer.
source                  1..113
                        mol_type = protein
                        organism = synthetic construct
SEQUENCE: 809
DIVMTQSPAF LSVTPGEKVT ITCKSSQSLL NSGNQKNYLT WYQQKPGQPP KLLIYWASTR  60
ESGVPDRFSG SGSGTDFTLT ISSLQAEDVA VYYCQNDYSY PLTFGQGTKL EIK         113

SEQ ID NO: 810          moltype = AA  length = 5
FEATURE                 Location/Qualifiers
REGION                  1..5
                        note = Synthetic polymer.
source                  1..5
                        mol_type = protein
                        organism = synthetic construct
SEQUENCE: 810
GGGGS                                                              5

SEQ ID NO: 811          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 811
GGGGSGGGGS                                                         10

SEQ ID NO: 812          moltype = AA  length = 15
FEATURE                 Location/Qualifiers
REGION                  1..15
                        note = Synthetic polymer.
source                  1..15
                        mol_type = protein
                        organism = synthetic construct
SEQUENCE: 812
GGGGSGGGGS GGGGS                                                   15

SEQ ID NO: 813          moltype = AA  length = 20
FEATURE                 Location/Qualifiers
REGION                  1..20
                        note = Synthetic polymer.
source                  1..20
                        mol_type = protein
                        organism = synthetic construct
SEQUENCE: 813
GGGGSGGGGS GGGGSGGGGS                                              20

SEQ ID NO: 814          moltype = AA  length = 25
FEATURE                 Location/Qualifiers
REGION                  1..25
                        note = Synthetic polymer.
source                  1..25
                        mol_type = protein
                        organism = synthetic construct
SEQUENCE: 814
GGGGSGGGGS GGGGSGGGGS GGGGS                                        25

SEQ ID NO: 815          moltype = AA  length = 30
FEATURE                 Location/Qualifiers
REGION                  1..30
                        note = Synthetic polymer.
source                  1..30
                        mol_type = protein
                        organism = synthetic construct
SEQUENCE: 815
GGGGSGGGGS GGGGSGGGGS GGGGSGGGGS                                   30

SEQ ID NO: 816          moltype = AA  length = 35
FEATURE                 Location/Qualifiers
REGION                  1..35
                        note = Synthetic polymer.
source                  1..35
                        mol_type = protein
                        organism = synthetic construct
SEQUENCE: 816
```

-continued

```
GGGGSGGGGS GGGGSGGGGS GGGGSGGGGS GGGGS                        35

SEQ ID NO: 817          moltype = AA  length = 40
FEATURE                 Location/Qualifiers
REGION                  1..40
                        note = Synthetic polymer.
source                  1..40
                        mol_type = protein
                        organism = synthetic construct
SEQUENCE: 817
GGGGSGGGGS GGGGSGGGGS GGGGSGGGGS GGGGSGGGGS                   40

SEQ ID NO: 818          moltype = AA  length = 16
FEATURE                 Location/Qualifiers
REGION                  1..16
                        note = Synthetic polymer.
source                  1..16
                        mol_type = protein
                        organism = synthetic construct
SEQUENCE: 818
GGSGGSGGGG SGGGGS                                             16

SEQ ID NO: 819          moltype = AA  length = 8
FEATURE                 Location/Qualifiers
REGION                  1..8
                        note = Synthetic polymer.
source                  1..8
                        mol_type = protein
                        organism = synthetic construct
SEQUENCE: 819
GGGGGGGG                                                      8

SEQ ID NO: 820          moltype = AA  length = 6
FEATURE                 Location/Qualifiers
REGION                  1..6
                        note = Synthetic polymer.
source                  1..6
                        mol_type = protein
                        organism = synthetic construct
SEQUENCE: 820
GGGGGG                                                        6

SEQ ID NO: 821          moltype = AA  length = 5
FEATURE                 Location/Qualifiers
REGION                  1..5
                        note = Synthetic polymer.
source                  1..5
                        mol_type = protein
                        organism = synthetic construct
SEQUENCE: 821
EAAAK                                                         5

SEQ ID NO: 822          moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 822
EAAAKEAAAK                                                    10

SEQ ID NO: 823          moltype = AA  length = 15
FEATURE                 Location/Qualifiers
REGION                  1..15
                        note = Synthetic polymer.
source                  1..15
                        mol_type = protein
                        organism = synthetic construct
SEQUENCE: 823
EAAAKEAAAK EAAAK                                              15

SEQ ID NO: 824          moltype = AA  length = 12
FEATURE                 Location/Qualifiers
REGION                  1..12
                        note = Synthetic polymer.
source                  1..12
                        mol_type = protein
                        organism = synthetic construct
```

```
SEQUENCE: 824
AEAAAKEAAA KA                                                12

SEQ ID NO: 825          moltype = AA  length = 17
FEATURE                 Location/Qualifiers
REGION                  1..17
                        note = Synthetic polymer.
source                  1..17
                        mol_type = protein
                        organism = synthetic construct
SEQUENCE: 825
AEAAAKEAAA KEAAAKA                                           17

SEQ ID NO: 826          moltype = AA  length = 22
FEATURE                 Location/Qualifiers
REGION                  1..22
                        note = Synthetic polymer.
source                  1..22
                        mol_type = protein
                        organism = synthetic construct
SEQUENCE: 826
AEAAAKEAAA KEAAAKEAAA KA                                     22

SEQ ID NO: 827          moltype = AA  length = 27
FEATURE                 Location/Qualifiers
REGION                  1..27
                        note = Synthetic polymer.
source                  1..27
                        mol_type = protein
                        organism = synthetic construct
SEQUENCE: 827
AEAAAKEAAA KEAAAKEAAA KEAAAKA                                27

SEQ ID NO: 828          moltype = AA  length = 46
FEATURE                 Location/Qualifiers
REGION                  1..46
                        note = Synthetic polymer.
source                  1..46
                        mol_type = protein
                        organism = synthetic construct
SEQUENCE: 828
AEAAAKEAAA KEAAAKEAAA KALEAEAAAK EAAAKEAAAK EAAAKA           46

SEQ ID NO: 829          moltype = AA  length = 5
FEATURE                 Location/Qualifiers
REGION                  1..5
                        note = Synthetic polymer.
source                  1..5
                        mol_type = protein
                        organism = synthetic construct
SEQUENCE: 829
PAPAP                                                        5

SEQ ID NO: 830          moltype = AA  length = 18
FEATURE                 Location/Qualifiers
REGION                  1..18
                        note = Synthetic polymer.
source                  1..18
                        mol_type = protein
                        organism = synthetic construct
SEQUENCE: 830
KESGSVSSEQ LAQFRSLD                                          18

SEQ ID NO: 831          moltype = AA  length = 14
FEATURE                 Location/Qualifiers
REGION                  1..14
                        note = Synthetic polymer.
source                  1..14
                        mol_type = protein
                        organism = synthetic construct
SEQUENCE: 831
EGKSSGSGSE SKST                                              14

SEQ ID NO: 832          moltype = AA  length = 12
FEATURE                 Location/Qualifiers
REGION                  1..12
                        note = Synthetic polymer.
source                  1..12
                        mol_type = protein
```

```
                        organism = synthetic construct
SEQUENCE: 832
GSAGSAAGSG EF                                                12

SEQ ID NO: 833          moltype = AA  length = 5
FEATURE                 Location/Qualifiers
REGION                  1..5
                        note = Synthetic polymer.
source                  1..5
                        mol_type = protein
                        organism = synthetic construct
SEQUENCE: 833
GGGSE                                                        5

SEQ ID NO: 834          moltype = AA  length = 5
FEATURE                 Location/Qualifiers
REGION                  1..5
                        note = Synthetic polymer.
source                  1..5
                        mol_type = protein
                        organism = synthetic construct
SEQUENCE: 834
GSESG                                                        5

SEQ ID NO: 835          moltype = AA  length = 5
FEATURE                 Location/Qualifiers
REGION                  1..5
                        note = Synthetic polymer.
source                  1..5
                        mol_type = protein
                        organism = synthetic construct
SEQUENCE: 835
GSEGS                                                        5

SEQ ID NO: 836          moltype = AA  length = 35
FEATURE                 Location/Qualifiers
REGION                  1..35
                        note = Synthetic polymer.
source                  1..35
                        mol_type = protein
                        organism = synthetic construct
SEQUENCE: 836
GEGGSGEGSS GEGSSSEGGG SEGGGSEGGG SEGGS                       35

SEQ ID NO: 837          moltype = DNA  length = 20
FEATURE                 Location/Qualifiers
misc_feature            1..20
                        note = Synthetic polymer.
source                  1..20
                        mol_type = other DNA
                        organism = synthetic construct
SEQUENCE: 837
ttatgcttcc ggctcgtatg                                        20

SEQ ID NO: 838          moltype = DNA  length = 29
FEATURE                 Location/Qualifiers
misc_feature            1..29
                        note = Synthetic polymer.
source                  1..29
                        mol_type = other DNA
                        organism = synthetic construct
SEQUENCE: 838
gatgtgcagc tgcaggagtc tggrggagg                              29

SEQ ID NO: 839          moltype = DNA  length = 34
FEATURE                 Location/Qualifiers
misc_feature            1..34
                        note = Synthetic polymer.
source                  1..34
                        mol_type = other DNA
                        organism = synthetic construct
SEQUENCE: 839
ctagtgcggc cgctgaggag acggtgacct gggt                        34

SEQ ID NO: 840          moltype = DNA  length = 22
FEATURE                 Location/Qualifiers
misc_feature            1..22
                        note = Synthetic polymer.
source                  1..22
```

```
                        mol_type = other DNA
                        organism = synthetic construct
SEQUENCE: 840
tcacacagga aacagctatg ac                                              22

SEQ ID NO: 841          moltype = DNA  length = 24
FEATURE                 Location/Qualifiers
misc_feature            1..24
                        note = Synthetic polymer.
source                  1..24
                        mol_type = other DNA
                        organism = synthetic construct
SEQUENCE: 841
cgccagggtt ttcccagtca cgac                                            24

SEQ ID NO: 842          moltype = AA  length = 138
FEATURE                 Location/Qualifiers
REGION                  1..138
                        note = Synthetic polymer.
source                  1..138
                        mol_type = protein
                        organism = synthetic construct
SEQUENCE: 842
QVQLQESGGG LVQAGDSLRL SCKGSGRNFG SYNMGWYRQA PGKEREFVAA VAWIGGTTYY  60
ADSVKGRFTI SRDNAERMVY LQMTNLKPED TAIYYCNADI ERRPLFGSWG PGTQVTVSSA  120
AAYPYDVPDY GSHHHHHH                                                138

SEQ ID NO: 843          moltype = AA  length = 355
FEATURE                 Location/Qualifiers
REGION                  1..355
                        note = Synthetic polymer.
source                  1..355
                        mol_type = protein
                        organism = synthetic construct
SEQUENCE: 843
QVQLQESGGG LVQTGGSLRL SCAASGSIFV GNAMGWYRQA LGNQRELVAG ITSDGTTYYP  60
DSVKGRFTIS RDNDKNTIYL QMNSLKPEDT AVYYCNLWPP RIGFASWGQG TQVTVSSVDG  120
GSGGSGGSGG SGGSGGSRSG GSGGSGGSGG SGGSGGSGGS GGSGGSGGSG GSGGSGGSAA  180
AMCDLPQTHS LGSRRTLMLL AQMRRISLFS CLKDRHDFGF PQEEFGNQFQ KAETIPVLHE  240
MIQQIFNLFS TKDSSAAWDE TLLDKFYTEL YQQLNDLEAC VIQGVGVTET PLMKEDSILA  300
VRKYFQRITL YLKEKKYSPC AWEVVRAEIM ASFSLSTNLQ ESLRSKELEH HHHHH       355

SEQ ID NO: 844          moltype = DNA  length = 429
FEATURE                 Location/Qualifiers
misc_feature            1..429
                        note = Synthetic polymer.
source                  1..429
                        mol_type = other DNA
                        organism = synthetic construct
SEQUENCE: 844
caggtgcagc tgcaggagtc tggggggagga ttggtagagg ctgagggctc tctgagactc  60
tcctgtgcag cctctggacg caccttcggt agctatgcca tgggctggtt ccgccaggct  120
ccaggaaagt cgcgcgagtt ggtcgcagct attagtagtg gtggtaccac atactatgca  180
gactctgtga agggccgatt caccatctcc agagacaacg ccaggaacac ggtgtatctg  240
caaacgaaca gcctgaaacc tgaggacacg gccgtttatt actgcgcagc tagaacaggg  300
agtgcctact acactaatcg tattgactgg ccctactggg gccaggggac ccaggtcacc  360
gtctcctcag cggccgcata cccgtacgac gttccggact acggttccca ccaccatcac  420
catcactag                                                          429

SEQ ID NO: 845          moltype = DNA  length = 429
FEATURE                 Location/Qualifiers
misc_feature            1..429
                        note = Synthetic polymer.
source                  1..429
                        mol_type = other DNA
                        organism = synthetic construct
SEQUENCE: 845
caggtgcagc tgcaggagtc tgggggagga ttggtagagg ctgagggctc tctgagactc  60
tcctgtgcag cctctggacg caccttcggt agctatgcca tgggctggtt ccgccaggct  120
ccaggaaagt cgcgcgagtt ggtcgcagct attagtagtg gtggtaccac atactatgca  180
gactctgtga agggccgatt caccatctcc agagacaacg ccaggaacac ggtgtatctg  240
caaacgaaca gcccgaaacc tgaggacacg gccgtttatt actgcgcagc tagaacaggg  300
agtgcctact acactaatcg tattgactgg ccctactggg gccaggggac ccaggtcacc  360
gtctcctcag cggccgcata cccgtacgac gttccggact acggttccca ccaccatcac  420
catcactag                                                          429

SEQ ID NO: 846          moltype = DNA  length = 429
FEATURE                 Location/Qualifiers
misc_feature            1..429
```

```
                        note = Synthetic polymer.
source                  1..429
                        mol_type = other DNA
                        organism = synthetic construct
SEQUENCE: 846
caggtgcagc tgcaggagtc tgggggagga ttggtggagg ctgagggctc tctgagactc  60
tcctgtgcag cctctggacg caccttcggt acctatgcgc tggcctggtt ccgccaggct  120
ccaggaaagt cgcgcgagtt ggtcgcagct attagtagtg gtggtagcac atactatgca  180
gactctgtga agggccgatt caccatctcc agagacaacg ccaggaacac ggtgtatctg  240
caaacgaaca gcctgaaacc tgaggacacg gccgtttatt actgcgcagc aaaaacaggg  300
agtgcctact acactaatcg tattgactgg ccctactggg gccaggggac ccaggtcacc  360
gtctcctcag cggccgcata cccgtacgac gttccggact acggttccca ccaccatcac  420
catcactag                                                          429

SEQ ID NO: 847          moltype = DNA  length = 429
FEATURE                 Location/Qualifiers
misc_feature            1..429
                        note = Synthetic polymer.
source                  1..429
                        mol_type = other DNA
                        organism = synthetic construct
SEQUENCE: 847
caggtgcagc tgcaggagtc tgggggagga ttggtgcagg ctgggggctc tctgagactc  60
tcctgtgcag cctctggacg caccttcagt agctatgcca tgggctggtt ccgccaggct  120
ccagggaagg agcgcgagtt ggtcgcagct attagtaatg gtggtagcgc atactatgca  180
gactctgtga agggccgatt caccatctcc agagacaacg ccaggaacac ggtgtatctg  240
caaacgaaca gcctgaaacc tgaggacacg gccgtttatt actgcgcagc tagaagaggg  300
agtgcctact acactaatcg tattgactgg ccctactggg gccaggggac ccaggtcacc  360
gtctcctcag cggccgcata cccgtacgac gttccggact acggttccca ccaccatcac  420
catcactag                                                          429

SEQ ID NO: 848          moltype = DNA  length = 429
FEATURE                 Location/Qualifiers
misc_feature            1..429
                        note = Synthetic polymer.
source                  1..429
                        mol_type = other DNA
                        organism = synthetic construct
SEQUENCE: 848
caggtgcagc tgcaggagtc tgggggaggc ttggtgcagg ctggggggtc tctgagactc  60
tcctgtgcag cctctggacg caccttcagt acgtatgcca tgggctggtt ccgccaggct  120
ccagggaagg agcgcgagtt ggtcgcagct attagtaatg gtggtagcgc atactatgca  180
gactctgtga agggccgatt caccatctcc agagacaacg ccaggaacac ggtgtatctg  240
caaacgaaca gcctgaaacc tgaggacacg gccgtttatt actgcgcagc tagaagaggg  300
agtgcctact acactaatcg tattgactgg ccctactggg gccaggggac ccaggtcacc  360
gtctcctcag cggccgcata cccgtacgac gttccggact acggttccca ccaccatcac  420
catcactag                                                          429

SEQ ID NO: 849          moltype = DNA  length = 429
FEATURE                 Location/Qualifiers
misc_feature            1..429
                        note = Synthetic polymer.
source                  1..429
                        mol_type = other DNA
                        organism = synthetic construct
SEQUENCE: 849
caggtgcagc tgcaggagtc tgggggagga ttggtagagg ctgagggctc tctgagactc  60
tcctgtatag cctctggacg caccttcggt acctatgcca tgggctggtt ccgccaggct  120
ccaggaaagg agcgcgagtt ggtcgcagct attagtagtg gtggtagcgc atattatgca  180
gactctgtga agggccgatt caccatctcc agagacaacg ccaggaacac ggtgtatctg  240
caaacgaaca gcctgaaacc tgaggacacg gctgtttatt actgcgcagc tagaagaggg  300
agtgcctact acactaatcg tattgattgg ccctactggg gccaggggac ccaggtcacc  360
gtctcctcag cggccgcata cccgtacgac gttccggact acggttccca ccaccatcac  420
catcactag                                                          429

SEQ ID NO: 850          moltype = DNA  length = 429
FEATURE                 Location/Qualifiers
misc_feature            1..429
                        note = Synthetic polymer.
source                  1..429
                        mol_type = other DNA
                        organism = synthetic construct
SEQUENCE: 850
caggtgcagc tgcaggagtc tggaggagga ttggtagagg ctgagggctc tctgagactc  60
tcctgtatag cctctggacg caccttcggt acctatgcca tgggctggtt ccgccaggct  120
ccaggaaagg agcgcgagtt ggtcgcagct attagtactg gtggtagcac atactatgca  180
gactctgtga agggccgatt caccatctcc agagacaacg ccaggaacac ggtgtatctg  240
caaacgaaca gcctgaaacc tgaggacacg gccgtttatt actgcgcagc tagaagaggt  300
agtgcctact acactaatca cgttgactgg ccctactggg gccaggggac ccaggtcacc  360
```

```
gtctcctcag cggccgcata cccgtacgac gttccggact acggttccca ccaccatcac  420
catcactag                                                          429

SEQ ID NO: 851         moltype = DNA  length = 429
FEATURE                Location/Qualifiers
misc_feature           1..429
                       note = Synthetic polymer.
source                 1..429
                       mol_type = other DNA
                       organism = synthetic construct
SEQUENCE: 851
caggtgcagc tgcaggagtc tgggggagga ttggtagagg ctgagggctc tctgagactc  60
tcctgtgcag cctctggacg cgccttcggt agctatgcca tgggctggtt ccgccaggct  120
ccaggcttgg agcgcgagct ggtcgcagct attagtagtg gtggtaccac atactatgca  180
gactctgtga agggccgatt caccatctcc agagacaacg ccaggaacac ggtgtatttg  240
caaacgaaca gcctgaaacc tgaggacacg gccgtttatt actgcgcagc tagaacaggg  300
ggtgccgcct acactaggcg tattgactgg ccctactggg gccaggggac ccaggtcacc  360
gtctcctcag cggccgcata cccgtacgac gttccggact acggttccca ccaccatcac  420
catcactag                                                          429

SEQ ID NO: 852         moltype = DNA  length = 429
FEATURE                Location/Qualifiers
misc_feature           1..429
                       note = Synthetic polymer.
source                 1..429
                       mol_type = other DNA
                       organism = synthetic construct
SEQUENCE: 852
caggtgcagc tgcaggagtc tgggggagga ttggtagagg ctgagggctc tctgagactc  60
tcctgtgcag cctctggacg caccttcggt agttatgcca tgggctggtt ccgccaggct  120
ccaggaaagg agcgcgagtt ggtcgcagct attagtagtg gtggtagcac attgtatgca  180
gactctgtga agggccgatt caccatctcc agagacaacg ccaagaacac ggtgtatctg  240
caaatgaaca gcctgaaacc tgaggacacg gccgtttatt actgcgcagc tagaagtggg  300
ggtgcctact acactgcccg tgttgactgg ccctactggg gccaggggac ccaggtcacc  360
gtctcctcag cggccgcata cccgtacgac gttccggact acggttccca ccaccatcac  420
catcactag                                                          429

SEQ ID NO: 853         moltype = DNA  length = 429
FEATURE                Location/Qualifiers
misc_feature           1..429
                       note = Synthetic polymer.
source                 1..429
                       mol_type = other DNA
                       organism = synthetic construct
SEQUENCE: 853
caggtgcagc tgcaggagtc tgggggagga ttggtagagg ctgagggctc tctgagactc  60
tcctgtgcag cctctggacg caccttcggt agttatgcca tgggctggtt ccgccaggct  120
ccaggaaagg agcgcgagtt ggtcgcagct attagtagtg gtggtagcac attgtatgca  180
ggctctgtga agggccgatt caccatttcc aaagacaacg ccaagaacac ggtgtatctg  240
caaatgaaca gcctgaaacc tgaggacacg gccgtttatt actgcgcagc tagaagtggg  300
ggtgcctact acactgcccg tgttgactgg ccctactggg gccaggggac ccaggtcacc  360
gtctcctcag cggccgcata cccgtacgac gttccggact acggttccca ccaccatcac  420
catcactag                                                          429

SEQ ID NO: 854         moltype = DNA  length = 429
FEATURE                Location/Qualifiers
misc_feature           1..429
                       note = Synthetic polymer.
source                 1..429
                       mol_type = other DNA
                       organism = synthetic construct
SEQUENCE: 854
caggtgcagc tgcaggagtc tgggggagga ttggtagagg ctgagggctc tccgagactc  60
tcctgtgcag cctctggacg caccttcggt agctatgcca tgggctggtt ccgccaggct  120
ccaggaaagg agcgcgagtt ggtcgcagct attagtagtg gtggtattac atactatgca  180
gactctgtga agggccgatt caccatctcc agagacaacg ccaagaacac ggtgtatctg  240
caaatgaaca gcctgaaacc tgaggacacg gccgtttatt actgcgcagc tagaagtggg  300
agtgcctact acactacccg tgttgactgg ccctactggg gccaggggac ccaggtcacc  360
gtctcctcag cggccgcata cccgtacgac gttccggact acggttccca ccaccatcac  420
catcactag                                                          429

SEQ ID NO: 855         moltype = DNA  length = 429
FEATURE                Location/Qualifiers
misc_feature           1..429
                       note = Synthetic polymer.
source                 1..429
                       mol_type = other DNA
                       organism = synthetic construct
SEQUENCE: 855
```

```
caggtgcagc tgcaggagtc tgggggagga ttggtagagg ctgagggctc tctgagactc  60
tcctgtgcag cctctggacg caccttcggt agctatgcca tgggctggtt ccgccaggct  120
gcaggaaagg agcgcgagtt ggtcgcagct attagtgctg gtggtagcac actctatgct  180
gacaatgtga agggccgatt caccatctcc agagacaacg ccaggaacac ggtgtatctg  240
ctatcgaaca gcctgaagcc tgaggacacg gccgtttatt actgcgcagc tagaagagga  300
agtgcctact acactaatca tattgactgg ccctactggg gccaggggac ccaggtcacc  360
gtctcctcag cggccgcata cccgtacgac gttccggact acggttccca ccaccatcac  420
catcactag                                                          429

SEQ ID NO: 856         moltype = DNA  length = 429
FEATURE                Location/Qualifiers
misc_feature           1..429
                       note = Synthetic polymer.
source                 1..429
                       mol_type = other DNA
                       organism = synthetic construct
SEQUENCE: 856
caggtgcagc tgcaggagtc tggaggaggc ttggtgcagc ctgggggttc tctgagactc  60
tcctgtgcag cctctggacg caccttcggt agctatgcca tgggctggtt ccgccaggct  120
gcaggaaagg agcgcgagtt ggtcgcagct attagtgctg gtggtagcac actctatgct  180
gacaatgtga agggccgatt caccatctcc agagacaacg ccaggaacac ggtgtatctg  240
ctatcgaaca gcctgaagcc tgaggacacg gccgtttatt actgcgcagc tagaagagga  300
agtgcctact acactaatca tattgactgg ccctactggg gccaggggac ccaggtcacc  360
gtctcctcag cggccgcata cccgtacgac gttccggact acggttccca ccaccatcac  420
catcactag                                                          429

SEQ ID NO: 857         moltype = DNA  length = 429
FEATURE                Location/Qualifiers
misc_feature           1..429
                       note = Synthetic polymer.
source                 1..429
                       mol_type = other DNA
                       organism = synthetic construct
SEQUENCE: 857
caggtgcagc tgcaggagtc tgggggaggc ttggtgcagg ctggggggtc tctgagactc  60
tcctgcgcag cctctggaaa catcgacagt atcgcttcca tgggctggta ccgccaggct  120
ccagggaagc agcgcgaatt ggtcgcagcg attagtgttg gtggtagcac atactatgca  180
gactctgtga agggccgatt caccatctcc agagacaacg ccaggaacac ggtgtatctg  240
caaacgaaca gcctgaagcc tgaggacacg gccgtttatt actgcgcagc tagaagaggg  300
agtgcctact acactagtcg tattgactgg ccctactggg gccaggggac ccaggtcacc  360
gtctcctcag cggccgcata cccgtacgac gttccggact acggttccca ccaccatcac  420
catcactag                                                          429

SEQ ID NO: 858         moltype = DNA  length = 429
FEATURE                Location/Qualifiers
misc_feature           1..429
                       note = Synthetic polymer.
source                 1..429
                       mol_type = other DNA
                       organism = synthetic construct
SEQUENCE: 858
caggtgcagc tgcaggagtc tggaggagga ttggtgcagg ctgagggctc tctgagactc  60
tcctgtgcag cctctggacg caccttcggt agctatgcca tgggctggtt ccgccaggct  120
ccagggaagg agcgcgagtt ggtcgcaggt attagtagtg gtggtattac aaactatgca  180
cactctgtga agggccgatt caccatctcc agagacattg acaagaacac ggtgttcctg  240
caaatgaaca gcctgaaacc tgaggacacg gccgtttatt actgtgcagc tagaagtggg  300
ggtgcctact acacttcccg tgttgactgg ccctactggg gccaggggac ccaggtcacc  360
gtctcctcag cggccgcata cccgtacgac gttccggact acggttccca ccaccatcac  420
catcactag                                                          429

SEQ ID NO: 859         moltype = DNA  length = 429
FEATURE                Location/Qualifiers
misc_feature           1..429
                       note = Synthetic polymer.
source                 1..429
                       mol_type = other DNA
                       organism = synthetic construct
SEQUENCE: 859
caggtgcagc tgcaggagtc tgggggagga ttggtgcagg ctggggactc tctgagactc  60
tcctgtgcag cctctggacg cactttcagt agctatgtca tgggctggtt ccgccaggtt  120
ccagggaagc agcgcgagtt ggtcgcagcg attactagtg gtcttagcac atactatgca  180
gactccctga agggccgatt caccatctcc agagacaacg ccaagaacac gatgtatctg  240
caaatgaaca gcctgaaact tgaggacacg gccgtttatt actgtgcagc cagggagggt  300
ggaggtatat ggactagttc tactcagtat gactactggg gccaggggac ccaggtcacc  360
gtctcctcag cggccgcata cccgtacgac gttccggact acggttccca ccaccatcac  420
catcactag                                                          429

SEQ ID NO: 860         moltype = DNA  length = 429
FEATURE                Location/Qualifiers
```

```
misc_feature           1..429
                       note = Synthetic polymer.
source                 1..429
                       mol_type = other DNA
                       organism = synthetic construct
SEQUENCE: 860
caggtgcagc tgcaggagtc tggaggagga ttggtgtagg ctgggggctc tctgagactc  60
tcctgtgcag cctctggacg caccttcagt gattatgcca tgggctggtt ccgccaggct  120
ccagggaagg agcgtgagtt tatagcaggt attagttggg ggggttcaag cacatactat  180
gcagactccg tgaagggccg attcaccatc tccagagaca acgccaagaa cacgatgtat  240
ctgcaaatga acagcctgaa acctgaggac acggccgttt attactgtgc agcgcgctta  300
agtggtgtaa gtagatccga ccggccgtat gactactggg gccaggggac ccaggtcacc  360
gtctcctcag cggccgcata cccgtacgac gttccggact acggttccca ccaccatcac  420
catcactag                                                          429

SEQ ID NO: 861         moltype = DNA  length = 405
FEATURE                Location/Qualifiers
misc_feature           1..405
                       note = Synthetic polymer.
source                 1..405
                       mol_type = other DNA
                       organism = synthetic construct
SEQUENCE: 861
caggtgcagc tgcaggagtc tgggggaggc ttggtgcagg ctgggggtc tctgagactc  60
tcctgtgcag tctctggaag actcttcagt gccaatacca tgggctggta ccgccaggct  120
ccagggaagc ggcgcgagtt ggtcgcgact attttgagta gtggtagcac aaactatgca  180
gactccgtga agggccgatt caccatctcc agagacgacg gcaagaacac ggtgtatctg  240
caaatgaaca gcctgaaacc tgacgacaca gccgtctatt actgtaattt cgcccccccg  300
cctgaggggt actggggcca ggggacccag gtcaccgtct cctcagcggc cgcatacccg  360
tacgacgttc cggactacgg ttcccaccac catcaccatc actag                  405

SEQ ID NO: 862         moltype = DNA  length = 405
FEATURE                Location/Qualifiers
misc_feature           1..405
                       note = Synthetic polymer.
source                 1..405
                       mol_type = other DNA
                       organism = synthetic construct
SEQUENCE: 862
caggtgcagc tgcaggagtc tgggggaggc ttggtgcagg ctgggggtc tctgagactc  60
tcctgtgcag tctctggaag actcttcagt gccaatacca tgggctggta ccgccaggct  120
ccagggaagc ggcgcgagtt ggtcgcgact attttgagta gcggtagcac aaactatgca  180
gactccgtga agggccgatt caccatctcc agagacgacg ccaagaacac ggtgtatctg  240
caaatgaaca gcctgaaacc tgaggacact gccgtctatt actgtaattt agcccccccg  300
cctgaggggt actggggcca ggggacccag gtcaccgtct cctcagcggc cgcatacccg  360
tacgacgttc cggactacgg ttcccaccac catcaccatc actag                  405

SEQ ID NO: 863         moltype = DNA  length = 405
FEATURE                Location/Qualifiers
misc_feature           1..405
                       note = Synthetic polymer.
source                 1..405
                       mol_type = other DNA
                       organism = synthetic construct
SEQUENCE: 863
caggtgcagc tgcaggagtc tgggggaggc ttggtgcagg ctgggggtc tctgagactc  60
tcctgtgcag tctctggaat tatctccagt atgaatgcca tgggctggta ccgccaggct  120
ccagggaagc ggcgcgagtt ggtcgcaggt cttggtagtg gggttagtac aacttatgca  180
gacgccgtga agggccgctt caccatctcc agagacaacg ccaagaacac gctgtatctg  240
caaatgaaca gcctgaaacc tgaggacaca gccgtctatt actgtaatcg atggcccccc  300
ccgtatgact actggggcca ggggacccag gtcaccgtct cctcagcggc cgcatacccg  360
tacgacgttc cggactacgg ttcccaccac catcaccatc actag                  405

SEQ ID NO: 864         moltype = DNA  length = 423
FEATURE                Location/Qualifiers
misc_feature           1..423
                       note = Synthetic polymer.
source                 1..423
                       mol_type = other DNA
                       organism = synthetic construct
SEQUENCE: 864
caggtgcagc tgcaggagtc tgggggaggc ttggtgcagg ctgggggtc tctgagactc  60
tcctgtgcag cctctggaag catcttcagt agcaatgcca tgggctggta ccgccaggcc  120
gcagggaagc ggcgcgagtt ggtcgcaggt atccgtagtg atggtaacac aaactatgta  180
gactccgtga agggccgatt caccatctcc agagaccgtg ccaagaacac ggtgtatctt  240
cagatgacca gcctaaaacc tgaggacacg gccgtctatt actgtaacta ctggcccccg  300
cccctacgac aagggggga ctatgcctac tggggccagg ggacccaggt caccgtctcc  360
tcagcggccg catacccgta cgacgttccg gactacggtt cccaccacca tcaccatcac  420
tag                                                                423
```

```
SEQ ID NO: 865         moltype = DNA  length = 429
FEATURE                Location/Qualifiers
misc_feature           1..429
                       note = Synthetic polymer.
source                 1..429
                       mol_type = other DNA
                       organism = synthetic construct
SEQUENCE: 865
caggtgcagc tgcaggagtc tggggggaggc ttggtgcagg ctggggggtc tctgagactc  60
tcctgtgcag cctctggacg cacctttagt atgtatgcca taggctggtt ccgccaggct  120
ccagggaagg agcgcgagtt ggtcgcaagt attagtagtg gtggtagcac aaactatgca  180
gactctgtga agggccgatt caccatctcc agagacaacg ccgagaaaac ggtgtatctg  240
caaatgatga gcctagaacc tgaagctacg ggtgtttatt actgtgcagc acgagacgga  300
tctgcattgt ataccgcaca tagcgactgg gactattggg gccaggggac ccaggtcacc  360
gtctcctcag cggccgcata cccgtacgac gttccggact acggttccca ccaccatcac  420
catcactag                                                         429

SEQ ID NO: 866         moltype = DNA  length = 429
FEATURE                Location/Qualifiers
misc_feature           1..429
                       note = Synthetic polymer.
source                 1..429
                       mol_type = other DNA
                       organism = synthetic construct
SEQUENCE: 866
caggtgcagc tgcaggagtc tggggggagga ttggtgcagc ctggggactc tctgagactc  60
tcctgtgcag cctctgaacg cacctttagt atgtatgcca taggctggtt ccgccaggct  120
ccagggaagg agcgcgagtt ggtcgcaggt attagtagtg gtggtagcac aaactatgca  180
gactctgtga agggccgatt caccatctcc agagacaacc ccaagaaaac ggtgtatctg  240
caaatgatga gcctagaacc tgaagacacg ggcgtttatt actgtgcagc acgatccgga  300
tctgcatact ttagtggacg ttactactgg aactattggg gccaggggac ccaggtcacc  360
gtctcctcag cggccgcata cccgtacgac gttccggact acggttccca ccaccatcac  420
catcactag                                                         429

SEQ ID NO: 867         moltype = DNA  length = 420
FEATURE                Location/Qualifiers
misc_feature           1..420
                       note = Synthetic polymer.
source                 1..420
                       mol_type = other DNA
                       organism = synthetic construct
SEQUENCE: 867
caggtgcagc tgcaggagtc tggggggaggc ttggtgcagg ctggggggtc tctgagactc  60
tcctgtgtag tctctggaac catcttgagt agcaattcca tgggctggta ccgccaggct  120
ccagggaagc gccgcgaatt ggtcgcaagt attagtacgg atggtagcac caactatgca  180
gactccgtga agggccgatt caccatctcc agagacaatg ccaagagcac ggtgtttctg  240
caaatgaaca gcctgaaacc tgaggacacg gccgtctatt actgtaattt ccatcccccc  300
gtcgttcggg attgggggga tacctactgg ggccagggga cccaggtcac cgtctcctca  360
gcggccgcat acccgtacga cgttccggac tacggttccc accaccatca ccatcactag  420

SEQ ID NO: 868         moltype = DNA  length = 411
FEATURE                Location/Qualifiers
misc_feature           1..411
                       note = Synthetic polymer.
source                 1..411
                       mol_type = other DNA
                       organism = synthetic construct
SEQUENCE: 868
caggtgcagc tgcaggagtc tggggggaggc ttggtgcagg ctggggggtc tctgagactc  60
tcctgtgcag cctctggaag catcttcgtt ggcaatgcca tgggctggta ccgccaggct  120
ctagggaacc agcgcgagtt ggtcgctggc attaccagtg atggtaccac atactatcca  180
gactccgtga agggccgatt caccatctcc agagacaatg acaagaacac gatatatctg  240
caaatgaaca gtctgaaacc tgaggacacg gccgtctatt actgtaattt atggcccccg  300
cgtataggct tcgcttcctg gggccagggg acccaggtca ccgtctcctc agcggccgca  360
tacccgtacg acgttccgga ctacggttcc caccaccatc accatcacta g          411

SEQ ID NO: 869         moltype = DNA  length = 411
FEATURE                Location/Qualifiers
misc_feature           1..411
                       note = Synthetic polymer.
source                 1..411
                       mol_type = other DNA
                       organism = synthetic construct
SEQUENCE: 869
caggtgcagc tgcaggagtc tggggggaggc ttggtgcggg ctggggggtc tctgagactc  60
tcctgtgcag cctctggaag catcttcgtt ggcaatgcca tgggctggta ccgccaggct  120
ctagggaacc agcgcgagtt ggtcgctggc attaccagtg atggtaccac atactatcca  180
gactccgtga agggccgatt caccatctcc agagacaatg acaagaacac gatatatctg  240
```

-continued

```
caaatgaaca gtctgaaacc tgaggacacg gccgtctatt actgtaattt atggcccccg   300
cgtataggct tcgcttcctg gggccagggg acccaggtca ccgtctcctc agcggccgca   360
tacccgtacg acgttccgga ctacggttcc caccaccatc accatcacta g            411

SEQ ID NO: 870            moltype = DNA   length = 411
FEATURE                   Location/Qualifiers
misc_feature              1..411
                          note = Synthetic polymer.
source                    1..411
                          mol_type = other DNA
                          organism = synthetic construct
SEQUENCE: 870
caggtgcagc tgcaggagtc tggggggaggc ttggtgcaga ctggggggtc tctgagactc   60
tcctgtgcag cctctggaag catcttcgtt ggcaatgcca tgggctggta ccgccaggct   120
ctagggaacc agcgcgagtt ggtcgctggc attaccagtg atggtaccac atactatcca   180
gactccgtga agggccgatt caccatctcc agagacaatg acaagaacac gatatatctg   240
caaatgaaca gtctgaaacc tgaggacacg gccgtctatt actgtaattt atggcccccg   300
cgtataggct tcgcttcctg gggccagggg acccaggtca ccgtctcctc agcggccgca   360
tacccgtacg acgttccgga ctacggttcc caccaccatc accatcacta g            411

SEQ ID NO: 871            moltype = DNA   length = 411
FEATURE                   Location/Qualifiers
misc_feature              1..411
                          note = Synthetic polymer.
source                    1..411
                          mol_type = other DNA
                          organism = synthetic construct
SEQUENCE: 871
caggtgcagc tgcaggagtc tggaggaggc ttggtgcaga ctggggggtc tctgagactc   60
tcctgtgcag cctctggaag catcttcgtt ggcaatgcca tgggctggta ccgccaggct   120
ctagggaacc agcgcgagtt ggtcgctggc attaccagtg atggtaccac atactatcca   180
gactccgtga agggccgatt caccatctcc agagacaatg acaagaacac gatatatctg   240
caaatgaaca gtctgaaacc tgaggacacg gccgtctatt actgtaattt atggcccccg   300
cgtataggct tcgcttcctg gggccagggg acccaggtca ccgtctcctc agcggccgca   360
tacccgtacg acgttccgga ctacggttcc caccaccatc accatcacta g            411

SEQ ID NO: 872            moltype = DNA   length = 411
FEATURE                   Location/Qualifiers
misc_feature              1..411
                          note = Synthetic polymer.
source                    1..411
                          mol_type = other DNA
                          organism = synthetic construct
SEQUENCE: 872
caggtgcagc tgcaggagtc tggggggaggc ttggtgcagg ctggggggtc tctgagactc   60
tcctgtgtag tctctggaag cttcgacagt cgcaatgcca tggcctggta ccgccaggct   120
ctagggaagg agcgcgtgtg ggtcgctggc attatcagtg atggtagcac aaactatgca   180
gacgccgtga agggccgatt caccatctcc agagacaatg acaagaatac ggtgtatctg   240
caaatgaaca gtctgaaacc tgaggacacg gccgtctatt actgcaatgc atggccccccg   300
cgtataggct tgggttcctg gggccagggg acccaggtca ccgtctcctc agcggccgca   360
tacccgtacg acgttccgga ctacggttcc caccaccatc accatcacta g            411

SEQ ID NO: 873            moltype = DNA   length = 411
FEATURE                   Location/Qualifiers
misc_feature              1..411
                          note = Synthetic polymer.
source                    1..411
                          mol_type = other DNA
                          organism = synthetic construct
SEQUENCE: 873
caggtgcagc tgcaggagtc tggggggaggc ttggtgcagg ctggggggtc tctgagactc   60
tcgtgtgcag cctctggaag catctccatg ctcaatagta tgggctggta ccgccaggct   120
ctagggaagc agcgcgagtt cgtcgctggc attaccagtg tgggcgcac aaactatgcg    180
gactccgtga agggccgatt cgccatctcc agagacaatg acaagaacac ggtgtatctg   240
caaatgaaca gtctgaaacc tgaggacacg gccgtctatt actgtaatac atggccccccg   300
cgtatagcgt tcgattcctg gggccagggg acccaggtca ccgtctcctc agcggccgca   360
tacccgtacg acgttccgga ctacggttcc caccaccatc accatcacta g            411

SEQ ID NO: 874            moltype = DNA   length = 408
FEATURE                   Location/Qualifiers
misc_feature              1..408
                          note = Synthetic polymer.
source                    1..408
                          mol_type = other DNA
                          organism = synthetic construct
SEQUENCE: 874
caggtgcagc tgcaggagtc tggggggaggc ttggtgcagg ctggggggtc tctgagactc   60
tcctgtgcag cctctggaac catgtccagt atcaatgcca tgggctggta ccgccaggct   120
ccagggaagc agcgcgagtt ggtcgcaggt attctaagtg atggtaccac aaagtatgtt   180
```

```
gaatccgtga agggccgatt caccatctcc agagacaatg ccaagaatac ggtgcatctg  240
caaatgaaca gcctgaaagt tgaggacacg gccgtctatt attgtaattt ttttcccccc  300
cctgtccctg cttcctgggg ccaggggacc caggtcaccg tctcctcagc ggccgcatac  360
ccgtacgacg ttccggacta cggttcccac caccatcacc atcactag               408

SEQ ID NO: 875         moltype = DNA  length = 405
FEATURE                Location/Qualifiers
misc_feature           1..405
                       note = Synthetic polymer.
source                 1..405
                       mol_type = other DNA
                       organism = synthetic construct
SEQUENCE: 875
caggtgcagc tgcaggagtc tggggaggc ttggtgcagg ctggggggtc tctgagactc  60
tcgtgtgcag cctctggaag cttcgacagt cgcaatgcca tgggctggta ccgccaggct  120
ccagggaagc gccgcgagtg ggtcgcaact attactactg atggtcgcac aaactatgca  180
gactccgtaa aggcccgatt caccgtctcc agagacaatg ccaagaacac ggtgtatctg  240
cagatgaaca gcctgaaacc agacgacacg gccgtctatt actgtaatgc agcgcctccg  300
atcttcaatt cctggggcca ggggacccag gtcaccgtct cctcagcggc cgcatacccg  360
tacgacgttc cggactacgg ttcccaccac catcaccatc actag               405

SEQ ID NO: 876         moltype = DNA  length = 405
FEATURE                Location/Qualifiers
misc_feature           1..405
                       note = Synthetic polymer.
source                 1..405
                       mol_type = other DNA
                       organism = synthetic construct
SEQUENCE: 876
caggtgcagc tgcaggagtc tggggaggc ttggtgcagg ctggggggtc tctgagactc  60
tcgtgtgcag cctctggagg cttcgacagt cgcaatgcca tgggctggta ccgccaggct  120
ccagggaagc gccgcgagtg ggtcgcaact attactagtg atggtcgcac aaactatgca  180
gactccgtga aggcccgatt caccatctcc agagacaatt ccaagaacac ggtgtatctg  240
cagatgaaca gcctgaaacc agaggacacg gccgtctatt actgtaatgc agcgcctccg  300
atcttcggtt cctggggcca ggggacccag gtcaccgtct cctcagcggc cgcatacccg  360
tacgacgttc cggactacgg ttcccaccac catcaccatc actag               405

SEQ ID NO: 877         moltype = DNA  length = 405
FEATURE                Location/Qualifiers
misc_feature           1..405
                       note = Synthetic polymer.
source                 1..405
                       mol_type = other DNA
                       organism = synthetic construct
SEQUENCE: 877
caggtgcagc tgcaggagtc tggaggaggc ttggtgcagg ctggggggtc tctgagactc  60
tcgtgtgcag cctctggaag catcgacagt cgcaatacca tgggctggta ccgccaggct  120
ccagggaagc gccgcgagtg ggtcgcaact attactactg gtggtcgcac aaactatgca  180
gactccgtga aggcccgatt caccatctcc agagacaatg ccaagaacac ggtgtatctg  240
cagatgaaca gcctgaaacc agaggacacg gccgtctatt actgtaatct agcgcctccg  300
atcttcaatt cctggggcca ggggacccag gtcaccgtct cctcagcggc cgcatacccg  360
tacgacgttc cggactacgg ttcccaccac catcaccatc actag               405

SEQ ID NO: 878         moltype = DNA  length = 405
FEATURE                Location/Qualifiers
misc_feature           1..405
                       note = Synthetic polymer.
source                 1..405
                       mol_type = other DNA
                       organism = synthetic construct
SEQUENCE: 878
caggtgcagc tgcaggagtc tggaggaggc ttggtgcggg ctggggggtc tctgagactc  60
tcgtgtgcag cctctggaac gttcgatagt cgcaatgcca tgggctggta ccgccaggct  120
ccagggaagc gccgcgagtg ggtcgcgact attactactg atggtcgcac aaactatgca  180
gactccgtga aggcccgatt caccatctcc agagacaatg ccaagaacac ggtgtatctg  240
cagatgaaca gcctgaaacc agaggacacg gccgtctatt actgtaatgc ggcgcctccg  300
atcttcggtt cctggggcca ggggacccag gtcaccgtct cctcagcggc cgcatacccg  360
tacgacgttc cggactacgg ttcccaccac catcaccatc actag               405

SEQ ID NO: 879         moltype = DNA  length = 405
FEATURE                Location/Qualifiers
misc_feature           1..405
                       note = Synthetic polymer.
source                 1..405
                       mol_type = other DNA
                       organism = synthetic construct
SEQUENCE: 879
caggtgcagc tgcaggagtc tggggaggc ttggtacagg ctggggggtc tctgagactc  60
tcgtgtgcag cctctggaag catcgacatt cgcaatgcca tgggctggta ccgccaggct  120
```

```
ccggggacgc gccgcgagtg ggtcgcaact attactacgg atggtcgcac aaactatgca  180
gactccgtga aggcccgatt caccatctcc agagacaatg ccaagaacac ggtgtatctg  240
cagatgaaca gcctgaaacc agaggacacg gccgtctatt actgtaattt agcgcctccg  300
atcttcggtt cctggggcca ggggacccag gtcaccgtct cctcagcggc cgcatacccg  360
tacgacgttc cggactacgg ttcccaccac catcaccatc actag                  405

SEQ ID NO: 880         moltype = DNA  length = 405
FEATURE                Location/Qualifiers
misc_feature           1..405
                       note = Synthetic polymer.
source                 1..405
                       mol_type = other DNA
                       organism = synthetic construct
SEQUENCE: 880
caggtgcagc tgcaggagtc tggggggggc ttggtgcggg ttggggggtc tctgagactc  60
tcgtgtgcag tttctggaag cttcgacagt cgcaacagca tgggctggta ccgccaggct  120
ccagggaagc gccgcgagtg ggtcgcaact attactagtg gtagtcgcac aaactatgca  180
gactccgtga aggcccgatt caccatctcc agagacaatg ccaagaacac ggtgtatctg  240
cagatggaca gcctgaaacc agaggacacg gccgtctatt actgtaatgc agcgcctccg  300
atcttcaatt cctggggcca ggggacccag gtcaccgtct cctcagcggc cgcatacccg  360
tacgacgttc cggactacgg ttcccaccac catcaccatc actag                  405

SEQ ID NO: 881         moltype = DNA  length = 405
FEATURE                Location/Qualifiers
misc_feature           1..405
                       note = Synthetic polymer.
source                 1..405
                       mol_type = other DNA
                       organism = synthetic construct
SEQUENCE: 881
caggtgcagc tgcaggagtc tgggggaggc ttggtgcagg ctggggggtc tctgagactc  60
tcctgtacag tcgctgaaag catcgacgtt cgcaatgcca tgggctggta ccgccaggct  120
ccagggaagc gccgcgagtg ggtcgcaact attactactg gtggacgcac aaactatgca  180
gactccgtga aggcccgatt caccatctcc agagacaatg ccaagaacac ggtgtatcta  240
cagatgaaca gcctgaaacc agaggacacg gccgtctatt attgtaatgc agcgcctccg  300
atcctcaatt cctggggcca ggggacccag gtcaccgtct cctcagcggc cgcatacccg  360
tacgacgttc cggactacgg ttcccaccac catcaccatc actag                  405

SEQ ID NO: 882         moltype = DNA  length = 414
FEATURE                Location/Qualifiers
misc_feature           1..414
                       note = Synthetic polymer.
source                 1..414
                       mol_type = other DNA
                       organism = synthetic construct
SEQUENCE: 882
caggtgcagc tgcaggagtc tggaggaggc ttggtgcagg ctggggggtc tctgagactc  60
tcctgtgtag cctctggaac catcttcagt agcggagcca tggccatggg ctggtaccgc  120
caggctccag ggaaacagcg cgagtgggtc gcaggtatta ctggtagtcg tacaacaacc  180
tatgcagact ccgtgaaggg ccgattcacc atctccagag acaacgccga gaacacggtt  240
tttctgcaaa tgaacaacct gaaatctgaa gacacagccg tctattactg taatctatgg  300
ccaccctcga ggcccgacca ctggggccag gggacccagg tcaccgtctc ctcagcggcc  360
gcatacccgt acgacgttcc ggactacggt tcccaccacc atcaccatca ctag        414

SEQ ID NO: 883         moltype = DNA  length = 405
FEATURE                Location/Qualifiers
misc_feature           1..405
                       note = Synthetic polymer.
source                 1..405
                       mol_type = other DNA
                       organism = synthetic construct
SEQUENCE: 883
caggtgcagc tgcaggagtc tgggggaggc ttggtgcagg ctggggggtc tctgagactc  60
tcctgtgtag cctctggaac catcagtagt ggagccatgg gctggtaccg ccaggttcca  120
gggaagcagc gcgagtgggt cgcaggtatt actggtagtc gtacaacaat gtatacagaa  180
tccgtgaagg gccgattcac catctccaga gacaacgccg agaacacggt tttctgcaa   240
atgaacaacc tgaaatctga agacacagcc gtctattact gtaatctatg gccaccctcg  300
aggcccgact actggggtca ggggacccag gtcaccgtct cctcagcggc cgcatacccg  360
tacgacgttc cggactacgg ttcccaccac catcaccatc actag                  405

SEQ ID NO: 884         moltype = DNA  length = 411
FEATURE                Location/Qualifiers
misc_feature           1..411
                       note = Synthetic polymer.
source                 1..411
                       mol_type = other DNA
                       organism = synthetic construct
SEQUENCE: 884
caggtgcagc tgcaggagtc tggaggagga ttggtgcagg ctgggggctc tctgagactc  60
```

-continued

```
tcctgtgcag cctctagaag catcttcagt atcggcacca tgggctggta ccgccaggct   120
ccagggaagc ggcgcgagtt ggtcgcattt attactgttg atcataatac atactataca   180
gactccgtga aaggccgatt caccatctcc acagagaatg acaagaacac ggtgtatctg   240
caaatgaaca gcctgaaacc tgaagatacg gccgtctatt actgtaatcg agctcctcca   300
tcgaccgacg gggatcgatg gggccagggg acccaggtca ccgtctcctc agcggccgca   360
tacccgtacg acgttccgga ctacggttcc caccaccatc accatcacta g            411
```

```
SEQ ID NO: 885              moltype = AA  length = 121
FEATURE                     Location/Qualifiers
REGION                      1..121
                            note = Synthetic polymer.
source                      1..121
                            mol_type = protein
                            organism = synthetic construct
SEQUENCE: 885
EVQLVESGGG LVQPGGSLRL SCAASGFTFS RYWMSWVRQA PGKGLEWVAN IKQDGSEKYY   60
VDSVKGRFTI SRDNAKNSLY LQMNSLRAED TAVYYCAREG GWFGELAFDY WGQGTLVTVS   120
S                                                                    121
```

```
SEQ ID NO: 886              moltype = AA  length = 108
FEATURE                     Location/Qualifiers
REGION                      1..108
                            note = Synthetic polymer.
source                      1..108
                            mol_type = protein
                            organism = synthetic construct
SEQUENCE: 886
EIVLTQSPGT LSLSPGERAT LSCRASQRVS SSYLAWYQQK PGQAPRLLIY DASSRATGIP   60
DRFSGSGSGT DFTLTISRLE PEDFAVYYCQ QYGSLPWTFG QGTKVEIK                108
```

```
SEQ ID NO: 887              moltype = AA  length = 448
FEATURE                     Location/Qualifiers
REGION                      1..448
                            note = Synthetic polymer.
source                      1..448
                            mol_type = protein
                            organism = synthetic construct
SEQUENCE: 887
EVQLVESGGG LVQPGGSLRL SCAASGFTFS DSWIHWVRQA PGKGLEWVAW ISPYGGSTYY   60
ADSVKGRFTI SADTSKNTAY LQMNSLRAED TAVYYCARRH WPGGFDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYAST   300
YRVVSVLTVL HQDWLNGKEY KCKVSNKALP APIEKTISKA KGQPREPQVY TLPPSREEMT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGK                                      448
```

```
SEQ ID NO: 888              moltype = AA  length = 214
FEATURE                     Location/Qualifiers
REGION                      1..214
                            note = Synthetic polymer.
source                      1..214
                            mol_type = protein
                            organism = synthetic construct
SEQUENCE: 888
DIQMTQSPSS LSASVGDRVT ITCRASQDVS TAVAWYQQKP GKAPKLLIYS ASFLYSGVPS   60
RFSGSGSGTD FTLTISSLQP EDFATYYCQQ YLYHPATFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214
```

```
SEQ ID NO: 889              moltype = AA  length = 450
FEATURE                     Location/Qualifiers
REGION                      1..450
                            note = Synthetic polymer.
source                      1..450
                            mol_type = protein
                            organism = synthetic construct
SEQUENCE: 889
EVQLLESGGG IYPSGGITFY LGTVTTVDYW DYFPEPVTVS YICNVNHKPS KDTLMISRTP   60
STYRVVSVLT VYTLPPSRDE LDSDGSFFLY LVQPGGSLRL ADTVKGRFTI GQGTLVTVSS   120
WNSGALTSGV NTKVDKKVEP EVTCVVVDVS VLHQDWLNGK LTKNQVSLTC SKLTVDKSRW   180
SCAASGFTFS SRDNSKNTLY ASTKGPSVFP HTFPAVLQSS KSCDKTHTCP HEDPEVKFNW   240
EYKCKVSNKA LVKGFYPSDI QQGNVFSCSV SYIMMWVRQA LQMNSLRAED LAPSSKSTSG   300
GLYSLSSVVT PCPAPELLGG YVDGVEVHNA LPAPIEKTIS AVEWESNGQP MHEALHNHYT   360
PGKGLEWVSS TAVYYCARIK GTAALGCLVK VPSSSLGTQT PSVFLFPPKP KTKPREEQYN   420
KAKGQPREPQ ENNYKTTPPV QKSLSLSPGK                                    450
```

```
SEQ ID NO: 890              moltype = AA  length = 216
FEATURE                     Location/Qualifiers
```

```
REGION                  1..216
                        note = Synthetic polymer.
source                  1..216
                        mol_type = protein
                        organism = synthetic construct
SEQUENCE: 890
QSALTQPASV SGSPGQSITI SCTGTSSDVG GYNYVSWYQQ HPGKAPKLMI YDVSNRPSGV  60
SNRFSGSKSG NTASLTISGL QAEDEADYYC SSYTSSSTRV FGTGTKVTVL GQPKANPTVT  120
LFPPSSEELQ ANKATLVCLI SDFYPGAVTV AWKADGSPVK AGVETTKPSK QSNNKYAASS  180
YLSLTPEQWK SHRSYSCQVT HEGSTVEKTV APTECS                            216

SEQ ID NO: 891          moltype = AA  length = 123
FEATURE                 Location/Qualifiers
REGION                  1..123
                        note = Synthetic polymer.
source                  1..123
                        mol_type = protein
                        organism = synthetic construct
SEQUENCE: 891
QVQLVQSGAE VKKPGSSVKV SCKTSGDTES TYAISWVRQA PGQGLEWMGG IIPIEGKAHY  60
AQKFQGRVTI TADESTSTAY MELSSLRSED TAVYFCARKF HEVSGSPFGM DVWGQGTTVT  120
VSS                                                                123

SEQ ID NO: 892          moltype = AA  length = 106
FEATURE                 Location/Qualifiers
REGION                  1..106
                        note = Synthetic polymer.
source                  1..106
                        mol_type = protein
                        organism = synthetic construct
SEQUENCE: 892
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TKVEIK                 106

SEQ ID NO: 893          moltype = AA  length = 117
FEATURE                 Location/Qualifiers
REGION                  1..117
                        note = Synthetic polymer.
source                  1..117
                        mol_type = protein
                        organism = synthetic construct
SEQUENCE: 893
QVQLVQSGAE VKKPGASVKV SCKASGYTFT DYGFSWVRQA PGQGLEWMGW ITAYNGNTNY  60
AQKLQGRVTM TTDTSTSTVY MELRSLRSDD TAVYYCARDY FYGMDVWGQG TTVTVSS     117

SEQ ID NO: 894          moltype = AA  length = 107
FEATURE                 Location/Qualifiers
REGION                  1..107
                        note = Synthetic polymer.
source                  1..107
                        mol_type = protein
                        organism = synthetic construct
SEQUENCE: 894
EIVLTQSPAT LSLSPGERAT LSCRASQSVS SYLVWYQQKP GQAPRLLIYD ASNRATGIPA  60
RFSGSGSGTD FTLTISSLEP EDFAVYYCQQ RSNWPRTFGQ GTKVEIK                107

SEQ ID NO: 895          moltype = AA  length = 118
FEATURE                 Location/Qualifiers
REGION                  1..118
                        note = Synthetic polymer.
source                  1..118
                        mol_type = protein
                        organism = synthetic construct
SEQUENCE: 895
QVQLVQSGAE VKKPGASVKV SCKASGYTFT SYDVHWVRQA PGQRLEWMGW LHADTGITKF  60
SQKFQGRVTI TRDTSASTAY MELSSLRSED TAVYYCARER IQLWFDYWGQ GTLVTVSS    118

SEQ ID NO: 896          moltype = AA  length = 107
FEATURE                 Location/Qualifiers
REGION                  1..107
                        note = Synthetic polymer.
source                  1..107
                        mol_type = protein
                        organism = synthetic construct
SEQUENCE: 896
DIQMTQSPSS LSASVGDRVT ITCRASQGIS SWLAWYQQKP EKAPKSLIYA ASSLQSGVPS  60
RFSGSGSGTD FTLTISSLQP EDFATYYCQQ YNSYPYTFGQ GTKLEIK                107

SEQ ID NO: 897          moltype = AA  length = 120
```

-continued

```
FEATURE                Location/Qualifiers
REGION                 1..120
                       note = Synthetic polymer.
source                 1..120
                       mol_type = protein
                       organism = synthetic construct
SEQUENCE: 897
QVQLVQSGAE VKKPGSSVKV SCKVSGGIFS TYAINWVRQA PGQGLEWMGG IIPIFGTANH  60
AQKFQGRVTI TADESTSTAY MELSSLRSED TAVYYCARDQ GIAAALFDYW GQGTLVTVSS  120

SEQ ID NO: 898         moltype = AA  length = 108
FEATURE                Location/Qualifiers
REGION                 1..108
                       note = Synthetic polymer.
source                 1..108
                       mol_type = protein
                       organism = synthetic construct
SEQUENCE: 898
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPWTFG QGTKVEIK             108

SEQ ID NO: 899         moltype = AA  length = 113
FEATURE                Location/Qualifiers
REGION                 1..113
                       note = Synthetic polymer.
source                 1..113
                       mol_type = protein
                       organism = synthetic construct
SEQUENCE: 899
EVQLVESGGG LVQPGRSLRL SCAVSGETFD DYVVHWVRQA PGKGLEWVSG ISGNSGNIGY  60
ADSVKGRFTI SRDNAKNSLY LQMNSLRAED TALYYCAVPF DYWGQGTLVT VSS         113

SEQ ID NO: 900         moltype = AA  length = 107
FEATURE                Location/Qualifiers
REGION                 1..107
                       note = Synthetic polymer.
source                 1..107
                       mol_type = protein
                       organism = synthetic construct
SEQUENCE: 900
DIQMTQSPSS LSASVGDRVT ITCRASQGIS SWLAWYQQKP EKAPKSLIYA ASSLQSGVPS  60
RFSGSGSGTD FTLTISSLQP EDFATYYCQQ YNSYPYTFGQ GTKLEIK              107

SEQ ID NO: 901         moltype = AA  length = 123
FEATURE                Location/Qualifiers
REGION                 1..123
                       note = Synthetic polymer.
source                 1..123
                       mol_type = protein
                       organism = synthetic construct
SEQUENCE: 901
QVQLVQSGAE VKKPGSSVKV SCKTSGDTFS SYAISWVRQA PGQGLEWMGG IIPIFGRAHY  60
AQKFQGRVTI TADESTSTAY MELSSLRSED TAVYFCARKF HEVSGSPFGM DVWGQGTTVT  120
VSS                                                              123

SEQ ID NO: 902         moltype = AA  length = 106
FEATURE                Location/Qualifiers
REGION                 1..106
                       note = Synthetic polymer.
source                 1..106
                       mol_type = protein
                       organism = synthetic construct
SEQUENCE: 902
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TKVEIK               106

SEQ ID NO: 903         moltype = AA  length = 123
FEATURE                Location/Qualifiers
REGION                 1..123
                       note = Synthetic polymer.
source                 1..123
                       mol_type = protein
                       organism = synthetic construct
SEQUENCE: 903
QVQLVQSGAE VKKPGSSVKV SCKTSGGTFS SYAISWVRQA PGQGLEWMGG IIPIFGKAHY  60
AQKFQGRVTI TADESTTTAY MELSSLRSED TAVYYCARKY DYVSGSPFGM DVWGQGTTVT  120
VSS                                                              123

SEQ ID NO: 904         moltype = AA  length = 106
```

-continued

```
FEATURE                 Location/Qualifiers
REGION                  1..106
                        note = Synthetic polymer.
source                  1..106
                        mol_type = protein
                        organism = synthetic construct
SEQUENCE: 904
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TKVEIK                106

SEQ ID NO: 905          moltype = AA  length = 121
FEATURE                 Location/Qualifiers
REGION                  1..121
                        note = Synthetic polymer.
source                  1..121
                        mol_type = protein
                        organism = synthetic construct
SEQUENCE: 905
QVQLVQSGAE VKKPGSSVKV SCKASGGTFS SYAINWVRQA PGQGLEWMGG IIPIFGSANY  60
AQKFQDRVTI TADESTSAAY MELSSLRSED TAVYYCARDS SGWSRYYMDV WGQGTTVTVS  120
S                                                                 121

SEQ ID NO: 906          moltype = AA  length = 106
FEATURE                 Location/Qualifiers
REGION                  1..106
                        note = Synthetic polymer.
source                  1..106
                        mol_type = protein
                        organism = synthetic construct
SEQUENCE: 906
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPFGGG TKVEIK                106

SEQ ID NO: 907          moltype = AA  length = 123
FEATURE                 Location/Qualifiers
REGION                  1..123
                        note = Synthetic polymer.
source                  1..123
                        mol_type = protein
                        organism = synthetic construct
SEQUENCE: 907
QVQLVQSGAE VKEPGSSVKV SCKASGGTFN SYAISWVRQA PGQGLEWMGG IIPLFGIAHY  60
AQKFQGRVTI TADESTNTAY MDLSSLRSED TAVYYCARKY SYVSGSPFGM DVWGQGTTVT  120
VSS                                                               123

SEQ ID NO: 908          moltype = AA  length = 106
FEATURE                 Location/Qualifiers
REGION                  1..106
                        note = Synthetic polymer.
source                  1..106
                        mol_type = protein
                        organism = synthetic construct
SEQUENCE: 908
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TRLEIK                106

SEQ ID NO: 909          moltype = AA  length = 121
FEATURE                 Location/Qualifiers
REGION                  1..121
                        note = Synthetic polymer.
source                  1..121
                        mol_type = protein
                        organism = synthetic construct
SEQUENCE: 909
EVQLVESGGG LVQPGRSLRL SCAASGITFD DYGMHWVRQA PGKGLEWVSG ISWNRGRIEY  60
ADSVKGRFTI SRDNAKNSLY LQMNSLRAED TALYYCAKGR FRYFDWFLDY WGQGTLVTVS  120
S                                                                 121

SEQ ID NO: 910          moltype = AA  length = 107
FEATURE                 Location/Qualifiers
REGION                  1..107
                        note = Synthetic polymer.
source                  1..107
                        mol_type = protein
                        organism = synthetic construct
SEQUENCE: 910
AIQLTQSPSS LSASVGDRVT ITCRASQGIS SALAWYQQKP GKAPKLLIYD ASSLESGVPS  60
RFSGSGSGTD FTLTISSLQP EDFATYYCQQ FNSYPFTFGP GTKVDIK               107
```

-continued

```
SEQ ID NO: 911          moltype = AA  length = 118
FEATURE                 Location/Qualifiers
REGION                  1..118
                        note = Synthetic polymer.
source                  1..118
                        mol_type = protein
                        organism = synthetic construct
SEQUENCE: 911
EVKLQESGPS LVKPSQTLSL TCSVTGYSIT SDYWNWIRKF PGNKLEYVGY ISYTGSTYYN  60
PSLKSRISIT RDTSKNQYYL QLNSVTSEDT ATYYCARYGG WLSPFDYWGQ GTTLTVSS    118

SEQ ID NO: 912          moltype = AA  length = 107
FEATURE                 Location/Qualifiers
REGION                  1..107
                        note = Synthetic polymer.
source                  1..107
                        mol_type = protein
                        organism = synthetic construct
SEQUENCE: 912
DIVMTQSHKL MSTSVGDRVS ITCKASQDVG TAVAWYQQKP GQSPKLLIYW ASTRHTGVPD  60
RFTGSGSGTD FTLTISNVQS EDLADYFCQQ DSSYPLTFGA GTKVELK               107

SEQ ID NO: 913          moltype = AA  length = 120
FEATURE                 Location/Qualifiers
REGION                  1..120
                        note = Synthetic polymer.
source                  1..120
                        mol_type = protein
                        organism = synthetic construct
SEQUENCE: 913
EVQLQESGPG LVAPSQSLSI TCTVSGFSLT TYSINWIRQP PGKGLEWLGV MWAGGGTNSN  60
SVLKSRLIIS KDNSKSQVFL KMNSLQTDDT ARYYCARYYG NSPYYAIDYW GQGTSVTVSS  120

SEQ ID NO: 914          moltype = AA  length = 107
FEATURE                 Location/Qualifiers
REGION                  1..107
                        note = Synthetic polymer.
source                  1..107
                        mol_type = protein
                        organism = synthetic construct
SEQUENCE: 914
DIVTTQSHKL MSTSVGDRVS ITCKASQDVG TAVAWYQQKP GQSPKLLIYW ASTRHTGVPD  60
RFTGSGSGTD FTLTISNVQS EDLADYFCQQ DSSYPLTFGA GTKVELK               107
```